(12) United States Patent
Malecova et al.

(10) Patent No.: US 11,999,955 B2
(45) Date of Patent: *Jun. 4, 2024

(54) COMPOSITIONS AND METHODS OF TREATING FACIOSCAPULOHUMERAL MUSCULAR DYSTROPHY

(71) Applicant: Avidity Biosciences, Inc., San Diego, CA (US)

(72) Inventors: Barbora Malecova, San Diego, CA (US); Rob Burke, Carlsbad, CA (US); David Sala Cano, San Diego, CA (US); Beatrice Diana Darimont, San Diego, CA (US)

(73) Assignee: AVIDITY BIOSCIENCES, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/052,898

(22) Filed: Nov. 4, 2022

(65) Prior Publication Data

US 2023/0340474 A1  Oct. 26, 2023

Related U.S. Application Data

(63) Continuation of application No. 17/200,612, filed on Mar. 12, 2021, now Pat. No. 11,555,190.

(60) Provisional application No. 63/066,655, filed on Aug. 17, 2020, provisional application No. 62/992,071, filed on Mar. 19, 2020.

(51) Int. Cl.
| | |
|---|---|
| C12N 15/113 | (2010.01) |
| A61K 31/7125 | (2006.01) |
| A61K 47/68 | (2017.01) |
| A61K 48/00 | (2006.01) |
| A61P 21/00 | (2006.01) |
| A61P 21/06 | (2006.01) |
| C07K 16/28 | (2006.01) |
| C07K 19/00 | (2006.01) |

(52) U.S. Cl.
CPC ........ *C12N 15/113* (2013.01); *A61K 31/7125* (2013.01); *A61K 47/6807* (2017.08); *A61K 47/6849* (2017.08); *A61K 47/6889* (2017.08); *A61K 48/005* (2013.01); *A61P 21/00* (2018.01); *A61P 21/06* (2018.01); *C07K 16/2881* (2013.01); *C07K 19/00* (2013.01); *C07K 2317/55* (2013.01); *C12N 2310/11* (2013.01); *C12N 2310/14* (2013.01); *C12N 2310/31* (2013.01); *C12N 2310/313* (2013.01); *C12N 2310/321* (2013.01); *C12N 2310/3231* (2013.01); *C12N 2310/3513* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 4,866,132 A | 9/1989 | Obligin et al. | |
| 4,921,963 A | 5/1990 | Skov et al. | |
| 5,064,849 A | 11/1991 | Suzuki et al. | |
| 5,142,047 A | 8/1992 | Summerton et al. | |
| 5,185,444 A | 2/1993 | Summerton et al. | |
| 5,208,020 A | 5/1993 | Chari et al. | |
| 5,256,334 A | 10/1993 | Smid et al. | |
| 5,334,711 A | 8/1994 | Sproat et al. | |
| 5,346,981 A | 9/1994 | Sarpeshkar et al. | |
| 5,416,064 A | 5/1995 | Chari et al. | |
| 5,627,053 A | 5/1997 | Usman et al. | |
| 5,700,825 A | 12/1997 | Hofer et al. | |
| 5,716,824 A | 2/1998 | Beigelman et al. | |
| 5,736,557 A | 4/1998 | Hofheinz et al. | |
| 5,849,738 A | 12/1998 | Lee et al. | |
| 5,872,107 A | 2/1999 | Schinazi et al. | |
| 5,889,136 A | 3/1999 | Scaringe et al. | |
| 5,898,031 A | 4/1999 | Crooke | |
| 5,939,045 A | 8/1999 | Suzuki et al. | |
| 5,945,439 A | 8/1999 | Richter et al. | |
| 6,008,400 A | 12/1999 | Scaringe et al. | |
| 6,107,094 A | 8/2000 | Crooke | |
| 6,111,086 A | 8/2000 | Scaringe | |
| 6,194,551 B1 | 2/2001 | Idusogie et al. | |
| 6,528,624 B1 | 3/2003 | Idusogie et al. | |
| 6,538,124 B1 | 3/2003 | Idusogie et al. | |
| 6,562,806 B1 | 5/2003 | Thurston et al. | |
| 6,608,192 B1 | 8/2003 | Thurston et al. | |
| 6,716,821 B2 | 4/2004 | Zhao et al. | |
| 6,821,783 B1 | 11/2004 | Comely et al. | |
| 6,849,272 B1 | 2/2005 | Langer et al. | |

(Continued)

FOREIGN PATENT DOCUMENTS

| | | |
|---|---|---|
| CA | 2123307 A1 | 6/1993 |
| CN | 110248963 A | 9/2019 |

(Continued)

OTHER PUBLICATIONS

Aartsma-Rus et al. Guidelines for antisense oligonucleotide design and insight into splice-modulating mechanisms. Mol Ther 17(3):548-53 (2009).

(Continued)

*Primary Examiner* — Aurora M Fontainhas
*Assistant Examiner* — Jennifer A Benavides
(74) *Attorney, Agent, or Firm* — WILSON SONSINI GOODRICH & ROSATI

(57) ABSTRACT

Disclosed herein are polynucleic acid molecules, pharmaceutical compositions, and methods for treating Facioscapulohumeral muscular dystrophy.

16 Claims, 22 Drawing Sheets
Specification includes a Sequence Listing.

(56) References Cited

U.S. PATENT DOCUMENTS

| | | |
|---|---|---|
| 6,884,869 B2 | 4/2005 | Senter et al. |
| 6,942,972 B2 | 9/2005 | Farooqui et al. |
| 7,049,311 B1 | 5/2006 | Thurston et al. |
| 7,056,704 B2 | 6/2006 | Tuschl et al. |
| 7,067,511 B2 | 6/2006 | Thurston et al. |
| 7,078,196 B2 | 7/2006 | Tuschl et al. |
| 7,132,519 B2 | 11/2006 | Monforte et al. |
| 7,244,724 B2 | 7/2007 | Liu et al. |
| 7,250,496 B2 | 7/2007 | Bentwich |
| 7,276,497 B2 | 10/2007 | Chari et al. |
| 7,351,855 B2 | 4/2008 | Coutts et al. |
| 7,364,731 B2 | 4/2008 | Idusogie et al. |
| 7,432,249 B2 | 10/2008 | Crooke |
| 7,432,250 B2 | 10/2008 | Crooke |
| 7,452,987 B2 | 11/2008 | Giese et al. |
| 7,459,547 B2 | 12/2008 | Zamore et al. |
| 7,498,298 B2 | 3/2009 | Doronina et al. |
| 7,521,232 B2 | 4/2009 | Moon |
| 7,528,126 B2 | 5/2009 | Howard et al. |
| 7,595,387 B2 | 9/2009 | Leake et al. |
| 7,612,062 B2 | 11/2009 | Gregson et al. |
| 7,629,321 B2 | 12/2009 | Crooke |
| 7,659,241 B2 | 2/2010 | Senter et al. |
| 7,691,997 B2 | 4/2010 | Khvorova et al. |
| 7,704,924 B2 | 4/2010 | Thurston et al. |
| 7,709,226 B2 | 5/2010 | Foote |
| 7,732,593 B2 | 6/2010 | Zamore et al. |
| 7,750,116 B1 | 7/2010 | Doronina et al. |
| 7,750,144 B2 | 7/2010 | Zamore et al. |
| 7,772,203 B2 | 8/2010 | Zamore et al. |
| 7,786,290 B2 | 8/2010 | Woppmann et al. |
| 7,829,693 B2 | 11/2010 | Kreutzer et al. |
| 7,833,992 B2 | 11/2010 | Vargeese et al. |
| 7,834,171 B2 | 11/2010 | Khvorova et al. |
| 7,850,975 B2 | 12/2010 | Mullis |
| 7,893,245 B2 | 2/2011 | Giese et al. |
| 7,923,547 B2 | 4/2011 | Mcswiggen et al. |
| 7,928,217 B2 | 4/2011 | Vornlocher et al. |
| 7,943,762 B2 | 5/2011 | Weller et al. |
| 7,964,566 B2 | 6/2011 | Doronina et al. |
| 8,084,582 B2 | 12/2011 | Dahiyat et al. |
| 8,084,598 B1 | 12/2011 | Bentwich |
| 8,090,542 B2 | 1/2012 | Khvorova et al. |
| 8,137,695 B2 | 3/2012 | Rozema et al. |
| 8,163,736 B2 | 4/2012 | Gauzy et al. |
| 8,202,979 B2 | 6/2012 | Mcswiggen et al. |
| 8,268,986 B2 | 9/2012 | Beigelman et al. |
| 8,273,866 B2 | 9/2012 | Mcswiggen et al. |
| 8,283,329 B2 | 10/2012 | Fire et al. |
| 8,288,352 B2 | 10/2012 | Doronina et al. |
| 8,304,530 B2 | 11/2012 | Zamore et al. |
| 8,309,704 B2 | 11/2012 | Zamore et al. |
| 8,309,705 B2 | 11/2012 | Zamore et al. |
| 8,324,370 B2 | 12/2012 | Giese et al. |
| 8,324,371 B2 | 12/2012 | Popplewell et al. |
| 8,329,892 B2 | 12/2012 | Zamore et al. |
| 8,334,373 B2 | 12/2012 | Vornlocher et al. |
| 8,361,979 B2 | 1/2013 | Aartsma-Rus et al. |
| 8,362,231 B2 | 1/2013 | Tuschl et al. |
| 8,372,968 B2 | 2/2013 | Tuschl et al. |
| 8,389,710 B2 | 3/2013 | Bruno et al. |
| 8,404,678 B2 | 3/2013 | Bouchard et al. |
| 8,420,391 B2 | 4/2013 | Tuschl et al. |
| 8,426,402 B2 | 4/2013 | Li et al. |
| 8,445,237 B2 | 5/2013 | Tuschl et al. |
| 8,461,325 B2 | 6/2013 | Popplewell et al. |
| 8,481,698 B2 | 7/2013 | Lieberman et al. |
| 8,501,703 B2 | 8/2013 | Bennett et al. |
| 8,501,930 B2 | 8/2013 | Rozema et al. |
| 8,501,934 B2 | 8/2013 | Howard et al. |
| 8,546,143 B2 | 10/2013 | Kreutzer et al. |
| 8,552,171 B2 | 10/2013 | Tuschl et al. |
| 8,557,292 B2 | 10/2013 | Davis et al. |
| 8,580,820 B2 | 11/2013 | Zanda et al. |
| 8,591,910 B2 | 11/2013 | Mullis |
| 8,604,184 B2 | 12/2013 | Mullis et al. |
| 8,609,105 B2 | 12/2013 | Senter et al. |
| 8,618,277 B2 | 12/2013 | Beigelman et al. |
| 8,632,997 B2 | 1/2014 | Tuschl et al. |
| 8,633,185 B2 | 1/2014 | Howard et al. |
| 8,648,185 B2 | 2/2014 | Mcswigen et al. |
| 8,691,786 B2 | 4/2014 | Rossi et al. |
| 8,697,688 B2 | 4/2014 | Howard et al. |
| 8,703,714 B2 | 4/2014 | Doronina et al. |
| 8,746,999 B2 | 6/2014 | Davis et al. |
| 8,765,930 B2 | 7/2014 | Tuschl et al. |
| 8,772,469 B2 | 7/2014 | Uhlmann et al. |
| 8,778,902 B2 | 7/2014 | Tuschl et al. |
| 8,790,922 B2 | 7/2014 | Tuschl et al. |
| 8,796,016 B2 | 8/2014 | Tuschl et al. |
| 8,796,443 B2 | 8/2014 | Khvorova et al. |
| 8,802,667 B2 | 8/2014 | Li et al. |
| 8,809,320 B2 | 8/2014 | Li et al. |
| 8,835,402 B2 | 9/2014 | Kole et al. |
| 8,846,875 B2 | 9/2014 | Schwartz et al. |
| 8,846,894 B2 | 9/2014 | Mcswiggen et al. |
| 8,853,384 B2 | 10/2014 | Tuschl et al. |
| 8,871,720 B2 | 10/2014 | Doronina et al. |
| 8,895,718 B2 | 11/2014 | Tuschl et al. |
| 8,895,721 B2 | 11/2014 | Tuschl et al. |
| 8,895,722 B2 | 11/2014 | Iversen et al. |
| 8,906,847 B2 | 12/2014 | Cleemann et al. |
| 8,933,044 B2 | 1/2015 | Tuschl et al. |
| 8,933,215 B2 | 1/2015 | Giese et al. |
| 8,936,910 B2 | 1/2015 | Mitsch et al. |
| 8,969,526 B2 | 3/2015 | Baehner et al. |
| 8,980,833 B2 | 3/2015 | Richter |
| 8,993,745 B2 | 3/2015 | Tuschl et al. |
| 9,012,138 B2 | 4/2015 | Tuschl et al. |
| 9,012,621 B2 | 4/2015 | Tuschl et al. |
| 9,078,911 B2 | 7/2015 | Lu |
| 9,089,614 B2 | 7/2015 | Lin et al. |
| 9,096,636 B2 | 8/2015 | Baker et al. |
| 9,096,877 B2 | 8/2015 | Johnson et al. |
| 9,139,828 B2 | 9/2015 | Platenburg et al. |
| 9,175,286 B2 | 11/2015 | Wilton et al. |
| 9,175,289 B2 | 11/2015 | Khvorova et al. |
| 9,181,551 B2 | 11/2015 | Mcswiggen et al. |
| 9,193,753 B2 | 11/2015 | Tuschl et al. |
| 9,212,364 B2 | 12/2015 | Sah et al. |
| 9,222,092 B2 | 12/2015 | Giese et al. |
| 9,228,187 B2 | 1/2016 | Wilton et al. |
| 9,242,013 B2 | 1/2016 | Howard et al. |
| 9,243,251 B2 | 1/2016 | Popplewell et al. |
| 9,243,252 B2 | 1/2016 | Popplewell et al. |
| 9,249,416 B2 | 2/2016 | Wilton et al. |
| 9,260,471 B2 | 2/2016 | Cancilla et al. |
| 9,284,551 B2 | 3/2016 | Puri et al. |
| 9,328,345 B2 | 5/2016 | Li et al. |
| 9,364,553 B2 | 6/2016 | Lee |
| 9,416,361 B2 | 8/2016 | Iversen et al. |
| 9,434,948 B2 | 9/2016 | Sazani et al. |
| 9,441,229 B2 | 9/2016 | Wilton et al. |
| 9,447,415 B2 | 9/2016 | Wilton et al. |
| 9,447,417 B2 | 9/2016 | Sazani et al. |
| 9,481,905 B2 | 11/2016 | Chen et al. |
| 9,499,818 B2 | 11/2016 | Van |
| 9,528,109 B2 | 12/2016 | De Kimpe et al. |
| 9,605,019 B2 | 3/2017 | Verdine et al. |
| 9,657,294 B2 | 5/2017 | Beigelman et al. |
| 9,695,211 B2 | 7/2017 | Wada et al. |
| 9,695,423 B2 | 7/2017 | Giese et al. |
| 9,708,406 B2 | 7/2017 | Zhang et al. |
| 9,732,344 B2 | 8/2017 | Beigelman et al. |
| 9,765,338 B2 | 9/2017 | Bennett et al. |
| 9,771,588 B2 | 9/2017 | Mcswiggen et al. |
| 9,796,974 B2 | 10/2017 | Rajeev et al. |
| 9,890,379 B2 | 2/2018 | De et al. |
| 9,926,557 B2 | 3/2018 | De et al. |
| 9,982,257 B2 | 5/2018 | Butler et al. |
| 10,000,754 B2 | 6/2018 | Beigelman et al. |
| 10,087,210 B2 | 10/2018 | Prakash et al. |
| 10,323,089 B2 | 6/2019 | Dengl et al. |
| 10,487,149 B2 | 11/2019 | Geall et al. |

(56) References Cited

U.S. PATENT DOCUMENTS

| | | |
|---|---|---|
| 10,550,188 B2 | 2/2020 | Geall et al. |
| 10,612,027 B2 | 4/2020 | Maier et al. |
| 10,787,519 B2 | 9/2020 | Geall et al. |
| 10,800,848 B2 | 10/2020 | Geall et al. |
| 10,865,445 B2 | 12/2020 | Van Der Maarel et al. |
| 10,881,743 B2 | 1/2021 | Geall et al. |
| 10,913,800 B2 | 2/2021 | Darimont et al. |
| 10,994,020 B2 | 5/2021 | Levin et al. |
| 11,028,179 B2 | 6/2021 | Darimont et al. |
| 11,110,180 B2 | 9/2021 | Geall et al. |
| 11,111,309 B2 | 9/2021 | Subramanian et al. |
| 11,179,472 B2 | 11/2021 | Levin et al. |
| 11,246,941 B2 | 2/2022 | Geall et al. |
| 11,253,607 B2 | 2/2022 | Geall et al. |
| 11,286,305 B2 | 3/2022 | Subramanian et al. |
| 11,504,391 B1 | 11/2022 | Schlegel et al. |
| 11,525,137 B2 | 11/2022 | Malecova et al. |
| 11,555,190 B2 | 1/2023 | Malecova et al. |
| 11,638,761 B2 | 5/2023 | Subramanian et al. |
| 2002/0142980 A1 | 10/2002 | Thompson et al. |
| 2003/0073207 A1 | 4/2003 | Akhtar et al. |
| 2004/0224893 A1 | 11/2004 | Wang et al. |
| 2007/0004665 A1 | 1/2007 | McSwiggen et al. |
| 2008/0097092 A1 | 4/2008 | Khvorova et al. |
| 2009/0092985 A1 | 4/2009 | Cardozo et al. |
| 2009/0149403 A1 | 6/2009 | Maclachlan et al. |
| 2009/0227655 A1 | 9/2009 | Khan |
| 2011/0039914 A1 | 2/2011 | Pavco et al. |
| 2011/0081362 A1 | 4/2011 | Elledge et al. |
| 2011/0263680 A1 | 10/2011 | Khvorova et al. |
| 2011/0263686 A1 | 10/2011 | Wilton et al. |
| 2011/0293512 A1 | 12/2011 | Violette et al. |
| 2011/0294753 A1 | 12/2011 | De et al. |
| 2011/0301218 A1 | 12/2011 | Bozzoni et al. |
| 2012/0065169 A1 | 3/2012 | Hanson et al. |
| 2012/0094299 A1 | 4/2012 | Ranum et al. |
| 2012/0122800 A1 | 5/2012 | Kadushin et al. |
| 2012/0172415 A1 | 7/2012 | Voit et al. |
| 2012/0270925 A1 | 10/2012 | Wilton et al. |
| 2013/0028919 A1 | 1/2013 | Howard et al. |
| 2013/0029900 A1 | 1/2013 | Widdison |
| 2013/0045520 A1 | 2/2013 | Woolf et al. |
| 2013/0052731 A1 | 2/2013 | Ma et al. |
| 2013/0164366 A1 | 6/2013 | Kreutzer et al. |
| 2013/0172238 A1 | 7/2013 | Mitsch et al. |
| 2013/0177579 A1 | 7/2013 | Lin et al. |
| 2013/0177631 A1 | 7/2013 | Kreutzer et al. |
| 2013/0217638 A1 | 8/2013 | Wessjohann et al. |
| 2013/0224228 A1 | 8/2013 | Jackson et al. |
| 2013/0309256 A1 | 11/2013 | Lyon et al. |
| 2013/0323268 A1 | 12/2013 | Chari et al. |
| 2014/0127239 A1 | 5/2014 | Howard |
| 2014/0194610 A1 | 7/2014 | Verdine et al. |
| 2014/0286970 A1 | 9/2014 | Jeffrey et al. |
| 2014/0288158 A1 | 9/2014 | Rajeev et al. |
| 2014/0294851 A1 | 10/2014 | Nguyen |
| 2014/0294868 A1 | 10/2014 | Howard et al. |
| 2014/0296321 A1 | 10/2014 | Iversen |
| 2014/0315862 A1 | 10/2014 | Kaye |
| 2014/0357700 A1 | 12/2014 | Rossi et al. |
| 2014/0363454 A1 | 12/2014 | Jackson et al. |
| 2015/0018540 A1 | 1/2015 | Prakash et al. |
| 2015/0037360 A1 | 2/2015 | Smith |
| 2015/0038554 A1 | 2/2015 | Brown |
| 2015/0038555 A1 | 2/2015 | Brown |
| 2015/0056220 A1 | 2/2015 | Chennamsetty et al. |
| 2015/0105539 A1 | 4/2015 | Miao et al. |
| 2015/0105540 A1 | 4/2015 | Miao et al. |
| 2015/0110791 A1 | 4/2015 | Zhang et al. |
| 2015/0111954 A1 | 4/2015 | Sliz et al. |
| 2015/0141492 A1 | 5/2015 | Tuschl et al. |
| 2015/0211006 A1 | 7/2015 | Butler et al. |
| 2015/0238516 A1 | 8/2015 | Dowdy et al. |
| 2015/0275212 A1 | 10/2015 | Albaek et al. |
| 2015/0366987 A1 | 12/2015 | Bodyak et al. |
| 2016/0002637 A1 | 1/2016 | Sazani et al. |
| 2016/0030332 A1 | 2/2016 | Lee et al. |
| 2016/0032288 A1 | 2/2016 | Tuschl et al. |
| 2016/0053262 A1 | 2/2016 | Platenburg et al. |
| 2016/0102135 A1 | 4/2016 | Escobar-Cabrera |
| 2016/0102148 A1 | 4/2016 | Park et al. |
| 2016/0193354 A1 | 7/2016 | Noe et al. |
| 2016/0298111 A1 | 10/2016 | Bestwick et al. |
| 2016/0304864 A1 | 10/2016 | De et al. |
| 2016/0304874 A1 | 10/2016 | Krauss |
| 2016/0304877 A1 | 10/2016 | Swayze et al. |
| 2016/0367687 A1 | 12/2016 | Manoharan et al. |
| 2017/0081425 A1 | 3/2017 | Colletti et al. |
| 2017/0107512 A1 | 4/2017 | De et al. |
| 2017/0204410 A1 | 7/2017 | Watanabe et al. |
| 2017/0204414 A1 | 7/2017 | Van et al. |
| 2017/0281795 A1 | 10/2017 | Geall et al. |
| 2017/0342416 A1 | 11/2017 | Mcswiggen et al. |
| 2018/0016574 A1 | 1/2018 | Bestwick et al. |
| 2018/0044675 A1 | 2/2018 | Watanabe et al. |
| 2018/0112214 A1 | 4/2018 | De et al. |
| 2018/0127758 A1 | 5/2018 | Bennett |
| 2018/0163209 A1 | 6/2018 | Bennett et al. |
| 2018/0305689 A1 | 10/2018 | Sætrom et al. |
| 2018/0344817 A1 | 12/2018 | Smith et al. |
| 2019/0062435 A1 | 2/2019 | Geall et al. |
| 2019/0062436 A1 | 2/2019 | Geall et al. |
| 2019/0240346 A1 | 8/2019 | Sugo et al. |
| 2019/0300903 A1 | 10/2019 | Harper et al. |
| 2020/0123261 A1 | 4/2020 | Geall et al. |
| 2020/0190523 A1 | 6/2020 | Mardinoglu et al. |
| 2020/0282074 A1 | 9/2020 | Levin et al. |
| 2021/0179720 A1 | 6/2021 | Geall et al. |
| 2021/0206868 A1 * | 7/2021 | Subramanian ......... A61P 21/00 |
| 2022/0324984 A1 | 10/2022 | Geall et al. |
| 2023/0279395 A1 | 9/2023 | Malecova et al. |
| 2023/0287420 A1 | 9/2023 | Malecova et al. |

FOREIGN PATENT DOCUMENTS

| | | |
|---|---|---|
| EP | 1144623 B1 | 8/2002 |
| EP | 0928290 B1 | 3/2005 |
| EP | 1214945 B1 | 6/2005 |
| EP | 1579015 A2 | 9/2005 |
| EP | 1352061 B1 | 5/2006 |
| EP | 1742958 A2 | 1/2007 |
| EP | 1407044 B1 | 9/2007 |
| EP | 1068241 B1 | 10/2007 |
| EP | 1550719 B1 | 12/2008 |
| EP | 2119783 A1 | 11/2009 |
| EP | 1349927 B1 | 3/2010 |
| EP | 1409670 B1 | 10/2010 |
| EP | 1633890 B1 | 10/2010 |
| EP | 2336317 A1 | 6/2011 |
| EP | 2361923 A2 | 8/2011 |
| EP | 2049664 B1 | 9/2011 |
| EP | 1608733 B1 | 12/2011 |
| EP | 1873259 B1 | 1/2012 |
| EP | 2278004 B1 | 10/2012 |
| EP | 2514758 A1 | 10/2012 |
| EP | 2580326 A1 | 4/2013 |
| EP | 2351852 B1 | 10/2013 |
| EP | 2195428 B1 | 12/2013 |
| EP | 2028278 B1 | 3/2014 |
| EP | 2348133 B1 | 7/2014 |
| EP | 2344637 B1 | 12/2014 |
| EP | 1633770 B1 | 4/2015 |
| EP | 2340310 B1 | 6/2015 |
| EP | 1423406 B2 | 11/2015 |
| EP | 2949752 A2 | 12/2015 |
| EP | 2548962 B1 | 1/2016 |
| EP | 3031920 A1 | 6/2016 |
| EP | 2421971 B1 | 7/2016 |
| EP | 2287306 B2 | 10/2016 |
| EP | 3030658 A4 | 3/2017 |
| EP | 2813582 B1 | 4/2017 |
| EP | 2287305 B2 | 11/2017 |
| EP | 2486141 B1 | 1/2018 |
| EP | 2902406 B1 | 1/2018 |

(56) References Cited

FOREIGN PATENT DOCUMENTS

| | | |
|---|---|---|
| EP | 2595664 B1 | 10/2018 |
| KR | 20140026045 A | 3/2014 |
| WO | WO-9104753 A1 | 4/1991 |
| WO | WO-9207065 A1 | 4/1992 |
| WO | WO-9315187 A1 | 8/1993 |
| WO | WO-9726270 A2 | 7/1997 |
| WO | WO-9734631 A1 | 9/1997 |
| WO | WO-9813526 A1 | 4/1998 |
| WO | WO-0149698 A1 | 7/2001 |
| WO | WO-2006000057 A1 | 1/2006 |
| WO | WO-2006006948 A2 | 1/2006 |
| WO | WO-2006128138 A2 | 11/2006 |
| WO | WO-2007021142 A1 | 2/2007 |
| WO | WO-2008036127 A2 | 3/2008 |
| WO | WO-2009099942 A2 | 8/2009 |
| WO | WO-2009099991 A2 | 8/2009 |
| WO | WO-2009108217 A2 | 9/2009 |
| WO | WO-2009126933 A2 | 10/2009 |
| WO | WO-2009129281 A2 | 10/2009 |
| WO | WO-2009144481 A2 | 12/2009 |
| WO | WO-2011003557 A1 | 1/2011 |
| WO | WO-2011009624 A1 | 1/2011 |
| WO | WO-2011150408 A2 | 12/2011 |
| WO | WO-2012012443 A2 | 1/2012 |
| WO | WO-2012092373 A2 | 7/2012 |
| WO | WO-2012125850 A1 | 9/2012 |
| WO | WO-2013166004 A2 | 11/2013 |
| WO | WO-2013166155 A1 | 11/2013 |
| WO | WO-2014080251 A1 | 5/2014 |
| WO | WO-2014140317 A2 | 9/2014 |
| WO | WO-2014145090 A1 | 9/2014 |
| WO | WO-2014154835 A2 | 10/2014 |
| WO | WO-2014177042 A1 | 11/2014 |
| WO | WO-2014189973 A2 | 11/2014 |
| WO | WO-2014197854 A1 | 12/2014 |
| WO | WO-2015021457 A2 | 2/2015 |
| WO | WO-2015038426 A1 | 3/2015 |
| WO | WO-2015057699 A2 | 4/2015 |
| WO | WO-2015069587 A2 | 5/2015 |
| WO | WO-2015084846 A1 | 6/2015 |
| WO | WO-2015107425 A2 | 7/2015 |
| WO | WO-2015113922 A1 | 8/2015 |
| WO | WO-2015200223 A1 | 12/2015 |
| WO | WO-2016028649 A1 | 2/2016 |
| WO | WO-2016081643 A1 | 5/2016 |
| WO | WO-2016187425 A1 | 11/2016 |
| WO | WO-2016207240 A1 | 12/2016 |
| WO | WO-2017007886 A2 | 1/2017 |
| WO | WO-2017148879 A1 | 9/2017 |
| WO | WO-2017173408 A1 | 10/2017 |
| WO | WO-2017192679 A1 | 11/2017 |
| WO | WO-2017221883 A1 | 12/2017 |
| WO | WO-2018129384 A1 | 7/2018 |
| WO | WO-2019060775 A1 | 3/2019 |
| WO | WO-2019071028 A1 | 4/2019 |
| WO | WO-2019113393 A1 | 6/2019 |
| WO | WO-2020028832 A1 | 2/2020 |
| WO | WO-2020132584 A1 | 6/2020 |
| WO | WO-2020142479 A1 | 7/2020 |
| WO | WO-2020203880 A1 | 10/2020 |
| WO | WO-2021188390 A1 | 9/2021 |
| WO | WO-2023043953 A1 | 3/2023 |

OTHER PUBLICATIONS

Aartsma-Rus et al. Progress in therapeutic antisense applications for neuromuscular disorders. Eur J Hum Genet 18(2):146-153 (2010).

Aartsma-Rus et al. Targeted exon skipping as a potential gene correction therapy for Duchenne muscular dystrophy. Neuromuscul Disord. 12 Suppl 1:S71-7 (2002).

Abramova et al. Novel oligonucleotide analogues based on morpholino nucleoside subunits-antisense technologies: new chemical possibilities. Indian Journal of Chemistry 48B:1721-1726 (2009).

Agarwal et al. A Pictet-Spengler ligation for protein chemical modification. PNAS 110(1):46-51 (2013).

Albarran et al. Efficient intracellular delivery of a pro-apoptotic peptide with a pH-responsive carrier. React Funct Polym 71:261-265 (2011).

Alegre et al. Effect of a Single Amino Acid Mutation on the Activating and Immunosuppressive Properties of a "Humanized" OKT3 Monoclonal Antibody. J Immunol 148:3461-3468 (1992).

Al-Lazikani et al.: Standard conformations for the canonical structures of immunoglobulins. J. Mol Biology 273(4):927-948 (1997).

Almagro et al. Humanization of antibodies. Front Biosci 13:1619-1633 (2008).

Arechavala-Gomeza et al. Comparative analysis of antisense oligonucleotide sequences for targeted skipping of exon 51 during dystrophin pre-mRNA splicing in human muscle. Hum Gene Ther. 18(9):798-810 (2007).

Axup et al. Synthesis of site-specific antibody-drug conjugates using unnatural amino acids. PNAS 109(40):16101-16106 (2012).

Ballangrud et al. Response of LNCaP Spheroids After Treatment With an Alpha-Particle Emitter (213Bi)-labeled Anti-Prostate-Specific Membrane Antigen Antibody (J591) Cancer Res. 61:2008-2014 (2001).

Baumer et al. Antibody-mediated delivery of anti-KRAS-siRNA in vivo overcomes therapy resistance in colon cancer. Clin Can Res 21(6):1383-1394 (2015).

Beduneau et al. Design of targeted lipid nanocapsules by conjugation of whole antibodies and antibody Fab' fragments. Biomaterials 28(33):4978-4990 (2007).

Beigelman et al. Chemical modification of hammerhead ribozymes. Catalytic activity and nuclease resistance. J Biol Chem 270:25702-25708 (1995).

Bell et al. Epidermal Growth Factor Receptor Mutations and Gene Amplification in Non-Small-Cell Lung Cancer: Molecular Analysis of the Ideal/Intact Gefitinib Trials. J Clin Oncol 23(31):8081-8092 (2005).

Bird et al. Single-chain antigen-binding proteins. Science 242:423-442 (1988).

Bjarne Udd et al., The myotonic dystrophies: molecular, clinical, and therapeutic challenges. Lancet Neurol. 11(10):891-905 (2012).

Blaney et al. Traceless solid-phase organic synthesis. Chem. Rev. 102:2607-2024 (2002.

Borchardt et al. Targeted actinium-225 in Vivo Generators for Therapy of Ovarian Cancer Cancer Res. 63:5084-50 (2003).

Brinkmann et al. The making of bispecific antibodies. MABS 9(2):182-212 (2017).

Bulmus et al. A new pH-responsive and glutathione-reactive, endosomal membrane-disruptive polymeric carrier for intracellular delivery of biomolecular drugs. J Controlled Release 93:105-120 (2003).

Burke et al. siRNA-mediated knockdown of P450 oxidoreductase in rats: a tool to reduce metabolism by CYPs and increase exposure of high clearance compounds. Pharm. Res. 31(12):3445-3460 (2014).

Burlina et al. Chemical engineering of RNase resistant and catalytically active hammerhead ribozymes. Bioorg Med Chem 5:1999-2010 (1997).

Carter et al. Antibody-drug conjugates for cancer therapy. Cancer J 14(3):154-69 (2008).

Casi et al. Antibody-drug conjugates: basic concepts, examples and future perspectives. J Control Release 161:422-428 (201).

Casi et al. Site-specific traceless coupling of potent cytotoxic drugs to recombinant antibodies for pharmacodelivery. J Am Chem Soc 134(13):5887-5892 (2012).

Casset et al. A peptide mimetic of an anti-CD4 monoclonal antibody by rational design. Biochemical and Biophysical Research Communication 307:198-205 (2003).

Castaneda et al. Acid-cleavable thiomaleamic acid linker for homogeneous antibody-drug conjugation, Chem. Commun. 49:8187-8189 (2013).

Certified JP2016-122187, filed on Jun. 20, 2016 (English counterpart US2019240346).

Certified U.S. Appl. No. 62/316,919, filed Apr. 1, 2016.

Chen et al. Real-time quantification of microRNAs by stem-loop RT-PCR. Nucleic Acids Res. 33:e179 (2005).

(56) References Cited

OTHER PUBLICATIONS

Chen et al. Selection and analysis of an optimized anti-VEGF antibody: Crystal structure of an affinity-matured Fab in complex with antigen. J Mol Bio 293:865-881 (1999).
Chen et al. Strand-specific 5'-O-methylation of siRNA duplexes controls guide strand selection and targeting specificity. RNA 14:263-274 (2008).
Chotha et al. Structural repertoire of the human VH segments. J.Mol.Biol. 227:799-817 (1992).
Chothia et al. Canonical structures for the hypervariable regions of immunoglobulins. J Mol Biol. 196(4):901-917 (1987).
Clackson et al. Making antibody fragments using phage display libraries. Nature 352(6336):624-628 (1991).
Colberre-Garapin et al. A new dominant hybrid selective marker for higher eukaryotic cells. J Mol Biol 150:1-14 (1981).
Cole et al. The EBV-hybridoma technique and its application to human lung cancer. In, Monoclonal Antibodies and Cancer Therapy (vol. 27, UCLA Symposia on Molecular and Cellular Biology, New Series) (eds. R.A. Reisfeld and S.Sell), New York: Alan R. Liss, Inc. pp. 77-96 (1985).
Co-pending U.S. Appl. No. 18/052,899, inventors Malecova; Barbora et al., filed Nov. 4, 2022.
Co-pending U.S. Appl. No. 18/052,900, inventors Malecova; Barbora et al., filed Nov. 4, 2022.
Crouse et al. Expression and amplification of engineered mouse dihydrofolate reductase minigenes. Mol Cell Biol 3(2):257-266 (1983).
Cuellar et al. Systematic evaluation of antibody-mediated siRNA delivery using an industrial platform of THIOMAB-siRNA conjugates. Nucleic Acids Res 43(2):1189-1203 (2015).
Dawson et al. Modulation of Reactivity in Native Chemical Ligation through the Use of Thiol Additives. J. Am. Chem. Soc. 119:4325-4329 (1997).
Dawson et al. Synthesis of proteins by native chemical ligation. Science 266(5186):776-779 (1994).
De Angelis et al. Chimeric snRNA molecules carrying antisense sequences against the splice junctions of exon 51 of the dystrophin pre-mRNA induce exon skipping and restoration of a dystrophin synthesis in Delta 48-50 DMD cells. PNAS USA 99:9456-9461 (2002).
De Pascalis et al. Grafting of "abbreviated" complementarity-determining regions containing specificity-determining residues essential for ligand contact to engineer a less immunogenic humanized monoclonal antibody. J Immunol. 169(6):3076-3084 (2002).
Debinski et al. Monovalent immunotoxin containing truncated form of Pseudomonas exotoxin as potent antitumor agent. Cancer Research 52(19):5379-5385 (1992).
Deleavey et al. Designing chemically modified oligonucleotides for targeted gene silencing. Chem Biol. 19(8):937-954 (2012).
Dietel et al. A 2015 update on predictive molecular pathology and its role in targeted cancer therapy: a review focussing on clinical relevance. Cancer Gene Ther 22(9):417-430 (2015).
Dimasi et al. Development of a trispecific antibody designed to simultaneously and efficiently target three different antigens on tumor cells. Mol Pharm 12(9):3490-3501 (2015).
Domingo et al. Transferrin receptor as a target for antibody—drug conjugates. Methods in Enzymology 112:238-247 (1985).
Duncan et al. A polymer-Triton X-100 conjugate capable of pH-dependent red blood cell lysis: a model system illustrating the possibility of drug delivery within acidic intracellular compartments. J Drug Target 2:341-347 (1994).
Earnshaw et al. Modified oligoribonucleotides as site-specific probes of RNA structure and function. Biopolymers (Nucleic Acid Sciences) 48:39-55 (1998).
Echigoya et al. In Silico Screening Based on Predictive Algorithms as a Design Tool for Exon Skipping Oligonucleotides in Duchenne Muscular Dystrophy. PLoS One 10(3):e0120058 (2015).
El-Sayed et al. Rational design of composition and activity correlations for pH-responsive and glutathione-reactive polymer therapeutics. J Control Release 104:417-427 (2005).

Feener et al. Alternative splicing of human dystrophin mRNA generates isoforms at the carboxy terminus. Nature 338:509-511 (Apr. 6, 1989).
Ferreboeuf et al. DUX4 and DUX4 downstream target genes are expressed in fetal FSHD muscles. Human Molecular Genetics 23(1):171-181 (2014).
Flanary et al. Antigen delivery with poly(propylacrylic acid) conjugation enhanced MHC-1 presentation and T-cell activation. Bioconjugate Chem. 20:241-248 (2009).
Gaziova et al. Chemically defined polyethylene glycol siRNA conjugates with enhanced gene silencing effect. Bioorg Med Chem 22(7):2320-2326 (2014).
Genbank HQ266760.1 A "*Homo sapiens* clone 34-15 double homeodomain protein DUX4-fl (DUX4) mRNA, complete cds" accessed from ncbi.nlm.nih.gov on Dec. 16, 2021 (2010).
Giorgetti et al. Rescue of Metabolic Alterations in AR113Q Skeletal Muscle by Peripheral Androgen Receptor Gene Silencing. Cell Rep 17(1):125-136 (2016).
Goldmacher et al. Antibody-drug conjugates: using monoclonal antibodies for delivery of cytotoxic payloads to cancer cells. Therapeutic Delivery 2:397-416 (2011).
Goldspiel et al. Human gene therapy. Clin Pharm 12:488-505 (1993).
Griffey et al. 2'-0-aminopropyl ribonucleotides: a zwitterionic modification that enhances the exonuclease resistance and biological activity of antisense oligonucleotides, J. Med. Chem. 39(26):5100-5109 (1997).
Hackeng et al. Protein synthesis by native chemical ligation: Expanded scope by using straightforward methodology. PNAS USA 96:10068-10073 (1999).
Hanes et al. In vitro selection and evolution of functional proteins by using ribosome display. PNAS USA 94:4937-4942 (1997).
Hejesen et al. A traceless aryl-triazene linker for DNA-directed chemistry. Org Biomol Chem 11(15):2493-2497 (2013).
Henry et al. pH-responsive poly(styrene-alt-maleic anhydride) alkylamide copolymers for intracellular drug delivery. Biomacromolecules 7:2407-2414 (2006).
Hitachi et al. Role of microRNAs in skeletal muscle hypertrophy. Front Physiol 16(4):408 (2014).
Hoffman et al. Restoring Dystrophin Expression in Duchenne Muscular Dystrophy Muscle: Progress in Exon Skipping and Stop Codon Read Through. Am J Pathol 179(1):12-22 (2011).
*Homo sapiens* DM1 protein kinase (DMPK), transcript variant 7, mRNA. NCBI reference sequence NM_001288766 (Mar. 12, 2019).
Hu et al. Site-specific Antibody-polymer Conjugates for siRNA Delivery. J Am Chem Soc 135(37):13885-13891 (2013).
Huang et al. Mechanisms of resistance to EGFR tyrosine kinase inhibitors. Acta Pharma Sinica B 5(5):390-401 (2015).
Hudson et al. Cellular delivery of hammerhead ribozymes conjugated to a transferrin receptor antibody. Int J Pharmaceuticals 182(1):49-58 (1999).
Huse et al. Generation of a large combinatorial library of the immunoglobulin repertoire in phage lambda. Science 246(4935):1275-1281 (1989).
Huston et al. Protein engineering of antibody binding sites: recovery of specific activity in an anti-digoxin single-chain Fv analogue produced in *Escherichia coli*. PNAS USA 85(16):5879-5883 (1988).
Idusogie, et al. Mapping of the C1q binding site on rituxan, a chimeric antibody with a human IgG1 Fc. J Immunol. Apr. 15, 2000;164(8):4178-84.
Idusogie.et al., EngineeredAntibodies with Increased Activity to Recruit Complement. J Immunol.166(4):2571-5 (2001).
Invivogen "RNA Interference" accessed from invivogen.com on Dec. 17, 2021 (2006).
Ishikawa et al. Preparation of monomeric Fab'—horseradish peroxidase conjugate using thiol groups in the hinge and its evaluation in enzyme immunoassay and immunohistochemical staining. Ann N Y Acad Sci. 420:74-89 (1983).
Iversen et al. Optimized siRNA-PEG conjugates for extended blood circulation and reduced urine excretion in mice. Theranostics 3(3):201-209 (2013).
Jancik et al. Clinical relevance of KRAS in human cancers. J Biomed Biotechnol 2010:150960 (13 pgs.) (2010).

(56) References Cited

OTHER PUBLICATIONS

Jearawiriyapaisarn et al. Sustained Dystrophin Expression Induced by Peptide-conjugated Morpholino Oligomers in the Muscles of mdx Mice. Mol Ther. 16(9): 1624-1629 (2008).
Jones et al. A cre-inducible DUX4 transgenic mouse model for investigating facioscapulohumeral muscular dystrophy. PLoS One 13(2):e0192657 (2018).
Jones et al. Poly(2-alkylacrylic acid) polymers deliver molecules to the cytosol by pH-sensitive disruption of endosomal vesicles. Biochem J 372:65-75 (2003).
Jones et al. Transgenic mice expressing tunable levels of DUX4 develop characteristic facioscapulohumeral muscular dystrophy-like pathophysiology ranging in severity. Skelet Muscle. 10(1):8 (2020).
Kabat et al. Attempts to Locate Complementarity-Determining Residues in the Variable Positions of Light and Heavy Chains. Ann. NY Acad. Sci. 190:382-391 (1971).
Kabat et al. Sequences of proteins of immunological interest. NIH Publ. No. 91-3242 1:647-669 (1991).
Kaneko et al. Optimizing Therapeutic Antibody Function: Progress With Fc Domain Engineering. Biodrugs 25(1):1-11 (2011).
Karpeisky et al. Highly efficient synthesis of 2'-O-amino nucleosides and their incorporation in hammerhead ribozymes. Tetrahedron Lett 39:1131-1134 (1998).
Khormaee et al. Endosomolytic anionic polymer for the cytoplasmic delivery of siRNAs in localized in vivo applications. Adv Funct Mater 23:565-574 (2013).
Kim et al. PEG conjugated VEGF siRNA for anti-angiogenic gene therapy. J Cont Rel 116:123-129 (2006).
Kohler et al. Continuous cultures of fused cells secreting antibody of predefined specificity. Nature 256:495-497 (1975).
Koizumi. ENA oligonucleotides as therapeutics. Curr Opin Mol Ther 8(2):144-149 (2006).
Kontermann et al. Bispecific antibodies. Drug Discov Today 20(7):838-847 (2015).
Kozbor et al. The production of monoclonal antibodies from human lymphocytes. Immunology Today 4:72-79 (1983).
Kutmeier et al. Assembly of humanized antibody genes from synthetic oligonucleotides using a single-round PCR. BioTechniques 17:242 (1994).
Lamminnnaki et al. Crystal structure of a recombinant anti-estradiol fab fragment in complex with 17Beta-Estradiol. J Biol Chem. 276:36687-36694 (2001).
Langlois et al. Cytoplasmic and Nuclear Retained DMPK mRNAS Are Targets for RNA Interference in Myotonic Dystrophy Cells. J biol Chem 280(17):16949-16954 (2005).
Lazar et al. Engineered antibody Fc variants with enhanced effector function. PNAS USA 103(11):4005-10 (2006).
Lee et al. Antisense PMO cocktails effectively skip dystrophin exons 45-55 in myotubes transdifferentiated from DMD patient fibroblasts. PLoS One 13(5):e0197084 (2018).
Lefranc et al. IMGT, the International ImMunoGene Tics Database. Nucleic Acids Res. 27:209-212 (1999).
Lefranc. The IMGT Unique Numbering for Immunoglobulins, T-Cell Receptors, and Ig-Like Domains. The Immunologist 7:132-136 (1999).
Leigh et al. The Human Plasma Proteome: History, Character, and Diagnostic Prospects. Mol Cell Proteomics 1:845-867 (2002).
Leroy et al. Epidermal growth factor receptor down-regulation triggers human myoblast differentiation. PLOS One 8(8):e71770 (2013).
Levin. Targeting Therapeutic Oligonucleotides. N Engl J Med 376:86-88 (2017).
Livak et al. Analysis of Relative Gene Expression Data Using RealTime Quantitative PCR and the 2-delta delta Ct Method. Methods 25:402-408 (2001).
Loakes. Survey and summary: The applications of universal DNA base analogues. Nucleic Acids Research 29:2437-2447 (2001).
Loh et al. A Survey of siRNA Nanoscal Delivery Patents. 11 Nanotechnology Law & Bus. (pp. 29-37) (2014).
Lowy et al., Isolation of transforming DNA: Cloning the hamster aprt gene. Cell 22:817-823 (1980).
Lyon et al. Self-hydrolyzing maleimides improve the stability and pharmacological properties of antibody-drug conjugates. Nat. Biotechnol. 32(10):1059-1062 (2014).
Maccallum et al.: Antibody-antigen interactions: contact analysis and binding site topography. J Mol Biol. 262(5):732-745 (1996).
Martin. Chapter 31. Protein Sequence and Structure Analysis of Antibody Variable Domains. in Antibody Engineering, Kontermann and Dübel, eds., pp. 422-439, Springer-Verlag, Berlin (2001).
Martinez et al. Single-stranded antisense siRNAs guide target RNA cleavage in RNAi. Cell 110(5):563-574 (2002).
Mcdevitt et al. Tumor Therapy With Targeted Atomic Nanogenerators. Science 294:1537-1540 (2001).
Mcenaney et al. Antibody-recruiting molecules: an emerging paradigm for engaging immune function in treating human disease. ACS Chem Biol. 7(7):1139-1151 (2012).
Mei et al. FBXO32 Targets c-Myc for Proteasomal Degradation and Inhibits c-Myc Activity. J Biol Chem 290:16202-16214 (2015).
Miyata et al. Polymer nanotechnology for nucleic acid delivery. Drug Delivery System 31(1):44-53 (2016) (English Abstract).
Moore et al. Engineered Fc variant antibodies with enhanced ability to recruit complement and mediate effector functions. mAbs 2(2):181-189 (2010).
Morgan et al. Human gene therapy. Ann Rev Biochem 62:191-217 (1993).
Morrison et al. Chimeric human antibody molecules: mouse antigen-binding domains with human constant region domains. PNAS USA 81(21):6851-6855 (1984).
Mulders et al. Molecular therapy in myotonic dystrophy: focus on RNA gain-of-function. Hum Mol Gen 19(R1):R90-R97 (2010).
Mulders et al. Supporting Information for Triplet-repeat oligonucleotide-mediated reversal of RNA toxicity in myotonic dystrophy. PNAS 106(33):13915-13920 (2009) (13 pgs).
Mulders et al. Triplet-repeat oligonucleotide-mediated reversal of RNA toxicity in myotonic dystrophy. PNAS 106(33):13915-13920 (2009).
Mulligan et al. Selection for animal cells that express the *Escherichia coli* gene coding for xanthine-guanine phosphoribosyltransferase. PNAS USA 78(4):2072-2076 (1981).
Mulligan. The basic science of gene therapy. Science 260(5110):926-932 (1993).
Muratovska et al. Conjugate for efficient delivery of short interfering RNA (siRNA) into mammalian cells. FEBS Lett. 558(1-3):63-8 (2004).
Naisbitt et al. Disposition of amodiaquine and related antimalarial agents in human neutrophils: implications for drug design. J Pharmacol Exp Ther 280:884-893 (1997).
Natsume et al. Engineered Antibodies of IgG1/IgG3 Mixed Isotype With Enhanced Cytotoxic Activities. Cancer Res 68(10):3863-72 (2008).
Neuberger et al. Recombinant antibodies possessing novel effector functions. Nature 312(5995):604-608 (1984).
Nielsen et al. Advances in targeted delivery of small interfering RNA using simple bioconjugates. Expert Opinion On Drug Delivery 11(5):791-822 (2014).
Normand-Sdiqui et al. Oligonucleotide delivery: Uptake of rat transferrin receptor antibody (OX / 26) conjugates into an in vitro immortalised cell line model of the blood, brain barrier. Int J Pharmaceuticals 163:63-71 (1998).
Obika et al. Synthesis of 2'-0,4'-C-methyleneuridine and -cytidine. Novel bicyclic nucleosides having a fixed C3'-endo sugar puckering. Tetrahedron Lett. 38(50):8735-8738 (1997).
O'Hare et al. Transformation of mouse fibroblasts to methotrexate resistance by a recombinant plasmid expressing a prokaryotic dihydrofolate reductase. PNAS USA 78:1527-1531 (1981).
Padlan et al. Structure of an antibody-antigen complex: Crystal structure of the HyHEL-10 Fab-lysozyme complex. PNAS USA 86:5938-5942 (1989).
Parmar et al. 5'-(E)-Vinylphosphonate: A Stable Phosphate Mimic Can Improve the RNAi Activity of siRNA-GalNAc Conjugates. Chembiochem 17(11):985-989 (2016).

(56) References Cited

OTHER PUBLICATIONS

PCT/US2017/025608 International Search Report and Written Opinion dated Jul. 10, 2017.
PCT/US2018/012672 International Search Report and Written Opinion dated May 24, 2018.
PCT/US2018/052289 International Search Report and Written Opinion dated Jan. 11, 2019.
PCT/US2018/054444 International Search Report and Written Opinion dated Feb. 15, 2019.
PCT/US2018/064359 International Search Report and Written Opinion dated Apr. 11, 2019.
PCT/US2019/068078 International Search Report and Written Opinion dated Apr. 24, 2020.
PCT/US2021/022214 International Search Report and Written Opinion dated Jun. 28, 2021.
PCT/US2021/024303 Invitation to Pay Additional Fees dated Jun. 24, 2021.
PCT/US2022/043705 International Search Report and Written Opinion dated Dec. 13, 2022.
Pei et al. Quantitative evaluation of siRNA delivery in vivo. RNA 16:2553-2563 (2010).
Perrault et al. Mixed deoxyribo- and ribo-oligonucleotides with catalytic activity. Nature 344:565-568 (1990).
Pieken et al. Kinetic characterization of ribonuclease-resistant 2'-modified hammerhead ribozymes. Science 253:314-317 (1991).
Pizzamiglio et al. Expression of iron-related proteins differentiate non-cancerous and cancerous breast tumors. Int J Mol Sci. 18(2):410 (2017).
Rangasamy et. al. New mechanism for release of endosomal contents: osmotic lysis via nigeri-cin-mediated K+/H+ exchange. Bioconjugate Chem. 29:1047-1059 (2018).
Rosager et al., Transferrin receptor-1 and ferritin heavy and light chains in astrocytic brain tu-mors: Expression and prognostic value. PLoS One 12:e0182954 (2017).
Rozema et al. Dynamic PolyConjugates for targeted in vivo delivery of siRNA to hepatocytes. PNAS USA 104(32):12982-12987 (2007).
Rudikoff et al. Single amino acid substitution altering antigen-binding specificity. PNAS USA 79:1979-1983 (1982).
Rychtarcikova et al. Tumorinitiating cells of breast and prostate origin show alterations in the expression of genes related to iron metabolism. Oncotarget. 8:6376-6398 (2017).
Sacheck et al. Rapid disuse and denervation atrophy involve transcriptional changes similar to those of muscle wasting during systemic diseases. The FASEB Journal 21:140-155 (2007).
Santerre et al. Expression of prokaryotic genes for hygromycin B and G418 resistance as dominant-selection markers in mouse L cells. Gene 30(1-3):147-156 (1984).
Sartori et al. Smad2 and 3 transcription factors control muscle mass in adulthood. Am J Physiol Cell Physiol 296:C1248-C1257 (2009).
Schnyder et al. Targeting of skeletal muscle in vitro using biotinylated immunoliposomes. Biochem J 377(Pt.1):61-67 (2004).
Schwarz et al. Evidence that siRNAs function as guides, not primers, in the *Drosophila* and human RNAi pathways. Molecular Cell 10:537-548 (2002).
Sekyere et al. Examination of the distribution of the transferrin homologue, melanotransferrin (tumour antigen p97), in mouse and human. Biochimica et Biophysica Acta 1722(2):131-142 (2005).
Shields et al. High Resolution Mapping of the Binding Site on Human IgG1 for FcγRI, FcγRII, FcγRIII, and FcRn and Design of IgG1 Variants with Improved Binding to the FcγR. J Biol Chem 276(9):6591-6604 (2001).
Singh et al. Recent developments in oligonucleotide conjugation. Chem Soc Rev 39(6):2054-2070 (2010).
Skerra et al. Assembly of a functional Immunoglobulin Fv fragment in *Escherichia coli*. Science 240(4855):1038-1041 (1988).
Stavenhagen et al. Enhancing the potency of therapeutic monoclonal antibodies via Fc optimization. Adv Enzyme Regul. 48:152-64 (2008).
Stavenhagen et al. Fc Optimization of Therapeutic Antibodies Enhances Their Ability to Kill Tumor Cells In vitro and Controls Tumor Expansion In vivo via Low-Affinity Activating Fcγ Receptors. Cancer Res 67(18):8882-91 (2007).
Stavenhagen et al. Fc optimization of therapeutic antibodies enhances their ability to kill tumor cells in vitro and controls tumor expansion in vivo via low-affinity activating Fcgamma receptors. Cancer Res. 67(18):8882-90 (2007).
Strop et al. Location matters: site of conjugation modulates stability and pharmacokinetics of antibody drug conjugates. Chem Biol 20(2):161-167 (2013).
Sugo et al. Development of antibody-siRNA conjugate targeted to cardiac and skeletal muscles. J Control release 237:1-13 (2016).
Summerton, et al. Morpholino antisense oligomers: design, preparation, and properties. Antisense Nucleic Acid Drug Dev. Jun. 1997;7(3):187-95.
Szybalska et al. Genetics of human cell line. IV. DNA-mediated heritable transformation of a biochemical trait. PNAS USA 48:2026-2034 (1962).
Takeda et al. Construction of chimaeric processed immunoglobulin genes containing mouse variable and human constant region sequences. Nature 314(6010):452-454 (1985).
Talasila et al. EGFR Wild-type Amplification and Activation Promote Invasion and Development of Glioblastoma Independent of Angiogenesis. Acta Neuropathol. 125(5):683-698 (2013).
Tolstoshev. Gene Therapy, Concepts, Current Trials and Future Directions. Ann. Rev. Pharmacol. Toxicol. 32:573-596 (1993).
Tramontano et al. Framework Residue 71 Is a Major Determinant of the Position and Conformation of the Second Hypervariable Region in the VH Domains of Immunoglobulins. J. Mol. Biol. 215(1):175-82 (1990).
Turner et al. The myotonic dystrophies: diagnosis and management. J Neurol Neurosurg Psychiatry 81:358-367 (2010).
U.S. Appl. No. 17/200,612 Office Action dated Apr. 20, 2022.
U.S. Appl. No. 17/200,612 Office Action dated Dec. 21, 2021.
U.S. Appl. No. 17/200,661 Office Action dated Jan. 31, 2022.
U.S. Appl. No. 17/200,661 Office Action dated May 23, 2022.
Usman et al. Exploiting the chemical synthesis of RNA. Trends Biochem Sci 17:334-339 (1992).
Vajdos et al. Comprehensive functional maps of the antigen-binding site of an anti-ErbB2 antibody obtained with shotgun scanning mutagenesis. J Mol Biol 320:415-428 (2002).
Verma et al. Modified oligonucleotides: synthesis and strategy for users. Annu Rev Biochem 67:99-134 (1998).
Vickers et al. Efficient Reduction of Target RNAs by Small Interfering RNA and RNase H-dependent Antisense Agents. J. Biol. Chem 278:7108-7118 (2003).
Walker et al. Improved cellular delivery of antisense oligonucleotides using transferrin receptor antibody-oligonucleotide conjugates. Pharmaceutical research 12(10):1548-1553 (1995).
Wallace et al. RNA interference inhibits DUX4-induced muscle toxicity in vivo: implications for a targeted FSHD therapy. Molecular Therapy 20.7 (2012): 1417-1423.
Ward et al. Binding activities of a repertoire of single immunoglobulin variable domains secreted from *Escherichia coli*. Nature 341(6242):544-546 (1989).
Watts et al. Chemically modified siRNA: tools and applications. Drug Discov Today 13(19-20):842-855 (2008).
Whiddon et al. Conservation and innovation in the DUX4-family gene network. Nat Genet. 49(6):935-940 (2017).
Wigler et al. Transfer of purified herpes virus thymidine kinase gene to cultured mouse cells. Cell 11:223-232 (1977).
Wigler et al. Transformation of mammalian cells with an amplifiable dominant-acting gene. PNAS USA 77:3567-3570 (1980).
Winkler. Oligonucleotide conjugates for therapeutic applications. Ther Del 4(7):791-809 (2013).
Wong et al. Co-injection of a targeted, reversibly masked endosomolytic polymer dramatically improves the efficacy of cholesterol-conjugated small interfering RNAs in vivo. Nucleic Acid Ther 22(6):380-390 (2012).
Wu et al. Building complex glycopeptides: Development of a cysteine-free native chemical ligation protocol. Angew. Chem. Int. Ed. 45:4116-4125 (2006).

(56) References Cited

OTHER PUBLICATIONS

Wu et al. Cell-penetrating peptides as transporters for morpholino oligomers: effects of amino acid composition on intracellular delivery and cytotoxicity. Nucleic Acids Res 35(15):5182-5191 (2007).
Wu et al. Delivery systems for gene therapy. Biotherapy 3:87-95 (1991).
Wu et al. Humanization of a murine monoclonal antibody by simultaneous optimization of framework and CDR residues. J.Mol. Biol. 294:151-162 (1999).
Wu et al. Site-specific chemical modification of recombinant proteins produced in mammalian cells by using the genetically encoded aldehyde tag. PNAS USA 106(9):3000-3005 (2009).
Xia et al. Intravenous siRNA of brain cancer with receptor targeting and avidin-biotin technology. Pharm Res 24(12):2309-16 (2007).
Xu et al. Delivery systems for siRNA drug development in cancer therapy. Asian Journal of Pharmaceutical Sciences 10(1):1-12 (2015).
Yazdi et al. Influence of cellular trafficking on protein synthesis inhibition of immunotoxins directed against the transferrin receptor. Cancer Res 55:3763-3771 (1995).
Yessine et al. Characterization of the membrane-destabilizing properties of different pH-sensitive methacrylic acid copolymers. Biochimica et Biophysica Acta 1613:28-38 (2003).
Yuan et al. Development of siRNA payloads to target KRAS-mutant cancer. Cancer Discov 4(10):1182-1197 (2014).
Zapata et al. Engineering linear F(ab')2 fragments for efficient production in *Escherichia coli* and enhanced antiproliferative activity. Protein Eng. 8(10):1057-1062 (1995).
Zhang et al. A remote arene-binding site on prostate specific membrane antigen revealed by antibody-recruiting small molecules. J Am Chem Soc. 132(36):12711-12716 (2010).
Darimont et al. 8-05 Abstract: A novel Antibody-Oligonucleotide Conjugate (AOC) platform enables efficient regulation of muscle targets in mice. Journal Of Cachexia, Sarcopenia And Muscle 8:999-1080 (2017).
Fortini et al. DNA damage response by single-strand breaks in terminally differentiated muscle cells and the control of muscle integrity. Cell Death Diff 19(11):1741-1749 (2012).
Malecova et al. DUX4 siRNA Optimization for the Development of an Antibody-Oligonucleotide Conjugate (AOC) for the Treatment of FSHD (P17-13.009). Neurology 98:(18 Supplement) (2022).
Mullard. Antibody-oligonucleotide conjugates enter the clinic. Nat Rev Drug Discov 21(1):6-8 (2022).
U.S. Appl. No. 17/243,362 Office Action dated Jul. 17, 2023.
U.S. Appl. No. 17/243,362 Office Action dated Mar. 16, 2023.
U.S. Appl. No. 17/932,653 Office Action dated Jul. 7, 2023.
U.S. Appl. No. 18/052,899 Office Action dated Jul. 5, 2023.
U.S. Appl. No. 18/052,899 Office Action dated Oct. 24, 2023.
U.S. Appl. No. 18/052,900 Office Action dated Dec. 14, 2023.
U.S. Appl. No. 18/052,900 Office Action dated Sep. 6, 2023.

* cited by examiner

MB06

-◇- KHDC1L  -✱- TRIM43  -○- LEUTX
-△- MBD3L2  -■- ZSCAN4

MB06

Calculations of the FSHD composite:
Dct = (Av. ct 5 DUX4 target genes) − (Av. ct 2 HKGs)
DDct = Dct (siDUX4) − Dct (mock)
Composite = 2^-DDct*100 (%)

DUX4 siRNA Library

Eliminate siRNAs with lower than 60% KD in at least one cell lines at 10nM

Eliminate siRNAs with ACTA1 expression < 70% in both cell lines

Eliminate siRNAs with null activity (<10% KD) at 0.5nM in both cell lines

COMPOSITIONS AND METHODS OF TREATING FACIOSCAPULOHUMERAL MUSCULAR DYSTROPHY

CROSS-REFERENCE

This application is a continuation of U.S. Application Ser. No. 17/200,612, filed on Mar. 12, 2021, which claims the benefit of U.S. Provisional Application No. 62/992,071 filed on Mar. 19, 2020, and U.S. Provisional Application No. 63/066,655 filed on Aug. 17, 2020, each of which is incorporated herein by reference in its entirety.

REFERENCE TO A SEQUENCE LISTING XML

This application contains a Sequence Listing which has been submitted electronically in XML format. The Sequence Listing XML is incorporated herein by reference. Said XML file, created on Nov. 17, 2022, is named 45532-742_301_SL.xml and is 1,928,393 bytes in size.

BACKGROUND OF THE DISCLOSURE

Gene suppression by RNA-induced gene silencing provides several levels of control: transcription inactivation, small interfering RNA (siRNA)-induced mRNA degradation, and siRNA-induced transcriptional attenuation. In some instances, RNA interference (RNAi) provides long lasting effect over multiple cell divisions. As such, RNAi represents a viable method useful for drug target validation, gene function analysis, pathway analysis, and disease therapeutics.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE DISCLOSURE

Disclosed herein, in certain embodiments, are polynucleic acid molecules and pharmaceutical compositions for modulating a gene associated with muscle atrophy, especially Facioscapulohumeral muscular dystrophy (FSHD). In some embodiments, also described herein are methods of treating muscle atrophy, especially FSHD, with a polynucleic acid molecule or a polynucleic acid molecule conjugate disclosed herein.

Disclosed herein, in certain embodiments, is a polynucleic acid molecule conjugate comprising an antibody or antigen binding fragment thereof conjugated to a polynucleic acid molecule that hybridizes to a target sequence of DUX4, and the polynucleic acid molecule conjugate mediates RNA interference against the DUX4. In certain embodiments, the antibody or antigen binding fragment thereof comprises a non-human antibody or binding fragment thereof, a human antibody or antigen binding fragment thereof, a humanized antibody or antigen binding fragment thereof, chimeric antibody or antigen binding fragment thereof, monoclonal antibody or antigen binding fragment thereof, monovalent Fab', divalent Fab2, single-chain variable fragment (scFv), diabody, minibody, nanobody, single-domain antibody (sdAb), or camelid antibody or antigen binding fragment thereof. In certain embodiments, the antibody or antigen binding fragment thereof is an anti-transferrin receptor antibody or antigen binding fragment thereof.

In certain embodiments, the polynucleic acid molecule comprises a sense strand and/or an antisense strand, and wherein the sense strand and/or the antisense strand each independently comprises at least one 2' modified nucleotide, at least one modified internucleotide linkage, or at least one inverted abasic moiety. In certain embodiments, the polynucleotide hybridizes to at least 8 contiguous bases of the target sequence of DUX4. In certain embodiments, the polynucleotide is from about 8 to about 50 nucleotides in length or from about 10 to about 30 nucleotides in length. In certain embodiments, the polynucleic acid molecule comprises a sense strand and/or an antisense strand, and the sense strand comprises at least 80%, at least 85%, at least 90%, at least 95%, at least 96%, at least 97%, at least 98%, at least 99% identical to a sequence selected from SEQ ID NOs: 1-70 or SEQ ID NOs: 141-210. Alternatively and/or additionally, the polynucleic acid molecule comprises a sense strand and/or an antisense strand, and the antisense strand comprises at least 80%, at least 85%, at least 90%, at least 95%, at least 96%, at least 97%, at least 98%, at least 99% identical to a sequence selected from SEQ ID NOs: 71-140 or SEQ ID NOs: 211-280.

In certain embodiments, the polynucleotide comprises at least one 2' modified nucleotide, and further the 2' modified nucleotide comprises 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified nucleotide, or comprises locked nucleic acid (LNA) or ethylene nucleic acid (ENA), or comprises a combination thereof. In certain embodiments, the at least one modified internucleotide linkage comprises a phosphorothioate linkage or a phosphorodithioate linkage. In certain embodiments, the polynucleic acid molecule comprises 3 or more 2' modified nucleotides selected from 2'-O-methyl and 2'-deoxy-2'-fluoro. In certain embodiments, the polynucleic acid molecule comprises a 5'-terminal vinylphosphonate modified nucleotide, such as those described in U.S. Publication No. 2019/0192681.

In certain embodiments, the 2' modified nucleotide is 2'-O-methyl modified nucleotide, and 2'-O-methyl modified nucleotide is at the 5'-end of the sense strand and/or the antisense strand. In some embodiments, the 2'-O-methyl modified nucleotide is a purine nucleotide, or the 2'-O-methyl modified nucleotide is a pyridine nucleotide. In certain embodiments, the sense and/or antisense strands comprise at least two, three, four consecutive the 2'-O-methyl modified nucleotides at the 5'-end.

In certain embodiments, the polynucleic acid molecule conjugate comprises a linker connecting the target cell binding moiety to the polynucleic acid moiety. In such embodiments, the linker is C1-C6 alkyl linker, or the linker is a homobifunctional linker or heterobifunctional linker, and comprises a maleimide group, a dipeptide moiety, a benzoic acid group, or its derivative thereof. Alternatively and/or additionally, the linker is a cleavable or non-cleavable linker. In certain embodiments, a ratio between the polynucleic acid moiety and the target cell binding moiety is about 1:1, 2:1, 3:1, or 4:1.

In certain embodiments, the polynucleic acid moiety mediates RNA interference against the human DUX4 and modulates symptoms of muscle dystrophy in a subject. In some embodiments, the RNA interference comprises reducing expression of the mRNA transcript of DUX4 gene at least 50%, at least 60%, or at least 70% or more compared to a quantity of the mRNA transcript of DUX4 gene in an untreated cell. Alternatively and/or additionally, the RNA interference comprises affecting expression of a marker gene selected from a group comprising or consisting of MBD3L2, TRIM43, PRAMEF1, ZSCAN4, KHDC1L, and LEUTX in a cell. In some embodiments, the affecting expression of the marker gene is reducing expression of the marker gene at least 20%, at least 30%, at least 40%, at least 50%, at least 60% or more. In some embodiments, the muscle dystrophy is Facioscapulohumeral muscular dystrophy (FSHD).

In certain embodiments, polynucleic acid molecule conjugate comprises a molecule of Formula (I): A-X—B, where A is the antibody or antigen binding fragment thereof. B is the polynucleic acid molecule that hybridizes to a target sequence of DUX4, X is a bond or a non-polymeric linker, which is conjugated to a cysteine residue of A.

Disclosed herein, in certain embodiments, is a pharmaceutical composition comprising a polynucleic acid molecule conjugate as described herein, and a pharmaceutically acceptable excipient. In some embodiments, the pharmaceutical composition is formulated as a nanoparticle formulation. In some embodiments, the pharmaceutical composition is formulated for parenteral, oral, intranasal, buccal, rectal, transdermal, or intravenous, subcutaneous, or intrathecal administration.

The symptoms of FSHD include affects on skeletal muscles. The skeletal muscles affected by FSHD include muscles around the eyes and mouth, muscle of the shoulders, muscle of the upper arms, muscle of the lower legs, abdominal muscles and hip muscles. In some instances, the symptoms of FSHD also affects vision and hearing. In some instances, the symptoms of FSHD also affect the function of the heart or lungs. In some instances, the symptoms of FSHD include muscle weakness, muscle atrophy, muscle dystrophy, pain inflammation, contractures, scioliosis, lordosis, hypoventilation, abnormalities of the retina, exposure to keratitis, mild hearing loss, and EMG abnormality. The term muscle atrophy as used herein refers to a wide range of muscle related effects of FSHD.

Disclosed herein, in certain embodiments, is a method for treating muscular dystrophy in a subject in need thereof by providing a polynucleic acid conjugate as described herein, and administering the polynucleic acid conjugate to the subject in need thereof to treat the muscular dystrophy. The polynucleic acid conjugate reduces a quantity of the mRNA transcript of human DUX4. In some embodiments, the polynucleic acid moiety mediates RNA interference against the human DUX4 modulates muscle atrophy in a subject. In certain embodiments, the RNA interference comprises affecting expression of a marker gene selected from a group comprising or consisting of MBD3L2, TRIM43, PRAMEF1, ZSCAN4, KHDC1L, and LEUTX in a cell affected by a muscle dystrophy. Preferably, the muscular dystrophy is Facioscapulohumeral muscular dystrophy (FSHD).

Disclosed herein, in certain embodiments, is a use of the polynucleic acid molecule conjugate or a pharmaceutical composition as described herein for treating in a subject diagnosed with or suspected to have Facioscapulohumeral muscular dystrophy (FSHD). Also disclosed herein, in certain embodiments, is a use of the polynucleic acid molecule conjugate or the pharmaceutical composition as described herein for manufacturing a medicament for treating in a subject diagnosed with or suspected to have Facioscapulohumeral muscular dystrophy (FSHD).

Disclosed herein, in certain embodiments, is a kit comprising the polynucleic acid molecule conjugate or the pharmaceutical composition as described herein.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings below. The patent application file contains at least one drawing executed in color. Copies of this patent application publication with color drawing(s) will be provided by the Office upon request and payment of the necessary fee.

DETAILED DESCRIPTION OF THE DISCLOSURE

Muscle atrophy is the loss of muscle mass or the progressive weakening and degeneration of muscles, such as skeletal or voluntary muscles that controls movement, cardiac muscles, and smooth muscles. Various pathophysiological conditions including disuse, starvation, cancer, diabetes, and renal failure, or treatment with glucocorticoids result in muscle atrophy and loss of strength. The phenotypical effects of muscle atrophy are induced by various molecular events, including inhibition of muscle protein synthesis, enhanced turnover of muscle proteins, abnormal regulation of satellite cells differentiation, and abnormal conversion of muscle fibers types.

FSHD is a rare, progressive and disabling disease for which there are no approved treatments. FSHD is one of the most common forms of muscular dystrophy and affects both sexes equally, with onset typically in teens and young adults. FSHD is characterized by progressive skeletal muscle loss that initially causes weakness in muscles in the face, shoulders, arms and trunk and progresses to weakness in muscles in lower extremities and the pelvic girdle. Skeletal muscle weakness results in significant physical limitations, including progressive loss of facial muscles that can cause an inability to smile or communicate, difficulty using arms for activities of daily living and difficulty getting out of bed, with many patients ultimately becoming dependent upon the use of a wheelchair for daily mobility activities. The majority of patients with FSHD also report experiencing chronic pain, anxiety and depression.

FSHD is caused by aberrant expression of a gene, DUX4, in skeletal muscle resulting in the inappropriate presence of DUX4 protein. DUX4 itself is a transcription factor that induces the expression of other genes and it is these inappropriately expressed downstream genes that result in the muscle pathology. Normally DUX4-driven gene expression is limited to germline and early stem cell development. In patients with FSHD, the DUX4 protein in skeletal muscle regulates other gene products, some of which are toxic to the muscle. Evidence of aberrant DUX4-driven gene expression is the major molecular signature that distinguishes muscle tissue affected by FSHD from healthy muscle. The result of aberrant DUX4 expression in FSHD is death of muscle and its replacement by fat, resulting in skeletal muscle weakness and progressive disability. Data suggest that reducing expression of the DUX4 gene and its downstream transcriptional program could provide a disease-modifying therapeutic approach for the treatment of FSHD at its root cause.

Figure 1:
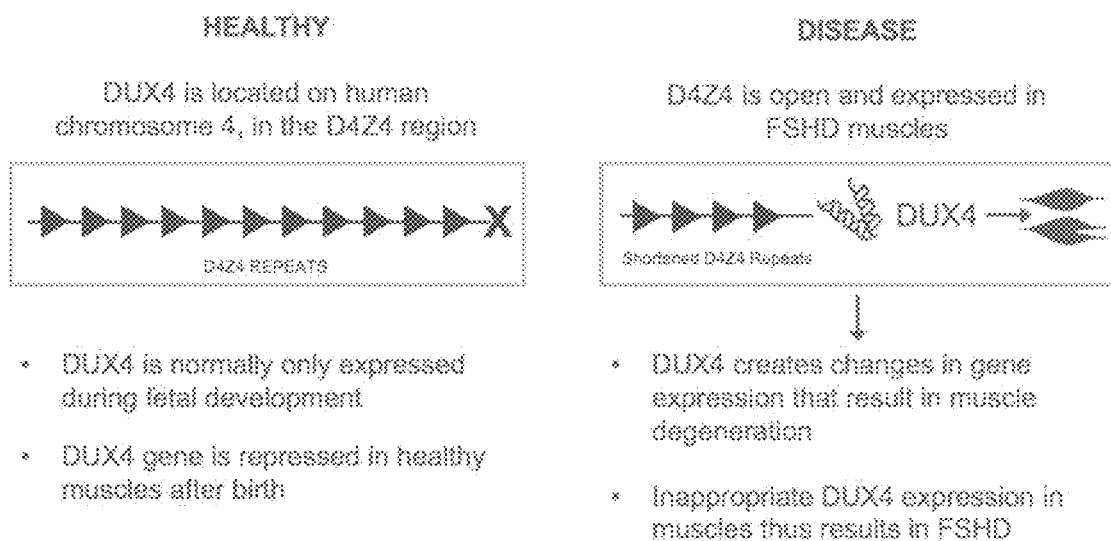
FIG. 1 illustrates a diagram of FSHD pathology.

There are two ways the DUX4 gene can be unsilenced, or de-repressed. In FSHD1, which comprises approximately 95% of FSHD patients, there are mutations that lead to the shortening of an array of DNA in a region near the end of the long arm of chromosome 4, known as D4Z4, which has repeats in the subtelomeric region of the chromosome. The D4Z4 region is abnormally shortened and contains between 1-10 repeats instead of the normal 11 to 100 repeats. This contraction causes hypomethylation of the D4Z4 region and de-repression of DUX4. Patients with FSHD2 do not have a meaningful D4Z4 repeat contraction, but have mutations in a regulatory gene, known as the SMCHD1 gene, that normally contributes to the repression of the DUX4 gene via DNA methylation. When that repression is lost due to the mutations of the SMCHD1 gene leading to the hypomethylation of the D4Z4 region, DUX4 is inappropriately expressed, inducing the disease state. FIG. 1 shows an illustrative diagram of FSHD pathology.

Nucleic acid (e.g., RNAi) therapy is a targeted therapy with high selectivity and specificity. However, in some instances, nucleic acid therapy is also hindered by poor intracellular uptake, limited blood stability and non-specific immune stimulation. To address these issues, various modifications of the nucleic acid composition are explored, such as for example, novel linkers for better stabilizing and/or lower toxicity, optimization of binding moiety for increased target specificity and/or target delivery, and nucleic acid polymer modifications for increased stability and/or reduced off-target effect.

In some embodiments, the arrangement or order of the different components that make-up the nucleic acid composition further effects intracellular uptake, stability, toxicity, efficacy, and/or non-specific immune stimulation. For example, if the nucleic acid component includes a binding moiety, a polymer, and a polynucleic acid molecule (or polynucleotide), the order or arrangement of the binding moiety, the polymer, and/or the polynucleic acid molecule (or polynucleotide) (e.g., binding moiety-polynucleic acid molecule-polymer, binding moiety-polymer-polynucleic acid molecule, or polymer-binding moiety-polynucleic acid molecule) further effects intracellular uptake, stability, toxicity, efficacy, and/or non-specific immune stimulation.

In some embodiments, described herein include polynucleic acid molecules and polynucleic acid molecule conjugates for the treatment of Facioscapulohumeral Muscular Dystrophy (FSHD) especially muscle dystrophy and/or muscle atrophy associated therewith. In some instances, the polynucleic acid molecule conjugates described herein enhance intracellular uptake, stability, and/or efficacy. In some cases, the polynucleic acid molecule conjugates comprise an antibody or antigen binding fragment thereof conjugated to a polynucleic acid molecule. In some cases, the polynucleic acid molecules that hybridize to target sequences of DUX4, preferably human DUX4.

Additional embodiments described herein include methods of treating FSHD, comprising administering to a subject a polynucleic acid molecule or a polynucleic acid molecule conjugate described herein.

Polynucleic Acid Molecules

In certain embodiments, a polynucleic acid molecule hybridizes to a target sequence of Double homeobox 4 (DUX4) gene. In some instances, a polynucleic acid molecule described herein hybridizes to a target sequence of human DUX4 gene (DUX4) and reduces DUX4 mRNA in muscle cells.

In some embodiments, the polynucleic acid molecule comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 1-70. In some embodiments, the polynucleic acid molecule comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 141-210. In some embodiments, the polynucleic acid molecule comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 71-140. In some embodiments, the polynucleic acid molecule comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 211-280.

In some embodiments, the polynucleic acid molecule comprises a first polynucleotide and a second polynucleotide. In some instances, the first polynucleotide comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 1-70. In some cases, the second polynucleotide comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 71-140. In some cases, the polynucleic acid molecule comprises a first polynucleotide and a second polynucleotide. In some instances, the first polynucleotide comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 141-210. In some cases, the second polynucleotide comprises a sequence having at least 50%, 55%, 60%, 65%, 70%, 75%, 80%, 85%, 90%, 95%. %*%, 97%, 98%, 99%, or 100/sequence identity to a sequence selected from SEQ ID NOs: 211-280.

In some embodiments, the polynucleic acid molecule comprises a sense strand (e.g., a passenger strand) and an antisense strand (e.g., a guide strand). In some instances, the sense strand (e.g., the passenger strand) comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 1-70. In some instances, the antisense strand (e.g., the guide strand) comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 71-140. In some embodiments, the polynucleic acid molecule comprises a sense strand (e.g., a passenger strand) and an antisense strand (e.g., a guide strand). In some instances, the sense strand (e.g., the passenger strand) comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 141-210. In some instances, the antisense strand (e.g., the guide strand) comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 211-280.

In some instances, the sense strand comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 1, 2, 3, 6, 14, 36, 52, 56, 61, 62, 63, 65, 66. In some instances, the antisense strand comprises a sequence having at least 50%, 55%, 60%, 65%, 70%, 75%, 80%, 85%, 90° %, 95%, 96%, 97%, 98%, 99%, or 100% sequence identity to a sequence selected from 71, 72, 73, 76, 84, 106, 122, 127, 131, 132, 133, 135, 136. In some instances, the siRNA comprises sense strand and antisense strand as presented in Table 11.

In some instances, the sense strand comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 141, 142, 143, 146, 176, 192, 196, 201, 202, 203, 205, 206. In some instances, the antisense strand comprises a sequence having at least 50%, 55%, 60%, 65%, 70%, 75%, 80%, 85%, 90%, 95%, 96%, 97%, 98%, 99%, or 100% sequence identity to a sequence selected from SEQ ID NOs: 211, 212, 213, 216, 246, 262, 266, 271, 272, 273, 275, 276. In some instances, the siRNA comprises sense strand and antisense strand as presented in Table 12.

In some embodiments, the polynucleic acid molecule described herein comprises RNA or DNA. In some cases, the polynucleic acid molecule comprises RNA. In some instances, RNA comprises short interfering RNA (siRNA), short hairpin RNA (shRNA), microRNA (miRNA), double-stranded RNA (dsRNA), transfer RNA (tRNA), ribosomal RNA (rRNA), or heterogeneous nuclear RNA (hnRNA). In some instances, RNA comprises shRNA. In some instances, RNA comprises miRNA. In some instances, RNA comprises dsRNA. In some instances. RNA comprises tRNA. In some instances, RNA comprises rRNA. In some instances, RNA comprises hnRNA. In some instances, the oligonucleotide is a phosphorodiamidate morpholino oligomers (PMO), which are short single-stranded oligonucleotide analogs that are built upon a backbone of morpholine rings connected by phosphorodiamidate linkages. In some instances, the RNA comprises siRNA. In some instances, the polynucleic acid molecule comprises siRNA.

In some embodiments, the polynucleic acid molecule is from about 8 to about 50 nucleotides in length. In some embodiments, the polynucleic acid molecule is from about 10 to about 50 nucleotides in length. In some instances, the polynucleic acid molecule is from about 10 to about 30, from about 15 to about 30, from about 18 to about 25, form about 18 to about 24, from about 19 to about 23, or from about 20 to about 22 nucleotides in length.

In some embodiments, the polynucleic acid molecule is about 50 nucleotides in length. In some instances, the polynucleic acid molecule is about 45 nucleotides in length. In some instances, the polynucleic acid molecule is about 40 nucleotides in length. In some instances, the polynucleic acid molecule is about 35 nucleotides in length. In some instances, the polynucleic acid molecule is about 30 nucleotides in length. In some instances, the polynucleic acid molecule is about 25 nucleotides in length. In some instances, the polynucleic acid molecule is about 20 nucleotides in length. In some instances, the polynucleic acid molecule is about 19 nucleotides in length. In some instances, the polynucleic acid molecule is about 18 nucleotides in length. In some instances, the polynucleic acid molecule is about 17 nucleotides in length. In some instances, the polynucleic acid molecule is about 16 nucleotides in length. In some instances, the polynucleic acid molecule is about 15 nucleotides in length. In some instances, the polynucleic acid molecule is about 14 nucleotides in length. In some instances, the polynucleic acid molecule is about 13 nucleotides in length. In some instances, the polynucleic acid molecule is about 12 nucleotides in length. In some instances, the polynucleic acid molecule is about 11 nucleotides in length. In some instances, the polynucleic acid molecule is about 10 nucleotides in length. In some instances, the polynucleic acid molecule is about 8 nucleotides in length. In some instances, the polynucleic acid molecule is between about 8 and about 50 nucleotides in length. In some instances, the polynucleic acid molecule is between about 10 and about 50 nucleotides in length. In some instances, the polynucleic acid molecule is between about 10 and about 45 nucleotides in length. In some instances, the polynucleic acid molecule is between about 10 and about 40 nucleotides in length. In some instances, the polynucleic acid molecule is between about 10 and about 35 nucleotides in length. In some instances, the polynucleic acid molecule is between about 10 and about 30 nucleotides in length. In some instances, the polynucleic acid molecule is between about 10 and about 25 nucleotides in length. In some instances, the polynucleic acid molecule is between about 10 and about 20 nucleotides in length. In some instances, the polynucleic acid molecule is between about 15 and about 25 nucleotides in length. In some instances, the polynucleic acid molecule is between about 15 and about 30 nucleotides in length. In some instances, the polynucleic acid molecule is between about 12 and about 30 nucleotides in length.

In some embodiments, the polynucleic acid molecule comprises a first polynucleotide. In some instances, the polynucleic acid molecule comprises a second polynucleotide. In some instances, the polynucleic acid molecule comprises a first polynucleotide and a second polynucleotide. In some instances, the first polynucleotide is a sense strand or passenger strand. In some instances, the second polynucleotide is an antisense strand or guide strand.

In some embodiments, the polynucleic acid molecule is a first polynucleotide. In some embodiments, the first polynucleotide is from about 8 to about 50 nucleotides in length. In some embodiments, the first polynucleotide is from about 10 to about 50 nucleotides in length. In some instances, the first polynucleotide is from about 10 to about 30, from about 15 to about 30, from about 18 to about 25, form about 18 to about 24, from about 19 to about 23, or from about 20 to about 22 nucleotides in length.

In some instances, the first polynucleotide is about 50 nucleotides in length. In some instances, the first polynucleotide is about 45 nucleotides in length. In some instances, the first polynucleotide is about 40 nucleotides in length. In some instances, the first polynucleotide is about 35 nucleotides in length. In some instances, the first polynucleotide is about 30 nucleotides in length. In some instances, the first polynucleotide is about 25 nucleotides in length. In some instances, the first polynucleotide is about 20 nucleotides in length. In some instances, the first polynucleotide is about 19 nucleotides in length. In some instances, the first polynucleotide is about 18 nucleotides in length. In some instances, the first polynucleotide is about 17 nucleotides in length. In some instances, the first polynucleotide is about 16 nucleotides in length. In some instances, the first polynucleotide is about 15 nucleotides in length. In some instances, the first polynucleotide is about 14 nucleotides in length. In some instances, the first polynucleotide is about 13 nucleotides in length. In some instances, the first polynucleotide is about 12 nucleotides in length. In some instances, the first polynucleotide is about 11 nucleotides in length. In some instances, the first polynucleotide is about 10 nucleotides in length. In some instances, the first polynucleotide is about 8 nucleotides in length. In some instances, the first polynucleotide is between about 8 and about 50 nucleotides in length. In some instances, the first polynucleotide is between about 10 and about 50 nucleotides in length. In some instances, the first polynucleotide is between about 10 and about 45 nucleotides in length. In some instances, the first polynucleotide is between about 10 and about 40 nucleotides in length. In some instances, the first polynucleotide is between about 10 and about 35 nucleotides in length. In some instances, the first polynucleotide is between about 10 and about 30 nucleotides in length. In some instances, the first polynucleotide is between about 10 and about 25 nucleotides in length. In some instances, the first polynucleotide is between about 10 and about 20 nucleotides in length. In some instances, the first polynucleotide is between about 15 and about 25 nucleotides in length. In some instances, the first polynucleotide is between about 15 and about 30 nucleotides in length. In some instances, the first polynucleotide is between about 12 and about 30 nucleotides in length.

In some embodiments, the polynucleic acid molecule is a second polynucleotide. In some embodiments, the second polynucleotide is from about 8 to about 50 nucleotides in length. In some embodiments, the second polynucleotide is from about 10 to about 50 nucleotides in length. In some instances, the second polynucleotide is from about 10 to about 30, from about 15 to about 30, from about 18 to about 25, form about 18 to about 24, from about 19 to about 23, or from about 20 to about 22 nucleotides in length.

In some instances, the second polynucleotide is about 50 nucleotides in length. In some instances, the second polynucleotide is about 45 nucleotides in length. In some instances, the second polynucleotide is about 40 nucleotides in length. In some instances, the second polynucleotide is about 35 nucleotides in length. In some instances, the second polynucleotide is about 30 nucleotides in length. In some instances, the second polynucleotide is about 25 nucleotides in length. In some instances, the second polynucleotide is about 20 nucleotides in length. In some instances, the second polynucleotide is about 19 nucleotides in length. In some instances, the second polynucleotide is about 18 nucleotides in length. In some instances, the second polynucleotide is about 17 nucleotides in length. In some instances, the second polynucleotide is about 16 nucleotides in length. In some instances, the second polynucleotide is about 15 nucleotides in length. In some instances, the second polynucleotide is about 14 nucleotides in length. In some instances, the second polynucleotide is about 13 nucleotides in length. In some instances, the second polynucleotide is about 12 nucleotides in length. In some instances, the second polynucleotide is about 11 nucleotides in length. In some instances, the second polynucleotide is about 10 nucleotides in length. In some instances, the second polynucleotide is about 8 nucleotides in length. In some instances, the second polynucleotide is between about 8 and about 50 nucleotides in length. In some instances, the second polynucleotide is between about 10 and about 50 nucleotides in length. In some instances, the second polynucleotide is between about 10 and about 45 nucleotides in length. In some instances, the second polynucleotide is between about 10 and about 40 nucleotides in length. In some instances, the second polynucleotide is between about 10 and about 35 nucleotides in length. In some instances, the second polynucleotide is between about 10 and about 30 nucleotides in length. In some instances, the second polynucleotide is between about 10 and about 25 nucleotides in length. In some instances, the second polynucleotide is between about 10 and about 20 nucleotides in length. In some instances, the second polynucleotide is between about 15 and about 25 nucleotides in length. In some instances, the second polynucleotide is between about 15 and about 30 nucleotides in length. In some instances, the second polynucleotide is between about 12 and about 30 nucleotides in length.

In some embodiments, the polynucleic acid molecule comprises a first polynucleotide and a second polynucleotide. In some instances, the polynucleic acid molecule further comprises a blunt terminus, an overhang, or a combination thereof. In some instances, the blunt terminus is a 5' blunt terminus, a 3' blunt terminus, or both. In some cases, the overhang is a 5' overhang, 3' overhang, or both. In some cases, the overhang comprises 1, 2, 3, 4, 5, 6, 7, 8, 9, or 10 non-base pairing nucleotides. In some cases, the overhang comprises 1, 2, 3, 4, 5, or 6 non-base pairing nucleotides. In some cases, the overhang comprises 1, 2, 3, or 4 non-base pairing nucleotides. In some cases, the overhang comprises 1 non-base pairing nucleotide. In some cases, the overhang comprises 2 non-base pairing nucleotides. In some cases, the overhang comprises 3 non-base pairing nucleotides. In some cases, the overhang comprises 4 non-base pairing nucleotides. In some embodiments, the polynucleic acid molecule comprises a sense strand and an antisense strand, and the antisense strand includes two non-base pairing nucleotides as an overhang at the 3'-end while the sense strand has no overhang. Optionally, in such embodiments, the non-base pairing nucleotides have a sequence of TT, dTdT, or UU. In some embodiments, the polynucleic acid molecule comprises a sense strand and an antisense strand, and the sense strand has one or more nucleotides at the 5'-end that are complementary to the antisense sequence.

In some embodiments, the sequence of the polynucleic acid molecule is at least 40%, 50%, 55%, 60%, 65%, 70%, 75%, 80%, 85%, 90%, 95%, 98%, 99%, or 99.5% complementary to a target sequence of DUX4. In some embodiments, the target sequence of DUX4 is a nucleic acid sequence of about 10-50 base pair length, about 15-50 base pair length, 15-40 base pair length, 15-30 base pair length, or 15-25 base pair length sequences in DUX4, in which the first nucleotide of the target sequence starts at any nucleotide in DUX4 mRNA transcript in the coding region, or in the 5' or 3'-untraslated region (UTR). For example, the first nucleotide of the target sequence can be selected so that it starts at the nucleic acid location (nal, number starting from the 5'-end of the full length of DUX mRNA, e.g., the 5-end first nucleotide is nal. 1) 1, nal 2, nal 3, nal 4, nal 5, nal 6, nal 7, nal 8, nal 9, nal 10, nal 11, nal 12, nal 13, nal 14, nal 15, nal 15, nal 16, nal 17, or any other nucleic acid location in the coding or noncoding regions (5' or 3'-untraslated region) of DUX mRNA. In some embodiments, the first nucleotide of the target sequence can be selected so that it starts at a location within, or between, nal 10-nal 15, nal 10-nal 20, nal 50-nal 60, nal 55-nal 65, nal 75-nal 85, nal 95-nal 105, nal 135-nal 145, nal 155-nal 165, nal 225-nal 235, nal 265-nal 275, nal 275-nal 285, nal 285-nal 295, nal 325-nal 335, nal 335-nal 345, nal 385-nal 395, nal 515-nal 525, nal 665-nal 675, nal 675-nal 685, nal 695-nal 705, nal 705-nal 715, nal 875-nal 885, nal 885-nal 895, nal 895-nal 905, nal 1035-nal 1045, nal 1045-nal 1055, nal 1125-nal 1135, nal 1135-nal 1145, nal 1145-nal 1155, nal 1155-nal 1165, nal 1125-nal 1135, nal 1155-nal 1165, nal 1225-nal 1235, nal 1235-nal 1245, nal 1275-nal 1285, nal 1285-nal 1295, nal 1305-nal 1315, nal 1125-nal 1135, nal 1155-nal 1165, nal 1225-nal 1235, nal 1235-nal 1245, nal 1275-nal 1285, nal 1285-nal 1295, nal 1305-nal 1315, nal 1315-nal 1325, nal 1335-nal 1345, nal 1345-nal 1355, nal 1525-nal 1535, nal 1535-nal 1545, nal 1605-nal 1615, nal 1615-c.1625, nal 1625-nal 1635.

In some embodiments, the sequence of the polynucleic acid molecule is at least 50% complementary to a target sequence described herein. In some embodiments, the sequence of the polynucleic acid molecule is at least 60% complementary to a target sequence described herein. In some embodiments, the sequence of the polynucleic acid molecule is at least 70% complementary to a target sequence described herein. In some embodiments, the sequence of the polynucleic acid molecule is at least 80% complementary to a target sequence described herein. In some embodiments, the sequence of the polynucleic acid molecule is at least 90% complementary to a target sequence described herein. In some embodiments, the sequence of the polynucleic acid molecule is at least 95% complementary to a target sequence described herein. In some embodiments, the sequence of the polynucleic acid molecule is at least 99% complementary to a target sequence described herein. In some instances, the sequence of the polynucleic acid molecule is 100% complementary to a target sequence described herein.

In some embodiments, the sequence of the polynucleic acid molecule has 5 or less mismatches to a target sequence described herein. In some embodiments, the sequence of the polynucleic acid molecule has 4 or less mismatches to a target sequence described herein. In some instances, the sequence of the polynucleic acid molecule has 3 or less mismatches to a target sequence described herein. In some cases, the sequence of the polynucleic acid molecule has 2 or less mismatches to a target sequence described herein. In some cases, the sequence of the polynucleic acid molecule has 1 or less mismatches to a target sequence described herein.

In some embodiments, a group of polynucleic acid molecules among all the polynucleic acid molecules potentially binds to the target sequence of DUX4 are selected to generate a polynucleic acid molecule library. In certain embodiments, such selection process is conducted in silico via one or more steps of eliminating less desirable polynucleic acid molecules from candidates. For example, in some embodiments, the selection process comprises an elimination step of one or more polynucleic acid molecule that has single nucleotide polymorphism (SNP) and/or MEF<−5. Alternatively and/or additionally, in some embodiments, the selection process comprises an elimination step of one or more polynucleic acid molecule with 0 and 1 mismatch (MM) in the human transcriptome (such that only hits allowed are DUX, DUX5, and DBET). Alternatively and/or additionally, in some embodiments, the selection process comprises an elimination step of one or more polynucleic acid molecule with 0 MM in the human intragenic regions (such that only hits allowed are DUX1. DUX5 and DBET pseudogenes). Alternatively and/or additionally, in some embodiments, the selection process comprises an elimination step of one or more polynucleic acid molecule with a MM to DUX4 human sequence used in FLExDUX4 FSHD mouse model. Alternatively and/or additionally, in some embodiments, the selection process comprises an elimination step of one or more polynucleic acid molecule predicted viability <60. Alternatively and/or additionally, such selection process comprises carrying forward one or more polynucleic acid molecule predicted viability ≥60. Alternatively and/or additionally, in some embodiments, the selection process comprises an elimination step of one or more polynucleic acid molecule with a match to a seed region of known miRNAs 1-1000. Alternatively and/or additionally, in some embodiments, the selection process comprises an elimination step of one or more polynucleic acid molecule with % GC content 75 and above. Alternatively and/or additionally, in some embodiments, the selection process comprises a selection step of 8 or less predicted off-target hits with 2 MM. In some embodiments, for the region 295-1132 (nal 295-1132), 12 or less predicted off-target hits with 2 MM is allowed.

In some embodiments, selection process is conducted in silico via one or more consecutive steps of eliminating less desirable polynucleic acid molecules from candidates. For example, in some embodiments, selection process begins with collecting candidate polynucleic acid molecules to generate a library. From the library, the first eliminating step comprises eliminating one or more polynucleic acid molecule that has single nucleotide polymorphism (SNP) and/or MEF<−5. Then, the second eliminating step comprises eliminating one or more polynucleic acid molecule with 0 and 1 MM in the human transcriptome (such that only hits allowed are DUX, DUX5, and DBET). Then, the third eliminating step comprises eliminating one or more polynucleic acid molecule with 0 MM in the human intragenic regions (such that only hits allowed are DUX1, DUX5 and DBET pseudogenes). Then, the next eliminating step comprises eliminating one or more polynucleic acid molecule with a MM to DUX4 human sequence used in FLExDUX4 FSHD mouse model. Then, the next step is carrying forward only or one or more polynucleic acid molecule with predicted viability >60. Next, the eliminating step comprises eliminating one or more polynucleic acid molecule with a match to a seed region of known miRNAs 1-1000. Then, the eliminating step continues with eliminating one or more polynucleic acid molecule with % GC content 75 and above. Then, the final selection process comprises with 8 or less predicted off-target hits with 2 MM, except for the region 295-1132, for which up to 12 hits are allowed.

In some embodiments, the specificity of the polynucleic acid molecule that hybridizes to a target sequence described herein is a 95%, 98%, 99%, 99.5% or 100% sequence complementarity of the polynucleic acid molecule to a target sequence. In some instances, the hybridization is a high stringent hybridization condition.

In some embodiments, the polynucleic acid molecule has reduced off-target effect. In some instances, "off-target" or "off-target effects" refer to any instance in which a polynucleic acid polymer directed against a given target causes an unintended effect by interacting either directly or indirectly with another mRNA sequence, a DNA sequence or a cellular protein or other moiety. In some instances, an "off-target effect" occurs when there is a simultaneous degradation of other transcripts due to partial homology or complementarity between that other transcript and the sense and/or antisense strand of the polynucleic acid molecule.

In some embodiments, the polynucleic acid molecule comprises natural or synthetic or artificial nucleotide analogues or bases. In some cases, the polynucleic acid molecule comprises combinations of DNA, RNA and/or nucleotide analogues. In some instances, the synthetic or artificial nucleotide analogues or bases comprise modifications at one or more of ribose moiety, phosphate moiety, nucleoside moiety, or a combination thereof.

In some embodiments, nucleotide analogues or artificial nucleotide base comprise a nucleic acid with a modification at a 2' hydroxyl group of the ribose moiety. In some instances, the modification includes an H, OR, R, halo, SH, SR, NH2, NHR, NR2, or CN, wherein R is an alkyl moiety. Exemplary alkyl moiety includes, but is not limited to, halogens, sulfurs, thiols, thioethers, thioesters, amines (primary, secondary, or tertiary), amides, ethers, esters, alcohols and oxygen. In some instances, the alkyl moiety further comprises a modification. In some instances, the modification comprises an azo group, a keto group, an aldehyde group, a carboxyl group, a nitro group, a nitroso, group, a nitrile group, a heterocycle (e.g., imidazole, hydrazino or hydroxylamino) group, an isocyanate or cyanate group, or a sulfur containing group (e.g., sulfoxide, sulfone, sulfide, and disulfide). In some instances, the alkyl moiety further comprises a hetero substitution. In some instances, the carbon of the heterocyclic group is substituted by a nitrogen, oxygen or sulfur. In some instances, the heterocyclic substitution includes but is not limited to, morpholino, imidazole, and pyrrolidino.

In some instances, the modification at the 2' hydroxyl group is a 2'-O-methyl modification or a 2'-O-methoxyethyl (2'-O-MOE) modification. In some cases, the 2'-O-methyl modification adds a methyl group to the 2' hydroxyl group of the ribose moiety whereas the 2'O-methoxyethyl modification adds a methoxyethyl group to the 2' hydroxyl group of the ribose moiety. Exemplary chemical structures of a 2'-O-methyl modification of an adenosine molecule and 2'O-methoxyethyl modification of an uridine are illustrated below.

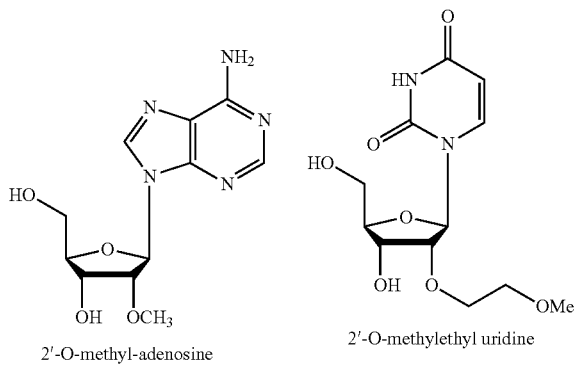

2'-O-methyl-adenosine

2'-O-methylethyl uridine

In some instances, the modification at the 2' hydroxyl group is a 2'-O-aminopropyl modification in which an extended amine group comprising a propyl linker binds the amine group to the 2' oxygen. In some instances, this modification neutralizes the phosphate derived overall negative charge of the oligonucleotide molecule by introducing one positive charge from the amine group per sugar and thereby improves cellular uptake properties due to its zwitterionic properties. An exemplary chemical structure of a 2'-O-aminopropyl nucleoside phosphoramidite is illustrated below.

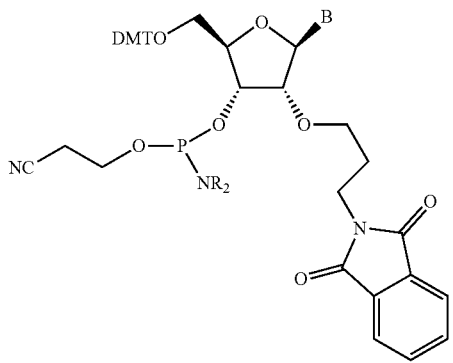

2'-O-aminopropyl nucleoside phosphoramidite

In some instances, the modification at the 2' hydroxyl group is a locked or bridged ribose modification (e.g., locked nucleic acid or LNA) in which the oxygen molecule bound at the 2' carbon is linked to the 4' carbon by a methylene group, thus forming a 2'-C,4'-C-oxy-methylene-linked bicyclic ribonucleotide monomer. Exemplary representations of the chemical structure of LNA are illustrated below. The representation shown to the left highlights the chemical connectivities of an LNA monomer. The representation shown to the right highlights the locked 3'-endo ($^3$E) conformation of the furanose ring of an LNA monomer.

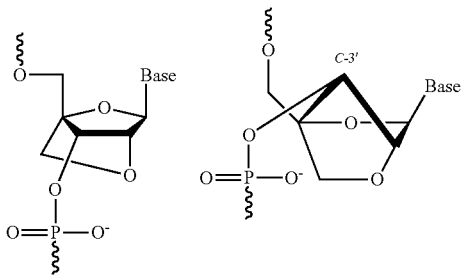

LNA (Locked Nucleic Acids)

In some instances, the modification at the 2' hydroxyl group comprises ethylene nucleic acids (ENA) such as for example 2'-4'-ethylene-bridged nucleic acid, which locks the sugar conformation into a $C_3$'-endo sugar puckering conformation. ENA are part of the bridged nucleic acids class of modified nucleic acids that also comprises LNA. Exemplary chemical structures of the ENA and bridged nucleic acids are illustrated below.

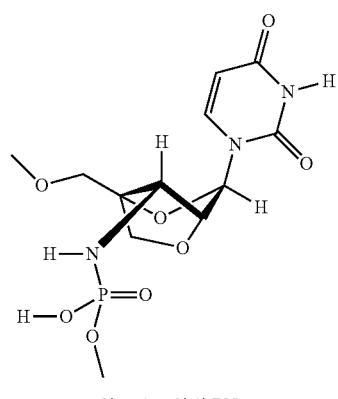

3'-amino-2',4'-BNA

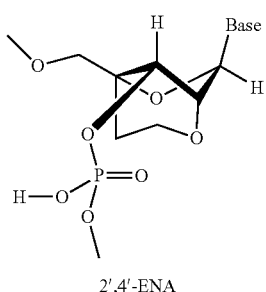

2',4'-ENA

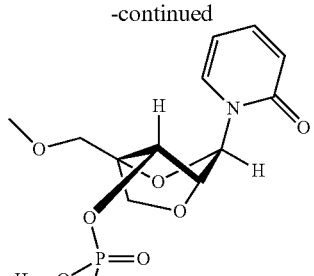

2',4'-BNA-2-pyridone

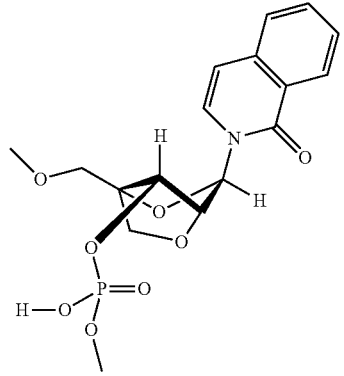

2',4'-BNA-1-isoquinolone

In some embodiments, additional modifications at the 2' hydroxyl group include 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA).

In some embodiments, nucleotide analogues comprise modified bases such as, but not limited to, 5-propynyluridine, 5-propynylcytidine, 6-methyladenine, 6-methylguanine, N, N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino) propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2, 2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4, 6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties, in some cases are or be based on, mannoses, arabinoses, glucopyranoses, galactopyranoses, 4'-thioribose, and other sugars, heterocycles, or carbocycles. The term nucleotide also includes what are known in the art as universal bases. By way of example, universal bases include but are not limited to 3-nitropyrrole, 5-nitroindole, or nebularine.

In some embodiments, nucleotide analogues further comprise morpholinos, peptide nucleic acids (PNAs), methylphosphonate nucleotides, thiolphosphonate nucleotides, 2'-fluoro N3-P5'-phosphoramidites, 1', 5'-anhydrohexitol nucleic acids (HNAs), or a combination thereof. Morpholino or phosphorodiamidate morpholino oligo (PMO) comprises synthetic molecules whose structure mimics natural nucleic acid structure by deviates from the normal sugar and phosphate structures. In some instances, the five member ribose ring is substituted with a six member morpholino ring containing four carbons, one nitrogen and one oxygen. In some cases, the ribose monomers are linked by a phosphordiamidate group instead of a phosphate group. In such cases, the backbone alterations remove all positive and negative charges making morpholinos neutral molecules capable of crossing cellular membranes without the aid of cellular delivery agents such as those used by charged oligonucleotides.

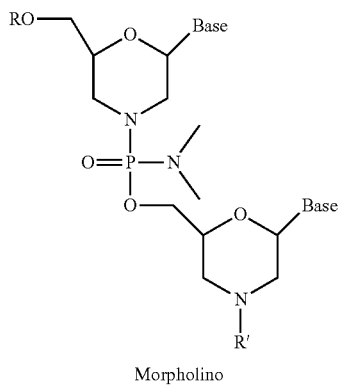

Morpholino

In some embodiments, peptide nucleic acid (PNA) does not contain sugar ring or phosphate linkage and the bases are attached and appropriately spaced by oligoglycine-like molecules, therefore, eliminating a backbone charge.

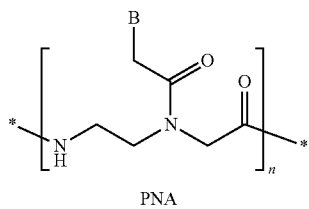

PNA

In some embodiments, one or more modifications optionally occur at the internucleotide linkage. In some instances, modified internucleotide linkage include, but is not limited to, phosphorothioates, phosphorodithioates, methylphosphonates, 5'-alkylenephosphonates, 5'-methylphosphonate, 3'-alkylene phosphonates, borontrifluoridates, borano phosphate esters and selenophosphates of 3'-5' linkage or 2'-5' linkage, phosphotriesters, thionoalkylphosphotriesters, hydrogen phosphonate linkages, alkyl phosphonates, alkylphosphonothioates, arylphosphonothioates, phosphoroselenoates, phosphorodiselenoates, phosphinates, phosphoramidates, 3'-alkylphosphoramidates, aminoalkylphosphoramidates, thionophosphoramidates, phosphoropiperazidates, phosphoroanilothioates, phosphoroanilidates, ketones, sulfones, sulfonamides, carbonates, carbamates, methylenehydrazos, methylenedimethylhydrazos, formacetals, thioformacetals, oximes, methyleneiminos, methylenemethyliminos, thioamidates, linkages with riboacetyl groups, aminoethyl glycine, silyl or siloxane linkages, alkyl or cycloalkyl linkages with or without heteroatoms of, for example, 1 to 10 carbons that are saturated or unsaturated and/or substituted and/or contain heteroatoms, linkages with morpholino structures, amides, polyamides wherein the bases are attached to the aza nitrogens of the backbone directly or indirectly, and combinations thereof. Phosphorothioate antisense oligonucleotides (PS ASO) are antisense oligonucleotides comprising a phosphorothioate linkage. An exemplary PS ASO is illustrated below.

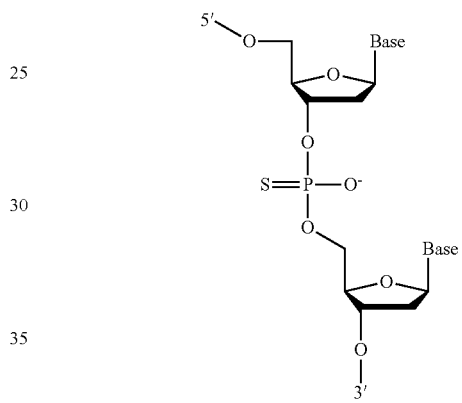

In some instances, the modification is a methyl or thiol modification such as methylphosphonate or thiolphosphonate modification. Exemplary thiolphosphonate nucleotide (left) and methylphosphonate nucleotide (right) are illustrated below.

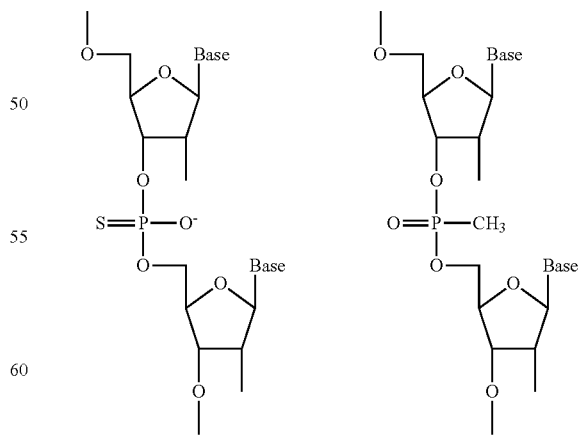

In some instances, a modified nucleotide includes, but is not limited to, 2'-fluoro N3-P5'-phosphoramidites illustrated as:

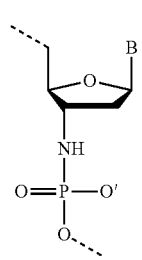

N3'-P5' Phosphoroamideate

In some instances, a modified nucleotide includes, but is not limited to, hexitol nucleic acid (or 1', 5'-anhydrohexitol nucleic acids (HNA)) illustrated as:

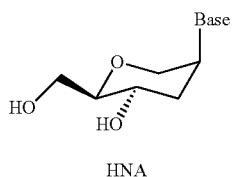

HNA

In some embodiments, one or more modifications further optionally include modifications of the ribose moiety, phosphate backbone and the nucleoside, or modifications of the nucleotide analogues at the 3' or the 5' terminus. For example, the 3' terminus optionally include a 3' cationic group, or by inverting the nucleoside at the 3'-terminus with a 3'-3' linkage. In another alternative, the 3'-terminus is optionally conjugated with an aminoalkyl group, e.g. a 3' C5-aminoalkyl dT. In an additional alternative, the 3'-terminus is optionally conjugated with an abasic site, e.g., with an apurinic or apyrimidinic site. In some instances, the 5'-terminus is conjugated with an aminoalkyl group. e.g. a 5'-O-alkylamino substituent. In some cases, the 5'-terminus is conjugated with an abasic site. e.g., with an apurinic or apyrimidinic site.

In some embodiments, the polynucleic acid molecule comprises one or more of the artificial nucleotide analogues described herein. In some instances, the polynucleic acid molecule comprises 1, 2, 3, 4, 5, 6, 7, 8, 9, 10, 11, 12, 13, 14, 15, 16, 17, 18, 20, 25, or more of the artificial nucleotide analogues described herein. In some embodiments, the artificial nucleotide analogues include 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the polynucleic acid molecule comprises 1, 2, 3, 4, 5, 6, 7, 8, 9, 10, 11, 12, 13, 14, 15, 16, 17, 18, 20, 25, or more of the artificial nucleotide analogues selected from 2'-O-methyl, 2'-O-methoxyethyl (2'-O-MOE), 2-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5-phosphoramidites, or a combination thereof. In some instances, the polynucleic acid molecule comprises 1, 2, 3, 4, 5, 6, 7, 8, 9, 10, 11, 12, 13, 14, 15, 16, 17, 18, 20, 25, or more of 2'-O-methyl modified nucleotides. In some instances, the polynucleic acid molecule comprises 1, 2, 3, 4, 5, 6, 7, 8, 9, 10, 11, 12, 13, 14, 15, 16, 17, 18, 20, 25, or more of 2'-O-methoxyethyl (2'-O-MOE) modified nucleotides. In some instances, the polynucleic acid molecule comprises 1, 2, 3, 4, 5, 6, 7, 8, 9, 10, 11, 12, 13, 14, 15, 16, 17, 18, 20, 25, or more of thiolphosphonate nucleotides.

In some instances, the polynucleic acid molecule comprises at least one of: from about 5% to about 100% modification, from about 10% to about 100% modification, from about 20% to about 100% modification, from about 30% to about 100% modification, from about 40% to about 100% modification, from about 50% to about 100% modification, from about 60% to about 100% modification, from about 70% to about 100% modification, from about 80% to about 100% modification, and from about 90% to about 100% modification.

In some cases, the polynucleic acid molecule comprises at least one of: from about 10% to about 90% modification, from about 20% to about 90% modification, from about 30% to about 90% modification, from about 40% to about 90% modification, from about 50% to about 90% modification, from about 60% to about 90% modification, from about 70% to about 90% modification, and from about 80% to about 100% modification.

In some cases, the polynucleic acid molecule comprises at least one of: from about 10% to about 80% modification, from about 20% to about 80% modification, from about 30% to about 80% modification, from about 40% to about 80% modification, from about 50% to about 80% modification, from about 60% to about 80% modification, and from about 70% to about 80% modification.

In some instances, the polynucleic acid molecule comprises at least one of: from about 10% to about 70% modification, from about 20% to about 70% modification, from about 30% to about 70% modification, from about 40% to about 70% modification, from about 50% to about 70% modification, and from about 60% to about 70% modification.

In some instances, the polynucleic acid molecule comprises at least one of: from about 10% to about 60% modification, from about 20% to about 60% modification, from about 30% to about 60% modification, from about 40% to about 60% modification, and from about 50% to about 60% modification.

In some cases, the polynucleic acid molecule comprises at least one of: from about 10% to about 50% modification, from about 20% to about 50% modification, from about 30% to about 50% modification, and from about 40% to about 50% modification.

In some cases, the polynucleic acid molecule comprises at least one of: from about 10% to about 40% modification, from about 20% to about 40% modification, and from about 30% to about 40% modification.

In some cases, the polynucleic acid molecule comprises at least one of: from about 10% to about 30% modification, and from about 20% to about 30% modification.

In some cases, the polynucleic acid molecule comprises from about 10% to about 20% modification.

In some cases, the polynucleic acid molecule comprises from about 15% to about 90%, from about 20% to about 80%, from about 30% to about 70%, or from about 40% to about 60% modifications.

In additional cases, the polynucleic acid molecule comprises at least about 15%, 20%, 30%, 40%, 50%, 60%, 70%, 80%, 90%, 95%, or 99% modification.

In some embodiments, the polynucleic acid molecule comprises at least about 1, about 2, about 3, about 4, about 5, about 6, about 7, about 8, about 9, about 10, about 11, about 12, about 13, about 14, about 15, about 16, about 17, about 18, about 19, about 20, about 21, about 22 or more modifications.

In some instances, the polynucleic acid molecule comprises at least about 1, about 2, about 3, about 4, about 5, about 6, about 7, about 8, about 9, about 10, about 11, about 12, about 13, about 14, about 15, about 16, about 17, about 18, about 19, about 20, about 21, about 22 or more modified nucleotides.

In some instances, from about 5 to about 100% of the polynucleic acid molecule comprise the artificial nucleotide analogues described herein. In some instances, about 5%, 10%, 15%, 20%, 25%, 30%, 35%, 40%, 45%, 50%, 55%, 60%, 65%, 70%, 75%, 80%, 85%, 90%, 95% or 100% of the polynucleic acid molecule comprise the artificial nucleotide analogues described herein. In some instances, about 5% of the polynucleic acid molecule comprises the artificial nucleotide analogues described herein. In some instances, about 10% of the polynucleic acid molecule comprises the artificial nucleotide analogues described herein. In some instances, about 15% of the polynucleic acid molecule comprises the artificial nucleotide analogues described herein. In some instances, about 20% of the polynucleic acid molecule comprises the artificial nucleotide analogues described herein. In some instances, about 25% of the polynucleic acid molecule comprises the artificial nucleotide analogues described herein. In some instances, about 30% of the polynucleic acid molecule comprises the artificial nucleotide analogues described herein. In some instances, about 35% of the polynucleic acid molecule comprises the artificial nucleotide analogues described herein. In some instances, about 40% of the polynucleic acid molecule comprises the artificial nucleotide analogues described herein. In some instances, about 45% of the polynucleic acid molecule comprises the artificial nucleotide analogues described herein. In some instances, about 50% of the polynucleic acid molecule comprises the artificial nucleotide analogues described herein. In some instances, about 55% of the polynucleic acid molecule comprises the artificial nucleotide analogues described herein. In some instances, about 60% of the polynucleic acid molecule comprises the artificial nucleotide analogues described herein. In some instances, about 65% of the polynucleic acid molecule comprises the artificial nucleotide analogues described herein. In some instances, about 70% of the polynucleic acid molecule comprises the artificial nucleotide analogues described herein. In some instances, about 75% of the polynucleic acid molecule comprises the artificial nucleotide analogues described herein. In some instances, about 80% of the polynucleic acid molecule comprises the artificial nucleotide analogues described herein. In some instances, about 85% of the polynucleic acid molecule comprises the artificial nucleotide analogues described herein. In some instances, about 90% of the polynucleic acid molecule comprises the artificial nucleotide analogues described herein. In some instances, about 95% of the polynucleic acid molecule comprises the artificial nucleotide analogues described herein. In some instances, about 96% of the polynucleic acid molecule comprises the artificial nucleotide analogues described herein. In some instances, about 97% of the polynucleic acid molecule comprises the artificial nucleotide analogues described herein. In some instances, about 98% of the polynucleic acid molecule comprises the artificial nucleotide analogues described herein. In some instances, about 99% of the polynucleic acid molecule comprises the artificial nucleotide analogues described herein. In some instances, about 100% of the polynucleic acid molecule comprises the artificial nucleotide analogues described herein. In some embodiments, the artificial nucleotide analogues include 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA. HNA, morpholino, methylphosphonate nucleotides, thiolphosphonate nucleotides, 2'-fluoro N3-P5'-phosphoramidites, or a combination thereof.

In some embodiments, the polynucleic acid molecule comprises from about 1 to about 25 modifications in which the modification comprises an artificial nucleotide analogues described herein. In some embodiments, the polynucleic acid molecule comprises about 1 modification in which the modification comprises an artificial nucleotide analogue described herein. In some embodiments, the polynucleic acid molecule comprises about 2 modifications in which the modifications comprise an artificial nucleotide analogue described herein. In some embodiments, the polynucleic acid molecule comprises about 3 modifications in which the modifications comprise an artificial nucleotide analogue described herein. In some embodiments, the polynucleic acid molecule comprises about 4 modifications in which the modifications comprise an artificial nucleotide analogue described herein. In some embodiments, the polynucleic acid molecule comprises about 5 modifications in which the modifications comprise an artificial nucleotide analogue described herein. In some embodiments, the polynucleic acid molecule comprises about 6 modifications in which the modifications comprise an artificial nucleotide analogue described herein. In some embodiments, the polynucleic acid molecule comprises about 7 modifications in which the modifications comprise an artificial nucleotide analogue described herein. In some embodiments, the polynucleic acid molecule comprises about 8 modifications in which the modifications comprise an artificial nucleotide analogue described herein. In some embodiments, the polynucleic acid molecule comprises about 9 modifications in which the modifications comprise an artificial nucleotide analogue described herein. In some embodiments, the polynucleic acid molecule comprises about 10 modifications in which the modifications comprise an artificial nucleotide analogue described herein. In some embodiments, the polynucleic acid molecule comprises about 11 modifications in which the modifications comprise an artificial nucleotide analogue described herein. In some embodiments, the polynucleic acid molecule comprises about 12 modifications in which the modifications comprise an artificial nucleotide analogue described herein. In some embodiments, the polynucleic acid molecule comprises about 13 modifications in which the modifications comprise an artificial nucleotide analogue described herein. In some embodiments, the polynucleic acid molecule comprises about 14 modifications in which the modifications comprise an artificial nucleotide analogue described herein. In some embodiments, the polynucleic acid molecule comprises about 15 modifications in which the modifications comprise an artificial nucleotide analogue described herein. In some embodiments, the polynucleic acid molecule comprises about 16 modifications in which the modifications comprise an artificial nucleotide analogue described herein. In some embodiments, the polynucleic acid molecule comprises about 17 modifications in which the modifications comprise an artificial nucleotide analogue described herein. In some embodiments, the polynucleic acid molecule comprises about 18 modifications in which the modifications comprise an artificial nucleotide analogue described herein. In some embodiments, the polynucleic acid molecule comprises about 19 modifications in which the modifications comprise an artificial nucleotide analogue described herein. In some embodiments, the polynucleic acid molecule comprises about 20 modifications in which the modifications comprise an artificial nucleotide analogue described herein. In some embodiments, the polynucleic acid molecule comprises about 21 modifications in which the modifications comprise an artificial nucleotide analogue described herein. In some embodiments, the polynucleic acid molecule comprises about 22 modifications in which the modifications comprise an artificial nucleotide analogue described herein. In some embodiments, the polynucleic acid molecule comprises about 23 modifications in which the modifications comprise an artificial nucleotide analogue described herein. In some embodiments, the polynucleic acid molecule comprises about 24 modifications in which the modifications comprise an artificial nucleotide analogue described herein. In some embodiments, the polynucleic acid molecule comprises about 25 modifications in which the modifications comprise an artificial nucleotide analogue described herein.

In some embodiments, a polynucleic acid molecule is assembled from two separate polynucleotides wherein one polynucleotide comprises the sense strand and the second polynucleotide comprises the antisense strand of the polynucleic acid molecule. In other embodiments, the sense strand is connected to the antisense strand via a linker molecule, which in some instances is a polynucleotide linker or a non-nucleotide linker.

In some embodiments, a polynucleic acid molecule comprises a sense strand and antisense strand, wherein pyrimidine nucleotides in the sense strand comprises 2'-O-methylpyrimidine nucleotides and purine nucleotides in the sense strand comprise 2'-deoxy purine nucleotides. In some embodiments, a polynucleic acid molecule comprises a sense strand and antisense strand, wherein pyrimidine nucleotides present in the sense strand comprise 2'-deoxy-2'-fluoro pyrimidine nucleotides and wherein purine nucleotides present in the sense strand comprise 2'-deoxy purine nucleotides.

In some embodiments, a polynucleic acid molecule comprises a sense strand and antisense strand, wherein the pyrimidine nucleotides when present in said antisense strand are 2'-deoxy-2'-fluoro pyrimidine nucleotides and the purine nucleotides when present in said antisense strand are 2'-O-methyl purine nucleotides.

In some embodiments, a polynucleic acid molecule comprises a sense strand and antisense strand, wherein the pyrimidine nucleotides when present in said antisense strand are 2'-deoxy-2'-fluoro pyrimidine nucleotides and wherein the purine nucleotides when present in said antisense strand comprise 2'-deoxy-purine nucleotides.

In some embodiments, a polynucleic acid molecule comprises a sense strand and antisense strand, and at least one of sense strand and antisense strands has a plurality of (e.g., two or more, three or more, four or more, five or more, six or more, seven or more, eight or more, etc) 2'-O-methyl or 2'-deoxy-2'-fluoro modified nucleotides. In some embodiments, where at least two out of the a plurality of 2'-O-methyl or 2'-deoxy-2'-fluoro modified nucleotides are consecutive nucleotides. In some embodiments, where consecutive 2'-O-methyl or 2'-deoxy-2'-fluoro modified nucleotides are located at the 5'-end of the sense strand and/or the antisense strand. In some embodiments, where consecutive 2'-O-methyl or 2'-deoxy-2'-fluoro modified nucleotides are located at the 3'-end of the sense strand and/or the antisense strand. In some embodiments, the sense strand of polynucleic acid molecule includes at least four, at least five, at least six consecutive 2'-O-methyl modified nucleotides at its 5' end and/or 3'end, or both. Optionally, in such embodiments, the sense strand of polynucleic acid molecule includes at least one, at least two, at least three, at least four 2'-deoxy-2'-fluoro modified nucleotides at the 3' end of the at least four, at least five, at least six consecutive 2'-O-methyl modified nucleotides at the polynucleotides' 5' end, or at the 5' end of the at least four, at least five, at least six consecutive 2'-O-methyl modified nucleotides at polynucleotides' 3' end. Also optionally, such at least two, at least three, at least four 2'-deoxy-2'-fluoro modified nucleotides are consecutive nucleotides.

In some embodiments, a polynucleic acid molecule comprises a sense strand and antisense strand, and at least one of sense strand and antisense strands has 2'-O-methyl modified nucleotide located at the 5'-end of the sense strand and/or the antisense strand. In some embodiments, at least one of sense strand and antisense strands has 2'-O-methyl modified nucleotide located at the 3'-end of the sense strand and/or the antisense strand. In some embodiments, the 2'-O-methyl modified nucleotide located at the 5'-end of the sense strand and/or the antisense strand is a purine nucleotide. In some embodiments, the 2'-O-methyl modified nucleotide located at the 5'-end of the sense strand and/or the antisense strand is a pyridine nucleotide.

In some embodiments, a polynucleic acid molecule comprises a sense strand and antisense strand, and the antisense strand has two or more consecutive 2'-deoxy-2'-fluoro modified nucleotides at 5'-end. In some embodiments, a polynucleic acid molecule comprises a sense strand and antisense strand, and the antisense strand has two or more consecutive 2'-O-methyl modified nucleotides at 3'-end. In some embodiments, a polynucleic acid molecule comprises a sense strand and antisense strand, and the antisense strand has at least 2, 3, 4, 5, 6, or 7 consecutive 2'-O-methyl modified nucleotides.

In some embodiments, a polynucleic acid molecule comprises a sense strand and antisense strand, and the sense strand comprises a nucleic acid of 5'-nsnsnnnnNfNfNfnnnnnnnnnsnsa-3' (lower case (n)=2'-O-Me (methyl), Nf=2'-F (fluoro); s=phosphorothioate backbone modification). In some embodiments, a polynucleic acid molecule comprises a sense strand and antisense strand, and the antisense strand comprises a nucleic acid of 5'-UfsNfsnnnNfnnnnnnnNfnNfnnnsusu-3' (lower case (n)=2'-O-Me (methyl), Nf=2'-F (fluoro); s=phosphorothioate backbone modification). In some embodiments, a polynucleic acid molecule comprises a sense strand and antisense strand, and the sense strand comprises a nucleic acid of 5'-nsnsnnnnNfNfNfnnnnnnnnnsnsa-3' (lower case (n)=2'-O-Me (methyl), Nf=2'-F (fluoro); s=phosphorothioate backbone modification) and the antisense strand comprises a nucleic acid of 5'-UfsNfsnnnNfnnnnnnnNfnNfnnnsusu-3' (lower case (n)=2'-O-Me (methyl), Nf=2'-F (fluoro); s=phosphorothioate backbone modification).

In some embodiments, a polynucleic acid molecule comprises a sense strand and antisense strand, wherein the sense strand includes a terminal cap moiety at the 5'-end, the 3'-end, or both of the 5' and 3' ends of the sense strand. In other embodiments, the terminal cap moiety is an inverted deoxy abasic moiety.

In some embodiments, a polynucleic acid molecule comprises a sense strand and an antisense strand, wherein the antisense strand comprises a glyceryl modification at the 3' end of the antisense strand.

In some embodiments, a polynucleic acid molecule comprises a sense strand and an antisense strand, in which the sense strand comprises one or more, for example, about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or about one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and in which the antisense strand comprises about 1 to about 10 or more, specifically about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10, or more, pyrimidine nucleotides of the sense and/or antisense strand are chemically-modified with 2'-deoxy, 2'-O-methyl and/or 2'-deoxy-2'-fluoro nucleotides, with or without one or more, for example about 1, 2, 3, 4, 5, 6, 7, 8, 9, 10, or more, phosphorothioate internucleotide linkages and/or a terminal cap molecule at the 3'-end, the 5'-end, or both of the 3'- and 5'-ends, being present in the same or different strand.

In some embodiments, a polynucleic acid molecule comprises a sense strand and an antisense strand, in which the sense strand comprises about 1 to about 25, for example, about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10, or more) 2'-deoxy, 2'-O-methyl, 2'-deoxy-2'-fluoro, and/or one or more (e.g., about 1, 2, 3, 4, 5, 6, 7, 8, 9, 10, or more) universal base modified nucleotides, and optionally a terminal cap molecule at the 3-end, the 5'-end, or both of the 3'- and 5'-ends of the sense strand; and in which the antisense strand comprises about 1 to about 25 or more, for example about 1, 2, 3, 4, 5, 6, 7, 8, 9, 10, 11, 12, 13, 14, 15, 16, 17, 18, 19, 20, or more phosphorothioate internucleotide linkages, and/or one or more (e.g. about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10, or more, pyrimidine nucleotides of the sense and/or antisense strand are chemically-modified with 2'-deoxy, 2'-O-methyl and/or 2'-deoxy-2'-fluoro nucleotides, with or without about 1 to about 25 or more, for example about 1, 2, 3, 4, 5, 6, 7, 8, 9, 10, 11, 12, 13, 14, 15, 16, 17, 18, 19, 20, or more phosphorothioate internucleotide linkages and/or a terminal cap molecule at the 3'-end, the 5'-end, or both of the 3'- and 5'-ends, being present in the same or different strand.

In some embodiments, a polynucleic acid molecule comprises a sense strand and an antisense strand, in which the antisense strand comprises one or more, for example, about 1, 2, 3, 4, 5, 6, 7, 8, 9, 10, 11, 12, 13, 14, 15, 16, 17, 18, 19, 20, or more phosphorothioate internucleotide linkages, and/or about one or more (e.g., about 1, 2, 3, 4, 5, 6, 7, 8, 9, 10 or more) 2'-deoxy, 2'-O-methyl, 2'-deoxy-2'-fluoro, and/or one or more (e.g. about 1, 2, 3, 4, 5, 6, 7, 8, 9, 10 or more) universal base modified nucleotides at the 3'-end, the 5'-end, or both of the 3'- and 5'-ends of the sense strand and/or antisense strand, and optionally a terminal cap molecule at the 3'-end, the 5'-end, or both of the 3'- and 5'-ends of the sense strand. In some embodiments, the antisense strand comprises about 1 to about 10 or more, specifically about 1, 2, 3, 4, 5, 6, 7, 8, 9, 10 or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g. about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10, 11, 12, 13, 14, 15, 16, 17, 18, 19, 20, or more pyrimidine nucleotides of the sense and/or antisense strand are chemically-modified with 2'-deoxy, 2'-O-methyl and/or 2'-deoxy-2'-fluoro nucleotides, with or without one or more, for example, about 1, 2, 3, 4, 5, 6, 7, 8, 9, 10 or more phosphorothioate internucleotide linkages and/or a terminal cap molecule at the 3'-end, the 5'-end, or both of the 3' and 5'-ends, being present in the same or different strand.

In some embodiments, a polynucleic acid molecule comprises a sense strand and an antisense strand, in which the antisense strand comprises about 1 to about 25 or more, for example, about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and the antisense strand comprises about 1 to about 25 or more, for example about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10 or more pyrimidine nucleotides of the sense and/or antisense strand are chemically-modified with 2'-deoxy, 2'-O-methyl and/or 2'-deoxy-2'-fluoro nucleotides, with or without about 1 to about 5, for example about 1, 2, 3, 4, 5 or more phosphorothioate internucleotide linkages and/or a terminal cap molecule at the 3'-end, the 5'-end, or both of the 3'- and 5'-ends, being present in the same or different strand.

In some embodiments, a polynucleic acid molecule described herein is a chemically-modified short interfering nucleic acid molecule having about 1 to about 25, for example, about 1, 2, 3, 4, 5, 6, 7, 8, 9, 10, 11, 12, 13, 14, 15, 16, 17, 18, 19, 20 or more phosphorothioate internucleotide linkages in each strand of the polynucleic acid molecule. In some embodiments, a polynucleic acid molecule comprises a sense strand and an antisense strand, and the antisense strand comprises a phosphate backbone modification at the 3' end of the antisense strand. Alternatively and/or additionally, a polynucleic acid molecule comprises a sense strand and an antisense strand, and the sense strand comprises a phosphate backbone modification at the 5' end of the antisense strand. In some instances, the phosphate backbone modification is a phosphorothioate. In some embodiments, the sense or antisense strand has three consecutive nucleosides that are coupled via two phosphorothioate backbone.

In another embodiment, a polynucleic acid molecule described herein comprises 2'-5' internucleotide linkages. In some instances, the 2'-5' internucleotide linkage(s) is at the 3'-end, the 5'-end, or both of the 3'- and 5'-ends of one or both sequence strands. In addition instances, the 2'-5' internucleotide linkage(s) is present at various other positions within one or both sequence strands, for example, about 1, 2, 3, 4, 5, 6, 7, 8, 9, 10, or more including every internucleotide linkage of a pyrimidine nucleotide in one or both strands of the polynucleic acid molecule comprise a 2'-5' internucleotide linkage, or about 1, 2, 3, 4, 5, 6, 7, 8, 9, 10, or more including every internucleotide linkage of a purine nucleotide in one or both strands of the polynucleic acid molecule comprise a 2'-5' internucleotide linkage.

In some embodiments, a polynucleic acid molecule is a single stranded polynucleic acid molecule that mediates RNAi activity in a cell or reconstituted in vitro system, wherein the polynucleic acid molecule comprises a single stranded polynucleotide having complementarity to a target nucleic acid sequence, and wherein one or more pyrimidine nucleotides present in the polynucleic acid are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any purine nucleotides present in the polynucleic acid are 2'-deoxy purine nucleotides (e.g., wherein all purine nucleotides are 2'-deoxy purine nucleotides or alternately a plurality of purine nucleotides are 2'-deoxy purine nucleotides), and a terminal cap modification, that is optionally present at the 3'-end, the 5'-end, or both of the 3' and 5'-ends of the antisense sequence, the polynucleic acid molecule optionally further comprising about 1 to about 4 (e.g., about 1, 2, 3, or 4) terminal 2'-deoxynucleotides at the 3'-end of the polynucleic acid molecule, wherein the terminal nucleotides further comprise one or more (e.g., 1, 2, 3, or 4) phosphorothioate internucleotide linkages, and wherein the polynucleic acid molecule optionally further comprises a terminal phosphate group, such as a 5'-terminal phosphate group.

In some cases, one or more of the artificial nucleotide analogues described herein are resistant toward nucleases such as for example ribonuclease such as RNase H, deoxyribonuclease such as DNase, or exonuclease such as 5'-3' exonuclease and 3'-5' exonuclease when compared to natural polynucleic acid molecules. In some instances, artificial nucleotide analogues comprising 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or combinations thereof are resistant toward nucleases such as for example ribonuclease such as RNase H, deoxyribonuclease such as DNase, or exonuclease such as 5'-3' exonuclease and 3'-5' exonuclease. In some instances, 2'-O-methyl modified polynucleic acid molecule is nuclease resistance (e.g., RNase H, DNase, 5'-3' exonuclease or 3'-5' exonuclease resistance). In some instances, 2'O-methoxyethyl (2'-O-MOE) modified polynucleic acid molecule is nuclease resistance (e.g., RNase H, DNase, 5'-3' exonuclease or 3'-5' exonuclease resistance). In some instances, 2'-O-aminopropyl modified polynucleic acid molecule is nuclease resistance (e.g., RNase H, DNase, 5'-3' exonuclease or 3'-5' exonuclease resistance). In some instances, 2'-deoxy modified polynucleic acid molecule is nuclease resistance (e.g., RNase H, DNase, 5'-3' exonuclease or 3'-5' exonuclease resistance). In some instances, 2'-deoxy-2'-fluoro modified polynucleic acid molecule is nuclease resistance (e.g., RNase H. DNase, 5'-3' exonuclease or 3'-5' exonuclease resistance). In some instances, 2'-O-aminopropyl (2'-O-AP) modified polynucleic acid molecule is nuclease resistance (e.g., RNase H, DNase, 5'-3' exonuclease or 3'-5' exonuclease resistance). In some instances, 2'-O-dimethylaminoethyl (2'-O-DMAOE) modified polynucleic acid molecule is nuclease resistance (e.g., RNase H, DNase, 5'-3' exonuclease or 3'-5' exonuclease resistance). In some instances, 2'-O-dimethylaminopropyl (2'-O-DMAP) modified polynucleic acid molecule is nuclease resistance (e.g., RNase H, DNase, 5'-3' exonuclease or 3'-5' exonuclease resistance). In some instances, 2'-O-dimethylaminoethyloxyethyl (2'-O-DMAEOE) modified polynucleic acid molecule is nuclease resistance (e.g. RNase H, DNase, 5'-3' exonuclease or 3'-5' exonuclease resistance). In some instances, 2'-O—N-methylacetamido (2'-O-NMA) modified polynucleic acid molecule is nuclease resistance (e.g., RNase H, DNase, 5'-3' exonuclease or 3'-5' exonuclease resistance). In some instances, LNA modified polynucleic acid molecule is nuclease resistance (e.g., RNase H, DNase, 5'-3' exonuclease or 3'-5' exonuclease resistance). In some instances, ENA modified polynucleic acid molecule is nuclease resistance (e.g., RNase H, DNase, 5'-3' exonuclease or 3'-5' exonuclease resistance). In some instances, HNA modified polynucleic acid molecule is nuclease resistance (e.g., RNase H. DNase, 5'-3' exonuclease or 3'-5' exonuclease resistance). In some instances, morpholinos is nuclease resistance (e.g., RNase H, DNase, 5'-3' exonuclease or 3'-5' exonuclease resistance). In some instances, PNA modified polynucleic acid molecule is resistant to nucleases (e.g., RNase H, DNase, 5'-3' exonuclease or 3'-5' exonuclease resistance). In some instances, methylphosphonate nucleotides modified polynucleic acid molecule is nuclease resistance (e.g., RNase H, DNase, 5'-3' exonuclease or 3'-5' exonuclease resistance). In some instances, thiolphosphonate nucleotides modified polynucleic acid molecule is nuclease resistance (e.g., RNase H, DNase, 5'-3' exonuclease or 3'-5' exonuclease resistance). In some instances, polynucleic acid molecule comprising 2'-fluoro N3-P5'-phosphoramidites is nuclease resistance (e.g., RNase H, DNase, 5'-3' exonuclease or 3'-5' exonuclease resistance). In some instances, the 5' conjugates described herein inhibit 5'-3' exonucleolytic cleavage. In some instances, the 3' conjugates described herein inhibit 3'-5' exonucleolytic cleavage.

In some embodiments, one or more of the artificial nucleotide analogues described herein have increased binding affinity toward their mRNA target relative to an equivalent natural polynucleic acid molecule. The one or more of the artificial nucleotide analogues comprising 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-

NMA) modified, LNA, ENA, PNA, HNA, morpholino, methylphosphonate nucleotides, thiolphosphonate nucleotides, or 2'-fluoro N3-P5'-phosphoramidites have increased binding affinity toward their mRNA target relative to an equivalent natural polynucleic acid molecule. In some instances, 2'-O-methyl modified polynucleic acid molecule has increased binding affinity toward their mRNA target relative to an equivalent natural polynucleic acid molecule. In some instances, 2'-O-methoxyethyl (2'-O-MOE) modified polynucleic acid molecule has increased binding affinity toward their mRNA target relative to an equivalent natural polynucleic acid molecule. In some instances, 2'-O-aminopropyl modified polynucleic acid molecule has increased binding affinity toward their mRNA target relative to an equivalent natural polynucleic acid molecule. In some instances, 2'-deoxy modified polynucleic acid molecule has increased binding affinity toward their mRNA target relative to an equivalent natural polynucleic acid molecule. In some instances, 2'-deoxy-2'-fluoro modified polynucleic acid molecule has increased binding affinity toward their mRNA target relative to an equivalent natural polynucleic acid molecule. In some instances, 2'-O-aminopropyl (2'-O-AP) modified polynucleic acid molecule has increased binding affinity toward their mRNA target relative to an equivalent natural polynucleic acid molecule. In some instances, 2'-O-dimethylaminoethyl (2'-O-DMAOE) modified polynucleic acid molecule has increased binding affinity toward their mRNA target relative to an equivalent natural polynucleic acid molecule. In some instances, 2'-O-dimethylaminopropyl (2'-O-DMAP) modified polynucleic acid molecule has increased binding affinity toward their mRNA target relative to an equivalent natural polynucleic acid molecule. In some instances, 2'-O-dimethylaminoethyloxyethyl (2'-O-DMAEOE) modified polynucleic acid molecule has increased binding affinity toward their mRNA target relative to an equivalent natural polynucleic acid molecule. In some instances, 2'-O—N-methylacetamido (2'-O-NMA) modified polynucleic acid molecule has increased binding affinity toward their mRNA target relative to an equivalent natural polynucleic acid molecule. In some instances, LNA modified polynucleic acid molecule has increased binding affinity toward their mRNA target relative to an equivalent natural polynucleic acid molecule. In some instances. ENA modified polynucleic acid molecule has increased binding affinity toward their mRNA target relative to an equivalent natural polynucleic acid molecule. In some instances, PNA modified polynucleic acid molecule has increased binding affinity toward their mRNA target relative to an equivalent natural polynucleic acid molecule. In some instances, HNA modified polynucleic acid molecule has increased binding affinity toward their mRNA target relative to an equivalent natural polynucleic acid molecule. In some instances, morpholino modified polynucleic acid molecule has increased binding affinity toward their mRNA target relative to an equivalent natural polynucleic acid molecule. In some instances, methylphosphonate nucleotides modified polynucleic acid molecule has increased binding affinity toward their mRNA target relative to an equivalent natural polynucleic acid molecule. In some instances, thiolphosphonate nucleotides modified polynucleic acid molecule has increased binding affinity toward their mRNA target relative to an equivalent natural polynucleic acid molecule. In some instances, polynucleic acid molecule comprising 2'-fluoro N3-P5'-phosphoramidites has increased binding affinity toward their mRNA target relative to an equivalent natural polynucleic acid molecule. In some cases, the increased affinity is illustrated with a lower Kd, a higher melt temperature (Tm), or a combination thereof.

In some embodiments, a polynucleic acid molecule described herein is a chirally pure (or stereo pure) polynucleic acid molecule, or a polynucleic acid molecule comprising a single enantiomer. In some instances, the polynucleic acid molecule comprises L-nucleotide. In some instances, the polynucleic acid molecule comprises D-nucleotides. In some instance, a polynucleic acid molecule composition comprises less than 30%, 25%, 20%, 15%, 10%, 5%, 4%, 3%, 2%, 1%, or less of its mirror enantiomer. In some cases, a polynucleic acid molecule composition comprises less than 30%, 25%, 20%, 15%, 10%, 5%, 4%, 3%, 2%, 1%, or less of a racemic mixture. In some instances, the polynucleic acid molecule is a polynucleic acid molecule described in: U.S. Patent Publication Nos: 2014/194610 and 2015/211006; and PCT Publication No: WO2015107425.

In some embodiments, a polynucleic acid molecule described herein is further modified to include an aptamer conjugating moiety. In some instances, the aptamer conjugating moiety is a DNA aptamer conjugating moiety. In some instances, the aptamer conjugating moiety is Alphamer (Centauri Therapeutics), which comprises an aptamer portion that recognizes a specific cell-surface target and a portion that presents a specific epitopes for attaching to circulating antibodies. In some instance, a polynucleic acid molecule described herein is further modified to include an aptamer conjugating moiety as described in: U.S. Pat. Nos. 8,604,184, 8,591,910, and 7,850,975.

In additional embodiments, a polynucleic acid molecule described herein is modified to increase its stability. In some embodiment, the polynucleic acid molecule is RNA (e.g., siRNA). In some instances, the polynucleic acid molecule is modified by one or more of the modifications described above to increase its stability. In some cases, the polynucleic acid molecule is modified at the 2' hydroxyl position, such as by 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-0-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modification or by a locked or bridged ribose conformation (e.g., LNA or ENA). In some cases, the polynucleic acid molecule is modified by 2'-O-methyl and/or 2'-O-methoxyethyl ribose. In some cases, the polynucleic acid molecule also includes morpholinos, PNAs, HNA, methylphosphonate nucleotides, thiolphosphonate nucleotides, and/or 2'-fluoro N3-P5'-phosphoramidites to increase its stability. In some instances, the polynucleic acid molecule is a chirally pure (or stereo pure) polynucleic acid molecule. In some instances, the chirally pure (or stereo pure) polynucleic acid molecule is modified to increase its stability. Suitable modifications to the RNA to increase stability for delivery will be apparent to the skilled person.

In some instances, the polynucleic acid molecule is a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. In some instances, the polynucleic acid molecule is assembled from two separate polynucleotides, where one strand is the sense strand and the other is the antisense strand, wherein the antisense and sense strands are self-complementary (e.g., each strand comprises nucleotide sequence that is complementary to nucleotide sequence in the other strand; such as where the antisense strand and sense strand form a duplex or double stranded structure, for example wherein the double stranded region is about 19, 20, 21, 22, 23, or more base pairs); the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof. Alternatively, the polynucleic acid molecule is assembled from a single oligonucleotide, where the self-complementary sense and antisense regions of the polynucleic acid molecule are linked by means of a nucleic acid based or non-nucleic acid-based linker(s).

In some cases, the polynucleic acid molecule is a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. In other cases, the polynucleic acid molecule is a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide is processed either in vivo or in vitro to generate an active polynucleic acid molecule capable of mediating RNAi. In additional cases, the polynucleic acid molecule also comprises a single-stranded polynucleotide having nucleotide sequence complementary to nucleotide sequence in a target nucleic acid molecule or a portion thereof (for example, where such polynucleic acid molecule does not require the presence within the polynucleic acid molecule of nucleotide sequence corresponding to the target nucleic acid sequence or a portion thereof), wherein the single stranded polynucleotide further comprises a terminal phosphate group, such as a 5'-phosphate (see for example Martinez et al., 2002, *Cell.*, 110, 563-574 and Schwarz et al., 2002, *Molecular Cell.* 10, 537-568), or 5', 3'-diphosphate.

In some instances, an asymmetric hairpin is a linear polynucleic acid molecule comprising an antisense region, a loop portion that comprises nucleotides or non-nucleotides, and a sense region that comprises fewer nucleotides than the antisense region to the extent that the sense region has enough complimentary nucleotides to base pair with the antisense region and form a duplex with loop. For example, an asymmetric hairpin polynucleic acid molecule comprises an antisense region having length sufficient to mediate RNAi in a cell or in vitro system (e.g. about 19 to about 22 nucleotides) and a loop region comprising about 4 to about 8 nucleotides, and a sense region having about 3 to about 18 nucleotides that are complementary to the antisense region. In some cases, the asymmetric hairpin polynucleic acid molecule also comprises a 5'-terminal phosphate group that is chemically modified. In additional cases, the loop portion of the asymmetric hairpin polynucleic acid molecule comprises nucleotides, non-nucleotides, linker molecules, or conjugate molecules.

In some embodiments, an asymmetric duplex is a polynucleic acid molecule having two separate strands comprising a sense region and an antisense region, wherein the sense region comprises fewer nucleotides than the antisense region to the extent that the sense region has enough complimentary nucleotides to base pair with the antisense region and form a duplex. For example, an asymmetric duplex polynucleic acid molecule comprises an antisense region having length sufficient to mediate RNAi in a cell or in vitro system (e.g., about 19 to about 22 nucleotides) and a sense region having about 3 to about 18 nucleotides that are complementary to the antisense region.

In some cases, a universal base refers to nucleotide base analogs that form base pairs with each of the natural DNA/RNA bases with little discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see for example Loakes, 2001, *Nucleic Acids Research.* 29, 2437-2447).

Polynucleic Acid Molecule Synthesis

In some embodiments, a polynucleic acid molecule described herein is constructed using chemical synthesis and/or enzymatic ligation reactions using procedures known in the art. For example, a polynucleic acid molecule is chemically synthesized using naturally occurring nucleotides or variously modified nucleotides designed to increase the biological stability of the molecules or to increase the physical stability of the duplex formed between the polynucleic acid molecule and target nucleic acids. Exemplary methods include those described in: U.S. Pat. Nos. 5,142,047; 5,185,444; 5,889,136; 6,008,400; and 6,111,086; PCT Publication No. WO2009099942; or European Publication NO. 1579015. Additional exemplary methods include those described in: Griffey et al., "2'-O-aminopropyl ribonucleotides: a zwitterionic modification that enhances the exonuclease resistance and biological activity of antisense oligonucleotides," *J. Med. Chem.* 39(26):5100-5109 (1997)); Obika, et al. "Synthesis of 2'-O,4'-C-methyleneuridine and -cytidine. Novel bicyclic nucleosides having a fixed C3, -endo sugar puckering". *Tetrahedron Letters* 38 (50): 8735 (1997); Koizumi, M. "ENA oligonucleotides as therapeutics". *Current opinion in molecular therapeutics* 8 (2): 144-149 (2006); and Abramova et al., "Novel oligonucleotide analogues based on morpholino nucleoside subunits-antisense technologies: new chemical possibilities," Indian Journal of Chemistry 48B:1721-1726 (2009). Alternatively, the polynucleic acid molecule is produced biologically using an expression vector into which a polynucleic acid molecule has been subcloned in an antisense orientation (i.e., RNA transcribed from the inserted polynucleic acid molecule will be of an antisense orientation to a target polynucleic acid molecule of interest).

In some embodiments, a polynucleic acid molecule is synthesized via a tandem synthesis methodology, wherein both strands are synthesized as a single contiguous oligonucleotide fragment or strand separated by a cleavable linker which is subsequently cleaved to provide separate fragments or strands that hybridize and permit purification of the duplex.

In some instances, a polynucleic acid molecule is also assembled from two distinct nucleic acid strands or fragments wherein one fragment includes the sense region and the second fragment includes the antisense region of the molecule.

Additional modification methods for incorporating, for example, sugar, base and phosphate modifications include: Eckstein et al., International Publication PCT No. WO 92/07065; Perrault et al. *Nature.* 1990, 344, 565-568; Pieken et al. *Science.* 1991, 253, 314-317; Usman and Cedergren, *Trends in Biochem. Sci.,* 1992, 17, 334-339; Usman et al. International Publication PCT No. WO 93/15187; Sproat, U.S. Pat. No. 5,334,711 and Beigelman et al., 1995, *J. Biol. Chem.,* 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, *Tetrahedron Lett.,* 39, 1131; Earnshaw and Gait, 1998, *Biopolymers (Nucleic Acid Sciences),* 48, 39-55; Verma and Eckstein, 1998, *Annu. Rev. Biochem.,* 67, 99-134; and Burlina et al., 1997, *Bioorg. Med. Chem.,* 5, 1999-2010. Such publications describe general methods and strategies to determine the location of incorporation of sugar, base and/or phosphate modifications and the like into nucleic acid molecules without modulating catalysis.

In some instances, while chemical modification of the polynucleic acid molecule internucleotide linkages with phosphorothioate, phosphorodithioate, and/or 5'-methylphosphonate linkages improves stability, excessive modifications sometimes cause toxicity or decreased activity. Therefore, when designing nucleic acid molecules, the amount of these internucleotide linkages in some cases is minimized. In such cases, the reduction in the concentration of these linkages lowers toxicity, increases efficacy and higher specificity of these molecules.

Polynucleic Acid Molecule Conjugates

In some embodiments, a polynucleic acid molecule (B) is further conjugated to a polypeptide (A) for delivery to a site of interest. In some instances, at least one polypeptide A is conjugated to at least one B. In some instances, the at least one polypeptide A is conjugated to the at least one B to form an A-B conjugate. In some embodiments, at least one A is conjugated to the 5' terminus of B, the 3' terminus of B, an internal site on B, or in any combinations thereof. In some instances, the at least one polypeptide A is conjugated to at least two B. In some instances, the at least one polypeptide A is conjugated to at least 2, 3, 4, 5, 6, 7, 8, or more B.

In some cases, a polynucleic acid molecule is conjugated to a polypeptide (A) and optionally a polymeric moiety (C). In some embodiments, at least one polypeptide A is conjugated at one terminus of at least one B while at least one C is conjugated at the opposite terminus of the at least one B to form an A-B-C conjugate. In some instances, at least one polypeptide A is conjugated at one terminus of the at least one B while at least one of C is conjugated at an internal site on the at least one B. In some instances, at least one polypeptide A is conjugated directly to the at least one C. In some instances, the at least one B is conjugated indirectly to the at least one polypeptide A via the at least one C to form an A-C-B conjugate.

In some instances, at least one B and/or at least one C, and optionally at least one D are conjugated to at least one polypeptide A. In some instances, the at least one B is conjugated at a terminus (e.g., a 5' terminus or a 3' terminus) to the at least one polypeptide A or are conjugated via an internal site to the at least one polypeptide A. In some cases, the at least one C is conjugated either directly to the at least one polypeptide A or indirectly via the at least one B. If indirectly via the at least one B, the at least one C is conjugated either at the same terminus as the at least one polypeptide A on B, at opposing terminus from the at least one polypeptide A, or independently at an internal site. In some instances, at least one additional polypeptide A is further conjugated to the at least one polypeptide A, to B, or to C. In additional instances, the at least one D is optionally conjugated either directly or indirectly to the at least one polypeptide A, to the at least one B, or to the at least one C. If directly to the at least one polypeptide A, the at least one D is also optionally conjugated to the at least one B to form an A-D-B conjugate or is optionally conjugated to the at least one B and the at least one C to form an A-D-B-C conjugate. In some instances, the at least one D is directly conjugated to the at least one polypeptide A and indirectly to the at least one B and the at least one C to form a D-A-B-C conjugate. If indirectly to the at least one polypeptide A, the at least one D is also optionally conjugated to the at least one B to form an A-B-D conjugate or is optionally conjugated to the at least one B and the at least one C to form an A-B-D-C conjugate. In some instances, at least one additional D is further conjugated to the at least one polypeptide A, to B, or to C.

Binding Moiety

In some embodiments, the binding moiety A is a polypeptide. In some instances, the polypeptide is an antibody or its fragment thereof. In some cases, the fragment is a binding fragment. In some instances, the antibody or antigen binding fragment thereof comprises a humanized antibody or antigen binding fragment thereof, murine antibody or antigen binding fragment thereof, chimeric antibody or antigen binding fragment thereof, monoclonal antibody or antigen binding fragment thereof, a binding fragment having a light chain domain and a heavy chain domain, a binding fragment having two light chain domains and two heavy chain domains, a binding fragment having two or more light chain domains and heavy chain domains, monovalent Fab', divalent Fab$_2$, F(ab)'$_3$ fragments, single-chain variable fragment (scFv), bis-scFv, (scFv)$_2$, diabody, minibody, nanobody, triabody, tetrabody, disulfide stabilized Fv protein (dsFv), single-domain antibody (sdAb), Ig NAR, camelid antibody or antigen binding fragment thereof, bispecific antibody or biding fragment thereof, or a chemically modified derivative thereof.

In some embodiments, the binding moiety A is a bispecific antibody or antigen binding fragment thereof. In some instances, the bispecific antibody is a trifunctional antibody or a bispecific mini-antibody. In some cases, the bispecific antibody is a trifunctional antibody. In some instances, the trifunctional antibody is a full length monoclonal antibody comprising binding sites for two different antigens.

In some cases, the bispecific antibody is a bispecific mini-antibody. In some instances, the bispecific mini-antibody comprises divalent Fab$_2$, F(ab)'$_3$ fragments, bis-scFv, (scFv)$_2$, diabody, minibody, triabody, tetrabody or a bi-specific T-cell engager (BiTE). In some embodiments, the bi-specific T-cell engager is a fusion protein that contains two single-chain variable fragments (scFvs) in which the two scFvs target epitopes of two different antigens.

In some embodiments, the binding moiety A is a bispecific mini-antibody. In some instances, A is a bispecific Fab$_2$. In some instances, A is a bispecific F(ab)'$_3$ fragment. In some cases, A is a bispecific bis-scFv. In some cases, A is a bispecific (scFv)$_2$. In some embodiments, A is a bispecific diabody. In some embodiments, A is a bispecific minibody. In some embodiments. A is a bispecific triabody. In other embodiments, A is a bispecific tetrabody. In other embodiments, A is a bi-specific T-cell engager (BiTE).

In some embodiments, the binding moiety A is a trispecific antibody. In some instances, the trispecific antibody comprises F(ab)′$_3$ fragments or a triabody. In some instances, A is a trispecific F(ab)′$_3$ fragment. In some cases, A is a triabody. In some embodiments, A is a trispecific antibody as described in Dimas, et al., "Development of a trispecific antibody designed to simultaneously and efficiently target three different antigens on tumor cells," *Mol. Pharmaceutics*, 12(9): 3490-3501 (2015).

In some embodiments, the binding moiety A is an antibody or antigen binding fragment thereof that recognizes a cell surface protein. In some instances, the binding moiety A is an antibody or antigen binding fragment thereof that recognizes a cell surface protein on a muscle cell. In some cases, the binding moiety A is an antibody or antigen binding fragment thereof that recognizes a cell surface protein on a skeletal muscle cell.

In some embodiments, exemplary antibodies include, but are not limited to, an anti-myosin antibody, an anti-transferrin receptor antibody, and an antibody that recognizes Muscle-Specific kinase (MuSK). In some instances, the antibody is an anti-transferrin receptor (anti-CD71) antibody.

In some embodiments, where the antibody is an anti-transferrin receptor (anti-CD71) antibody, the anti-transferrin antibody specifically binds to a transferrin receptor (TfR), preferably, specifically binds to transferrin receptor 1 (TfR1), or more preferably, specifically binds to human transferrin receptor 1 (TfR1) (or human CD71).

In some instances, the anti-transferrin receptor antibody comprises a variable heavy chain (VH) region and a variable light chain (VL) region, wherein the VH region comprises HCDR1 sequence comprising SEQ ID NO: 281; HCDR2 sequence EINPIX$_1$GRSNYAX$_2$KFQG (SEQ ID NO: 406), wherein X$_1$ is selected from N or Q and X$_2$ is selected from Q or E; and HCDR3 sequence comprising SEQ ID NO: 283.

In some embodiments, the VH region of the anti-transferrin receptor antibody comprises HCDR1, HCDR2, and HCDR3 sequences selected from Table 1.

TABLE 1

| Name | HCDR1 | SEQ ID NO: | HCDR2 | SEQ ID NO: | HCDR3 | SEQ ID NO: |
|---|---|---|---|---|---|---|
| 13E4_VH1 | YTFTNYW MH | 281 | EINPINGRSNY AQKFQG | 282 | GTRAMHY | 283 |
| 13E4_VH2* | YTFTNYW MH | 281 | EINPINGRSNY AEKFQG | 284 | GTRAMHY | 283 |
| 13E4_VH3 | YTFTNYW MH | 281 | EINPIQGRSNY AEKFQG | 285 | GTRAMHY | 283 |

*13E4_VH2 shares the same HCDR1, HCDR2, and HCDR3 sequences with anti-transferrin receptor antibody 13E4_VH4

In some embodiments, the VH region comprises HCDR1 sequence comprising SEQ ID NO: 281; HCDR2 sequence comprising SEQ ID NO: 282, 284, or 285; and HCDR3 sequence comprising SEQ ID NO: 283. In some instances, the VH region comprises HCDR1 sequence comprising SEQ ID NO: 281, HCDR2 sequence comprising SEQ ID NO: 282, and HCDR3 sequence comprising SEQ ID NO: 283. In some instances, the VH region comprises HCDR1 sequence comprising SEQ ID NO: 281, HCDR2 sequence comprising SEQ ID NO: 284, and HCDR3 sequence comprising SEQ ID NO: 283. In some instances, the VH region comprises HCDR1 sequence comprising SEQ ID NO: 281, HCDR2 sequence comprising SEQ ID NO: 285, and HCDR3 sequence comprising SEQ ID NO: 283.

In some embodiments, the VL region of the anti-transferrin receptor antibody comprises LCDR1 sequence RTSENIYX$_3$NLA (SEQ ID NO: 407), LCDR2 sequence AX$_4$TNLAX$_5$ (SEQ ID NO: 408), and LCDR3 sequence QHFWGTPLTX$_6$ (SEQ ID NO: 409), wherein X$_3$ is selected from N or S, X$_4$ is selected from A or G, X$_5$ is selected from D or E, and X$_6$ is present or absence, and if present, is F.

In some embodiments, the VL region of the anti-transferrin receptor antibody comprises LCDR1, LCDR2, and LCDR3 sequences selected from Table 2.

TABLE 2

| Name | LCDR1 | SEQ ID NO: | LCDR2 | SEQ ID NO: | LCDR3 | SEQ ID NO: |
|---|---|---|---|---|---|---|
| 13E4_VL1* | RTSENIYN NLA | 286 | AATNLAD | 287 | QHFWGTPLT | 288 |
| 13E4_VL3 | RTSENIYN NLA | 286 | AATNLAE | 289 | QHFWGTPLTF | 290 |
| 13E4_VL4 | RTSENIYS NLA | 291 | AGTNLAD | 292 | QHFWGTPLTF | 290 |

*13E4_VL1 shares the same LCDR1, LCDR2, and LCDR3 sequences with anti-transferrin receptor antibody 13E4_VL2

In some instances, the VL region comprises LCDR1 sequence RTSENIYX$_3$NLA (SEQ ID NO: 407), LCDR2 sequence comprising SEQ ID NO: 287, 289, or 292, and LCDR3 sequence comprising SEQ ID NO: 288 or 290, wherein X$_3$ is selected from N or S.

In some instances, the VL region comprises LCDR1 sequence comprising SEQ ID NO: 286 or 291, LCDR2 sequence AX$_4$TNLAX$_5$ (SEQ ID NO: 408), and LCDR3 sequence comprising SEQ ID NO: 288 or 290, wherein X$_4$ is selected from A or G, and X$_5$ is selected from D or E.

In some instances, the VL region comprises LCDR1 sequence comprising SEQ ID NO: 286 or 291, LCDR2 sequence SEQ ID NO: 287, 289, or 292, and LCDR3 sequence QHFWGTPLTX$_6$ (SEQ ID NO: 409), wherein X$_6$ is present or absence, and if present, is F.

In some instances, the VL region comprises LCDR1 sequence comprising SEQ ID NO: 286, LCDR2 sequence AATNLAX$_5$ (SEQ ID NO: 410), and LCDR3 sequence QHFWGTPLTX$_6$ (SEQ ID NO: 409), wherein X$_5$ is selected from D or E and X$_6$ is present or absence, and if present, is F.

In some instances, the VL region comprises LCDR1 sequence comprising SEQ ID NO: 286, LCDR2 sequence comprising SEQ ID NO: 287, and LCDR3 sequence comprising SEQ ID NO: 288.

In some instances, the VL region comprises LCDR1 sequence comprising SEQ ID NO: 286, LCDR2 sequence comprising SEQ ID NO: 289, and LCDR3 sequence comprising SEQ ID NO: 290.

In some instances, the VL region comprises LCDR1 sequence comprising SEQ ID NO: 291, LCDR2 sequence comprising SEQ ID NO: 292, and LCDR3 sequence comprising SEQ ID NO: 290.

In some embodiments, the anti-transferrin receptor antibody comprises a VH region and a VL region, wherein the VH region comprises HCDR1 sequence comprising SEQ ID NO: 281; HCDR2 sequence EINPIX$_1$GRSNYAX$_2$KFQG (SEQ ID NO: 406), wherein X$_1$ is selected from N or Q and X$_2$ is selected from Q or E; and HCDR3 sequence comprising SEQ ID NO: 283; and the VL region comprises LCDR1 sequence RTSENIYX$_3$NLA (SEQ ID NO: 407), LCDR2 sequence AX$_4$TNLAX$_5$ (SEQ ID NO: 408), and LCDR3 sequence QHFWGTPLTX$_6$ (SEQ ID NO: 409), wherein X$_3$ is selected from N or S, X$_4$ is selected from A or G. X$_5$ is selected from D or E, and X$_6$ is present or absence, and if present, is F.

In some instances, the anti-transferrin receptor antibody comprises a VH region and a VL region, wherein the VH region comprises HCDR1 sequence comprising SEQ ID NO: 281; HCDR2 sequence EINPIX$_1$GRSNYAX$_2$KFQG (SEQ ID NO: 406), wherein X$_1$ is selected from N or Q and X$_2$ is selected from Q or E; and HCDR3 sequence comprising SEQ ID NO: 283; and the VL region comprises LCDR1 sequence RTSENIYX$_3$NLA (SEQ ID NO: 407), LCDR2 sequence comprising SEQ ID NO: 287, 289, or 292, and LCDR3 sequence comprising SEQ ID NO: 288 or 290, wherein X$_3$ is selected from N or S.

In some instances, the anti-transferrin receptor antibody comprises a VH region and a VL region, wherein the VH region comprises HCDR1 sequence comprising SEQ ID NO: 281; HCDR2 sequence EINPIX$_1$GRSNYAX$_2$KFQG (SEQ ID NO: 406), wherein X$_1$ is selected from N or Q and X$_2$ is selected from Q or E; and HCDR3 sequence comprising SEQ ID NO: 283; and the VL region comprises LCDR1 sequence comprising SEQ ID NO: 286 or 291, LCDR2 sequence AX$_4$TNLAX$_5$ (SEQ ID NO: 408), and LCDR3 sequence comprising SEQ ID NO: 288 or 290, wherein X$_4$ is selected from A or G, and X$_5$ is selected from D or E.

In some instances, the anti-transferrin receptor antibody comprises a VH region and a VL region, wherein the VH region comprises HCDR1 sequence comprising SEQ ID NO: 281; HCDR2 sequence EINPIX$_1$GRSNYAX$_2$KFQG (SEQ ID NO: 406), wherein X$_1$ is selected from N or Q and X$_2$ is selected from Q or E; and HCDR3 sequence comprising SEQ ID NO: 283; and the VL region comprises LCDR1 sequence comprising SEQ ID NO: 286 or 291, LCDR2 sequence SEQ ID NO: 287, 289, or 292, and LCDR3 sequence QHFWGTPLTX$_6$ (SEQ ID NO: 409), wherein X$_6$ is present or absence, and if present, is F.

In some instances, the anti-transferrin receptor antibody comprises a VH region and a VL region, wherein the VH region comprises HCDR1 sequence comprising SEQ ID NO: 281; HCDR2 sequence EINPIX$_1$GRSNYAX$_2$KFQG (SEQ ID NO: 406), wherein X$_1$ is selected from N or Q and X$_2$ is selected from Q or E; and HCDR3 sequence comprising SEQ ID NO: 283; and the VL region comprises LCDR1 sequence comprising SEQ ID NO: 286, LCDR2 sequence AATNLAX$_5$ (SEQ ID NO: 410), and LCDR3 sequence QHFWGTPLTX$_6$ (SEQ ID NO: 409), wherein X$_5$ is selected from D or E and X$_6$ is present or absence, and if present, is F.

In some instances, the anti-transferrin receptor antibody comprises a VH region and a VL region, wherein the VH region comprises HCDR1 sequence comprising SEQ ID NO: 281; HCDR2 sequence EINPIX$_1$GRSNYAX$_2$KFQG (SEQ ID NO: 406), wherein X$_1$ is selected from N or Q and X$_2$ is selected from Q or E; and HCDR3 sequence comprising SEQ ID NO: 283; and the VL region comprises LCDR1 sequence comprising SEQ ID NO: 286, LCDR2 sequence comprising SEQ ID NO: 287, and LCDR3 sequence comprising SEQ ID NO: 288.

In some instances, the anti-transferrin receptor antibody comprises a VH region and a VL region, wherein the VH region comprises HCDR1 sequence comprising SEQ ID NO: 281; HCDR2 sequence EINPIX$_1$GRSNYAX$_2$KFQG (SEQ ID NO: 406), wherein X$_1$ is selected from N or Q and X$_2$ is selected from Q or E; and HCDR3 sequence comprising SEQ ID NO: 283; and the VL region comprises LCDR1 sequence comprising SEQ ID NO: 286, LCDR2 sequence comprising SEQ ID NO: 289, and LCDR3 sequence comprising SEQ ID NO: 290.

In some instances, the anti-transferrin receptor antibody comprises a VH region and a VL region, wherein the VH region comprises HCDR1 sequence comprising SEQ ID NO: 281; HCDR2 sequence EINPIX$_1$GRSNYAX$_2$KFQG (SEQ ID NO: 406), wherein X$_1$ is selected from N or Q and X$_2$ is selected from Q or E; and HCDR3 sequence comprising SEQ ID NO: 283; and the VL region comprises LCDR1 sequence comprising SEQ ID NO: 291, LCDR2 sequence comprising SEQ ID NO: 292, and LCDR3 sequence comprising SEQ ID NO: 290.

In some instances, the anti-transferrin receptor antibody comprises a VH region and a VL region, in which the VH region comprises HCDR1 sequence comprising SEQ ID NO: 281, HCDR2 sequence comprising SEQ ID NO: 282, and HCDR3 sequence comprising SEQ ID NO: 283; and the VL region comprises LCDR1 sequence RTSENIYX$_3$NLA (SEQ ID NO: 407), LCDR2 sequence comprising SEQ ID NO: 287, 289, or 292, and LCDR3 sequence comprising SEQ ID NO: 288 or 290, wherein X$_3$ is selected from N or S.

In some instances, the anti-transferrin receptor antibody comprises a VH region and a VL region, in which the VH region comprises HCDR1 sequence comprising SEQ ID NO: 281, HCDR2 sequence comprising SEQ ID NO: 282, and HCDR3 sequence comprising SEQ ID NO: 283; and the VL region comprises LCDR1 sequence comprising SEQ ID NO: 286 or 291, LCDR2 sequence AX$_4$TNLAX$_5$ (SEQ ID NO: 408), and LCDR3 sequence comprising SEQ ID NO: 288 or 290, wherein X$_4$ is selected from A or G, and X$_5$ is selected from D or E.

In some instances, the anti-transferrin receptor antibody comprises a VH region and a VL region, in which the VH region comprises HCDR1 sequence comprising SEQ ID NO: 281, HCDR2 sequence comprising SEQ ID NO: 2, and HCDR3 sequence comprising SEQ ID NO: 283; and the VL region comprises LCDR1 sequence comprising SEQ ID NO: 286 or 291, LCDR2 sequence SEQ ID NO: 287, 289, or 292, and LCDR3 sequence QHFWGTPLTX$_6$ (SEQ ID NO: 409), wherein X$_b$ is present or absence, and if present, is F.

In some instances, the anti-transferrin receptor antibody comprises a VH region and a VL region, in which the VH region comprises HCDR1 sequence comprising SEQ ID NO: 281, HCDR2 sequence comprising SEQ ID NO: 282, and HCDR3 sequence comprising SEQ ID NO: 283; and the VL region comprises LCDR1 sequence comprising SEQ ID NO: 286, LCDR2 sequence AATNLAX$_5$ (SEQ ID NO: 410), and LCDR3 sequence QHFWGTPLTX$_6$ (SEQ ID NO: 409), wherein X$_5$ is selected from D or E and X$_6$ is present or absence, and if present, is F.

In some instances, the anti-transferrin receptor antibody comprises a VH region and a VL region, in which the VH region comprises HCDR1 sequence comprising SEQ ID NO: 281, HCDR2 sequence comprising SEQ ID NO: 282, and HCDR3 sequence comprising SEQ ID NO: 283; and the VL region comprises LCDR1 sequence comprising SEQ ID NO: 286, LCDR2 sequence comprising SEQ ID NO: 287, and LCDR3 sequence comprising SEQ ID NO: 288.

In some instances, the anti-transferrin receptor antibody comprises a VH region and a VL region, in which the VH region comprises HCDR1 sequence comprising SEQ ID NO: 281, HCDR2 sequence comprising SEQ ID NO: 282, and HCDR3 sequence comprising SEQ ID NO: 283; and the VL region comprises LCDR1 sequence comprising SEQ ID NO: 286, LCDR2 sequence comprising SEQ ID NO: 289, and LCDR3 sequence comprising SEQ ID NO: 290.

In some instances, the anti-transferrin receptor antibody comprises a VH region and a VL region, in which the VH region comprises HCDR1 sequence comprising SEQ ID NO: 281, HCDR2 sequence comprising SEQ ID NO: 282, and HCDR3 sequence comprising SEQ ID NO: 283; and the VL region comprises LCDR1 sequence comprising SEQ ID NO: 291, LCDR2 sequence comprising SEQ ID NO: 292, and LCDR3 sequence comprising SEQ ID NO: 290.

In some instances, the anti-transferrin receptor antibody comprises a VH region and a VL region, in which the VH region comprises HCDR1 sequence comprising SEQ ID NO: 281, HCDR2 sequence comprising SEQ ID NO: 284, and HCDR3 sequence comprising SEQ ID NO: 283; and the VL region comprises LCDR1 sequence RTSENIYX$_3$NLA (SEQ ID NO: 407), LCDR2 sequence comprising SEQ ID NO: 287, 289, or 292, and LCDR3 sequence comprising SEQ ID NO: 288 or 290, wherein X$_3$ is selected from N or S.

In some instances, the anti-transferrin receptor antibody comprises a VH region and a VL region, in which the VH region comprises HCDR1 sequence comprising SEQ ID NO: 281, HCDR2 sequence comprising SEQ ID NO: 284, and HCDR3 sequence comprising SEQ ID NO: 283; and the VL region comprises LCDR1 sequence comprising SEQ ID NO: 286 or 291, LCDR2 sequence AX$_4$TNLAX$_5$ (SEQ ID NO: 408), and LCDR3 sequence comprising SEQ ID NO: 288 or 290, wherein X$_4$ is selected from A or G, and X$_5$ is selected from D or E.

In some instances, the anti-transferrin receptor antibody comprises a VH region and a VL region, in which the VH region comprises HCDR1 sequence comprising SEQ ID NO: 281, HCDR2 sequence comprising SEQ ID NO: 284, and HCDR3 sequence comprising SEQ ID NO: 283; and the VL region comprises LCDR1 sequence comprising SEQ ID NO: 286 or 291, LCDR2 sequence SEQ ID NO: 287, 289, or 292, and LCDR3 sequence QHFWGTPLTX$_6$ (SEQ ID NO: 409), wherein X$_6$ is present or absence, and if present, is F.

In some instances, the anti-transferrin receptor antibody comprises a VH region and a VL region, in which the VH region comprises HCDR1 sequence comprising SEQ ID NO: 281, HCDR2 sequence comprising SEQ ID NO: 284, and HCDR3 sequence comprising SEQ ID NO: 283; and the VL region comprises LCDR1 sequence comprising SEQ ID NO: 286, LCDR2 sequence AATNLAX$_5$ (SEQ ID NO: 410), and LCDR3 sequence QHFWGTPLTX$_6$ (SEQ ID NO: 409), wherein X$_5$ is selected from D or E and X$_6$ is present or absence, and if present, is F.

In some instances, the anti-transferrin receptor antibody comprises a VH region and a VL region, in which the VH region comprises HCDR1 sequence comprising SEQ ID NO: 281, HCDR2 sequence comprising SEQ ID NO: 284, and HCDR3 sequence comprising SEQ ID NO: 283; and the VL region comprises LCDR1 sequence comprising SEQ ID NO: 286, LCDR2 sequence comprising SEQ ID NO: 287, and LCDR3 sequence comprising SEQ ID NO: 288.

In some instances, the anti-transferrin receptor antibody comprises a VH region and a VL region, in which the VH region comprises HCDR1 sequence comprising SEQ ID NO: 281, HCDR2 sequence comprising SEQ ID NO; 284, and HCDR3 sequence comprising SEQ ID NO: 283; and the VL region comprises LCDR1 sequence comprising SEQ ID NO: 286, LCDR2 sequence comprising SEQ ID NO: 289, and LCDR3 sequence comprising SEQ ID NO:290.

In some instances, the anti-transferrin receptor antibody comprises a VH region and a VL region, in which the VH region comprises HCDR1 sequence comprising SEQ ID NO: 281, HCDR2 sequence comprising SEQ ID NO: 284, and HCDR3 sequence comprising SEQ ID NO: 283; and the VL region comprises LCDR1 sequence comprising SEQ ID NO: 291, LCDR2 sequence comprising SEQ ID NO: 292, and LCDR3 sequence comprising SEQ ID NO: 290.

In some instances, the anti-transferrin receptor antibody comprises a VH region and a VL region, in which the VH region comprises HCDR1 sequence comprising SEQ ID NO: 281, HCDR2 sequence comprising SEQ ID NO: 285, and HCDR3 sequence comprising SEQ ID NO: 283; and the VL region comprises LCDR1 sequence RTSENIYX$_3$NLA (SEQ ID NO: 407), LCDR2 sequence comprising SEQ ID NO: 287, 289, or 29, and LCDR3 sequence comprising SEQ ID NO: 288 or 290, wherein X$_3$ is selected from N or S.

In some instances, the anti-transferrin receptor antibody comprises a VH region and a VL region, in which the VH region comprises HCDR1 sequence comprising SEQ ID NO: 281, HCDR2 sequence comprising SEQ ID NO: 285, and HCDR3 sequence comprising SEQ ID NO: 283; and the VL region comprises LCDR1 sequence comprising SEQ ID NO: 286 or 291, LCDR2 sequence AX$_4$TNLAX$_5$ (SEQ ID NO: 408), and LCDR3 sequence comprising SEQ ID NO: 288 or 290, wherein X$_4$ is selected from A or G, and X$_5$ is selected from D or E.

In some instances, the anti-transferrin receptor antibody comprises a VH region and a VL region, in which the VH region comprises HCDR1 sequence comprising SEQ ID NO: 281, HCDR2 sequence comprising SEQ ID NO: 285, and HCDR3 sequence comprising SEQ ID NO: 283; and the VL region comprises LCDR1 sequence comprising SEQ ID NO: 286 or 291, LCDR2 sequence SEQ ID NO: 287, 289, or 292, and LCDR3 sequence QHFWGTPLTX$_6$ (SEQ ID NO: 409), wherein X$_6$ is present or absence, and if present, is F.

In some instances, the anti-transferrin receptor antibody comprises a VH region and a VL region, in which the VH region comprises HCDR1 sequence comprising SEQ ID NO: 281, HCDR2 sequence comprising SEQ ID NO: 285, and HCDR3 sequence comprising SEQ ID NO: 283 and the VL region comprises LCDR1 sequence comprising SEQ ID NO: 286, LCDR2 sequence AATNLAX$_5$ (SEQ ID NO: 410), and LCDR3 sequence QHFWGTPLTX$_6$ (SEQ ID NO: 409), wherein X$_5$ is selected from D or E and X$_6$ is present or absence, and if present, is F.

In some instances, the anti-transferrin receptor antibody comprises a VH region and a VL region, in which the VH region comprises HCDR1 sequence comprising SEQ ID NO: 281, HCDR2 sequence comprising SEQ ID NO: 285, and HCDR3 sequence comprising SEQ ID NO: 283; and the VL region comprises LCDR1 sequence comprising SEQ ID NO: 286, LCDR2 sequence comprising SEQ ID NO: 287, and LCDR3 sequence comprising SEQ ID NO: 288.

In some instances, the anti-transferrin receptor antibody comprises a VH region and a VL region, in which the VH region comprises HCDR1 sequence comprising SEQ ID NO: 281, HCDR2 sequence comprising SEQ ID NO: 285, and HCDR3 sequence comprising SEQ ID NO: 283; and the VL region comprises LCDR1 sequence comprising SEQ ID NO: 286, LCDR2 sequence comprising SEQ ID NO: 289, and LCDR3 sequence comprising SEQ ID NO: 290.

In some instances, the anti-transferrin receptor antibody comprises a VH region and a VL region, in which the VH region comprises HCDR1 sequence comprising SEQ ID NO: 281, HCDR2 sequence comprising SEQ ID NO: 285, and HCDR3 sequence comprising SEQ ID NO: 283; and the VL region comprises LCDR1 sequence comprising SEQ ID NO: 291, LCDR2 sequence comprising SEQ ID NO: 292, and LCDR3 sequence comprising SEQ ID NO: 290.

In some embodiments, the anti-transferrin receptor antibody comprises a VH region and a VL region in which the sequence of the VH region comprises about 80%, 85%, 90%, 95%, 96% 97%, 98%, 99%, or 100% sequence identity to SEQ ID NOs: 293-296 and the sequence of the VL region comprises about 80%, 85%, 90%, 95%, 96% 97%, 98%, 99%, or 100% sequence identity to SEQ ID NOs: 298-301.

In some embodiments, the VH region comprises a sequence selected from SEQ ID NOs: 293-296 (Table 3) and the VL region comprises a sequence selected from SEQ ID NOs: 298-301 (Table 4). The underlined regions in Table 3 and Table 4 denote the respective CDR1, CDR2, or CDR3 sequence.

TABLE 3

| NAME | VH SEQUENCE | SEQ ID NO: |
|---|---|---|
| 13E4_VH1 | QVQLVQSGAEVKKPGASVKVSCKASGYTFTNYWMHWVRQAPGQGLEW MGEINPINGRSNYAQKFQGRVTLTVDTSISTAYMELSRLRSDDTAVY YCARGTRAMHYWGQGTLVTVSS | 293 |
| 13E4_VH2 | QVQLVQSGAEVKKPGASVKVSCKASGYTFTNYWMHWVRQAPGQGLEW IGEINPINGRSNYAEKFQGRVTLTVDTSSSTAYMELSRLRSDDTAVY YCARGTRAMHYWGQGTLVTVSS | 294 |
| 13E4_VH3 | QVQLVQSGAEVKKPGASVKVSCKASGYTFTNYWMHWVRQAPGQGLEW MGEINPIQGRSNYAEKFQGRVTLTVDTSSSTAYMELSSLRSEDTATY YCARGTRAMHYWGQGTLVTVSS | 295 |
| 13E4_VH4 | QVQLVQSGAEVKKPGASVKVSCKASGYTFTNYWMHWVRQAPGQGLEW MGEINPINGRSNYAEKFQGRVTLTVDTSSSTAYMELSSLRSEDTATY YCARGTRAMHYWGQGTLVTVSS | 296 |
| 13E4_VH | QVQLQQPGAELVKPGASVKLSCKASGYTFTNYWMHWVKQRPGQGLEW IGEINPINGRSNYGERFKTKATLTVDKSSSTAYMQLSSLTSEDSAVY YCARGTRAMHYWGQGTSVTVSS | 297 |

TABLE 4

| NAME | VL SEQUENCE | SEQ ID NO: |
|---|---|---|
| 13E4_VL1 | DIQMTQSPSSLSASVGDRVTITCRTSENIYNNLAWYQQKPGKSPKLLIYAA TNLADGVPSRFSGSGSGTDYTLTISSLQPEDFATYYCQHFWGTPLTFGGGT KVEIK | 298 |
| 13E4_VL2 | DIQMTQSPSSLSASVGDRVTITCRTSENIYNNLAWYQQKPGKAPKLLIYA ATNLADGVPSRFSGSGSGTDYTLTISSLQPEDFATYYCQHFWGTPLTFGG GTKVEIK | 299 |
| 13E4_VL3 | DIQMTQSPSSLSASVGDRVTITCRTSENIYNNLAWYQQKPGKAPKLLIYA ATNLAEGVPSRFSGSGSGTDYTLTISSLQPEDFATYYCQHFWGTPLTFGGG TKVEIK | 300 |
| 13E4_VL4 | DIQMTQSPSSLSASVGDRVTITCRTSENIYSNLAWYQQKPGKAPKLLIYAG TNLADGVPSRFSGSGSGTDYTLTISSLQPEDFANYYCQHFWGTPLTFGGG TKVEIK | 301 |
| 13E4_VL | DIQMTQSPASLSVSVGETVTITCRTSENIYNNLAWYQQKQGKSPQLLVYA ATNLADGVPSRFSGSGSGTQYSLKINSLQSEDFGNYYCQHFWGTPLTFGA GTKLELK | 302 |

In some embodiments, the anti-transferrin receptor antibody comprises a VH region and a VL region as illustrated in Table 5.

TABLE 5

| | 13E4_VH1 (SEQ ID NO: 13) | 13E4_VH2 (SEQ ID NO: 14) | 13E4_VH3 (SEQ ID NO: 15) | 13E4_VH4 (SEQ ID NO: 16) |
|---|---|---|---|---|
| 13E4_VL1 (SEQ ID NO: 298) | SEQ ID NO: 293 + SEQ ID NO: 298 | SEQ ID NO: 294 + SEQ ID NO: 298 | SEQ ID NO: 295 + SEQ ID NO: 298 | SEQ ID NO: 296 + SEQ ID NO: 298 |
| 13E4_VL2 (SEQ ID NO: 299) | SEQ ID NO: 293 + SEQ ID NO: 299 | SEQ ID NO: 294 + SEQ ID NO: 299 | SEQ ID NO: 295 + SEQ ID NO: 299 | SEQ ID NO: 296 + SEQ ID NO: 299 |
| 13E4_VL3 (SEQ ID NO: 300) | SEQ ID NO: 293 + SEQ ID NO: 300 | SEQ ID NO: 294 + SEQ ID NO: 300 | SEQ ID NO: 295 + SEQ ID NO: 300 | SEQ ID NO: 296 + SEQ ID NO: 300 |
| 13E4_VL4 (SEQ ID NO: 301) | SEQ ID NO: 293 + SEQ ID NO: 301 | SEQ ID NO: 294 + SEQ ID NO: 301 | SEQ ID NO: 295 + SEQ ID NO: 301 | SEQ ID NO: 296 + SEQ ID NO: 301 |

In some embodiments, an anti-transferrin receptor antibody described herein comprises an IgG framework, an IgA framework, an IgE framework, or an IgM framework. In some instances, the anti-transferrin receptor antibody comprises an IgG framework (e.g., IgG1, IgG2, IgG3, or IgG4). In some cases, the anti-transferrin receptor antibody comprises an IgG1 framework. In some cases, the anti-transferrin receptor antibody comprises an IgG2 (e.g., an IgG2a or IgG2b) framework. In some cases, the anti-transferrin receptor antibody comprises an IgG2a framework. In some cases, the anti-transferrin receptor antibody comprises an IgG2b framework. In some cases, the anti-transferrin receptor antibody comprises an IgG3 framework. In some cases, the anti-transferrin receptor antibody comprises an IgG4 framework.

In some cases, an anti-transferrin receptor antibody comprises one or more mutations in a framework region, e.g., in the CH1 domain, CH2 domain, CH3 domain, hinge region, or a combination thereof. In some instances, the one or more mutations are to stabilize the antibody and/or to increase half-life. In some instances, the one or more mutations are to modulate Fc receptor interactions, to reduce or eliminate Fc effector functions such as FcγR, antibody-dependent cell-mediated cytotoxicity (ADCC), or complement-dependent cytotoxicity (CDC). In additional instances, the one or more mutations are to modulate glycosylation.

In some embodiments, the one or more mutations are located in the Fc region. In some instances, the Fc region comprises a mutation at residue position L234, L235, or a combination thereof. In some instances, the mutations comprise L234 and L235. In some instances, the mutations comprise L234A and L235A. In some cases, the residue positions are in reference to IgG1.

In some instances, the Fc region comprises a mutation at residue position L234, L235, D265, N297, K322, L328, or P329, or a combination thereof. In some instances, the mutations comprise L234 and L235 in combination with a mutation at residue position K322, L328, or P329. In some cases, the Fc region comprises mutations at L234, L235, and K322. In some cases, the Fc region comprises mutations at L234, L235, and L328. In some cases, the Fc region comprises mutations at L234, L235, and P329. In some cases, the Fc region comprises mutations at D265 and N297. In some cases, the residue position is in reference to IgG1.

In some instances, the Fc region comprises L234A, L235A, D265A, N297G, K322G, L328R, or P329G, or a combination thereof. In some instances, the Fc region comprises L234A and L235A in combination with K322G, L328R, or P329G. In some cases, the Fc region comprises L234A, L235A, and K322G. In some cases, the Fc region comprises L234A, L235A, and L328R. In some cases, the Fc region comprises L234A, L235A, and P329G. In some cases, the Fc region comprises D265A and N297G. In some cases, the residue position is in reference to IgG1.

In some instances, the Fc region comprises a mutation at residue position L235, L236, D265, N297, K322, L328, or P329, or a combination of the mutations. In some instances, the Fc region comprises mutations at L235 and L236. In some instances, the Fc region comprises mutations at L235 and L236 in combination with a mutation at residue position K322, L328, or P329. In some cases, the Fc region comprises mutations at L235. L236, and K322. In some cases, the Fc region comprises mutations at L235, L236, and L328. In some cases, the Fc region comprises mutations at L235. L236, and P329. In some cases, the Fc region comprises mutations at D265 and N297. In some cases, the residue position is in reference to IgG2b.

In some embodiments, the Fc region comprises L235A, L236A, D265A, N297G, K322G, L328R. or P329G, or a combination thereof. In some instances, the Fc region comprises L235A and L236A. In some instances, the Fc region comprises L235A and L236A in combination with K322G, L328R, or P329G. In some cases, the Fc region comprises L235A, L236A, and K322G. In some cases, the Fc region comprises L235A, L236A, and L328R. In some cases, the Fc region comprises L235A, L236A, and P329G. In some cases, the Fc region comprises D265A and N297G. In some cases, the residue position is in reference to IgG2b.

In some embodiments, the Fc region comprises a mutation at residue position L233, L234, D264, N296, K321, L327, or P328, wherein the residues correspond to positions 233, 234, 264, 296, 321, 327, and 328 of SEQ ID NO: 303. In some instances, the Fc region comprises mutations at L233 and L234. In some instances, the Fc region comprises mutations at L233 and L234 in combination with a mutation at residue position K321, L327, or P328. In some cases, the Fc region comprises mutations at L233, L234, and K321. In some cases, the Fc region comprises mutations at L233, L234, and L327. In some cases, the Fc region comprises mutations at L233, L234, and K321. In some cases, the Fc region comprises mutations at L233, L234, and P328. In some instances, the Fc region comprises mutations at D264 and N296. In some cases, equivalent positions to residue L233, L234, D264, N296, K321, L327, or P328 in an IgG1, IgG2, IgG3, or IgG4 framework are contemplated. In some cases, mutations to a residue that corresponds to residue L233, L234, D264, N296, K321, L327, or P328 of SEQ ID NO: 23 in an IgG1, IgG2, or IgG4 framework are also contemplated.

In some embodiments, the Fc region comprises L233A, L234A, D264A, N296G, K321G, L327R, or P328G, wherein the residues correspond to positions 233, 234, 264, 296, 321, 327, and 328 of SEQ ID NO: 303. In some instances, the Fc region comprises L233A and L234A. In some instances, the Fc region comprises L233A and L234A in combination with K321G, L327R, or P328G. In some cases, the Fc region comprises L233A, L234A, and K321G. In some cases, the Fc region comprises L233A. L234A, and L327R. In some cases, the Fc region comprises L233A, L234A, and K321G. In some cases, the Fc region comprises L233A, L234A, and P328G. In some instances, the Fc region comprises D264A and N2% G.

In some embodiments, the human IgG constant region is modified to alter antibody-dependent cellular cytotoxicity (ADCC) and/or complement-dependent cytotoxicity (CDC), e.g., with an amino acid modification described in Natsume et al., 2008 *Cancer Res*, 68(10): 3863-72; Idusogie el al., 2001 *J Immunol*, 166(4): 2571-5; Moore et al., 2010 *mAbs*, 2(2): 181-189; Lazar et al., 2006 *PNAS*, 103(11): 4005-4010, Shields et al., 2001 *JBC*, 276(9): 6591-6604; Stavenhagen et al., 2007 *Cancer Res*. 67(18): 8882-8890; Stavenhagen et al., 2008 *Advan. Enzyme Regul.*, 48: 152-164; Alegre et al, 1992 *J Immunol*, 148: 3461-3468; Reviewed in Kaneko and Niwa, 2011 Biodrugs, 25(1): 1-11.

In some embodiments, an anti-transferrin receptor antibody described herein is a full-length antibody, comprising a heavy chain (HC) and a light chain (LC). In some cases, the heavy chain (HC) comprises a sequence selected from Table 6. In some cases, the light chain (LC) comprises a sequence selected from Table 7. The underlined region denotes the respective CDRs.

TABLE 6

| NAME | HC SEQUENCE | SEQ ID NO: |
|---|---|---|
| 13E4_VH1 | QVQLVQSGAEVKKPGASVKVSCKASGYTFTNYWMHWVRQAPGQGLE WMGEINPINGRSNYAQKFQGRVTLTVDTSISTAYMELSRLRSDDTAVY YCARGTRAMHYWGQGTLVTVSSASTKGPSVFPLAPSSKSTSGGTAALG CLVKDYFPEPVTVSWNSGALTSGVHTFPAVLQSSGLYSLSSVVTVPSSS LGTQTYICNVNHKPSNTKVDKRVEPKSCDKTHTCPPCPAPELLGGPSVF LFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTIS KAKGQPREPQVYTLPPSREEMTKNQVSLTCLVKGFYPSDIAVEWESNG QPENNYKTTPPVLDSDGSFFLYSKLTVDKSRWQQGNVFSCSVMHEALH NHYTQKSLSLSPG | 303 |
| 13E4_VH1_a | QVQLVQSGAEVKKPGASVKVSCKASGYTFTNYWMHWVRQAPGQGLE WMGEINPINGRSNYAQKFQGRVTLTVDTSISTAYMELSRLRSDDTAVY YCARGTRAMHYWGQGTLVTVSSASTKGPSVFPLAPSSKSTSGGTAALG CLVKDYFPEPVTVSWNSGALTSGVHTFPAVLQSSGLYSLSSVVTVPSSS LGTQTYICNVNHKPSNTKVDKRVEPKSCDKTHTCPPCPAPEAAGGPSVF LFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTIS KAKGQPREPQVYTLPPSREEMTKNQVSLTCLVKGFYPSDIAVEWESNG QPENNYKTTPPVLDSDGSFFLYSKLTVDKSRWQQGNVFSCSVMHEALH NHYTQKSLSLSPG | 304 |
| 13E4_VH1_b | QVQLVQSGAEVKKPGASVKVSCKASGYTFTNYWMHWVRQAPGQGLE WMGEINPINGRSNYAQKFQGRVTLTVDTSISTAYMELSRLRSDDTAVY YCARGTRAMHYWGQGTLVTVSSASTKGPSVFPLAPSSKSTSGGTAALG CLVKDYFPEPVTVSWNSGALTSGVHTFPAVLQSSGLYSLSSVVTVPSSS LGTQTYICNVNHKPSNTKVDKRVEPKSCDKTHTCPPCPAPEAAGGPSVF LFPPKPKDTLMISRTPEVTCVVVDVSHEDPEVKFNWYVDGVEVHNAKT KPREEQYNSTYRVVSVLTVLHQDWLNGKEYKCGVSNKALPAPIEKTIS KAKGQPREPQVYTLPPSREEMTKNQVSLTCLVKGFYPSDIAVEWESNG QPENNYKTTPPVLDSDGSFFLYSKLTVDKSRWQQGNVFSCSVMHEALH NHYTQKSLSLSPG | 305 |
| 13E4_VH1_c | QVQLVQSGAEVKKPGASVKVSCKASGYTFTNYWMHWVRQAPGQGLE WMGEINPINGRSNYAQKFQGRVTLTVDTSISTAYMELSRLRSDDTAVY YCARGTRAMHYWGQGTLVTVSSASTKGPSVFPLAPSSKSTSGGTAALG CLVKDYFPEPVTVSWNSGALTSGVHTFPAVLQSSGLYSLSSVVTVPSSS LGTQTYICNVNHKPSNTKVDKRVEPKSCDKTHTCPPCPAPEAAGGPSVF LFPPKPKDTLMISRTPEVTCVVVDVSHEDPEVKFNWYVDGVEVHNAKT KPREEQYNSTYRVVSVLTVLHQDWLNGKEYKCKVSNKARPAPIEKTIS KAKGQPREPQVYTLPPSREEMTKNQVSLTCLVKGFYPSDIAVEWESNG QPENNYKTTPPVLDSDGSFFLYSKLTVDKSRWQQGNVFSCSVMHEALH NHYTQKSLSLSPG | 306 |
| 13E4_VH1_d | QVQLVQSGAEVKKPGASVKVSCKASGYTFTNYWMHWVRQAPGQGLE WMGEINPINGRSNYAQKFQGRVTLTVDTSISTAYMELSRLRSDDTAVY YCARGTRAMHYWGQGTLVTVSSASTKGPSVFPLAPSSKSTSGGTAALG CLVKDYFPEPVTVSWNSGALTSGVHTFPAVLQSSGLYSLSSVVTVPSSS LGTQTYICNVNHKPSNTKVDKRVEPKSCDKTHTCPPCPAPEAAGGPSVF LFPPKPKDTLMISRTPEVTCVVVDVSHEDPEVKFNWYVDGVEVHNAKT KPREEQYNSTYRVVSVLTVLHQDWLNGKEYKCKVSNKALGAPIEKTIS KAKGQPREPQVYTLPPSREEMTKNQVSLTCLVKGFYPSDIAVEWESNG QPENNYKTTPPVLDSDGSFFLYSKLTVDKSRWQQGNVFSCSVMHEALH NHYTQKSLSLSPG | 307 |
| 13E4_VH1_e | QVQLVQSGAEVKKPGASVKVSCKASGYTFTNYWMHWVRQAPGQGLE WMGEINPINGRSNYAQKFQGRVTLTVDTSISTAYMELSRLRSDDTAVY YCARGTRAMHYWGQGTLVTVSSASTKGPSVFPLAPSSKSTSGGTAALG CLVKDYFPEPVTVSWNSGALTSGVHTFPAVLQSSGLYSLSSVVTVPSSS LGTQTYICNVNHKPSNTKVDKRVEPKSCDKTHTCPPCPAPELLGGPSVF LFPPKPKDTLMISRTPEVTCVVVAVSHEDPEVKFNWYVDGVEVHNAKT KPREEQYGSTYRVVSVLTVLHQDWLNGKEYKCKVSNKALPAPIEKTIS | 308 |

TABLE 6-continued

| NAME | HC SEQUENCE | SEQ ID NO: |
|---|---|---|
| | KAKGQPREPQVYTLPPSREEMTKNQVSLTCLVKGFYPSDIAVEWESNG QPENNYKTTPPVLDSDGSFFLYSKLTVDKSRWQQGNVFSCSVMHEALH NHYTQKSLSLSPG | |
| 13E4_VH2 | QVQLVQSGAEVKKPGASVKVSCKASGYTFTNYWMHWVRQAPGQGLE WIGEINPINGRSNYAEKFQGRVTLTVDTSSSTAYMELSRLRSDDTAVYY CARGTRAMHYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKRVEPKSCDKTHTCPPCPAPELLGGPSVFL FPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISK AKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHN HYTQKSLSLSPG | 309 |
| 13E4_VH2_a | QVQLVQSGAEVKKPGASVKVSCKASGYTFTNYWMHWVRQAPGQGLE WIGEINPINGRSNYAEKFQGRVTLTVDTSSSTAYMELSRLRSDDTAVYY CARGTRAMHYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKRVEPKSCDKTHTCPPCPAPEAAGGPSVFL FPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISK AKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHN HYTQKSLSLSPG | 310 |
| 13E4_VH2_b | QVQLVQSGAEVKKPGASVKVSCKASGYTFTNYWMHWVRQAPGQGLE WIGEINPINGRSNYAEKFQGRVTLTVDTSSSTAYMELSRLRSDDTAVYY CARGTRAMHYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKRVEPKSCDKTHTCPPCPAPEAAGGPSVFL FPPKPKDTLMISRTPEVTCVVVDVSHEDPEVKFNWYVDGVEVHNAKTK PREEQYNSTYRVVSVLTVLHQDWLNGKEYKCGVSNKALPAPIEKTISK AKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHN HYTQKSLSLSPG | 311 |
| 13E4_VH2_c | QVQLVQSGAEVKKPGASVKVSCKASGYTFTNYWMHWVRQAPGQGLE WIGEINPINGRSNYAEKFQGRVTLTVDTSSSTAYMELSRLRSDDTAVYY CARGTRAMHYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKRVEPKSCDKTHTCPPCPAPEAAGGPSVFL FPPKPKDTLMISRTPEVTCVVVDVSHEDPEVKFNWYVDGVEVHNAKTK PREEQYNSTYRVVSVLTVLHQDWLNGKEYKCKVSNKARPAPIEKTISK AKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHN HYTQKSLSLSPG | 312 |
| 13E4_VH2_d | QVQLVQSGAEVKKPGASVKVSCKASGYTFTNYWMHWVRQAPGQGLE WIGEINPINGRSNYAEKFQGRVTLTVDTSSSTAYMELSRLRSDDTAVYY CARGTRAMHYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKRVEPKSCDKTHTCPPCPAPEAAGGPSVFL FPPKPKDTLMISRTPEVTCVVVDVSHEDPEVKFNWYVDGVEVHNAKTK PREEQYNSTYRVVSVLTVLHQDWLNGKEYKCKVSNKALGAPIEKTISK AKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHN HYTQKSLSLSPG | 313 |
| 13E4_VH2_e | QVQLVQSGAEVKKPGASVKVSCKASGYTFTNYWMHWVRQAPGQGLE WIGEINPINGRSNYAEKFQGRVTLTVDTSSSTAYMELSRLRSDDTAVYY CARGTRAMHYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKRVEPKSCDKTHTCPPCPAPELLGGPSVFL FPPKPKDTLMISRTPEVTCVVVAVSHEDPEVKFNWYVDGVEVHNAKTK PREEQYGSTYRVVSVLTVLHQDWLNGKEYKCKVSNKALPAPIEKTISK AKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHN HYTQKSLSLSPG | 314 |
| 13E4_VH3 | QVQLVQSGAEVKKPGASVKVSCKASGYTFTNYWMHWVRQAPGQGLE WMGEINPIQGRSNYAEKFQGRVTLTVDTSSSTAYMELSSLRSEDTATYY CARGTRAMHYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKRVEPKSCDKTHTCPPCPAPELLGGPSVFL FPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISK | 315 |

TABLE 6-continued

| NAME | HC SEQUENCE | SEQ ID NO: |
|---|---|---|
| | AKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHN HYTQKSLSLSPG | |
| 13E4_VH3_a | QVQLVQSGAEVKKPGASVKVSCKASGYTFTNYWMHWVRQAPGQGLE WMGEINPIQGRSNYAEKFQGRVTLTVDTSSSTAYMELSSLRSEDTATYY CARGTRAMHYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKRVEPKSCDKTHTCPPCPAPEAAGGPSVFL FPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISK AKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHN HYTQKSLSLSPG | 316 |
| 13E4_VH3_b | QVQLVQSGAEVKKPGASVKVSCKASGYTFTNYWMHWVRQAPGQGLE WMGEINPIQGRSNYAEKFQGRVTLTVDTSSSTAYMELSSLRSEDTATYY CARGTRAMHYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKRVEPKSCDKTHTCPPCPAPEAAGGPSVFL FPPKPKDTLMISRTPEVTCVVVDVSHEDPEVKFNWYVDGVEVHNAKTK PREEQYNSTYRVVSVLTVLHQDWLNGKEYKCGVSNKALPAPIEKTISK AKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHN HYTQKSLSLSPG | 317 |
| 13E4_VH3_c | QVQLVQSGAEVKKPGASVKVSCKASGYTFTNYWMHWVRQAPGQGLE WMGEINPIQGRSNYAEKFQGRVTLTVDTSSSTAYMELSSLRSEDTATYY CARGTRAMHYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKRVEPKSCDKTHTCPPCPAPEAAGGPSVFL FPPKPKDTLMISRTPEVTCVVVDVSHEDPEVKFNWYVDGVEVHNAKTK PREEQYNSTYRVVSVLTVLHQDWLNGKEYKCKVSNKARPAPIEKTISK AKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHN HYTQKSLSLSPG | 318 |
| 13E4_VH3_d | QVQLVQSGAEVKKPGASVKVSCKASGYTFTNYWMHWVRQAPGQGLE WMGEINPIQGRSNYAEKFQGRVTLTVDTSSSTAYMELSSLRSEDTATYY CARGTRAMHYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKRVEPKSCDKTHTCPPCPAPEAAGGPSVFL FPPKPKDTLMISRTPEVTCVVVDVSHEDPEVKFNWYVDGVEVHNAKTK PREEQYNSTYRVVSVLTVLHQDWLNGKEYKCKVSNKALGAPIEKTISK AKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHN HYTQKSLSLSPG | 319 |
| 13E4_VH3_e | QVQLVQSGAEVKKPGASVKVSCKASGYTFTNYWMHWVRQAPGQGLE WMGEINPIQGRSNYAEKFQGRVTLTVDTSSSTAYMELSSLRSEDTATYY CARGTRAMHYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKRVEPKSCDKTHTCPPCPAPELLGGPSVFL FPPKPKDTLMISRTPEVTCVVVAVSHEDPEVKFNWYVDGVEVHNAKTK PREEQYGSTYRVVSVLTVLHQDWLNGKEYKCKVSNKALPAPIEKTISK AKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHN HYTQKSLSLSPG | 320 |
| 13E4_VH4 | QVQLVQSGAEVKKPGASVKVSCKASGYTFTNYWMHWVRQAPGQGLE WMGEINPINGRSNYAEKFQGRVTLTVDTSSSTAYMELSSLRSEDTATYY CARGTRAMHYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKRVEPKSCDKTHTCPPCPAPELLGGPSVFL FPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISK AKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHN HYTQKSLSLSPG | 321 |
| 13E4_VH4_a | QVQLVQSGAEVKKPGASVKVSCKASGYTFTNYWMHWVRQAPGQGLE WMGEINPINGRSNYAEKFQGRVTLTVDTSSSTAYMELSSLRSEDTATYY CARGTRAMHYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKRVEPKSCDKTHTCPPCPAPEAAGGPSVFL FPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISK | 322 |

TABLE 6-continued

| NAME | HC SEQUENCE | SEQ ID NO: |
|---|---|---|
| | AKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHN HYTQKSLSLSPG | |
| 13E4_VH4_b | QVQLVQSGAEVKKPGASVKVSCKASGYTFTNYWMHWVRQAPGQGLE WMGEINPINGRSNYAEKFQGRVTLTVDTSSSTAYMELSSLRSEDTATYY CARGTRAMHYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKRVEPKSCDKTHTCPPCPAPEAAGGPSVFL FPPKPKDTLMISRTPEVTCVVVDVSHEDPEVKFNWYVDGVEVHNAKTK PREEQYNSTYRVVSVLTVLHQDWLNGKEYKCGVSNKALPAPIEKTISK AKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHN HYTQKSLSLSPG | 323 |
| 13E4_VH4_c | QVQLVQSGAEVKKPGASVKVSCKASGYTFTNYWMHWVRQAPGQGLE WMGEINPINGRSNYAEKFQGRVTLTVDTSSSTAYMELSSLRSEDTATYY CARGTRAMHYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKRVEPKSCDKTHTCPPCPAPEAAGGPSVFL FPPKPKDTLMISRTPEVTCVVVDVSHEDPEVKFNWYVDGVEVHNAKTK PREEQYNSTYRVVSVLTVLHQDWLNGKEYKCKVSNKARPAPIEKTISK AKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHN HYTQKSLSLSPG | 324 |
| 13E4_VH4_d | QVQLVQSGAEVKKPGASVKVSCKASGYTFTNYWMHWVRQAPGQGLE WMGEINPINGRSNYAEKFQGRVTLTVDTSSSTAYMELSSLRSEDTATYY CARGTRAMHYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKRVEPKSCDKTHTCPPCPAPEAAGGPSVFL FPPKPKDTLMISRTPEVTCVVVDVSHEDPEVKFNWYVDGVEVHNAKTK PREEQYNSTYRVVSVLTVLHQDWLNGKEYKCKVSNKALGAPIEKTISK AKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHN HYTQKSLSLSPG | 325 |
| 13E4_VH4_e | QVQLVQSGAEVKKPGASVKVSCKASGYTFTNYWMHWVRQAPGQGLE WMGEINPINGRSNYAEKFQGRVTLTVDTSSSTAYMELSSLRSEDTATYY CARGTRAMHYWGQGTLVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKRVEPKSCDKTHTCPPCPAPELLGGPSVFL FPPKPKDTLMISRTPEVTCVVVAVSHEDPEVKFNWYVDGVEVHNAKTK PREEQYGSTYRVVSVLTVLHQDWLNGKEYKCKVSNKALPAPIEKTISK AKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHN HYTQKSLSLSPG | 326 |

TABLE 7

| NAME | LC SEQUENCE | SEQ ID NO: |
|---|---|---|
| 13E4_VL1 | DIQMTQSPSSLSASVGDRVTITCRTSENIYNNLAWYQQKPGKSPKLLIYA ATNLADGVPSRFSGSGSGTDYTLTISSLQPEDFATYYCQHFWGTPLTFG GGTKVEIKRTVAAPSVFIFPPSDEQLKSGTASVVCLLNNFYPREAKVQW KVDNALQSGNSQESVTEQDSKDSTYSLSSTLTLSKADYEKHKVYACEV THQGLSSPVTKSFNRGEC | 327 |
| 13E4_VL2 | DIQMTQSPSSLSASVGDRVTITCRTSENIYNNLAWYQQKPGKAPKLLIY AATNLADGVPSRFSGSGSGTDYTLTISSLQPEDFATYYCQHFWGTPLTF GGGTKVEIKRTVAAPSVFIFPPSDEQLKSGTASVVCLLNNFYPREAKVQ WKVDNALQSGNSQESVTEQDSKDSTYSLSSTLTLSKADYEKHKVYACE VTHQGLSSPVTKSFNRGEC | 328 |
| 13E4_VL3 | DIQMTQSPSSLSASVGDRVTITCRTSENIYNNLAWYQQKPGKAPKLLIY AATNLAEGVPSRFSGSGSGTDYTLTISSLQPEDFATYYCQHFWGTPLTF GGGTKVEIKRTVAAPSVFIFPPSDEQLKSGTASVVCLLNNFYPREAKVQ WKVDNALQSGNSQESVTEQDSKDSTYSLSSTLTLSKADYEKHKVYACE VTHQGLSSPVTKSFNRGEC | 329 |
| 13E4_VL4 | DIQMTQSPSSLSASVGDRVTITCRTSENIYSNLAWYQQKPGKAPKLLIYA GTNLADGVPSRFSGSGSGTDYTLTISSLQPEDFANYYCQHFWGTPLTFG | 330 |

TABLE 7-continued

| NAME | LC SEQUENCE | SEQ ID NO: |
|------|-------------|------------|
| | GGTKVEIKRTVAAPSVFIFPPSDEQLKSGTASVVCLLNNFYPREAKVQW KVDNALQSGNSQESVTEQDSKDSTYSLSSTLTLSKADYEKHKVYACEV THQGLSSPVTKSFNRGEC | |

In some embodiments, an anti-transferrin receptor antibody described herein has an improved serum half-life compared to a reference anti-transferrin receptor antibody. In some instances, the improved serum half-life is at least 30 minutes, 1 hour, 1.5 hour, 2 hours, 3 hours, 4 hours, 5 hours, 6 hours, 7 hours, 8 hours, 9 hours, 10 hours, 12 hours, 18 hours, 24 hours, 2 days, 3 days, 4 days, 5 days, 6 days, 7 days, 14 days, 30 days, or longer than reference anti-transferrin receptor antibody.

In some embodiments, the binding moiety A is conjugated to a polynucleic acid molecule (B) non-specifically. In some instances, the binding moiety A is conjugated to a polynucleic acid molecule (B) via a lysine residue or a cysteine residue, in a non-site specific manner. In some instances, the binding moiety A is conjugated to a polynucleic acid molecule (B) via a lysine residue (e.g., lysine residue present in the binding moiety A) in a non-site specific manner. In some cases, the binding moiety A is conjugated to a polynucleic acid molecule (B) via a cysteine residue (e.g., cysteine residue present in the binding moiety A) in a non-site specific manner.

In some embodiments, the binding moiety A is conjugated to a polynucleic acid molecule (B) in a site-specific manner. In some instances, the binding moiety A is conjugated to a polynucleic acid molecule (B) through a lysine residue, a cysteine residue, at the 5'-terminus, at the 3'-terminus, an unnatural amino acid, or an enzyme-modified or enzyme-catalyzed residue, via a site-specific manner. In some instances, the binding moiety A is conjugated to a polynucleic acid molecule (B) through a lysine residue (e.g., lysine residue present in the binding moiety A) via a site-specific manner. In some instances, the binding moiety A is conjugated to a polynucleic acid molecule (B) through a cysteine residue (e.g., cysteine residue present in the binding moiety A) via a site-specific manner. In some instances, the binding moiety A is conjugated to a polynucleic acid molecule (B) at the 5'-terminus via a site-specific manner. In some instances, the binding moiety A is conjugated to a polynucleic acid molecule (B) at the 3'-terminus via a site-specific manner. In some instances, the binding moiety A is conjugated to a polynucleic acid molecule (B) through an unnatural amino acid via a site-specific manner. In some instances, the binding moiety A is conjugated to a polynucleic acid molecule (B) through an enzyme-modified or enzyme-catalyzed residue via a site-specific manner.

In some embodiments, one or more polynucleic acid molecule (B) is conjugated to a binding moiety A. In some instances, about 1, 2, 3, 4, 5, 6, 7, 8, 9, 10, 11, 12, 13, 14, 15, 16, or more polynucleic acid molecules are conjugated to one binding moiety A. In some instances, about 1 polynucleic acid molecule is conjugated to one binding moiety A. In some instances, about 2 polynucleic acid molecules are conjugated to one binding moiety A. In some instances, about 3 polynucleic acid molecules are conjugated to one binding moiety A. In some instances, about 4 polynucleic acid molecules are conjugated to one binding moiety A. In some instances, about 5 polynucleic acid molecules are conjugated to one binding moiety A. In some instances, about 6 polynucleic acid molecules are conjugated to one binding moiety A. In some instances, about 7 polynucleic acid molecules are conjugated to one binding moiety A. In some instances, about 8 polynucleic acid molecules are conjugated to one binding moiety A. In some instances, about 9 polynucleic acid molecules are conjugated to one binding moiety A. In some instances, about 10 polynucleic acid molecules are conjugated to one binding moiety A. In some instances, about 11 polynucleic acid molecules are conjugated to one binding moiety A. In some instances, about 12 polynucleic acid molecules are conjugated to one binding moiety A. In some instances, about 13 polynucleic acid molecules are conjugated to one binding moiety A. In some instances, about 14 polynucleic acid molecules are conjugated to one binding moiety A. In some instances, about 15 polynucleic acid molecules are conjugated to one binding moiety A. In some instances, about 16 polynucleic acid molecules are conjugated to one binding moiety A. In some cases, the one or more polynucleic acid molecules are the same. In other cases, the one or more polynucleic acid molecules are different.

In some embodiments, the number of polynucleic acid molecule (B) conjugated to a binding moiety A forms a ratio. In some instances, the ratio is referred to as a DAR (drug-to-antibody) ratio, in which the drug as referred to herein is the polynucleic acid molecule (B). In some instances, the DAR ratio of the polynucleic acid molecule (B) to binding moiety A is about 1, 2, 3, 4, 5, 6, 7, 8, 9, 10, 11, 12, 13, 14, 15, 16, or greater. In some instances, the DAR ratio of the polynucleic acid molecule (B) to binding moiety A is about 1 or greater. In some instances, the DAR ratio of the polynucleic acid molecule (B) to binding moiety A is about 2 or greater. In some instances, the DAR ratio of the polynucleic acid molecule (B) to binding moiety A is about 3 or greater. In some instances, the DAR ratio of the polynucleic acid molecule (B) to binding moiety A is about 4 or greater. In some instances, the DAR ratio of the polynucleic acid molecule (B) to binding moiety A is about 5 or greater. In some instances, the DAR ratio of the polynucleic acid molecule (B) to binding moiety A is about 6 or greater. In some instances, the DAR ratio of the polynucleic acid molecule (B) to binding moiety A is about 7 or greater. In some instances, the DAR ratio of the polynucleic acid molecule (B) to binding moiety A is about 8 or greater. In some instances, the DAR ratio of the polynucleic acid molecule (B) to binding moiety A is about 9 or greater. In some instances, the DAR ratio of the polynucleic acid molecule (B) to binding moiety A is about 10 or greater. In some instances, the DAR ratio of the polynucleic acid molecule (B) to binding moiety A is about 11 or greater. In some instances, the DAR ratio of the polynucleic acid molecule (B) to binding moiety A is about 12 or greater.

In some instances, the DAR ratio of the polynucleic acid molecule (B) to binding moiety A is about 1, 2, 3, 4, 5, 6, 7, 8, 9, 10, 11, 12, 13, 14, 15, or 16. In some instances, the DAR ratio of the polynucleic acid molecule (B) to binding moiety A is about 1. In some instances, the DAR ratio of the polynucleic acid molecule (B) to binding moiety A is about 2. In some instances, the DAR ratio of the polynucleic acid molecule (B) to binding moiety A is about 3. In some instances, the DAR ratio of the polynucleic acid molecule (B) to binding moiety A is about 4. In some instances, the DAR ratio of the polynucleic acid molecule (B) to binding moiety A is about 5. In some instances, the DAR ratio of the polynucleic acid molecule (B) to binding moiety A is about 6. In some instances, the DAR ratio of the polynucleic acid molecule (B) to binding moiety A is about 7. In some instances, the DAR ratio of the polynucleic acid molecule (B) to binding moiety A is about 8. In some instances, the DAR ratio of the polynucleic acid molecule (B) to binding moiety A is about 9. In some instances, the DAR ratio of the polynucleic acid molecule (B) to binding moiety A is about 10. In some instances, the DAR ratio of the polynucleic acid molecule (B) to binding moiety A is about 11. In some instances, the DAR ratio of the polynucleic acid molecule (B) to binding moiety A is about 12. In some instances, the DAR ratio of the polynucleic acid molecule (B) to binding moiety A is about 13. In some instances, the DAR ratio of the polynucleic acid molecule (B) to binding moiety A is about 14. In some instances, the DAR ratio of the polynucleic acid molecule (B) to binding moiety A is about 15. In some instances, the DAR ratio of the polynucleic acid molecule (B) to binding moiety A is about 16.

In some instances, the DAR ratio of the polynucleic acid molecule (B) to binding moiety A is 1, 2, 3, 4, 5, 6, 7, 8, 9, 10, 11, 12, 13, 14, 15, or 16. In some instances, the DAR ratio of the polynucleic acid molecule (B) to binding moiety A is 1. In some instances, the DAR ratio of the polynucleic acid molecule (B) to binding moiety A is 2. In some instances, the DAR ratio of the polynucleic acid molecule (B) to binding moiety A is 4. In some instances, the DAR ratio of the polynucleic acid molecule (B) to binding moiety A is 6. In some instances, the DAR ratio of the polynucleic acid molecule (B) to binding moiety A is 8. In some instances, the DAR ratio of the polynucleic acid molecule (B) to binding moiety A is 12.

In some instances, a conjugate comprising polynucleic acid molecule (B) and binding moiety A has improved activity as compared to a conjugate comprising polynucleic acid molecule (B) without a binding moiety A. In some instances, improved activity results in enhanced biologically relevant functions, e.g., improved stability, affinity, binding, functional activity, and efficacy in treatment or prevention of a disease state. In some instances, the disease state is a result of one or more mutated exons of a gene. In some instances, the conjugate comprising polynucleic acid molecule (B) and binding moiety A results in increased exon skipping of the one or more mutated exons as compared to the conjugate comprising polynucleic acid molecule (B) without a binding moiety A. In some instances, exon skipping is increased by at least or about 5%, 10%, 20%, 25%, 30%, 40%, 50%, 60%, 70%, 80%, 90%, 95%, or more than 95% in the conjugate comprising polynucleic acid molecule (B) and binding moiety A as compared to the conjugate comprising polynucleic acid molecule (B) without a binding moiety A.

In some embodiments, an antibody or antigen binding fragment is further modified using conventional techniques known in the art, for example, by using amino acid deletion, insertion, substitution, addition, and/or by recombination and/or any other modification (e.g., posttranslational and chemical modifications, such as glycosylation and phosphorylation) known in the art either alone or in combination. In some instances, the modification further comprises a modification for modulating interaction with Fc receptors. In some instances, the one or more modifications include those described in, for example, International Publication No. WO97/34631, which discloses amino acid residues involved in the interaction between the Fc domain and the FcRn receptor. Methods for introducing such modifications in the nucleic acid sequence underlying the amino acid sequence of an antibody or antigen binding fragment is well known to the person skilled in the art.

In some instances, an antigen binding fragment further encompasses its derivatives and includes polypeptide sequences containing at least one CDR.

In some instances, the term "single-chain" as used herein means that the first and second domains of a bi-specific single chain construct are covalently linked, preferably in the form of a co-linear amino acid sequence encodable by a single nucleic acid molecule.

In some instances, a bispecific single chain antibody construct relates to a construct comprising two antibody derived binding domains. In such embodiments, bi-specific single chain antibody construct is tandem bi-scFv or diabody. In some instances, a scFv contains a VH and VL domain connected by a linker peptide. In some instances, linkers are of a length and sequence sufficient to ensure that each of the first and second domains can, independently from one another, retain their differential binding specificities.

In some embodiments, binding to or interacting with as used herein defines a binding/interaction of at least two antigen-interaction-sites with each other. In some instances, antigen-interaction-site defines a motif of a polypeptide that shows the capacity of specific interaction with a specific antigen or a specific group of antigens. In some cases, the binding/interaction is also understood to define a specific recognition. In such cases, specific recognition refers to that the antibody or its antigen binding fragment is capable of specifically interacting with and/or binding to at least two amino acids of each of a target molecule. For example, specific recognition relates to the specificity of the antibody molecule, or to its ability to discriminate between the specific regions of a target molecule. In additional instances, the specific interaction of the antigen-interaction-site with its specific antigen results in an initiation of a signal, e.g. due to the induction of a change of the conformation of the antigen, an oligomerization of the antigen, etc. In further embodiments, the binding is exemplified by the specificity of a "key-lock-principle". Thus in some instances, specific motifs in the amino acid sequence of the antigen-interaction-site and the antigen bind to each other as a result of their primary, secondary or tertiary structure as well as the result of secondary modifications of said structure. In such cases, the specific interaction of the antigen-interaction-site with its specific antigen results as well in a simple binding of the site to the antigen.

In some instances, specific interaction further refers to a reduced cross-reactivity of the antibody or antigen binding fragment or a reduced off-target effect. For example, the antibody or antigen binding fragment that bind to the polypeptide/protein of interest but do not or do not essentially bind to any of the other polypeptides are considered as specific for the polypeptide/protein of interest. Examples for the specific interaction of an antigen-interaction-site with a specific antigen comprise the specificity of a ligand for its receptor, for example, the interaction of an antigenic determinant (epitope) with the antigenic binding site of an antibody.

Additional Binding Moieties

In some embodiments, the binding moiety is a plasma protein. In some instances, the plasma protein comprises albumin. In some instances, the binding moiety A is albumin. In some instances, albumin is conjugated by one or more of a conjugation chemistry described herein to a polynucleic acid molecule. In some instances, albumin is conjugated by native ligation chemistry to a polynucleic acid molecule. In some instances, albumin is conjugated by lysine conjugation to a polynucleic acid molecule.

In some instances, the binding moiety is a steroid. Exemplary steroids include cholesterol, phospholipids, di- and triacylglycerols, fatty acids, hydrocarbons that are saturated, unsaturated, comprise substitutions, or combinations thereof. In some instances, the steroid is cholesterol. In some instances, the binding moiety is cholesterol. In some instances, cholesterol is conjugated by one or more of a conjugation chemistry described herein to a polynucleic acid molecule. In some instances, cholesterol is conjugated by native ligation chemistry to a polynucleic acid molecule. In some instances, cholesterol is conjugated by lysine conjugation to a polynucleic acid molecule.

In some instances, the binding moiety is a polymer, including but not limited to polynucleic acid molecule aptamers that bind to specific surface markers on cells. In this instance the binding moiety is a polynucleic acid that does not hybridize to a target gene or mRNA, but instead is capable of selectively binding to a cell surface marker similarly to an antibody binding to its specific epitope of a cell surface marker.

In some cases, the binding moiety is a peptide. In some cases, the peptide comprises between about 1 and about 3 kDa. In some cases, the peptide comprises between about 1.2 and about 2.8 kDa, about 1.5 and about 2.5 kDa, or about 1.5 and about 2 kDa. In some instances, the peptide is a bicyclic peptide. In some cases, the bicyclic peptide is a constrained bicyclic peptide. In some instances, the binding moiety is a bicyclic peptide (e.g., bicycles from Bicycle Therapeutics).

In additional cases, the binding moiety is a small molecule. In some instances, the small molecule is an antibody-recruiting small molecule. In some cases, the antibody-recruiting small molecule comprises a target-binding terminus and an antibody-binding terminus, in which the target-binding terminus is capable of recognizing and interacting with a cell surface receptor. For example, in some instances, the target-binding terminus comprising a glutamate urea compound enables interaction with PSMA, thereby, enhances an antibody interaction with a cell that expresses PSMA. In some instances, a binding moiety is a small molecule described in Zhang et al., "A remote arene-binding site on prostate specific membrane antigen revealed by antibody-recruiting small molecules," J Am Chem Soc. 132(36): 12711-12716 (2010); or McEnaney, et al., "Antibody-recruiting molecules: an emerging paradigm for engaging immune function in treating human disease," ACS Chem Biol. 7(7): 1139-1151 (2012).

Production of Antibodies or Antigen Binding Fragment Thereof

In some embodiments, polypeptides described herein (e.g., antibodies and antigen binding fragments) are produced using any method known in the art to be useful for the synthesis of polypeptides (e.g., antibodies), in particular, by chemical synthesis or by recombinant expression, and are preferably produced by recombinant expression techniques.

In some instances, an antibody or antigen binding fragment thereof is expressed recombinantly, and the nucleic acid encoding the antibody or antigen binding fragment is assembled from chemically synthesized oligonucleotides (e.g., as described in Kutmeier et al., 1994. *BioTechniques* 17:242), which involves the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody is optionally generated from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

In some instances, an antibody or its antigen binding is optionally generated by immunizing an animal, such as a rabbit, to generate polyclonal antibodies or, more preferably, by generating monoclonal antibodies, e.g., as described by Kohler and Milstein (1975. *Nature* 256:495-497) or, as described by Kozbor et al. (1983. *Immunology Today* 4:72) or Cole et al. (1985 in *Monoclonal Antibodies and Cancer Therapy*, Alan R. Liss, Inc., pp. 77-96). Alternatively, a clone encoding at least the Fab portion of the antibody is optionally obtained by screening Fab expression libraries (e.g., as described in Huse et al., 1989. *Science* 246:1275-1281) for clones of Fab fragments that bind the specific antigen or by screening antibody libraries (See, e.g., Clackson et al., 1991. *Nature* 352:624; Hane et al., 1997 *Proc. Natl. Acad. Sci. USA* 94:4937).

In some embodiments, techniques developed for the production of "chimeric antibodies" (Morrison et al., 1984, *Proc. Natl. Acad. Sci.* 81:851-855; Neuberger et al., 1984. *Nature* 312:604-608; Takeda et al., 1985, *Nature* 314:452-454) by splicing genes from a mouse antibody molecule of appropriate antigen specificity together with genes from a human antibody molecule of appropriate biological activity are used. A chimeric antibody is a molecule in which different portions are derived from different animal species, such as those having a variable region derived from a murine monoclonal antibody and a human immunoglobulin constant region, e.g., humanized antibodies.

In some embodiments, techniques described for the production of single chain antibodies (U.S. Pat. No. 4,694,778; Bird, 1988. *Science* 242:423-42; Huston et al., 1988. *Proc. Natl. Acad. Sci. USA* 85:5879-5883; and Ward et al., 1989. *Nature* 334:544-54) are adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* are also optionally used (Skerra et al., 1988. *Science* 242:1038-1041).

In some embodiments, an expression vector comprising the nucleotide sequence of an antibody or the nucleotide sequence of an antibody is transferred to a host cell by conventional techniques (e.g., electroporation, liposomal transfection, and calcium phosphate precipitation), and the transfected cells are then cultured by conventional techniques to produce the antibody. In specific embodiments, the expression of the antibody is regulated by a constitutive, an inducible or a tissue, specific promoter.

In some embodiments, a variety of host-expression vector systems is utilized to express an antibody or its antigen binding fragment described herein. Such host-expression systems represent vehicles by which the coding sequences of the antibody is produced and subsequently purified, but also represent cells that are, when transformed or transfected with the appropriate nucleotide coding sequences, express an antibody or its antigen binding fragment in situ. These include, but are not limited to, microorganisms such as bacteria (e.g. *E. coli* and *B. subtilis*) transformed with recombinant bacteriophage DNA, plasmid DNA or cosmid DNA expression vectors containing an antibody or its antigen binding fragment coding sequences; yeast (e.g., *Saccharomyces Pichia*) transformed with recombinant yeast expression vectors containing an antibody or its antigen binding fragment coding sequences; insect cell systems infected with recombinant virus expression vectors (e.g., baculovirus) containing an antibody or its antigen binding fragment coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing an antibody or its antigen binding fragment coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g. the adenovirus late promoter; the vaccinia virus 7.5K promoter).

For long-term, high-yield production of recombinant proteins, stable expression is preferred. In some instances, cell lines that stably express an antibody are optionally engineered. Rather than using expression vectors that contain viral origins of replication, host cells are transformed with DNA controlled by appropriate expression control elements (e.g., promoter, enhancer, sequences, transcription terminators, polyadenylation sites, etc.), and a selectable marker. Following the introduction of the foreign DNA, engineered cells are then allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn are cloned and expanded into cell lines. This method can advantageously be used to engineer cell lines which express the antibody or its antigen binding fragments.

In some instances, a number of selection systems are used, including but not limited to the herpes simplex virus thymidine kinase (Wigler et al., 1977, *Cell* 11:223), hypoxanthine-guanine phosphoribosyltransferase (Szybalska & Szybalski, 192, *Proc. Natl. Acad. Sci. USA* 48:202), and adenine phosphoribosyltransferase (Lowy et al., 1980, *Cell* 22:817) genes are employed in tk-, hgprt- or aprt-cells, respectively. Also, antimetabolite resistance are used as the basis of selection for the following genes: dhfr, which confers resistance to methotrexate (Wigler et al., 1980, *Proc. Natl. Acad Sci. USA* 77:357; O'Hare et al., 1981, *Proc. Natl. Acad Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (*Clinical Pharmacy* 12:488-505; Wu and Wu, 1991, *Biotherapy* 3:87-95; Tolstoshev, 1993. *Ann. Rev. Pharmacol. Toxicol.* 32:573-596; Mulligan, 1993. *Science* 260:926-932; and Morgan and Anderson, 1993, *Ann. Rev. Biochem.* 62:191-217; May, 1993. *TIB TECH* 11(5):155-215) and hygro, which confers resistance to hygromycin (Santerre et al., 1984, *Gene* 30:147). Methods commonly known in the art of recombinant DNA technology which can be used are described in Ausubel et al. (eds., 1993, *Current Protocols m Molecular Biology*, John Wiley & Sons, NY; Kriegler, 1990, *Gene Transfer and Expression*, *A Laboratory Manual*, Stockton Press, NY; and in Chapters 12 and 13, Dracopoli et al. (eds), 1994, *Current Protocols in Human Genetics*, John Wiley & Sons, NY.; Colberre-Garapin et al., 1981, *J. Mol. Biol.* 150:1).

In some instances, the expression levels of an antibody are increased by vector amplification (for a review, see Bebbington and Hentschel, *The use of vectors based on gene amplification for the expression of cloned genes in mammalian cells in DNA cloning*, Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (Crouse et al., 1983, *Mol. Cell Biol.* 3:257).

In some instances, any method known in the art for purification or analysis of an antibody or antibody conjugates is used, for example, by chromatography (e.g., ion exchange, affinity, particularly by affinity for the specific antigen after Protein A, and sizing column chromatography), centrifugation, differential solubility, or by any other standard technique for the purification of proteins. Exemplary chromatography methods included, but are not limited to, strong anion exchange chromatography, hydrophobic interaction chromatography, size exclusion chromatography, and fast protein liquid chromatography.

Conjugation Chemistry

In some embodiments, a polynucleic acid molecule B is conjugated to a binding moiety. In some embodiments, a polynucleic acid molecule B is conjugated to a binding moiety in a formula A-X—B (X is a linker conjugating A and B). In some instances, the binding moiety comprises amino acids, peptides, polypeptides, proteins, antibodies, antigens, toxins, hormones, lipids, nucleotides, nucleosides, sugars, carbohydrates, polymers such as polyethylene glycol and polypropylene glycol, as well as analogs or derivatives of all of these classes of substances. Additional examples of binding moiety also include steroids, such as cholesterol, phospholipids, di- and triacylglycerols, fatty acids, hydrocarbons (e.g., saturated, unsaturated, or contains substitutions), enzyme substrates, biotin, digoxigenin, and polysaccharides. In some instances, the binding moiety is an antibody or antigen binding fragment thereof. In some instances, the polynucleic acid molecule is further conjugated to a polymer, and optionally an endosomolytic moiety.

In some embodiments, the polynucleic acid molecule is conjugated to the binding moiety by a chemical ligation process. In some instances, the polynucleic acid molecule is conjugated to the binding moiety by a native ligation. In some instances, the conjugation is as described in: Dawson, et al. "Synthesis of proteins by native chemical ligation." *Science* 1994, 266, 776-779; Dawson, et al. "Modulation of Reactivity in Native Chemical Ligation through the Use of Thiol Additives," *J. Am. Chem. Soc.* 1997, 119, 4325-4329; Hackeng, et al. "Protein synthesis by native chemical ligation: Expanded scope by using straightforward methodology," *Proc. Natl. Acad Sci. USA* 1999, 96, 10068-10073; or Wu, et al. "Building complex glycopeptides: Development of a cysteine-free native chemical ligation protocol," *Angew. Chem. Int. Ed.* 2006, 45, 4116-4125. In some instances, the conjugation is as described in U.S. Pat. No. 8,936,910. In some embodiments, the polynucleic acid molecule is conjugated to the binding moiety either site-specifically or non-specifically via native ligation chemistry.

In some instances, the polynucleic acid molecule is conjugated to the binding moiety by a site-directed method utilizing a "traceless" coupling technology (Philochem). In some instances, the "traceless" coupling technology utilizes an N-terminal 1,2-aminothiol group on the binding moiety which is then conjugate with a polynucleic acid molecule containing an aldehyde group. (see Casi et al., "Site-specific traceless coupling of potent cytotoxic drugs to recombinant antibodies for pharmacodelivery," *JACS* 134(13): 5887-5892 (2012))

In some instances, the polynucleic acid molecule is conjugated to the binding moiety by a site-directed method utilizing an unnatural amino acid incorporated into the binding moiety. In some instances, the unnatural amino acid comprises p-acetylphenylalanine (pAcPhe). In some instances, the keto group of pAcPhe is selectively coupled to an alkoxy-amine derivatived conjugating moiety to form an oxime bond. (see Axup et al., "Synthesis of site-specific antibody-drug conjugates using unnatural amino acids," *PNAS* 109(40): 16101-16106 (2012)).

In some instances, the polynucleic acid molecule is conjugated to the binding moiety by a site-directed method utilizing an enzyme-catalyzed process. In some instances, the site-directed method utilizes SMARTag™ technology (Catalent, Inc.). In some instances, the SMARTag™ technology comprises generation of a formylglycine (FGly) residue from cysteine by formylglycine-generating enzyme (FGE) through an oxidation process under the presence of an aldehyde tag and the subsequent conjugation of FGIy to an alkylhydraine-functionalized polynucleic acid molecule via hydrazino-Pictet-Spengler (HIPS) ligation. (see Wu et al., "Site-specific chemical modification of recombinant proteins produced in mammalian cells by using the genetically encoded aldehyde tag," PNAS 106(9): 3000-3005 (2009); Agarwal, et al., "A Pictet-Spengler ligation for protein chemical modification," PNAS 110(1): 46-51 (2013))

In some instances, the enzyme-catalyzed process comprises microbial transglutaminase (mTG). In some cases, the polynucleic acid molecule is conjugated to the binding moiety utilizing a microbial transglutaminase-catalyzed process. In some instances, mTG catalyzes the formation of a covalent bond between the amide side chain of a glutamine within the recognition sequence and a primary amine of a functionalized polynucleic acid molecule. In some instances, mTG is produced from *Streptomyces mobarensis*. (see Strop et al., "Location matters: site of conjugation modulates stability and pharmacokinetics of antibody drug conjugates," *Chemistry and Biology* 20(2) 161-167 (2013))

In some instances, the polynucleic acid molecule is conjugated to the binding moiety by a method as described in PCT Publication No. WO2014/140317, which utilizes a sequence-specific transpeptidase.

In some instances, the polynucleic acid molecule is conjugated to the binding moiety by a method as described in U.S. Patent Publication Nos. 2015/0105539 and 2015/0105540.

Polymer Conjugating Moiety

In some embodiments, a polymer moiety C is further conjugated to a polynucleic acid molecule described herein, a binding moiety described herein, or in combinations thereof. In some instances, a polymer moiety C is conjugated a polynucleic acid molecule in a formula A-$X_1$—B—$X_2$—C ($X_1$, $X_2$ as two linkers conjugating A and B, B and C, respectively). In some cases, a polymer moiety C is conjugated to a binding moiety. In other cases, a polymer moiety C is conjugated to a polynucleic acid molecule-binding moiety molecule. In additional cases, a polymer moiety C is conjugated, as illustrated supra.

In some instances, the polymer moiety C is a natural or synthetic polymer, consisting of long chains of branched or unbranched monomers, and/or cross-linked network of monomers in two or three dimensions. In some instances, the polymer moiety C includes a polysaccharide, lignin, rubber, or polyalkylen oxide (e.g., polyethylene glycol). In some instances, the at least one polymer moiety C includes, but is not limited to, alpha-, omega-dihydroxylpolyethyleneglycol, biodegradable lactone-based polymer, e.g. polyacrylic acid, polylactide acid (PLA), poly(glycolic acid) (PGA), polypropylene, polystyrene, polyolefin, polyamide, polycyanoacrylate, polyimide, polyethylene terephthalate (also known as poly(ethylene terephthalate), PET, PETG, or PETE), polytetramethylene glycol (PTG), or polyurethane as well as mixtures thereof. As used herein, a mixture refers to the use of different polymers within the same compound as well as in reference to block copolymers. In some cases, block copolymers are polymers wherein at least one section of a polymer is build up from monomers of another polymer. In some instances, the polymer moiety C comprises polyalkylene oxide. In some instances, the polymer moiety C comprises PEG. In some instances, the polymer moiety C comprises polyethylene imide (PEI) or hydroxy ethyl starch (HES).

In some instances, C is a PEG moiety. In some instances, the PEG moiety is conjugated at the 5' terminus of the polynucleic acid molecule while the binding moiety is conjugated at the 3' terminus of the polynucleic acid molecule. In some instances, the PEG moiety is conjugated at the 3' terminus of the polynucleic acid molecule while the binding moiety is conjugated at the 5' terminus of the polynucleic acid molecule. In some instances, the PEG moiety is conjugated to an internal site of the polynucleic acid molecule. In some instances, the PEG moiety, the binding moiety, or a combination thereof, are conjugated to an internal site of the polynucleic acid molecule. In some instances, the conjugation is a direct conjugation. In some instances, the conjugation is via native ligation.

In some embodiments, the polyalkylene oxide (e.g., PEG) is a polydisperse or monodisperse compound. In some instances, polydisperse material comprises disperse distribution of different molecular weight of the material, characterized by mean weight (weight average) size and dispersity. In some instances, the monodisperse PEG comprises one size of molecules. In some embodiments, C is poly- or monodispersed polyalkylene oxide (e.g., PEG) and the indicated molecular weight represents an average of the molecular weight of the polyalkylene oxide, e.g., PEG, molecules.

In some embodiments, the molecular weight of the polyalkylene oxide (e.g. PEG) is about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da.

In some embodiments, C is polyalkylene oxide (e.g., PEG) and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100.000 Da. In some embodiments, C is PEG and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some instances, the molecular weight of C is about 200 Da. In some instances, the molecular weight of C is about 300 Da. In some instances, the molecular weight of C is about 400 Da. In some instances, the molecular weight of C is about 500 Da. In some instances, the molecular weight of C is about 600 Da. In some instances, the molecular weight of C is about 700 Da. In some instances, the molecular weight of C is about 800 Da. In some instances, the molecular weight of C is about 900 Da. In some instances, the molecular weight of C is about 1000 Da. In some instances, the molecular weight of C is about 1100 Da. In some instances, the molecular weight of C is about 1200 Da. In some instances, the molecular weight of C is about 1300 Da. In some instances, the molecular weight of C is about 1400 Da. In some instances, the molecular weight of C is about 1450 Da. In some instances, the molecular weight of C is about 1500 Da. In some instances, the molecular weight of C is about 1600 Da. In some instances, the molecular weight of C is about 1700 Da. In some instances, the molecular weight of C is about 1800 Da. In some instances, the molecular weight of C is about 1900 Da. In some instances, the molecular weight of C is about 2000 Da. In some instances, the molecular weight of C is about 2100 Da. In some instances, the molecular weight of C is about 2200 Da. In some instances, the molecular weight of C is about 2300 Da. In some instances, the molecular weight of C is about 2400 Da. In some instances, the molecular weight of C is about 2500 Da. In some instances, the molecular weight of C is about 2600 Da. In some instances, the molecular weight of C is about 2700 Da. In some instances, the molecular weight of C is about 2800 Da. In some instances, the molecular weight of C is about 2900 Da. In some instances, the molecular weight of C is about 3000 Da. In some instances, the molecular weight of C is about 3250 Da. In some instances, the molecular weight of C is about 3350 Da. In some instances, the molecular weight of C is about 3500 Da. In some instances, the molecular weight of C is about 3750 Da. In some instances, the molecular weight of C is about 4000 Da. In some instances, the molecular weight of C is about 4250 Da. In some instances, the molecular weight of C is about 4500 Da. In some instances, the molecular weight of C is about 4600 Da. In some instances, the molecular weight of C is about 4750 Da. In some instances, the molecular weight of C is about 5000 Da. In some instances, the molecular weight of C is about 5500 Da. In some instances, the molecular weight of C is about 6000 Da. In some instances, the molecular weight of C is about 6500 Da. In some instances, the molecular weight of C is about 7000 Da. In some instances, the molecular weight of C is about 7500 Da. In some instances, the molecular weight of C is about 8000 Da. In some instances, the molecular weight of C is about 10,000 Da. In some instances, the molecular weight of C is about 12,000 Da. In some instances, the molecular weight of C is about 20,000 Da. In some instances, the molecular weight of C is about 35,000 Da. In some instances, the molecular weight of C is about 40,000 Da. In some instances, the molecular weight of C is about 50,000 Da. In some instances, the molecular weight of C is about 60,000 Da. In some instances, the molecular weight of C is about 100,000 Da.

In some embodiments, the polyalkylene oxide (e.g., PEG) comprises discrete ethylene oxide units (e.g., four to about 48 ethylene oxide units). In some instances, the polyalkylene oxide comprising the discrete ethylene oxide units is a linear chain. In other cases, the polyalkylene oxide comprising the discrete ethylene oxide units is a branched chain.

In some instances, the polymer moiety C is a polyalkylene oxide (e.g., PEG) comprising discrete ethylene oxide units. In some cases, the polymer moiety C comprises between about 4 and about 48 ethylene oxide units. In some cases, the polymer moiety C comprises about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, or about 48 ethylene oxide units.

In some instances, the polymer moiety C is a discrete PEG comprising, e.g., between about 4 and about 48 ethylene oxide units. In some cases, the polymer moiety C is a discrete PEG comprising, e.g., about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, or about 48 ethylene oxide units. In some cases, the polymer moiety C is a discrete PEG comprising, e.g., about 4 ethylene oxide units. In some cases, the polymer moiety C is a discrete PEG comprising, e.g., about 5 ethylene oxide units. In some cases, the polymer moiety C is a discrete PEG comprising, e.g., about 6 ethylene oxide units. In some cases, the polymer moiety C is a discrete PEG comprising, e.g., about 7 ethylene oxide units. In some cases, the polymer moiety C is a discrete PEG comprising, e.g., about 8 ethylene oxide units. In some cases, the polymer moiety C is a discrete PEG comprising, e.g., about 9 ethylene oxide units. In some cases, the polymer moiety C is a discrete PEG comprising, e.g., about 10 ethylene oxide units. In some cases, the polymer moiety C is a discrete PEG comprising, e.g., about 11 ethylene oxide units. In some cases, the polymer moiety C is a discrete PEG comprising, e.g., about 12 ethylene oxide units. In some cases, the polymer moiety C is a discrete PEG comprising, e.g., about 13 ethylene oxide units. In some cases, the polymer moiety C is a discrete PEG comprising, e.g., about 14 ethylene oxide units. In some cases, the polymer moiety C is a discrete PEG comprising, e.g., about 15 ethylene oxide units. In some cases, the polymer moiety C is a discrete PEG comprising. e.g., about 16 ethylene oxide units. In some cases, the polymer moiety C is a discrete PEG comprising, e.g., about 17 ethylene oxide units. In some cases, the polymer moiety C is a discrete PEG comprising, e.g., about 18 ethylene oxide units. In some cases, the polymer moiety C is a discrete PEG comprising, e.g., about 19 ethylene oxide units. In some cases, the polymer moiety C is a discrete PEG comprising, e.g., about 20 ethylene oxide units. In some cases, the polymer moiety C is a discrete PEG comprising, e.g., about 21 ethylene oxide units. In some cases, the polymer moiety C is a discrete PEG comprising, e.g., about 22 ethylene oxide units. In some cases, the polymer moiety C is a discrete PEG comprising, e.g., about 23 ethylene oxide units. In some cases, the polymer moiety C is a discrete PEG comprising, e.g., about 24 ethylene oxide units. In some cases, the polymer moiety C is a discrete PEG comprising. e.g., about 25 ethylene oxide units. In some cases, the polymer moiety C is a discrete PEG comprising, e.g., about 26 ethylene oxide units. In some cases, the polymer moiety C is a discrete PEG comprising, e.g., about 27 ethylene oxide units. In some cases, the polymer moiety C is a discrete PEG comprising, e.g., about 28 ethylene oxide units. In some cases, the polymer moiety C is a discrete PEG comprising, e.g., about 29 ethylene oxide units. In some cases, the polymer moiety C is a discrete PEG comprising, e.g., about 30 ethylene oxide units. In some cases, the polymer moiety C is a discrete PEG comprising, e.g., about 31 ethylene oxide units. In some cases, the polymer moiety C is a discrete PEG comprising, e.g., about 32 ethylene oxide units. In some cases, the polymer moiety C is a discrete PEG comprising, e.g., about 33 ethylene oxide units. In some cases, the polymer moiety C is a discrete PEG comprising, e.g., about 34 ethylene oxide units. In some cases, the polymer moiety C is a discrete PEG comprising, e.g., about 35 ethylene oxide units. In some cases, the polymer moiety C is a discrete PEG comprising, e.g., about 36 ethylene oxide units. In some cases, the polymer moiety C is a discrete PEG comprising, e.g., about 37 ethylene oxide units. In some cases, the polymer moiety C is a discrete PEG comprising, e.g., about 38 ethylene oxide units. In some cases, the polymer moiety C is a discrete PEG comprising, e.g., about 39 ethylene oxide units. In some cases, the polymer moiety C is a discrete PEG comprising, e.g., about 40 ethylene oxide units. In some cases, the polymer moiety C is a discrete PEG comprising, e.g., about 41 ethylene oxide units. In some cases, the polymer moiety C is a discrete PEG comprising, e.g., about 42 ethylene oxide units. In some cases, the polymer moiety C is a discrete PEG comprising, e.g., about 43 ethylene oxide units. In some cases, the polymer moiety C is a discrete PEG comprising, e.g., about 44 ethylene oxide units. In some cases, the polymer moiety C is a discrete PEG comprising, e.g., about 45 ethylene oxide units. In some cases, the polymer moiety C is a discrete PEG comprising, e.g., about 46 ethylene oxide units. In some cases, the polymer moiety C is a discrete PEG comprising, e.g., about 47 ethylene oxide units. In some cases, the polymer moiety C is a discrete PEG comprising, e.g., about 48 ethylene oxide units.

In some cases, the polymer moiety C is dPEG® (Quanta Biodesign Ltd).

In some embodiments, the polymer moiety C comprises a cationic mucic acid-based polymer (cMAP). In some instances, cMAP comprises one or more subunit of at least one repeating subunit, and the subunit structure is represented as Formula (V):

Formula V

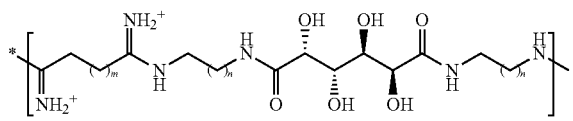

wherein m is independently at each occurrence 1, 2, 3, 4, 5, 6, 7, 8, 9, or 10, preferably 4-6 or 5; and n is independently at each occurrence 1, 2, 3, 4, or 5. In some embodiments, m and n are, for example, about 10.

In some instances, cMAP is further conjugated to a PEG moiety, generating a cMAP-PEG copolymer, an mPEG-cMAP-PEGm triblock polymer, or a cMAP-PEG-cMAP triblock polymer. In instances, the PEG moiety is in a range of from about 500 Da to about 50,000 Da. In some instances, the PEG moiety is in a range of from about 500 Da to about 1000 Da, greater than 1000 Da to about 5000 Da, greater than 5000 Da to about 10,000 Da, greater than 10,000 to about 25,000 Da, greater than 25,000 Da to about 50,000 Da, or any combination of two or more of these ranges.

In some instances, the polymer moiety C is cMAP-PEG copolymer, an mPEG-cMAP-PEGm triblock polymer, or a cMAP-PEG-cMAP triblock polymer. In some cases, the polymer moiety C is cMAP-PEG copolymer. In other cases, the polymer moiety C is an mPEG-cMAP-PEGm triblock polymer. In additional cases, the polymer moiety C is a cMAP-PEG-cMAP triblock polymer.

In some embodiments, the polymer moiety C is conjugated to the polynucleic acid molecule, the binding moiety, and optionally to the endosomolytic moiety as illustrated supra.

Endosomolytic or Cell Membrane Penetration Moiety

In some embodiments, a molecule of Formula (I): A-X$_1$—B—X$_2$—C, further comprises an additional conjugating moiety. In some instances, the additional conjugating moiety is an endosomolytic moiety and/or a cell membrane penetration moiety. In some cases, the endosomolytic moiety is a cellular compartmental release component, such as a compound capable of releasing from any of the cellular compartments known in the art, such as the endosome, lysosome, endoplasmic reticulum (ER), Golgi apparatus, microtubule, peroxisome, or other vesicular bodies with the cell. In some cases, the endosomolytic moiety comprises an endosomolytic polypeptide, an endosomolytic polymer, an endosomolytic lipid, or an endosomolytic small molecule. In some cases, the endosomolytic moiety comprises an endosomolytic polypeptide. In other cases, the endosomolytic moiety comprises an endosomolytic polymer. In some cases, the cell membrane penetration moiety comprises a cell penetrating peptide (CPP). In other cases, the cell membrane penetration moiety comprises a cell penetrating lipid. In other cases, the cell membrane penetration moiety comprises a cell penetrating small molecule.

Endosomolytic and Cell Membrane Penetration Polypeptides

In some embodiments, a molecule of Formula (I): A-X$_1$—B—X$_2$—C, is further conjugated with an endosomolytic polypeptide. In some cases, the endosomolytic polypeptide is a pH-dependent membrane active peptide. In some cases, the endosomolytic polypeptide is an amphipathic polypeptide. In additional cases, the endosomolytic polypeptide is a peptidomimetic. In some instances, the endosomolytic polypeptide comprises INF, melittin, meucin, or their respective derivatives thereof. In some instances, the endosomolytic polypeptide comprises INF or its derivatives thereof. In other cases, the endosomolytic polypeptide comprises melittin or its derivatives thereof. In additional cases, the endosomolytic polypeptide comprises meucin or its derivatives thereof.

In some instances, INF7 is a 24 residue polypeptide those sequence comprises CGIFGEIEELIEEGLENLIDWGNA (SEQ ID NO: 331), or GLFEAIEGFIENGWEG-MIDGWYGC (SEQ ID NO: 332). In some instances, INF7 or its derivatives comprise a sequence of: GLFEAIEGFIEN-GWEGMIWDYGSGSCG (SEQ ID NO: 333), GLFEAIEG-FIENGWEGMIDG WYG-(PEG)6-NH2 (SEQ ID NO: 334), or GLFEAIEGFIENGWEGMIWDYG-SGSC-K(GalNAc)2 (SEQ ID NO: 335).

In some cases, melittin is a 26 residue polypeptide those sequence comprises CLIGAILKVLATGLPTLISWIKNK- RKQ (SEQ ID NO. 336), or GIGAVLKVLTTGLPAL-ISWIKRKRQQ (SEQ ID NO: 337) In some instances, melittin comprises a polypeptide sequence as described in U.S. Pat. No. 8,501,930.

In some instances, meucin is an antimicrobial peptide (AMP) derived from the venom gland of the scorpion Mesobuthus eupeus. In some instances, meucin comprises of meucin-13 those sequence comprises IFGAIAGLLKNIF-NH$_2$ (SEQ ID NO: 338) and meucin-18 those sequence comprises FFGHLFKLATKIIPSLFQ (SEQ ID NO: 339).

In some instances, the endosomolytic polypeptide comprises a polypeptide in which its sequence is at least 50%, 60%, 70%, 80%, 90%, 95%, or 99% sequence identity to INF7 or its derivatives thereof, melittin or its derivatives thereof, or meucin or its derivatives thereof. In some instances, the endosomolytic moiety comprises INF7 or its derivatives thereof, melittin or its derivatives thereof, or meucin or its derivatives thereof.

In some instances, the endosomolytic moiety is INF7 or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 331-335. In some cases, the endosomolytic moiety comprises a polypeptide having at least 50%, 55%, 60%, 65%, 70%, 75%, 80%, 85%, 90°,%, 95%, 96%, 97%, 98%, 99%, or 100% sequence identity to SEQ ID NO: 331. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 332-335. In some cases, the endosomolytic moiety comprises SEQ ID NO: 331. In some cases, the endosomolytic moiety comprises SEQ ID NO: 332-335. In some cases, the endosomolytic moiety consists of SEQ ID NO: 331. In some cases, the endosomolytic moiety consists of SEQ ID NO: 332-335.

In some instances, the endosomolytic moiety is melittin or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 336 or 337. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 336. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 337. In some cases, the endosomolytic moiety comprises SEQ ID NO: 286. In some cases, the endosomolytic moiety comprises SEQ ID NO: 337. In some cases, the endosomolytic moiety consists of SEQ ID NO: 336. In some cases, the endosomolytic moiety consists of SEQ ID NO: 337.

In some instances, the endosomolytic moiety is meucin or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 338 or 339. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 338. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 339. In some cases, the endosomolytic moiety comprises SEQ ID NO: 338. In some cases, the endosomolytic moiety comprises SEQ ID NO: 339. In some cases, the endosomolytic moiety consists of SEQ ID NO: 338. In some cases, the endosomolytic moiety consists of SEQ ID NO: 339.

In some instances, the endosomolytic moiety comprises a sequence as illustrated in Table 8

TABLE 8

| NAME | ORIGIN | AMINO ACID SEQUENCE | SEQ ID NO: | TYPE |
| --- | --- | --- | --- | --- |
| Pep-1 | NLS from Simian Virus 40 large antigen and Reverse transcriptase of HIV | KETWWETWWTEWSQPKKKRKV | 340 | Primary amphipathic |
| pVEC | VE-cadherin | LLIILRRRRIRKQAHAHSK | 341 | Primary amphipathic |
| VT5 | Synthetic peptide | DPKGDPKGVTVTVTVTVTGKGDPKPD | 342 | β-sheet amphipathic |
| C105Y | 1-antitrypsin | CSIPPEVKFNKPFVYLI | 343 | — |
| Transportan | Galanin and mastoparan | GWTLNSAGYLLGKINLKALAALAKKIL | 344 | Primary amphipathic |
| TP10 | Galanin and mastoparan | AGYLLGKINLKALAALAKKIL | 345 | Primary amphipathic |
| MPG | A hydrophobic domain from the fusion sequence of HIV gp41 and NLS of SV40 T antigen | GALFLGFLGAAGSTMGA | 346 | β-sheet amphipathic |
| gH625 | Glycoprotein gH of HSV type I | HGLASTLTRWAHYNALIRAF | 347 | Secondary amphipathic α-helical |

TABLE 8-continued

| NAME | ORIGIN | AMINO ACID SEQUENCE | SEQ ID NO: | TYPE |
|---|---|---|---|---|
| CADY | PPTG1 peptide | GLWRALWRLLRSLWRLLWRA | 348 | Secondary amphipathic α-helical |
| GALA | Synthetic peptide | WEAALAEALAEALAEHLAEALAE ALEALAA | 349 | Secondary amphipathic α-helical |
| INF | Influenza HA2 fusion peptide | GLFEAIEGFIENGWEGMIDGWYGC | 350 | Secondary amphipathic α-helical/ pH-dependent membrane active peptide |
| HA2E5-TAT | Influenza HA2 subunit of influenza virus X31 strain fusion peptide | GLFGAIAGFIENGWEGMIDGWYG | 351 | Secondary amphipathic α-helical/ pH-dependent membrane active peptide |
| HA2-penetratin | Influenza HA2 subunit of influenza virus X31 strain fusion peptide | GLFGAIAGFIENGWEGMIDGRQIKI WFQNRRMKW KK-amide | 352 | pH-dependent membrane active peptide |
| HA-K4 | Influenza HA2 subunit of influenza virus X31 strain fusion peptide | GLFGAIAGFIENGWEGMIDG-SSKKKK | 353 | pH-dependent membrane active peptide |
| HA2E4 | Influenza HA2 subunit of influenza virus X31 strain fusion peptide | GLFEAIAGFIENGWEGMIDGGGYC | 354 | pH-dependent membrane active peptide |
| H5WYG | HA2 analogue | GLFHAIAHFIHGGWHGLIHGWYG | 355 | pH-dependent membrane active peptide |
| GALA-INF3-(PEG)6-NH | INF3 fusion peptide | GLFEAIEGFIENGWEGLAEALAEAL EALAA-(PEG)6-NH2 | 356 | pH-dependent membrane active peptide |
| CM18-TAT11 | Cecropin-A-Melittin$_{2-12}$ (CM$_{18}$) fusion peptide | KWKLFKKIGAVLKVLTIG-YGRKKRRQRRR | 357 | pH-dependent membrane active peptide |

In some cases, the endosomolytic moiety comprises a Bak BH3 polypeptide which induces apoptosis through antagonization of suppressor targets such as Bcl-2 and/or Bcl-x$_L$. In some instances, the endosomolytic moiety comprises a Bak BH3 polypeptide described in Albarran, et al., "Efficient intracellular delivery of a pro-apoptotic peptide with a pH-responsive carrier," Reactive & Functional Polymers 71: 261-265 (2011).

In some instances, the endosomolytic moiety comprises a polypeptide (e.g., a cell-penetrating polypeptide) as described in PCT Publication Nos. WO20131166155 or WO2015/069587.

Endosomolytic Lipids

In some embodiments, the endosomolytic moiety is a lipid (e.g., a fusogenic lipid). In some embodiments, a molecule of Formula (I): A-X$_1$—B—X$_2$—C, is further conjugated with an endosomolytic lipid (e.g., fusogenic lipid). Exemplary fusogenic lipids include 1,2-dileoyl-sn-3-phosphoethanolamine (DOPE), phosphatidylethanolamine (POPE), palmitoyloleoylphosphatidvlcholine (POPC), (6Z, 9Z,28Z,31Z)-heptatriaconta-6,9,28,31-tetraen-19-ol (Di-Lin), N-methyl(2,2-di((9Z,12Z)-octadeca-9,12-dienyl)-1,3-dioxolan-4-yl)methanamine (DLin-k-DMA) and N-methyl-2-(2,2-di((9Z,12Z)-octadeca-9,12-dienyl)-1,3-dioxolan-4-yl)ethanamine (XTC).

In some instances, an endosomolytic moiety is a lipid (e.g., a fusogenic lipid) described in PCT Publication No. WO09/126,933.

Endosomolytic Small Molecules

In some embodiments, the endosomolytic moiety is a small molecule. In some embodiments, a molecule of Formula (I). A-X$_1$—B—X$_2$—C, is further conjugated with an endosomolytic small molecule. Exemplary small molecules suitable as endosomolytic moieties include, but are not limited to, quinine, chloroquine, hydroxychloroquines, amodiaquins (camoquines), amopyroquines, primaquines, mefloquines, nivaquines, halofantrines, quinone imines, or a combination thereof. In some instances, quinoline endosomolytic moieties include, but are not limited to, 7-chloro-4-(4-diethylamino-1-methylbutyl-amino)quinoline (chloroquine); 7-chloro-4-(4-ethyl-(2-hydroxyethyl)-amino-1-methylbutyl-amino)quinoline (hydroxychloroquine); 7-fluoro-4-(4-diethylamino-1-methylbutyl-amino)quinoline; 4-(4-diethylamino-1-methylbutylamino) quinoline; 7-hydroxy-4-(4-diethyl-amino-1-methylbutylamino)quinoline; 7-chloro-4-(4-diethylamino-1-butylamino)quinoline (desmethylchloroquine); 7-fluoro-4-(4-diethylamino-1-butylamino)quinoline; 4-(4-diethyl-amino-1-butylamino) quinoline; 7-hydroxy-4-(4-diethylamino-1-butylamino)quinoline; 7-chloro-4-(1-carboxy-4-diethylamino-1-butylamino)quinoline; 7-fluoro-4-(1-carboxy-4-diethyl-amino-1-butylamino)quinoline; 4-(1-carboxy-4-diethylamino-1-butylamino) quinoline; 7-hydroxy-4-(1-carboxy-4-diethylamino-1-butylamino)quinoline; 7-chloro-4-(1-carboxy-4-diethylamino-1-methylbutylamino) quinoline; 7-fluoro-4-(1-carboxy-4-diethyl-amino-1-methylbutylamino)quinoline; 4-(1-carboxy-4-diethylamino-1-methylbutylamino)quinoline; 7-hydroxy-4-(1-carboxy-4-diethylamino-1-methylbutylamino)quinoline; 7-fluoro-4-(4-ethyl-(2-hydroxyethyl)-amino-1-methylbutylamino) quinoline; 4-(4-ethyl-(2-hydroxy-ethyl)-amino-1-methylbutylamino-)quinoline; 7-hydroxy-4-(4-ethyl-(2-hydroxyethyl)-amino-1-methylbutylamino)quinoline; hydroxychloroquine phosphate; 7-chloro-4-(4-ethyl-(2-hydroxyethyl-1)-amino-1-butylamino)quinoline (desmethylhydroxychloroquine); 7-fluoro-4-(4-ethyl-(2-hydroxyethyl)-amino-1-butylamino)quinoline; 4-(4-ethyl-(2-hydroxyethyl)-amino-1-butylamino)quinoline; 7-hydroxy-4-(4-ethyl-(2-hydroxyethyl)-amino-1-butylamino)quinoline; 7-chloro-4-(1-carboxy-4-ethyl-(2-hydroxyethyl)-amino-1-butylamino)quinoline; 7-fluoro-4-(1-carboxy-4-ethyl-(2-hydroxyethyl)-amino-1-butylamino)quinoline; 4-(1-carboxy-4-ethyl-(2-hydroxyethyl)-amino-1-butylamino)quinoline; 7-hydroxy-4-(1-carboxy-4-ethyl-(2-hydroxyethyl)-amino-1-butylamino)quinoline; 7-chloro-4-(1-carboxy-4-ethyl-(2-hydroxyethyl)-amino-1-methylbutylamino)quinoline; 7-fluoro-4-(1-carboxy-4-ethyl-(2-hydroxyethyl)-amino-1-methylbutylamino) quinoline; 4-(1-carboxy-4-ethyl-(2-hydroxyethyl)-amino-1-methylbutylamino)quinoline; 7-hydroxy-4-(1-carboxy-4-ethyl-(2-hydroxyethyl)-amino-1-methylbutylamino) quinoline; 8-[(4-aminopentyl)amino]-6-methoxydihydrochloride quinoline; 1-acetyl-1,2,3,4-tetrahydroquinoline; 8-[(4-aminopentyl)amino]-6-methoxyquinoline dihydrochloride; 1-butyryl-1,2,3,4-tetrahydroquinoline; 3-chloro-4-(4-hydroxy-alpha,alpha'-bis(2-methyl-1-pyrrolidinyl)-2,5-xylidinoquinoline, 4-[(4-diethyl-amino)-1-methylbutyl-amino]-6-methoxyquinoline; 3-fluoro-4-(4-hydroxy-alpha,alpha'-bis(2-methyl-1-pyrrolidinyl)-2,5-xylidinoquinoline, 4-[(4-diethylamino)-1-methylbutyl-amino]-6-methoxyquinoline; 4-(4-hydroxy-alpha, alpha'-bis(2-methyl-1-pyrrolidinyl)-2,5-xylidinoquinoline; 4-[(4-diethylamino)-1-methylbutyl-amino]-6-methoxyquinoline; 3,4-dihydro-1-(2H)-quinolinecarboxyaldehyde; 1,1'-pentamethylene diquinoleinium diiodide; 8-quinolinol sulfate and amino, aldehyde, carboxylic, hydroxyl, halogen, keto, sulfhydryl and vinyl derivatives or analogs thereof. In some instances, an endosomolytic moiety is a small molecule described in Naisbitt et al (1997, J Pharmacol Exp Therapy 280:884-893) and in U.S. Pat. No. 5,736,557.

Cell Penetrating Polypeptide (CPP)

In some embodiments, cell penetrating polypeptide comprises positively charged short peptides with 5-30 amino acids. In some embodiments, cell penetrating polypeptide comprises arginine or lysine rich amino acid sequences. In some embodiments, cell penetrating polypeptide includes any polypeptide or combination thereof listed in Table 9

TABLE 9

| Peptide | Sequence | SEQ ID NO |
| --- | --- | --- |
| Antennapedia Penetratin (43-58) | RQIKIWFQNRRMKWKK | 358 |
| HIV-1 TAT protein (48-60) | GRKKRRQRRRPPQ | 359 |
| pVEC Cadherin (615-632) | LLIILRRRIRKQAHAHSK | 360 |
| Transportan Galanine/Mastoparan | GWTLNSAGYLLGKINLKALAALAKKIL | 361 |
| MPG HIV-gp41/SV40 T-antigen | GALFLGFLGAAGSTMGAWSQPKKKRKV | 362 |
| Pep-1 HIV-reverse transcriptase/SV40 T-antigen | KETWWETWWTEWSQPKKKRKV | 363 |
| Polyarginines | R(n); 6 < n < 12 | 364 |
| MAP | KLALKLALKALKAALKLA | 365 |
| R6W3 | RRWWRRWRR | 366 |
| NLS | CGYGPKKKRKVGG | 367 |
| 8-lysines | KKKKKKKK | 368 |
| ARF (1-22) | MVRRFLVTLRIRRACGPPRVRV | 369 |
| Azurin-p28 | LSTAADMQGVVTDGMASGLDKDYLKPDD | 370 |

Linkers

In some embodiments, a linker described herein is a cleavable linker or a non-cleavable linker. In some instances, the linker is a cleavable linker. In other instances, the linker is a non-cleavable linker.

In some cases, the linker is a non-polymeric linker. A non-polymeric linker refers to a linker that does not contain a repeating unit of monomers generated by a polymerization process. Exemplary non-polymeric linkers include, but are not limited to, $C_1$-$C_6$ alkyl group (e.g., a $C_5$, $C_4$, $C_3$, $C_2$, or $C_1$ alkyl group), homobifunctional cross linkers, heterobifunctional cross linkers, peptide linkers, traceless linkers, self-immolative linkers, maleimide-based linkers, or combinations thereof. In some cases, the non-polymeric linker comprises a $C_1$-$C_6$ alkyl group (e.g. a $C_5$, $C_4$, $C_3$, $C_2$, or $C_1$ alkyl group), a homobifunctional cross linker, a heterobifunctional cross linker, a peptide linker, a traceless linker, a self-immolative linker, a maleimide-based linker, or a combination thereof. In additional cases, the non-polymeric linker does not comprise more than two of the same type of linkers, e.g., more than two homobifunctional cross linkers, or more than two peptide linkers. In further cases, the non-polymeric linker optionally comprises one or more reactive functional groups.

In some instances, the non-polymeric linker does not encompass a polymer that is described above. In some instances, the non-polymeric linker does not encompass a polymer encompassed by the polymer moiety C. In some cases, the non-polymeric linker does not encompass a polyalkylene oxide (e.g., PEG). In some cases, the non-polymeric linker does not encompass a PEG.

In some instances, the linker comprises a homobifunctional linker. Exemplary homobifunctional linkers include, but are not limited to, Lomant's reagent dithiobis (succinimidylpropionate) DSP, 3'3'-dithiobis(sulfosuccinimidyl proprionate (DTSSP), disuccinimidyl suberate (DSS), bis (sulfosuccinimidyl)suberate (BS), disuccinimidyl tartrate (DST), disulfosuccinimidyl tartrate (sulfo DST), ethylene glycobis(succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide).

In some embodiments, the linker comprises a heterobifunctional linker. Exemplary heterobifunctional linker include, but are not limited to, amine-reactive and sulfhydryl cross-linkers such as N-succinimidyl 3-(2-pyridyldithio) propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMBs), N-(γ-maleimidobutyryloxy)sulfosuccinimide ester (sulfo-GMBs), succinimidyl 6-((iodoacetyl)amino)hexanoate (sIAX), succinimidyl 6-[6-(((iodoacetyl)amino) hexanoyl)amino]hexanoate (sIAXX), succinimidyl 4-(((iodoacetyl)amino)methyl)cyclohexane-1-carboxylate (sIAC), succinimidyl 6-((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl) butyric acid hydrazide (MPBH), 4-(N-maleimidomethyl) cyclohexane-1-carboxyl-hydrazide-8 ($M_2C_2H$), 3-(2-pyridyldithio)propionyl hydrazide (PDPH), amine-reactive and photoreactive cross-linkers such as N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido)hexanoate (sulfo-NHs-LC-AsA), sulfosuccinimidyl-2-(p-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(p-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), p-nitrophenyl diazopyruvate (pNPDP), p-nitrophenyl-2-diazo-3,3,3-trifluoropropionate (PNP-DTP), sulfhydryl-reactive and photoreactive cross-linkers such as 1-(p-Azidosalicylamido)-4-(iodoacetamido) butane (AsIB), N-[4-(p-azidosalicylamido)butyl]-3'-(2'-pyridyldithio)propionamide (APDP), benzophenone-4-iodoacetamide, benzophenone-4-maleimide carbonyl-reactive and photoreactive cross-linkers such as p-azidobenzoyl hydrazide (ABH), carboxylate-reactive and photoreactive cross-linkers such as 4-(p-azidosalicylamido) butylamine (AsBA), and arginine-reactive and photoreactive cross-linkers such as p-azidophenyl glyoxal (APG).

In some instances, the linker comprises a reactive functional group. In some cases, the reactive functional group comprises a nucleophilic group that is reactive to an electrophilic group present on a binding moiety. Exemplary electrophilic groups include carbonyl groups-such as aldehyde, ketone, carboxylic acid, ester, amide, enone, acyl halide or acid anhydride. In some embodiments, the reactive functional group is aldehyde. Exemplary nucleophilic groups include hydrazide, oxime, amino, hydrazine, thiosemicarbazone, hydrazine carboxylate, and arylhydrazide.

In some embodiments, the linker comprises a maleimide group. In some instances, the maleimide group is also referred to as a maleimide spacer. In some instances, the maleimide group further encompasses a caproic acid, forming maleimidocaproyl (mc). In some cases, the linker comprises maleimidocaproyl (mc). In some cases, the linker is maleimidocaproyl (mc). In other instances, the maleimide group comprises a maleimidomethyl group, such as succinimidyl-4-(N-maleimidomethyl)cyclohexane-1-carboxylate (sMCC) or sulfosuccinimidyl-4-(N-maleimidomethyl)cyclohexane-1-carboxylate (sulfo-sMCC) described above.

In some embodiments, the maleimide group is a self-stabilizing maleimide. In some instances, the self-stabilizing maleimide utilizes diaminopropionic acid (DPR) to incorporate a basic amino group adjacent to the maleimide to provide intramolecular catalysis of tiosuccinimide ring hydrolysis, thereby eliminating maleimide from undergoing an elimination reaction through a retro-Michael reaction. In some instances, the self-stabilizing maleimide is a maleimide group described in Lyon et al., "Self-hydrolyzing maleimides improve the stability and pharmacological properties of antibody-drug conjugates," Nat. Biotechnol. 32(10): 1059-1062 (2014). In some instances, the linker comprises a self-stabilizing maleimide. In some instances, the linker is a self-stabilizing maleimide.

In some embodiments, the linker comprises a peptide moiety. In some instances, the peptide moiety comprises at least 2, 3, 4, 5, or 6 more amino acid residues. In some instances, the peptide moiety comprises at most 2, 3, 4, 5, 6, 7, or 8 amino acid residues. In some instances, the peptide moiety comprises about 2, about 3, about 4, about 5, or about 6 amino acid residues. In some instances, the peptide moiety is a cleavable peptide moiety (e.g., either enzymatically or chemically). In some instances, the peptide moiety is a non-cleavable peptide moiety. In some instances, the peptide moiety comprises Val-Cit (valine-citrulline). Gly-Gly-Phe-Gly (SEQ ID NO: 403), Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 404), or Gly-Phe-Leu-Gly (SEQ ID NO: 410). In some instances, the linker comprises a peptide moiety such as: Val-Cit (valine-citrulline), Gly-Gly-Phe-Gly, Phe-Lys. Val-Lys, Gly-Phe-Lys, Phe-Phe-Lys, Ala-Lys. Val-Arg, Phe-Cit, Phe-Arg, Leu-Cit, Ile-Cit, Trp-Cit, Phe-Ala, Ala-Leu-Ala-Leu, or Gly-Phe-Leu-Gly (SEQ ID NO: 405). In some cases, the linker comprises Val-Cit. In some cases, the linker is Val-Cit.

In some embodiments, the linker comprises a benzoic acid group, or its derivatives thereof. In some instances, the benzoic acid group or its derivatives thereof comprise paraaminobenzoic acid (PABA). In some instances, the benzoic acid group or its derivatives thereof comprise gamma-aminobutyric acid (GABA).

In some embodiments, the linker comprises one or more of a maleimide group, a peptide moiety, and/or a benzoic acid group, in any combination. In some embodiments, the linker comprises a combination of a maleimide group, a peptide moiety, and/or a benzoic acid group. In some instances, the maleimide group is maleimidocaproyl (mc). In some instances, the peptide group is val-cit. In some instances, the benzoic acid group is PABA. In some instances, the linker comprises a mc-val-cit group. In some cases, the linker comprises a val-cit-PABA group. In additional cases, the linker comprises a mc-val-cit-PABA group.

In some embodiments, the linker is a self-immolative linker or a self-elimination linker. In some cases, the linker is a self-immolative linker. In other cases, the linker is a self-elimination linker (e.g., a cyclization self-elimination linker). In some instances, the linker comprises a linker described in U.S. Pat. No. 9,089,614 or PCT Publication NO. WO2015038426.

In some embodiments, the linker is a dendritic type linker. In some instances, the dendritic type linker comprises a branching, multifunctional linker moiety. In some instances, the dendritic type linker is used to increase the molar ratio of polynucleotide B to the binding moiety A. In some instances, the dendritic type linker comprises PAMAM dendrimers.

In some embodiments, the linker is a traceless linker or a linker in which after cleavage does not leave behind a linker moiety (e.g., an atom or a linker group) to a binding moiety A, a polynucleotide B, a polymer C, or an endosomolytic moiety D. Exemplary traceless linkers include, but are not limited to, germanium linkers, silicium linkers, sulfur linkers, selenium linkers, nitrogen linkers, phosphorus linkers, boron linkers, chromium linkers, or phenylhydrazide linker. In some cases, the linker is a traceless aryl-triazene linker as described in Hejesen, et al., "A traceless aryl-triazene linker for DNA-directed chemistry." Org Biomol Chem 11(15): 2493-2497 (2013). In some instances, the linker is a traceless linker described in Blaney, et al., "Traceless solid-phase organic synthesis," Chem. Rev. 102: 2607-2024 (2002). In some instances, a linker is a traceless linker as described in U.S. Pat. No. 6,821,783.

In some instances, the linker is a linker described in U.S. Pat. Nos. 6,884,869; 7,498,298; 8,288,352; 8,609,105; or 8,697,688; U.S. Patent Publication NOs. 2014/0127239; 2013/028919; 2014/286970; 2013/0309256; 2015/037360; or 2014/0294851; or PCT Publication NOs. WO2015057699; WO2014080251; WO2014197854; WO2014145090; or WO2014177042.

In some embodiments, $X_1$ and $X_2$ are each independently a bond or a non-polymeric linker. In some instances, $X_1$ and $X_2$ are each independently a bond. In some cases, $X_1$ and $X_2$ are each independently a non-polymeric linker.

In some instances, $X_1$ is a bond or a non-polymeric linker. In some instances, $X_1$ is a bond. In some instances, $X_1$ is a non-polymeric linker. In some instances, the linker is a $C_1$-$C_6$ alkyl group. In some cases, $X_1$ is a $C_1$-$C_6$ alkyl group, such as for example, a $C_5$, $C_4$, $C_3$, $C_2$, or $C_1$ alkyl group. In some cases, the $C_1$-$C_6$ alkyl group is an unsubstituted $C_1$-$C_6$ alkyl group. As used in the context of a linker, and in particular in the context of $X_1$, alkyl means a saturated straight or branched hydrocarbon radical containing up to six carbon atoms. In some instances, $X_1$ includes a homobifunctional linker or a heterobifunctional linker described supra. In some cases, $X_1$ includes a heterobifunctional linker. In some cases, $X_1$ includes sMCC. In other instances. $X_1$ includes a heterobifunctional linker optionally conjugated to a $C_1$-$C_6$ alkyl group. In other instances, $X_1$ includes sMCC optionally conjugated to a $C_1$-$C_6$ alkyl group. In additional instances, $X_1$ does not include a homobifunctional linker or a heterobifunctional linker described supra.

In some instances, $X_2$ is a bond or a linker. In some instances, $X_2$ is a bond. In other cases, $X_2$ is a linker. In additional cases, $X_2$ is a non-polymeric linker. In some embodiments, $X_2$ is a $C_1$-$C_6$ alkyl group. In some instances, $X_2$ is a homobifunctional linker or a heterobifunctional linker described supra. In some instances, $X_2$ is a homobifunctional linker described supra. In some instances, $X_2$ is a heterobifunctional linker described supra. In some instances, $X_2$ comprises a maleimide group, such as maleimidocaproyl (mc) or a self-stabilizing maleimide group described above. In some instances, $X_2$ comprises a peptide moiety, such as Val-Cit. In some instances, $X_2$ comprises a benzoic acid group, such as PABA. In additional instances, $X_2$ comprises a combination of a maleimide group, a peptide moiety, and/or a benzoic acid group. In additional instances, $X_2$ comprises a mc group. In additional instances, $X_2$ comprises a mc-val-cit group. In additional instances, $X_2$ comprises a val-cit-PABA group. In additional instances, $X_2$ comprises a mc-val-cit-PABA group.

Methods of Use

Muscle atrophy refers to a loss of muscle mass and/or to a progressive weakening and degeneration of muscles. In some cases, the loss of muscle mass and/or the progressive weakening and degeneration of muscles occurs due to a high rate of protein degradation, a low rate of protein synthesis, or a combination of both. In some cases, a high rate of muscle protein degradation is due to muscle protein catabolism (i.e., the breakdown of muscle protein in order to use amino acids as substrates for gluconeogenesis).

In one embodiment, muscle atrophy refers to a significant loss in muscle strength. By significant loss in muscle strength is meant a reduction of strength in diseased, injured, or unused muscle tissue in a subject relative to the same muscle tissue in a control subject. In an embodiment, a significant loss in muscle strength is a reduction in strength of at least 10%, at least 15%, at least 20%, at least 25%, at least 30%, at least 35%, at least 40%, at least 45%, at least 50%, or more relative to the same muscle tissue in a control subject. In another embodiment, by significant loss in muscle strength is meant a reduction of strength in unused muscle tissue relative to the muscle strength of the same muscle tissue in the same subject prior to a period of nonuse. In an embodiment, a significant loss in muscle strength is a reduction of at least 10%, at least 15%, at least 20%, at least 25%, at least 30%, at least 35%, at least 40%, at least 45%, at least 50%, or more relative to the muscle strength of the same muscle tissue in the same subject prior to a period of nonuse.

In another embodiment, muscle atrophy refers to a significant loss in muscle mass. By significant loss in muscle mass is meant a reduction of muscle volume in diseased, injured, or unused muscle tissue in a subject relative to the same muscle tissue in a control subject. In an embodiment, a significant loss of muscle volume is at least 10%, at least 15%, at least 20%, at least 25%, at least 30%, at least 35%, at least 40%, at least 45%, at least 50%, or more relative to the same muscle tissue in a control subject. In another embodiment, by significant loss in muscle mass is meant a reduction of muscle volume in unused muscle tissue relative to the muscle volume of the same muscle tissue in the same subject prior to a period of nonuse. In an embodiment, a significant loss in muscle tissue is at least 10%, at least 15%, at least 20%, at least 25%, at least 30%, at least 35%, at least 40%, at least 45%, at least 50%, or more relative to the muscle volume of the same muscle tissue in the same subject prior to a period of nonuse. Muscle volume is optionally measured by evaluating the cross-section area of a muscle such as by Magnetic Resonance Imaging (e.g. by a muscle volume/cross-section area (CSA) MRI method).

In some embodiments, described herein is a method of treating muscle atrophy in a subject, which comprises providing polynucleic acid molecule described herein and administering to the subject a therapeutically effective amount of a polynucleic acid molecule described herein or a polynucleic acid molecule conjugate described herein to reduces a quantity of the mRNA transcript of human DUX4. In some instances, the muscle atrophy is associated with Facioscapulohumeral muscular dystrophy (FSHD). The polynucleic acid moiety mediates RNA interference against the human DUX4 as to modulating muscle atrophy in a subject. In some embodiments, expression of one or more marker genes that are affected by DUX4 expression is also altered or modulated (e.g., decreased) by the decreased expression of human DUX4. The marker genes includes, but not limited to, MBD3L2, TRIM43, PRAMEF1, ZSCAN4, KHDC1L, and LEUTX. In some embodiments, the expression of one or more marker genes is decreased at least 10%, 15%, 20%, 25%, 30%, 35%, 40%, 45%, or 50% compared to untreated cells. In some embodiments, the expression of one or more marker genes, as a group or a composite, is decreased at least 10%, 15%, 20%, 25%, 30%, 35%, 40%, 45%, or 50% compared to untreated cells.

In some embodiments, described herein is a method of treating muscle atrophy in a subject, which comprises providing an siRNA antibody conjugate described herein and administering to the subject a therapeutically effective amount of the siRNA antibody conjugate described herein and reducing the levels of mRNA transcript of human DUX4 in said subject. In some instances, the muscle atrophy is associated with FSHD. The siRNA antibody conjugate mediates RNA interference against the human DUX4 mRNA as to treat muscle atrophy in the subject, which comprises administering to the subject a therapeutically effective amount of the siRNA antibody conjugate described herein and reducing the levels of mRNA transcript of human DUX4 in said subject.

In some embodiments, described herein is a method of treating muscle atrophy in a subject, which comprises providing a DUX4siRNA antibody conjugate (DUX4 siRNA-conjugate or DUX4-AOC) described herein and administering to the subject a therapeutically effective amount of the DUX4 siRNA antibody conjugate described herein and reducing the levels of mRNA transcript of human DUX4 in said subject. In some instances, the muscle atrophy is associated with FSHD. The DUX4 siRNA antibody conjugate mediates RNA interference against the human DUX4 mRNA as to treat muscle atrophy in the subject, which comprises administering to the subject a therapeutically effective amount of the DUX4 siRNA antibody conjugate described herein and reducing the levels of mRNA transcript of human DUX4 in said subject.

In some embodiments, described herein is a method of treating FSHD in a subject, which comprises providing a DUX4 siRNA antibody conjugate (DUX4 siRNA conjugate or DUX4-AOC) described herein and administering to the subject a therapeutically effective amount of the DUX4 siRNA antibody conjugate described herein and reducing the levels of mRNA transcript of human DUX4 in said subject. In some instances, the FSHD is FSHD type 1 (FSHD1). In some instances, the FSHD is FSHD type 2. The DUX4 siRNA antibody conjugate mediates RNA interference against the human DUX4 mRNA as to treat FSHD in the subject, which comprises administering to the subject a therapeutically effective amount of the DUX4 siRNA-conjugate described herein and reducing the levels of mRNA transcript of human DUX4 in said subject. In some embodiments, expression levels of one or more marker genes that are affected by DUX4 expression are also altered or modulated by the decreased expression levels of human DUX4. The DUX4 biomarker genes include but are not limited to MBD3L2, TRIM43, PRAMEF1, ZSCAN4, KHDC1L, and LEUTX.

In some embodiments, described herein is a method of alleviating symptoms in a subject with FSHD, which comprises providing a DUX siRNA antibody conjugate (DUX4-siRNA conjugate or DUX4-AOC) described herein and administering to the subject a therapeutically effective amount of the siRNA conjugate described herein by reducing the levels of mRNA transcript of human DUX4. In some instances, the FSHD is FSHD type 1 (FSHD1). In some instances, the FSHD is FSHD type 2. In another embodiments, described herein is a method of alleviating symptoms in a FSHD patient, which comprises providing an siRNA conjugate described herein and administering to the FSHD patient a therapeutically effective amount of the siRNA conjugate describes herein by reducing the levels of mRNA transcript of human DUX4 or reducing the levels of DUX4 protein.

In some instances, the symptoms of FSHD affect skeletal muscles. The skeletal muscles affected by FSHD include muscles around the eyes and mouth, muscle of the shoulders, muscle of the upper arms, muscle of the lower legs, abdominal muscles and hip muscles. In some instances, the symptoms of FSHD also affects vision and hearing. In some instances, the symptoms of FSHD also affect the function of the heart or lungs. In some instances, the symptoms of FSHD include muscle weakness, muscle atrophy, muscle dystrophy, pain inflammation, contractures, scioliosis, lordosis, hypoventilation, abnormalities of the retina, exposure to keratitis, mild hearing loss, and EMG abnormality.

In some embodiments, described herein is a method of improving skeletal muscle functions in a FSHD patient comprising the step of administering to the FSHD patient a therapeutically effective amount of the siRNA conjugate described herein by reducing the levels of mRNA transcript of human DUX4 or reducing the levels of DUX4 protein. In some instances, FSHD is FSHD type 1 (FSHD1). In some instances, FSHD is FSHD type 2. In some embodiments, described herein is a method of improving skeletal muscle functions, vision, hearing, heart functions or lung functions in a patient suffering from FSHD comprising the step of administering to the FSHD patient a therapeutically effective amount of the siRNA conjugate described herein by reducing the levels of mRNA transcript of human DUX4 or reducing the levels of DUX4 protein.

In some embodiments, described herein is a method of treating FSHD in a subject, which comprises providing an antisense oligonucleotide (ASO) antibody conjugate (ASO conjugate) described herein and administering to the subject a therapeutically effective amount of the ASO-antibody conjugate described herein and reducing the levels of mRNA transcript of human DUX4 in said subject. In some instances, FSHD is FSHD type 1 (FSHD1). In some instances, FSHD is FSHD type 2. The ASO-conjugate mediates RNA interference against the human DUX4 mRNA as to treat FSHD in the subject, which comprises administering to the subject a therapeutically effective amount of the ASO-antibody conjugate described herein and reducing the levels of mRNA transcript of human DUX4 in said subject. In some embodiments, expression levels of one or more marker genes that are affected by DUX4 expression is also altered or modulated by the decreased expression levels of human DUX4. The DUX4 biomarker genes include but are not limited to MBD3L2, TRIM43, PRAMEF1. ZSCAN4, KHDC1L, and LEUTX.

In some embodiments, described herein is a method of treating FSHD in a subject. In some instances, the FSHD subject suffers from FSHD1. In other instances, the FSHD subject suffers from FSHD2. In another embodiment, the FSHD subject has muscle cells abnormally expressing DUX4 protein caused by the genetic and epigenetic molecular changes in the D4Z4 region of the long arm of chromosome 4. The genetic molecular changes in the muscle cells are mutations leading to the contraction of the D4Z4 region containing 1-10 repeats instead of the normal 11 to 100 repeats of chromosome 4 of the FSHD subject. The epigenetic molecular changes in the muscle cells are changes leading to the hypomethylation of the D4Z4 region of chromosome 4 of the FSHD subject. In some instances, the muscle cells are skeletal muscle cells.

Pharmaceutical Formulation

In some embodiments, the pharmaceutical formulations described herein are administered to a subject by multiple administration routes, including but not limited to, parenteral (e.g., intravenous, subcutaneous, intramuscular), oral, intranasal, buccal, rectal, or transdermal administration routes. In some instances, the pharmaceutical composition describe herein is formulated for parenteral (e.g., intravenous, subcutaneous, intramuscular, intra-arterial, intraperitoneal, intrathecal, intracerebral, intracerebroventricular, or intracranial) administration. In other instances, the pharmaceutical composition describe herein is formulated for oral administration. In still other instances, the pharmaceutical composition describe herein is formulated for intranasal administration.

In some embodiments, the pharmaceutical formulations include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations (e.g., nanoparticle formulations), and mixed immediate and controlled release formulations.

In some instances, the pharmaceutical formulation includes multiparticulate formulations. In some instances, the pharmaceutical formulation includes nanoparticle formulations. In some instances, nanoparticles comprise cMAP, cyclodextrin, or lipids. In some cases, nanoparticles comprise solid lipid nanoparticles, polymeric nanoparticles, self-emulsifying nanoparticles, liposomes, microemulsions, or micellar solutions. Additional exemplary nanoparticles include, but are not limited to, paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes and quantum dots. In some instances, a nanoparticle is a metal nanoparticle, e.g., a nanoparticle of scandium, titanium, vanadium, chromium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum, gold, gadolinium, aluminum, gallium, indium, tin, thallium, lead, bismuth, magnesium, calcium, strontium, barium, lithium, sodium, potassium, boron, silicon, phosphorus, germanium, arsenic, antimony, and combinations, alloys or oxides thereof.

In some instances, a nanoparticle includes a core or a core and a shell, as in a core-shell nanoparticle.

In some instances, a nanoparticle is further coated with molecules for attachment of functional elements (e.g., with one or more of a polynucleic acid molecule or binding moiety described herein). In some instances, a coating comprises chondroitin sulfate, dextran sulfate, carboxymethyl dextran, alginic acid, pectin, carragheenan, fucoidan, agaropectin, porphyran, karaya gum, gellan gum, xanthan gum, hyaluronic acids, glucosamine, galactosamine, chitin (or chitosan), polyglutamic acid, polyaspartic acid, lysozyme, cytochrome C, ribonuclease, trypsinogen, chymotrypsinogen, α-chymotrypsin, polylysine, polyarginine, histone, protamine, ovalbumin or dextrin or cyclodextrin. In some instances, a nanoparticle comprises a graphene-coated nanoparticle.

In some cases, a nanoparticle has at least one dimension of less than about 500 nm, 400 nm, 300 nm, 200 nm, or 100 nm.

In some instances, the nanoparticle formulation comprises paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes or quantum dots. In some instances, a polynucleic acid molecule or a binding moiety described herein is conjugated either directly or indirectly to the nanoparticle. In some instances, at least 1, 5, 10, 15, 20, 30, 40, 50, 60, 70, 80, 90, 100 or more polynucleic acid molecules or binding moieties described herein are conjugated either directly or indirectly to a nanoparticle.

In some embodiments, the pharmaceutical formulation comprises a delivery vector, e.g., a recombinant vector, the delivery of the polynucleic acid molecule into cells. In some instances, the recombinant vector is DNA plasmid. In other instances, the recombinant vector is a viral vector. Exemplary viral vectors include vectors derived from adeno-associated virus, retrovirus, adenovirus, or alphavirus. In some instances, the recombinant vectors capable of expressing the polynucleic acid molecules provide stable expression in target cells. In additional instances, viral vectors are used that provide for transient expression of polynucleic acid molecules.

In some embodiments, the pharmaceutical formulation includes a carrier or carrier materials selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerine, magnesium silicate, polyvinylpyrrolidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa: Mack Publishing Company, 1995); Hoover, John E., Remington's Pharmaceutical Sciences, Mack Publishing Co., Easton, Pennsylvania 1975; Liberman, H. A., and Lachman, L., Eds., *Pharmaceutical Dosage Forms*, Marcel Decker, New York, N.Y., 1980; and *Pharmaceutical Dosage Forms* and Drug Delivery Systems, Seventh Ed. (Lippincott Williams & Wilkins 1999).

In some instances, the pharmaceutical formulation further includes pH adjusting agents or buffering agents which include acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some instances, the pharmaceutical formulation further includes diluent which are used to stabilize compounds because they provide a more stable environment. Salts dissolved in buffered solutions (which also provide pH control or maintenance) are utilized as diluents in the art, including, but not limited to a phosphate buffered saline solution. In certain instances, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

In some cases, the pharmaceutical formulation includes disintegration agents or disintegrants to facilitate the breakup or disintegration of a substance. The term "disintegrate" include both the dissolution and dispersion of the dosage form when contacted with gastrointestinal fluid. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia® and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked poly vinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In some instances, the pharmaceutical formulation includes filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

Lubricants and glidants are also optionally included in the pharmaceutical formulations described herein for preventing, reducing or inhibiting adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax®, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

Plasticizers include compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. Plasticizers also function as dispersing agents or wetting agents.

Solubilizers include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

Stabilizers include compounds such as any antioxidation agents, buffers, acids, preservatives and the like.

Suspending agents include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol has a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g. Pluronic® (BASF), and the like. Additional surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. Sometimes, surfactants is included to enhance physical stability or for other purposes.

Viscosity enhancing agents include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

Wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Therapeutic Regimens

In some embodiments, the pharmaceutical compositions described herein are administered for therapeutic applications. In some embodiments, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, once in two months, once in three months, once in four months, once in five months, once in six months or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In some embodiments, one or more pharmaceutical compositions are administered simultaneously, sequentially, or at an interval period of time. In some embodiments, one or more pharmaceutical compositions are administered simultaneously. In some cases, one or more pharmaceutical compositions are administered sequentially. In additional cases, one or more pharmaceutical compositions are administered at an interval period of time (e.g., the first administration of a first pharmaceutical composition is on day one followed by an interval of at least 1, 2, 3, 4, 5, or more days prior to the administration of at least a second pharmaceutical composition).

In some embodiments, two or more different pharmaceutical compositions are co-administered. In some instances, the two or more different pharmaceutical compositions are co-administered simultaneously. In some cases, the two or more different pharmaceutical compositions are co-administered sequentially without a gap of time between administrations. In other cases, the two or more different pharmaceutical compositions are co-administered sequentially with a gap of about 0.5 hour, 1 hour, 2 hour, 3 hour, 12 hours, 1 day, 2 days, or more between administrations.

In the case wherein the patient's status does improve, upon the doctor's discretion the administration of the composition is given continuously; alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages is altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Kits/Article of Manufacture

Disclosed herein, in certain embodiments, are kits and articles of manufacture for use with one or more of the compositions and methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include target nucleic acid molecule described herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

The term "therapeutically effective amount" relates to an amount of a polynucleic acid molecule conjugate that is sufficient to provide a desired therapeutic effect in a mammalian subject. In some cases, the amount is single or multiple dose administration to a patient (such as a human) for treating, preventing, preventing the onset of, curing, delaying, reducing the severity of, ameliorating at least one symptom of a disorder or recurring disorder, or prolonging the survival of the patient beyond that expected in the absence of such treatment. Naturally, dosage levels of the particular polynucleic acid molecule conjugate employed to provide a therapeutically effective amount vary in dependence of the type of injury, the age, the weight, the gender, the medical condition of the subject, the severity of the condition, the route of administration, and the particular inhibitor employed. In some instances, therapeutically effective amounts of polynucleic acid molecule conjugate, as described herein, is estimated initially from cell culture and animal models. For example, $IC_{50}$ values determined in cell culture methods optionally serve as a starting point in animal models, while ICs values determined in animal models are optionally used to find a therapeutically effective dose in humans.

Skeletal muscle, or voluntary muscle, is generally anchored by tendons to bone and is generally used to effect skeletal movement such as locomotion or in maintaining posture. Although some control of skeletal muscle is generally maintained as an unconscious reflex (e.g., postural muscles or the diaphragm), skeletal muscles react to conscious control. Smooth muscle, or involuntary muscle, is found within the walls of organs and structures such as the esophagus, stomach, intestines, uterus, urethra, and blood vessels.

Skeletal muscle is further divided into two broad types: Type I (or "slow twitch") and Type II (or "fast twitch"). Type I muscle fibers are dense with capillaries and are rich in mitochondria and myoglobin, which gives Type I muscle tissue a characteristic red color. In some cases, Type I muscle fibers carries more oxygen and sustain aerobic activity using fats or carbohydrates for fuel. Type I muscle fibers contract for long periods of time but with little force. Type II muscle fibers are further subdivided into three major subtypes (IIa, IIx, and IIb) that vary in both contractile speed and force generated. Type II muscle fibers contract quickly and powerfully but fatigue very rapidly, and therefore produce only short, anaerobic bursts of activity before muscle contraction becomes painful.

Unlike skeletal muscle, smooth muscle is not under conscious control.

Cardiac muscle is also an involuntary muscle but more closely resembles skeletal muscle in structure and is found only in the heart. Cardiac and skeletal muscles are striated in that they contain sarcomeres that are packed into highly regular arrangements of bundles. By contrast, the myofibrils of smooth muscle cells are not arranged in sarcomeres and therefore are not striated.

Muscle cells encompass any cells that contribute to muscle tissue. Exemplary muscle cells include myoblasts, satellite cells, myotubes, and myofibril tissues.

As used here, muscle force is proportional to the cross-sectional area (CSA), and muscle velocity is proportional to muscle fiber length. Thus, comparing the cross-sectional areas and muscle fibers between various kinds of muscles is capable of providing an indication of muscle atrophy. Various methods are known in the art to measure muscle strength and muscle weight, see, for example, "Musculoskeletal assessment; Joint range of motion and manual muscle strength" by Hazel M. Clarkson, published by Lippincott Williams & Wilkins, 200). The production of tomographic images from selected muscle tissues by computed axial tomography and sonographic evaluation are additional methods of measuring muscle mass.

The term antibody oligonucleotide conjugate (AOC) refers to an antibody conjugated to a nucleotide.

The term siRNA conjugate or siRNAantibody conjugate refers to an antibody conjugated to a siRNA.

The term DUX4 siRNA-conjugate or DUX4 siRNAantibody conjugate refers to an antibody conjugated to a siRNA hybridizing to a target sequence of the human DUX4 mRNA.

The term DUX4-AOC refers to an antibody conjugated to an siRNA hybridizing to a target sequence of the human DUX4 mRNA.

EXAMPLES

These examples are provided for illustrative purposes only and not to limit the scope of the claims provided herein.

Figure 2:
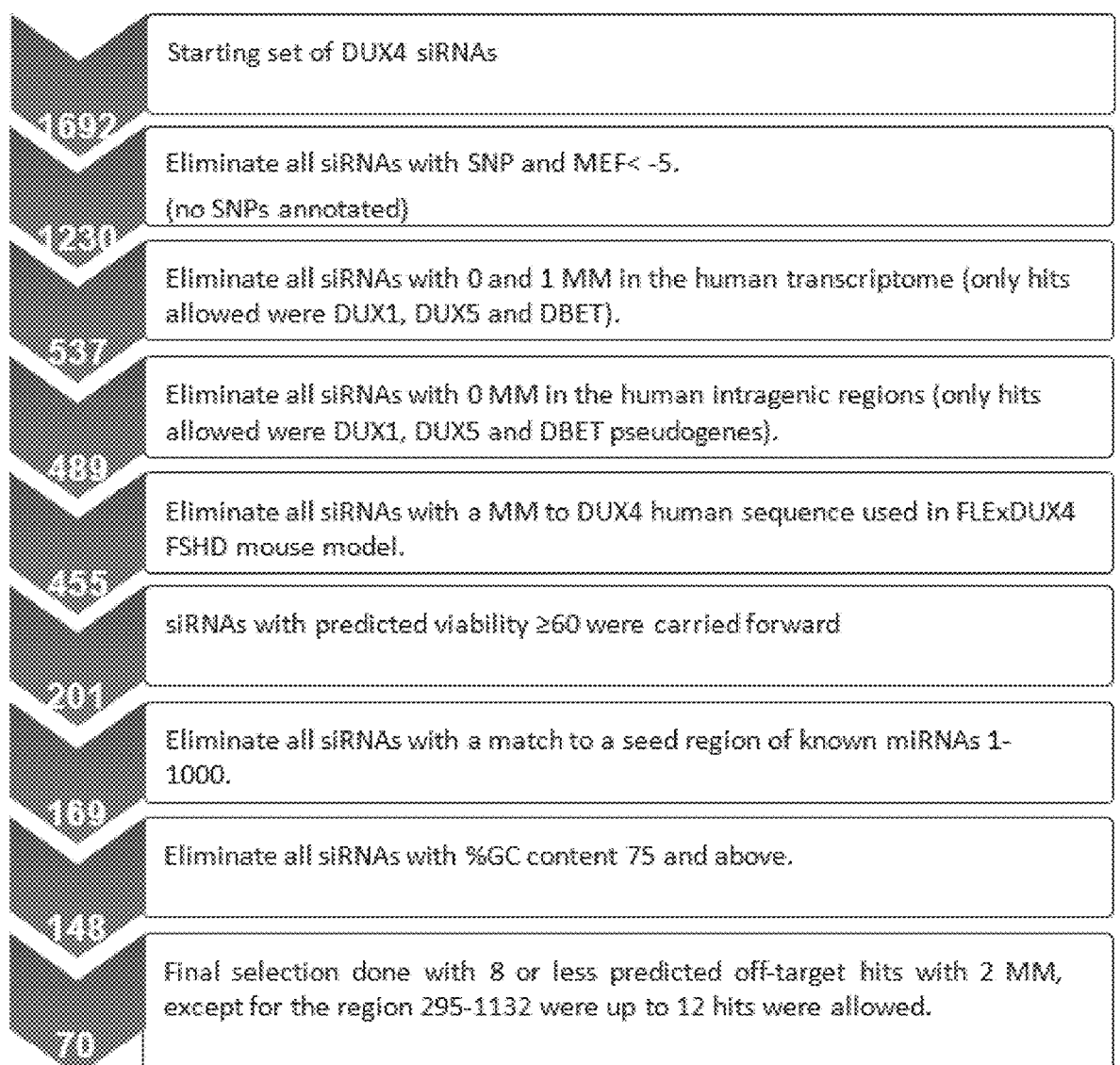
FIG. 2 shows a flowchart diagram of in silico selection of DUX4 siRNA.
Figure 3:
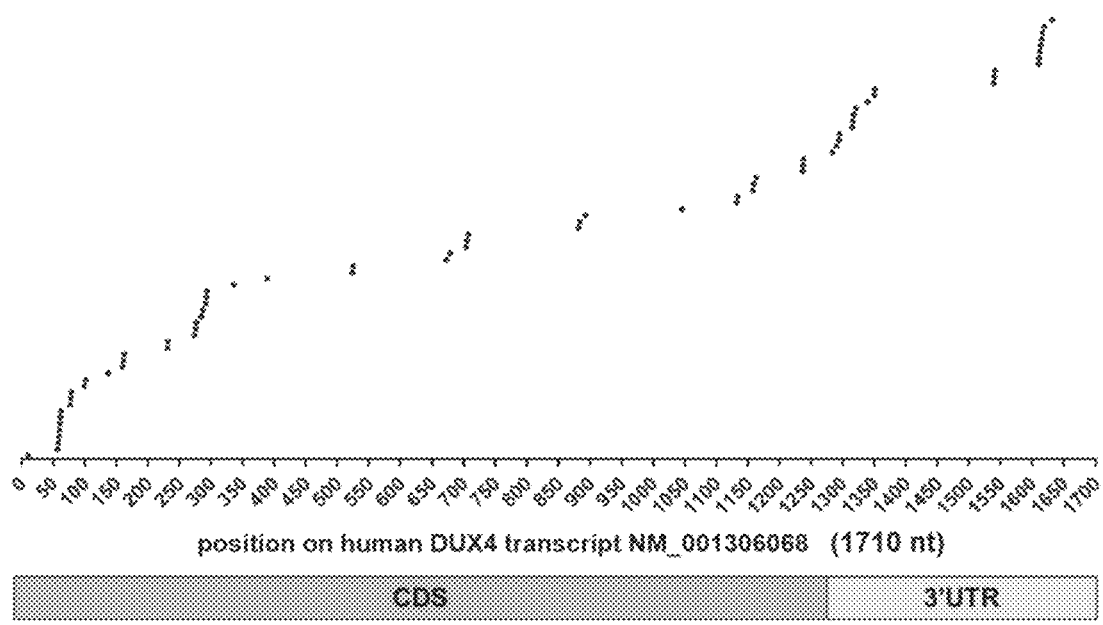
FIG. 3 illustrates the location and numbers of selected DUX4 siRNA in the DUX4 mRNA transcript.

Example 1. Bioinformatic siRNA Library Design Against Human Full Length DUX4 Transcript FIG. 2 shows a flowchart of in silico selection process of DUX4 siRNA. Sequences of all siRNAs that can binds to DUX4, or a pre-determined region of the DUX4 are collected to generate a starting set of DUX4 siRNA. From the starting set of DUX siRNAs, the first eliminating step comprises eliminating one or more DUX siRNAs that has single nucleotide polymorphism (SNP) and/or MEF<−5. Then, the second eliminating step comprises eliminating DUX siRNAs with 0 and 1 MM in the human transcriptome (such that only hits allowed are DUX, DUX5, and DBET). Then, the third eliminating step comprises eliminating DUX siRNAs with 0 mismatch (MM) in the human intragenic regions (such that only hits allowed are DUX1, DUX5 and DBET pseudogenes). Then, the next eliminating step comprises eliminating DUX siRNAs with a MM to DUX4 human sequence used in FLExDUX4 FSHD mouse model. Then, the next step is carrying forward only or one or more DUX siRNAs with predicted viability >60. Next, the eliminating step comprises eliminating one or more DUX siRNAs with a match to a seed region of known miRNAs 1-1000. Then, the eliminating step continues with eliminating DUX siRNAs molecule with % GC content 75 and above. Then, the final selection process comprises with 8 or less predicted off-target hits with 2 MM, except for the region 295-1132, for which up to 12 hits are allowed. Using such series of selection steps, final 70 candidate DUX siRNAs could be selected from a starting set of 1694 DUX siRNAs. FIG. 3 shows the location and numbers of such selected DUX4 siRNA in the DUX4 mRNA transcript (NM_001306068).

Identified siRNA candidates share common characteristics in their sequences as shown below Table 10 The identified siRNAs have mostly 2'-O-Me modifications, with 2'-F modifications only located on sense strand at positions 7, 8, 9 and 2-'F only located on antisense strand at positions 1, 2, 6, 14, 16. Also, the identified siRNAs comprises 4 thioate modifications on each strand, located at the final 2 linkages of each 5' and 3' terminus. The identified siRNAs further comprises "Uf" at the first position of 5' end of the antisense strand, regardless of the actual target mRNA sequence (coupled with "a" at the last position at the 3' end of the sense strand). The identified siRNAs further comprises "uu" overhang at the 3' end of the antisense strand only, with no overhang at the 3' end of the sense strand. The optimization of the identified siRNAs may comprise a vinyl phosphonate nucleotide, an inverted abasic moiety, or an amine linker to the passenger strand or the guide strand.

TABLE 10

| duplex name | sense strand sequence (5'-3') (passenger strand) | antisense strand sequence (5'-3') (guide strand) |
|---|---|---|
| DUX4 template | nsnsnnnnNfNfNfnnnnnnnnsnsa | UfsNfsnnnNfnnnnnnnNfnNfnnnsusu | vpN = vinyl phosphonate 21-MOE;
upper case (N) = 2'-OH (ribo);
lower case (n) = 2'-O-Me (methyl) dN = 2'-H (deoxy);
Nf = 2'-F (fluoro);
s = phosphorothioate backbone modification;
iB = inverted abasic Tables 11, 12, and 13 illustrate identified siRNA candidates for the regulation of human DUX4.

TABLE 11

| Name | 19mer start site | SEQ ID NO | sense/passenger_seq (5'-3') | SEQ ID NO | antisense/guide_seq (5'-3') |
|---|---|---|---|---|---|
| NM_001306068_11_29 | 11 | 1 | cgacaccctcggacagcac | 71 | gtgctgtccgagggtgtcg |
| NM_001306068_57_75 | 57 | 2 | acggcgacggagactcgtt | 72 | aacgagtctccgtcgccgt |
| NM_001306068_58_76 | 58 | 3 | cggcgacggagactcgttt | 73 | aaacgagtctccgtcgccg |
| NM_001306068_59_77 | 59 | 4 | ggcgacggagactcgtttg | 74 | caaacgagtctccgtcgcc |
| NM_001306068_60_78 | 60 | 5 | gcgacggagactcgtttgg | 75 | ccaaacgagtctccgtcgc |
| NM_001306068_61_79 | 61 | 6 | cgacggagactcgtttgga | 76 | tccaaacgagtctccgtcg |
| NM_001306068_62_80 | 62 | 7 | gacggagactcgtttggac | 77 | gtccaaacgagtctccgtc |
| NM_001306068_63_81 | 63 | 8 | acggagactcgtttggacc | 78 | ggtccaaacgagtctccgt |
| NM_001306068_77_95 | 77 | 9 | ggaccccgagccaaagcga | 79 | tcgctttggctcggggtcc |
| NM_001306068_78_96 | 78 | 10 | gaccccgagccaaagcgag | 80 | ctcgctttggctcggggtc |
| NM_001306068_79_97 | 79 | 11 | accccgagccaaagcgagg | 81 | cctcgctttggctcggggt |
| NM_001306068_99_117 | 99 | 12 | cctgcgagcctgctttgag | 82 | ctcaaagcaggctcgcagg |
| NM_001306068_102_120 | 102 | 13 | gcgagcctgctttgagcgg | 83 | ccgctcaaagcaggctcgc |
| NM_001306068_137_155 | 137 | 14 | tcgccaccagagaacggct | 84 | agccgttctctggtggcga |
| NM_001306068_160_178 | 160 | 15 | caggccatcggcattccgg | 85 | ccggaatgccgatggcctg |
| NM_001306068_162_180 | 162 | 16 | ggccatcggcattccggag | 86 | ctccggaatgccgatggcc |
| NM_001306068_163_181 | 163 | 17 | gccatcggcattccggagc | 87 | gctccggaatgccgatggc |
| NM_001306068_231_249 | 231 | 18 | gcaccggcgggaatctcgg | 88 | ccgagattcccgccggtgc |
| NM_001306068_232_250 | 232 | 19 | caccggcgggaatctcggc | 89 | gccgagattcccgccggtg |
| NM_001306068_274_292 | 274 | 20 | ccagaaggccggcgaaagc | 90 | gctttcgccggccttctgg |
| NM_001306068_276_294 | 276 | 21 | agaaggccggcgaaagcgg | 91 | ccgctttcgccggccttct |
| NM_001306068_277_295 | 277 | 22 | gaaggccggcgaaagcgga | 92 | tccgctttcgccggccttc |
| NM_001306068_285_303 | 285 | 23 | gcgaaagcggaccgccgtc | 93 | gacggcggtccgctttcgc |
| NM_001306068_287_305 | 287 | 24 | gaaagcggaccgccgtcac | 94 | gtgacggcggtccgctttc |
| NM_001306068_292_310 | 292 | 25 | cggaccgccgtcaccggat | 95 | atccggtgacggcggtccg |
| NM_001306068_293_311 | 293 | 26 | ggaccgccgtcaccggatc | 96 | gatccggtgacggcggtcc |
| NM_001306068_294_312 | 294 | 27 | gaccgccgtcaccggatcc | 97 | ggatccggtgacggcggtc |
| NM_001306068_389_407 | 389 | 28 | agacgggcctcccggagtc | 98 | gactccgggaggcccgtct |
| NM_001306068_524_542 | 524 | 29 | cctcgtgggtcgccttcgc | 99 | gcgaaggcgacccacgagg |

TABLE 11-continued

| Name | 19mer start site | SEQ ID NO | sense/passenger_seq (5'-3') | SEQ ID NO | antisense/guide_seq (5'-3') |
|---|---|---|---|---|---|
| NM_001306068_525_543 | 525 | 30 | ctcgtgggtcgccttcgcc | 100 | ggcgaaggcgacccacgag |
| NM_001306068_679_697 | 679 | 31 | gagggatctcccaacctg | 101 | caggttgggagatcccctc |
| NM_001306068_704_722 | 704 | 32 | cgcgcggggatttcgccta | 102 | taggcgaaatccccgcgcg |
| NM_001306068_705_723 | 705 | 33 | gcgcggggatttcgcctac | 103 | gtaggcgaaatccccgcgc |
| NM_001306068_708_726 | 708 | 34 | cggggatttcgcctacgcc | 104 | ggcgtaggcgaaatccccg |
| NM_001306068_893_911 | 893 | 35 | tgcttgcgccacccacgtc | 105 | gacgtgggtggcgcaagca |
| NM_001306068_1132_1150 | 1132 | 36 | ctggcgagcccggagtttc | 106 | gaaactccgggctcgccag |
| NM_001306068_1134_1152 | 1134 | 37 | ggcgagcccggagtttctg | 107 | cagaaactccgggctcgcc |
| NM_001306068_1158_1176 | 1158 | 38 | ggcgcaacctctcctagaa | 108 | ttctaggagaggttgcgcc |
| NM_001306068_1159_1177 | 1159 | 39 | gcgcaacctctcctagaaa | 109 | tttctaggagaggttgcgc |
| NM_001306068_1163_1181 | 1163 | 40 | aacctctcctagaaacgga | 110 | tccgtttctaggagaggtt |
| NM_001306068_1236_1254 | 1236 | 41 | cagcgaggaagaataccgg | 111 | ccggtattcttcctcgctg |
| NM_001306068_1237_1255 | 1237 | 42 | agcgaggaagaataccggg | 112 | cccggtattcttcctcgct |
| NM_001306068_1238_1256 | 1238 | 43 | gcgaggaagaataccgggc | 113 | gcccggtattcttcctcgc |
| NM_001306068_1284_1302 | 1284 | 44 | gttgggacggggtcgggtg | 114 | cacccgaccccgtcccaac |
| NM_001306068_1290_1308 | 1290 | 45 | acggggtcggtggttcgg | 115 | ccgaaccacccgacccccgt |
| NM_001306068_1294_1312 | 1294 | 46 | ggtcgggtggttcggggca | 116 | tgccccgaaccacccgacc |
| NM_001306068_1295_1313 | 1295 | 47 | gtcgggtggttcggggcag | 117 | ctgccccgaaccacccgac |
| NM_001306068_1315_1333 | 1315 | 48 | gcggtggcctctctttcgc | 118 | gcgaaagagaggccaccgc |
| NM_001306068_1316_1334 | 1316 | 49 | cggtggcctctctttcgcg | 119 | cgcgaaagagaggccaccg |
| NM_001306068_1317_1335 | 1317 | 50 | ggtggcctctctttcgcgg | 120 | ccgcgaaagagaggccacc |
| NM_001306068_1321_1339 | 1321 | 51 | gcctctcttcgcggggaa | 121 | ttccccgcgaaagagaggc |
| NM_001306068_1340_1358 | 1340 | 52 | cacctggctggctacggag | 122 | ctccgtagccagccaggtg |
| NM_001306068_1350_1368 | 1350 | 53 | gctacggaggggcgtgtct | 123 | agacacgcccctccgtagc |
| NM_001306068_1351_1369 | 1351 | 54 | ctacggaggggcgtgtctc | 124 | gagacacgcccctccgtag |
| NM_001306068_1539_1557 | 1539 | 55 | acgtgcaagggagctcgct | 125 | agcgagctcccttgcacgt |
| NM_001306068_1540_1558 | 1540 | 56 | cgtgcaagggagctcgctg | 126 | cagcgagctcccttgcacg |
| NM_001306068_1541_1559 | 1541 | 57 | gtgcaagggagctcgctgg | 127 | ccagcgagctcccttgcac |
| NM_001306068_1610_1628 | 1610 | 58 | caccttccgacgctgtcta | 128 | tagacagcgtcggaaggtg |
| NM_001306068_1611_1629 | 1611 | 59 | accttccgacgctgtctag | 129 | ctagacagcgtcggaaggt |
| NM_001306068_1612_1630 | 1612 | 60 | ccttccgacgctgtctagg | 130 | cctagacagcgtcggaagg |
| NM_001306068_1613_1631 | 1613 | 61 | cttccgacgctgtctaggc | 131 | gcctagacagcgtcggaag |
| NM_001306068_1615_1633 | 1615 | 62 | tccgacgctgtctaggcaa | 132 | ttgcctagacagcgtcgga |
| NM_001306068_1616_1634 | 1616 | 63 | ccgacgctgtctaggcaaa | 133 | tttgcctagacagcgtcgg |
| NM_001306068_1619_1637 | 1619 | 64 | acgctgtctaggcaaacct | 134 | aggtttgcctagacagcgt |
| NM_001306068_1632_1650 | 1632 | 65 | aaacctggattagagttac | 135 | gtaactctaatccaggttt |
| NM_001306068_336_354 | 336 | 66 | ctttgagaaggatcgcttt | 136 | aaagcgatccttctcaaag |
| NM_001306068_672_690 | 672 | 67 | gccggcagaggggatctcc | 137 | ggagatcccctctgccggc |

TABLE 11-continued

| Name | 19mer start site | SEQ ID NO | sense/passenger_seq (5'-3') | SEQ ID NO | antisense/guide_seq (5'-3') |
| --- | --- | --- | --- | --- | --- |
| NM_001306068_882_900 | 882 | 68 | gggccaaggggtgcttgcg | 138 | cgcaagcacccccttggccc |
| NM_001306068_884_902 | 884 | 69 | gccaaggggtgcttgcgcc | 139 | ggcgcaagcacccccttggc |
| NM_001306068_1045_1063 | 1045 | 70 | atgcaaggcatcccggcgc | 140 | gcgccgggatgccttgcat |

TABLE 12

| Name | 19mer start site | SEQ ID NO | sense/passenger_seq (5'-3') | SEQ ID NO | antisense/guide_seq (5'-3') |
| --- | --- | --- | --- | --- | --- |
| NM_001306068_11_29 | 11 | 141 | csgsacacCfCfUfcggacagcsasa | 211 | UfsUfsgcuGfuccgaggGfuGfucgsusu |
| NM_001306068_57_75 | 57 | 142 | ascsggcgAfCfGfgagacucgsusa | 212 | UfsAfscgaGfucuccguCfgCfcgususu |
| NM_001306068_58_76 | 58 | 143 | csgsgcgaCfGfGfagacucgususa | 213 | UfsAfsacgAfgucuccgUfcGfccgsusu |
| NM_001306068_59_77 | 59 | 144 | gsgscgacGfGfAfgacucguususa | 214 | UfsAfsaacGfagucuccGfuCfgccsusu |
| NM_001306068_60_78 | 60 | 145 | gscsgacgGfAfGfacucguuusgsa | 215 | UfsCfsaaaCfgagucucCfgUfcgcsusu |
| NM_001306068_61_79 | 61 | 146 | csgsacggAfGfAfcucguuugsgsa | 216 | UfsCfscaaAfcgagucuCfcGfucgsusu |
| NM_001306068_62_80 | 62 | 147 | gsascggaGfAfCfucguuuggsasa | 217 | UfsUfsccaAfacgagucUfcCfgucsusu |
| NM_001306068_63_81 | 63 | 148 | ascsggagAfCfUfcguuuggascsa | 218 | UfsGfsuccAfaacgaguCfuCfcgususu |
| NM_001306068_77_95 | 77 | 149 | gsgsacccCfGfAfgccaaagcsgsa | 219 | UfsCfsgcuUfuggcucgGfgGfuccsusu |
| NM_001306068_78_96 | 78 | 150 | gsasccccGfAfGfccaaagcgsasa | 220 | UfsUfscgcUfuuggcucGfgGfgucsusu |
| NM_001306068_79_97 | 79 | 151 | ascscccgAfGfCfcaaagcgasgsa | 221 | UfsCfsucgCfuuuggcuCfgGfgususu |
| NM_001306068_99_117 | 99 | 152 | cscsugcgAfGfCfcugcuuugsasa | 222 | UfsUfscaaAfgcaggcuCfgCfaggsusu |
| NM_001306068_102_120 | 102 | 153 | gscsgagcCfUfGfcuuugagcsgsa | 223 | UfsCfsgcuCfaaagcagGfcUfcgcsusu |
| NM_001306068_137_155 | 137 | 154 | uscsgccaCfCfAfgagaacggscsa | 224 | UfsGfsccgUfucucuggUfgGfcgasusu |
| NM_001306068_160_178 | 160 | 155 | csasggccAfUfCfggcauuccsgsa | 225 | UfsCfsggaAfugccgauGfgCfcugsusu |
| NM_001306068_162_180 | 162 | 156 | gsgsccauCfGfGfcauuccggsasa | 226 | UfsUfsccgGfaaugccgAfuGfgccsusu |
| NM_001306068_163_181 | 163 | 157 | gscscaucGfGfCfauuccggasgsa | 227 | UfsCfsuccGfaaugccGfaUfggcsusu |
| NM_001306068_231_249 | 231 | 158 | gscsaccgGfCfGfggaaucucsgsa | 228 | UfsCfsgagAfuucccgcCfgGfugcsusu |
| NM_001306068_232_250 | 232 | 159 | csasccggCfGfGfgaaucucgsgsa | 229 | UfsCfscgaGfauucccgCfcGfgugsusu |
| NM_001306068_274_292 | 274 | 160 | cscsagaaGfGfCfcggcgaaasgsa | 230 | UfsCfsuuuCfgccggccUfuCfuggsusu |

TABLE 12-continued

| Name | 19mer start site | SEQ ID NO | sense/passenger_seq (5'-3') | SEQ ID NO | antisense/guide_seq (5'-3') |
|---|---|---|---|---|---|
| NM_001306068_276_294 | 276 | 161 | asgsaaggCfCfGfgcgaaagcsgsa | 231 | UfsCfsgcuUfucgccggCfcUfucususu |
| NM_001306068_277_295 | 277 | 162 | gsasaggcCfGfGfcgaaagcgsgsa | 232 | UfsCfscgcUfuucgccgGfcCfuucsusu |
| NM_001306068_285_303 | 285 | 163 | gscsgaaaGfCfGfgaccgccgsusa | 233 | UfsAfscggCfgguccgcUfuUfcgcsusu |
| NM_001306068_287_305 | 287 | 164 | gsasaagcGfGfAfccgccgucsasa | 234 | UfsUfsgacGfgcgguccGfcUfuucsusu |
| NM_001306068_292_310 | 292 | 165 | csgsgaccGfCfCfgucaccggsasa | 235 | UfsUfsccgGfugacggcGfgUfccgsusu |
| NM_001306068_293_311 | 293 | 166 | gsgsaccgCfCfGfucaccggasusa | 236 | UfsAfsuccGfgugacggCfgGfuccsusu |
| NM_001306068_294_312 | 294 | 167 | gsasccgcCfGfUfcaccggauscsa | 237 | UfsGfsaucCfggugacgGfcGfgucsusu |
| NM_001306068_389_407 | 389 | 168 | asgsacggGfCfCfucccggagsusa | 238 | UfsAfscucCfgggaggcCfcGfucususu |
| NM_001306068_524_542 | 524 | 169 | cscsucguGfGfGfucgccuucsgsa | 239 | UfsCfsgaaGfgcgacccAfcGfaggsusu |
| NM_001306068_525_543 | 525 | 170 | csuscgugGfGfUfcgccuucgscsa | 240 | UfsGfscgaAfggcgaccCfaCfgagsusu |
| NM_001306068_679_697 | 679 | 171 | gsasggggAfUfCfucccaaccsusa | 241 | UfsAfsgguUfgggagauCfcCfcucsusu |
| NM_001306068_704_722 | 704 | 172 | csgscgcgGfGfGfauuucgccsusa | 242 | UfsAfsggcGfaaaucccCfgCfgcgsusu |
| NM_001306068_705_723 | 705 | 173 | gscsgcggGfGfAfuuucgccusasa | 243 | UfsUfsaggCfgaaauccCfcGfcgcsusu |
| NM_001306068_708_726 | 708 | 174 | csgsgggaUfUfUfcgccuacgscsa | 244 | UfsGfscguAfggcgaaaUfcCfccgsusu |
| NM_001306068_893_911 | 893 | 175 | usgscuugCfGfCfcacccacgsusa | 245 | UfsAfscguGfgguggcgCfaAfgcasusu |
| NM_001306068_1132_1150 | 1132 | 176 | csusggcgAfGfCfccggaguususa | 246 | UfsAfsaacUfccgggcuCfgCfcagsusu |
| NM_001306068_1134_1152 | 1134 | 177 | gsgscgagCfCfCfggaguuucsusa | 247 | UfsAfsgaaAfcucccggGfcUfCfgccsusu |
| NM_001306068_1158_1176 | 1158 | 178 | gsgscgcaAfCfCfucuccuagsasa | 248 | UfsUfscuaGfgagagguUfgCfgccsusu |
| NM_001306068_1159_1177 | 1159 | 179 | gscsgcaaCfCfUfcuccuagasasa | 249 | UfsUfsucuAfggagaggUfuGfcgcsusu |
| NM_001306068_1163_1181 | 1163 | 180 | asasccucUfCfCfuagaaacgsgsa | 250 | UfsCfscguUfucuaggaGfaGfguususu |
| NM_001306068_1236_1254 | 1236 | 181 | csasgcgaGfGfAfagaauuaccsgsa | 251 | UfsCfsgguAfuucuuccUfcGfcugsusu |
| NM_001306068_1237_1255 | 1237 | 182 | asgscgagGfAfAfgaauaccsgsa | 252 | UfsCfsggUfauucuucCfuCfgcususu |
| NM_001306068_1238_1256 | 1238 | 183 | gscsgaggAfAfGfaauaccggsgsa | 253 | UfsCfsccgGfuauucuuCfcUfcgcsusu |
| NM_001306068_1284_1302 | 1284 | 184 | gsusugggAfCfGfggguCfgggsusa | 254 | UfsAfsccCfacccguCfcCfaacsusu |
| NM_001306068_1290_1308 | 1290 | 185 | ascsggggUfCfGfggguguucsgsa | 255 | UfsCfsgaaCfcacccgaCfcCfcgususu |

TABLE 12-continued

| Name | 19mer start site | SEQ ID NO | sense/passenger_seq (5'-3') | SEQ ID NO | antisense/guide_seq (5'-3') |
|---|---|---|---|---|---|
| NM_001306068_1294_1312 | 1294 | 186 | gsgsucggGfUfGfguucggggscsa | 256 | UfsGfscccCfgaaccacCfcGfaccsusu |
| NM_001306068_1295_1313 | 1295 | 187 | gsuscgggUfGfGfuucggggcsasa | 257 | UfsUfsgccCfcgaaccaCfcCfgacsusu |
| NM_001306068_1315_1333 | 1315 | 188 | gscsggugGfCfCfucucuuucsgsa | 258 | UfsCfsgaaAfgagaggcCfaCfcgcsusu |
| NM_001306068_1316_1334 | 1316 | 189 | csgsguggCfCfUfcucuuucgscsa | 259 | UfsGfscgaAfagagaggCfcAfccgsusu |
| NM_001306068_1317_1335 | 1317 | 190 | gsgsuggcCfUfCfucuuucgcsgsa | 260 | UfsCfsgcgAfaagagagGfcCfaccsusu |
| NM_001306068_1321_1339 | 1321 | 191 | gscsucuCfUfUfucgcggggsasa | 261 | UfsUfscccCfgcgaaagAfgAfggcsusu |
| NM_001306068_1340_1358 | 1340 | 192 | csasccugGfCfUfggcuacggsasa | 262 | UfsUfsccgUfagccagcCfaGfgugsusu |
| NM_001306068_1350_1368 | 1350 | 193 | gscsuacgGfAfGfgggcguguscsa | 263 | UfsGfsacaCfgccccucCfgUfagcsusu |
| NM_001306068_1351_1369 | 1351 | 194 | csusacggAfGfGfggcgugucsusa | 264 | UfsAfsgacAfcgccccuCfcGfuagsusu |
| NM_001306068_1539_1557 | 1539 | 195 | ascsgugcAfAfGfggagcucgscsa | 265 | UfsGfscgaGfcuccccuuGfcAfcgususu |
| NM_001306068_1540_1558 | 1540 | 196 | csgsugcaAfGfGfgagcucgcsusa | 266 | UfsAfsgcgAfgcucccuUfgCfacgsusu |
| NM_001306068_1541_1559 | 1541 | 197 | gsusgcaaGfGfGfagcucgcusgsa | 267 | UfsCfsagcGfagcucccUfuGfcacsusu |
| NM_001306068_1610_1628 | 1610 | 198 | csasccuuCfCfGfacgcugucsusa | 268 | UfsAfsgacAfgcgucggAfaGfgugsusu |
| NM_001306068_1611_1629 | 1611 | 199 | ascscuuCfGfAfcgcugucusasa | 269 | UfsUfsagaCfagcgucgGfaAfggusu |
| NM_001306068_1612_1630 | 1612 | 200 | cscsuuccGfAfCfgcugucuasgsa | 270 | UfsCfsuagAfcagcgucGfgAfaggsusu |
| NM_001306068_1613_1631 | 1613 | 201 | csusuccgAfCfGfcugucuagsgsa | 271 | UfsCfscuaGfacagcguCfgGfaagsusu |
| NM_001306068_1615_1633 | 1615 | 202 | uscscgacGfCfUfgucuaggcsasa | 272 | UfsUfsgccUfagacagcGfuCfggasusu |
| NM_001306068_1616_1634 | 1616 | 203 | cscsgacgCfUfGfucuaggcasasa | 273 | UfsUfsugcCfuagacagCfgUfcggsusu |
| NM_001306068_1619_1637 | 1619 | 204 | ascsgcugUfCfUfaggcaaacscsa | 274 | UfsGfsguuUfgccuagaCfaGfcgususu |
| NM_001306068_1632_1650 | 1632 | 205 | asasaccuGfGfAfuuuagaguusasa | 275 | UfsUfsaacUfcuaauccAfgGfuuususu |
| NM_001306068_336_354 | 336 | 206 | csusuugaGfAfAfggaucgcususa | 276 | UfsAfsagcGfauccuucUfcAfaagsusu |
| NM_001306068_672_690 | 672 | 207 | gscscggcAfGfAfgggauscsa | 277 | UfsGfsagaUfcccucuGfcCfggcsusu |
| NM_001306068_882_900 | 882 | 208 | gsgsgccaAfGfGfggugcuugscsa | 278 | UfsGfscaaGfcaccccuUfgGfcccsusu |

TABLE 12-continued

| Name | 19mer start site | SEQ ID NO | sense/passenger_seq (5'-3') | SEQ ID NO | antisense/guide_seq (5'-3') |
|---|---|---|---|---|---|
| NM_001306068_884_902 | 884 | 209 | gscscaagGfGfGfugcuu gcgscsa | 279 | UfsGfscgcAfagcacccC fuUfggcsusu |
| NM_001306068_1045_1063 | 1045 | 210 | asusgcaaGfGfCfauccc ggcsgsa | 280 | UfsCfsgccGfggaugcc UfuGfcaususu | vpN = vinyl phosphonate 2'-MOE; upper case (N) = 2'-OH (ribo); lower case (n) = 2'-O-Me (methyl) dN = 2'-H (deoxy); Nf = 2'-F (fluoro); s = phosphorothioate backbone modification; iB = inverted abasic

TABLE 13

| SEQ ID NO | sense/passenger seq (5'-3') | SEQ ID NO | antisense/guide seq (5'-3') |
|---|---|---|---|
| 371 | CTGCCTCTCCACCAGCCCA | 372 | TGGGCTGGTGGAGAGGCAG |
| 373 | GCAGAGATGGAGAGAGGAA | 374 | TTCCTCTCTCCATCTCTGC |
| 375 | GCGGTTTCCTCCGGGACAA | 376 | TTGTCCCGGAGGAAACCGC |
| 377 | GGACGACGGAGGCGTGATT | 378 | AATCACGCCTCCGTCGTCC |
| 379 | CGGGCACCCGGAAACATGCAGGGAA | 380 | TTCCCTGCATGTTTCCGGGTGCCCG |
| 381 | CCGGAAACATGCAGGGAAG | 382 | CTTCCCTGCATGTTTCCGG |
| 383 | GAAATGAACGAGAGCCACA | 384 | TGTGGCTCTCGTTCATTTC |
| 385 | TGGCACACTCAAGACTCCCACGGAG | 386 | CTCCGTGGGAGTCTTGAGTGTGCCA |
| 387 | CCACGGAGGTTCAGTTCCA | 388 | TGGAACTGAACCTCCGTGG |
| 389 | ACCACCACCACCACCACCA | 390 | TGGTGGTGGTGGTGGTGGT |
| 391 | CGCCATTCATGAAGGGGTG | 392 | CACCCCTTCATGAATGGCG |
| 393 | CATGAAGGGGTGGAGCCTG | 394 | CAGGCTCCACCCCTTCATG |
| 395 | GAGCCTGCTTTGAGCGGAA | 396 | TTCCGCTCAAAGCAGGCTC |
| 397 | CCGAGCCTTTGAGAAGGATCGCTTT | 398 | AAAGCGATCCTTCTCAAAGGCTCGG |
| 399 | GGCAGGGCGCCCGCGCAGG | 400 | CCTGCGCGGGCGCCCTGCC |
| 401 | GATGATTAGTTCAGAGATA | 402 | TATCTCTGAACTAATCATC |

Example 2. siRNA Sequences and Synthesis

All siRNA single strands were fully assembled on solid phase using standard phosphoramidite chemistry and purified over HPLC. Purified single strands were duplexed to get the double stranded siRNA. All the siRNA passenger strand contains conjugation handles in different formats, $C_6$—$NH_2$ and/or $C_6$—SH, one at each end of the strand. The conjugation handle or handles were connected to the siRNA passenger strand or siRNA guide strand via inverted abasic phosphodiester or phosphorothioate. Below are representative structures of the formats used in the in vivo experiments.

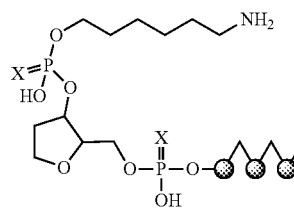
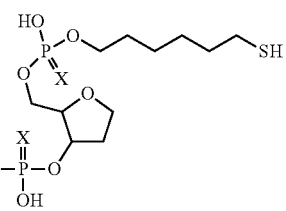

X = O or S

5' end

X = O or S

3' end

A representative structure of siRNA with C6-$NH_2$ conjugation handle at the 5' end and $C_6$—SH at 3'end of the passenger strand or guide strand.

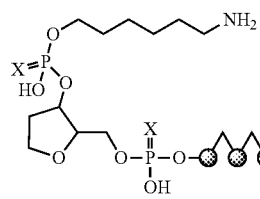
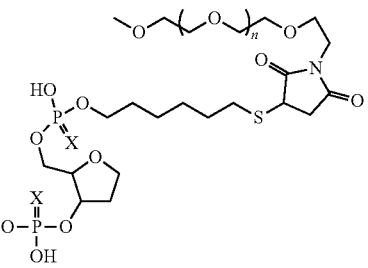

X = O or S

5' end

X = O or S

3' end

A representative structure of siRNA passenger strand or guide strand with $C_6$—$NH_2$ conjugation handle at the 5' end and C6-S-PEG at 3' end.

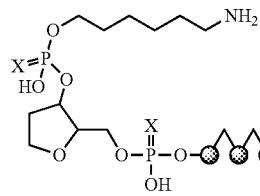
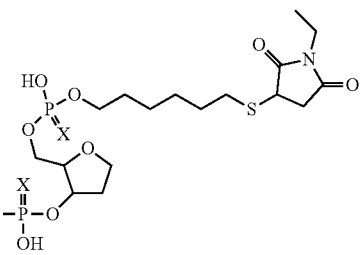

X = O or S

5' end

X = O or S

3' end

A representative structure of siRNA passenger strand or guide strand with C_6—NH_2 conjugation handle at the 5' end and C_6—S-NEM at 3' end.

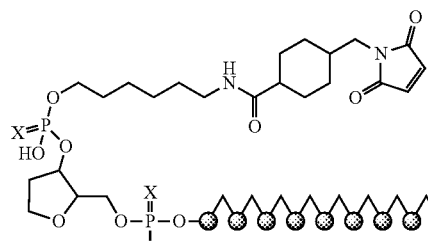

5' end

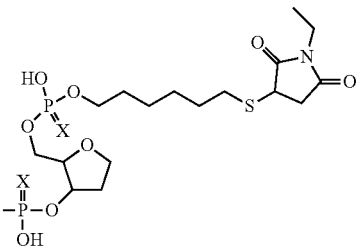

3' end

A representative structure of siRNA passenger strand with C6-N-SMCC conjugation handle at the 5' end and C_6—S-NEM at 3' end.

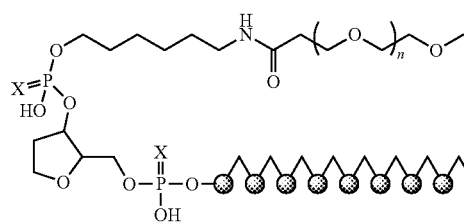

5' end

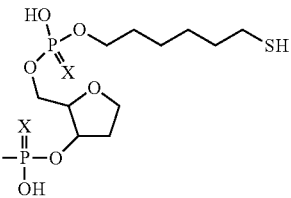

3' end

A representative structure of siRNA passenger strand or guide strand with PEG at the 5' end and C_6—SH at 3' end.

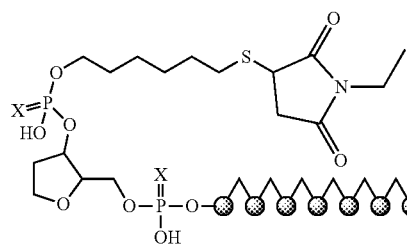

5' end

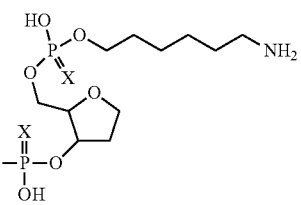

3' end

A representative structure of siRNA passenger strand or guide strand with $C_6$-S-NEM at the 5' end and $C_6$—$NH_2$ conjugation handle at 3' end.

Example 3. Conjugate Synthesis

The following structures illustrate exemplary A-$X_1$—B—$X_2$-Y (Formula I) architectures described herein.

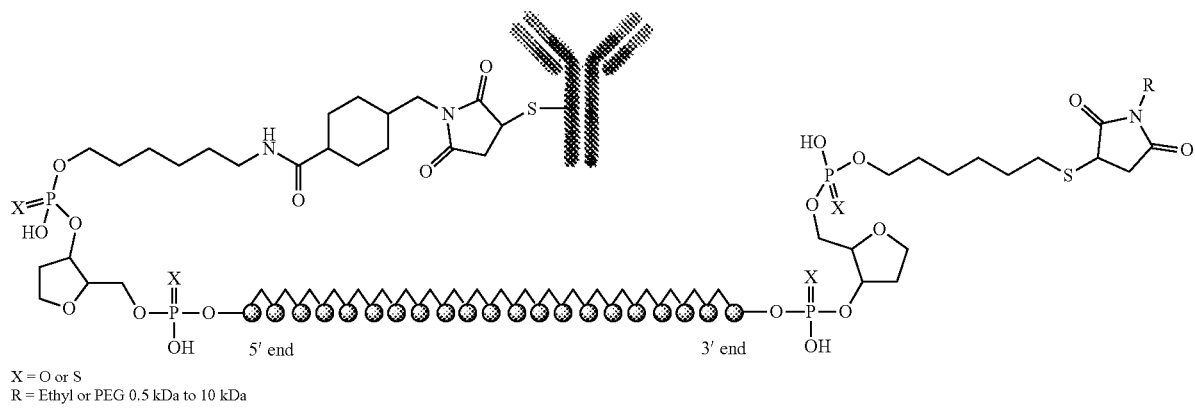

X = O or S
R = Ethyl or PEG 0.5 kDa to 10 kDa

Architecture-1: Antibody-Cys-SMCC-5'-passenger strand. This conjugate was generated by antibody inter-chain cysteine conjugation to maleimide (SMCC) at the 5' end of passenger strand.

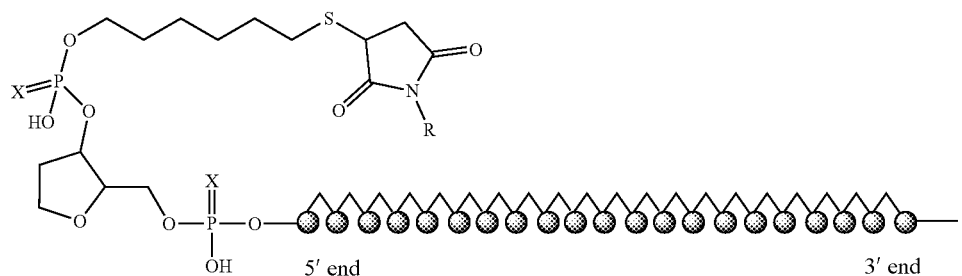

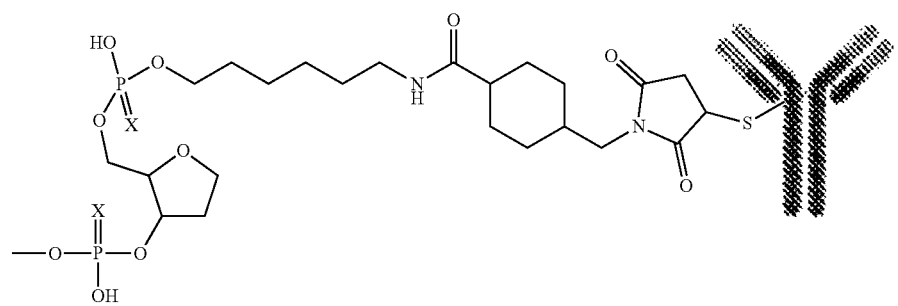

X = O or S
R = Ethyl or PEG 0.5 kDa to 10kDa

Architecture-2: Antibody-Cys-SMCC-3'-Passenger strand. This conjugate was generated by antibody inter-chain cysteine conjugation to maleimide (SMCC) at the 3' end of passenger strand.

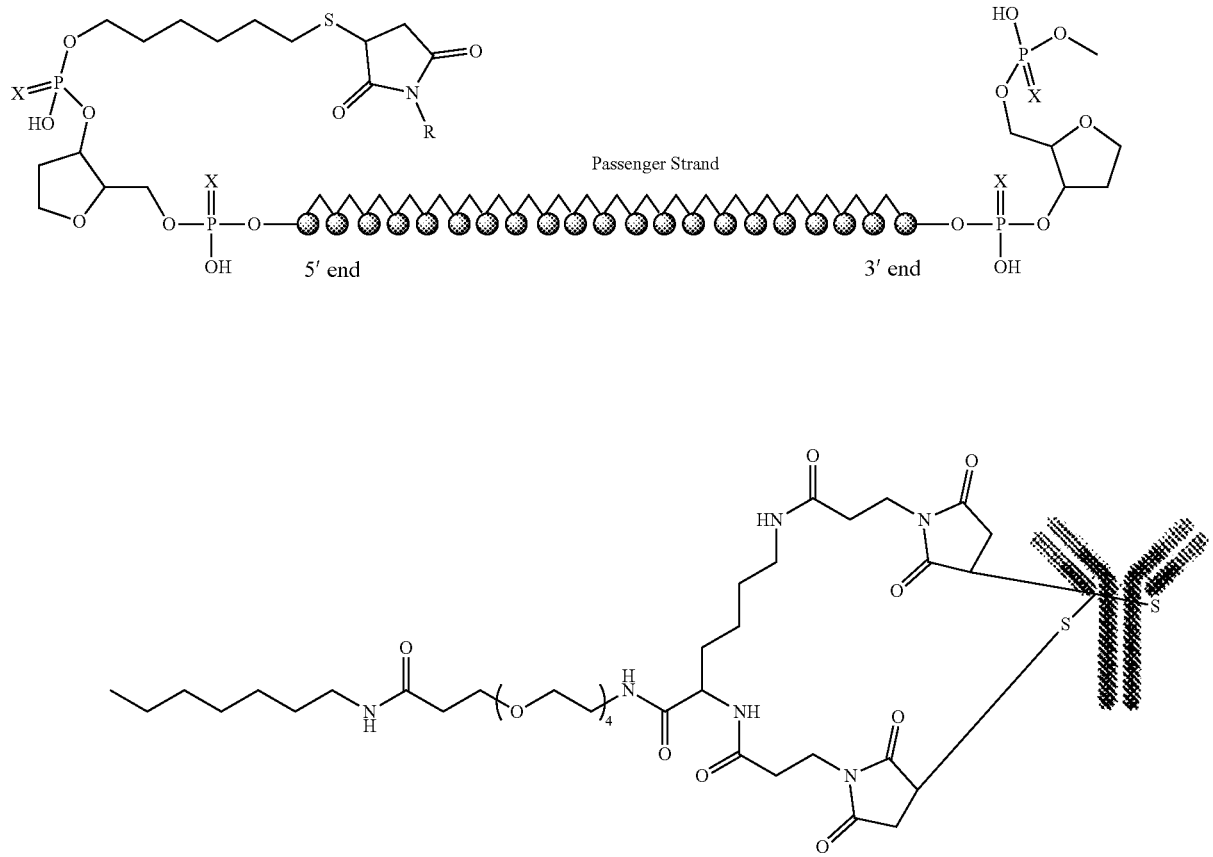

X = O or S
R = Ethyl or PEG 0.5 kDa to 10kDa

ASC Architecture-3: Antibody-Cys-bisMal-3'-Passenger strand. This conjugate was generated by antibody inter-chain cysteine conjugation to bismaleimide (bisMal) linker at the 3' end of passenger strand.

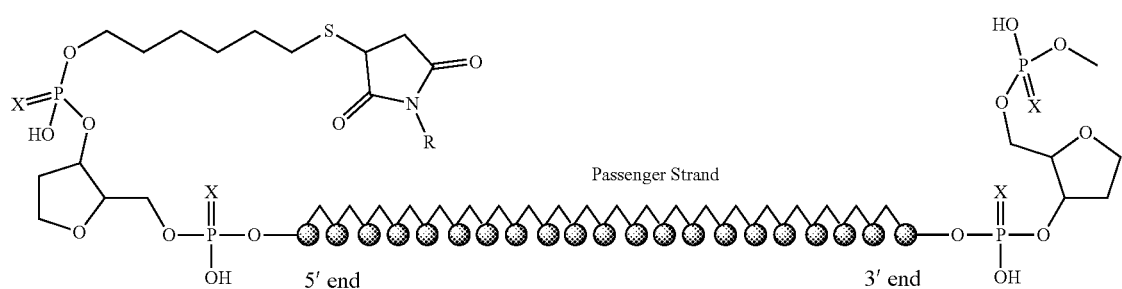

-continued
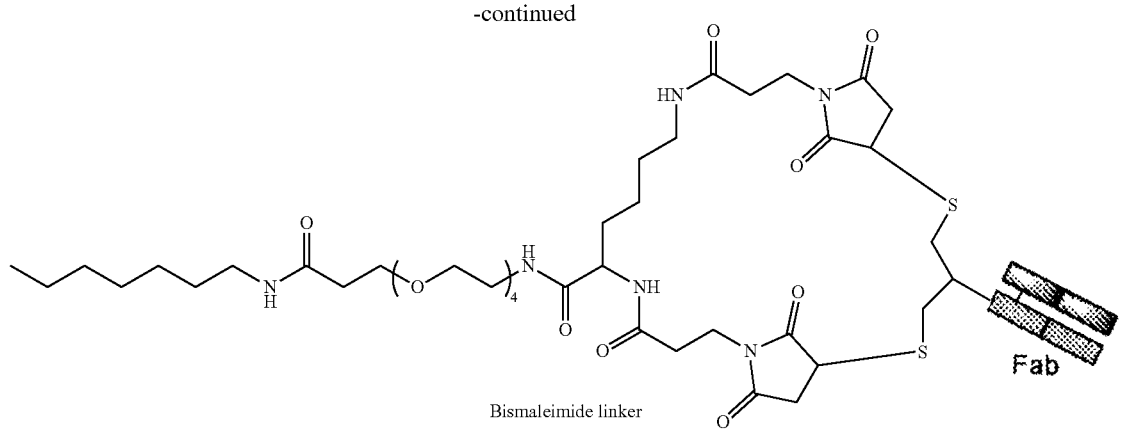
Bismaleimide linker
X = O or S
R = Ethyl or PEG 0.5 kDa to 10kDa
ASC Architecture-4: A model structure of the Fab-Cys-bisMal-3'-Passenger strand. This conjugate was generated by Fab inter-chain cysteine conjugation to bismaleimide (bisMal) linker at the 3' end of passenger strand.

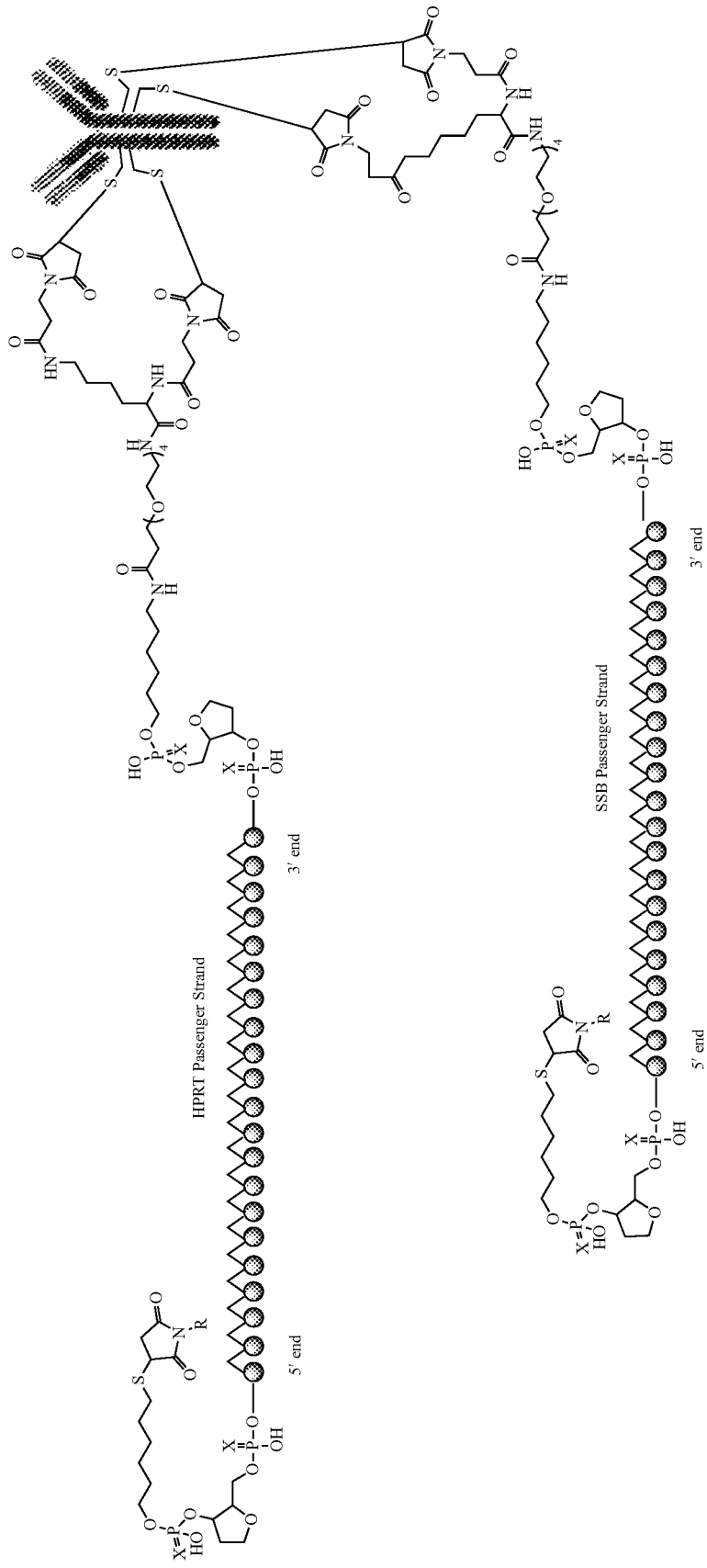
X = O or S
R = Ethyl or PEG 0.5 kDa to 10kDa

ASC Architecture-5. A model structure of the antibody siRNA conjugate with two different siRNAs attached to one antibody molecule. This conjugate was generated by conjugating a mixture of SSB and HPRT siRNAs to the reduced mAb inter-chain cysteines to bismaleimide (bisMal) linker at the 3' end of passenger strand of each siRNA.

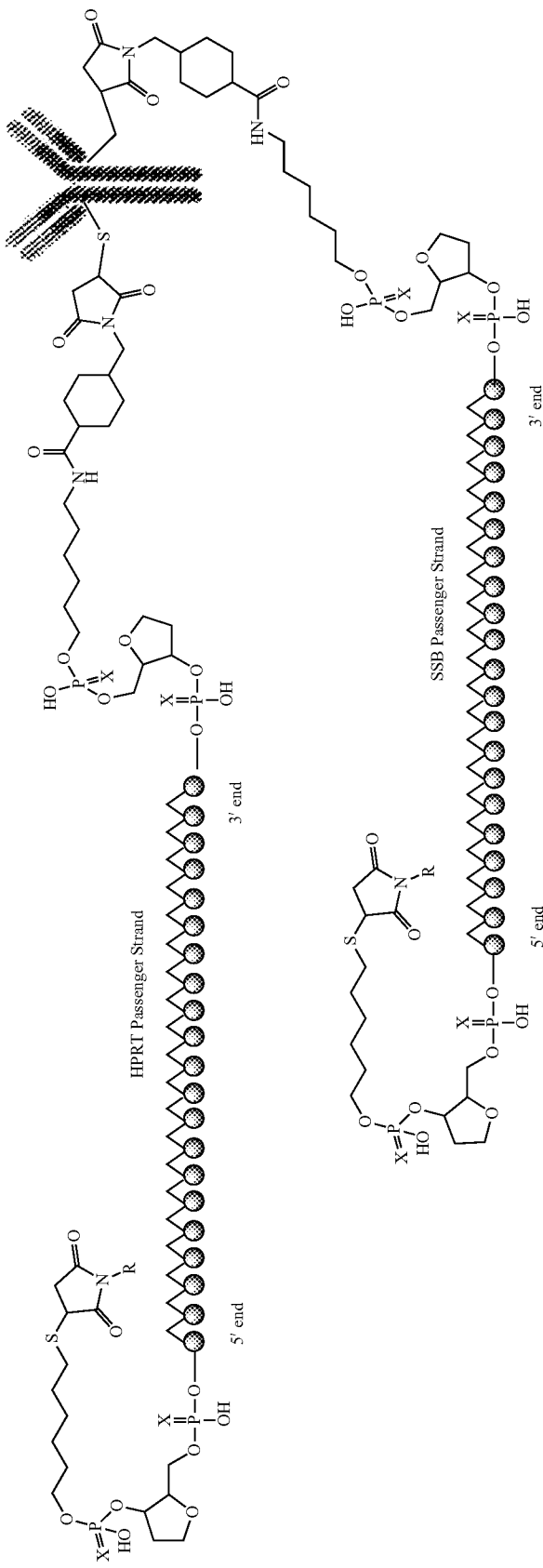
X = O or S
R = Ethyl or PEG 0.5 kDa to 10kDa

ASC Architecture-6: A model structure of the antibody siRNA conjugate with two different siRNAs attached. This conjugate was generated by conjugating a mixture of SSB and HPRT siRNAs to the reduced mAb inter-chain cysteines to maleimide (SMCC) linker at the 3' end of passenger strand of each siRNA.

Example 3.1 Antibody siRNA Conjugate Synthesis Using SMCC Linker

Synthesis scheme-1: Antibody-Cys-SMCC-siRNA-PEG conjugates via antibody cysteine conjugation

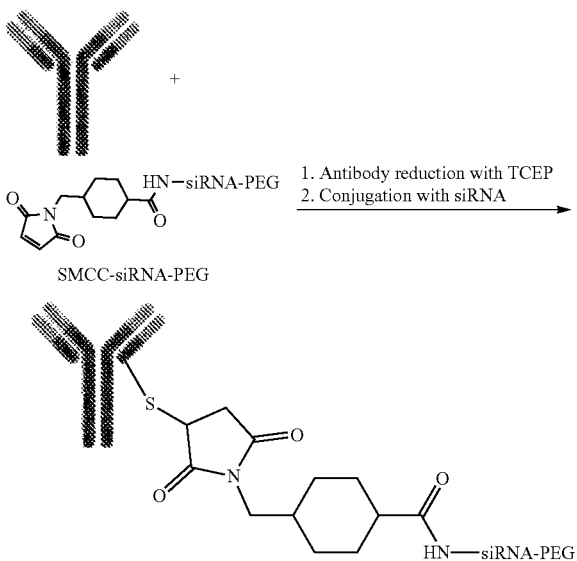

Step 1: Antibody Interchain Disulfide Reduction with TCEP

Antibody was buffer exchanged with borax buffer (pH 8) and made up to 10 mg/ml concentration. To this solution, 2 equivalents of TCEP in water was added and rotated for 2 hours at RT. The resultant reaction mixture was buffer exchanged with pH 7.4 PBS containing 5 mM EDTA and added to a solution of SMCC-C6-siRNA or SMCC-C6-siRNA-C6-NHCO-PEG-XkDa (2 equivalents) (X=0.5 kDa to 10 kDa) in pH 7.4 PBS containing 5 mM EDTA at RT and rotated overnight. Analysis of the reaction mixture by analytical SAX column chromatography showed antibody siRNA conjugate along with unreacted antibody and siRNA.

Step 2: Purification

The crude reaction mixture was purified by AKTA explorer FPLC using anion exchange chromatography method-1 as described in Example 3.4. Fractions containing DAR1 and DAR>2 antibody-siRNA-PEG conjugates were separated, concentrated and buffer exchanged with pH 7.4 PBS.

Step 3: Analysis of the Purified Conjugate

The isolated conjugates were characterized by SEC, SAX chromatography and SDS-PAGE. The purity of the conjugate was assessed by analytical HPLC using either anion exchange chromatography method-2 or anion exchange chromatography method-3. Both methods are described in Example 3.4. Isolated DAR1 conjugates are typically eluted at 9.0±0.3 min on analytical SAX method and are greater than 90% pure. The typical DAR>2 cysteine conjugate contains more than 85% DAR2 and less than 15% DAR3.

Example 3.2. Antibody siRNA Conjugate Synthesis Using Bis-Maleimide (BisMal) Linker Synthesis scheme-2: Antibody-Cys-BisMal-siRNA-PEG conjugates.

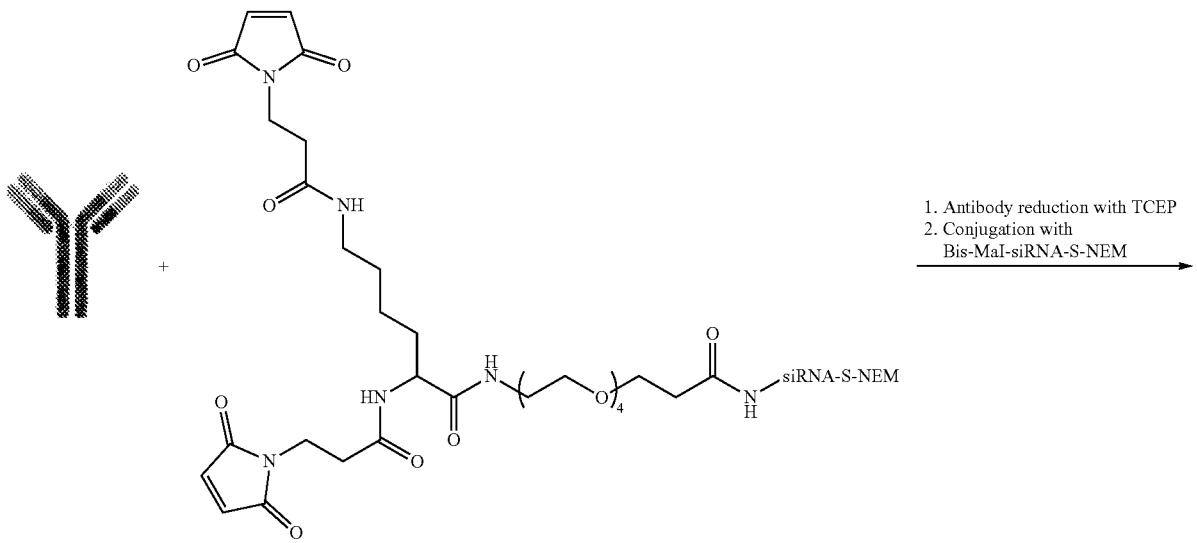

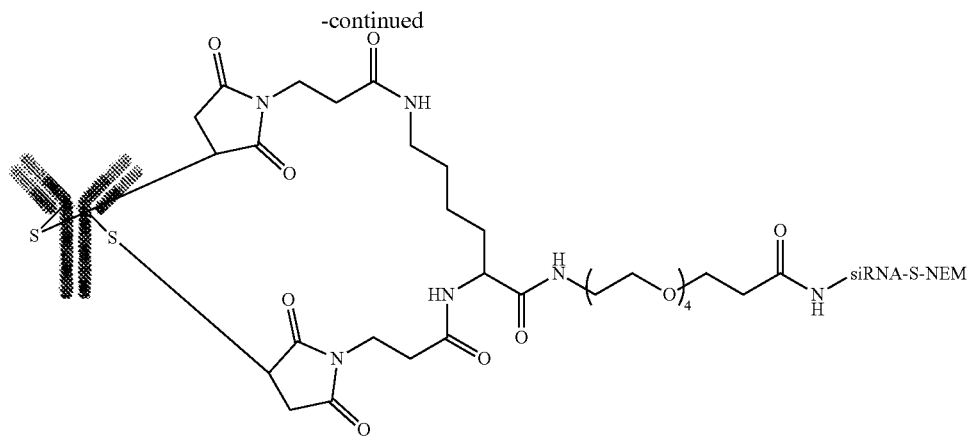

Step 1: Antibody Reduction with TCEP

Antibody was buffer exchanged with borax buffer (pH 8) and made up to 5 mg/ml concentration. To this solution, 2 equivalents of TCEP in water was added and rotated for 2 hours at RT. The resultant reaction mixture was exchanged with pH 7.4 PBS containing 5 mM EDTA and added to a solution of BisMal-C6-siRNA-C6-S-NEM (2 equivalents) in pH 7.4 PBS containing 5 mM EDTA at RT and kept at 4° C. overnight. Analysis of the reaction mixture by analytical SAX column chromatography showed antibody siRNA conjugate along with unreacted antibody and siRNA.

Step 2: Purification

The crude reaction mixture was purified by AKTA explorer FPLC using anion exchange chromatography method-1. Fractions containing DAR1 and DAR2 antibody-siRNA conjugates were separated, concentrated and buffer exchanged with pH 7.4 PBS.

Step-3: Analysis of the Purified Conjugate

The isolated conjugates were characterized by either mass spec or SDS-PAGE. The purity of the conjugate was assessed by analytical HPLC using either anion exchange chromatography method-2 or 3 as well as size exclusion chromatography method-1.

Example 3.3. Fab' Generation from mAb and Conjugation to siRNA

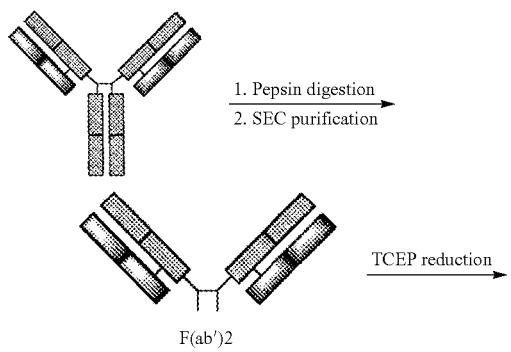

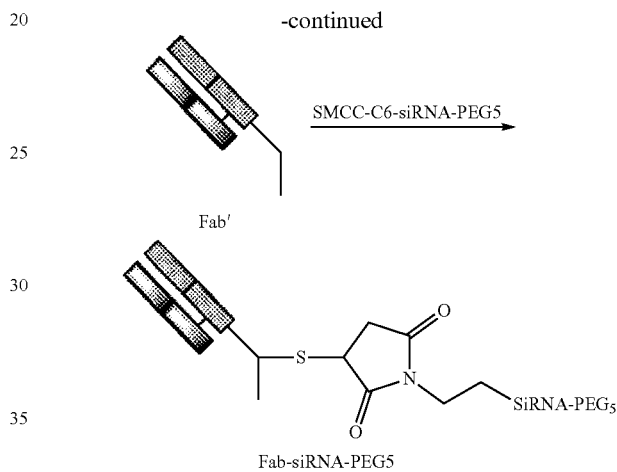

Step 1: Antibody Digestion with Pepsin

Antibody was buffer exchanged with pH 4.0, 20 mM sodium acetate/acetic acid buffer and made up to 5 mg/ml concentration. Immobilized pepsin (Thermo Scientific, Prod #20343) was added and incubated for 3 hours at 37° C. The reaction mixture was filtered using 30 kDa MWCO Amicon spin filters and pH 7.4 PBS. The retentate was collected and purified using size exclusion chromatography to isolate F(ab')2. The collected F(ab')2 was then reduced by 10 equivalents of TCEP and conjugated with SMCC-$C_6$-siRNA-PEG5 at room temperature in pH 7.4 PBS. Analysis of reaction mixture on SAX chromatography showed Fab-siRNA conjugate along with unreacted Fab and siRNA-PEG.

Step 2: Purification

The crude reaction mixture was purified by AKTA explorer FPLC using anion exchange chromatography method-1. Fractions containing DAR1 and DAR2 Fab-siRNA conjugates were separated, concentrated and buffer exchanged with pH 7.4 PBS.

Step-3: Analysis of the Purified Conjugate

The characterization and purity of the isolated conjugate was assessed by analytical HPLC using anion exchange chromatography method-2 or 3 as well as by SEC method-1.

Example 3.4. Purification and Analytical Methods

Anion Exchange Chromatography Method (SAX)-1.
1. Column: Tosoh Bioscience, TSKGel SuperQ-5PW, 21.5 mm ID×15 cm, 13 um
2. Solvent A: 20 mM TRIS buffer, pH 8.0; Solvent B: 20 mM TRIS, 1.5 M NaCl, pH 8.0; Flow Rate: 6.0 ml/min
3. Gradient:

| a. | % A | % B | Column Volume |
|---|---|---|---|
| b. | 100 | 0 | 1.00 |
| c. | 60 | 40 | 18.00 |
| d. | 40 | 60 | 2.00 |
| e. | 40 | 60 | 5.00 |
| f. | 0 | 100 | 2.00 |
| g. | 100 | 0 | 2.00 |

Anion Exchange Chromatography (SAX) Method-2
1. Column: Thermo Scientific, ProPac™ SAX-10, Bio LC™, 4×250 mm
2. Solvent A: 80% 10 mM TRIS pH 8, 20% ethanol; Solvent B: 80% 10 mM TRIS pH 8, 20% ethanol, 1.5 M NaCl; Flow Rate: 0.75 ml/min
3. Gradient:

| a. | Time | % A | % B |
|---|---|---|---|
| b. | 0.0 | 90 | 10 |
| c. | 3.00 | 90 | 10 |
| d. | 11.00 | 40 | 60 |
| e. | 23.00 | 40 | 60 |
| f. | 25.00 | 90 | 10 |
| g. | 30.00 | 90 | 10 |

Anion Exchange Chromatography (SAX) Method-3
1. Column: Thermo Scientific, ProPac™ SAX-10, Bio LC™, 4×250 mm
2. Solvent A: 80% 10 mM TRIS pH 8, 20% ethanol; Solvent B: 80% 10 mM TRIS pH 8, 20% ethanol, 1.5 M NaCl
3. Flow Rate; 0.75 ml/min
4. Gradient:

| a. | Time | % A | % B |
|---|---|---|---|
| b. | 0.0 | 90 | 10 |
| c. | 3.00 | 90 | 10 |
| d. | 11.00 | 40 | 60 |
| e. | 13.00 | 40 | 60 |
| f. | 15.00 | 90 | 10 |
| g. | 20.00 | 90 | 10 |

Size Exclusion Chromatography (SEC) Method-1
1. Column: TOSOH Biosciences, TSKgelG3000SW XL, 7.8×300 mm, 5 µM
2. Mobile phase: 150 mM phosphate buffer
3. Flow Rate: 1.0 ml/min for 15 mins Example 3.5. Antibody siRNA Conjugate Synthesis Using Bis-Maleimide (BisMal) Linker Step 1: Antibody Reduction with TCEP Antibody was buffer exchanged with 25 mM borate buffer (pH 8) with 1 mM DTPA and made up to 10 mg/ml concentration. To this solution, 4 equivalents of TCEP in the same borate buffer were added and incubated for 2 hours at 37° C. The resultant reaction mixture was combined with a solution of BisMal-siRNA (1.25 equivalents) in pH 6.0 10 mM acetate buffer at RT and kept at 4° C. overnight. Analysis of the reaction mixture by analytical SAX column chromatography showed antibody siRNA conjugate along with unreacted antibody and siRNA. The reaction mixture was treated with 10 EQ of N-ethylmaleimide (in DMSO at 10 mg/mL) to cap any remaining free cysteine residues.

Step 2: Purification

The crude reaction mixture was purified by AKTA Pure FPLC using anion exchange chromatography (SAX) method-1. Fractions containing DAR1 and DAR2 antibody-siRNA conjugates were isolated, concentrated and buffer exchanged with pH 7.4 PBS.

Anion Exchange Chromatography Method (SAX)-1.
Column: Tosoh Bioscience, TSKGel SuperQ-5PW, 21.5 mm ID×15 cm, 13 um
Solvent A: 20 mM TRIS buffer, pH 8.0; Solvent B: 20 mM TRIS, 1.5 M NaCl, pH 8.0; Flow Rate: 6.0 ml/min
Gradient:

| a. | % A | % B | Column Volume |
|---|---|---|---|
| b. | 100 | 0 | 1 |
| c. | 81 | 19 | 0.5 |
| d. | 50 | 50 | 13 |
| e. | 40 | 60 | 0.5 |
| f | 0 | 100 | 0.5 |
| g. | 100 | 0 | 2 |

Anion Exchange Chromatography (SAX) Method-2
Column: Thermo Scientific, ProPac™ SAX-10, Bio LC™, 4×250 mm
Solvent A: 80% 10 mM TRIS pH 8, 20% ethanol; Solvent B: 80% 10 mM TRIS pH 8, 20% ethanol, 1.5 M NaCl; Flow Rate: 0.75 ml/min
Gradient:

| a. | Time | % A | % B |
|---|---|---|---|
| b. | 0.0 | 90 | 10 |
| c. | 3.00 | 90 | 10 |
| d. | 11.00 | 40 | 60 |
| e. | 14.00 | 40 | 60 |
| f | 15.00 | 20 | 80 |
| g. | 16.00 | 90 | 10 |
| h. | 20.00 | 90 | 10 |

Example 4. Expression Profile of DUX4 in Myonuclei

Figure 4:
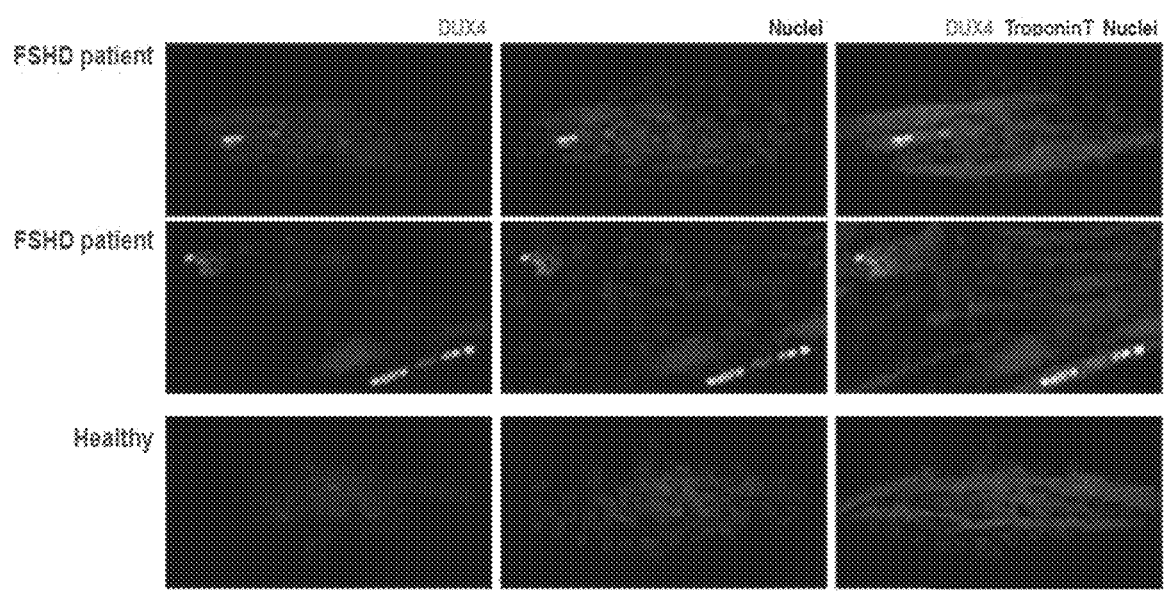
FIG. 4 shows immunofluorescent detection of DUX4 expression in myonuclei.

Myotubes derived from a healthy individual and FSHD patient were evaluated for DUX4 expression. As shown in FIG. 4, myotubes were immunostained to detect DUX4 expression. Muscle cells' nuclei and cytoplasm were immunostained by labeling DAPI (4',6-diamidino-2-phenylindole) and troponin T. As shown, DUX4 expression could be detected in low and sporadic manner—in less than 1% of myonuclei—indicating that detecting of DUX4 expression directly from the cell can be challenging in determining the effect of DUX4 siRNA activity.

Figure 5:
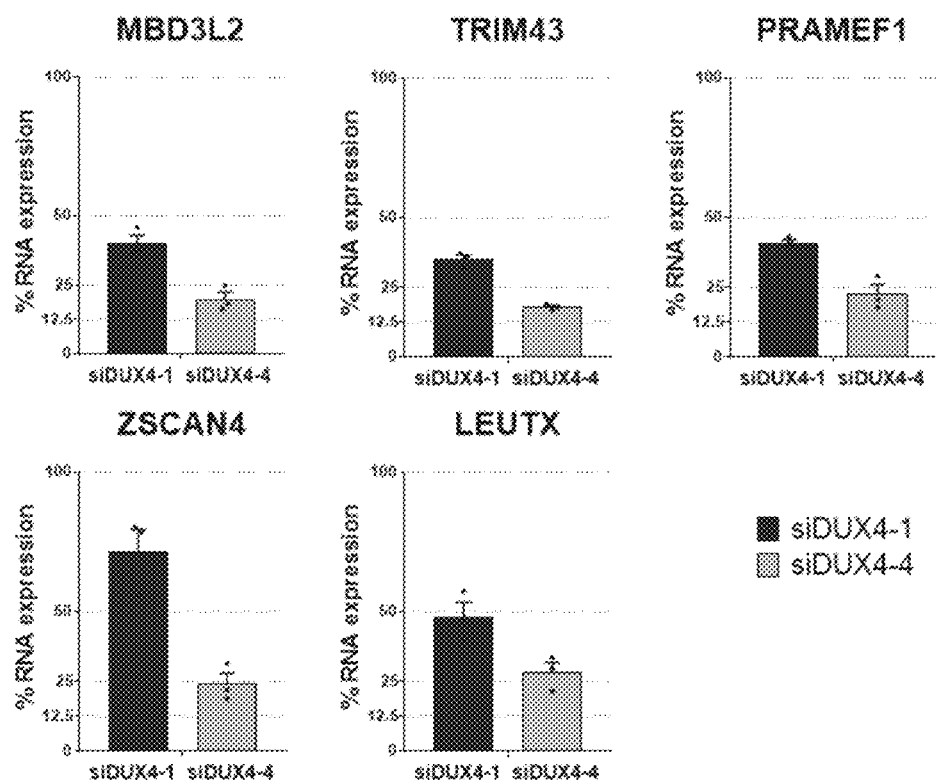
FIG. 5 shows bar graphs of siRNA-mediated reduction of DUX4-target biomarker gene expressions.

Example 5. Expression Profiles of DUX4-Dependent Marker Genes in FSHD Donor Muscle Cells with DUX4 siRNA Treatment Two DUX4 siRNAs (siDUX4-1 and siDUX4-4 are disclosed in Geng L N et al. *Dev. Cell,* 2012) were used to treat the diseased muscle cells (FSHD donor muscle cells), and RNA expression level of five DUX4-dependent biomarker genes were quantitated, as shown in bar graphs in FIG. 5. As shown, both siDUX4-1 and siDUX4-4 substantially reduced the expression of MBD3L2. TRIM43, PRAMEF1, ZSCAN4, and LEUTX compared to the baseline (100%). More specifically, siDUX4-4 reduced the expression of MBD3L2, TRIM43, PRAMEF1, ZSCAN4, and LEUTX at least ~75% compared to the baseline (100%). DUX4-target genes as biomarkers were sensitive to measure siRNA-mediated downregulation of DUX4.

Figure 6A:
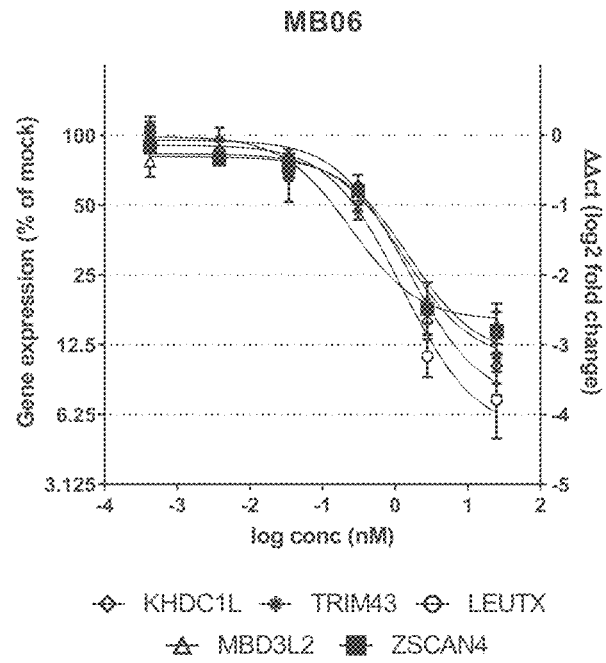
FIGS. 6A-B show graphs of the siRNA-mediated reduction of DUX4-target biomarker gene expressions in cultured FSHD primary myotubes and a FSHD composite of the siRNA-mediated reduction of DUX4-target biomarker gene expressions in cultured FSHD primary myotubes
Figure 6B:
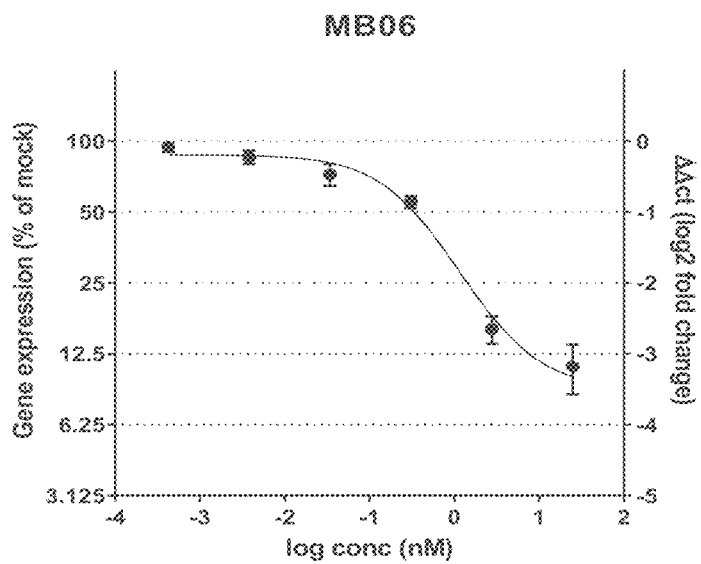

Example 6. DUX4 siRNA-Mediated Reduction of 5 DUX4-Target Biomarker Gene Expressions and a FSHD Composite of DUX4-Target Biomarker Genes in Cultured FSHD Primary Myotubes FSHD1 patient-derived primary myoblasts (MB06) were used to validate the FSHD composite as a reliable surrogate biomarker to assess DUX4 siRNA activity with the published 2 DUX4 siRNAs, siDUX4-1 and siDUX4-4 (Geng L N et al, *Dev. Cell,* 2012) in a dose dependent concentration. FSHD primary myoblasts (MB06 (FSHD1)) were grown in recommended media. Prior to seeding, 96-well tissue culture plates (Costar) were coated with 50 µL of 1% Matrigel per well for at least 2 hours at 37° C., and washed 2× with PBS. After coating, myoblasts were seeded in quadruplicate at 4000 cells/well without antibiotics and maintained 24 h prior to transfection. On the day of transfection, the DUX4-4 siRNA was formulated with commercially available transfection reagent Lipofectamine RNAiMAX (Life Technologies) and OptiMEM (Life Technologies) according to the manufacturer's "forward transfection" instructions. DUX4-4 siRNA was synthesized by Integrated DNA Technologies (IDT). Myoblasts were transfected with DUX4-4 siRNA at a high concentration of 25 nM with 9-fold serial dilutions. 24 hours post transfection, myogenic differentiation was induced with 15% KOSR-containing differentiation medium. Myotubes were collected in Trizol 4 days after inducing differentiation and stored at −80'C until processing. RNA isolation was performed using Direct-zol-96 RNA isolation kit (Zymo) according to the manufacturer's instructions. 100-500 ng of purified RNA was converted to cDNA using High-Capacity cDNA Reverse Transcription Kit (Applied Biosystems) using SimpliAmp Thermal Cycler (Applied Biosystems). cDNA was analyzed by qPCR using TaqMan Fast Universal Master Mix II (Thermo Fisher) and TaqMan probes (Thermo Fisher) in duplicates, using QuantStudio 6 or 7 Flex Real-Time PCR instruments (Applied Biosystems). Data were analyzed by QuantStudio™ Real-Time PCR Software v1.3 (Applied Biosystems). The expression levels of 5 DUX4-target genes were evaluated: MBD3L2, ZSCAN4, LEUTX, KHDC1L, and TRIM43. DUX4-target gene expression was normalized to a composite of two reference genes: AHSA1 and RPL27. The percentage of target mRNA expression was determined relative to mock treated cells by using the $2^{-\Delta\Delta Ct}$ method (Livak and Schmittgen, *Methods* 2001). FIG. 6A-B show DUX4 siRNA-mediated reduction of 5 DUX4-target biomarker gene expressions in cultured FSHD primary myotubes. DUX4 siRNA reduced the expression of 5 individual DUX4-target biomarker genes (MBD3L2. ZSCAN4, LEUTX, KHDC1L, and TRIM43) (FIG. 6A) or as a FSHD composite of the 5 DUX4-target biomarker genes (FIG. 6B) in cultured FSHD primary myotubes.

Example 7. DUX4 siRNA Library Screening—First Round at 2 Concentrations (10 and 0.5 nM) in MB02 and MB06

In this example, 70 DUX4 siRNAs were screened for their activity in two FSHD primary myoblast cell lines (MB02 (FSHD1) and MB06 (FSHD1)) to identify more desirable siRNA candidates. Cells were plated at a density of 4,000 cells/well (MW96) and then transfected in four replicates with DUX4 siRNAs, as well as a tool siRNA as control. Transfection was performed 24 hours after plating at 10 nM concentration. Myogenic differentiation was induced 2 days after plating (24 hours after transfection) with 15% KOSR (in DMEM/F-12) medium. Samples were harvested 3 or 4 days after inducing differentiation, depending on the cell line. DUX4-downstream target gene expression was evaluated by RT-qPCR (normalized to a composite AHSA1 and RPL27 housekeeping gene expression value). Data shown in this example are represented as mean FSHD Composite−/+ SEM. N=4.

Figure 7:
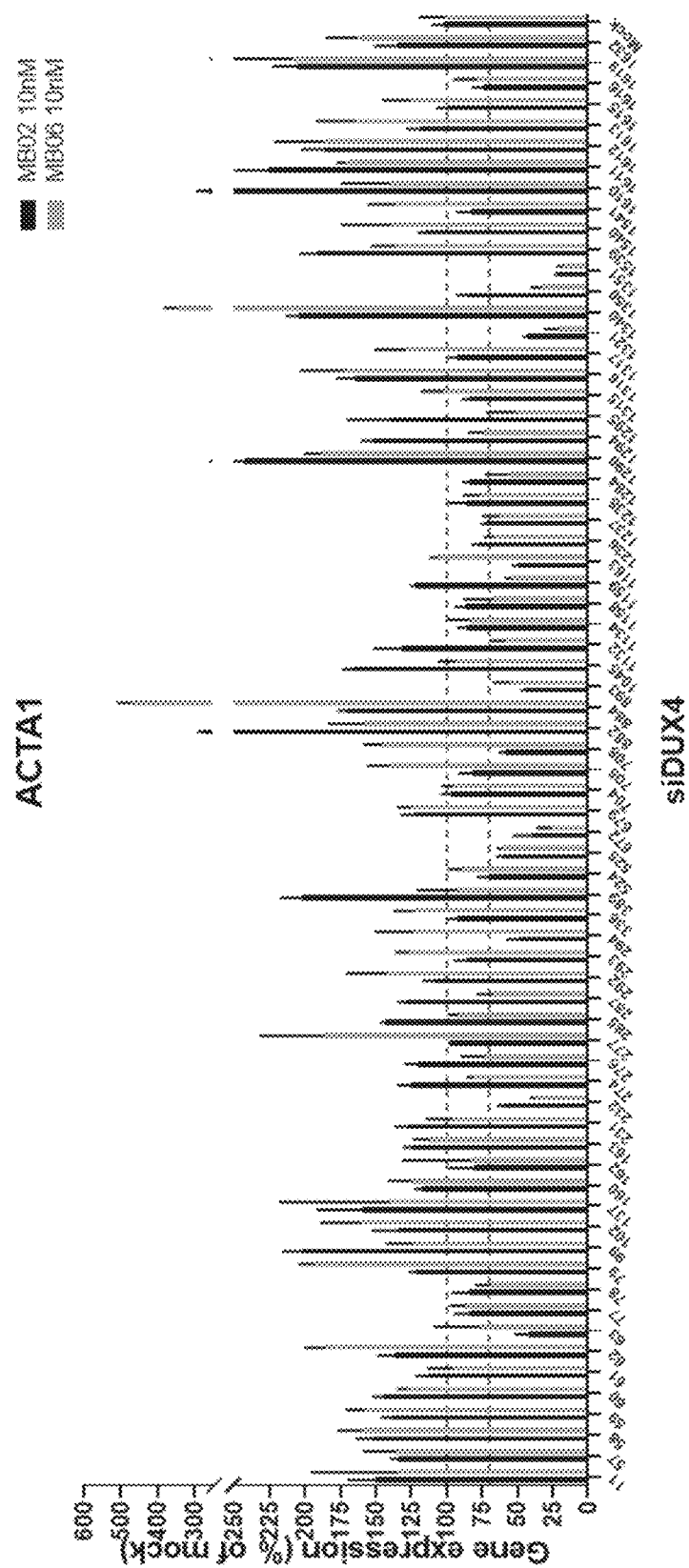
FIG. 7 shows a bar graph of ACTA1 gene expression in myotubes with treatment of DUX4 siRNA at a concentration of 10 nM.

FIG. 7 shows a bar graph of assessment of myotubes differentiation and viability at 10 nM concentration of siDUX4 by monitoring ACTA1 expression in MB02 (FSHD1) and MB06 (FSHD1) cell lines.

Figure 8:
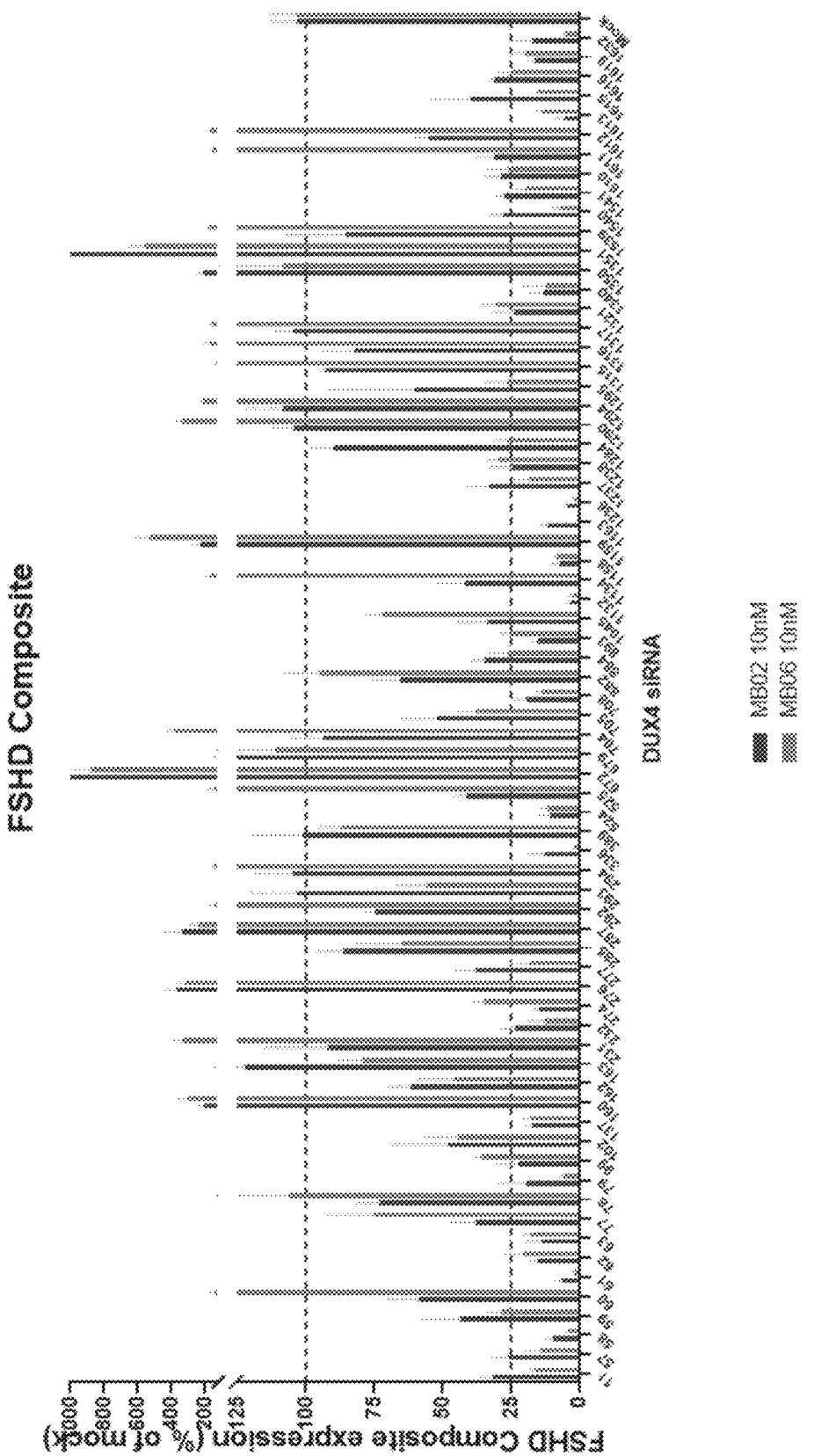
FIG. 8 shows FSHD composite expression in myotubes with treatment of DUX4 siRNA at a concentration of 10 nM.

FIG. 8 shows a bar graph of screening for activity at 10 nM Concentration of 70 DUX4 siRNAs by measuring FSHD composite expression (Calculations of the FSHD composite: Dct=(Av. ct 4 DUX4 target genes)−(Av. ct 2 HKGs), DDct=Dct (siDUX4)−Dct (mock), Composite=2^-DDct*100(%)).

Figure 9:
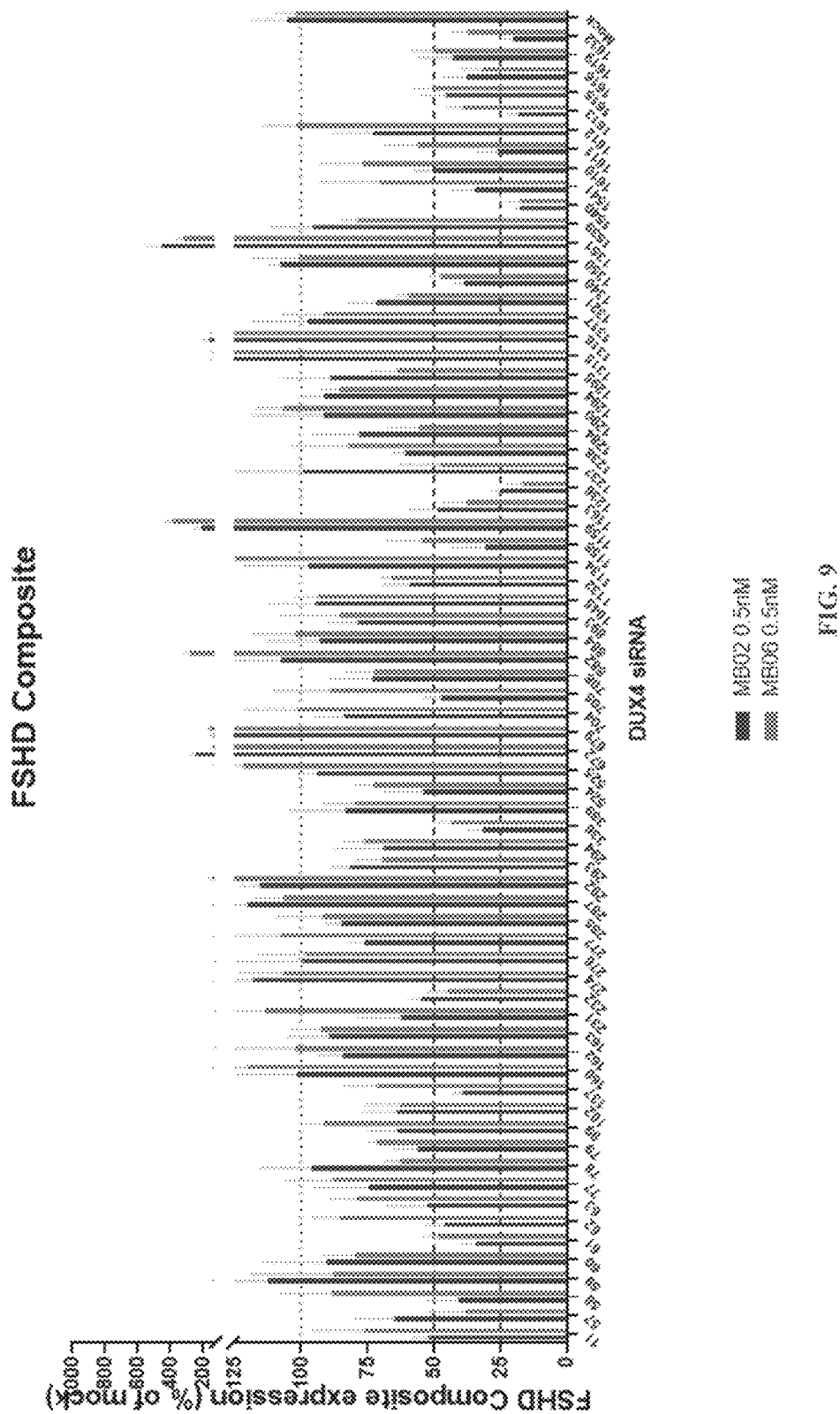
FIG. 9 shows FSHD composite expression in myotubes with treatment of DUX4 siRNA at a concentration of 0.5 nM.

FIG. 9 shows a bar graph of screening for activity at 0.5 nM Concentration of 70 DUX4 siRNAs by measuring FSHD composite expression. As used herein. FSHD Composite is made of 4 DUX4-target genes: MBD3L29 ZSCAN4, LEUTX, KHDC1L. As shown in Table 15, downregulation of FSHD composite expression is well correlated with downregulation of individual genes in the composite when normalized to HKG composite (AHSA1, RPL27) (n=4), indicating that the effective downregulation of FSHD composite expression is a good indicator to DUX4 siRNA potency.

TABLE 15

| siRNA | MB02 | | | | | | | MB06 |
| | FSHD Composite | KHDC1l | LEUTX | MDB3L2 | ZSCAN4 | AHSA1 | RPl27 | FSHD Composite |
|---|---|---|---|---|---|---|---|---|
| 11 | 31.75 | 32.33 | 27.01 | 47.47 | 30.27 | 109.58 | 91.38 | 16.09 |
| 57 | 25.85 | 22.62 | 27.70 | 42.22 | 20.85 | 97.29 | 103.31 | 14.22 |
| 58 | 9.78 | 12.44 | 13.10 | 5.88 | 7.11 | 97.37 | 103.29 | 4.10 |
| 59 | 43.49 | 44.17 | 43.50 | 45.55 | 45.97 | 105.40 | 94.78 | 28.22 |

TABLE 15-continued

| | | | | | | | | |
|---|---|---|---|---|---|---|---|---|
| 60 | 58.45 | 59.45 | 55.13 | 69.75 | 57.17 | 94.97 | 105.61 | 140.69 |
| 61 | 6.34 | 7.32 | 2.83 | 11.18 | 9.93 | 90.50 | 113.77 | 1.73 |
| 62 | 15.44 | 18.56 | 12.97 | 25.33 | 12.82 | 100.38 | 102.07 | 20.45 |
| 63 | 13.73 | 29.72 | 11.40 | 14.50 | 10.07 | 85.09 | 118.35 | 17.87 |
| 77 | 37.74 | 32.95 | 30.95 | 47.38 | 45.61 | 94.54 | 105.59 | 75.08 |
| 78 | 72.97 | 59.09 | 58.98 | 102.78 | 83.09 | 100.39 | 100.53 | 106.34 |
| 79 | 19.50 | 12.62 | 19.45 | 34.83 | 24.75 | 108.94 | 95.53 | 5.72 |
| 99 | 22.26 | 16.41 | 19.77 | 35.04 | 25.06 | 92.52 | 109.14 | 35.72 |
| 102 | 48.17 | 39.31 | 49.89 | 65.85 | 45.69 | 101.19 | 100.20 | 44.10 |
| 137 | 17.49 | 14.10 | 11.02 | 25.26 | 31.37 | 93.65 | 107.00 | 17.65 |
| 160 | 201.88 | 205.52 | 215.56 | 241.34 | 167.58 | 97.09 | 103.95 | 300.78 |
| 162 | 61.62 | 51.74 | 58.79 | 91.54 | 57.24 | 105.98 | 93.58 | 45.68 |
| 163 | 122.38 | 115.49 | 111.83 | 111.99 | 154.49 | 88.53 | 113.03 | 79.05 |
| 231 | 91.73 | 95.05 | 89.58 | 106.78 | 91.32 | 97.74 | 102.50 | 337.97 |
| 232 | 23.56 | 25.81 | 22.38 | 33.70 | 17.65 | 102.82 | 98.35 | 12.55 |
| 274 | 14.70 | 12.58 | 7.62 | 26.42 | 21.88 | 95.39 | 106.34 | 34.53 |
| 276 | 355.14 | 295.05 | 459.25 | 349.12 | 397.99 | 104.97 | 96.57 | 319.52 |
| 277 | 37.91 | 43.98 | 41.85 | 40.48 | 38.05 | 108.35 | 94.03 | 18.43 |
| 285 | 86.15 | 108.25 | 75.54 | 78.48 | 98.14 | 88.18 | 114.79 | 65.05 |
| 287 | 339.10 | 407.15 | 355.95 | 331.14 | 282.13 | 99.11 | 101.55 | 239.05 |
| 292 | 74.54 | 55.24 | 70.23 | 99.22 | 71.01 | 99.83 | 100.24 | 141.85 |
| 293 | 103.15 | 93.51 | 103.54 | 114.07 | 115.31 | 95.28 | 104.03 | 55.65 |
| 294 | 104.91 | 113.05 | 114.54 | 112.24 | 92.48 | 92.28 | 108.55 | 147.19 |
| 335 | 12.62 | 12.47 | 13.75 | 15.54 | 14.57 | 100.38 | 100.54 | 1.77 |
| 289 | 101.16 | 143.98 | 74.83 | 103.37 | 105.53 | 91.50 | 110.54 | 87.13 |
| 524 | 10.70 | 7.90 | 5.81 | 18.87 | 20.05 | 102.71 | 97.55 | 11.57 |
| 525 | 41.37 | 44.14 | 45.56 | 39.27 | 41.85 | 100.52 | 100.49 | 147.51 |
| 672 | 1105.70 | 976.91 | 1558.44 | 1316.38 | 778.03 | 102.53 | 97.86 | 875.88 |
| 679 | 126.54 | 165.55 | 124.45 | 112.83 | 118.55 | 84.77 | 118.50 | 111.13 |
| 704 | 93.68 | 93.39 | 94.12 | 118.54 | 85.98 | 100.74 | 100.94 | 382.40 |
| 705 | 52.22 | 52.53 | 39.24 | 70.91 | 49.46 | 100.96 | 99.96 | 37.85 |
| 708 | 19.24 | 27.41 | 17.79 | 21.23 | 14.34 | 105.74 | 95.27 | 13.86 |
| 882 | 65.40 | 41.13 | 61.93 | 118.03 | 64.59 | 108.83 | 93.30 | 95.03 |
| 884 | 34.58 | 28.82 | 25.19 | 51.92 | 42.17 | 106.64 | 95.66 | 25.97 |
| 893 | 15.06 | 12.73 | 13.13 | 23.42 | 14.15 | 80.16 | 124.98 | 25.57 |
| 1045 | 33.86 | 28.20 | 32.38 | 42.01 | 42.10 | 102.03 | 99.58 | 72.20 |
| 1132 | 3.20 | 4.19 | 1.89 | 42.6 | 4.64 | 92.42 | 110.66 | 2.17 |
| 1134 | 41.73 | 31.74 | 27.87 | 62.98 | 58.37 | 97.67 | 103.39 | 165.18 |
| 1158 | 7.01 | 6.51 | 4.48 | 13.33 | 9.47 | 91.29 | 109.76 | 8.01 |
| 1159 | 226.21 | 152.73 | 154.74 | 292.83 | 401.40 | 82.15 | 126.63 | 525.79 |
| 1163 | 11.52 | 15.00 | 8.01 | 15.75 | 10.55 | 94.55 | 106.71 | 0.62 |
| 1236 | 4.22 | 3.32 | 1.94 | 8.35 | 8.47 | 82.34 | 121.73 | 1.85 |
| 1237 | 32.87 | 31.02 | 25.17 | 43.61 | 38.79 | 97.35 | 102.99 | 18.02 |
| 1238 | 24.43 | 25.07 | 19.03 | 35.16 | 24.46 | 105.02 | 95.44 | 29.53 |
| 1284 | 90.11 | 83.12 | 84.62 | 106.45 | 100.99 | 98.75 | 106.13 | 26.55 |
| 1290 | 104.36 | 97.53 | 102.02 | 118.57 | 109.73 | 100.22 | 101.46 | 335.73 |
| 1294 | 108.34 | 91.38 | 115.59 | 177.24 | 78.03 | 114.67 | 88.47 | 210.94 |
| 1295 | 60.35 | 60.16 | 43.80 | 96.21 | 55.94 | 69.18 | 145.68 | 26.36 |
| 1315 | 92.84 | 85.02 | 96.47 | 111.78 | 83.44 | 107.21 | 93.35 | 132.47 |
| 1316 | 82.53 | 68.66 | 62.91 | 154.83 | 71.10 | 97.30 | 103.65 | 170.76 |
| 1317 | 104.92 | 105.43 | 101.20 | 112.07 | 112.09 | 97.95 | 105.07 | 155.72 |
| 1321 | 23.72 | 20.71 | 13.75 | 44.87 | 29.79 | 87.40 | 115.65 | 30.38 |
| 1340 | 13.06 | 14.55 | 14.52 | 14.04 | 12.12 | 76.27 | 131.90 | 12.24 |
| 1350 | 207.49 | 155.67 | 224.45 | 254.19 | 222.09 | 103.71 | 96.95 | 108.59 |
| 1351 | 2217.65 | 1074.92 | 2732.04 | 3210.96 | 2752.93 | 135.49 | 75.80 | 556.04 |
| 1539 | 85.20 | 76.82 | 87.54 | 121.01 | 73.71 | 98.65 | 102.96 | 174.37 |
| 1540 | 27.76 | 27.63 | 21.74 | 39.45 | 27.56 | 99.84 | 100.4 | 6.96 |
| 1541 | 27.45 | 23.47 | 21.75 | 36.77 | 33.40 | 94.71 | 106.55 | 19.68 |
| 1610 | 28.54 | 14.04 | 21.45 | 56.20 | 41.60 | 102.33 | 98.02 | 26.04 |
| 1611 | 31.12 | 23.09 | 26.42 | 59.28 | 27.96 | 96.38 | 104.00 | 148.02 |
| 1612 | 55.31 | 46.84 | 46.05 | 91.02 | 53.05 | 104.00 | 97.07 | 166.82 |
| 1613 | 5.18 | 6.53 | 1.37 | 8.42 | 9.92 | 96.50 | 106.13 | 13.55 |
| 1615 | 39.81 | 36.59 | 35.01 | 62.94 | 35.85 | 103.77 | 97.50 | 15.05 |
| 1616 | 31.13 | 28.01 | 32.41 | 33.99 | 31.93 | 94.67 | 106 96 | 24.95 |
| 1619 | 16.06 | 11.42 | 7.09 | 38.40 | 25.85 | 96.42 | 104.14 | 19.69 |
| 1632 | 17.02 | 21.17 | 23.00 | 26.39 | 8.73 | 109.10 | 92.79 | 4.83 |

| | | MB06 | | | | | |
|---|---|---|---|---|---|---|---|
| | siRNA | KHDC11 | LEUTX | MBD3L2 | ZSCAN4 | AHSA1 | RPI27 |
| | 11 | 8.38 | 11.09 | 23.82 | 33.31 | 114.05 | 90.97 |
| | 57 | 12.15 | 10.51 | 18.81 | 19.54 | 89.28 | 115.02 |
| | 58 | 2.57 | 2.37 | 6.05 | 11.34 | 10.19 | 105.55 |
| | 59 | 22.48 | 29.71 | 33.29 | 32.50 | 117.04 | 88.15 |
| | 60 | 122.45 | 142.62 | 155.90 | 150.70 | 116.93 | 4.15 |
| | 61 | 1.57 | 1.08 | 1.78 | 4.58 | 9.85 | 114.58 |
| | 62 | 10.45 | 15.63 | 37.90 | 32.54 | 101.13 | 102.58 |
| | 63 | 21.42 | 13.53 | 24.40 | 16.06 | 83.35 | 122.84 |
| | 77 | 53.88 | 58.53 | 78.07 | 112.37 | 111.85 | 93.58 |

TABLE 15-continued

| | | | | | | |
|---|---|---|---|---|---|---|
| 78 | 79.97 | 85.79 | 123.98 | 154.02 | 103.95 | 101.34 |
| 79 | 7.19 | 3.78 | 5.70 | 8.23 | 99.32 | 104.82 |
| 99 | 25.35 | 26.35 | 40.43 | 63.61 | 99.65 | 104.80 |
| 102 | 57.01 | 39.54 | 42.83 | 40.52 | 90.72 | 119.87 |
| 137 | 1.24 | 12.00 | 21.07 | 33.17 | 98.95 | 105.09 |
| 160 | 306.57 | 304.41 | 294.44 | 312.89 | 108.55 | 100.20 |
| 162 | 29.38 | 37.70 | 55.89 | 73.25 | 105.10 | 97.57 |
| 163 | 63.62 | 72.05 | 62.17 | 144.47 | 95.43 | 109.30 |
| 231 | 283.17 | 379.63 | 352.81 | 354.24 | 115.95 | 92.45 |
| 232 | 11.16 | 9.33 | 15.35 | 17.15 | 92.25 | 109.99 |
| 274 | 26.94 | 29.25 | 37.69 | 50.61 | 103.83 | 99.85 |
| 276 | 337.69 | 319.51 | 228.18 | 44.51 | 199.52 | 110.28 |
| 277 | 17.38 | 16.75 | 19.54 | 22.05 | 100.75 | 102.23 |
| 285 | 53.72 | 56.52 | 72.14 | 71.55 | 102.87 | 103.35 |
| 287 | 253.18 | 231.21 | 228.18 | 257.25 | 101.75 | 102.15 |
| 292 | 143.88 | 135.19 | 159.14 | 135.01 | 103.00 | 105.57 |
| 293 | 40.83 | 48.59 | 71.53 | 70.82 | 103.57 | 100.30 |
| 294 | 163.93 | 152.23 | 129.50 | 154.54 | 104.25 | 104.91 |
| 335 | 1.85 | 0.74 | 2.24 | 3.69 | 105.87 | 100.27 |
| 289 | 87.19 | 61.30 | 80.98 | 139.82 | 97.28 | 110.00 |
| 524 | 8.50 | 7.01 | 13.83 | 22.05 | 125.94 | 84.71 |
| 525 | 131.00 | 168.52 | 148.43 | 149.22 | 115.00 | 89.05 |
| 672 | 932.45 | 950.25 | 747.57 | 916.32 | 95.33 | 105.59 |
| 679 | 89.15 | 108.25 | 119.11 | 139.93 | 108.59 | 99.35 |
| 704 | 345.98 | 392.90 | 385.90 | 415.94 | 110.04 | 98.08 |
| 705 | 40.55 | 22.82 | 47.40 | 50.42 | 95.14 | 108.51 |
| 708 | 12.61 | 8.91 | 21.99 | 16.45 | 110.19 | 98.33 |
| 882 | 51.51 | 92.26 | 137.90 | 135.15 | 126.73 | 85.08 |
| 884 | 22.07 | 25.24 | 23.84 | 38.18 | 121.69 | 88.93 |
| 893 | 22.57 | 17.56 | 18.86 | 61.47 | 74.41 | 151.83 |
| 1045 | 55.02 | 62.24 | 73.95 | 110.04 | 112.74 | 93.00 |
| 1132 | 1.38 | 1.22 | 2.33 | 4.89 | 110.80 | 95.16 |
| 1134 | 124.57 | 138.47 | 238.72 | 194.16 | 120.19 | 96.87 |
| 1158 | 6.27 | 3.33 | 14.17 | 16.01 | 103.69 | 100.97 |
| 1159 | 246.31 | 419.47 | 961.82 | 840.11 | 109.42 | 94.92 |
| 1163 | 0.71 | 0.24 | 1.16 | 1.49 | 114.57 | 93.45 |
| 1236 | 1.56 | 0.70 | 2.59 | 4.72 | 83.65 | 125.55 |
| 1237 | 15.99 | 12.24 | 19.83 | 28.35 | 86.15 | 127.14 |
| 1238 | 23.79 | 22.54 | 35.10 | 43.41 | 106.57 | 101.82 |
| 1284 | 26.17 | 21.71 | 21.91 | 47.85 | 105.06 | 107.66 |
| 1290 | 277.05 | 410.94 | 346.25 | 336.63 | 129.53 | 81.28 |
| 1294 | 212.54 | 213.33 | 192.41 | 237.66 | 104.07 | 108.48 |
| 1295 | 19.44 | 20.39 | 39.85 | 33.69 | 80.55 | 134.12 |
| 1315 | 131.69 | 120.09 | 124.25 | 162.31 | 102.73 | 107.96 |
| 1316 | 141.70 | 168.39 | 207.31 | 175.30 | 116.86 | 93.87 |
| 1317 | 136.41 | 146.45 | 192.41 | 163.46 | 116.80 | 89.59 |
| 1321 | 22.32 | 20.48 | 43.92 | 44.59 | 91.46 | 115.30 |
| 1340 | 16.78 | 10.49 | 8.35 | 17.48 | 80.76 | 135.39 |
| 1350 | 73.33 | 116.32 | 128.51 | 130.28 | 111.71 | 94.61 |
| 1351 | 409.02 | 572.93 | 604.80 | 690.63 | 124.43 | 89.12 |
| 1539 | 162.38 | 150.76 | 180.05 | 217.16 | 105.72 | 100.85 |
| 1540 | 10.19 | 3.38 | 8.01 | 9.77 | 95.47 | 111.96 |
| 1541 | 13.08 | 13.65 | 27.71 | 34.20 | 104.27 | 100.39 |
| 1610 | 14.84 | 20.65 | 28.45 | 59.48 | 111.99 | 98.08 |
| 1611 | 126.75 | 169.36 | 178.77 | 128.62 | 115.44 | 90.38 |
| 1612 | 149.98 | 188.56 | 161.52 | 174.12 | 123.98 | 87.12 |
| 1613 | 10.97 | 6.06 | 22.26 | 24.00 | 110.12 | 94.54 |
| 1615 | 10.29 | 8.06 | 20.20 | 34.44 | 98.28 | 107.83 |
| 1616 | 15.42 | 15.50 | 31.87 | 59.94 | 104.72 | 99.75 |
| 1619 | 15.64 | 10.91 | 33.63 | 30.66 | 103.27 | 106.14 |
| 1632 | 6.04 | 2.20 | 7.24 | 6.80 | 101.92 | 104.27 |

Figure 10:
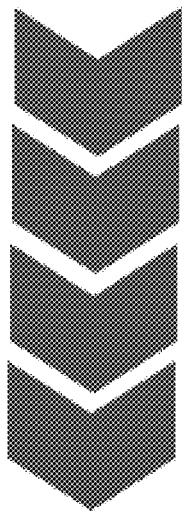
FIG. 10 shows a flowchart diagram of the selection of DUX4 top 28 siRNAs based on data from initial screening.
Figure 11A:
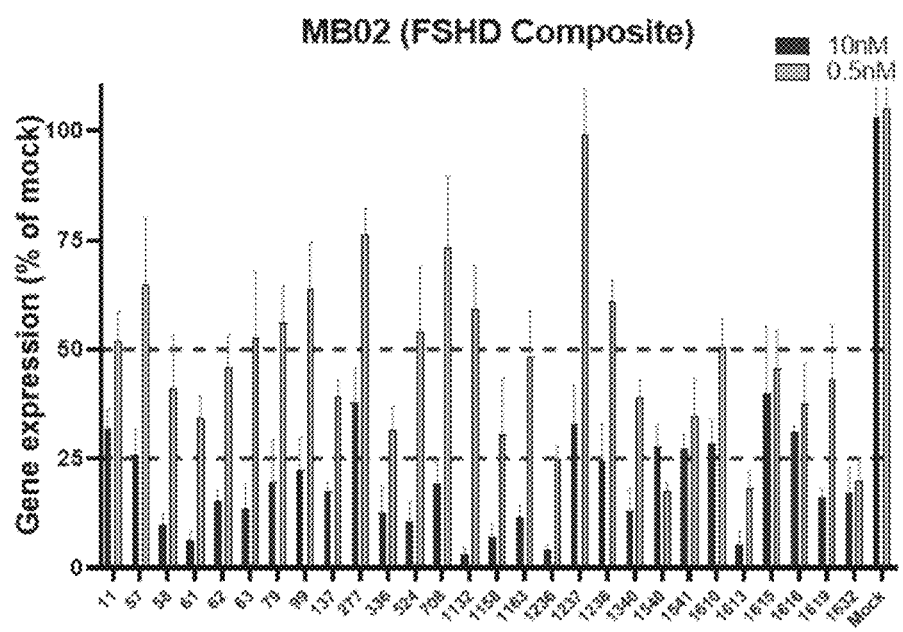
FIGS. 11A-B show FSHD composite expression in two FSHD primary myotubes upon treatment with DUX4 siRNAs at a concentration of 10 nM and 0.5 nM.
Figure 11B:
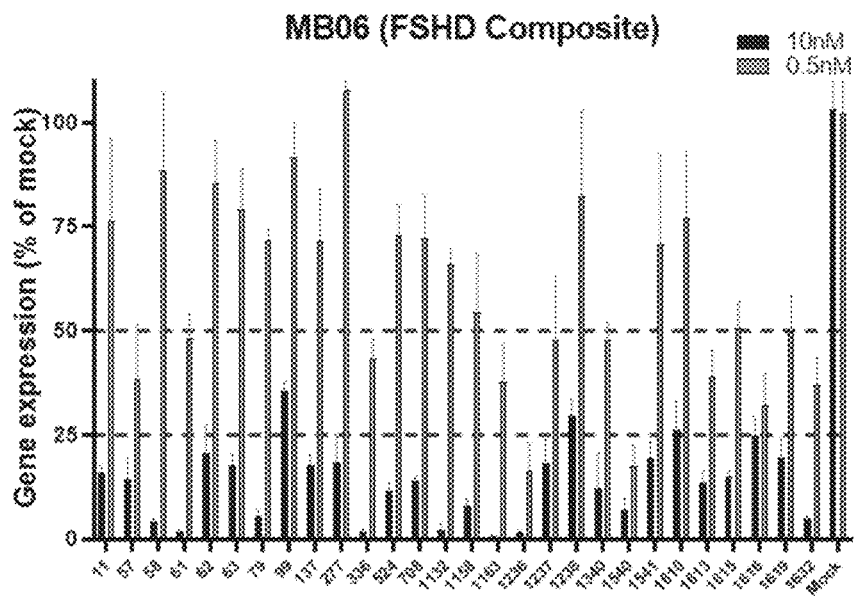

As shown in FIG. 10, from the DUX4 siRNA library with 70 siRNA candidates 37 candidates were eliminated that have lower than 70% KD in at least one cell lines at 10 nM. Then, 3 additional siRNA candidates were eliminated that resulted in ACTA1 expression less than 70% in both cell lines. Then, 2 additional siRNA candidates with null activity (<10% KD) at 0.5 nM in both cell lines were eliminated, resulting in total 28 siRNA candidates left for the next screening process. Table 16 lists such selected 28 DUX4 siRNAs and the downregulation of FSHD composite expression in two cell lines at the concentration of 10 nM and 0.5 nM of the selected 28 DUX4 siRNAs (also shown as bar graphs in FIGS. 11A and 11B).

TABLE 16

| | FSHD Composite (% Mock) | | | |
|---|---|---|---|---|
| siRNA | MB02—10 nM | MB02—0.5 nM | MB06—10 nM | MB06—0.5 nM |
| 11 | 31.76 | 51.87 | 16.09 | 76.24 |
| 57 | 25.86 | 64.82 | 14.22 | 38.21 |
| 58 | 9.78 | 40.95 | 4.10 | 88.52 |
| 61 | 6.34 | 34.34 | 1.73 | 48.20 |
| 62 | 15.44 | 45.95 | 20.46 | 85.52 |
| 63 | 13.73 | 52.64 | 17.87 | 79.18 |
| 79 | 19.50 | 56.01 | 5.72 | 71.70 |
| 99 | 22.26 | 63.90 | 35.72 | 91.67 |

TABLE 16-continued

| | FSHD Composite (% Mock) | | | |
|---|---|---|---|---|
| siRNA | MB02—10 nM | MB02—0.5 nM | MB06—10 nM | MB06—0.5 nM |
| 137 | 17.49 | 39.13 | 17.66 | 71.37 |
| 277 | 37.91 | 76.29 | 18.43 | 107.75 |
| 336 | 12.62 | 31.51 | 1.77 | 43.22 |
| 524 | 10.70 | 53.98 | 11.57 | 73.00 |
| 708 | 19.24 | 73.21 | 13.86 | 72.29 |
| 1132 | 3.20 | 59.37 | 2.17 | 66.00 |
| 1158 | 7.01 | 30.58 | 8.01 | 5440 |
| 1163 | 11.52 | 48.46 | 0.62 | 37.70 |
| 1236 | 4.22 | 25.00 | 1.85 | 16.55 |
| 1237 | 32.87 | 99.25 | 18.02 | 47.65 |
| 1238 | 24.43 | 60.92 | 29.53 | 82.40 |
| 1340 | 13.06 | 38.81 | 12.24 | 47.63 |
| 1540 | 27.76 | 17.63 | 6.96 | 17.57 |
| 1541 | 27.45 | 34.55 | 19.68 | 70.70 |
| 1610 | 28.54 | 50.65 | 26.04 | 76.91 |
| 1613 | 5.18 | 18.30 | 13.55 | 39.25 |
| 1615 | 39.81 | 45.49 | 15.05 | 50.57 |
| 1616 | 31.13 | 37.63 | 24.95 | 32.25 |
| 1619 | 16.06 | 42.95 | 19.69 | 49.95 |
| 1632 | 17.02 | 20.07 | 4.83 | 37.10 |

Figure 12:
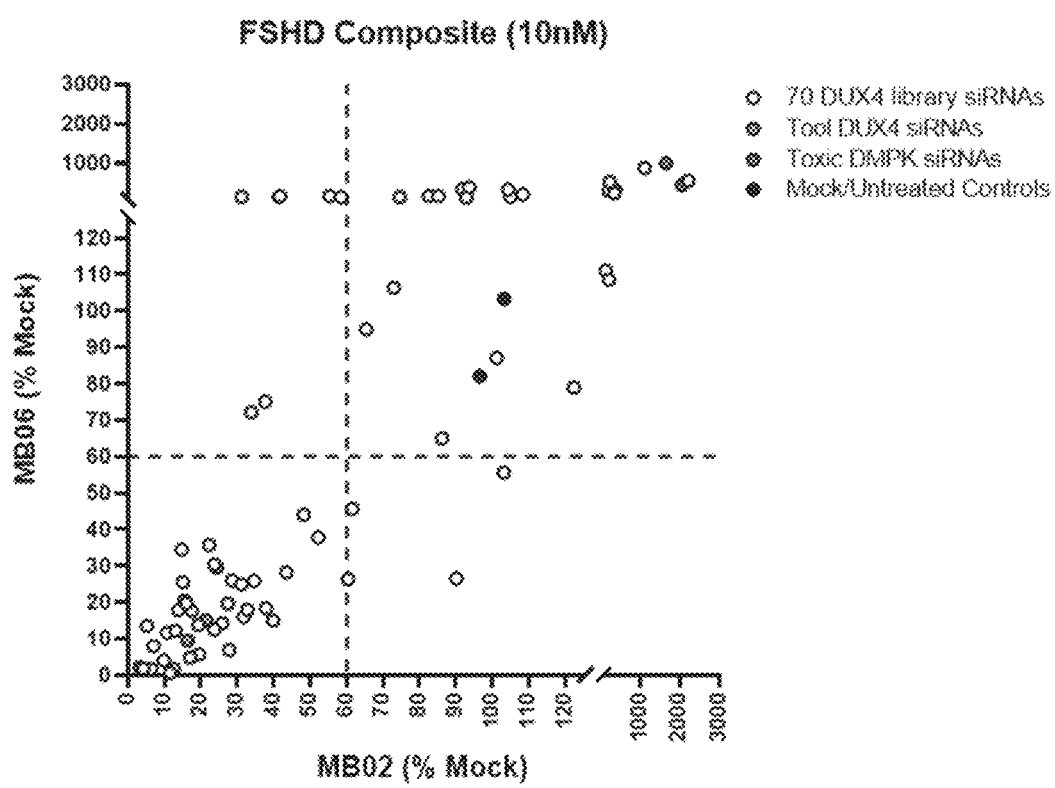
FIG. 12 shows a KD correlation analysis identifying DUX4 siRNA effective in one or more FSHD primary myotubes.

Databases of human polymorphisms are not reliable in repeats and it is possible that polymorphic positions may be missed. Thus, in this round of selection, siRNAs that show poor performance in one of two myoblast cell lines were eliminated for a purpose of validating that selected DUX4 siRNAs are active in a variety of FSHD-patient derived myoblasts. FIG. 12 shows distribution of 70 siRNAs by their efficacies of downregulating FSHD composite in two myoblast cell lines. KD correlation analysis identified ~10% of DUX4 siRNAs that worked only in one of the two FSHD primary myoblast cell lines used in the full library screening.

Example 8. DUX4 siRNA Library Screening—Second Round at 10 nM in Four Different Patient-Derived Primary Myoblast Cell Lines In this example, a total of 9 high quality FSHD patient-derived primary myoblast cell lines (6 FSHD1, 3 FSHD2) were used. Conditions that allow reliable detection of DUX4 target gene expression in FSHD myotubes in-house were established by culturing the cells in Differentiation medium (15% KOSR in DMEM/F-12). Time-point was selected specifically for each cell line. All 9 FSHD cell lines showed a concentration-dependent response to a tool DUX4 siRNA.

Figure 13:
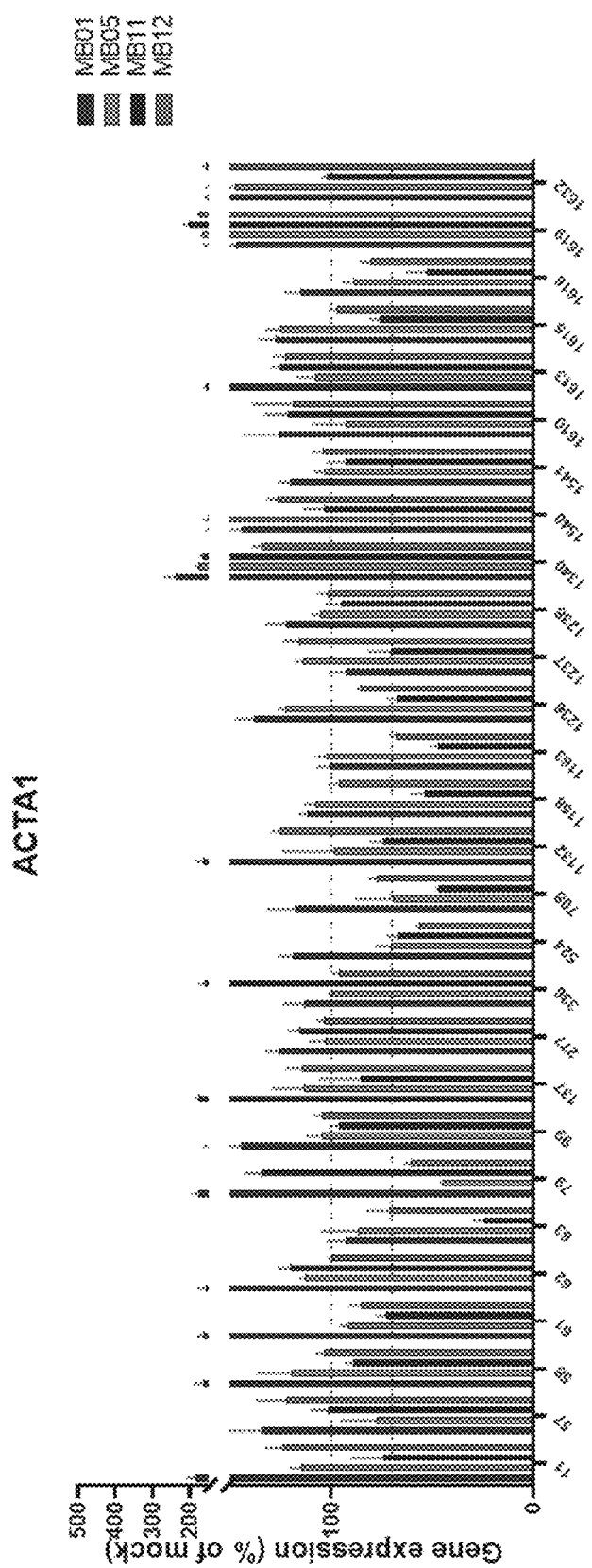
FIG. 13 shows ACTA1 gene expression in patient-derived myotubes with treatment of DUX4 siRNA at a concentration of 10 nM.
Figure 14:
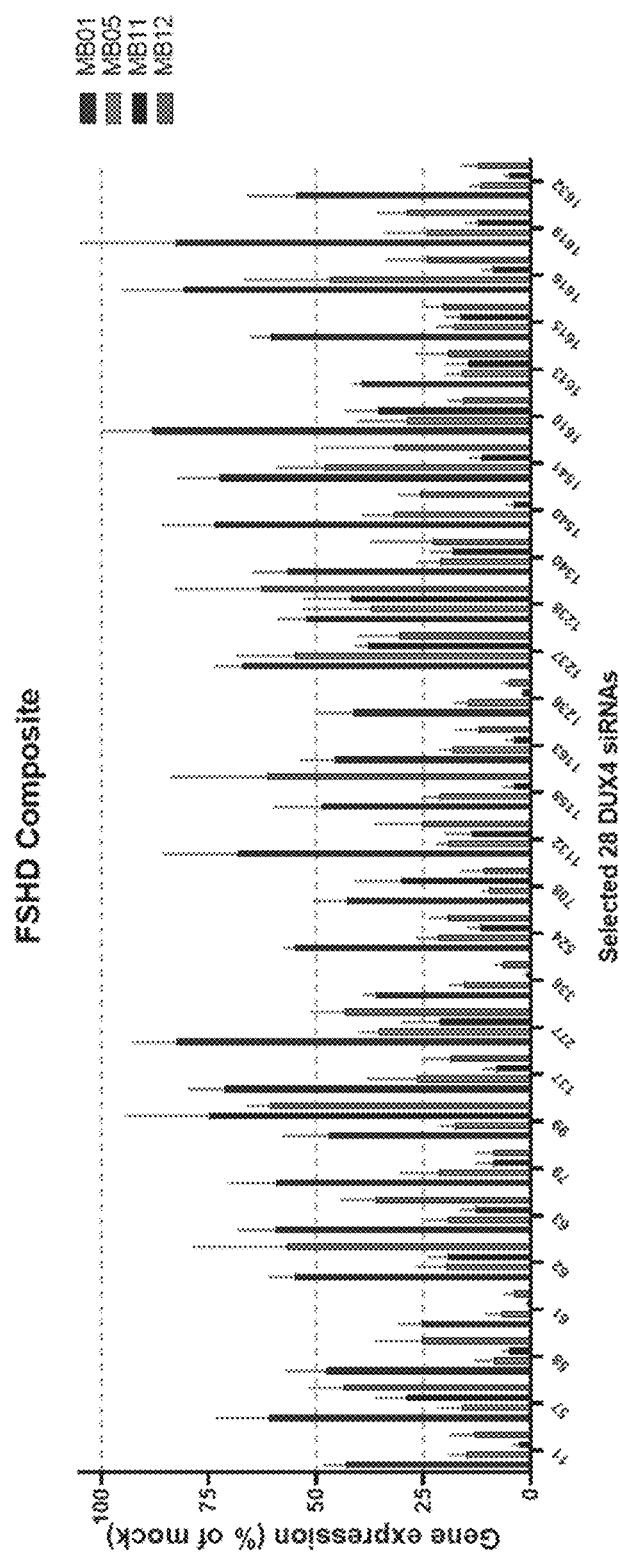
FIG. 14 shows FSHD composite expression in patient-derived myotubes with treatment of DUX4 siRNA at a concentration of 10 nM.
Figure 15:
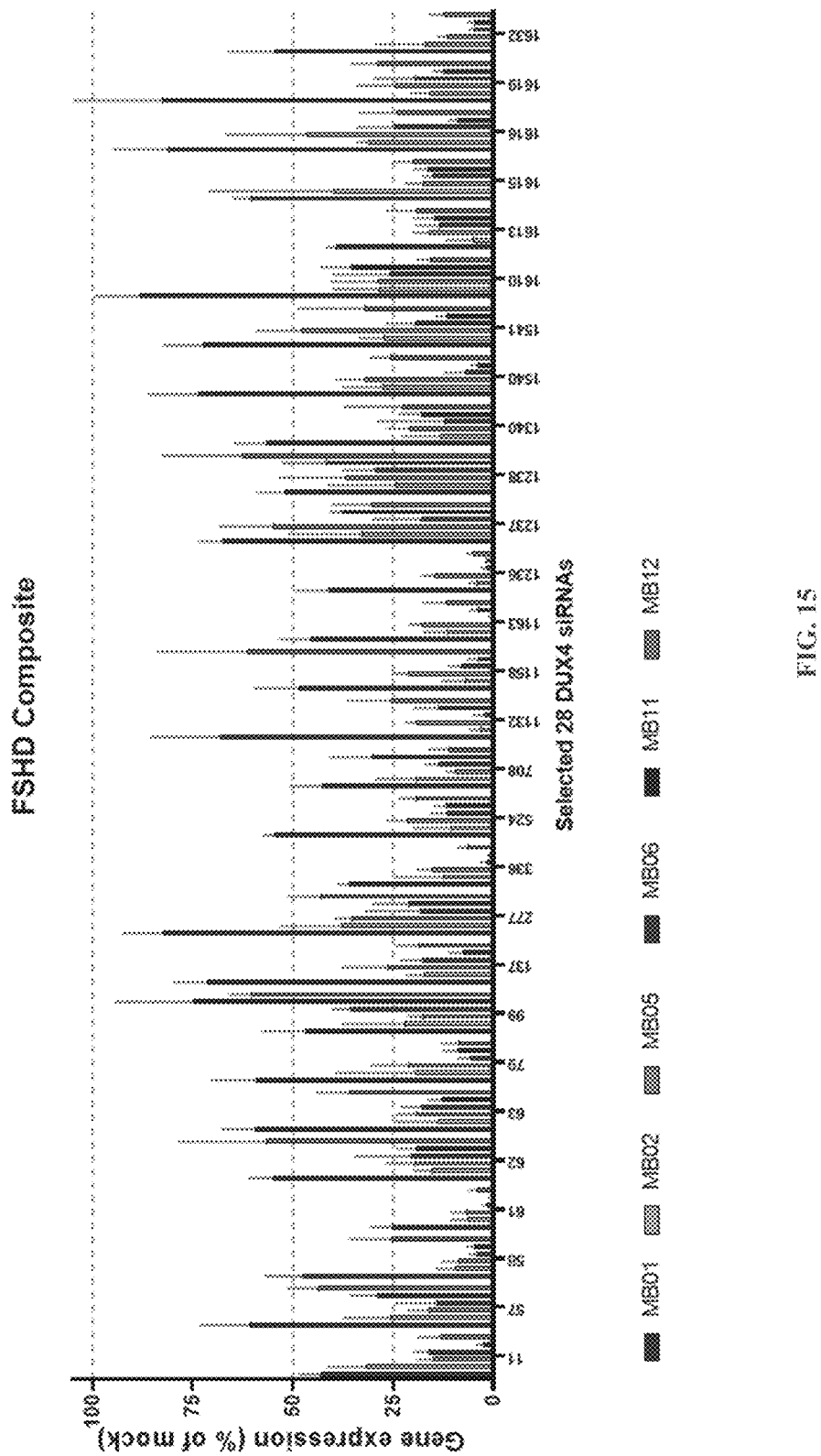
FIG. 15 shows FSHD composite expression in 6 patient-derived myotubes with treatment of DUX4 siRNA.

FIG. 13 shows a bar graph of ACTA1 expression levels in four different patient-derived primary myoblast cell lines (MB01, MB05, MB11, MB12). Most of the top 28 DUX4 siRNAs did not effect ACTA1 expression levels in these cell lines, while a few siRNAs showed more than 30% reduction in ACTA1 expression levels in the additional 4 FSHD primary cell lines tested (8 in MB11, 3 in MB05, 3 in MB12, and none in MB01). In addition, as shown in FIG. 14, the top 28 DUX4 siRNAs showed activity in all four additional FSHD primary cell lines. Several siRNAs showed more than 75% KD in three lines: MB05, MB11, MB12. KD levels were overall lower in MB01. FIG. 15 shows the top 28 DUX4 siRNAs' activity at 10 nM concentration in all FSHD cell lines (MB01, MB02, MB05, MB06, MB11, MB12).

Top 14 DUX4 siRNAs were selected from top 28 DUX4 siRNAs. Selection of such top 14 DUX4 siRNAs were i) siRNAs that showed no or minimal cell toxicity (visual identification and evaluation of ACTA1 expression levels), and ii) siRNAs that displayed the best activity at both 10 nM and 0.5 nM concentrations. Table 17 lists the top 14 DUX4 siRNAs and downregulation of FSHD composite expression in six primary FSHD cell lines (MB01, MB02, MB05, MB06, MB11, MB12) at the concentration of 10 nM and 0.5 nM of the selected 14 DUX4 siRNAs, and downregulation of ACTA1 expression in six primary FSHD cell lines at the concentration of 10 nM. Table 18 lists the top 14 DUX4 siRNAs and downregulation of FSHD composite expression in all 9 FSHD primary myotubes.

TABLE 17

| | FSHD Composite (% Mock) | | | | | | | | ACTA 1 (% Mock) | | | | | |
|---|---|---|---|---|---|---|---|---|---|---|---|---|---|---|
| | 10 nM | | | | | | 0.5 nM | | 10 nM | | | | | |
| siRNA | MB01 | MB02 | MB05 | MB06 | MB11 | MB12 | MB02 | MB06 | MB01 | MB02 | MB05 | MB06 | MB11 | MB12 |
| 11 | 43.10 | 31.76 | 15.02 | 16.09 | 2.66 | 13.06 | 51.87 | 76.24 | 182.43 | 149.99 | 114.72 | 134.18 | 74.18 | 123.86 |
| 57 | 60.89 | 25.86 | 16.05 | 14.22 | 29.01 | 43.75 | 64.82 | 38.21 | 134.81 | 133.87 | 77.42 | 136.08 | 101.53 | 122.19 |
| 58 | 47.60 | 9.78 | 8.74 | 4.10 | 5.00 | 25.30 | 40.95 | 88.52 | 164.25 | 152.35 | 119.96 | 159.71 | 89.04 | 103.74 |
| 61 | 25.54 | 6.34 | 6.82 | 1.73 | 0.63 | 4.11 | 34.34 | 48.20 | 161.47 | 112.20 | 91.46 | 95.20 | 73.28 | 85.37 |
| 137 | 71.58 | 17.49 | 26.43 | 17.66 | 7.90 | 18.69 | 39.13 | 71.37 | 175.58 | 159.65 | 113.40 | 140.40 | 85.80 | 114.48 |
| 336 | 36.05 | 12.62 | 15.53 | 1.77 | 0.96 | 6.47 | 31.51 | 43.22 | 113.53 | 92.45 | 99.88 | 123.50 | 159.92 | 96.08 |
| 1132 | 68.25 | 3.20 | 19.20 | 2.17 | 13.69 | 25.30 | 59.37 | 66.00 | 162.91 | 132.10 | 98.43 | 59.31 | 74.15 | 125.51 |
| 1340 | 56.58 | 13.06 | 21.04 | 12.24 | 18.09 | 22.73 | 38.81 | 47.63 | 237.27 | 204.96 | 176.84 | 346.51 | 167.31 | 134.73 |
| 1540 | 73.69 | 27.76 | 32.13 | 6.96 | 3.91 | 25.71 | 17.63 | 17.57 | 144.35 | 114.80 | 152.76 | 139.56 | 103.36 | 126.51 |
| 1613 | 39.26 | 5.18 | 16.04 | 13.55 | 14.70 | 19.28 | 18.30 | 39.25 | 155.21 | 119.51 | 107.74 | 164.23 | 125.38 | 122.92 |
| 1615 | 60.45 | 39.81 | 17.82 | 15.05 | 16.36 | 20.41 | 45.49 | 50.57 | 127.69 | 100.20 | 125.61 | 125.54 | 76.09 | 97.17 |
| 1616 | 81.11 | 31.13 | 46.69 | 29.45 | 8.98 | 24.15 | 37.63 | 32.25 | 115.10 | 74.43 | 89.58 | 77.81 | 52.83 | 80.71 |
| 1619 | 82.83 | 16.06 | 24.32 | 19.69 | 12.41 | 28.99 | 42.95 | 49.95 | 147.16 | 205.75 | 165.69 | 208.77 | 203.81 | 172.31 |
| 1632 | 54.74 | 17.02 | 11.74 | 4.83 | 4.99 | 12.45 | 20.07 | 37.10 | 151.01 | 135.47 | 147.94 | 162.22 | 101.99 | 157.04 |

TABLE 18

FSHD Composite (% Mock)

| | 10 nM | | | | | | | | | 0.5 nM | |
|---|---|---|---|---|---|---|---|---|---|---|---|
| siRNA | MB01 | MB02 | MB03 | MB04 | MB05 | MB06 | MB10 | MB11 | MB12 | MB02 | MB06 |
| 11 | 43.10 | 31.76 | 22.99 | 5.61 | 15.02 | 16.09 | 19.78 | 2.66 | 13.06 | 51.87 | 76.24 |
| 57 | 60.89 | 25.86 | 35.58 | 81.33 | 16.05 | 14.22 | 33.53 | 29.01 | 43.75 | 64.82 | 38.21 |
| 58 | 47.60 | 9.78 | 17.90 | 0.72 | 8.74 | 4.10 | 22.29 | 5.00 | 25.30 | 40.95 | 88.52 |
| 61 | 25.54 | 6.34 | 12.59 | 0.59 | 6.82 | 1.73 | 16.50 | 0.63 | 4.11 | 34.34 | 48.10 |
| 137 | 71.58 | 17.49 | 25.94 | 0.37 | 26.43 | 17.66 | 26.87 | 7.90 | 18.69 | 39.13 | 71.37 |
| 336 | 36.05 | 12.62 | 15.99 | 0.13 | 15.53 | 1.77 | 11.35 | 0.96 | 6.47 | 31.51 | 43.22 |
| 1132 | 68.25 | 3.20 | 15.18 | 8.72 | 19.20 | 2.17 | 34.72 | 13.69 | 25.30 | 59.37 | 66.00 |
| 1340 | 56.58 | 13.06 | 41.13 | 13.67 | 21.04 | 12.24 | 35.26 | 18.09 | 22.73 | 38.81 | 47.63 |
| 1540 | 73.69 | 27.76 | 39.02 | 6.94 | 32.13 | 6.96 | 27.94 | 3.910 | 25.71 | 17.63 | 17.57 |
| 1613 | 39.16 | 5.18 | 13.19 | 76.57 | 16.04 | 13.55 | 84.76 | 14.70 | 19.28 | 18.30 | 39.25 |
| 1615 | 60.45 | 39.81 | 34.04 | 12.48 | 17.82 | 15.05 | 41.32 | 16.36 | 20.41 | 45.49 | 50.57 |
| 1616 | 81.11 | 31.13 | 36.27 | 13.99 | 46.99 | 24.95 | 72.30 | 8.98 | 24.15 | 37.63 | 32.25 |
| 1619 | 82.83 | 16.06 | 40.97 | 3.88 | 24.32 | 19.69 | 41.16 | 12.41 | 28.99 | 42.95 | 49.95 |
| 1632 | 54.74 | 17.02 | 19.15 | 4.02 | 11.74 | 4.83 | 28.31 | 4.99 | 12.45 | 20.07 | 37.10 |

ACTA 1 (% Mock)
10 nM

| siRNA | MB01 | MB02 | MB03 | MB04 | MB05 | MB06 | MB10 | MB11 | MB12 |
|---|---|---|---|---|---|---|---|---|---|
| 11 | 182.43 | 149.99 | 94.53 | 252.83 | 114.72 | 134.18 | 113.25 | 74.18 | 123.86 |
| 57 | 134.81 | 133.87 | 135.56 | 83.84 | 77.42 | 136.08 | 104.46 | 101.53 | 122.19 |
| 58 | 164.25 | 152.35 | 201.75 | 146.25 | 119.9 | 159.71 | 82.38 | 89.04 | 103.74 |
| 61 | 161.47 | 112.20 | 170.49 | 97.32 | 91.46 | 95.20 | 108.30 | 73.28 | 85.37 |
| 137 | 175.58 | 159.65 | 92.10 | 197.01 | 113.4 | 140.40 | 71.16 | 85.80 | 114.48 |
| 336 | 113.53 | 92.45 | 99.01 | 476.86 | 99.88 | 123.50 | 93.80 | 159.92 | 96.08 |
| 1132 | 162.91 | 132.10 | 149.30 | 109.39 | 98.43 | 59.31 | 103.20 | 74.15 | 125.51 |
| 1340 | 237.27 | 204.96 | 182.92 | 279.19 | 176.84 | 346.51 | 160.47 | 167.31 | 134.73 |
| 1540 | 144.35 | 114.80 | 92.99 | 101.69 | 152.76 | 139.56 | 56.11 | 103.36 | 126.51 |
| 1613 | 155.21 | 119.51 | 160.42 | 289.09 | 107.74 | 164.23 | 102.70 | 125.38 | 122.92 |
| 1615 | 127.69 | 100.20 | 97.77 | 146.44 | 125.61 | 125 | 45.03 | 76.09 | 97.17 |
| 1616 | 115.10 | 74.43 | 74.24 | 84.55 | 89.58 | 77.81 | 46.80 | 52.83 | 80.71 |
| 1619 | 147.16 | 205.75 | 155.05 | 967.98 | 165.69 | 208.77 | 88.92 | 203.81 | 172.31 |
| 1632 | 151.01 | 135.47 | 113.22 | 531.53 | 147.94 | 162.22 | 155.60 | 101.99 | 157.04 |

Example 9. Top 14 DUX4 siRNAs Evaluated for Potency in Concentration Response in MB02, MB05 and MB06

The goal of the experiments in this example is to select 8 siRNAs with best Emax and potency for off-target analysis. Three FSHD primary myoblast cell lines (MB02, MB05, MB06) were used. Cells were plated at a density of 4,000 cells/well (MW96) and transfected in quadruplicates with selected 14 DUX4 siRNAs. Transfection was performed 24 hours after plating. Myogenic differentiation was induced 2 days after plating (24 hours after transfection) with 15% KOSR (in DMEM/F-12) medium. Samples were harvested 3 or 4 day's after inducing differentiation, depending on the cell line. DUX4-downstream target gene expression was evaluated by RT-qPCR (normalized to a composite AHSA1 and RPL27 housekeeping gene expression value). Data represented as mean−/+SEM. N=4.

Figure 16A:
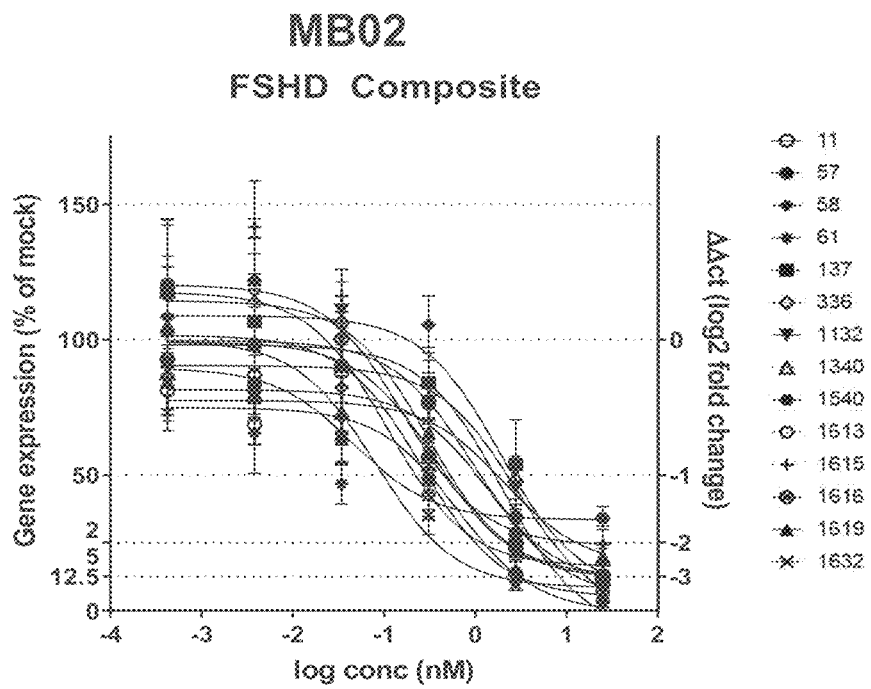
FIGS. 16A-C show graphs of FSHD composite expression in 3 patient-derived myotubes with treatment of 14 selected DUX4 siRNAs.
Figure 16B:
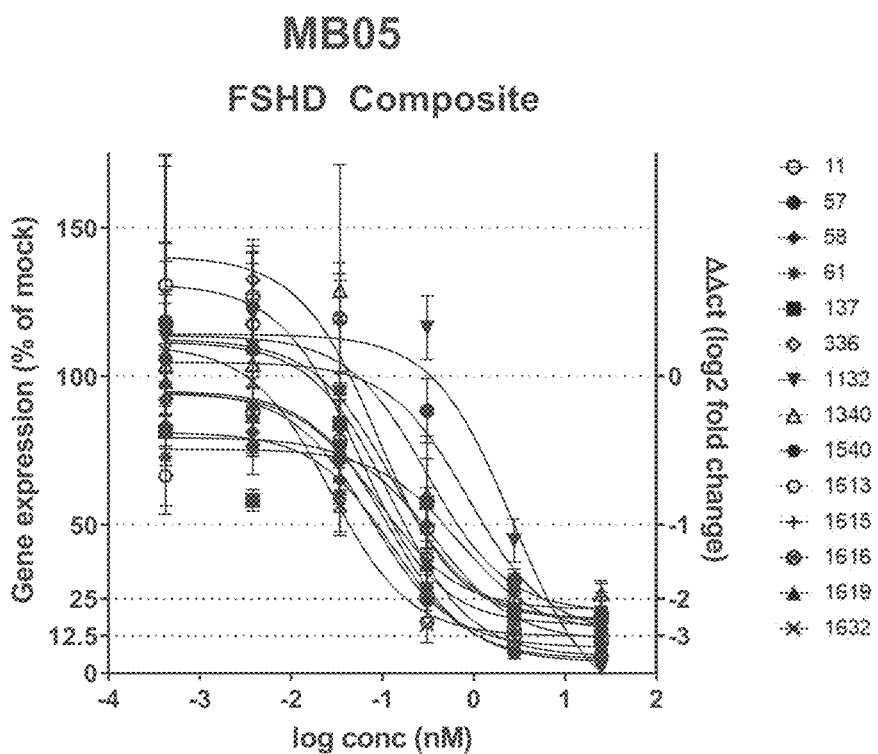
Figure 16C:
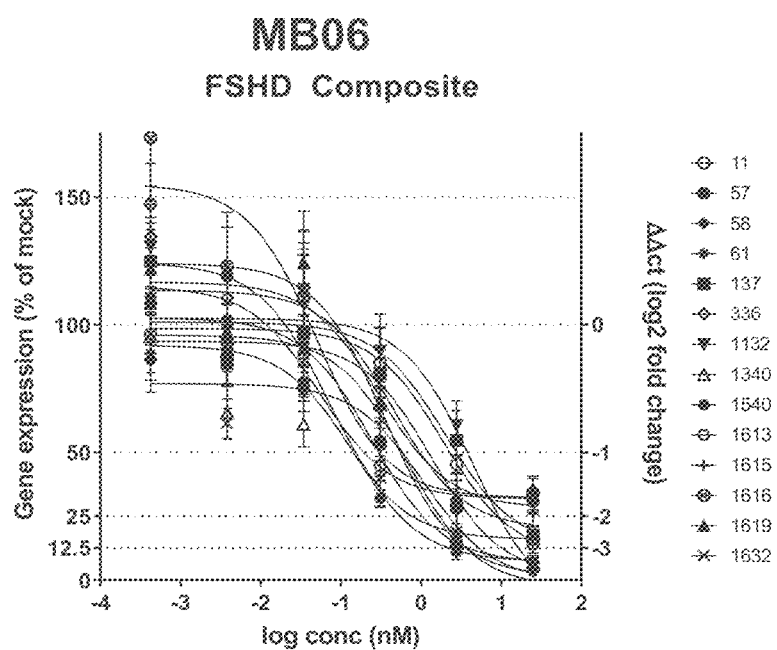
Figure 17A:
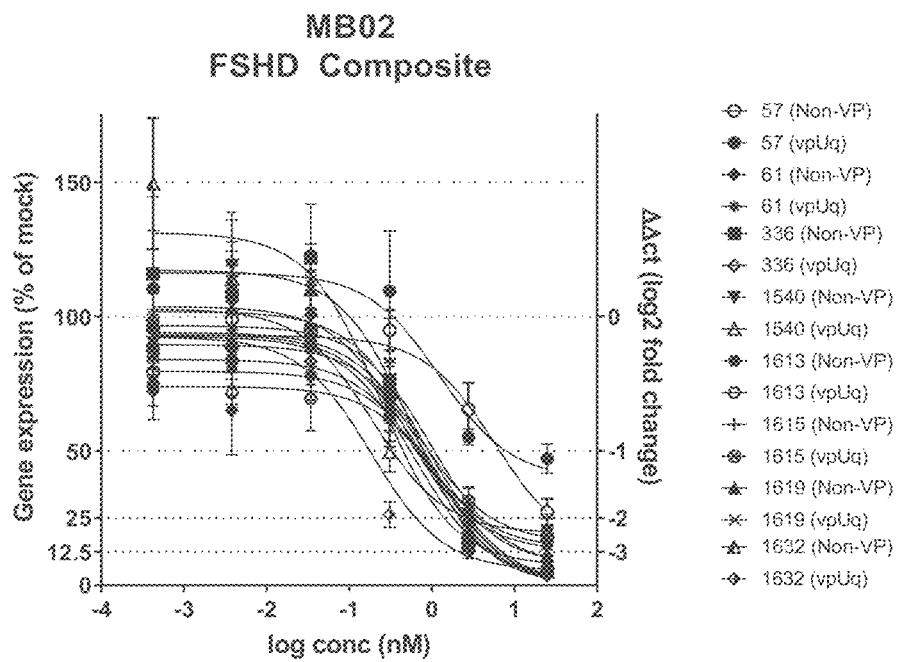
FIGS. 17 A-C show graphs of FSHD composite expression in 3 FSHD patient-derived myotubes with treatment of 8 selected DUX4 siRNAs.
Figure 17B:
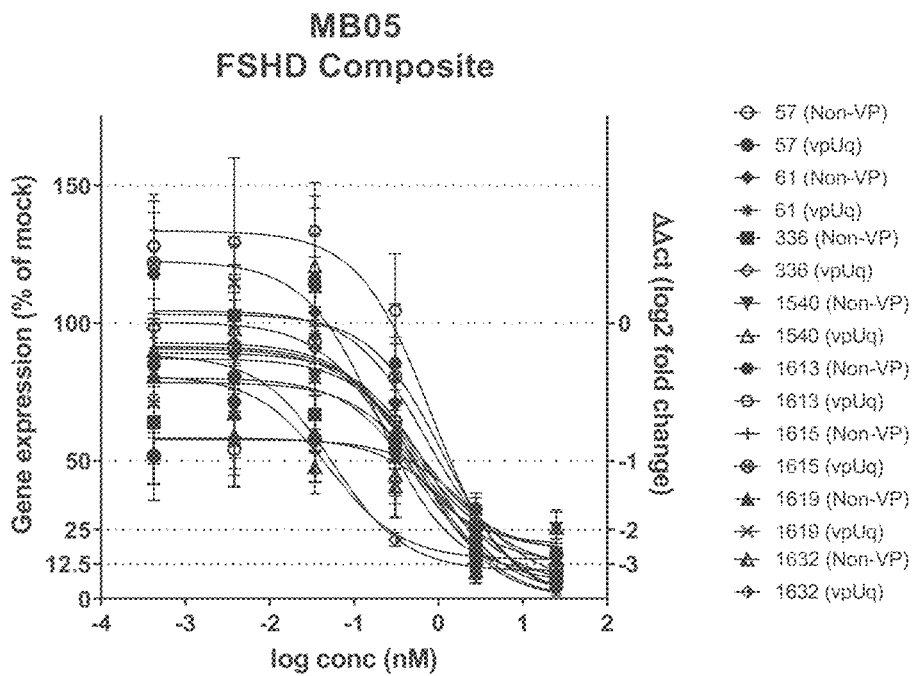
Figure 17C:
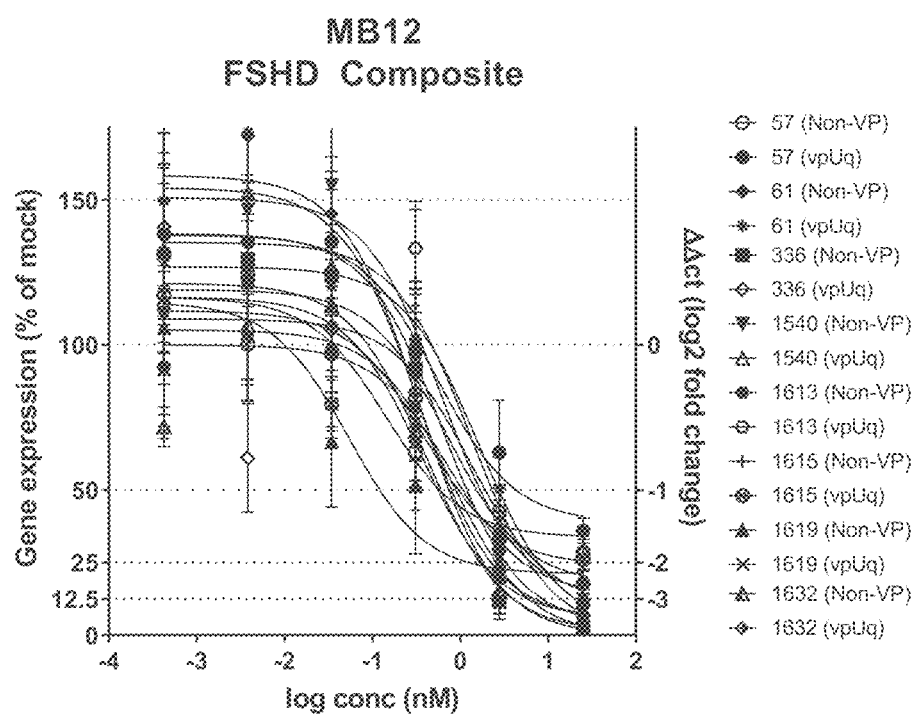

FIGS. 16A-C show concentration response of 14 selected DUX4 siRNA in three FSHD patient-derived primary myotubes—MB02, MB05, MB06, respectively. DUX-4-target gene expression was reduced more than 75% by most of the top 14 DUX4 siRNAs in three FSHD patient-derived primary myoblast lines. It was also observed that differences on potency among siRNAs ranged between 60 to 100-fold depending on the cell lines. Tables 19-22 show potency of DUX4 siRNAs evaluated in three FSHD patient-derived primary myotubes based on FSHD composite.

TABLE 19

MB02

| siRNA | Max KD (%)* | IC50 (nM) |
|---|---|---|
| 11 | 95.54 | 1.506 |
| 57 | 90.06 | 0.918 |
| 58 | 100.00 | 1.969 |
| 61 | 100.00 | 0.639 |
| 137 | 93.30 | 1.903 |
| 336 | 83.74 | 0.110 |
| 1132 | 100.00 | 2.830 |
| 1340 | 83.69 | 2.137 |
| 1540 | 66.47 | 0.047 |
| 1613 | 95.09 | 0.259 |
| 1615 | 76.01 | 0.166 |
| 1616 | 88.05 | 0.372 |
| 1619 | 87.10 | 0.306 |
| 1632 | 91.52 | 0.082 |

TABLE 20

MB05

| siRNA | Max KD (%)* | IC50 (nM) |
|---|---|---|
| 11 | 83.78 | 0.055 |
| 57 | 86.86 | 0.870 |
| 58 | 89.08 | 0.375 |
| 61 | 95.24 | 0.127 |
| 137 | 86.13 | 0.673 |

TABLE 20-continued

MB05

| siRNA | Max KD (%)* | IC50 (nM) |
|---|---|---|
| 336 | 94.35 | 0.127 |
| 1132 | 100.00 | 2.666 |
| 1340 | 79.53 | 0.309 |
| 1540 | 91.33 | 0.075 |
| 1613 | 96.23 | 0.118 |
| 1615 | 82.43 | 0.091 |
| 1616 | 81.99 | 0.130 |
| 1619 | 78.60 | 0.091 |
| 1632 | 87.59 | 0.027 |

TABLE 21

MB06

| siRNA | Max KD (%)* | IC50 (nM) |
|---|---|---|
| 11 | 90.75 | 1.923 |
| 57 | 68.18 | 0.054 |
| 58 | 98.45 | 1.374 |
| 61 | 100.00 | 0.665 |
| 137 | 87.25 | 2.018 |
| 336 | 98.53 | 0.359 |
| 1132 | 100.00 | 4.482 |
| 1340 | 100.00 | 1.090 |
| 1540 | 92.71 | 0.145 |
| 1613 | 84.07 | 0.070 |
| 1615 | 80.01 | 0.457 |
| 1616 | 67.81 | 0.051 |
| 1619 | 71.83 | 0.299 |
| 1632 | 93.15 | 0.243 |

TABLE 22

All lines together

| siRNA | Av. Max KD (%)* | Av. IC50 (nM) |
|---|---|---|
| 11 | 90.02 | 1.161 |
| 57 | 81.70 | 0.614 |
| 58 | 95.84 | 1.239 |
| 61 | 98.41 | 0.477 |
| 137 | 88.89 | 1.531 |
| 336 | 92.21 | 0.199 |
| 1132 | 100.00 | 3.326 |
| 1340 | 87.74 | 1.179 |
| 1540 | 83.50 | 0.089 |
| 1613 | 91.80 | 0.149 |
| 1615 | 79.48 | 0.238 |
| 1616 | 79.28 | 0.184 |
| 1619 | 79.18 | 0.232 |
| 1632 | 90.76 | 0.117 |

Example 11

Antibody-DUX4 siRNA conjugates (DUX4-AOCs) mediated reduction of FSHD composite (composite of DUX4-target biomarker genes) expression in cultured FSHD primary myotubes.

The in vitro concentration-response potency and maximum efficacy of 16 DUX4-AOCs (8 vpUq AOCs or 8 Non-VP AOCs) were assessed in FSHD1 patient-derived primary myotubes (MB06). The guide strand of the DUX4 siRNA of the AOCs was either with vinylphophonate at the 5' of the strand (vpUq) or without vinylphosphonate at the 5' end of the strand (Non-VP).

The human IgG1 antibody against human TfR1 was expressed in CHO stable pools, created by transfecting the CHOK1SV GS-KO host cell line with a double gene vector. The antibody was captured from cell culture supernatant using protein A affinity chromatography. The resultant antibody was further purified using hydrophobic interaction chromatography (to reduce aggregates) and anion exchange chromatography (to reduce host cell DNA & endotoxin). The final antibody was buffer exchanged into either PBS or 50 mM sodium citrate buffer. pH 6.5 at a concentration of 20 mg/mL. The purity of the antibody was assessed by size exclusion chromatography.

The guide and fully complementary RNA passenger strands were assembled on solid phase using standard phos-pharamidite chemistry and purified over HPLC. Purified single strands were duplexed to obtain double stranded siRNA. The guide strand was produced with a vinylphosphonate modified nucleotide structures at the 5'end. The passenger strand had a conjugation handle on the 5' end via a phosphorothioate-inverted abasic-phosphodiester linker.

Antibody oligonucleotide conjugates (AOCs) were generated using a random cysteine conjugation method. The interchain disulfide bonds of the antibody were partially reduced with TCEP prior to conjugation with a maleimide linker-siRNA. The reaction mixture was purified using strong anion exchange chromatography to ensure a drug-antibody ratio (DAR) equal to 1 (i.e., one siRNA molecule per one antibody molecule). Collected AOC fractions were concentrated, buffer exchanged into PBS and sterile filtered using a 0.2 µm filter. The purity of AOCs was assessed using strong anion exchange chromatography, size exclusion chromatography, and SDS-PAGE.

FSHD primary myoblasts (MB06 (FSHD1)) were grown in recommended media. Prior to seeding, 96-well tissue culture plates (Costar) were coated with 50 µL of 1% Matrigel per well for at least 2 hours at 37° C., and washed 2× with PBS. After coating, myoblasts were seeded in quadruplicate at 4000 cells/well. 2 days after plating, myogenic differentiation was induced with 15% KOSR-containing differentiation medium. 24 hours after inducing differentiation, siDUX4-AOCs were added in the medium at a high concentration of 100 nM with 10-fold serial dilutions. Untreated cells were maintained as a relative control. After 3 days of incubation with DUX4-AOCs, myotubes were collected in Trizol and stored at −80° C. until processing. RNA isolation was performed using Direct-zol-96 RNA isolation kit (Zymo) according to the manufacturer's instructions. 100-500 ng of purified RNA was converted to cDNA using High-Capacity cDNA Reverse Transcription Kit (Applied Biosystems) using SimpliAmp Thermal Cycler (Applied Biosystems). cDNA was analyzed by qPCR using TaqMan Fast Universal Master Mix II (Thermo Fisher) and TaqMan probes (Thermo Fisher) in duplicates, using QuantStudio 6 or 7 Flex Real-Time PCR instruments (Applied Biosystems). Data were analyzed by QuantStudio™ Real-Time PCR Software v1.3 (Applied Biosystems). DUX4-target gene expression levels were evaluated by calculating the FSHD Composite score, which integrated the expression levels of 4 DUX4-target genes (MBD3L2, ZSCAN4, LEUTX, and KHDC1L) normalized to two reference genes (AHSA1 and RPL27).

Figure 18A:
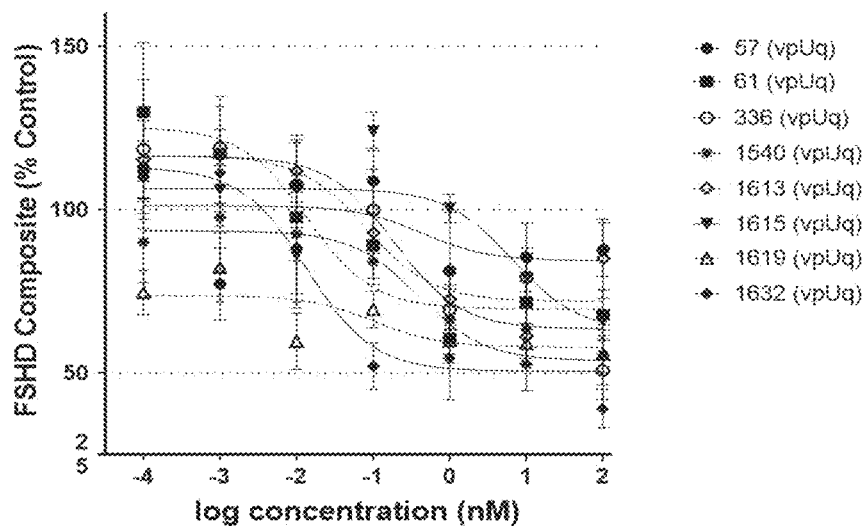
FIGS. 18 A-B show graphs of FSHD composite expression in cultured FSHD primary myotubes with treatment of 8 antibody DUX4-siRNA conjugates (DUX4-AOCs) without vinylphosphonate or 8 antibody DUX4-siRNA conjugates with vinylphosphonate.
Figure 18B:
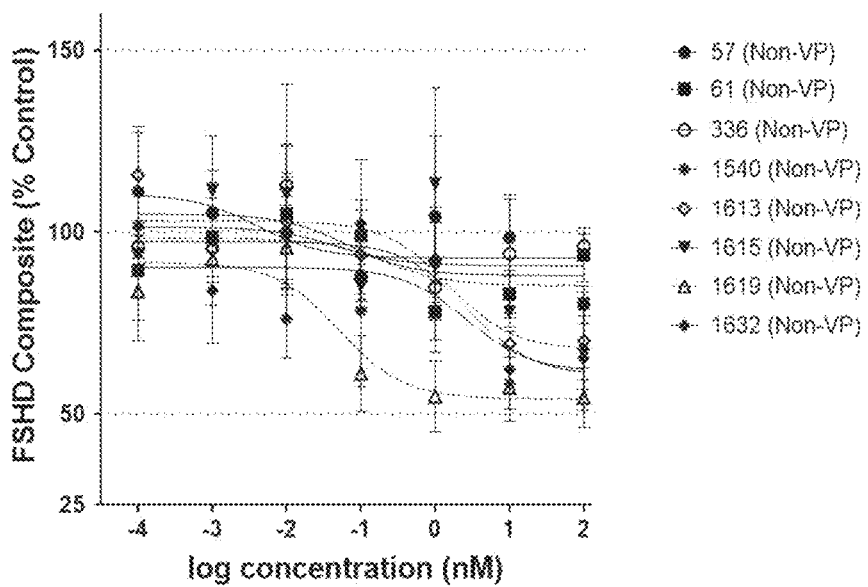

FIGS. 18A-B show the dose response curve of DUX4-AOCs mediated reduction of DUX4-target biomarker gene expressions in cultured FSHD primary myotubes. Most DUX4-AOCs with vinylphosphonate (FIG. 18A) and several DUX4-AOCs without vinylphosphonate (FIG. 18B) reduced the expression of the FSHD composite of 4 DUX4-target biomarker genes (MBD3L2, ZSCAN4, LEUTX, and KHDC1L) in FSHD1 patient-derived primary myotubes.

Overall, DUX4-AOCs reduced the expression of DUX4-target biomarker gene expressions and the presence of vinylphosphonate on the DUX4 siRNA in the AOCs facilitated the reduction of the DUX4-target biomarker gene expressions.

Example 12. Malat1-siRNA AOC Mediated In Vivo Reduction of Nuclear Localized lnc-RNA Malat1 mRNA Levels in 3 Different Murine Skeletal Muscles Wild type female CD-1 mice (approximately 6-8 weeks old) were dosed once by a single IV bolus injection in the tail vein at 5 mL/kg body weight, of either Malat1 or Scramble AOCs, in which the siRNA was conjugated to murine anti-Transferrin Receptor (mTfR1) antibody, at doses 0.3, 1, 3, 6 mg/kg body weight (siRNA amount). Muscle tissue samples were collected 2 weeks post treatment in tubes containing ceramic beads, flash frozen in liquid nitrogen, and then homogenized in 1 mL cold Trizol using a FastPrep-24 (MP Biomedicals). Homogenate supernatants were used for RNA isolation using Direct-zol-96 RNA isolation kit (Zymo) according to the manufacturer's instructions. 100-500 ng of purified RNA was converted to cDNA using High-Capacity cDNA Reverse Transcription Kit (Applied Biosystems) using SimpliAmp Thermal Cycler (Applied Biosystems). cDNA was analyzed by qPCR using TaqMan Fast Universal Master Mix II (Thermo Fisher) and TaqMan probes (Thermo Fisher) in duplicates, using QuantStudio 6 or 7 Flex Real-Time PCR instruments (Applied Biosystems). Data were analyzed by QuantStudio™ Real-Time PCR Software v1.3 (Applied Biosystems). The target gene expression was normalized to a reference gene Ppib. The percentage of target mRNA expression in treatment samples was determined relative to the control treatment using the $2^{-\Delta\Delta Ct}$ method. Data are represented as % of PBS control (mean±SEM; N=4 for siMalat1 and siScramble AOCs, N=5 for PBS groups).

Figure 19:
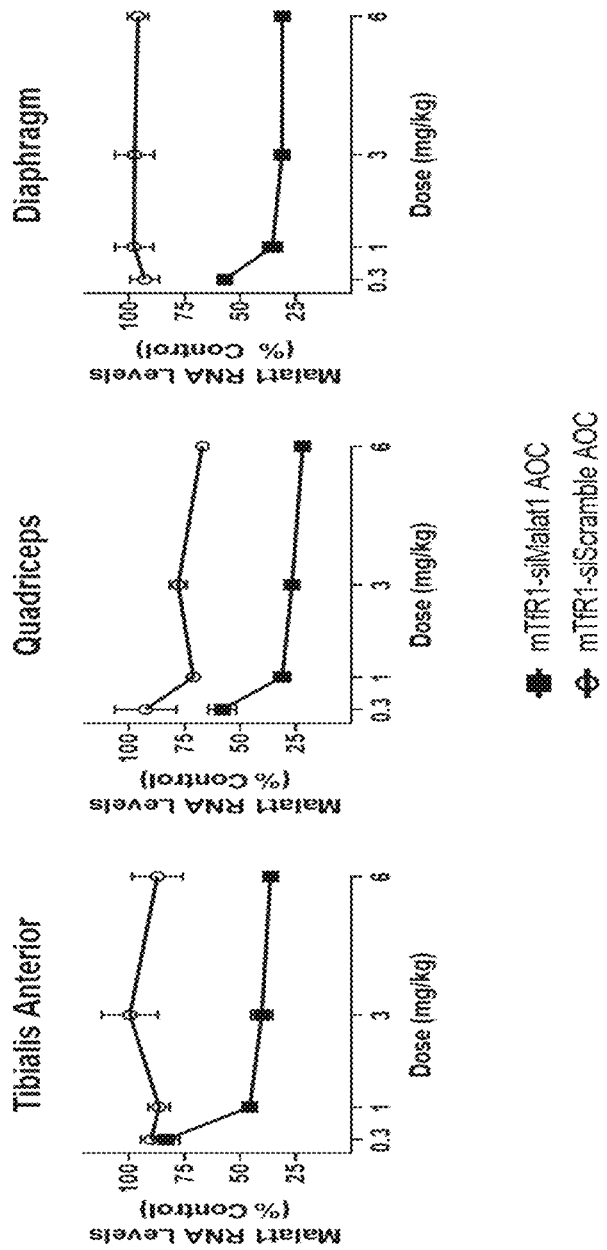
FIG. 19 shows graphs of the AOC-mediated in vivo reduction of nuclear localized lnc-RNA Malat1 levels in skeletal muscles in mice.

FIG. 19 shows Malat1 siRNA-AOC-mediated in vivo reduction of nuclear localized lnc-RNA Malat1 levels in skeletal muscles in mice. A single administration of up to 6 mg/kg of Malat1 siRNA-AOC (siRNA dose) in mice reduced nuclear Malat1 expression up to 80% in skeletal muscle 2 weeks post-dose. The reduction of nuclear Malat1 mRNA expression levels indicate the in vivo ability of AOCs to target nuclear RNAs for degradation.

Example 13. Sustained AOC-Mediated in Ivo Reduction of SSB mRNA Levels in Murine Skeletal Muscles with a Single Dose of 3 mg/kg siRNA AOC During an 8-Week Period Wild type male C57BL/6 mice (approximately 12-16 weeks old) were dosed once by a single IV bolus injection in the tail vein at 5 mL/kg body weight of either without vinylphosphonate (Non-VP) or with vinylphosphonate (vpUq) Ssb siRNA conjugated to murine anti-TfR1 (mTfR1) antibody at 3 mg/kg body weight (siRNA amount) dose. Gastrocnemius muscles were collected at the following time-points after dosing: day 1, 7, 14, 28, 43 and 57. Muscles were placed in tubes containing ceramic beads, flash frozen in liquid nitrogen, and then homogenized in 1 mL cold Trizol using a FastPrep-24 (MP Biomedicals). Homogenate supernatants were used for RNA isolation using Direct-zol-96 RNA isolation kit (Zymo) according to the manufacturer's instructions. 100-5(0) ng of purified RNA was converted to cDNA using High-Capacity cDNA Reverse Transcription Kit (Applied Biosystems) using SimpliAmp Thermal Cycler (Applied Biosystems). cDNA was analyzed by qPCR using TaqMan Fast Universal Master Mix 11 (Thermo Fisher) and TaqMan probes (Thermo Fisher) in duplicates, using QuantStudio 6 or 7 Flex Real-Time PCR instruments (Applied Biosystems). Data were analyzed by QuantStudio™ Real-Time PCR Software v1.3 (Applied Biosystems). Ssb gene expression was normalized to the reference gene Ppib. The percentage of target mRNA expression in treatment samples was determined relative to the control treatment (PBS) using the $2^{-\Delta\Delta Ct}$ method. Data are represented as % of PBS control (mean±SEM; N=4 for siSsb-AOCs. N=3-5 for PBS groups).

Figure 20:
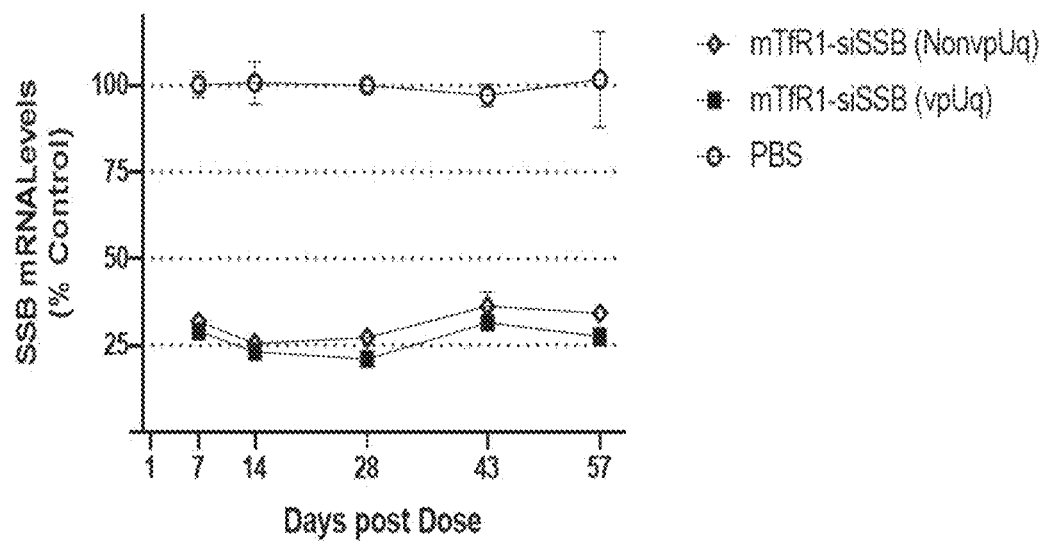
FIG. 20 shows a graph of the sustained SSB-AOC-mediated in vivo reduction of SSB mRNA levels in murine skeletal muscles with a single dose of 3 mg/kg siRNA during an 8-week period.

FIG. 20 shows SSB siRNA-AOC-mediated in vivo reduction of SSB mRNA levels in murine skeletal muscles with a single dose of 3 mg/kg siRNA during an 8-week period. The sustained AOC-mediated in vivo reduction of SSB mRNA expression levels was achieved in a mouse skeletal muscle after a 3 mg/kg (siRNA dose) single administration of both without vinylphosphonate (non-VP) and with vinylphosphonate (vpUq) SSB siRNA-AOCs.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

SEQUENCE LISTING

```
Sequence total quantity: 410
SEQ ID NO: 1            moltype = DNA  length = 19
FEATURE                 Location/Qualifiers
source                  1..19
                        mol_type = other DNA
                        organism = synthetic construct
SEQUENCE: 1
cgacaccctc ggacagcac                                                19

SEQ ID NO: 2            moltype = DNA  length = 19
FEATURE                 Location/Qualifiers
source                  1..19
                        mol_type = other DNA
```

```
                            organism = synthetic construct
SEQUENCE: 2
acggcgacgg agactcgtt                                                           19

SEQ ID NO: 3            moltype = DNA  length = 19
FEATURE                 Location/Qualifiers
source                  1..19
                        mol_type = other DNA
                        organism = synthetic construct
SEQUENCE: 3
cggcgacgga gactcgttt                                                           19

SEQ ID NO: 4            moltype = DNA  length = 19
FEATURE                 Location/Qualifiers
source                  1..19
                        mol_type = other DNA
                        organism = synthetic construct
SEQUENCE: 4
ggcgacggag actcgtttg                                                           19

SEQ ID NO: 5            moltype = DNA  length = 19
FEATURE                 Location/Qualifiers
source                  1..19
                        mol_type = other DNA
                        organism = synthetic construct
SEQUENCE: 5
gcgacggaga ctcgtttgg                                                           19

SEQ ID NO: 6            moltype = DNA  length = 19
FEATURE                 Location/Qualifiers
source                  1..19
                        mol_type = other DNA
                        organism = synthetic construct
SEQUENCE: 6
cgacggagac tcgtttgga                                                           19

SEQ ID NO: 7            moltype = DNA  length = 19
FEATURE                 Location/Qualifiers
source                  1..19
                        mol_type = other DNA
                        organism = synthetic construct
SEQUENCE: 7
gacggagact cgtttggac                                                           19

SEQ ID NO: 8            moltype = DNA  length = 19
FEATURE                 Location/Qualifiers
source                  1..19
                        mol_type = other DNA
                        organism = synthetic construct
SEQUENCE: 8
acggagactc gtttggacc                                                           19

SEQ ID NO: 9            moltype = DNA  length = 19
FEATURE                 Location/Qualifiers
source                  1..19
                        mol_type = other DNA
                        organism = synthetic construct
SEQUENCE: 9
ggaccccgag ccaaagcga                                                           19

SEQ ID NO: 10           moltype = DNA  length = 19
FEATURE                 Location/Qualifiers
source                  1..19
                        mol_type = other DNA
                        organism = synthetic construct
SEQUENCE: 10
gaccccgagc caaagcgag                                                           19

SEQ ID NO: 11           moltype = DNA  length = 19
FEATURE                 Location/Qualifiers
source                  1..19
                        mol_type = other DNA
                        organism = synthetic construct
SEQUENCE: 11
accccgagcc aaagcgagg                                                           19

SEQ ID NO: 12           moltype = DNA  length = 19
FEATURE                 Location/Qualifiers
source                  1..19
```

```
                        mol_type = other DNA
                        organism = synthetic construct
SEQUENCE: 12
cctgcgagcc tgctttgag                                            19

SEQ ID NO: 13           moltype = DNA   length = 19
FEATURE                 Location/Qualifiers
source                  1..19
                        mol_type = other DNA
                        organism = synthetic construct
SEQUENCE: 13
gcgagcctgc tttgagcgg                                            19

SEQ ID NO: 14           moltype = DNA   length = 19
FEATURE                 Location/Qualifiers
source                  1..19
                        mol_type = other DNA
                        organism = synthetic construct
SEQUENCE: 14
tcgccaccag agaacggct                                            19

SEQ ID NO: 15           moltype = DNA   length = 19
FEATURE                 Location/Qualifiers
source                  1..19
                        mol_type = other DNA
                        organism = synthetic construct
SEQUENCE: 15
caggccatcg gcattccgg                                            19

SEQ ID NO: 16           moltype = DNA   length = 19
FEATURE                 Location/Qualifiers
source                  1..19
                        mol_type = other DNA
                        organism = synthetic construct
SEQUENCE: 16
ggccatcggc attccggag                                            19

SEQ ID NO: 17           moltype = DNA   length = 19
FEATURE                 Location/Qualifiers
source                  1..19
                        mol_type = other DNA
                        organism = synthetic construct
SEQUENCE: 17
gccatcggca ttccggagc                                            19

SEQ ID NO: 18           moltype = DNA   length = 19
FEATURE                 Location/Qualifiers
source                  1..19
                        mol_type = other DNA
                        organism = synthetic construct
SEQUENCE: 18
gcaccggcgg gaatctcgg                                            19

SEQ ID NO: 19           moltype = DNA   length = 19
FEATURE                 Location/Qualifiers
source                  1..19
                        mol_type = other DNA
                        organism = synthetic construct
SEQUENCE: 19
caccggcggg aatctcggc                                            19

SEQ ID NO: 20           moltype = DNA   length = 19
FEATURE                 Location/Qualifiers
source                  1..19
                        mol_type = other DNA
                        organism = synthetic construct
SEQUENCE: 20
ccagaaggcc ggcgaaagc                                            19

SEQ ID NO: 21           moltype = DNA   length = 19
FEATURE                 Location/Qualifiers
source                  1..19
                        mol_type = other DNA
                        organism = synthetic construct
SEQUENCE: 21
agaaggccgg cgaaagcgg                                            19

SEQ ID NO: 22           moltype = DNA   length = 19
FEATURE                 Location/Qualifiers
```

```
source                      1..19
                            mol_type = other DNA
                            organism = synthetic construct
SEQUENCE: 22
gaaggccggc gaaagcgga                                                    19

SEQ ID NO: 23               moltype = DNA   length = 19
FEATURE                     Location/Qualifiers
source                      1..19
                            mol_type = other DNA
                            organism = synthetic construct
SEQUENCE: 23
gcgaaagcgg accgccgtc                                                    19

SEQ ID NO: 24               moltype = DNA   length = 19
FEATURE                     Location/Qualifiers
source                      1..19
                            mol_type = other DNA
                            organism = synthetic construct
SEQUENCE: 24
gaaagcggac cgccgtcac                                                    19

SEQ ID NO: 25               moltype = DNA   length = 19
FEATURE                     Location/Qualifiers
source                      1..19
                            mol_type = other DNA
                            organism = synthetic construct
SEQUENCE: 25
cggaccgccg tcaccggat                                                    19

SEQ ID NO: 26               moltype = DNA   length = 19
FEATURE                     Location/Qualifiers
source                      1..19
                            mol_type = other DNA
                            organism = synthetic construct
SEQUENCE: 26
ggaccgccgt caccggatc                                                    19

SEQ ID NO: 27               moltype = DNA   length = 19
FEATURE                     Location/Qualifiers
source                      1..19
                            mol_type = other DNA
                            organism = synthetic construct
SEQUENCE: 27
gaccgccgtc accggatcc                                                    19

SEQ ID NO: 28               moltype = DNA   length = 19
FEATURE                     Location/Qualifiers
source                      1..19
                            mol_type = other DNA
                            organism = synthetic construct
SEQUENCE: 28
agacgggcct cccggagtc                                                    19

SEQ ID NO: 29               moltype = DNA   length = 19
FEATURE                     Location/Qualifiers
source                      1..19
                            mol_type = other DNA
                            organism = synthetic construct
SEQUENCE: 29
cctcgtgggt cgccttcgc                                                    19

SEQ ID NO: 30               moltype = DNA   length = 19
FEATURE                     Location/Qualifiers
source                      1..19
                            mol_type = other DNA
                            organism = synthetic construct
SEQUENCE: 30
ctcgtgggtc gccttcgcc                                                    19

SEQ ID NO: 31               moltype = DNA   length = 19
FEATURE                     Location/Qualifiers
source                      1..19
                            mol_type = other DNA
                            organism = synthetic construct
SEQUENCE: 31
gagggatct cccaacctg                                                     19

SEQ ID NO: 32               moltype = DNA   length = 19
```

```
FEATURE                 Location/Qualifiers
source                  1..19
                        mol_type = other DNA
                        organism = synthetic construct
SEQUENCE: 32
cgcgcgggga tttcgccta                                                    19

SEQ ID NO: 33           moltype = DNA   length = 19
FEATURE                 Location/Qualifiers
source                  1..19
                        mol_type = other DNA
                        organism = synthetic construct
SEQUENCE: 33
gcgcgggat ttcgcctac                                                     19

SEQ ID NO: 34           moltype = DNA   length = 19
FEATURE                 Location/Qualifiers
source                  1..19
                        mol_type = other DNA
                        organism = synthetic construct
SEQUENCE: 34
cggggatttc gcctacgcc                                                    19

SEQ ID NO: 35           moltype = DNA   length = 19
FEATURE                 Location/Qualifiers
source                  1..19
                        mol_type = other DNA
                        organism = synthetic construct
SEQUENCE: 35
tgcttgcgcc acccacgtc                                                    19

SEQ ID NO: 36           moltype = DNA   length = 19
FEATURE                 Location/Qualifiers
source                  1..19
                        mol_type = other DNA
                        organism = synthetic construct
SEQUENCE: 36
ctggcgagcc cggagtttc                                                    19

SEQ ID NO: 37           moltype = DNA   length = 19
FEATURE                 Location/Qualifiers
source                  1..19
                        mol_type = other DNA
                        organism = synthetic construct
SEQUENCE: 37
ggcgagcccg gagtttctg                                                    19

SEQ ID NO: 38           moltype = DNA   length = 19
FEATURE                 Location/Qualifiers
source                  1..19
                        mol_type = other DNA
                        organism = synthetic construct
SEQUENCE: 38
ggcgcaacct ctcctagaa                                                    19

SEQ ID NO: 39           moltype = DNA   length = 19
FEATURE                 Location/Qualifiers
source                  1..19
                        mol_type = other DNA
                        organism = synthetic construct
SEQUENCE: 39
gcgcaacctc tcctagaaa                                                    19

SEQ ID NO: 40           moltype = DNA   length = 19
FEATURE                 Location/Qualifiers
source                  1..19
                        mol_type = other DNA
                        organism = synthetic construct
SEQUENCE: 40
aacctctcct agaaacgga                                                    19

SEQ ID NO: 41           moltype = DNA   length = 19
FEATURE                 Location/Qualifiers
source                  1..19
                        mol_type = other DNA
                        organism = synthetic construct
SEQUENCE: 41
cagcgaggaa gaataccgg                                                    19
```

-continued

| | | |
|---|---|---|
| SEQ ID NO: 42<br>FEATURE<br>source | moltype = DNA   length = 19<br>Location/Qualifiers<br>1..19<br>mol_type = other DNA<br>organism = synthetic construct | |
| SEQUENCE: 42<br>agcgaggaag aataccggg | | 19 |
| SEQ ID NO: 43<br>FEATURE<br>source | moltype = DNA   length = 19<br>Location/Qualifiers<br>1..19<br>mol_type = other DNA<br>organism = synthetic construct | |
| SEQUENCE: 43<br>gcgaggaaga ataccgggc | | 19 |
| SEQ ID NO: 44<br>FEATURE<br>source | moltype = DNA   length = 19<br>Location/Qualifiers<br>1..19<br>mol_type = other DNA<br>organism = synthetic construct | |
| SEQUENCE: 44<br>gttgggacgg ggtcgggtg | | 19 |
| SEQ ID NO: 45<br>FEATURE<br>source | moltype = DNA   length = 19<br>Location/Qualifiers<br>1..19<br>mol_type = other DNA<br>organism = synthetic construct | |
| SEQUENCE: 45<br>acggggtcgg gtggttcgg | | 19 |
| SEQ ID NO: 46<br>FEATURE<br>source | moltype = DNA   length = 19<br>Location/Qualifiers<br>1..19<br>mol_type = other DNA<br>organism = synthetic construct | |
| SEQUENCE: 46<br>ggtcgggtgg ttcggggca | | 19 |
| SEQ ID NO: 47<br>FEATURE<br>source | moltype = DNA   length = 19<br>Location/Qualifiers<br>1..19<br>mol_type = other DNA<br>organism = synthetic construct | |
| SEQUENCE: 47<br>gtcgggtggt tcggggcag | | 19 |
| SEQ ID NO: 48<br>FEATURE<br>source | moltype = DNA   length = 19<br>Location/Qualifiers<br>1..19<br>mol_type = other DNA<br>organism = synthetic construct | |
| SEQUENCE: 48<br>gcggtggcct ctctttcgc | | 19 |
| SEQ ID NO: 49<br>FEATURE<br>source | moltype = DNA   length = 19<br>Location/Qualifiers<br>1..19<br>mol_type = other DNA<br>organism = synthetic construct | |
| SEQUENCE: 49<br>cggtggcctc tctttcgcg | | 19 |
| SEQ ID NO: 50<br>FEATURE<br>source | moltype = DNA   length = 19<br>Location/Qualifiers<br>1..19<br>mol_type = other DNA<br>organism = synthetic construct | |
| SEQUENCE: 50<br>ggtggcctct ctttcgcgg | | 19 |
| SEQ ID NO: 51<br>FEATURE<br>source | moltype = DNA   length = 19<br>Location/Qualifiers<br>1..19<br>mol_type = other DNA<br>organism = synthetic construct | |
| SEQUENCE: 51<br>gcctctcttt cgcggggaa | | 19 |

```
SEQ ID NO: 52            moltype = DNA  length = 19
FEATURE                  Location/Qualifiers
source                   1..19
                         mol_type = other DNA
                         organism = synthetic construct SEQUENCE: 52
cacctggctg gctacggag                                                      19

SEQ ID NO: 53            moltype = DNA  length = 19
FEATURE                  Location/Qualifiers
source                   1..19
                         mol_type = other DNA
                         organism = synthetic construct SEQUENCE: 53
gctacggagg ggcgtgtct                                                      19

SEQ ID NO: 54            moltype = DNA  length = 19
FEATURE                  Location/Qualifiers
source                   1..19
                         mol_type = other DNA
                         organism = synthetic construct SEQUENCE: 54
ctacggaggg gcgtgtctc                                                      19

SEQ ID NO: 55            moltype = DNA  length = 19
FEATURE                  Location/Qualifiers
source                   1..19
                         mol_type = other DNA
                         organism = synthetic construct SEQUENCE: 55
acgtgcaagg gagctcgct                                                      19

SEQ ID NO: 56            moltype = DNA  length = 19
FEATURE                  Location/Qualifiers
source                   1..19
                         mol_type = other DNA
                         organism = synthetic construct SEQUENCE: 56
cgtgcaaggg agctcgctg                                                      19

SEQ ID NO: 57            moltype = DNA  length = 19
FEATURE                  Location/Qualifiers
source                   1..19
                         mol_type = other DNA
                         organism = synthetic construct SEQUENCE: 57
gtgcaaggga gctcgctgg                                                      19

SEQ ID NO: 58            moltype = DNA  length = 19
FEATURE                  Location/Qualifiers
source                   1..19
                         mol_type = other DNA
                         organism = synthetic construct SEQUENCE: 58
caccttccga cgctgtcta                                                      19

SEQ ID NO: 59            moltype = DNA  length = 19
FEATURE                  Location/Qualifiers
source                   1..19
                         mol_type = other DNA
                         organism = synthetic construct SEQUENCE: 59
accttccgac gctgtctag                                                      19

SEQ ID NO: 60            moltype = DNA  length = 19
FEATURE                  Location/Qualifiers
source                   1..19
                         mol_type = other DNA
                         organism = synthetic construct SEQUENCE: 60
ccttccgacg ctgtctagg                                                      19

SEQ ID NO: 61            moltype = DNA  length = 19
FEATURE                  Location/Qualifiers
source                   1..19
                         mol_type = other DNA
                         organism = synthetic construct

SEQUENCE: 61
```

```
cttccgacgc tgtctaggc                                                    19

SEQ ID NO: 62           moltype = DNA   length = 19
FEATURE                 Location/Qualifiers
source                  1..19
                        mol_type = other DNA
                        organism = synthetic construct SEQUENCE: 62
tccgacgctg tctaggcaa                                                    19

SEQ ID NO: 63           moltype = DNA   length = 19
FEATURE                 Location/Qualifiers
source                  1..19
                        mol_type = other DNA
                        organism = synthetic construct SEQUENCE: 63
ccgacgctgt ctaggcaaa                                                    19

SEQ ID NO: 64           moltype = DNA   length = 19
FEATURE                 Location/Qualifiers
source                  1..19
                        mol_type = other DNA
                        organism = synthetic construct SEQUENCE: 64
acgctgtcta ggcaaacct                                                    19

SEQ ID NO: 65           moltype = DNA   length = 19
FEATURE                 Location/Qualifiers
source                  1..19
                        mol_type = other DNA
                        organism = synthetic construct SEQUENCE: 65
aaacctggat tagagttac                                                    19

SEQ ID NO: 66           moltype = DNA   length = 19
FEATURE                 Location/Qualifiers
source                  1..19
                        mol_type = other DNA
                        organism = synthetic construct SEQUENCE: 66
ctttgagaag gatcgcttt                                                    19

SEQ ID NO: 67           moltype = DNA   length = 19
FEATURE                 Location/Qualifiers
source                  1..19
                        mol_type = other DNA
                        organism = synthetic construct SEQUENCE: 67
gccggcagag gggatctcc                                                    19

SEQ ID NO: 68           moltype = DNA   length = 19
FEATURE                 Location/Qualifiers
source                  1..19
                        mol_type = other DNA
                        organism = synthetic construct SEQUENCE: 68
gggccaaggg gtgcttgcg                                                    19

SEQ ID NO: 69           moltype = DNA   length = 19
FEATURE                 Location/Qualifiers
source                  1..19
                        mol_type = other DNA
                        organism = synthetic construct SEQUENCE: 69
gccaaggggt gcttgcgcc                                                    19

SEQ ID NO: 70           moltype = DNA   length = 19
FEATURE                 Location/Qualifiers
source                  1..19
                        mol_type = other DNA
                        organism = synthetic construct SEQUENCE: 70
atgcaaggca tcccggcgc                                                    19

SEQ ID NO: 71           moltype = DNA   length = 19
FEATURE                 Location/Qualifiers
source                  1..19
                        mol_type = other DNA
                        organism = synthetic construct
```

```
SEQUENCE: 71
gtgctgtccg agggtgtcg                                                                  19

SEQ ID NO: 72           moltype = DNA  length = 19
FEATURE                 Location/Qualifiers
source                  1..19
                        mol_type = other DNA
                        organism = synthetic construct
SEQUENCE: 72
aacgagtctc cgtcgccgt                                                                  19

SEQ ID NO: 73           moltype = DNA  length = 19
FEATURE                 Location/Qualifiers
source                  1..19
                        mol_type = other DNA
                        organism = synthetic construct
SEQUENCE: 73
aaacgagtct ccgtcgccg                                                                  19

SEQ ID NO: 74           moltype = DNA  length = 19
FEATURE                 Location/Qualifiers
source                  1..19
                        mol_type = other DNA
                        organism = synthetic construct
SEQUENCE: 74
caaacgagtc tccgtcgcc                                                                  19

SEQ ID NO: 75           moltype = DNA  length = 19
FEATURE                 Location/Qualifiers
source                  1..19
                        mol_type = other DNA
                        organism = synthetic construct
SEQUENCE: 75
ccaaacgagt ctccgtcgc                                                                  19

SEQ ID NO: 76           moltype = DNA  length = 19
FEATURE                 Location/Qualifiers
source                  1..19
                        mol_type = other DNA
                        organism = synthetic construct
SEQUENCE: 76
tccaaacgag tctccgtcg                                                                  19

SEQ ID NO: 77           moltype = DNA  length = 19
FEATURE                 Location/Qualifiers
source                  1..19
                        mol_type = other DNA
                        organism = synthetic construct
SEQUENCE: 77
gtccaaacga gtctccgtc                                                                  19

SEQ ID NO: 78           moltype = DNA  length = 19
FEATURE                 Location/Qualifiers
source                  1..19
                        mol_type = other DNA
                        organism = synthetic construct
SEQUENCE: 78
ggtccaaacg agtctccgt                                                                  19

SEQ ID NO: 79           moltype = DNA  length = 19
FEATURE                 Location/Qualifiers
source                  1..19
                        mol_type = other DNA
                        organism = synthetic construct
SEQUENCE: 79
tcgctttggc tcggggtcc                                                                  19

SEQ ID NO: 80           moltype = DNA  length = 19
FEATURE                 Location/Qualifiers
source                  1..19
                        mol_type = other DNA
                        organism = synthetic construct
SEQUENCE: 80
ctcgctttgg ctcggggtc                                                                  19

SEQ ID NO: 81           moltype = DNA  length = 19
FEATURE                 Location/Qualifiers
source                  1..19
                        mol_type = other DNA
```

```
                                  -continued
                    organism = synthetic construct
SEQUENCE: 81
cctcgctttg gctcgsggt                                              19

SEQ ID NO: 82       moltype = DNA  length = 19
FEATURE             Location/Qualifiers
source              1..19
                    mol_type = other DNA
                    organism = synthetic construct
SEQUENCE: 82
ctcaaagcag gctcgcagg                                              19

SEQ ID NO: 83       moltype = DNA  length = 19
FEATURE             Location/Qualifiers
source              1..19
                    mol_type = other DNA
                    organism = synthetic construct
SEQUENCE: 83
ccgctcaaag caggctcgc                                              19

SEQ ID NO: 84       moltype = DNA  length = 19
FEATURE             Location/Qualifiers
source              1..19
                    mol_type = other DNA
                    organism = synthetic construct
SEQUENCE: 84
agccgttctc tggtggcga                                              19

SEQ ID NO: 85       moltype = DNA  length = 19
FEATURE             Location/Qualifiers
source              1..19
                    mol_type = other DNA
                    organism = synthetic construct
SEQUENCE: 85
ccggaatgcc gatggcctg                                              19

SEQ ID NO: 86       moltype = DNA  length = 19
FEATURE             Location/Qualifiers
source              1..19
                    mol_type = other DNA
                    organism = synthetic construct
SEQUENCE: 86
ctccggaatg ccgatggcc                                              19

SEQ ID NO: 87       moltype = DNA  length = 19
FEATURE             Location/Qualifiers
source              1..19
                    mol_type = other DNA
                    organism = synthetic construct
SEQUENCE: 87
gctccggaat gccgatggc                                              19

SEQ ID NO: 88       moltype = DNA  length = 19
FEATURE             Location/Qualifiers
source              1..19
                    mol_type = other DNA
                    organism = synthetic construct
SEQUENCE: 88
ccgagattcc cgccggtgc                                              19

SEQ ID NO: 89       moltype = DNA  length = 19
FEATURE             Location/Qualifiers
source              1..19
                    mol_type = other DNA
                    organism = synthetic construct
SEQUENCE: 89
gccgagattc cgccggtg                                               19

SEQ ID NO: 90       moltype = DNA  length = 19
FEATURE             Location/Qualifiers
source              1..19
                    mol_type = other DNA
                    organism = synthetic construct
SEQUENCE: 90
gctttcgccg gccttctgg                                              19

SEQ ID NO: 91       moltype = DNA  length = 19
FEATURE             Location/Qualifiers
source              1..19
```

-continued

```
                        mol_type = other DNA
                        organism = synthetic construct
SEQUENCE: 91
ccgctttcgc cggccttct                                                      19

SEQ ID NO: 92           moltype = DNA   length = 19
FEATURE                 Location/Qualifiers
source                  1..19
                        mol_type = other DNA
                        organism = synthetic construct
SEQUENCE: 92
tccgctttcg ccggccttc                                                      19

SEQ ID NO: 93           moltype = DNA   length = 19
FEATURE                 Location/Qualifiers
source                  1..19
                        mol_type = other DNA
                        organism = synthetic construct
SEQUENCE: 93
gacggcggtc cgctttcgc                                                      19

SEQ ID NO: 94           moltype = DNA   length = 19
FEATURE                 Location/Qualifiers
source                  1..19
                        mol_type = other DNA
                        organism = synthetic construct
SEQUENCE: 94
gtgacggcgg tccgctttc                                                      19

SEQ ID NO: 95           moltype = DNA   length = 19
FEATURE                 Location/Qualifiers
source                  1..19
                        mol_type = other DNA
                        organism = synthetic construct
SEQUENCE: 95
atccggtgac ggcggtccg                                                      19

SEQ ID NO: 96           moltype = DNA   length = 19
FEATURE                 Location/Qualifiers
source                  1..19
                        mol_type = other DNA
                        organism = synthetic construct
SEQUENCE: 96
gatccggtga cggcggtcc                                                      19

SEQ ID NO: 97           moltype = DNA   length = 19
FEATURE                 Location/Qualifiers
source                  1..19
                        mol_type = other DNA
                        organism = synthetic construct
SEQUENCE: 97
ggatccggtg acggcggtc                                                      19

SEQ ID NO: 98           moltype = DNA   length = 19
FEATURE                 Location/Qualifiers
source                  1..19
                        mol_type = other DNA
                        organism = synthetic construct
SEQUENCE: 98
gactccggga ggcccgtct                                                      19

SEQ ID NO: 99           moltype = DNA   length = 19
FEATURE                 Location/Qualifiers
source                  1..19
                        mol_type = other DNA
                        organism = synthetic construct
SEQUENCE: 99
gcgaaggcga cccacgagg                                                      19

SEQ ID NO: 100          moltype = DNA   length = 19
FEATURE                 Location/Qualifiers
source                  1..19
                        mol_type = other DNA
                        organism = synthetic construct
SEQUENCE: 100
ggcgaaggcg acccacgag                                                      19

SEQ ID NO: 101          moltype = DNA   length = 19
FEATURE                 Location/Qualifiers
```

| | | |
|---|---|---|
| source | 1..19<br>mol_type = other DNA<br>organism = synthetic construct | |
| SEQUENCE: 101<br>caggttggga gatccctc | | 19 |
| SEQ ID NO: 102<br>FEATURE<br>source | moltype = DNA   length = 19<br>Location/Qualifiers<br>1..19<br>mol_type = other DNA<br>organism = synthetic construct | |
| SEQUENCE: 102<br>taggcgaaat ccccgcgcg | | 19 |
| SEQ ID NO: 103<br>FEATURE<br>source | moltype = DNA   length = 19<br>Location/Qualifiers<br>1..19<br>mol_type = other DNA<br>organism = synthetic construct | |
| SEQUENCE: 103<br>gtaggcgaaa tccccgcgc | | 19 |
| SEQ ID NO: 104<br>FEATURE<br>source | moltype = DNA   length = 19<br>Location/Qualifiers<br>1..19<br>mol_type = other DNA<br>organism = synthetic construct | |
| SEQUENCE: 104<br>ggcgtaggcg aaatccccg | | 19 |
| SEQ ID NO: 105<br>FEATURE<br>source | moltype = DNA   length = 19<br>Location/Qualifiers<br>1..19<br>mol_type = other DNA<br>organism = synthetic construct | |
| SEQUENCE: 105<br>gacgtgggtg gcgcaagca | | 19 |
| SEQ ID NO: 106<br>FEATURE<br>source | moltype = DNA   length = 19<br>Location/Qualifiers<br>1..19<br>mol_type = other DNA<br>organism = synthetic construct | |
| SEQUENCE: 106<br>gaaactccgg gctcgccag | | 19 |
| SEQ ID NO: 107<br>FEATURE<br>source | moltype = DNA   length = 19<br>Location/Qualifiers<br>1..19<br>mol_type = other DNA<br>organism = synthetic construct | |
| SEQUENCE: 107<br>cagaaactcc gggctcgcc | | 19 |
| SEQ ID NO: 108<br>FEATURE<br>source | moltype = DNA   length = 19<br>Location/Qualifiers<br>1..19<br>mol_type = other DNA<br>organism = synthetic construct | |
| SEQUENCE: 108<br>ttctaggaga ggttgcgcc | | 19 |
| SEQ ID NO: 109<br>FEATURE<br>source | moltype = DNA   length = 19<br>Location/Qualifiers<br>1..19<br>mol_type = other DNA<br>organism = synthetic construct | |
| SEQUENCE: 109<br>tttctaggag aggttgcgc | | 19 |
| SEQ ID NO: 110<br>FEATURE<br>source | moltype = DNA   length = 19<br>Location/Qualifiers<br>1..19<br>mol_type = other DNA<br>organism = synthetic construct | |
| SEQUENCE: 110<br>tccgtttcta ggagaggtt | | 19 |
| SEQ ID NO: 111 | moltype = DNA   length = 19 | |

```
FEATURE              Location/Qualifiers
source               1..19
                     mol_type = other DNA
                     organism = synthetic construct
SEQUENCE: 111
ccggtattct tcctcgctg                                                    19

SEQ ID NO: 112       moltype = DNA   length = 19
FEATURE              Location/Qualifiers
source               1..19
                     mol_type = other DNA
                     organism = synthetic construct
SEQUENCE: 112
cccggtattc ttcctcgct                                                    19

SEQ ID NO: 113       moltype = DNA   length = 19
FEATURE              Location/Qualifiers
source               1..19
                     mol_type = other DNA
                     organism = synthetic construct
SEQUENCE: 113
gcccggtatt cttcctcgc                                                    19

SEQ ID NO: 114       moltype = DNA   length = 19
FEATURE              Location/Qualifiers
source               1..19
                     mol_type = other DNA
                     organism = synthetic construct
SEQUENCE: 114
cacccgaccc cgtcccaac                                                    19

SEQ ID NO: 115       moltype = DNA   length = 19
FEATURE              Location/Qualifiers
source               1..19
                     mol_type = other DNA
                     organism = synthetic construct
SEQUENCE: 115
ccgaaccacc cgaccccgt                                                    19

SEQ ID NO: 116       moltype = DNA   length = 19
FEATURE              Location/Qualifiers
source               1..19
                     mol_type = other DNA
                     organism = synthetic construct
SEQUENCE: 116
tgccccgaac cacccgacc                                                    19

SEQ ID NO: 117       moltype = DNA   length = 19
FEATURE              Location/Qualifiers
source               1..19
                     mol_type = other DNA
                     organism = synthetic construct
SEQUENCE: 117
ctgccccgaa ccacccgac                                                    19

SEQ ID NO: 118       moltype = DNA   length = 19
FEATURE              Location/Qualifiers
source               1..19
                     mol_type = other DNA
                     organism = synthetic construct
SEQUENCE: 118
gcgaaagaga ggccaccgc                                                    19

SEQ ID NO: 119       moltype = DNA   length = 19
FEATURE              Location/Qualifiers
source               1..19
                     mol_type = other DNA
                     organism = synthetic construct
SEQUENCE: 119
cgcgaaagag aggccaccg                                                    19

SEQ ID NO: 120       moltype = DNA   length = 19
FEATURE              Location/Qualifiers
source               1..19
                     mol_type = other DNA
                     organism = synthetic construct
SEQUENCE: 120
ccgcgaaaga gaggccacc                                                    19
```

| | | |
|---|---|---|
| SEQ ID NO: 121<br>FEATURE<br>source | moltype = DNA   length = 19<br>Location/Qualifiers<br>1..19<br>mol_type = other DNA<br>organism = synthetic construct | |
| SEQUENCE: 121<br>ttccccgcga aagagaggc | | 19 |
| SEQ ID NO: 122<br>FEATURE<br>source | moltype = DNA   length = 19<br>Location/Qualifiers<br>1..19<br>mol_type = other DNA<br>organism = synthetic construct | |
| SEQUENCE: 122<br>ctccgtagcc agccaggtg | | 19 |
| SEQ ID NO: 123<br>FEATURE<br>source | moltype = DNA   length = 19<br>Location/Qualifiers<br>1..19<br>mol_type = other DNA<br>organism = synthetic construct | |
| SEQUENCE: 123<br>agacacgccc ctccgtagc | | 19 |
| SEQ ID NO: 124<br>FEATURE<br>source | moltype = DNA   length = 19<br>Location/Qualifiers<br>1..19<br>mol_type = other DNA<br>organism = synthetic construct | |
| SEQUENCE: 124<br>gagacacgcc cctccgtag | | 19 |
| SEQ ID NO: 125<br>FEATURE<br>source | moltype = DNA   length = 19<br>Location/Qualifiers<br>1..19<br>mol_type = other DNA<br>organism = synthetic construct | |
| SEQUENCE: 125<br>agcgagctcc cttgcacgt | | 19 |
| SEQ ID NO: 126<br>FEATURE<br>source | moltype = DNA   length = 19<br>Location/Qualifiers<br>1..19<br>mol_type = other DNA<br>organism = synthetic construct | |
| SEQUENCE: 126<br>cagcgagctc ccttgcacg | | 19 |
| SEQ ID NO: 127<br>FEATURE<br>source | moltype = DNA   length = 19<br>Location/Qualifiers<br>1..19<br>mol_type = other DNA<br>organism = synthetic construct | |
| SEQUENCE: 127<br>ccagcgagct cccttgcac | | 19 |
| SEQ ID NO: 128<br>FEATURE<br>source | moltype = DNA   length = 19<br>Location/Qualifiers<br>1..19<br>mol_type = other DNA<br>organism = synthetic construct | |
| SEQUENCE: 128<br>tagacagcgt cggaaggtg | | 19 |
| SEQ ID NO: 129<br>FEATURE<br>source | moltype = DNA   length = 19<br>Location/Qualifiers<br>1..19<br>mol_type = other DNA<br>organism = synthetic construct | |
| SEQUENCE: 129<br>ctagacagcg tcggaaggt | | 19 |
| SEQ ID NO: 130<br>FEATURE<br>source | moltype = DNA   length = 19<br>Location/Qualifiers<br>1..19<br>mol_type = other DNA<br>organism = synthetic construct | |
| SEQUENCE: 130<br>cctagacagc gtcggaagg | | 19 |

```
SEQ ID NO: 131         moltype = DNA  length = 19
FEATURE                Location/Qualifiers
source                 1..19
                       mol_type = other DNA
                       organism = synthetic construct
SEQUENCE: 131
gcctagacag cgtcggaag                                              19

SEQ ID NO: 132         moltype = DNA  length = 19
FEATURE                Location/Qualifiers
source                 1..19
                       mol_type = other DNA
                       organism = synthetic construct
SEQUENCE: 132
ttgcctagac agcgtcgga                                              19

SEQ ID NO: 133         moltype = DNA  length = 19
FEATURE                Location/Qualifiers
source                 1..19
                       mol_type = other DNA
                       organism = synthetic construct
SEQUENCE: 133
tttgcctaga cagcgtcgg                                              19

SEQ ID NO: 134         moltype = DNA  length = 19
FEATURE                Location/Qualifiers
source                 1..19
                       mol_type = other DNA
                       organism = synthetic construct
SEQUENCE: 134
aggtttgcct agacagcgt                                              19

SEQ ID NO: 135         moltype = DNA  length = 19
FEATURE                Location/Qualifiers
source                 1..19
                       mol_type = other DNA
                       organism = synthetic construct
SEQUENCE: 135
gtaactctaa tccaggttt                                              19

SEQ ID NO: 136         moltype = DNA  length = 19
FEATURE                Location/Qualifiers
source                 1..19
                       mol_type = other DNA
                       organism = synthetic construct
SEQUENCE: 136
aaagcgatcc ttctcaaag                                              19

SEQ ID NO: 137         moltype = DNA  length = 19
FEATURE                Location/Qualifiers
source                 1..19
                       mol_type = other DNA
                       organism = synthetic construct
SEQUENCE: 137
ggagatcccc tctgccggc                                              19

SEQ ID NO: 138         moltype = DNA  length = 19
FEATURE                Location/Qualifiers
source                 1..19
                       mol_type = other DNA
                       organism = synthetic construct
SEQUENCE: 138
cgcaagcacc ccttggccc                                              19

SEQ ID NO: 139         moltype = DNA  length = 19
FEATURE                Location/Qualifiers
source                 1..19
                       mol_type = other DNA
                       organism = synthetic construct
SEQUENCE: 139
ggcgcaagca ccccttggc                                              19

SEQ ID NO: 140         moltype = DNA  length = 19
FEATURE                Location/Qualifiers
source                 1..19
                       mol_type = other DNA
                       organism = synthetic construct
SEQUENCE: 140
```

```
gcgccgggat gccttgcat                                                    19

SEQ ID NO: 141          moltype = RNA  length = 19
FEATURE                 Location/Qualifiers
source                  1..19
                        mol_type = other RNA
                        organism = synthetic construct
modified_base           1
                        mod_base = OTHER
                        note = 2'-O-methylcytidine phosphorothioate
modified_base           2
                        mod_base = OTHER
                        note = 2'-O-methylguanosine phosphorothioate
modified_base           3
                        mod_base = OTHER
                        note = 2'-O-methyladenosine
modified_base           4
                        mod_base = OTHER
                        note = 2'-O-methylcytidine
modified_base           5
                        mod_base = OTHER
                        note = 2'-O-methyladenosine
modified_base           6
                        mod_base = OTHER
                        note = 2'-O-methylcytidine
modified_base           7
                        mod_base = OTHER
                        note = 2'-fluorocytidine
modified_base           8
                        mod_base = OTHER
                        note = 2'-fluorocytidine
modified_base           9
                        mod_base = OTHER
                        note = 2'-fluorouridine
modified_base           10
                        mod_base = OTHER
                        note = 2'-O-methylcytidine
modified_base           11
                        mod_base = OTHER
                        note = 2'-O-methylguanosine
modified_base           12
                        mod_base = OTHER
                        note = 2'-O-methylguanosine
modified_base           13
                        mod_base = OTHER
                        note = 2'-O-methyladenosine
modified_base           14
                        mod_base = OTHER
                        note = 2'-O-methylcytidine
modified_base           15
                        mod_base = OTHER
                        note = 2'-O-methyladenosine
modified_base           16
                        mod_base = OTHER
                        note = 2'-O-methylguanosine
modified_base           17
                        mod_base = OTHER
                        note = 2'-O-methylcytidine phosphorothioate
modified_base           18
                        mod_base = OTHER
                        note = 2'-O-methyladenosine phosphorothioate
modified_base           19
                        mod_base = OTHER
                        note = 2'-O-methyladenosine
SEQUENCE: 141
cgacaccctc ggacagcaa                                                    19

SEQ ID NO: 142          moltype = RNA  length = 19
FEATURE                 Location/Qualifiers
source                  1..19
                        mol_type = other RNA
                        organism = synthetic construct
modified_base           1
                        mod_base = OTHER
                        note = 2'-O-methyladenosine phosphorothioate
modified_base           2
                        mod_base = OTHER
                        note = 2'-O-methylcytidine phosphorothioate
modified_base           3
```

|                    |                                                              |
| ------------------ | ------------------------------------------------------------ |
|                    | mod_base = OTHER                                             |
|                    | note = 2'-O-methylguanosine                                  |
| modified_base      | 4                                                            |
|                    | mod_base = OTHER                                             |
|                    | note = 2'-O-methylguanosine                                  |
| modified_base      | 5                                                            |
|                    | mod_base = OTHER                                             |
|                    | note = 2'-O-methylcytidine                                   |
| modified_base      | 6                                                            |
|                    | mod_base = OTHER                                             |
|                    | note = 2'-O-methylguanosine                                  |
| modified_base      | 7                                                            |
|                    | mod_base = OTHER                                             |
|                    | note = 2'-fluoroadenosine                                    |
| modified_base      | 8                                                            |
|                    | mod_base = OTHER                                             |
|                    | note = 2'-fluorocytidine                                     |
| modified_base      | 9                                                            |
|                    | mod_base = OTHER                                             |
|                    | note = 2'-fluoroguanosine                                    |
| modified_base      | 10                                                           |
|                    | mod_base = OTHER                                             |
|                    | note = 2'-O-methylguanosine                                  |
| modified_base      | 11                                                           |
|                    | mod_base = OTHER                                             |
|                    | note = 2'-O-methyladenosine                                  |
| modified_base      | 12                                                           |
|                    | mod_base = OTHER                                             |
|                    | note = 2'-O-methylguanosine                                  |
| modified_base      | 13                                                           |
|                    | mod_base = OTHER                                             |
|                    | note = 2'-O-methyladenosine                                  |
| modified_base      | 14                                                           |
|                    | mod_base = OTHER                                             |
|                    | note = 2'-O-methylcytidine                                   |
| modified_base      | 15                                                           |
|                    | mod_base = OTHER                                             |
|                    | note = 2'-O-methyluridine                                    |
| modified_base      | 16                                                           |
|                    | mod_base = OTHER                                             |
|                    | note = 2'-O-methylcytidine                                   |
| modified_base      | 17                                                           |
|                    | mod_base = OTHER                                             |
|                    | note = 2'-O-methylguanosine phosphorothioate                 |
| modified_base      | 18                                                           |
|                    | mod_base = OTHER                                             |
|                    | note = 2'-O-methyluridine phosphorothioate                   |
| modified_base      | 19                                                           |
|                    | mod_base = OTHER                                             |
|                    | note = 2'-O-methyladenosine                                  |
| SEQUENCE: 142      |                                                              |
| acggcgacgg agactcgta |                                                          19 |
|                    |                                                              |
| SEQ ID NO: 143     | moltype = RNA   length = 19                                  |
| FEATURE            | Location/Qualifiers                                          |
| source             | 1..19                                                        |
|                    | mol_type = other RNA                                         |
|                    | organism = synthetic construct                               |
| modified_base      | 1                                                            |
|                    | mod_base = OTHER                                             |
|                    | note = 2'-O-methylcytidine phosphorothioate                  |
| modified_base      | 2                                                            |
|                    | mod_base = OTHER                                             |
|                    | note = 2'-O-methylguanosine phosphorothioate                 |
| modified_base      | 3                                                            |
|                    | mod_base = OTHER                                             |
|                    | note = 2'-O-methylguanosine                                  |
| modified_base      | 4                                                            |
|                    | mod_base = OTHER                                             |
|                    | note = 2'-O-methylcytidine                                   |
| modified_base      | 5                                                            |
|                    | mod_base = OTHER                                             |
|                    | note = 2'-O-methylguanosine                                  |
| modified_base      | 6                                                            |
|                    | mod_base = OTHER                                             |
|                    | note = 2'-O-methyladenosine                                  |
| modified_base      | 7                                                            |
|                    | mod_base = OTHER                                             |
|                    | note = 2'-fluorocytidine                                     |

```
modified_base      8
                   mod_base = OTHER
                   note = 2'-fluoroguanosine
modified_base      9
                   mod_base = OTHER
                   note = 2'-fluoroguanosine
modified_base      10
                   mod_base = OTHER
                   note = 2'-O-methyladenosine
modified_base      11
                   mod_base = OTHER
                   note = 2'-O-methylguanosine
modified_base      12
                   mod_base = OTHER
                   note = 2'-O-methyladenosine
modified_base      13
                   mod_base = OTHER
                   note = 2'-O-methylcytidine
modified_base      14
                   mod_base = OTHER
                   note = 2'-O-methyluridine
modified_base      15
                   mod_base = OTHER
                   note = 2'-O-methylcytidine
modified_base      16
                   mod_base = OTHER
                   note = 2'-O-methylguanosine
modified_base      17
                   mod_base = OTHER
                   note = 2'-O-methyluridine phosphorothioate
modified_base      18
                   mod_base = OTHER
                   note = 2'-O-methyluridine phosphorothioate
modified_base      19
                   mod_base = OTHER
                   note = 2'-O-methyladenosine
SEQUENCE: 143
cggcgacgga gactcgtta                                             19

SEQ ID NO: 144     moltype = RNA  length = 19
FEATURE            Location/Qualifiers
source             1..19
                   mol_type = other RNA
                   organism = synthetic construct
modified_base      1
                   mod_base = OTHER
                   note = 2'-O-methylguanosine phosphorothioate
modified_base      2
                   mod_base = OTHER
                   note = 2'-O-methylguanosine phosphorothioate
modified_base      3
                   mod_base = OTHER
                   note = 2'-O-methylcytidine
modified_base      4
                   mod_base = OTHER
                   note = 2'-O-methylguanosine
modified_base      5
                   mod_base = OTHER
                   note = 2'-O-methyladenosine
modified_base      6
                   mod_base = OTHER
                   note = 2'-O-methylcytidine
modified_base      7
                   mod_base = OTHER
                   note = 2'-fluoroguanosine
modified_base      8
                   mod_base = OTHER
                   note = 2'-fluoroguanosine
modified_base      9
                   mod_base = OTHER
                   note = 2'-fluoroadenosine
modified_base      10
                   mod_base = OTHER
                   note = 2'-O-methylguanosine
modified_base      11
                   mod_base = OTHER
                   note = 2'-O-methyladenosine
modified_base      12
                   mod_base = OTHER
```

```
                        note = 2'-O-methylcytidine
modified_base           13
                        mod_base = OTHER
                        note = 2'-O-methyluridine
modified_base           14
                        mod_base = OTHER
                        note = 2'-O-methylcytidine
modified_base           15
                        mod_base = OTHER
                        note = 2'-O-methylguanosine
modified_base           16
                        mod_base = OTHER
                        note = 2'-O-methyluridine
modified_base           17
                        mod_base = OTHER
                        note = 2'-O-methyluridine phosphorothioate
modified_base           18
                        mod_base = OTHER
                        note = 2'-O-methyluridine phosphorothioate
modified_base           19
                        mod_base = OTHER
                        note = 2'-O-methyladenosine
SEQUENCE: 144
ggcgacggag actcgttta                                              19

SEQ ID NO: 145          moltype = RNA   length = 19
FEATURE                 Location/Qualifiers
source                  1..19
                        mol_type = other RNA
                        organism = synthetic construct
modified_base           1
                        mod_base = OTHER
                        note = 2'-O-methylguanosine phosphorothioate
modified_base           2
                        mod_base = OTHER
                        note = 2'-O-methylcytidine phosphorothioate
modified_base           3
                        mod_base = OTHER
                        note = 2'-O-methylguanosine
modified_base           4
                        mod_base = OTHER
                        note = 2'-O-methyladenosine
modified_base           5
                        mod_base = OTHER
                        note = 2'-O-methylcytidine
modified_base           6
                        mod_base = OTHER
                        note = 2'-O-methylguanosine
modified_base           7
                        mod_base = OTHER
                        note = 2'-fluoroguanosine
modified_base           8
                        mod_base = OTHER
                        note = 2'-fluoroadenosine
modified_base           9
                        mod_base = OTHER
                        note = 2'-fluoroguanosine
modified_base           10
                        mod_base = OTHER
                        note = 2'-O-methyladenosine
modified_base           11
                        mod_base = OTHER
                        note = 2'-O-methylcytidine
modified_base           12
                        mod_base = OTHER
                        note = 2'-O-methyluridine
modified_base           13
                        mod_base = OTHER
                        note = 2'-O-methylcytidine
modified_base           14
                        mod_base = OTHER
                        note = 2'-O-methylguanosine
modified_base           15
                        mod_base = OTHER
                        note = 2'-O-methyluridine
modified_base           16
                        mod_base = OTHER
                        note = 2'-O-methyluridine
modified_base           17
```

|                | |                                              |    |
|----------------|-|----------------------------------------------|----|
|                | | mod_base = OTHER                             |    |
|                | | note = 2'-O-methyluridine phosphorothioate   |    |
| modified_base  | | 18                                           |    |
|                | | mod_base = OTHER                             |    |
|                | | note = 2'-O-methylguanosine phosphorothioate |    |
| modified_base  | | 19                                           |    |
|                | | mod_base = OTHER                             |    |
|                | | note = 2'-O-methyladenosine                  |    |
| SEQUENCE: 145  | |                                              |    |
| gcgacggaga ctcgtttga | |                                        | 19 |

| | |
|---|---|
| SEQ ID NO: 146 | moltype = RNA  length = 19 |
| FEATURE | Location/Qualifiers |
| source | 1..19 |
| | mol_type = other RNA |
| | organism = synthetic construct |
| modified_base | 1 |
| | mod_base = OTHER |
| | note = 2'-O-methylcytidine phosphorothioate |
| modified_base | 2 |
| | mod_base = OTHER |
| | note = 2'-O-methylguanosine phosphorothioate |
| modified_base | 3 |
| | mod_base = OTHER |
| | note = 2'-O-methyladenosine |
| modified_base | 4 |
| | mod_base = OTHER |
| | note = 2'-O-methylcytidine |
| modified_base | 5 |
| | mod_base = OTHER |
| | note = 2'-O-methylguanosine |
| modified_base | 6 |
| | mod_base = OTHER |
| | note = 2'-O-methylguanosine |
| modified_base | 7 |
| | mod_base = OTHER |
| | note = 2'-fluoroadenosine |
| modified_base | 8 |
| | mod_base = OTHER |
| | note = 2'-fluoroguanosine |
| modified_base | 9 |
| | mod_base = OTHER |
| | note = 2'-fluoroadenosine |
| modified_base | 10 |
| | mod_base = OTHER |
| | note = 2'-O-methylcytidine |
| modified_base | 11 |
| | mod_base = OTHER |
| | note = 2'-O-methyluridine |
| modified_base | 12 |
| | mod_base = OTHER |
| | note = 2'-O-methylcytidine |
| modified_base | 13 |
| | mod_base = OTHER |
| | note = 2'-O-methylguanosine |
| modified_base | 14 |
| | mod_base = OTHER |
| | note = 2'-O-methyluridine |
| modified_base | 15 |
| | mod_base = OTHER |
| | note = 2'-O-methyluridine |
| modified_base | 16 |
| | mod_base = OTHER |
| | note = 2'-O-methyluridine |
| modified_base | 17 |
| | mod_base = OTHER |
| | note = 2'-O-methylguanosine phosphorothioate |
| modified_base | 18 |
| | mod_base = OTHER |
| | note = 2'-O-methylguanosine phosphorothioate |
| modified_base | 19 |
| | mod_base = OTHER |
| | note = 2'-O-methyladenosine |

| | | |
|---|---|---|
| SEQUENCE: 146 | | |
| cgacggagac tcgtttgga | | 19 |

| | |
|---|---|
| SEQ ID NO: 147 | moltype = RNA  length = 19 |
| FEATURE | Location/Qualifiers |
| source | 1..19 |

```
                          mol_type = other RNA
                          organism = synthetic construct
modified_base             1
                          mod_base = OTHER
                          note = 2'-O-methylguanosine phosphorothioate
modified_base             2
                          mod_base = OTHER
                          note = 2'-O-methyladenosine phosphorothioate
modified_base             3
                          mod_base = OTHER
                          note = 2'-O-methylcytidine
modified_base             4
                          mod_base = OTHER
                          note = 2'-O-methylguanosine
modified_base             5
                          mod_base = OTHER
                          note = 2'-O-methylguanosine
modified_base             6
                          mod_base = OTHER
                          note = 2'-O-methyladenosine
modified_base             7
                          mod_base = OTHER
                          note = 2'-fluoroguanosine
modified_base             8
                          mod_base = OTHER
                          note = 2'-fluoroadenosine
modified_base             9
                          mod_base = OTHER
                          note = 2'-fluorocytidine
modified_base             10
                          mod_base = OTHER
                          note = 2'-O-methyluridine
modified_base             11
                          mod_base = OTHER
                          note = 2'-O-methylcytidine
modified_base             12
                          mod_base = OTHER
                          note = 2'-O-methylguanosine
modified_base             13
                          mod_base = OTHER
                          note = 2'-O-methyluridine
modified_base             14
                          mod_base = OTHER
                          note = 2'-O-methyluridine
modified_base             15
                          mod_base = OTHER
                          note = 2'-O-methyluridine
modified_base             16
                          mod_base = OTHER
                          note = 2'-O-methylguanosine
modified_base             17
                          mod_base = OTHER
                          note = 2'-O-methylguanosine phosphorothioate
modified_base             18
                          mod_base = OTHER
                          note = 2'-O-methyladenosine phosphorothioate
modified_base             19
                          mod_base = OTHER
                          note = 2'-O-methyladenosine
SEQUENCE: 147
gacggagact cgtttggaa                                                    19

SEQ ID NO: 148            moltype = RNA   length = 19
FEATURE                   Location/Qualifiers
source                    1..19
                          mol_type = other RNA
                          organism = synthetic construct
modified_base             1
                          mod_base = OTHER
                          note = 2'-O-methyladenosine phosphorothioate
modified_base             2
                          mod_base = OTHER
                          note = 2'-O-methylcytidine phosphorothioate
modified_base             3
                          mod_base = OTHER
                          note = 2'-O-methylguanosine
modified_base             4
                          mod_base = OTHER
                          note = 2'-O-methylguanosine
```

|   |   |
|---|---|
| modified_base | 5<br>mod_base = OTHER<br>note = 2'-O-methyladenosine |
| modified_base | 6<br>mod_base = OTHER<br>note = 2'-O-methylguanosine |
| modified_base | 7<br>mod_base = OTHER<br>note = 2'-fluoroadenosine |
| modified_base | 8<br>mod_base = OTHER<br>note = 2'-fluorocytidine |
| modified_base | 9<br>mod_base = OTHER<br>note = 2'-fluorouridine |
| modified_base | 10<br>mod_base = OTHER<br>note = 2'-O-methylcytidine |
| modified_base | 11<br>mod_base = OTHER<br>note = 2'-O-methylguanosine |
| modified_base | 12<br>mod_base = OTHER<br>note = 2'-O-methyluridine |
| modified_base | 13<br>mod_base = OTHER<br>note = 2'-O-methyluridine |
| modified_base | 14<br>mod_base = OTHER<br>note = 2'-O-methyluridine |
| modified_base | 15<br>mod_base = OTHER<br>note = 2'-O-methylguanosine |
| modified_base | 16<br>mod_base = OTHER<br>note = 2'-O-methylguanosine |
| modified_base | 17<br>mod_base = OTHER<br>note = 2'-O-methyladenosine phosphorothioate |
| modified_base | 18<br>mod_base = OTHER<br>note = 2'-O-methylcytidine phosphorothioate |
| modified_base | 19<br>mod_base = OTHER<br>note = 2'-O-methyladenosine |
| SEQUENCE: 148<br>acggagactc gtttggaca | 19 |
| SEQ ID NO: 149<br>FEATURE<br>source | moltype = RNA   length = 19<br>Location/Qualifiers<br>1..19<br>mol_type = other RNA<br>organism = synthetic construct |
| modified_base | 1<br>mod_base = OTHER<br>note = 2'-O-methylguanosine phosphorothioate |
| modified_base | 2<br>mod_base = OTHER<br>note = 2'-O-methylguanosine phosphorothioate |
| modified_base | 3<br>mod_base = OTHER<br>note = 2'-O-methyladenosine |
| modified_base | 4<br>mod_base = OTHER<br>note = 2'-O-methylcytidine |
| modified_base | 5<br>mod_base = OTHER<br>note = 2'-O-methylcytidine |
| modified_base | 6<br>mod_base = OTHER<br>note = 2'-O-methylcytidine |
| modified_base | 7<br>mod_base = OTHER<br>note = 2'-fluorocytidine |
| modified_base | 8<br>mod_base = OTHER<br>note = 2'-fluoroguanosine |
| modified_base | 9<br>mod_base = OTHER |

```
                        note = 2'-fluoroadenosine
modified_base           10
                        mod_base = OTHER
                        note = 2'-O-methylguanosine
modified_base           11
                        mod_base = OTHER
                        note = 2'-O-methylcytidine
modified_base           12
                        mod_base = OTHER
                        note = 2'-O-methylcytidine
modified_base           13
                        mod_base = OTHER
                        note = 2'-O-methyladenosine
modified_base           14
                        mod_base = OTHER
                        note = 2'-O-methyladenosine
modified_base           15
                        mod_base = OTHER
                        note = 2'-O-methyladenosine
modified_base           16
                        mod_base = OTHER
                        note = 2'-O-methylguanosine
modified_base           17
                        mod_base = OTHER
                        note = 2'-O-methylcytidine phosphorothioate
modified_base           18
                        mod_base = OTHER
                        note = 2'-O-methylguanosine phosphorothioate
modified_base           19
                        mod_base = OTHER
                        note = 2'-O-methyladenosine
SEQUENCE: 149
ggaccccgag ccaaagcga                                                  19

SEQ ID NO: 150          moltype = RNA   length = 19
FEATURE                 Location/Qualifiers
source                  1..19
                        mol_type = other RNA
                        organism = synthetic construct
modified_base           1
                        mod_base = OTHER
                        note = 2'-O-methylguanosine phosphorothioate
modified_base           2
                        mod_base = OTHER
                        note = 2'-O-methyladenosine phosphorothioate
modified_base           3
                        mod_base = OTHER
                        note = 2'-O-methylcytidine
modified_base           4
                        mod_base = OTHER
                        note = 2'-O-methylcytidine
modified_base           5
                        mod_base = OTHER
                        note = 2'-O-methylcytidine
modified_base           6
                        mod_base = OTHER
                        note = 2'-O-methylcytidine
modified_base           7
                        mod_base = OTHER
                        note = 2'-fluoroguanosine
modified_base           8
                        mod_base = OTHER
                        note = 2'-fluoroadenosine
modified_base           9
                        mod_base = OTHER
                        note = 2'-fluoroguanosine
modified_base           10
                        mod_base = OTHER
                        note = 2'-O-methylcytidine
modified_base           11
                        mod_base = OTHER
                        note = 2'-O-methylcytidine
modified_base           12
                        mod_base = OTHER
                        note = 2'-O-methyladenosine
modified_base           13
                        mod_base = OTHER
                        note = 2'-O-methyladenosine
modified_base           14
```

```
                        mod_base = OTHER
                        note = 2'-O-methyladenosine
modified_base           15
                        mod_base = OTHER
                        note = 2'-O-methylguanosine
modified_base           16
                        mod_base = OTHER
                        note = 2'-O-methylcytidine
modified_base           17
                        mod_base = OTHER
                        note = 2'-O-methylguanosine phosphorothioate
modified_base           18
                        mod_base = OTHER
                        note = 2'-O-methyladenosine phosphorothioate
modified_base           19
                        mod_base = OTHER
                        note = 2'-O-methyladenosine
SEQUENCE: 150
gaccccgagc caaagcgaa                                                    19

SEQ ID NO: 151          moltype = RNA  length = 19
FEATURE                 Location/Qualifiers
source                  1..19
                        mol_type = other RNA
                        organism = synthetic construct
modified_base           1
                        mod_base = OTHER
                        note = 2'-O-methyladenosine phosphorothioate
modified_base           2
                        mod_base = OTHER
                        note = 2'-O-methylcytidine phosphorothioate
modified_base           3
                        mod_base = OTHER
                        note = 2'-O-methylcytidine
modified_base           4
                        mod_base = OTHER
                        note = 2'-O-methylcytidine
modified_base           5
                        mod_base = OTHER
                        note = 2'-O-methylcytidine
modified_base           6
                        mod_base = OTHER
                        note = 2'-O-methylguanosine
modified_base           7
                        mod_base = OTHER
                        note = 2'-fluoroadenosine
modified_base           8
                        mod_base = OTHER
                        note = 2'-fluoroguanosine
modified_base           9
                        mod_base = OTHER
                        note = 2'-fluorocytidine
modified_base           10
                        mod_base = OTHER
                        note = 2'-O-methylcytidine
modified_base           11
                        mod_base = OTHER
                        note = 2'-O-methyladenosine
modified_base           12
                        mod_base = OTHER
                        note = 2'-O-methyladenosine
modified_base           13
                        mod_base = OTHER
                        note = 2'-O-methyladenosine
modified_base           14
                        mod_base = OTHER
                        note = 2'-O-methylguanosine
modified_base           15
                        mod_base = OTHER
                        note = 2'-O-methylcytidine
modified_base           16
                        mod_base = OTHER
                        note = 2'-O-methylguanosine
modified_base           17
                        mod_base = OTHER
                        note = 2'-O-methyladenosine phosphorothioate
modified_base           18
                        mod_base = OTHER
                        note = 2'-O-methylguanosine phosphorothioate
```

```
modified_base              19
                           mod_base = OTHER
                           note = 2'-O-methyladenosine
SEQUENCE: 151
accccgagcc aaagcgaga                                               19

SEQ ID NO: 152             moltype = RNA   length = 19
FEATURE                    Location/Qualifiers
source                     1..19
                           mol_type = other RNA
                           organism = synthetic construct
modified_base              1
                           mod_base = OTHER
                           note = 2'-O-methylcytidine phosphorothioate
modified_base              2
                           mod_base = OTHER
                           note = 2'-O-methylcytidine phosphorothioate
modified_base              3
                           mod_base = OTHER
                           note = 2'-O-methyluridine
modified_base              4
                           mod_base = OTHER
                           note = 2'-O-methylguanosine
modified_base              5
                           mod_base = OTHER
                           note = 2'-O-methylcytidine
modified_base              6
                           mod_base = OTHER
                           note = 2'-O-methylguanosine
modified_base              7
                           mod_base = OTHER
                           note = 2'-fluoroadenosine
modified_base              8
                           mod_base = OTHER
                           note = 2'-fluoroguanosine
modified_base              9
                           mod_base = OTHER
                           note = 2'-fluorocytidine
modified_base              10
                           mod_base = OTHER
                           note = 2'-O-methylcytidine
modified_base              11
                           mod_base = OTHER
                           note = 2'-O-methyluridine
modified_base              12
                           mod_base = OTHER
                           note = 2'-O-methylguanosine
modified_base              13
                           mod_base = OTHER
                           note = 2'-O-methylcytidine
modified_base              14
                           mod_base = OTHER
                           note = 2'-O-methyluridine
modified_base              15
                           mod_base = OTHER
                           note = 2'-O-methyluridine
modified_base              16
                           mod_base = OTHER
                           note = 2'-O-methyluridine
modified_base              17
                           mod_base = OTHER
                           note = 2'-O-methylguanosine phosphorothioate
modified_base              18
                           mod_base = OTHER
                           note = 2'-O-methyladenosine phosphorothioate
modified_base              19
                           mod_base = OTHER
                           note = 2'-O-methyladenosine
SEQUENCE: 152
cctgcgagcc tgctttgaa                                               19

SEQ ID NO: 153             moltype = RNA   length = 19
FEATURE                    Location/Qualifiers
source                     1..19
                           mol_type = other RNA
                           organism = synthetic construct
modified_base              1
                           mod_base = OTHER
                           note = 2'-O-methylguanosine phosphorothioate
```

```
modified_base       2
                    mod_base = OTHER
                    note = 2'-O-methylcytidine phosphorothioate
modified_base       3
                    mod_base = OTHER
                    note = 2'-O-methylguanosine
modified_base       4
                    mod_base = OTHER
                    note = 2'-O-methyladenosine
modified_base       5
                    mod_base = OTHER
                    note = 2'-O-methylguanosine
modified_base       6
                    mod_base = OTHER
                    note = 2'-O-methylcytidine
modified_base       7
                    mod_base = OTHER
                    note = 2'-fluorocytidine
modified_base       8
                    mod_base = OTHER
                    note = 2'-fluorouridine
modified_base       9
                    mod_base = OTHER
                    note = 2'-fluoroguanosine
modified_base       10
                    mod_base = OTHER
                    note = 2'-O-methylcytidine
modified_base       11
                    mod_base = OTHER
                    note = 2'-O-methyluridine
modified_base       12
                    mod_base = OTHER
                    note = 2'-O-methyluridine
modified_base       13
                    mod_base = OTHER
                    note = 2'-O-methyluridine
modified_base       14
                    mod_base = OTHER
                    note = 2'-O-methylguanosine
modified_base       15
                    mod_base = OTHER
                    note = 2'-O-methyladenosine
modified_base       16
                    mod_base = OTHER
                    note = 2'-O-methylguanosine
modified_base       17
                    mod_base = OTHER
                    note = 2'-O-methylcytidine phosphorothioate
modified_base       18
                    mod_base = OTHER
                    note = 2'-O-methylguanosine phosphorothioate
modified_base       19
                    mod_base = OTHER
                    note = 2'-O-methyladenosine
SEQUENCE: 153
gcgagcctgc tttgagcga                                              19

SEQ ID NO: 154      moltype = RNA   length = 19
FEATURE             Location/Qualifiers
source              1..19
                    mol_type = other RNA
                    organism = synthetic construct
modified_base       1
                    mod_base = OTHER
                    note = 2'-O-methyluridine phosphorothioate
modified_base       2
                    mod_base = OTHER
                    note = 2'-O-methylcytidine phosphorothioate
modified_base       3
                    mod_base = OTHER
                    note = 2'-O-methylguanosine
modified_base       4
                    mod_base = OTHER
                    note = 2'-O-methylcytidine
modified_base       5
                    mod_base = OTHER
                    note = 2'-O-methylcytidine
modified_base       6
                    mod_base = OTHER
```

```
                       note = 2'-O-methyladenosine
modified_base          7
                       mod_base = OTHER
                       note = 2'-fluorocytidine
modified_base          8
                       mod_base = OTHER
                       note = 2'-fluorocytidine
modified_base          9
                       mod_base = OTHER
                       note = 2'-fluoroadenosine
modified_base          10
                       mod_base = OTHER
                       note = 2'-O-methylguanosine
modified_base          11
                       mod_base = OTHER
                       note = 2'-O-methyladenosine
modified_base          12
                       mod_base = OTHER
                       note = 2'-O-methylguanosine
modified_base          13
                       mod_base = OTHER
                       note = 2'-O-methyladenosine
modified_base          14
                       mod_base = OTHER
                       note = 2'-O-methyladenosine
modified_base          15
                       mod_base = OTHER
                       note = 2'-O-methylcytidine
modified_base          16
                       mod_base = OTHER
                       note = 2'-O-methylguanosine
modified_base          17
                       mod_base = OTHER
                       note = 2'-O-methylguanosine phosphorothioate
modified_base          18
                       mod_base = OTHER
                       note = 2'-O-methylcytidine phosphorothioate
modified_base          19
                       mod_base = OTHER
                       note = 2'-O-methyladenosine
SEQUENCE: 154
tcgccaccag agaacggca                                                       19

SEQ ID NO: 155         moltype = RNA   length = 19
FEATURE                Location/Qualifiers
source                 1..19
                       mol_type = other RNA
                       organism = synthetic construct
modified_base          1
                       mod_base = OTHER
                       note = 2'-O-methylcytidine phosphorothioate
modified_base          2
                       mod_base = OTHER
                       note = 2'-O-methyladenosine phosphorothioate
modified_base          3
                       mod_base = OTHER
                       note = 2'-O-methylguanosine
modified_base          4
                       mod_base = OTHER
                       note = 2'-O-methylguanosine
modified_base          5
                       mod_base = OTHER
                       note = 2'-O-methylcytidine
modified_base          6
                       mod_base = OTHER
                       note = 2'-O-methylcytidine
modified_base          7
                       mod_base = OTHER
                       note = 2'-fluoroadenosine
modified_base          8
                       mod_base = OTHER
                       note = 2'-fluorouridine
modified_base          9
                       mod_base = OTHER
                       note = 2'-fluorocytidine
modified_base          10
                       mod_base = OTHER
                       note = 2'-O-methylguanosine
modified_base          11
```

|  |  |
|---|---|
|  | mod_base = OTHER |
|  | note = 2'-O-methylguanosine |
| modified_base | 12 |
|  | mod_base = OTHER |
|  | note = 2'-O-methylcytidine |
| modified_base | 13 |
|  | mod_base = OTHER |
|  | note = 2'-O-methyladenosine |
| modified_base | 14 |
|  | mod_base = OTHER |
|  | note = 2'-O-methyluridine |
| modified_base | 15 |
|  | mod_base = OTHER |
|  | note = 2'-O-methyluridine |
| modified_base | 16 |
|  | mod_base = OTHER |
|  | note = 2'-O-methylcytidine |
| modified_base | 17 |
|  | mod_base = OTHER |
|  | note = 2'-O-methylcytidine phosphorothioate |
| modified_base | 18 |
|  | mod_base = OTHER |
|  | note = 2'-O-methylguanosine phosphorothioate |
| modified_base | 19 |
|  | mod_base = OTHER |
|  | note = 2'-O-methyladenosine |

SEQUENCE: 155
caggccatcg gcattccga                                                19

| SEQ ID NO: 156 | moltype = RNA   length = 19 |
|---|---|
| FEATURE | Location/Qualifiers |
| source | 1..19 |
|  | mol_type = other RNA |
|  | organism = synthetic construct |
| modified_base | 1 |
|  | mod_base = OTHER |
|  | note = 2'-O-methylguanosine phosphorothioate |
| modified_base | 2 |
|  | mod_base = OTHER |
|  | note = 2'-O-methylguanosine phosphorothioate |
| modified_base | 3 |
|  | mod_base = OTHER |
|  | note = 2'-O-methylcytidine |
| modified_base | 4 |
|  | mod_base = OTHER |
|  | note = 2'-O-methylcytidine |
| modified_base | 5 |
|  | mod_base = OTHER |
|  | note = 2'-O-methyladenosine |
| modified_base | 6 |
|  | mod_base = OTHER |
|  | note = 2'-O-methyluridine |
| modified_base | 7 |
|  | mod_base = OTHER |
|  | note = 2'-fluorocytidine |
| modified_base | 8 |
|  | mod_base = OTHER |
|  | note = 2'-fluoroguanosine |
| modified_base | 9 |
|  | mod_base = OTHER |
|  | note = 2'-fluoroguanosine |
| modified_base | 10 |
|  | mod_base = OTHER |
|  | note = 2'-O-methylcytidine |
| modified_base | 11 |
|  | mod_base = OTHER |
|  | note = 2'-O-methyladenosine |
| modified_base | 12 |
|  | mod_base = OTHER |
|  | note = 2'-O-methyluridine |
| modified_base | 13 |
|  | mod_base = OTHER |
|  | note = 2'-O-methyluridine |
| modified_base | 14 |
|  | mod_base = OTHER |
|  | note = 2'-O-methylcytidine |
| modified_base | 15 |
|  | mod_base = OTHER |
|  | note = 2'-O-methylcytidine |

| | | |
|---|---|---|
| modified_base | 16 | |
| | mod_base = OTHER | |
| | note = 2'-O-methylguanosine | |
| modified_base | 17 | |
| | mod_base = OTHER | |
| | note = 2'-O-methylguanosine phosphorothioate | |
| modified_base | 18 | |
| | mod_base = OTHER | |
| | note = 2'-O-methyladenosine phosphorothioate | |
| modified_base | 19 | |
| | mod_base = OTHER | |
| | note = 2'-O-methyladenosine | |
| SEQUENCE: 156 | | |
| ggccatcggc attccggaa | | 19 |
| SEQ ID NO: 157 | moltype = RNA length = 19 | |
| FEATURE | Location/Qualifiers | |
| source | 1..19 | |
| | mol_type = other RNA | |
| | organism = synthetic construct | |
| modified_base | 1 | |
| | mod_base = OTHER | |
| | note = 2'-O-methylguanosine phosphorothioate | |
| modified_base | 2 | |
| | mod_base = OTHER | |
| | note = 2'-O-methylcytidine phosphorothioate | |
| modified_base | 3 | |
| | mod_base = OTHER | |
| | note = 2'-O-methylcytidine | |
| modified_base | 4 | |
| | mod_base = OTHER | |
| | note = 2'-O-methyladenosine | |
| modified_base | 5 | |
| | mod_base = OTHER | |
| | note = 2'-O-methyluridine | |
| modified_base | 6 | |
| | mod_base = OTHER | |
| | note = 2'-O-methylcytidine | |
| modified_base | 7 | |
| | mod_base = OTHER | |
| | note = 2'-fluoroguanosine | |
| modified_base | 8 | |
| | mod_base = OTHER | |
| | note = 2'-fluoroguanosine | |
| modified_base | 9 | |
| | mod_base = OTHER | |
| | note = 2'-fluorocytidine | |
| modified_base | 10 | |
| | mod_base = OTHER | |
| | note = 2'-O-methyladenosine | |
| modified_base | 11 | |
| | mod_base = OTHER | |
| | note = 2'-O-methyluridine | |
| modified_base | 12 | |
| | mod_base = OTHER | |
| | note = 2'-O-methyluridine | |
| modified_base | 13 | |
| | mod_base = OTHER | |
| | note = 2'-O-methylcytidine | |
| modified_base | 14 | |
| | mod_base = OTHER | |
| | note = 2'-O-methylcytidine | |
| modified_base | 15 | |
| | mod_base = OTHER | |
| | note = 2'-O-methylguanosine | |
| modified_base | 16 | |
| | mod_base = OTHER | |
| | note = 2'-O-methylguanosine | |
| modified_base | 17 | |
| | mod_base = OTHER | |
| | note = 2'-O-methyladenosine phosphorothioate | |
| modified_base | 18 | |
| | mod_base = OTHER | |
| | note = 2'-O-methylguanosine phosphorothioate | |
| modified_base | 19 | |
| | mod_base = OTHER | |
| | note = 2'-O-methyladenosine | |
| SEQUENCE: 157 | | |
| gccatcggca ttccggaga | | 19 |

```
SEQ ID NO: 158         moltype = RNA   length = 19
FEATURE                Location/Qualifiers
source                 1..19
                       mol_type = other RNA
                       organism = synthetic construct
modified_base          1
                       mod_base = OTHER
                       note = 2'-O-methylguanosine phosphorothioate
modified_base          2
                       mod_base = OTHER
                       note = 2'-O-methylcytidine phosphorothioate
modified_base          3
                       mod_base = OTHER
                       note = 2'-O-methyladenosine
modified_base          4
                       mod_base = OTHER
                       note = 2'-O-methylcytidine
modified_base          5
                       mod_base = OTHER
                       note = 2'-O-methylcytidine
modified_base          6
                       mod_base = OTHER
                       note = 2'-O-methylguanosine
modified_base          7
                       mod_base = OTHER
                       note = 2'-fluoroguanosine
modified_base          8
                       mod_base = OTHER
                       note = 2'-fluorocytidine
modified_base          9
                       mod_base = OTHER
                       note = 2'-fluoroguanosine
modified_base          10
                       mod_base = OTHER
                       note = 2'-O-methylguanosine
modified_base          11
                       mod_base = OTHER
                       note = 2'-O-methylguanosine
modified_base          12
                       mod_base = OTHER
                       note = 2'-O-methyladenosine
modified_base          13
                       mod_base = OTHER
                       note = 2'-O-methyladenosine
modified_base          14
                       mod_base = OTHER
                       note = 2'-O-methyluridine
modified_base          15
                       mod_base = OTHER
                       note = 2'-O-methylcytidine
modified_base          16
                       mod_base = OTHER
                       note = 2'-O-methyluridine
modified_base          17
                       mod_base = OTHER
                       note = 2'-O-methylcytidine phosphorothioate
modified_base          18
                       mod_base = OTHER
                       note = 2'-O-methylguanosine phosphorothioate
modified_base          19
                       mod_base = OTHER
                       note = 2'-O-methyladenosine
SEQUENCE: 158
gcaccggcgg gaatctcga                                                      19

SEQ ID NO: 159         moltype = RNA   length = 19
FEATURE                Location/Qualifiers
source                 1..19
                       mol_type = other RNA
                       organism = synthetic construct
modified_base          1
                       mod_base = OTHER
                       note = 2'-O-methylcytidine phosphorothioate
modified_base          2
                       mod_base = OTHER
                       note = 2'-O-methyladenosine phosphorothioate
modified_base          3
                       mod_base = OTHER
```

```
                        note = 2'-O-methylcytidine
modified_base           4
                        mod_base = OTHER
                        note = 2'-O-methylcytidine
modified_base           5
                        mod_base = OTHER
                        note = 2'-O-methylguanosine
modified_base           6
                        mod_base = OTHER
                        note = 2'-O-methylguanosine
modified_base           7
                        mod_base = OTHER
                        note = 2'-fluorocytidine
modified_base           8
                        mod_base = OTHER
                        note = 2'-fluoroguanosine
modified_base           9
                        mod_base = OTHER
                        note = 2'-fluoroguanosine
modified_base           10
                        mod_base = OTHER
                        note = 2'-O-methylguanosine
modified_base           11
                        mod_base = OTHER
                        note = 2'-O-methyladenosine
modified_base           12
                        mod_base = OTHER
                        note = 2'-O-methyladenosine
modified_base           13
                        mod_base = OTHER
                        note = 2'-O-methyluridine
modified_base           14
                        mod_base = OTHER
                        note = 2'-O-methylcytidine
modified_base           15
                        mod_base = OTHER
                        note = 2'-O-methyluridine
modified_base           16
                        mod_base = OTHER
                        note = 2'-O-methylcytidine
modified_base           17
                        mod_base = OTHER
                        note = 2'-O-methylguanosine phosphorothioate
modified_base           18
                        mod_base = OTHER
                        note = 2'-O-methylguanosine phosphorothioate
modified_base           19
                        mod_base = OTHER
                        note = 2'-O-methyladenosine
SEQUENCE: 159
caccggcggg aatctcgga                                                   19

SEQ ID NO: 160          moltype = RNA   length = 19
FEATURE                 Location/Qualifiers
source                  1..19
                        mol_type = other RNA
                        organism = synthetic construct
modified_base           1
                        mod_base = OTHER
                        note = 2'-O-methylcytidine phosphorothioate
modified_base           2
                        mod_base = OTHER
                        note = 2'-O-methylcytidine phosphorothioate
modified_base           3
                        mod_base = OTHER
                        note = 2'-O-methyladenosine
modified_base           4
                        mod_base = OTHER
                        note = 2'-O-methylguanosine
modified_base           5
                        mod_base = OTHER
                        note = 2'-O-methyladenosine
modified_base           6
                        mod_base = OTHER
                        note = 2'-O-methyladenosine
modified_base           7
                        mod_base = OTHER
                        note = 2'-fluoroguanosine
modified_base           8
```

```
                        mod_base = OTHER
                        note = 2'-fluoroguanosine
modified_base           9
                        mod_base = OTHER
                        note = 2'-fluorocytidine
modified_base           10
                        mod_base = OTHER
                        note = 2'-O-methylcytidine
modified_base           11
                        mod_base = OTHER
                        note = 2'-O-methylguanosine
modified_base           12
                        mod_base = OTHER
                        note = 2'-O-methylguanosine
modified_base           13
                        mod_base = OTHER
                        note = 2'-O-methylcytidine
modified_base           14
                        mod_base = OTHER
                        note = 2'-O-methylguanosine
modified_base           15
                        mod_base = OTHER
                        note = 2'-O-methyladenosine
modified_base           16
                        mod_base = OTHER
                        note = 2'-O-methyladenosine
modified_base           17
                        mod_base = OTHER
                        note = 2'-O-methyladenosine phosphorothioate
modified_base           18
                        mod_base = OTHER
                        note = 2'-O-methylguanosine phosphorothioate
modified_base           19
                        mod_base = OTHER
                        note = 2'-O-methyladenosine
SEQUENCE: 160
ccagaaggcc ggcgaaaga                                                19

SEQ ID NO: 161          moltype = RNA   length = 19
FEATURE                 Location/Qualifiers
source                  1..19
                        mol_type = other RNA
                        organism = synthetic construct
modified_base           1
                        mod_base = OTHER
                        note = 2'-O-methyladenosine phosphorothioate
modified_base           2
                        mod_base = OTHER
                        note = 2'-O-methylguanosine phosphorothioate
modified_base           3
                        mod_base = OTHER
                        note = 2'-O-methyladenosine
modified_base           4
                        mod_base = OTHER
                        note = 2'-O-methyladenosine
modified_base           5
                        mod_base = OTHER
                        note = 2'-O-methylguanosine
modified_base           6
                        mod_base = OTHER
                        note = 2'-O-methylguanosine
modified_base           7
                        mod_base = OTHER
                        note = 2'-fluorocytidine
modified_base           8
                        mod_base = OTHER
                        note = 2'-fluorocytidine
modified_base           9
                        mod_base = OTHER
                        note = 2'-fluoroguanosine
modified_base           10
                        mod_base = OTHER
                        note = 2'-O-methylguanosine
modified_base           11
                        mod_base = OTHER
                        note = 2'-O-methylcytidine
modified_base           12
                        mod_base = OTHER
                        note = 2'-O-methylguanosine
```

```
modified_base        13
                     mod_base = OTHER
                     note = 2'-O-methyladenosine
modified_base        14
                     mod_base = OTHER
                     note = 2'-O-methyladenosine
modified_base        15
                     mod_base = OTHER
                     note = 2'-O-methyladenosine
modified_base        16
                     mod_base = OTHER
                     note = 2'-O-methylguanosine
modified_base        17
                     mod_base = OTHER
                     note = 2'-O-methylcytidine phosphorothioate
modified_base        18
                     mod_base = OTHER
                     note = 2'-O-methylguanosine phosphorothioate
modified_base        19
                     mod_base = OTHER
                     note = 2'-O-methyladenosine
SEQUENCE: 161
agaaggccgg cgaaagcga                                                       19

SEQ ID NO: 162       moltype = RNA   length = 19
FEATURE              Location/Qualifiers
source               1..19
                     mol_type = other RNA
                     organism = synthetic construct
modified_base        1
                     mod_base = OTHER
                     note = 2'-O-methylguanosine phosphorothioate
modified_base        2
                     mod_base = OTHER
                     note = 2'-O-methyladenosine phosphorothioate
modified_base        3
                     mod_base = OTHER
                     note = 2'-O-methyladenosine
modified_base        4
                     mod_base = OTHER
                     note = 2'-O-methylguanosine
modified_base        5
                     mod_base = OTHER
                     note = 2'-O-methylguanosine
modified_base        6
                     mod_base = OTHER
                     note = 2'-O-methylcytidine
modified_base        7
                     mod_base = OTHER
                     note = 2'-fluorocytidine
modified_base        8
                     mod_base = OTHER
                     note = 2'-fluoroguanosine
modified_base        9
                     mod_base = OTHER
                     note = 2'-fluoroguanosine
modified_base        10
                     mod_base = OTHER
                     note = 2'-O-methylcytidine
modified_base        11
                     mod_base = OTHER
                     note = 2'-O-methylguanosine
modified_base        12
                     mod_base = OTHER
                     note = 2'-O-methyladenosine
modified_base        13
                     mod_base = OTHER
                     note = 2'-O-methyladenosine
modified_base        14
                     mod_base = OTHER
                     note = 2'-O-methyladenosine
modified_base        15
                     mod_base = OTHER
                     note = 2'-O-methylguanosine
modified_base        16
                     mod_base = OTHER
                     note = 2'-O-methylcytidine
modified_base        17
                     mod_base = OTHER
```

```
                      note = 2'-O-methylguanosine phosphorothioate
modified_base         18
                      mod_base = OTHER
                      note = 2'-O-methylguanosine phosphorothioate
modified_base         19
                      mod_base = OTHER
                      note = 2'-O-methyladenosine
SEQUENCE: 162
gaaggccggc gaaagcgga                                                    19

SEQ ID NO: 163        moltype = RNA  length = 19
FEATURE               Location/Qualifiers
source                1..19
                      mol_type = other RNA
                      organism = synthetic construct
modified_base         1
                      mod_base = OTHER
                      note = 2'-O-methylguanosine phosphorothioate
modified_base         2
                      mod_base = OTHER
                      note = 2'-O-methylcytidine phosphorothioate
modified_base         3
                      mod_base = OTHER
                      note = 2'-O-methylguanosine
modified_base         4
                      mod_base = OTHER
                      note = 2'-O-methyladenosine
modified_base         5
                      mod_base = OTHER
                      note = 2'-O-methyladenosine
modified_base         6
                      mod_base = OTHER
                      note = 2'-O-methyladenosine
modified_base         7
                      mod_base = OTHER
                      note = 2'-fluoroguanosine
modified_base         8
                      mod_base = OTHER
                      note = 2'-fluorocytidine
modified_base         9
                      mod_base = OTHER
                      note = 2'-fluoroguanosine
modified_base         10
                      mod_base = OTHER
                      note = 2'-O-methylguanosine
modified_base         11
                      mod_base = OTHER
                      note = 2'-O-methyladenosine
modified_base         12
                      mod_base = OTHER
                      note = 2'-O-methylcytidine
modified_base         13
                      mod_base = OTHER
                      note = 2'-O-methylcytidine
modified_base         14
                      mod_base = OTHER
                      note = 2'-O-methylguanosine
modified_base         15
                      mod_base = OTHER
                      note = 2'-O-methylcytidine
modified_base         16
                      mod_base = OTHER
                      note = 2'-O-methylcytidine
modified_base         17
                      mod_base = OTHER
                      note = 2'-O-methylguanosine phosphorothioate
modified_base         18
                      mod_base = OTHER
                      note = 2'-O-methyluridine phosphorothioate
modified_base         19
                      mod_base = OTHER
                      note = 2'-O-methyladenosine
SEQUENCE: 163
gcgaaagcgg accgccgta                                                    19

SEQ ID NO: 164        moltype = RNA  length = 19
FEATURE               Location/Qualifiers
source                1..19
                      mol_type = other RNA
```

```
                        organism = synthetic construct
modified_base           1
                        mod_base = OTHER
                        note = 2'-O-methylguanosine phosphorothioate
modified_base           2
                        mod_base = OTHER
                        note = 2'-O-methyladenosine phosphorothioate
modified_base           3
                        mod_base = OTHER
                        note = 2'-O-methyladenosine
modified_base           4
                        mod_base = OTHER
                        note = 2'-O-methyladenosine
modified_base           5
                        mod_base = OTHER
                        note = 2'-O-methylguanosine
modified_base           6
                        mod_base = OTHER
                        note = 2'-O-methylcytidine
modified_base           7
                        mod_base = OTHER
                        note = 2'-fluoroguanosine
modified_base           8
                        mod_base = OTHER
                        note = 2'-fluoroguanosine
modified_base           9
                        mod_base = OTHER
                        note = 2'-fluoroadenosine
modified_base           10
                        mod_base = OTHER
                        note = 2'-O-methylcytidine
modified_base           11
                        mod_base = OTHER
                        note = 2'-O-methylcytidine
modified_base           12
                        mod_base = OTHER
                        note = 2'-O-methylguanosine
modified_base           13
                        mod_base = OTHER
                        note = 2'-O-methylcytidine
modified_base           14
                        mod_base = OTHER
                        note = 2'-O-methylcytidine
modified_base           15
                        mod_base = OTHER
                        note = 2'-O-methylguanosine
modified_base           16
                        mod_base = OTHER
                        note = 2'-O-methyluridine
modified_base           17
                        mod_base = OTHER
                        note = 2'-O-methylcytidine phosphorothioate
modified_base           18
                        mod_base = OTHER
                        note = 2'-O-methyladenosine phosphorothioate
modified_base           19
                        mod_base = OTHER
                        note = 2'-O-methyladenosine
SEQUENCE: 164
gaaagcggac cgccgtcaa                                              19

SEQ ID NO: 165          moltype = RNA   length = 19
FEATURE                 Location/Qualifiers
source                  1..19
                        mol_type = other RNA
                        organism = synthetic construct
modified_base           1
                        mod_base = OTHER
                        note = 2'-O-methylcytidine phosphorothioate
modified_base           2
                        mod_base = OTHER
                        note = 2'-O-methylguanosine phosphorothioate
modified_base           3
                        mod_base = OTHER
                        note = 2'-O-methylguanosine
modified_base           4
                        mod_base = OTHER
                        note = 2'-O-methyladenosine
modified_base           5
```

|  |  |
|---|---|
|  | mod_base = OTHER |
|  | note = 2'-O-methylcytidine |
| modified_base | 6 |
|  | mod_base = OTHER |
|  | note = 2'-O-methylcytidine |
| modified_base | 7 |
|  | mod_base = OTHER |
|  | note = 2'-fluoroguanosine |
| modified_base | 8 |
|  | mod_base = OTHER |
|  | note = 2'-fluorocytidine |
| modified_base | 9 |
|  | mod_base = OTHER |
|  | note = 2'-fluorocytidine |
| modified_base | 10 |
|  | mod_base = OTHER |
|  | note = 2'-O-methylguanosine |
| modified_base | 11 |
|  | mod_base = OTHER |
|  | note = 2'-O-methyluridine |
| modified_base | 12 |
|  | mod_base = OTHER |
|  | note = 2'-O-methylcytidine |
| modified_base | 13 |
|  | mod_base = OTHER |
|  | note = 2'-O-methyladenosine |
| modified_base | 14 |
|  | mod_base = OTHER |
|  | note = 2'-O-methylcytidine |
| modified_base | 15 |
|  | mod_base = OTHER |
|  | note = 2'-O-methylcytidine |
| modified_base | 16 |
|  | mod_base = OTHER |
|  | note = 2'-O-methylguanosine |
| modified_base | 17 |
|  | mod_base = OTHER |
|  | note = 2'-O-methylguanosine phosphorothioate |
| modified_base | 18 |
|  | mod_base = OTHER |
|  | note = 2'-O-methyladenosine phosphorothioate |
| modified_base | 19 |
|  | mod_base = OTHER |
|  | note = 2'-O-methyladenosine |

SEQUENCE: 165
cggaccgccg tcaccggaa                                             19

| SEQ ID NO: 166 | moltype = RNA  length = 19 |
|---|---|
| FEATURE | Location/Qualifiers |
| source | 1..19 |
|  | mol_type = other RNA |
|  | organism = synthetic construct |
| modified_base | 1 |
|  | mod_base = OTHER |
|  | note = 2'-O-methylguanosine phosphorothioate |
| modified_base | 2 |
|  | mod_base = OTHER |
|  | note = 2'-O-methylguanosine phosphorothioate |
| modified_base | 3 |
|  | mod_base = OTHER |
|  | note = 2'-O-methyladenosine |
| modified_base | 4 |
|  | mod_base = OTHER |
|  | note = 2'-O-methylcytidine |
| modified_base | 5 |
|  | mod_base = OTHER |
|  | note = 2'-O-methylcytidine |
| modified_base | 6 |
|  | mod_base = OTHER |
|  | note = 2'-O-methylguanosine |
| modified_base | 7 |
|  | mod_base = OTHER |
|  | note = 2'-fluorocytidine |
| modified_base | 8 |
|  | mod_base = OTHER |
|  | note = 2'-fluorocytidine |
| modified_base | 9 |
|  | mod_base = OTHER |
|  | note = 2'-fluoroguanosine |

| | |
|---|---|
| modified_base | 10<br>mod_base = OTHER<br>note = 2'-O-methyluridine |
| modified_base | 11<br>mod_base = OTHER<br>note = 2'-O-methylcytidine |
| modified_base | 12<br>mod_base = OTHER<br>note = 2'-O-methyladenosine |
| modified_base | 13<br>mod_base = OTHER<br>note = 2'-O-methylcytidine |
| modified_base | 14<br>mod_base = OTHER<br>note = 2'-O-methylcytidine |
| modified_base | 15<br>mod_base = OTHER<br>note = 2'-O-methylguanosine |
| modified_base | 16<br>mod_base = OTHER<br>note = 2'-O-methylguanosine |
| modified_base | 17<br>mod_base = OTHER<br>note = 2'-O-methyladenosine phosphorothioate |
| modified_base | 18<br>mod_base = OTHER<br>note = 2'-O-methyluridine phosphorothioate |
| modified_base | 19<br>mod_base = OTHER<br>note = 2'-O-methyladenosine |
| SEQUENCE: 166 | |
| ggaccgccgt caccggata | 19 |
| SEQ ID NO: 167<br>FEATURE<br>source | moltype = RNA length = 19<br>Location/Qualifiers<br>1..19<br>mol_type = other RNA<br>organism = synthetic construct |
| modified_base | 1<br>mod_base = OTHER<br>note = 2'-O-methylguanosine phosphorothioate |
| modified_base | 2<br>mod_base = OTHER<br>note = 2'-O-methyladenosine phosphorothioate |
| modified_base | 3<br>mod_base = OTHER<br>note = 2'-O-methylcytidine |
| modified_base | 4<br>mod_base = OTHER<br>note = 2'-O-methylcytidine |
| modified_base | 5<br>mod_base = OTHER<br>note = 2'-O-methylguanosine |
| modified_base | 6<br>mod_base = OTHER<br>note = 2'-O-methylcytidine |
| modified_base | 7<br>mod_base = OTHER<br>note = 2'-fluorocytidine |
| modified_base | 8<br>mod_base = OTHER<br>note = 2'-fluoroguanosine |
| modified_base | 9<br>mod_base = OTHER<br>note = 2'-fluorouridine |
| modified_base | 10<br>mod_base = OTHER<br>note = 2'-O-methylcytidine |
| modified_base | 11<br>mod_base = OTHER<br>note = 2'-O-methyladenosine |
| modified_base | 12<br>mod_base = OTHER<br>note = 2'-O-methylcytidine |
| modified_base | 13<br>mod_base = OTHER<br>note = 2'-O-methylcytidine |
| modified_base | 14<br>mod_base = OTHER |

|  |  |
|---|---|
|  | note = 2'-O-methylguanosine |
| modified_base | 15 |
|  | mod_base = OTHER |
|  | note = 2'-O-methylguanosine |
| modified_base | 16 |
|  | mod_base = OTHER |
|  | note = 2'-O-methyladenosine |
| modified_base | 17 |
|  | mod_base = OTHER |
|  | note = 2'-O-methyluridine phosphorothioate |
| modified_base | 18 |
|  | mod_base = OTHER |
|  | note = 2'-O-methylcytidine phosphorothioate |
| modified_base | 19 |
|  | mod_base = OTHER |
|  | note = 2'-O-methyladenosine |
| SEQUENCE: 167 |  |
| gaccgccgtc accggatca | 19 |
| SEQ ID NO: 168 | moltype = RNA  length = 19 |
| FEATURE | Location/Qualifiers |
| source | 1..19 |
|  | mol_type = other RNA |
|  | organism = synthetic construct |
| modified_base | 1 |
|  | mod_base = OTHER |
|  | note = 2'-O-methyladenosine phosphorothioate |
| modified_base | 2 |
|  | mod_base = OTHER |
|  | note = 2'-O-methylguanosine phosphorothioate |
| modified_base | 3 |
|  | mod_base = OTHER |
|  | note = 2'-O-methyladenosine |
| modified_base | 4 |
|  | mod_base = OTHER |
|  | note = 2'-O-methylcytidine |
| modified_base | 5 |
|  | mod_base = OTHER |
|  | note = 2'-O-methylguanosine |
| modified_base | 6 |
|  | mod_base = OTHER |
|  | note = 2'-O-methylguanosine |
| modified_base | 7 |
|  | mod_base = OTHER |
|  | note = 2'-fluoroguanosine |
| modified_base | 8 |
|  | mod_base = OTHER |
|  | note = 2'-fluorocytidine |
| modified_base | 9 |
|  | mod_base = OTHER |
|  | note = 2'-fluorocytidine |
| modified_base | 10 |
|  | mod_base = OTHER |
|  | note = 2'-O-methyluridine |
| modified_base | 11 |
|  | mod_base = OTHER |
|  | note = 2'-O-methylcytidine |
| modified_base | 12 |
|  | mod_base = OTHER |
|  | note = 2'-O-methylcytidine |
| modified_base | 13 |
|  | mod_base = OTHER |
|  | note = 2'-O-methylcytidine |
| modified_base | 14 |
|  | mod_base = OTHER |
|  | note = 2'-O-methylguanosine |
| modified_base | 15 |
|  | mod_base = OTHER |
|  | note = 2'-O-methylguanosine |
| modified_base | 16 |
|  | mod_base = OTHER |
|  | note = 2'-O-methyladenosine |
| modified_base | 17 |
|  | mod_base = OTHER |
|  | note = 2'-O-methylguanosine phosphorothioate |
| modified_base | 18 |
|  | mod_base = OTHER |
|  | note = 2'-O-methyluridine phosphorothioate |
| modified_base | 19 | mod_base = OTHER
                        note = 2'-O-methyladenosine
SEQUENCE: 168
agacgggcct cccggagta                                                       19

SEQ ID NO: 169          moltype = RNA   length = 19
FEATURE                 Location/Qualifiers
source                  1..19
                        mol_type = other RNA
                        organism = synthetic construct
modified_base           1
                        mod_base = OTHER
                        note = 2'-O-methylcytidine phosphorothioate
modified_base           2
                        mod_base = OTHER
                        note = 2'-O-methylcytidine phosphorothioate
modified_base           3
                        mod_base = OTHER
                        note = 2'-O-methyluridine
modified_base           4
                        mod_base = OTHER
                        note = 2'-O-methylcytidine
modified_base           5
                        mod_base = OTHER
                        note = 2'-O-methylguanosine
modified_base           6
                        mod_base = OTHER
                        note = 2'-O-methyluridine
modified_base           7
                        mod_base = OTHER
                        note = 2'-fluoroguanosine
modified_base           8
                        mod_base = OTHER
                        note = 2'-fluoroguanosine
modified_base           9
                        mod_base = OTHER
                        note = 2'-fluoroguanosine
modified_base           10
                        mod_base = OTHER
                        note = 2'-O-methyluridine
modified_base           11
                        mod_base = OTHER
                        note = 2'-O-methylcytidine
modified_base           12
                        mod_base = OTHER
                        note = 2'-O-methylguanosine
modified_base           13
                        mod_base = OTHER
                        note = 2'-O-methylcytidine
modified_base           14
                        mod_base = OTHER
                        note = 2'-O-methylcytidine
modified_base           15
                        mod_base = OTHER
                        note = 2'-O-methyluridine
modified_base           16
                        mod_base = OTHER
                        note = 2'-O-methyluridine
modified_base           17
                        mod_base = OTHER
                        note = 2'-O-methylcytidine phosphorothioate
modified_base           18
                        mod_base = OTHER
                        note = 2'-O-methylguanosine phosphorothioate
modified_base           19
                        mod_base = OTHER
                        note = 2'-O-methyladenosine
SEQUENCE: 169
cctcgtgggt cgccttcga                                                       19

SEQ ID NO: 170          moltype = RNA   length = 19
FEATURE                 Location/Qualifiers
source                  1..19
                        mol_type = other RNA
                        organism = synthetic construct
modified_base           1
                        mod_base = OTHER
                        note = 2'-O-methylcytidine phosphorothioate
modified_base           2

|              |                                                                                  |
|--------------|----------------------------------------------------------------------------------|
|              | mod_base = OTHER<br>note = 2'-O-methyluridine phosphorothioate                   |
| modified_base | 3<br>mod_base = OTHER<br>note = 2'-O-methylcytidine                             |
| modified_base | 4<br>mod_base = OTHER<br>note = 2'-O-methylguanosine                            |
| modified_base | 5<br>mod_base = OTHER<br>note = 2'-O-methyluridine                              |
| modified_base | 6<br>mod_base = OTHER<br>note = 2'-O-methylguanosine                            |
| modified_base | 7<br>mod_base = OTHER<br>note = 2'-fluoroguanosine                              |
| modified_base | 8<br>mod_base = OTHER<br>note = 2'-fluoroguanosine                              |
| modified_base | 9<br>mod_base = OTHER<br>note = 2'-fluorouridine                                |
| modified_base | 10<br>mod_base = OTHER<br>note = 2'-O-methylcytidine                            |
| modified_base | 11<br>mod_base = OTHER<br>note = 2'-O-methylguanosine                           |
| modified_base | 12<br>mod_base = OTHER<br>note = 2'-O-methylcytidine                            |
| modified_base | 13<br>mod_base = OTHER<br>note = 2'-O-methylcytidine                            |
| modified_base | 14<br>mod_base = OTHER<br>note = 2'-O-methyluridine                             |
| modified_base | 15<br>mod_base = OTHER<br>note = 2'-O-methyluridine                             |
| modified_base | 16<br>mod_base = OTHER<br>note = 2'-O-methylcytidine                            |
| modified_base | 17<br>mod_base = OTHER<br>note = 2'-O-methylguanosine phosphorothioate          |
| modified_base | 18<br>mod_base = OTHER<br>note = 2'-O-methylcytidine phosphorothioate           |
| modified_base | 19<br>mod_base = OTHER<br>note = 2'-O-methyladenosine                           |

SEQUENCE: 170
ctcgtgggtc gccttcgca                                                              19

| SEQ ID NO: 171 | moltype = RNA  length = 19                                                    |
|----------------|-------------------------------------------------------------------------------|
| FEATURE        | Location/Qualifiers                                                           |
| source         | 1..19<br>mol_type = other RNA<br>organism = synthetic construct               |
| modified_base  | 1<br>mod_base = OTHER<br>note = 2'-O-methylguanosine phosphorothioate         |
| modified_base  | 2<br>mod_base = OTHER<br>note = 2'-O-methyladenosine phosphorothioate         |
| modified_base  | 3<br>mod_base = OTHER<br>note = 2'-O-methylguanosine                          |
| modified_base  | 4<br>mod_base = OTHER<br>note = 2'-O-methylguanosine                          |
| modified_base  | 5<br>mod_base = OTHER<br>note = 2'-O-methylguanosine                          |
| modified_base  | 6<br>mod_base = OTHER<br>note = 2'-O-methylguanosine                          |

```
modified_base       7
                    mod_base = OTHER
                    note = 2'-fluoroadenosine
modified_base       8
                    mod_base = OTHER
                    note = 2'-fluorouridine
modified_base       9
                    mod_base = OTHER
                    note = 2'-fluorocytidine
modified_base       10
                    mod_base = OTHER
                    note = 2'-O-methyluridine
modified_base       11
                    mod_base = OTHER
                    note = 2'-O-methylcytidine
modified_base       12
                    mod_base = OTHER
                    note = 2'-O-methylcytidine
modified_base       13
                    mod_base = OTHER
                    note = 2'-O-methylcytidine
modified_base       14
                    mod_base = OTHER
                    note = 2'-O-methyladenosine
modified_base       15
                    mod_base = OTHER
                    note = 2'-O-methyladenosine
modified_base       16
                    mod_base = OTHER
                    note = 2'-O-methylcytidine
modified_base       17
                    mod_base = OTHER
                    note = 2'-O-methylcytidine phosphorothioate
modified_base       18
                    mod_base = OTHER
                    note = 2'-O-methyluridine phosphorothioate
modified_base       19
                    mod_base = OTHER
                    note = 2'-O-methyladenosine
SEQUENCE: 171
gaggggatct cccaaccta                                                        19

SEQ ID NO: 172      moltype = RNA   length = 19
FEATURE             Location/Qualifiers
source              1..19
                    mol_type = other RNA
                    organism = synthetic construct
modified_base       1
                    mod_base = OTHER
                    note = 2'-O-methylcytidine phosphorothioate
modified_base       2
                    mod_base = OTHER
                    note = 2'-O-methylguanosine phosphorothioate
modified_base       3
                    mod_base = OTHER
                    note = 2'-O-methylcytidine
modified_base       4
                    mod_base = OTHER
                    note = 2'-O-methylguanosine
modified_base       5
                    mod_base = OTHER
                    note = 2'-O-methylcytidine
modified_base       6
                    mod_base = OTHER
                    note = 2'-O-methylguanosine
modified_base       7
                    mod_base = OTHER
                    note = 2'-fluoroguanosine
modified_base       8
                    mod_base = OTHER
                    note = 2'-fluoroguanosine
modified_base       9
                    mod_base = OTHER
                    note = 2'-fluoroguanosine
modified_base       10
                    mod_base = OTHER
                    note = 2'-O-methyladenosine
modified_base       11
                    mod_base = OTHER
```

```
                          note = 2'-O-methyluridine
modified_base             12
                          mod_base = OTHER
                          note = 2'-O-methyluridine
modified_base             13
                          mod_base = OTHER
                          note = 2'-O-methyluridine
modified_base             14
                          mod_base = OTHER
                          note = 2'-O-methylcytidine
modified_base             15
                          mod_base = OTHER
                          note = 2'-O-methylguanosine
modified_base             16
                          mod_base = OTHER
                          note = 2'-O-methylcytidine
modified_base             17
                          mod_base = OTHER
                          note = 2'-O-methylcytidine phosphorothioate
modified_base             18
                          mod_base = OTHER
                          note = 2'-O-methyluridine phosphorothioate
modified_base             19
                          mod_base = OTHER
                          note = 2'-O-methyladenosine
SEQUENCE: 172
cgcgcgggga tttcgccta                                                    19

SEQ ID NO: 173            moltype = RNA   length = 19
FEATURE                   Location/Qualifiers
source                    1..19
                          mol_type = other RNA
                          organism = synthetic construct
modified_base             1
                          mod_base = OTHER
                          note = 2'-O-methylguanosine phosphorothioate
modified_base             2
                          mod_base = OTHER
                          note = 2'-O-methylcytidine phosphorothioate
modified_base             3
                          mod_base = OTHER
                          note = 2'-O-methylguanosine
modified_base             4
                          mod_base = OTHER
                          note = 2'-O-methylcytidine
modified_base             5
                          mod_base = OTHER
                          note = 2'-O-methylguanosine
modified_base             6
                          mod_base = OTHER
                          note = 2'-O-methylguanosine
modified_base             7
                          mod_base = OTHER
                          note = 2'-fluoroguanosine
modified_base             8
                          mod_base = OTHER
                          note = 2'-fluoroguanosine
modified_base             9
                          mod_base = OTHER
                          note = 2'-fluoroadenosine
modified_base             10
                          mod_base = OTHER
                          note = 2'-O-methyluridine
modified_base             11
                          mod_base = OTHER
                          note = 2'-O-methyluridine
modified_base             12
                          mod_base = OTHER
                          note = 2'-O-methyluridine
modified_base             13
                          mod_base = OTHER
                          note = 2'-O-methylcytidine
modified_base             14
                          mod_base = OTHER
                          note = 2'-O-methylguanosine
modified_base             15
                          mod_base = OTHER
                          note = 2'-O-methylcytidine
modified_base             16
```

|  |  |
|---|---|
|  | mod_base = OTHER |
|  | note = 2'-O-methylcytidine |
| modified_base | 17 |
|  | mod_base = OTHER |
|  | note = 2'-O-methyluridine phosphorothioate |
| modified_base | 18 |
|  | mod_base = OTHER |
|  | note = 2'-O-methyladenosine phosphorothioate |
| modified_base | 19 |
|  | mod_base = OTHER |
|  | note = 2'-O-methyladenosine |

SEQUENCE: 173  
gcgcggggat ttcgcctaa                                                              19

| SEQ ID NO: 174 | moltype = RNA  length = 19 |
|---|---|
| FEATURE | Location/Qualifiers |
| source | 1..19 |
|  | mol_type = other RNA |
|  | organism = synthetic construct |
| modified_base | 1 |
|  | mod_base = OTHER |
|  | note = 2'-O-methylcytidine phosphorothioate |
| modified_base | 2 |
|  | mod_base = OTHER |
|  | note = 2'-O-methylguanosine phosphorothioate |
| modified_base | 3 |
|  | mod_base = OTHER |
|  | note = 2'-O-methylguanosine |
| modified_base | 4 |
|  | mod_base = OTHER |
|  | note = 2'-O-methylguanosine |
| modified_base | 5 |
|  | mod_base = OTHER |
|  | note = 2'-O-methylguanosine |
| modified_base | 6 |
|  | mod_base = OTHER |
|  | note = 2'-O-methyladenosine |
| modified_base | 7 |
|  | mod_base = OTHER |
|  | note = 2'-fluorouridine |
| modified_base | 8 |
|  | mod_base = OTHER |
|  | note = 2'-fluorouridine |
| modified_base | 9 |
|  | mod_base = OTHER |
|  | note = 2'-fluorouridine |
| modified_base | 10 |
|  | mod_base = OTHER |
|  | note = 2'-O-methylcytidine |
| modified_base | 11 |
|  | mod_base = OTHER |
|  | note = 2'-O-methylguanosine |
| modified_base | 12 |
|  | mod_base = OTHER |
|  | note = 2'-O-methylcytidine |
| modified_base | 13 |
|  | mod_base = OTHER |
|  | note = 2'-O-methylcytidine |
| modified_base | 14 |
|  | mod_base = OTHER |
|  | note = 2'-O-methyluridine |
| modified_base | 15 |
|  | mod_base = OTHER |
|  | note = 2'-O-methyladenosine |
| modified_base | 16 |
|  | mod_base = OTHER |
|  | note = 2'-O-methylcytidine |
| modified_base | 17 |
|  | mod_base = OTHER |
|  | note = 2'-O-methylguanosine phosphorothioate |
| modified_base | 18 |
|  | mod_base = OTHER |
|  | note = 2'-O-methylcytidine phosphorothioate |
| modified_base | 19 |
|  | mod_base = OTHER |
|  | note = 2'-O-methyladenosine |

SEQUENCE: 174  
cggggatttc gcctacgca                                                              19

```
SEQ ID NO: 175          moltype = RNA  length = 19
FEATURE                 Location/Qualifiers
source                  1..19
                        mol_type = other RNA
                        organism = synthetic construct
modified_base           1
                        mod_base = OTHER
                        note = 2'-O-methyluridine phosphorothioate
modified_base           2
                        mod_base = OTHER
                        note = 2'-O-methylguanosine phosphorothioate
modified_base           3
                        mod_base = OTHER
                        note = 2'-O-methylcytidine
modified_base           4
                        mod_base = OTHER
                        note = 2'-O-methyluridine
modified_base           5
                        mod_base = OTHER
                        note = 2'-O-methyluridine
modified_base           6
                        mod_base = OTHER
                        note = 2'-O-methylguanosine
modified_base           7
                        mod_base = OTHER
                        note = 2'-fluorocytidine
modified_base           8
                        mod_base = OTHER
                        note = 2'-fluoroguanosine
modified_base           9
                        mod_base = OTHER
                        note = 2'-fluorocytidine
modified_base           10
                        mod_base = OTHER
                        note = 2'-O-methylcytidine
modified_base           11
                        mod_base = OTHER
                        note = 2'-O-methyladenosine
modified_base           12
                        mod_base = OTHER
                        note = 2'-O-methylcytidine
modified_base           13
                        mod_base = OTHER
                        note = 2'-O-methylcytidine
modified_base           14
                        mod_base = OTHER
                        note = 2'-O-methylcytidine
modified_base           15
                        mod_base = OTHER
                        note = 2'-O-methyladenosine
modified_base           16
                        mod_base = OTHER
                        note = 2'-O-methylcytidine
modified_base           17
                        mod_base = OTHER
                        note = 2'-O-methylguanosine phosphorothioate
modified_base           18
                        mod_base = OTHER
                        note = 2'-O-methyluridine phosphorothioate
modified_base           19
                        mod_base = OTHER
                        note = 2'-O-methyladenosine
SEQUENCE: 175
tgcttgcgcc acccacgta                                                    19

SEQ ID NO: 176          moltype = RNA  length = 19
FEATURE                 Location/Qualifiers
source                  1..19
                        mol_type = other RNA
                        organism = synthetic construct
modified_base           1
                        mod_base = OTHER
                        note = 2'-O-methylcytidine phosphorothioate
modified_base           2
                        mod_base = OTHER
                        note = 2'-O-methyluridine phosphorothioate
modified_base           3
                        mod_base = OTHER
                        note = 2'-O-methylguanosine
```

| | |
|---|---|
| modified_base | 4<br>mod_base = OTHER<br>note = 2'-O-methylguanosine |
| modified_base | 5<br>mod_base = OTHER<br>note = 2'-O-methylcytidine |
| modified_base | 6<br>mod_base = OTHER<br>note = 2'-O-methylguanosine |
| modified_base | 7<br>mod_base = OTHER<br>note = 2'-fluoroadenosine |
| modified_base | 8<br>mod_base = OTHER<br>note = 2'-fluoroguanosine |
| modified_base | 9<br>mod_base = OTHER<br>note = 2'-fluorocytidine |
| modified_base | 10<br>mod_base = OTHER<br>note = 2'-O-methylcytidine |
| modified_base | 11<br>mod_base = OTHER<br>note = 2'-O-methylcytidine |
| modified_base | 12<br>mod_base = OTHER<br>note = 2'-O-methylguanosine |
| modified_base | 13<br>mod_base = OTHER<br>note = 2'-O-methylguanosine |
| modified_base | 14<br>mod_base = OTHER<br>note = 2'-O-methyladenosine |
| modified_base | 15<br>mod_base = OTHER<br>note = 2'-O-methylguanosine |
| modified_base | 16<br>mod_base = OTHER<br>note = 2'-O-methyluridine |
| modified_base | 17<br>mod_base = OTHER<br>note = 2'-O-methyluridine phosphorothioate |
| modified_base | 18<br>mod_base = OTHER<br>note = 2'-O-methyluridine phosphorothioate |
| modified_base | 19<br>mod_base = OTHER<br>note = 2'-O-methyladenosine |
| SEQUENCE: 176 | |
| ctggcgagcc cggagttta | 19 |
| SEQ ID NO: 177<br>FEATURE<br>source | moltype = RNA length = 19<br>Location/Qualifiers<br>1..19<br>mol_type = other RNA<br>organism = synthetic construct |
| modified_base | 1<br>mod_base = OTHER<br>note = 2'-O-methylguanosine phosphorothioate |
| modified_base | 2<br>mod_base = OTHER<br>note = 2'-O-methylguanosine phosphorothioate |
| modified_base | 3<br>mod_base = OTHER<br>note = 2'-O-methylcytidine |
| modified_base | 4<br>mod_base = OTHER<br>note = 2'-O-methylguanosine |
| modified_base | 5<br>mod_base = OTHER<br>note = 2'-O-methyladenosine |
| modified_base | 6<br>mod_base = OTHER<br>note = 2'-O-methylguanosine |
| modified_base | 7<br>mod_base = OTHER<br>note = 2'-fluorocytidine |
| modified_base | 8<br>mod_base = OTHER |

```
                        note = 2'-fluorocytidine
modified_base           9
                        mod_base = OTHER
                        note = 2'-fluorocytidine
modified_base           10
                        mod_base = OTHER
                        note = 2'-O-methylguanosine
modified_base           11
                        mod_base = OTHER
                        note = 2'-O-methylguanosine
modified_base           12
                        mod_base = OTHER
                        note = 2'-O-methyladenosine
modified_base           13
                        mod_base = OTHER
                        note = 2'-O-methylguanosine
modified_base           14
                        mod_base = OTHER
                        note = 2'-O-methyluridine
modified_base           15
                        mod_base = OTHER
                        note = 2'-O-methyluridine
modified_base           16
                        mod_base = OTHER
                        note = 2'-O-methyluridine
modified_base           17
                        mod_base = OTHER
                        note = 2'-O-methylcytidine phosphorothioate
modified_base           18
                        mod_base = OTHER
                        note = 2'-O-methyluridine phosphorothioate
modified_base           19
                        mod_base = OTHER
                        note = 2'-O-methyladenosine
SEQUENCE: 177
ggcgagcccg gagtttcta                                                  19

SEQ ID NO: 178          moltype = RNA  length = 19
FEATURE                 Location/Qualifiers
source                  1..19
                        mol_type = other RNA
                        organism = synthetic construct
modified_base           1
                        mod_base = OTHER
                        note = 2'-O-methylguanosine phosphorothioate
modified_base           2
                        mod_base = OTHER
                        note = 2'-O-methylguanosine phosphorothioate
modified_base           3
                        mod_base = OTHER
                        note = 2'-O-methylcytidine
modified_base           4
                        mod_base = OTHER
                        note = 2'-O-methylguanosine
modified_base           5
                        mod_base = OTHER
                        note = 2'-O-methylcytidine
modified_base           6
                        mod_base = OTHER
                        note = 2'-O-methyladenosine
modified_base           7
                        mod_base = OTHER
                        note = 2'-fluoroadenosine
modified_base           8
                        mod_base = OTHER
                        note = 2'-fluorocytidine
modified_base           9
                        mod_base = OTHER
                        note = 2'-fluorocytidine
modified_base           10
                        mod_base = OTHER
                        note = 2'-O-methyluridine
modified_base           11
                        mod_base = OTHER
                        note = 2'-O-methylcytidine
modified_base           12
                        mod_base = OTHER
                        note = 2'-O-methyluridine
modified_base           13
```

|                | mod_base = OTHER |
|----------------|------------------|
|                | note = 2'-O-methylcytidine |
| modified_base  | 14 |
|                | mod_base = OTHER |
|                | note = 2'-O-methylcytidine |
| modified_base  | 15 |
|                | mod_base = OTHER |
|                | note = 2'-O-methyluridine |
| modified_base  | 16 |
|                | mod_base = OTHER |
|                | note = 2'-O-methyladenosine |
| modified_base  | 17 |
|                | mod_base = OTHER |
|                | note = 2'-O-methylguanosine phosphorothioate |
| modified_base  | 18 |
|                | mod_base = OTHER |
|                | note = 2'-O-methyladenosine phosphorothioate |
| modified_base  | 19 |
|                | mod_base = OTHER |
|                | note = 2'-O-methyladenosine |

SEQUENCE: 178 ggcgcaacct ctcctagaa                                                 19

| SEQ ID NO: 179 | moltype = RNA  length = 19 |
|----------------|-----------------------------|
| FEATURE        | Location/Qualifiers |
| source         | 1..19 |
|                | mol_type = other RNA |
|                | organism = synthetic construct |
| modified_base  | 1 |
|                | mod_base = OTHER |
|                | note = 2'-O-methylguanosine phosphorothioate |
| modified_base  | 2 |
|                | mod_base = OTHER |
|                | note = 2'-O-methylcytidine phosphorothioate |
| modified_base  | 3 |
|                | mod_base = OTHER |
|                | note = 2'-O-methylguanosine |
| modified_base  | 4 |
|                | mod_base = OTHER |
|                | note = 2'-O-methylcytidine |
| modified_base  | 5 |
|                | mod_base = OTHER |
|                | note = 2'-O-methyladenosine |
| modified_base  | 6 |
|                | mod_base = OTHER |
|                | note = 2'-O-methyladenosine |
| modified_base  | 7 |
|                | mod_base = OTHER |
|                | note = 2'-fluorocytidine |
| modified_base  | 8 |
|                | mod_base = OTHER |
|                | note = 2'-fluorocytidine |
| modified_base  | 9 |
|                | mod_base = OTHER |
|                | note = 2'-fluorouridine |
| modified_base  | 10 |
|                | mod_base = OTHER |
|                | note = 2'-O-methylcytidine |
| modified_base  | 11 |
|                | mod_base = OTHER |
|                | note = 2'-O-methyluridine |
| modified_base  | 12 |
|                | mod_base = OTHER |
|                | note = 2'-O-methylcytidine |
| modified_base  | 13 |
|                | mod_base = OTHER |
|                | note = 2'-O-methylcytidine |
| modified_base  | 14 |
|                | mod_base = OTHER |
|                | note = 2'-O-methyluridine |
| modified_base  | 15 |
|                | mod_base = OTHER |
|                | note = 2'-O-methyladenosine |
| modified_base  | 16 |
|                | mod_base = OTHER |
|                | note = 2'-O-methylguanosine |
| modified_base  | 17 |
|                | mod_base = OTHER |
|                | note = 2'-O-methyladenosine phosphorothioate |

| | |
|---|---|
| modified_base | 18<br>mod_base = OTHER<br>note = 2'-O-methyladenosine phosphorothioate |
| modified_base | 19<br>mod_base = OTHER<br>note = 2'-O-methyladenosine |
| SEQUENCE: 179 | |
| gcgcaacctc tcctagaaa | 19 |
| SEQ ID NO: 180<br>FEATURE<br>source | moltype = RNA length = 19<br>Location/Qualifiers<br>1..19<br>mol_type = other RNA<br>organism = synthetic construct |
| modified_base | 1<br>mod_base = OTHER<br>note = 2'-O-methyladenosine phosphorothioate |
| modified_base | 2<br>mod_base = OTHER<br>note = 2'-O-methyladenosine phosphorothioate |
| modified_base | 3<br>mod_base = OTHER<br>note = 2'-O-methylcytidine |
| modified_base | 4<br>mod_base = OTHER<br>note = 2'-O-methylcytidine |
| modified_base | 5<br>mod_base = OTHER<br>note = 2'-O-methyluridine |
| modified_base | 6<br>mod_base = OTHER<br>note = 2'-O-methylcytidine |
| modified_base | 7<br>mod_base = OTHER<br>note = 2'-fluorouridine |
| modified_base | 8<br>mod_base = OTHER<br>note = 2'-fluorocytidine |
| modified_base | 9<br>mod_base = OTHER<br>note = 2'-fluorocytidine |
| modified_base | 10<br>mod_base = OTHER<br>note = 2'-O-methyluridine |
| modified_base | 11<br>mod_base = OTHER<br>note = 2'-O-methyladenosine |
| modified_base | 12<br>mod_base = OTHER<br>note = 2'-O-methylguanosine |
| modified_base | 13<br>mod_base = OTHER<br>note = 2'-O-methyladenosine |
| modified_base | 14<br>mod_base = OTHER<br>note = 2'-O-methyladenosine |
| modified_base | 15<br>mod_base = OTHER<br>note = 2'-O-methyladenosine |
| modified_base | 16<br>mod_base = OTHER<br>note = 2'-O-methylcytidine |
| modified_base | 17<br>mod_base = OTHER<br>note = 2'-O-methylguanosine phosphorothioate |
| modified_base | 18<br>mod_base = OTHER<br>note = 2'-O-methylguanosine phosphorothioate |
| modified_base | 19<br>mod_base = OTHER<br>note = 2'-O-methyladenosine |
| SEQUENCE: 180 | |
| aacctctcct agaaacgga | 19 |
| SEQ ID NO: 181<br>FEATURE<br>source | moltype = RNA length = 19<br>Location/Qualifiers<br>1..19<br>mol_type = other RNA<br>organism = synthetic construct |

| | |
|---|---|
| modified_base | 1<br>mod_base = OTHER<br>note = 2'-O-methylcytidine phosphorothioate |
| modified_base | 2<br>mod_base = OTHER<br>note = 2'-O-methyladenosine phosphorothioate |
| modified_base | 3<br>mod_base = OTHER<br>note = 2'-O-methylguanosine |
| modified_base | 4<br>mod_base = OTHER<br>note = 2'-O-methylcytidine |
| modified_base | 5<br>mod_base = OTHER<br>note = 2'-O-methylguanosine |
| modified_base | 6<br>mod_base = OTHER<br>note = 2'-O-methyladenosine |
| modified_base | 7<br>mod_base = OTHER<br>note = 2'-fluoroguanosine |
| modified_base | 8<br>mod_base = OTHER<br>note = 2'-fluoroguanosine |
| modified_base | 9<br>mod_base = OTHER<br>note = 2'-fluoroadenosine |
| modified_base | 10<br>mod_base = OTHER<br>note = 2'-O-methyladenosine |
| modified_base | 11<br>mod_base = OTHER<br>note = 2'-O-methylguanosine |
| modified_base | 12<br>mod_base = OTHER<br>note = 2'-O-methyladenosine |
| modified_base | 13<br>mod_base = OTHER<br>note = 2'-O-methyladenosine |
| modified_base | 14<br>mod_base = OTHER<br>note = 2'-O-methyluridine |
| modified_base | 15<br>mod_base = OTHER<br>note = 2'-O-methyladenosine |
| modified_base | 16<br>mod_base = OTHER<br>note = 2'-O-methylcytidine |
| modified_base | 17<br>mod_base = OTHER<br>note = 2'-O-methylcytidine phosphorothioate |
| modified_base | 18<br>mod_base = OTHER<br>note = 2'-O-methylguanosine phosphorothioate |
| modified_base | 19<br>mod_base = OTHER<br>note = 2'-O-methyladenosine |

SEQUENCE: 181
cagcgaggaa gaataccga                    19

| | |
|---|---|
| SEQ ID NO: 182<br>FEATURE<br>source | moltype = RNA  length = 19<br>Location/Qualifiers<br>1..19<br>mol_type = other RNA<br>organism = synthetic construct |
| modified_base | 1<br>mod_base = OTHER<br>note = 2'-O-methyladenosine phosphorothioate |
| modified_base | 2<br>mod_base = OTHER<br>note = 2'-O-methylguanosine phosphorothioate |
| modified_base | 3<br>mod_base = OTHER<br>note = 2'-O-methylcytidine |
| modified_base | 4<br>mod_base = OTHER<br>note = 2'-O-methylguanosine |
| modified_base | 5<br>mod_base = OTHER |

```
                        note = 2'-O-methyladenosine
modified_base           6
                        mod_base = OTHER
                        note = 2'-O-methylguanosine
modified_base           7
                        mod_base = OTHER
                        note = 2'-fluoroguanosine
modified_base           8
                        mod_base = OTHER
                        note = 2'-fluoroadenosine
modified_base           9
                        mod_base = OTHER
                        note = 2'-fluoroadenosine
modified_base           10
                        mod_base = OTHER
                        note = 2'-O-methylguanosine
modified_base           11
                        mod_base = OTHER
                        note = 2'-O-methyladenosine
modified_base           12
                        mod_base = OTHER
                        note = 2'-O-methyladenosine
modified_base           13
                        mod_base = OTHER
                        note = 2'-O-methyluridine
modified_base           14
                        mod_base = OTHER
                        note = 2'-O-methyladenosine
modified_base           15
                        mod_base = OTHER
                        note = 2'-O-methylcytidine
modified_base           16
                        mod_base = OTHER
                        note = 2'-O-methylcytidine
modified_base           17
                        mod_base = OTHER
                        note = 2'-O-methylguanosine phosphorothioate
modified_base           18
                        mod_base = OTHER
                        note = 2'-O-methylguanosine phosphorothioate
modified_base           19
                        mod_base = OTHER
                        note = 2'-O-methyladenosine
SEQUENCE: 182
agcgaggaag aataccgga                                                 19

SEQ ID NO: 183          moltype = RNA   length = 19
FEATURE                 Location/Qualifiers
source                  1..19
                        mol_type = other RNA
                        organism = synthetic construct
modified_base           1
                        mod_base = OTHER
                        note = 2'-O-methylguanosine phosphorothioate
modified_base           2
                        mod_base = OTHER
                        note = 2'-O-methylcytidine phosphorothioate
modified_base           3
                        mod_base = OTHER
                        note = 2'-O-methylguanosine
modified_base           4
                        mod_base = OTHER
                        note = 2'-O-methyladenosine
modified_base           5
                        mod_base = OTHER
                        note = 2'-O-methylguanosine
modified_base           6
                        mod_base = OTHER
                        note = 2'-O-methylguanosine
modified_base           7
                        mod_base = OTHER
                        note = 2'-fluoroadenosine
modified_base           8
                        mod_base = OTHER
                        note = 2'-fluoroadenosine
modified_base           9
                        mod_base = OTHER
                        note = 2'-fluoroguanosine
modified_base           10
```

```
                              mod_base = OTHER
                              note = 2'-O-methyladenosine
modified_base                 11
                              mod_base = OTHER
                              note = 2'-O-methyladenosine
modified_base                 12
                              mod_base = OTHER
                              note = 2'-O-methyluridine
modified_base                 13
                              mod_base = OTHER
                              note = 2'-O-methyladenosine
modified_base                 14
                              mod_base = OTHER
                              note = 2'-O-methylcytidine
modified_base                 15
                              mod_base = OTHER
                              note = 2'-O-methylcytidine
modified_base                 16
                              mod_base = OTHER
                              note = 2'-O-methylguanosine
modified_base                 17
                              mod_base = OTHER
                              note = 2'-O-methylguanosine phosphorothioate
modified_base                 18
                              mod_base = OTHER
                              note = 2'-O-methylguanosine phosphorothioate
modified_base                 19
                              mod_base = OTHER
                              note = 2'-O-methyladenosine
SEQUENCE: 183
gcgaggaaga ataccggga                                                      19

SEQ ID NO: 184                moltype = RNA   length = 19
FEATURE                       Location/Qualifiers
source                        1..19
                              mol_type = other RNA
                              organism = synthetic construct
modified_base                 1
                              mod_base = OTHER
                              note = 2'-O-methylguanosine phosphorothioate
modified_base                 2
                              mod_base = OTHER
                              note = 2'-O-methyluridine phosphorothioate
modified_base                 3
                              mod_base = OTHER
                              note = 2'-O-methyluridine
modified_base                 4
                              mod_base = OTHER
                              note = 2'-O-methylguanosine
modified_base                 5
                              mod_base = OTHER
                              note = 2'-O-methylguanosine
modified_base                 6
                              mod_base = OTHER
                              note = 2'-O-methylguanosine
modified_base                 7
                              mod_base = OTHER
                              note = 2'-fluoroadenosine
modified_base                 8
                              mod_base = OTHER
                              note = 2'-fluorocytidine
modified_base                 9
                              mod_base = OTHER
                              note = 2'-fluoroguanosine
modified_base                 10
                              mod_base = OTHER
                              note = 2'-O-methylguanosine
modified_base                 11
                              mod_base = OTHER
                              note = 2'-O-methylguanosine
modified_base                 12
                              mod_base = OTHER
                              note = 2'-O-methylguanosine
modified_base                 13
                              mod_base = OTHER
                              note = 2'-O-methyluridine
modified_base                 14
                              mod_base = OTHER
                              note = 2'-O-methylcytidine
```

```
modified_base       15
                    mod_base = OTHER
                    note = 2'-O-methylguanosine
modified_base       16
                    mod_base = OTHER
                    note = 2'-O-methylguanosine
modified_base       17
                    mod_base = OTHER
                    note = 2'-O-methylguanosine phosphorothioate
modified_base       18
                    mod_base = OTHER
                    note = 2'-O-methyluridine phosphorothioate
modified_base       19
                    mod_base = OTHER
                    note = 2'-O-methyladenosine
SEQUENCE: 184
gttgggacgg ggtcgggta                                              19

SEQ ID NO: 185      moltype = RNA   length = 19
FEATURE             Location/Qualifiers
source              1..19
                    mol_type = other RNA
                    organism = synthetic construct
modified_base       1
                    mod_base = OTHER
                    note = 2'-O-methyladenosine phosphorothioate
modified_base       2
                    mod_base = OTHER
                    note = 2'-O-methylcytidine phosphorothioate
modified_base       3
                    mod_base = OTHER
                    note = 2'-O-methylguanosine
modified_base       4
                    mod_base = OTHER
                    note = 2'-O-methylguanosine
modified_base       5
                    mod_base = OTHER
                    note = 2'-O-methylguanosine
modified_base       6
                    mod_base = OTHER
                    note = 2'-O-methylguanosine
modified_base       7
                    mod_base = OTHER
                    note = 2'-fluorouridine
modified_base       8
                    mod_base = OTHER
                    note = 2'-fluorocytidine
modified_base       9
                    mod_base = OTHER
                    note = 2'-fluoroguanosine
modified_base       10
                    mod_base = OTHER
                    note = 2'-O-methylguanosine
modified_base       11
                    mod_base = OTHER
                    note = 2'-O-methylguanosine
modified_base       12
                    mod_base = OTHER
                    note = 2'-O-methyluridine
modified_base       13
                    mod_base = OTHER
                    note = 2'-O-methylguanosine
modified_base       14
                    mod_base = OTHER
                    note = 2'-O-methylguanosine
modified_base       15
                    mod_base = OTHER
                    note = 2'-O-methyluridine
modified_base       16
                    mod_base = OTHER
                    note = 2'-O-methyluridine
modified_base       17
                    mod_base = OTHER
                    note = 2'-O-methylcytidine phosphorothioate
modified_base       18
                    mod_base = OTHER
                    note = 2'-O-methylguanosine phosphorothioate
modified_base       19
                    mod_base = OTHER
```

```
                        note = 2'-O-methyladenosine
SEQUENCE: 185
acggggtcgg gtggttcga                                                   19

SEQ ID NO: 186          moltype = RNA  length = 19
FEATURE                 Location/Qualifiers
source                  1..19
                        mol_type = other RNA
                        organism = synthetic construct
modified_base           1
                        mod_base = OTHER
                        note = 2'-O-methylguanosine phosphorothioate
modified_base           2
                        mod_base = OTHER
                        note = 2'-O-methylguanosine phosphorothioate
modified_base           3
                        mod_base = OTHER
                        note = 2'-O-methyluridine
modified_base           4
                        mod_base = OTHER
                        note = 2'-O-methylcytidine
modified_base           5
                        mod_base = OTHER
                        note = 2'-O-methylguanosine
modified_base           6
                        mod_base = OTHER
                        note = 2'-O-methylguanosine
modified_base           7
                        mod_base = OTHER
                        note = 2'-fluoroguanosine
modified_base           8
                        mod_base = OTHER
                        note = 2'-fluorouridine
modified_base           9
                        mod_base = OTHER
                        note = 2'-fluoroguanosine
modified_base           10
                        mod_base = OTHER
                        note = 2'-O-methylguanosine
modified_base           11
                        mod_base = OTHER
                        note = 2'-O-methyluridine
modified_base           12
                        mod_base = OTHER
                        note = 2'-O-methyluridine
modified_base           13
                        mod_base = OTHER
                        note = 2'-O-methylcytidine
modified_base           14
                        mod_base = OTHER
                        note = 2'-O-methylguanosine
modified_base           15
                        mod_base = OTHER
                        note = 2'-O-methylguanosine
modified_base           16
                        mod_base = OTHER
                        note = 2'-O-methylguanosine
modified_base           17
                        mod_base = OTHER
                        note = 2'-O-methylguanosine phosphorothioate
modified_base           18
                        mod_base = OTHER
                        note = 2'-O-methylcytidine phosphorothioate
modified_base           19
                        mod_base = OTHER
                        note = 2'-O-methyladenosine
SEQUENCE: 186
ggtcgggtgg ttcggggca                                                   19

SEQ ID NO: 187          moltype = RNA  length = 19
FEATURE                 Location/Qualifiers
source                  1..19
                        mol_type = other RNA
                        organism = synthetic construct
modified_base           1
                        mod_base = OTHER
                        note = 2'-O-methylguanosine phosphorothioate
modified_base           2
                        mod_base = OTHER
```

```
                          note = 2'-O-methyluridine phosphorothioate
modified_base             3
                          mod_base = OTHER
                          note = 2'-O-methylcytidine
modified_base             4
                          mod_base = OTHER
                          note = 2'-O-methylguanosine
modified_base             5
                          mod_base = OTHER
                          note = 2'-O-methylguanosine
modified_base             6
                          mod_base = OTHER
                          note = 2'-O-methylguanosine
modified_base             7
                          mod_base = OTHER
                          note = 2'-fluorouridine
modified_base             8
                          mod_base = OTHER
                          note = 2'-fluoroguanosine
modified_base             9
                          mod_base = OTHER
                          note = 2'-fluoroguanosine
modified_base             10
                          mod_base = OTHER
                          note = 2'-O-methyluridine
modified_base             11
                          mod_base = OTHER
                          note = 2'-O-methyluridine
modified_base             12
                          mod_base = OTHER
                          note = 2'-O-methylcytidine
modified_base             13
                          mod_base = OTHER
                          note = 2'-O-methylguanosine
modified_base             14
                          mod_base = OTHER
                          note = 2'-O-methylguanosine
modified_base             15
                          mod_base = OTHER
                          note = 2'-O-methylguanosine
modified_base             16
                          mod_base = OTHER
                          note = 2'-O-methylguanosine
modified_base             17
                          mod_base = OTHER
                          note = 2'-O-methylcytidine phosphorothioate
modified_base             18
                          mod_base = OTHER
                          note = 2'-O-methyladenosine phosphorothioate
modified_base             19
                          mod_base = OTHER
                          note = 2'-O-methyladenosine
SEQUENCE: 187
gtcgggtggt tcggggcaa                                                  19

SEQ ID NO: 188            moltype = RNA   length = 19
FEATURE                   Location/Qualifiers
source                    1..19
                          mol_type = other RNA
                          organism = synthetic construct
modified_base             1
                          mod_base = OTHER
                          note = 2'-O-methylguanosine phosphorothioate
modified_base             2
                          mod_base = OTHER
                          note = 2'-O-methylcytidine phosphorothioate
modified_base             3
                          mod_base = OTHER
                          note = 2'-O-methylguanosine
modified_base             4
                          mod_base = OTHER
                          note = 2'-O-methylguanosine
modified_base             5
                          mod_base = OTHER
                          note = 2'-O-methyluridine
modified_base             6
                          mod_base = OTHER
                          note = 2'-O-methylguanosine
modified_base             7
```

| | | |
|---|---|---|
| | | mod_base = OTHER |
| | | note = 2'-fluoroguanosine |
| modified_base | 8 | |
| | | mod_base = OTHER |
| | | note = 2'-fluorocytidine |
| modified_base | 9 | |
| | | mod_base = OTHER |
| | | note = 2'-fluorocytidine |
| modified_base | 10 | |
| | | mod_base = OTHER |
| | | note = 2'-O-methyluridine |
| modified_base | 11 | |
| | | mod_base = OTHER |
| | | note = 2'-O-methylcytidine |
| modified_base | 12 | |
| | | mod_base = OTHER |
| | | note = 2'-O-methyluridine |
| modified_base | 13 | |
| | | mod_base = OTHER |
| | | note = 2'-O-methylcytidine |
| modified_base | 14 | |
| | | mod_base = OTHER |
| | | note = 2'-O-methyluridine |
| modified_base | 15 | |
| | | mod_base = OTHER |
| | | note = 2'-O-methyluridine |
| modified_base | 16 | |
| | | mod_base = OTHER |
| | | note = 2'-O-methyluridine |
| modified_base | 17 | |
| | | mod_base = OTHER |
| | | note = 2'-O-methylcytidine phosphorothioate |
| modified_base | 18 | |
| | | mod_base = OTHER |
| | | note = 2'-O-methylguanosine phosphorothioate |
| modified_base | 19 | |
| | | mod_base = OTHER |
| | | note = 2'-O-methyladenosine |
| SEQUENCE: 188 | | |
| gcggtggcct ctctttcga | | 19 |
| | | |
| SEQ ID NO: 189 | moltype = RNA  length = 19 | |
| FEATURE | Location/Qualifiers | |
| source | 1..19 | |
| | | mol_type = other RNA |
| | | organism = synthetic construct |
| modified_base | 1 | |
| | | mod_base = OTHER |
| | | note = 2'-O-methylcytidine phosphorothioate |
| modified_base | 2 | |
| | | mod_base = OTHER |
| | | note = 2'-O-methylguanosine phosphorothioate |
| modified_base | 3 | |
| | | mod_base = OTHER |
| | | note = 2'-O-methylguanosine |
| modified_base | 4 | |
| | | mod_base = OTHER |
| | | note = 2'-O-methyluridine |
| modified_base | 5 | |
| | | mod_base = OTHER |
| | | note = 2'-O-methylguanosine |
| modified_base | 6 | |
| | | mod_base = OTHER |
| | | note = 2'-O-methylguanosine |
| modified_base | 7 | |
| | | mod_base = OTHER |
| | | note = 2'-fluorocytidine |
| modified_base | 8 | |
| | | mod_base = OTHER |
| | | note = 2'-fluorocytidine |
| modified_base | 9 | |
| | | mod_base = OTHER |
| | | note = 2'-fluorouridine |
| modified_base | 10 | |
| | | mod_base = OTHER |
| | | note = 2'-O-methylcytidine |
| modified_base | 11 | |
| | | mod_base = OTHER |
| | | note = 2'-O-methyluridine |

|   |   |
|---|---|
| modified_base | 12<br>mod_base = OTHER<br>note = 2'-O-methylcytidine |
| modified_base | 13<br>mod_base = OTHER<br>note = 2'-O-methyluridine |
| modified_base | 14<br>mod_base = OTHER<br>note = 2'-O-methyluridine |
| modified_base | 15<br>mod_base = OTHER<br>note = 2'-O-methyluridine |
| modified_base | 16<br>mod_base = OTHER<br>note = 2'-O-methylcytidine |
| modified_base | 17<br>mod_base = OTHER<br>note = 2'-O-methylguanosine phosphorothioate |
| modified_base | 18<br>mod_base = OTHER<br>note = 2'-O-methylcytidine phosphorothioate |
| modified_base | 19<br>mod_base = OTHER<br>note = 2'-O-methyladenosine |

SEQUENCE: 189
cggtggcctc tctttcgca                                                     19

|   |   |
|---|---|
| SEQ ID NO: 190 | moltype = RNA   length = 19 |
| FEATURE | Location/Qualifiers |
| source | 1..19<br>mol_type = other RNA<br>organism = synthetic construct |
| modified_base | 1<br>mod_base = OTHER<br>note = 2'-O-methylguanosine phosphorothioate |
| modified_base | 2<br>mod_base = OTHER<br>note = 2'-O-methylguanosine phosphorothioate |
| modified_base | 3<br>mod_base = OTHER<br>note = 2'-O-methyluridine |
| modified_base | 4<br>mod_base = OTHER<br>note = 2'-O-methylguanosine |
| modified_base | 5<br>mod_base = OTHER<br>note = 2'-O-methylguanosine |
| modified_base | 6<br>mod_base = OTHER<br>note = 2'-O-methylcytidine |
| modified_base | 7<br>mod_base = OTHER<br>note = 2'-fluorocytidine |
| modified_base | 8<br>mod_base = OTHER<br>note = 2'-fluorouridine |
| modified_base | 9<br>mod_base = OTHER<br>note = 2'-fluorocytidine |
| modified_base | 10<br>mod_base = OTHER<br>note = 2'-O-methyluridine |
| modified_base | 11<br>mod_base = OTHER<br>note = 2'-O-methylcytidine |
| modified_base | 12<br>mod_base = OTHER<br>note = 2'-O-methyluridine |
| modified_base | 13<br>mod_base = OTHER<br>note = 2'-O-methyluridine |
| modified_base | 14<br>mod_base = OTHER<br>note = 2'-O-methyluridine |
| modified_base | 15<br>mod_base = OTHER<br>note = 2'-O-methylcytidine |
| modified_base | 16<br>mod_base = OTHER |

```
                        note = 2'-O-methylguanosine
modified_base           17
                        mod_base = OTHER
                        note = 2'-O-methylcytidine phosphorothioate
modified_base           18
                        mod_base = OTHER
                        note = 2'-O-methylguanosine phosphorothioate
modified_base           19
                        mod_base = OTHER
                        note = 2'-O-methyladenosine
SEQUENCE: 190
ggtggcctct ctttcgcga                                                       19

SEQ ID NO: 191          moltype = RNA   length = 19
FEATURE                 Location/Qualifiers
source                  1..19
                        mol_type = other RNA
                        organism = synthetic construct
modified_base           1
                        mod_base = OTHER
                        note = 2'-O-methylguanosine phosphorothioate
modified_base           2
                        mod_base = OTHER
                        note = 2'-O-methylcytidine phosphorothioate
modified_base           3
                        mod_base = OTHER
                        note = 2'-O-methylcytidine
modified_base           4
                        mod_base = OTHER
                        note = 2'-O-methyluridine
modified_base           5
                        mod_base = OTHER
                        note = 2'-O-methylcytidine
modified_base           6
                        mod_base = OTHER
                        note = 2'-O-methyluridine
modified_base           7
                        mod_base = OTHER
                        note = 2'-fluorocytidine
modified_base           8
                        mod_base = OTHER
                        note = 2'-fluorouridine
modified_base           9
                        mod_base = OTHER
                        note = 2'-fluorouridine
modified_base           10
                        mod_base = OTHER
                        note = 2'-O-methyluridine
modified_base           11
                        mod_base = OTHER
                        note = 2'-O-methylcytidine
modified_base           12
                        mod_base = OTHER
                        note = 2'-O-methylguanosine
modified_base           13
                        mod_base = OTHER
                        note = 2'-O-methylcytidine
modified_base           14
                        mod_base = OTHER
                        note = 2'-O-methylguanosine
modified_base           15
                        mod_base = OTHER
                        note = 2'-O-methylguanosine
modified_base           16
                        mod_base = OTHER
                        note = 2'-O-methylguanosine
modified_base           17
                        mod_base = OTHER
                        note = 2'-O-methylguanosine phosphorothioate
modified_base           18
                        mod_base = OTHER
                        note = 2'-O-methyladenosine phosphorothioate
modified_base           19
                        mod_base = OTHER
                        note = 2'-O-methyladenosine
SEQUENCE: 191
gcctctcttt cgcggggaa                                                       19

SEQ ID NO: 192          moltype = RNA   length = 19
```

```
FEATURE              Location/Qualifiers
source               1..19
                     mol_type = other RNA
                     organism = synthetic construct
modified_base        1
                     mod_base = OTHER
                     note = 2'-O-methylcytidine phosphorothioate
modified_base        2
                     mod_base = OTHER
                     note = 2'-O-methyladenosine phosphorothioate
modified_base        3
                     mod_base = OTHER
                     note = 2'-O-methylcytidine
modified_base        4
                     mod_base = OTHER
                     note = 2'-O-methylcytidine
modified_base        5
                     mod_base = OTHER
                     note = 2'-O-methyluridine
modified_base        6
                     mod_base = OTHER
                     note = 2'-O-methylguanosine
modified_base        7
                     mod_base = OTHER
                     note = 2'-fluoroguanosine
modified_base        8
                     mod_base = OTHER
                     note = 2'-fluorocytidine
modified_base        9
                     mod_base = OTHER
                     note = 2'-fluorouridine
modified_base        10
                     mod_base = OTHER
                     note = 2'-O-methylguanosine
modified_base        11
                     mod_base = OTHER
                     note = 2'-O-methylguanosine
modified_base        12
                     mod_base = OTHER
                     note = 2'-O-methylcytidine
modified_base        13
                     mod_base = OTHER
                     note = 2'-O-methyluridine
modified_base        14
                     mod_base = OTHER
                     note = 2'-O-methyladenosine
modified_base        15
                     mod_base = OTHER
                     note = 2'-O-methylcytidine
modified_base        16
                     mod_base = OTHER
                     note = 2'-O-methylguanosine
modified_base        17
                     mod_base = OTHER
                     note = 2'-O-methylguanosine phosphorothioate
modified_base        18
                     mod_base = OTHER
                     note = 2'-O-methyladenosine phosphorothioate
modified_base        19
                     mod_base = OTHER
                     note = 2'-O-methyladenosine
SEQUENCE: 192
cacctggctg gctacggaa                                              19

SEQ ID NO: 193       moltype = RNA   length = 19
FEATURE              Location/Qualifiers
source               1..19
                     mol_type = other RNA
                     organism = synthetic construct
modified_base        1
                     mod_base = OTHER
                     note = 2'-O-methylguanosine phosphorothioate
modified_base        2
                     mod_base = OTHER
                     note = 2'-O-methylcytidine phosphorothioate
modified_base        3
                     mod_base = OTHER
                     note = 2'-O-methyluridine
modified_base        4
```

|                | mod_base = OTHER |
|                | note = 2'-O-methyladenosine |
| modified_base | 5 |
|                | mod_base = OTHER |
|                | note = 2'-O-methylcytidine |
| modified_base | 6 |
|                | mod_base = OTHER |
|                | note = 2'-O-methylguanosine |
| modified_base | 7 |
|                | mod_base = OTHER |
|                | note = 2'-fluoroguanosine |
| modified_base | 8 |
|                | mod_base = OTHER |
|                | note = 2'-fluoroadenosine |
| modified_base | 9 |
|                | mod_base = OTHER |
|                | note = 2'-fluoroguanosine |
| modified_base | 10 |
|                | mod_base = OTHER |
|                | note = 2'-O-methylguanosine |
| modified_base | 11 |
|                | mod_base = OTHER |
|                | note = 2'-O-methylguanosine |
| modified_base | 12 |
|                | mod_base = OTHER |
|                | note = 2'-O-methylguanosine |
| modified_base | 13 |
|                | mod_base = OTHER |
|                | note = 2'-O-methylcytidine |
| modified_base | 14 |
|                | mod_base = OTHER |
|                | note = 2'-O-methylguanosine |
| modified_base | 15 |
|                | mod_base = OTHER |
|                | note = 2'-O-methyluridine |
| modified_base | 16 |
|                | mod_base = OTHER |
|                | note = 2'-O-methylguanosine |
| modified_base | 17 |
|                | mod_base = OTHER |
|                | note = 2'-O-methyluridine phosphorothioate |
| modified_base | 18 |
|                | mod_base = OTHER |
|                | note = 2'-O-methylcytidine phosphorothioate |
| modified_base | 19 |
|                | mod_base = OTHER |
|                | note = 2'-O-methyladenosine |

SEQUENCE: 193
gctacggagg ggcgtgtca                                                    19

| SEQ ID NO: 194 | moltype = RNA   length = 19 |
| FEATURE | Location/Qualifiers |
| source | 1..19 |
|                | mol_type = other RNA |
|                | organism = synthetic construct |
| modified_base | 1 |
|                | mod_base = OTHER |
|                | note = 2'-O-methylcytidine phosphorothioate |
| modified_base | 2 |
|                | mod_base = OTHER |
|                | note = 2'-O-methyluridine phosphorothioate |
| modified_base | 3 |
|                | mod_base = OTHER |
|                | note = 2'-O-methyladenosine |
| modified_base | 4 |
|                | mod_base = OTHER |
|                | note = 2'-O-methylcytidine |
| modified_base | 5 |
|                | mod_base = OTHER |
|                | note = 2'-O-methylguanosine |
| modified_base | 6 |
|                | mod_base = OTHER |
|                | note = 2'-O-methylguanosine |
| modified_base | 7 |
|                | mod_base = OTHER |
|                | note = 2'-fluoroadenosine |
| modified_base | 8 |
|                | mod_base = OTHER |
|                | note = 2'-fluoroguanosine |

```
                    modified_base    9
                                     mod_base = OTHER
                                     note = 2'-fluoroguanosine
                    modified_base    10
                                     mod_base = OTHER
                                     note = 2'-O-methylguanosine
                    modified_base    11
                                     mod_base = OTHER
                                     note = 2'-O-methylguanosine
                    modified_base    12
                                     mod_base = OTHER
                                     note = 2'-O-methylcytidine
                    modified_base    13
                                     mod_base = OTHER
                                     note = 2'-O-methylguanosine
                    modified_base    14
                                     mod_base = OTHER
                                     note = 2'-O-methyluridine
                    modified_base    15
                                     mod_base = OTHER
                                     note = 2'-O-methylguanosine
                    modified_base    16
                                     mod_base = OTHER
                                     note = 2'-O-methyluridine
                    modified_base    17
                                     mod_base = OTHER
                                     note = 2'-O-methylcytidine phosphorothioate
                    modified_base    18
                                     mod_base = OTHER
                                     note = 2'-O-methyluridine phosphorothioate
                    modified_base    19
                                     mod_base = OTHER
                                     note = 2'-O-methyladenosine
SEQUENCE: 194
ctacggaggg gcgtgtcta                                                          19

SEQ ID NO: 195         moltype = RNA   length = 19
FEATURE                Location/Qualifiers
source                 1..19
                       mol_type = other RNA
                       organism = synthetic construct
                    modified_base    1
                                     mod_base = OTHER
                                     note = 2'-O-methyladenosine phosphorothioate
                    modified_base    2
                                     mod_base = OTHER
                                     note = 2'-O-methylcytidine phosphorothioate
                    modified_base    3
                                     mod_base = OTHER
                                     note = 2'-O-methylguanosine
                    modified_base    4
                                     mod_base = OTHER
                                     note = 2'-O-methyluridine
                    modified_base    5
                                     mod_base = OTHER
                                     note = 2'-O-methylguanosine
                    modified_base    6
                                     mod_base = OTHER
                                     note = 2'-O-methylcytidine
                    modified_base    7
                                     mod_base = OTHER
                                     note = 2'-fluoroadenosine
                    modified_base    8
                                     mod_base = OTHER
                                     note = 2'-fluoroadenosine
                    modified_base    9
                                     mod_base = OTHER
                                     note = 2'-fluoroguanosine
                    modified_base    10
                                     mod_base = OTHER
                                     note = 2'-O-methylguanosine
                    modified_base    11
                                     mod_base = OTHER
                                     note = 2'-O-methylguanosine
                    modified_base    12
                                     mod_base = OTHER
                                     note = 2'-O-methyladenosine
                    modified_base    13
                                     mod_base = OTHER
```

```
                        note = 2'-O-methylguanosine
modified_base           14
                        mod_base = OTHER
                        note = 2'-O-methylcytidine
modified_base           15
                        mod_base = OTHER
                        note = 2'-O-methyluridine
modified_base           16
                        mod_base = OTHER
                        note = 2'-O-methylcytidine
modified_base           17
                        mod_base = OTHER
                        note = 2'-O-methylguanosine phosphorothioate
modified_base           18
                        mod_base = OTHER
                        note = 2'-O-methylcytidine phosphorothioate
modified_base           19
                        mod_base = OTHER
                        note = 2'-O-methyladenosine
SEQUENCE: 195
acgtgcaagg gagctcgca                                               19

SEQ ID NO: 196          moltype = RNA  length = 19
FEATURE                 Location/Qualifiers
source                  1..19
                        mol_type = other RNA
                        organism = synthetic construct
modified_base           1
                        mod_base = OTHER
                        note = 2'-O-methylcytidine phosphorothioate
modified_base           2
                        mod_base = OTHER
                        note = 2'-O-methylguanosine phosphorothioate
modified_base           3
                        mod_base = OTHER
                        note = 2'-O-methyluridine
modified_base           4
                        mod_base = OTHER
                        note = 2'-O-methylguanosine
modified_base           5
                        mod_base = OTHER
                        note = 2'-O-methylcytidine
modified_base           6
                        mod_base = OTHER
                        note = 2'-O-methyladenosine
modified_base           7
                        mod_base = OTHER
                        note = 2'-fluoroadenosine
modified_base           8
                        mod_base = OTHER
                        note = 2'-fluoroguanosine
modified_base           9
                        mod_base = OTHER
                        note = 2'-fluoroguanosine
modified_base           10
                        mod_base = OTHER
                        note = 2'-O-methylguanosine
modified_base           11
                        mod_base = OTHER
                        note = 2'-O-methyladenosine
modified_base           12
                        mod_base = OTHER
                        note = 2'-O-methylguanosine
modified_base           13
                        mod_base = OTHER
                        note = 2'-O-methylcytidine
modified_base           14
                        mod_base = OTHER
                        note = 2'-O-methyluridine
modified_base           15
                        mod_base = OTHER
                        note = 2'-O-methylcytidine
modified_base           16
                        mod_base = OTHER
                        note = 2'-O-methylguanosine
modified_base           17
                        mod_base = OTHER
                        note = 2'-O-methylcytidine phosphorothioate
modified_base           18
```

|                | mod_base = OTHER |
|                | note = 2'-O-methyluridine phosphorothioate |
| modified_base  | 19 |
|                | mod_base = OTHER |
|                | note = 2'-O-methyladenosine |
| SEQUENCE: 196  |    |
| cgtgcaaggg agctcgcta | 19 |

| SEQ ID NO: 197 | moltype = RNA   length = 19 |
| FEATURE        | Location/Qualifiers |
| source         | 1..19 |
|                | mol_type = other RNA |
|                | organism = synthetic construct |
| modified_base  | 1 |
|                | mod_base = OTHER |
|                | note = 2'-O-methylguanosine phosphorothioate |
| modified_base  | 2 |
|                | mod_base = OTHER |
|                | note = 2'-O-methyluridine phosphorothioate |
| modified_base  | 3 |
|                | mod_base = OTHER |
|                | note = 2'-O-methylguanosine |
| modified_base  | 4 |
|                | mod_base = OTHER |
|                | note = 2'-O-methylcytidine |
| modified_base  | 5 |
|                | mod_base = OTHER |
|                | note = 2'-O-methyladenosine |
| modified_base  | 6 |
|                | mod_base = OTHER |
|                | note = 2'-O-methyladenosine |
| modified_base  | 7 |
|                | mod_base = OTHER |
|                | note = 2'-fluoroguanosine |
| modified_base  | 8 |
|                | mod_base = OTHER |
|                | note = 2'-fluoroguanosine |
| modified_base  | 9 |
|                | mod_base = OTHER |
|                | note = 2'-fluoroguanosine |
| modified_base  | 10 |
|                | mod_base = OTHER |
|                | note = 2'-O-methyladenosine |
| modified_base  | 11 |
|                | mod_base = OTHER |
|                | note = 2'-O-methylguanosine |
| modified_base  | 12 |
|                | mod_base = OTHER |
|                | note = 2'-O-methylcytidine |
| modified_base  | 13 |
|                | mod_base = OTHER |
|                | note = 2'-O-methyluridine |
| modified_base  | 14 |
|                | mod_base = OTHER |
|                | note = 2'-O-methylcytidine |
| modified_base  | 15 |
|                | mod_base = OTHER |
|                | note = 2'-O-methylguanosine |
| modified_base  | 16 |
|                | mod_base = OTHER |
|                | note = 2'-O-methylcytidine |
| modified_base  | 17 |
|                | mod_base = OTHER |
|                | note = 2'-O-methyluridine phosphorothioate |
| modified_base  | 18 |
|                | mod_base = OTHER |
|                | note = 2'-O-methylguanosine phosphorothioate |
| modified_base  | 19 |
|                | mod_base = OTHER |
|                | note = 2'-O-methyladenosine |
| SEQUENCE: 197  |    |
| gtgcaaggga gctcgctga | 19 |

| SEQ ID NO: 198 | moltype = RNA   length = 19 |
| FEATURE        | Location/Qualifiers |
| source         | 1..19 |
|                | mol_type = other RNA |
|                | organism = synthetic construct |
| modified_base  | 1 |

|   |   |
|---|---|
| | mod_base = OTHER |
| | note = 2'-O-methylcytidine phosphorothioate |
| modified_base | 2 |
| | mod_base = OTHER |
| | note = 2'-O-methyladenosine phosphorothioate |
| modified_base | 3 |
| | mod_base = OTHER |
| | note = 2'-O-methylcytidine |
| modified_base | 4 |
| | mod_base = OTHER |
| | note = 2'-O-methylcytidine |
| modified_base | 5 |
| | mod_base = OTHER |
| | note = 2'-O-methyluridine |
| modified_base | 6 |
| | mod_base = OTHER |
| | note = 2'-O-methyluridine |
| modified_base | 7 |
| | mod_base = OTHER |
| | note = 2'-fluorocytidine |
| modified_base | 8 |
| | mod_base = OTHER |
| | note = 2'-fluorocytidine |
| modified_base | 9 |
| | mod_base = OTHER |
| | note = 2'-fluoroguanosine |
| modified_base | 10 |
| | mod_base = OTHER |
| | note = 2'-O-methyladenosine |
| modified_base | 11 |
| | mod_base = OTHER |
| | note = 2'-O-methylcytidine |
| modified_base | 12 |
| | mod_base = OTHER |
| | note = 2'-O-methylguanosine |
| modified_base | 13 |
| | mod_base = OTHER |
| | note = 2'-O-methylcytidine |
| modified_base | 14 |
| | mod_base = OTHER |
| | note = 2'-O-methyluridine |
| modified_base | 15 |
| | mod_base = OTHER |
| | note = 2'-O-methylguanosine |
| modified_base | 16 |
| | mod_base = OTHER |
| | note = 2'-O-methyluridine |
| modified_base | 17 |
| | mod_base = OTHER |
| | note = 2'-O-methylcytidine phosphorothioate |
| modified_base | 18 |
| | mod_base = OTHER |
| | note = 2'-O-methyluridine phosphorothioate |
| modified_base | 19 |
| | mod_base = OTHER |
| | note = 2'-O-methyladenosine |
| SEQUENCE: 198 | |
| caccttccga cgctgtcta | 19 |
| | |
| SEQ ID NO: 199 | moltype = RNA   length = 19 |
| FEATURE | Location/Qualifiers |
| source | 1..19 |
| | mol_type = other RNA |
| | organism = synthetic construct |
| modified_base | 1 |
| | mod_base = OTHER |
| | note = 2'-O-methyladenosine phosphorothioate |
| modified_base | 2 |
| | mod_base = OTHER |
| | note = 2'-O-methylcytidine phosphorothioate |
| modified_base | 3 |
| | mod_base = OTHER |
| | note = 2'-O-methylcytidine |
| modified_base | 4 |
| | mod_base = OTHER |
| | note = 2'-O-methyluridine |
| modified_base | 5 |
| | mod_base = OTHER |
| | note = 2'-O-methyluridine |

| | | |
|---|---|---|
| modified_base | 6 | |
| | mod_base = OTHER | |
| | note = 2'-O-methylcytidine | |
| modified_base | 7 | |
| | mod_base = OTHER | |
| | note = 2'-fluorocytidine | |
| modified_base | 8 | |
| | mod_base = OTHER | |
| | note = 2'-fluoroguanosine | |
| modified_base | 9 | |
| | mod_base = OTHER | |
| | note = 2'-fluoroadenosine | |
| modified_base | 10 | |
| | mod_base = OTHER | |
| | note = 2'-O-methylcytidine | |
| modified_base | 11 | |
| | mod_base = OTHER | |
| | note = 2'-O-methylguanosine | |
| modified_base | 12 | |
| | mod_base = OTHER | |
| | note = 2'-O-methylcytidine | |
| modified_base | 13 | |
| | mod_base = OTHER | |
| | note = 2'-O-methyluridine | |
| modified_base | 14 | |
| | mod_base = OTHER | |
| | note = 2'-O-methylguanosine | |
| modified_base | 15 | |
| | mod_base = OTHER | |
| | note = 2'-O-methyluridine | |
| modified_base | 16 | |
| | mod_base = OTHER | |
| | note = 2'-O-methylcytidine | |
| modified_base | 17 | |
| | mod_base = OTHER | |
| | note = 2'-O-methyluridine phosphorothioate | |
| modified_base | 18 | |
| | mod_base = OTHER | |
| | note = 2'-O-methyladenosine phosphorothioate | |
| modified_base | 19 | |
| | mod_base = OTHER | |
| | note = 2'-O-methyladenosine | |
| SEQUENCE: 199 | | |
| accttccgac gctgtctaa | | 19 |
| | | |
| SEQ ID NO: 200 | moltype = RNA  length = 19 | |
| FEATURE | Location/Qualifiers | |
| source | 1..19 | |
| | mol_type = other RNA | |
| | organism = synthetic construct | |
| modified_base | 1 | |
| | mod_base = OTHER | |
| | note = 2'-O-methylcytidine phosphorothioate | |
| modified_base | 2 | |
| | mod_base = OTHER | |
| | note = 2'-O-methylcytidine phosphorothioate | |
| modified_base | 3 | |
| | mod_base = OTHER | |
| | note = 2'-O-methyluridine | |
| modified_base | 4 | |
| | mod_base = OTHER | |
| | note = 2'-O-methyluridine | |
| modified_base | 5 | |
| | mod_base = OTHER | |
| | note = 2'-O-methylcytidine | |
| modified_base | 6 | |
| | mod_base = OTHER | |
| | note = 2'-O-methylcytidine | |
| modified_base | 7 | |
| | mod_base = OTHER | |
| | note = 2'-fluoroguanosine | |
| modified_base | 8 | |
| | mod_base = OTHER | |
| | note = 2'-fluoroadenosine | |
| modified_base | 9 | |
| | mod_base = OTHER | |
| | note = 2'-fluorocytidine | |
| modified_base | 10 | |
| | mod_base = OTHER | |

```
                        note = 2'-O-methylguanosine
modified_base           11
                        mod_base = OTHER
                        note = 2'-O-methylcytidine
modified_base           12
                        mod_base = OTHER
                        note = 2'-O-methyluridine
modified_base           13
                        mod_base = OTHER
                        note = 2'-O-methylguanosine
modified_base           14
                        mod_base = OTHER
                        note = 2'-O-methyluridine
modified_base           15
                        mod_base = OTHER
                        note = 2'-O-methylcytidine
modified_base           16
                        mod_base = OTHER
                        note = 2'-O-methyluridine
modified_base           17
                        mod_base = OTHER
                        note = 2'-O-methyladenosine phosphorothioate
modified_base           18
                        mod_base = OTHER
                        note = 2'-O-methylguanosine phosphorothioate
modified_base           19
                        mod_base = OTHER
                        note = 2'-O-methyladenosine
SEQUENCE: 200
ccttccgacg ctgtctaga                                                   19

SEQ ID NO: 201          moltype = RNA  length = 19
FEATURE                 Location/Qualifiers
source                  1..19
                        mol_type = other RNA
                        organism = synthetic construct
modified_base           1
                        mod_base = OTHER
                        note = 2'-O-methylcytidine phosphorothioate
modified_base           2
                        mod_base = OTHER
                        note = 2'-O-methyluridine phosphorothioate
modified_base           3
                        mod_base = OTHER
                        note = 2'-O-methyluridine
modified_base           4
                        mod_base = OTHER
                        note = 2'-O-methylcytidine
modified_base           5
                        mod_base = OTHER
                        note = 2'-O-methylcytidine
modified_base           6
                        mod_base = OTHER
                        note = 2'-O-methylguanosine
modified_base           7
                        mod_base = OTHER
                        note = 2'-fluoroadenosine
modified_base           8
                        mod_base = OTHER
                        note = 2'-fluorocytidine
modified_base           9
                        mod_base = OTHER
                        note = 2'-fluoroguanosine
modified_base           10
                        mod_base = OTHER
                        note = 2'-O-methylcytidine
modified_base           11
                        mod_base = OTHER
                        note = 2'-O-methyluridine
modified_base           12
                        mod_base = OTHER
                        note = 2'-O-methylguanosine
modified_base           13
                        mod_base = OTHER
                        note = 2'-O-methyluridine
modified_base           14
                        mod_base = OTHER
                        note = 2'-O-methylcytidine
modified_base           15
```

```
                        mod_base = OTHER
                        note = 2'-O-methyluridine
modified_base           16
                        mod_base = OTHER
                        note = 2'-O-methyladenosine
modified_base           17
                        mod_base = OTHER
                        note = 2'-O-methylguanosine phosphorothioate
modified_base           18
                        mod_base = OTHER
                        note = 2'-O-methylguanosine phosphorothioate
modified_base           19
                        mod_base = OTHER
                        note = 2'-O-methyladenosine
SEQUENCE: 201
cttccgacgc tgtctagga                                                       19

SEQ ID NO: 202          moltype = RNA   length = 19
FEATURE                 Location/Qualifiers
source                  1..19
                        mol_type = other RNA
                        organism = synthetic construct
modified_base           1
                        mod_base = OTHER
                        note = 2'-O-methyluridine phosphorothioate
modified_base           2
                        mod_base = OTHER
                        note = 2'-O-methylcytidine phosphorothioate
modified_base           3
                        mod_base = OTHER
                        note = 2'-O-methylcytidine
modified_base           4
                        mod_base = OTHER
                        note = 2'-O-methylguanosine
modified_base           5
                        mod_base = OTHER
                        note = 2'-O-methyladenosine
modified_base           6
                        mod_base = OTHER
                        note = 2'-O-methylcytidine
modified_base           7
                        mod_base = OTHER
                        note = 2'-fluoroguanosine
modified_base           8
                        mod_base = OTHER
                        note = 2'-fluorocytidine
modified_base           9
                        mod_base = OTHER
                        note = 2'-fluorouridine
modified_base           10
                        mod_base = OTHER
                        note = 2'-O-methylguanosine
modified_base           11
                        mod_base = OTHER
                        note = 2'-O-methyluridine
modified_base           12
                        mod_base = OTHER
                        note = 2'-O-methylcytidine
modified_base           13
                        mod_base = OTHER
                        note = 2'-O-methyluridine
modified_base           14
                        mod_base = OTHER
                        note = 2'-O-methyladenosine
modified_base           15
                        mod_base = OTHER
                        note = 2'-O-methylguanosine
modified_base           16
                        mod_base = OTHER
                        note = 2'-O-methylguanosine
modified_base           17
                        mod_base = OTHER
                        note = 2'-O-methylcytidine phosphorothioate
modified_base           18
                        mod_base = OTHER
                        note = 2'-O-methyladenosine phosphorothioate
modified_base           19
                        mod_base = OTHER
                        note = 2'-O-methyladenosine
```

```
SEQUENCE: 202
tccgacgctg tctaggcaa                                            19

SEQ ID NO: 203            moltype = RNA  length = 19
FEATURE                   Location/Qualifiers
source                    1..19
                          mol_type = other RNA
                          organism = synthetic construct
modified_base             1
                          mod_base = OTHER
                          note = 2'-O-methylcytidine phosphorothioate
modified_base             2
                          mod_base = OTHER
                          note = 2'-O-methylcytidine phosphorothioate
modified_base             3
                          mod_base = OTHER
                          note = 2'-O-methylguanosine
modified_base             4
                          mod_base = OTHER
                          note = 2'-O-methyladenosine
modified_base             5
                          mod_base = OTHER
                          note = 2'-O-methylcytidine
modified_base             6
                          mod_base = OTHER
                          note = 2'-O-methylguanosine
modified_base             7
                          mod_base = OTHER
                          note = 2'-fluorocytidine
modified_base             8
                          mod_base = OTHER
                          note = 2'-fluorouridine
modified_base             9
                          mod_base = OTHER
                          note = 2'-fluoroguanosine
modified_base             10
                          mod_base = OTHER
                          note = 2'-O-methyluridine
modified_base             11
                          mod_base = OTHER
                          note = 2'-O-methylcytidine
modified_base             12
                          mod_base = OTHER
                          note = 2'-O-methyluridine
modified_base             13
                          mod_base = OTHER
                          note = 2'-O-methyladenosine
modified_base             14
                          mod_base = OTHER
                          note = 2'-O-methylguanosine
modified_base             15
                          mod_base = OTHER
                          note = 2'-O-methylguanosine
modified_base             16
                          mod_base = OTHER
                          note = 2'-O-methylcytidine
modified_base             17
                          mod_base = OTHER
                          note = 2'-O-methyladenosine phosphorothioate
modified_base             18
                          mod_base = OTHER
                          note = 2'-O-methyladenosine phosphorothioate
modified_base             19
                          mod_base = OTHER
                          note = 2'-O-methyladenosine
SEQUENCE: 203
ccgacgctgt ctaggcaaa                                            19

SEQ ID NO: 204            moltype = RNA  length = 19
FEATURE                   Location/Qualifiers
source                    1..19
                          mol_type = other RNA
                          organism = synthetic construct
modified_base             1
                          mod_base = OTHER
                          note = 2'-O-methyladenosine phosphorothioate
modified_base             2
                          mod_base = OTHER
                          note = 2'-O-methylcytidine phosphorothioate
```

```
modified_base      3
                   mod_base = OTHER
                   note = 2'-O-methylguanosine
modified_base      4
                   mod_base = OTHER
                   note = 2'-O-methylcytidine
modified_base      5
                   mod_base = OTHER
                   note = 2'-O-methyluridine
modified_base      6
                   mod_base = OTHER
                   note = 2'-O-methylguanosine
modified_base      7
                   mod_base = OTHER
                   note = 2'-fluorouridine
modified_base      8
                   mod_base = OTHER
                   note = 2'-fluorocytidine
modified_base      9
                   mod_base = OTHER
                   note = 2'-fluorouridine
modified_base      10
                   mod_base = OTHER
                   note = 2'-O-methyladenosine
modified_base      11
                   mod_base = OTHER
                   note = 2'-O-methylguanosine
modified_base      12
                   mod_base = OTHER
                   note = 2'-O-methylguanosine
modified_base      13
                   mod_base = OTHER
                   note = 2'-O-methylcytidine
modified_base      14
                   mod_base = OTHER
                   note = 2'-O-methyladenosine
modified_base      15
                   mod_base = OTHER
                   note = 2'-O-methyladenosine
modified_base      16
                   mod_base = OTHER
                   note = 2'-O-methyladenosine
modified_base      17
                   mod_base = OTHER
                   note = 2'-O-methylcytidine phosphorothioate
modified_base      18
                   mod_base = OTHER
                   note = 2'-O-methylcytidine phosphorothioate
modified_base      19
                   mod_base = OTHER
                   note = 2'-O-methyladenosine
SEQUENCE: 204
acgctgtcta ggcaaaacca                                              19

SEQ ID NO: 205     moltype = RNA   length = 19
FEATURE            Location/Qualifiers
source             1..19
                   mol_type = other RNA
                   organism = synthetic construct
modified_base      1
                   mod_base = OTHER
                   note = 2'-O-methyladenosine phosphorothioate
modified_base      2
                   mod_base = OTHER
                   note = 2'-O-methyladenosine phosphorothioate
modified_base      3
                   mod_base = OTHER
                   note = 2'-O-methyladenosine
modified_base      4
                   mod_base = OTHER
                   note = 2'-O-methylcytidine
modified_base      5
                   mod_base = OTHER
                   note = 2'-O-methylcytidine
modified_base      6
                   mod_base = OTHER
                   note = 2'-O-methyluridine
modified_base      7
                   mod_base = OTHER
```

```
                        note = 2'-fluoroguanosine
modified_base           8
                        mod_base = OTHER
                        note = 2'-fluoroguanosine
modified_base           9
                        mod_base = OTHER
                        note = 2'-fluoroadenosine
modified_base           10
                        mod_base = OTHER
                        note = 2'-O-methyluridine
modified_base           11
                        mod_base = OTHER
                        note = 2'-O-methyluridine
modified_base           12
                        mod_base = OTHER
                        note = 2'-O-methyladenosine
modified_base           13
                        mod_base = OTHER
                        note = 2'-O-methylguanosine
modified_base           14
                        mod_base = OTHER
                        note = 2'-O-methyladenosine
modified_base           15
                        mod_base = OTHER
                        note = 2'-O-methylguanosine
modified_base           16
                        mod_base = OTHER
                        note = 2'-O-methyluridine
modified_base           17
                        mod_base = OTHER
                        note = 2'-O-methyluridine phosphorothioate
modified_base           18
                        mod_base = OTHER
                        note = 2'-O-methyladenosine phosphorothioate
modified_base           19
                        mod_base = OTHER
                        note = 2'-O-methyladenosine
SEQUENCE: 205
aaacctggat tagagttaa                                                  19

SEQ ID NO: 206          moltype = RNA   length = 19
FEATURE                 Location/Qualifiers
source                  1..19
                        mol_type = other RNA
                        organism = synthetic construct
modified_base           1
                        mod_base = OTHER
                        note = 2'-O-methylcytidine phosphorothioate
modified_base           2
                        mod_base = OTHER
                        note = 2'-O-methyluridine phosphorothioate
modified_base           3
                        mod_base = OTHER
                        note = 2'-O-methyluridine
modified_base           4
                        mod_base = OTHER
                        note = 2'-O-methyluridine
modified_base           5
                        mod_base = OTHER
                        note = 2'-O-methylguanosine
modified_base           6
                        mod_base = OTHER
                        note = 2'-O-methyladenosine
modified_base           7
                        mod_base = OTHER
                        note = 2'-fluoroguanosine
modified_base           8
                        mod_base = OTHER
                        note = 2'-fluoroadenosine
modified_base           9
                        mod_base = OTHER
                        note = 2'-fluoroadenosine
modified_base           10
                        mod_base = OTHER
                        note = 2'-O-methylguanosine
modified_base           11
                        mod_base = OTHER
                        note = 2'-O-methylguanosine
modified_base           12
```

```
                        mod_base = OTHER
                        note = 2'-O-methyladenosine
modified_base           13
                        mod_base = OTHER
                        note = 2'-O-methyluridine
modified_base           14
                        mod_base = OTHER
                        note = 2'-O-methylcytidine
modified_base           15
                        mod_base = OTHER
                        note = 2'-O-methylguanosine
modified_base           16
                        mod_base = OTHER
                        note = 2'-O-methylcytidine
modified_base           17
                        mod_base = OTHER
                        note = 2'-O-methyluridine phosphorothioate
modified_base           18
                        mod_base = OTHER
                        note = 2'-O-methyluridine phosphorothioate
modified_base           19
                        mod_base = OTHER
                        note = 2'-O-methyladenosine
SEQUENCE: 206
ctttgagaag gatcgctta                                                 19

SEQ ID NO: 207          moltype = RNA   length = 19
FEATURE                 Location/Qualifiers
source                  1..19
                        mol_type = other RNA
                        organism = synthetic construct
modified_base           1
                        mod_base = OTHER
                        note = 2'-O-methylguanosine phosphorothioate
modified_base           2
                        mod_base = OTHER
                        note = 2'-O-methylcytidine phosphorothioate
modified_base           3
                        mod_base = OTHER
                        note = 2'-O-methylcytidine
modified_base           4
                        mod_base = OTHER
                        note = 2'-O-methylguanosine
modified_base           5
                        mod_base = OTHER
                        note = 2'-O-methylguanosine
modified_base           6
                        mod_base = OTHER
                        note = 2'-O-methylcytidine
modified_base           7
                        mod_base = OTHER
                        note = 2'-fluoroadenosine
modified_base           8
                        mod_base = OTHER
                        note = 2'-fluoroguanosine
modified_base           9
                        mod_base = OTHER
                        note = 2'-fluoroadenosine
modified_base           10
                        mod_base = OTHER
                        note = 2'-O-methylguanosine
modified_base           11
                        mod_base = OTHER
                        note = 2'-O-methylguanosine
modified_base           12
                        mod_base = OTHER
                        note = 2'-O-methylguanosine
modified_base           13
                        mod_base = OTHER
                        note = 2'-O-methylguanosine
modified_base           14
                        mod_base = OTHER
                        note = 2'-O-methyladenosine
modified_base           15
                        mod_base = OTHER
                        note = 2'-O-methyluridine
modified_base           16
                        mod_base = OTHER
                        note = 2'-O-methylcytidine
```

| | |
|---|---|
| modified_base | 17<br>mod_base = OTHER<br>note = 2'-O-methyluridine phosphorothioate |
| modified_base | 18<br>mod_base = OTHER<br>note = 2'-O-methylcytidine phosphorothioate |
| modified_base | 19<br>mod_base = OTHER<br>note = 2'-O-methyladenosine |
| SEQUENCE: 207 | |
| gccggcagag gggatctca | 19 |
| | |
| SEQ ID NO: 208<br>FEATURE<br>source | moltype = RNA length = 19<br>Location/Qualifiers<br>1..19<br>mol_type = other RNA<br>organism = synthetic construct |
| modified_base | 1<br>mod_base = OTHER<br>note = 2'-O-methylguanosine phosphorothioate |
| modified_base | 2<br>mod_base = OTHER<br>note = 2'-O-methylguanosine phosphorothioate |
| modified_base | 3<br>mod_base = OTHER<br>note = 2'-O-methylguanosine |
| modified_base | 4<br>mod_base = OTHER<br>note = 2'-O-methylcytidine |
| modified_base | 5<br>mod_base = OTHER<br>note = 2'-O-methylcytidine |
| modified_base | 6<br>mod_base = OTHER<br>note = 2'-O-methyladenosine |
| modified_base | 7<br>mod_base = OTHER<br>note = 2'-fluoroadenosine |
| modified_base | 8<br>mod_base = OTHER<br>note = 2'-fluoroguanosine |
| modified_base | 9<br>mod_base = OTHER<br>note = 2'-fluoroguanosine |
| modified_base | 10<br>mod_base = OTHER<br>note = 2'-O-methylguanosine |
| modified_base | 11<br>mod_base = OTHER<br>note = 2'-O-methylguanosine |
| modified_base | 12<br>mod_base = OTHER<br>note = 2'-O-methyluridine |
| modified_base | 13<br>mod_base = OTHER<br>note = 2'-O-methylguanosine |
| modified_base | 14<br>mod_base = OTHER<br>note = 2'-O-methylcytidine |
| modified_base | 15<br>mod_base = OTHER<br>note = 2'-O-methyluridine |
| modified_base | 16<br>mod_base = OTHER<br>note = 2'-O-methyluridine |
| modified_base | 17<br>mod_base = OTHER<br>note = 2'-O-methylguanosine phosphorothioate |
| modified_base | 18<br>mod_base = OTHER<br>note = 2'-O-methylcytidine phosphorothioate |
| modified_base | 19<br>mod_base = OTHER<br>note = 2'-O-methyladenosine |
| SEQUENCE: 208 | |
| gggccaaggg gtgcttgca | 19 |
| | |
| SEQ ID NO: 209<br>FEATURE | moltype = RNA length = 19<br>Location/Qualifiers |

| | | |
|---|---|---|
| source | 1..19 | |
| | mol_type = other RNA | |
| | organism = synthetic construct | |
| modified_base | 1 | |
| | mod_base = OTHER | |
| | note = 2'-O-methylguanosine phosphorothioate | |
| modified_base | 2 | |
| | mod_base = OTHER | |
| | note = 2'-O-methylcytidine phosphorothioate | |
| modified_base | 3 | |
| | mod_base = OTHER | |
| | note = 2'-O-methylcytidine | |
| modified_base | 4 | |
| | mod_base = OTHER | |
| | note = 2'-O-methyladenosine | |
| modified_base | 5 | |
| | mod_base = OTHER | |
| | note = 2'-O-methyladenosine | |
| modified_base | 6 | |
| | mod_base = OTHER | |
| | note = 2'-O-methylguanosine | |
| modified_base | 7 | |
| | mod_base = OTHER | |
| | note = 2'-fluoroguanosine | |
| modified_base | 8 | |
| | mod_base = OTHER | |
| | note = 2'-fluoroguanosine | |
| modified_base | 9 | |
| | mod_base = OTHER | |
| | note = 2'-fluoroguanosine | |
| modified_base | 10 | |
| | mod_base = OTHER | |
| | note = 2'-O-methyluridine | |
| modified_base | 11 | |
| | mod_base = OTHER | |
| | note = 2'-O-methylguanosine | |
| modified_base | 12 | |
| | mod_base = OTHER | |
| | note = 2'-O-methylcytidine | |
| modified_base | 13 | |
| | mod_base = OTHER | |
| | note = 2'-O-methyluridine | |
| modified_base | 14 | |
| | mod_base = OTHER | |
| | note = 2'-O-methyluridine | |
| modified_base | 15 | |
| | mod_base = OTHER | |
| | note = 2'-O-methylguanosine | |
| modified_base | 16 | |
| | mod_base = OTHER | |
| | note = 2'-O-methylcytidine | |
| modified_base | 17 | |
| | mod_base = OTHER | |
| | note = 2'-O-methylguanosine phosphorothioate | |
| modified_base | 18 | |
| | mod_base = OTHER | |
| | note = 2'-O-methylcytidine phosphorothioate | |
| modified_base | 19 | |
| | mod_base = OTHER | |
| | note = 2'-O-methyladenosine | |
| SEQUENCE: 209 | | |
| gccaaggggt gcttgcgca | | 19 |
| | | |
| SEQ ID NO: 210 | moltype = RNA   length = 19 | |
| FEATURE | Location/Qualifiers | |
| source | 1..19 | |
| | mol_type = other RNA | |
| | organism = synthetic construct | |
| modified_base | 1 | |
| | mod_base = OTHER | |
| | note = 2'-O-methyladenosine phosphorothioate | |
| modified_base | 2 | |
| | mod_base = OTHER | |
| | note = 2'-O-methyluridine phosphorothioate | |
| modified_base | 3 | |
| | mod_base = OTHER | |
| | note = 2'-O-methylguanosine | |
| modified_base | 4 | |
| | mod_base = OTHER | |

```
                      note = 2'-O-methylcytidine
modified_base         5
                      mod_base = OTHER
                      note = 2'-O-methyladenosine
modified_base         6
                      mod_base = OTHER
                      note = 2'-O-methyladenosine
modified_base         7
                      mod_base = OTHER
                      note = 2'-fluoroguanosine
modified_base         8
                      mod_base = OTHER
                      note = 2'-fluoroguanosine
modified_base         9
                      mod_base = OTHER
                      note = 2'-fluorocytidine
modified_base         10
                      mod_base = OTHER
                      note = 2'-O-methyladenosine
modified_base         11
                      mod_base = OTHER
                      note = 2'-O-methyluridine
modified_base         12
                      mod_base = OTHER
                      note = 2'-O-methylcytidine
modified_base         13
                      mod_base = OTHER
                      note = 2'-O-methylcytidine
modified_base         14
                      mod_base = OTHER
                      note = 2'-O-methylcytidine
modified_base         15
                      mod_base = OTHER
                      note = 2'-O-methylguanosine
modified_base         16
                      mod_base = OTHER
                      note = 2'-O-methylguanosine
modified_base         17
                      mod_base = OTHER
                      note = 2'-O-methylcytidine phosphorothioate
modified_base         18
                      mod_base = OTHER
                      note = 2'-O-methylguanosine phosphorothioate
modified_base         19
                      mod_base = OTHER
                      note = 2'-O-methyladenosine
SEQUENCE: 210
atgcaaggca tcccggcga                                                  19

SEQ ID NO: 211        moltype = RNA   length = 21
FEATURE               Location/Qualifiers
source                1..21
                      mol_type = other RNA
                      organism = synthetic construct
modified_base         1
                      mod_base = OTHER
                      note = 2'-fluorouridine phosphorothioate
modified_base         2
                      mod_base = OTHER
                      note = 2'-fluorouridine phosphorothioate
modified_base         3
                      mod_base = OTHER
                      note = 2'-O-methylguanosine
modified_base         4
                      mod_base = OTHER
                      note = 2'-O-methylcytidine
modified_base         5
                      mod_base = OTHER
                      note = 2'-O-methyluridine
modified_base         6
                      mod_base = OTHER
                      note = 2'-fluoroguanosine
modified_base         7
                      mod_base = OTHER
                      note = 2'-O-methyluridine
modified_base         8
                      mod_base = OTHER
                      note = 2'-O-methylcytidine
modified_base         9
```

|  |  |
|---|---|
|  | mod_base = OTHER |
|  | note = 2'-O-methylcytidine |
| modified_base | 10 |
|  | mod_base = OTHER |
|  | note = 2'-O-methylguanosine |
| modified_base | 11 |
|  | mod_base = OTHER |
|  | note = 2'-O-methyladenosine |
| modified_base | 12 |
|  | mod_base = OTHER |
|  | note = 2'-O-methylguanosine |
| modified_base | 13 |
|  | mod_base = OTHER |
|  | note = 2'-O-methylguanosine |
| modified_base | 14 |
|  | mod_base = OTHER |
|  | note = 2'-fluoroguanosine |
| modified_base | 15 |
|  | mod_base = OTHER |
|  | note = 2'-O-methyluridine |
| modified_base | 16 |
|  | mod_base = OTHER |
|  | note = 2'-fluoroguanosine |
| modified_base | 17 |
|  | mod_base = OTHER |
|  | note = 2'-O-methyluridine |
| modified_base | 18 |
|  | mod_base = OTHER |
|  | note = 2'-O-methylcytidine |
| modified_base | 19 |
|  | mod_base = OTHER |
|  | note = 2'-O-methylguanosine phosphorothioate |
| modified_base | 20 |
|  | mod_base = OTHER |
|  | note = 2'-O-methyluridine phosphorothioate |
| modified_base | 21 |
|  | mod_base = OTHER |
|  | note = 2'-O-methyluridine |
| SEQUENCE: 211 |  |
| ttgctgtccg agggtgtcgt t | 21 |
|  |  |
| SEQ ID NO: 212 | moltype = RNA  length = 21 |
| FEATURE | Location/Qualifiers |
| source | 1..21 |
|  | mol_type = other RNA |
|  | organism = synthetic construct |
| modified_base | 1 |
|  | mod_base = OTHER |
|  | note = 2'-fluorouridine phosphorothioate |
| modified_base | 2 |
|  | mod_base = OTHER |
|  | note = 2'-fluoroadenosine phosphorothioate |
| modified_base | 3 |
|  | mod_base = OTHER |
|  | note = 2'-O-methylcytidine |
| modified_base | 4 |
|  | mod_base = OTHER |
|  | note = 2'-O-methylguanosine |
| modified_base | 5 |
|  | mod_base = OTHER |
|  | note = 2'-O-methyladenosine |
| modified_base | 6 |
|  | mod_base = OTHER |
|  | note = 2'-fluoroguanosine |
| modified_base | 7 |
|  | mod_base = OTHER |
|  | note = 2'-O-methyluridine |
| modified_base | 8 |
|  | mod_base = OTHER |
|  | note = 2'-O-methylcytidine |
| modified_base | 9 |
|  | mod_base = OTHER |
|  | note = 2'-O-methyluridine |
| modified_base | 10 |
|  | mod_base = OTHER |
|  | note = 2'-O-methylcytidine |
| modified_base | 11 |
|  | mod_base = OTHER |
|  | note = 2'-O-methylcytidine |

```
modified_base        12
                     mod_base = OTHER
                     note = 2'-O-methylguanosine
modified_base        13
                     mod_base = OTHER
                     note = 2'-O-methyluridine
modified_base        14
                     mod_base = OTHER
                     note = 2'-fluorocytidine
modified_base        15
                     mod_base = OTHER
                     note = 2'-O-methylguanosine
modified_base        16
                     mod_base = OTHER
                     note = 2'-fluorocytidine
modified_base        17
                     mod_base = OTHER
                     note = 2'-O-methylcytidine
modified_base        18
                     mod_base = OTHER
                     note = 2'-O-methylguanosine
modified_base        19
                     mod_base = OTHER
                     note = 2'-O-methyluridine phosphorothioate
modified_base        20
                     mod_base = OTHER
                     note = 2'-O-methyluridine phosphorothioate
modified_base        21
                     mod_base = OTHER
                     note = 2'-O-methyluridine
SEQUENCE: 212
tacgagtctc cgtcgccgtt t                                              21

SEQ ID NO: 213       moltype = RNA  length = 21
FEATURE              Location/Qualifiers
source               1..21
                     mol_type = other RNA
                     organism = synthetic construct
modified_base        1
                     mod_base = OTHER
                     note = 2'-fluorouridine phosphorothioate
modified_base        2
                     mod_base = OTHER
                     note = 2'-fluoroadenosine phosphorothioate
modified_base        3
                     mod_base = OTHER
                     note = 2'-O-methyladenosine
modified_base        4
                     mod_base = OTHER
                     note = 2'-O-methylcytidine
modified_base        5
                     mod_base = OTHER
                     note = 2'-O-methylguanosine
modified_base        6
                     mod_base = OTHER
                     note = 2'-fluoroadenosine
modified_base        7
                     mod_base = OTHER
                     note = 2'-O-methylguanosine
modified_base        8
                     mod_base = OTHER
                     note = 2'-O-methyluridine
modified_base        9
                     mod_base = OTHER
                     note = 2'-O-methylcytidine
modified_base        10
                     mod_base = OTHER
                     note = 2'-O-methyluridine
modified_base        11
                     mod_base = OTHER
                     note = 2'-O-methylcytidine
modified_base        12
                     mod_base = OTHER
                     note = 2'-O-methylcytidine
modified_base        13
                     mod_base = OTHER
                     note = 2'-O-methylguanosine
modified_base        14
                     mod_base = OTHER
```

|     |     |
| --- | --- |
|  | note = 2'-fluorouridine |
| modified_base | 15 |
|  | mod_base = OTHER |
|  | note = 2'-O-methylcytidine |
| modified_base | 16 |
|  | mod_base = OTHER |
|  | note = 2'-fluoroguanosine |
| modified_base | 17 |
|  | mod_base = OTHER |
|  | note = 2'-O-methylcytidine |
| modified_base | 18 |
|  | mod_base = OTHER |
|  | note = 2'-O-methylcytidine |
| modified_base | 19 |
|  | mod_base = OTHER |
|  | note = 2'-O-methylguanosine phosphorothioate |
| modified_base | 20 |
|  | mod_base = OTHER |
|  | note = 2'-O-methyluridine phosphorothioate |
| modified_base | 21 |
|  | mod_base = OTHER |
|  | note = 2'-O-methyluridine |
| SEQUENCE: 213 | |
| taacgagtct ccgtcgccgt t | 21 |
| SEQ ID NO: 214 | moltype = RNA length = 21 |
| FEATURE | Location/Qualifiers |
| source | 1..21 |
|  | mol_type = other RNA |
|  | organism = synthetic construct |
| modified_base | 1 |
|  | mod_base = OTHER |
|  | note = 2'-fluorouridine phosphorothioate |
| modified_base | 2 |
|  | mod_base = OTHER |
|  | note = 2'-fluoroadenosine phosphorothioate |
| modified_base | 3 |
|  | mod_base = OTHER |
|  | note = 2'-O-methyladenosine |
| modified_base | 4 |
|  | mod_base = OTHER |
|  | note = 2'-O-methyladenosine |
| modified_base | 5 |
|  | mod_base = OTHER |
|  | note = 2'-O-methylcytidine |
| modified_base | 6 |
|  | mod_base = OTHER |
|  | note = 2'-fluoroguanosine |
| modified_base | 7 |
|  | mod_base = OTHER |
|  | note = 2'-O-methyladenosine |
| modified_base | 8 |
|  | mod_base = OTHER |
|  | note = 2'-O-methylguanosine |
| modified_base | 9 |
|  | mod_base = OTHER |
|  | note = 2'-O-methyluridine |
| modified_base | 10 |
|  | mod_base = OTHER |
|  | note = 2'-O-methylcytidine |
| modified_base | 11 |
|  | mod_base = OTHER |
|  | note = 2'-O-methyluridine |
| modified_base | 12 |
|  | mod_base = OTHER |
|  | note = 2'-O-methylcytidine |
| modified_base | 13 |
|  | mod_base = OTHER |
|  | note = 2'-O-methylcytidine |
| modified_base | 14 |
|  | mod_base = OTHER |
|  | note = 2'-fluoroguanosine |
| modified_base | 15 |
|  | mod_base = OTHER |
|  | note = 2'-O-methyluridine |
| modified_base | 16 |
|  | mod_base = OTHER |
|  | note = 2'-fluorocytidine |
| modified_base | 17 |

```
                         mod_base = OTHER
                         note = 2'-O-methylguanosine
modified_base            18
                         mod_base = OTHER
                         note = 2'-O-methylcytidine
modified_base            19
                         mod_base = OTHER
                         note = 2'-O-methylcytidine phosphorothioate
modified_base            20
                         mod_base = OTHER
                         note = 2'-O-methyluridine phosphorothioate
modified_base            21
                         mod_base = OTHER
                         note = 2'-O-methyluridine
SEQUENCE: 214
taaacgagtc tccgtcgcct t                                            21

SEQ ID NO: 215           moltype = RNA  length = 21
FEATURE                  Location/Qualifiers
source                   1..21
                         mol_type = other RNA
                         organism = synthetic construct
modified_base            1
                         mod_base = OTHER
                         note = 2'-fluorouridine phosphorothioate
modified_base            2
                         mod_base = OTHER
                         note = 2'-fluorocytidine phosphorothioate
modified_base            3
                         mod_base = OTHER
                         note = 2'-O-methyladenosine
modified_base            4
                         mod_base = OTHER
                         note = 2'-O-methyladenosine
modified_base            5
                         mod_base = OTHER
                         note = 2'-O-methyladenosine
modified_base            6
                         mod_base = OTHER
                         note = 2'-fluorocytidine
modified_base            7
                         mod_base = OTHER
                         note = 2'-O-methylguanosine
modified_base            8
                         mod_base = OTHER
                         note = 2'-O-methyladenosine
modified_base            9
                         mod_base = OTHER
                         note = 2'-O-methylguanosine
modified_base            10
                         mod_base = OTHER
                         note = 2'-O-methyluridine
modified_base            11
                         mod_base = OTHER
                         note = 2'-O-methylcytidine
modified_base            12
                         mod_base = OTHER
                         note = 2'-O-methyluridine
modified_base            13
                         mod_base = OTHER
                         note = 2'-O-methylcytidine
modified_base            14
                         mod_base = OTHER
                         note = 2'-fluorocytidine
modified_base            15
                         mod_base = OTHER
                         note = 2'-O-methylguanosine
modified_base            16
                         mod_base = OTHER
                         note = 2'-fluorouridine
modified_base            17
                         mod_base = OTHER
                         note = 2'-O-methylcytidine
modified_base            18
                         mod_base = OTHER
                         note = 2'-O-methylguanosine
modified_base            19
                         mod_base = OTHER
                         note = 2'-O-methylcytidine phosphorothioate
```

| | | |
|---|---|---|
| modified_base | 20 | |
| | mod_base = OTHER | |
| | note = 2'-O-methyluridine phosphorothioate | |
| modified_base | 21 | |
| | mod_base = OTHER | |
| | note = 2'-O-methyluridine | |
| SEQUENCE: 215 | | |
| tcaaacgagt ctccgtcgct t | | 21 |
| | | |
| SEQ ID NO: 216 | moltype = RNA  length = 21 | |
| FEATURE | Location/Qualifiers | |
| source | 1..21 | |
| | mol_type = other RNA | |
| | organism = synthetic construct | |
| modified_base | 1 | |
| | mod_base = OTHER | |
| | note = 2'-fluorouridine phosphorothioate | |
| modified_base | 2 | |
| | mod_base = OTHER | |
| | note = 2'-fluorocytidine phosphorothioate | |
| modified_base | 3 | |
| | mod_base = OTHER | |
| | note = 2'-O-methylcytidine | |
| modified_base | 4 | |
| | mod_base = OTHER | |
| | note = 2'-O-methyladenosine | |
| modified_base | 5 | |
| | mod_base = OTHER | |
| | note = 2'-O-methyladenosine | |
| modified_base | 6 | |
| | mod_base = OTHER | |
| | note = 2'-fluoroadenosine | |
| modified_base | 7 | |
| | mod_base = OTHER | |
| | note = 2'-O-methylcytidine | |
| modified_base | 8 | |
| | mod_base = OTHER | |
| | note = 2'-O-methylguanosine | |
| modified_base | 9 | |
| | mod_base = OTHER | |
| | note = 2'-O-methyladenosine | |
| modified_base | 10 | |
| | mod_base = OTHER | |
| | note = 2'-O-methylguanosine | |
| modified_base | 11 | |
| | mod_base = OTHER | |
| | note = 2'-O-methyluridine | |
| modified_base | 12 | |
| | mod_base = OTHER | |
| | note = 2'-O-methylcytidine | |
| modified_base | 13 | |
| | mod_base = OTHER | |
| | note = 2'-O-methyluridine | |
| modified_base | 14 | |
| | mod_base = OTHER | |
| | note = 2'-fluorocytidine | |
| modified_base | 15 | |
| | mod_base = OTHER | |
| | note = 2'-O-methylcytidine | |
| modified_base | 16 | |
| | mod_base = OTHER | |
| | note = 2'-fluoroguanosine | |
| modified_base | 17 | |
| | mod_base = OTHER | |
| | note = 2'-O-methyluridine | |
| modified_base | 18 | |
| | mod_base = OTHER | |
| | note = 2'-O-methylcytidine | |
| modified_base | 19 | |
| | mod_base = OTHER | |
| | note = 2'-O-methylguanosine phosphorothioate | |
| modified_base | 20 | |
| | mod_base = OTHER | |
| | note = 2'-O-methyluridine phosphorothioate | |
| modified_base | 21 | |
| | mod_base = OTHER | |
| | note = 2'-O-methyluridine | |
| SEQUENCE: 216 | | |
| tccaaacgag tctccgtcgt t | | 21 |

```
SEQ ID NO: 217         moltype = RNA  length = 21
FEATURE                Location/Qualifiers
source                 1..21
                       mol_type = other RNA
                       organism = synthetic construct
modified_base          1
                       mod_base = OTHER
                       note = 2'-fluorouridine phosphorothioate
modified_base          2
                       mod_base = OTHER
                       note = 2'-fluorouridine phosphorothioate
modified_base          3
                       mod_base = OTHER
                       note = 2'-O-methylcytidine
modified_base          4
                       mod_base = OTHER
                       note = 2'-O-methylcytidine
modified_base          5
                       mod_base = OTHER
                       note = 2'-O-methyladenosine
modified_base          6
                       mod_base = OTHER
                       note = 2'-fluoroadenosine
modified_base          7
                       mod_base = OTHER
                       note = 2'-O-methyladenosine
modified_base          8
                       mod_base = OTHER
                       note = 2'-O-methylcytidine
modified_base          9
                       mod_base = OTHER
                       note = 2'-O-methylguanosine
modified_base          10
                       mod_base = OTHER
                       note = 2'-O-methyladenosine
modified_base          11
                       mod_base = OTHER
                       note = 2'-O-methylguanosine
modified_base          12
                       mod_base = OTHER
                       note = 2'-O-methyluridine
modified_base          13
                       mod_base = OTHER
                       note = 2'-O-methylcytidine
modified_base          14
                       mod_base = OTHER
                       note = 2'-fluorouridine
modified_base          15
                       mod_base = OTHER
                       note = 2'-O-methylcytidine
modified_base          16
                       mod_base = OTHER
                       note = 2'-fluorocytidine
modified_base          17
                       mod_base = OTHER
                       note = 2'-O-methylguanosine
modified_base          18
                       mod_base = OTHER
                       note = 2'-O-methyluridine
modified_base          19
                       mod_base = OTHER
                       note = 2'-O-methylcytidine phosphorothioate
modified_base          20
                       mod_base = OTHER
                       note = 2'-O-methyluridine phosphorothioate
modified_base          21
                       mod_base = OTHER
                       note = 2'-O-methyluridine
SEQUENCE: 217
ttccaaacga gtctccgtct t                                             21

SEQ ID NO: 218         moltype = RNA  length = 21
FEATURE                Location/Qualifiers
source                 1..21
                       mol_type = other RNA
                       organism = synthetic construct
modified_base          1
                       mod_base = OTHER
```

```
                        note = 2'-fluorouridine phosphorothioate
modified_base           2
                        mod_base = OTHER
                        note = 2'-fluoroguanosine phosphorothioate
modified_base           3
                        mod_base = OTHER
                        note = 2'-O-methyluridine
modified_base           4
                        mod_base = OTHER
                        note = 2'-O-methylcytidine
modified_base           5
                        mod_base = OTHER
                        note = 2'-O-methylcytidine
modified_base           6
                        mod_base = OTHER
                        note = 2'-fluoroadenosine
modified_base           7
                        mod_base = OTHER
                        note = 2'-O-methyladenosine
modified_base           8
                        mod_base = OTHER
                        note = 2'-O-methyladenosine
modified_base           9
                        mod_base = OTHER
                        note = 2'-O-methylcytidine
modified_base           10
                        mod_base = OTHER
                        note = 2'-O-methylguanosine
modified_base           11
                        mod_base = OTHER
                        note = 2'-O-methyladenosine
modified_base           12
                        mod_base = OTHER
                        note = 2'-O-methylguanosine
modified_base           13
                        mod_base = OTHER
                        note = 2'-O-methyluridine
modified_base           14
                        mod_base = OTHER
                        note = 2'-fluorocytidine
modified_base           15
                        mod_base = OTHER
                        note = 2'-O-methyluridine
modified_base           16
                        mod_base = OTHER
                        note = 2'-fluorocytidine
modified_base           17
                        mod_base = OTHER
                        note = 2'-O-methylcytidine
modified_base           18
                        mod_base = OTHER
                        note = 2'-O-methylguanosine
modified_base           19
                        mod_base = OTHER
                        note = 2'-O-methyluridine phosphorothioate
modified_base           20
                        mod_base = OTHER
                        note = 2'-O-methyluridine phosphorothioate
modified_base           21
                        mod_base = OTHER
                        note = 2'-O-methyluridine
SEQUENCE: 218
tgtccaaacg agtctccgtt t                                              21

SEQ ID NO: 219          moltype = RNA   length = 21
FEATURE                 Location/Qualifiers
source                  1..21
                        mol_type = other RNA
                        organism = synthetic construct
modified_base           1
                        mod_base = OTHER
                        note = 2'-fluorouridine phosphorothioate
modified_base           2
                        mod_base = OTHER
                        note = 2'-fluorocytidine phosphorothioate
modified_base           3
                        mod_base = OTHER
                        note = 2'-O-methylguanosine
modified_base           4
```

|                | mod_base = OTHER |
|                | note = 2'-O-methylcytidine |
| modified_base | 5 |
|                | mod_base = OTHER |
|                | note = 2'-O-methyluridine |
| modified_base | 6 |
|                | mod_base = OTHER |
|                | note = 2'-fluorouridine |
| modified_base | 7 |
|                | mod_base = OTHER |
|                | note = 2'-O-methyluridine |
| modified_base | 8 |
|                | mod_base = OTHER |
|                | note = 2'-O-methylguanosine |
| modified_base | 9 |
|                | mod_base = OTHER |
|                | note = 2'-O-methylguanosine |
| modified_base | 10 |
|                | mod_base = OTHER |
|                | note = 2'-O-methylcytidine |
| modified_base | 11 |
|                | mod_base = OTHER |
|                | note = 2'-O-methyluridine |
| modified_base | 12 |
|                | mod_base = OTHER |
|                | note = 2'-O-methylcytidine |
| modified_base | 13 |
|                | mod_base = OTHER |
|                | note = 2'-O-methylguanosine |
| modified_base | 14 |
|                | mod_base = OTHER |
|                | note = 2'-fluoroguanosine |
| modified_base | 15 |
|                | mod_base = OTHER |
|                | note = 2'-O-methylguanosine |
| modified_base | 16 |
|                | mod_base = OTHER |
|                | note = 2'-fluoroguanosine |
| modified_base | 17 |
|                | mod_base = OTHER |
|                | note = 2'-O-methyluridine |
| modified_base | 18 |
|                | mod_base = OTHER |
|                | note = 2'-O-methylcytidine |
| modified_base | 19 |
|                | mod_base = OTHER |
|                | note = 2'-O-methylcytidine phosphorothioate |
| modified_base | 20 |
|                | mod_base = OTHER |
|                | note = 2'-O-methyluridine phosphorothioate |
| modified_base | 21 |
|                | mod_base = OTHER |
|                | note = 2'-O-methyluridine |

SEQUENCE: 219
tcgctttggc tcggggtcct t    21

| SEQ ID NO: 220 | moltype = RNA   length = 21 |
| FEATURE | Location/Qualifiers |
| source | 1..21 |
|        | mol_type = other RNA |
|        | organism = synthetic construct |
| modified_base | 1 |
|                | mod_base = OTHER |
|                | note = 2'-fluorouridine phosphorothioate |
| modified_base | 2 |
|                | mod_base = OTHER |
|                | note = 2'-fluorouridine phosphorothioate |
| modified_base | 3 |
|                | mod_base = OTHER |
|                | note = 2'-O-methylcytidine |
| modified_base | 4 |
|                | mod_base = OTHER |
|                | note = 2'-O-methylguanosine |
| modified_base | 5 |
|                | mod_base = OTHER |
|                | note = 2'-O-methylcytidine |
| modified_base | 6 |
|                | mod_base = OTHER |
|                | note = 2'-fluorouridine |

```
modified_base       7
                    mod_base = OTHER
                    note = 2'-O-methyluridine
modified_base       8
                    mod_base = OTHER
                    note = 2'-O-methyluridine
modified_base       9
                    mod_base = OTHER
                    note = 2'-O-methylguanosine
modified_base       10
                    mod_base = OTHER
                    note = 2'-O-methylguanosine
modified_base       11
                    mod_base = OTHER
                    note = 2'-O-methylcytidine
modified_base       12
                    mod_base = OTHER
                    note = 2'-O-methyluridine
modified_base       13
                    mod_base = OTHER
                    note = 2'-O-methylcytidine
modified_base       14
                    mod_base = OTHER
                    note = 2'-fluoroguanosine
modified_base       15
                    mod_base = OTHER
                    note = 2'-O-methylguanosine
modified_base       16
                    mod_base = OTHER
                    note = 2'-fluoroguanosine
modified_base       17
                    mod_base = OTHER
                    note = 2'-O-methylguanosine
modified_base       18
                    mod_base = OTHER
                    note = 2'-O-methyluridine
modified_base       19
                    mod_base = OTHER
                    note = 2'-O-methylcytidine phosphorothioate
modified_base       20
                    mod_base = OTHER
                    note = 2'-O-methyluridine phosphorothioate
modified_base       21
                    mod_base = OTHER
                    note = 2'-O-methyluridine
SEQUENCE: 220
ttcgctttgg ctcgggtct t                                              21

SEQ ID NO: 221      moltype = RNA   length = 21
FEATURE             Location/Qualifiers
source              1..21
                    mol_type = other RNA
                    organism = synthetic construct
modified_base       1
                    mod_base = OTHER
                    note = 2'-fluorouridine phosphorothioate
modified_base       2
                    mod_base = OTHER
                    note = 2'-fluorocytidine phosphorothioate
modified_base       3
                    mod_base = OTHER
                    note = 2'-O-methyluridine
modified_base       4
                    mod_base = OTHER
                    note = 2'-O-methylcytidine
modified_base       5
                    mod_base = OTHER
                    note = 2'-O-methylguanosine
modified_base       6
                    mod_base = OTHER
                    note = 2'-fluorocytidine
modified_base       7
                    mod_base = OTHER
                    note = 2'-O-methyluridine
modified_base       8
                    mod_base = OTHER
                    note = 2'-O-methyluridine
modified_base       9
                    mod_base = OTHER
```

```
                        note = 2'-O-methyluridine
modified_base           10
                        mod_base = OTHER
                        note = 2'-O-methylguanosine
modified_base           11
                        mod_base = OTHER
                        note = 2'-O-methylguanosine
modified_base           12
                        mod_base = OTHER
                        note = 2'-O-methylcytidine
modified_base           13
                        mod_base = OTHER
                        note = 2'-O-methyluridine
modified_base           14
                        mod_base = OTHER
                        note = 2'-fluorocytidine
modified_base           15
                        mod_base = OTHER
                        note = 2'-O-methylguanosine
modified_base           16
                        mod_base = OTHER
                        note = 2'-fluoroguanosine
modified_base           17
                        mod_base = OTHER
                        note = 2'-O-methylguanosine
modified_base           18
                        mod_base = OTHER
                        note = 2'-O-methylguanosine
modified_base           19
                        mod_base = OTHER
                        note = 2'-O-methyluridine phosphorothioate
modified_base           20
                        mod_base = OTHER
                        note = 2'-O-methyluridine phosphorothioate
modified_base           21
                        mod_base = OTHER
                        note = 2'-O-methyluridine
SEQUENCE: 221
tctcgctttg gctcggggtt t                                              21

SEQ ID NO: 222          moltype = RNA   length = 21
FEATURE                 Location/Qualifiers
source                  1..21
                        mol_type = other RNA
                        organism = synthetic construct
modified_base           1
                        mod_base = OTHER
                        note = 2'-fluorouridine phosphorothioate
modified_base           2
                        mod_base = OTHER
                        note = 2'-fluorouridine phosphorothioate
modified_base           3
                        mod_base = OTHER
                        note = 2'-O-methylcytidine
modified_base           4
                        mod_base = OTHER
                        note = 2'-O-methyladenosine
modified_base           5
                        mod_base = OTHER
                        note = 2'-O-methyladenosine
modified_base           6
                        mod_base = OTHER
                        note = 2'-fluoroadenosine
modified_base           7
                        mod_base = OTHER
                        note = 2'-O-methylguanosine
modified_base           8
                        mod_base = OTHER
                        note = 2'-O-methylcytidine
modified_base           9
                        mod_base = OTHER
                        note = 2'-O-methyladenosine
modified_base           10
                        mod_base = OTHER
                        note = 2'-O-methylguanosine
modified_base           11
                        mod_base = OTHER
                        note = 2'-O-methylguanosine
modified_base           12
```

```
                        mod_base = OTHER
                        note = 2'-O-methylcytidine
modified_base           13
                        mod_base = OTHER
                        note = 2'-O-methyluridine
modified_base           14
                        mod_base = OTHER
                        note = 2'-fluorocytidine
modified_base           15
                        mod_base = OTHER
                        note = 2'-O-methylguanosine
modified_base           16
                        mod_base = OTHER
                        note = 2'-fluorocytidine
modified_base           17
                        mod_base = OTHER
                        note = 2'-O-methyladenosine
modified_base           18
                        mod_base = OTHER
                        note = 2'-O-methylguanosine
modified_base           19
                        mod_base = OTHER
                        note = 2'-O-methylguanosine phosphorothioate
modified_base           20
                        mod_base = OTHER
                        note = 2'-O-methyluridine phosphorothioate
modified_base           21
                        mod_base = OTHER
                        note = 2'-O-methyluridine
SEQUENCE: 222
ttcaaagcag gctcgcaggt t                                              21

SEQ ID NO: 223          moltype = RNA   length = 21
FEATURE                 Location/Qualifiers
source                  1..21
                        mol_type = other RNA
                        organism = synthetic construct
modified_base           1
                        mod_base = OTHER
                        note = 2'-fluorouridine phosphorothioate
modified_base           2
                        mod_base = OTHER
                        note = 2'-fluorocytidine phosphorothioate
modified_base           3
                        mod_base = OTHER
                        note = 2'-O-methylguanosine
modified_base           4
                        mod_base = OTHER
                        note = 2'-O-methylcytidine
modified_base           5
                        mod_base = OTHER
                        note = 2'-O-methyluridine
modified_base           6
                        mod_base = OTHER
                        note = 2'-fluorocytidine
modified_base           7
                        mod_base = OTHER
                        note = 2'-O-methyladenosine
modified_base           8
                        mod_base = OTHER
                        note = 2'-O-methyladenosine
modified_base           9
                        mod_base = OTHER
                        note = 2'-O-methyladenosine
modified_base           10
                        mod_base = OTHER
                        note = 2'-O-methylguanosine
modified_base           11
                        mod_base = OTHER
                        note = 2'-O-methylcytidine
modified_base           12
                        mod_base = OTHER
                        note = 2'-O-methyladenosine
modified_base           13
                        mod_base = OTHER
                        note = 2'-O-methylguanosine
modified_base           14
                        mod_base = OTHER
                        note = 2'-fluoroguanosine
```

```
modified_base        15
                     mod_base = OTHER
                     note = 2'-O-methylcytidine
modified_base        16
                     mod_base = OTHER
                     note = 2'-fluorouridine
modified_base        17
                     mod_base = OTHER
                     note = 2'-O-methylcytidine
modified_base        18
                     mod_base = OTHER
                     note = 2'-O-methylguanosine
modified_base        19
                     mod_base = OTHER
                     note = 2'-O-methylcytidine phosphorothioate
modified_base        20
                     mod_base = OTHER
                     note = 2'-O-methyluridine phosphorothioate
modified_base        21
                     mod_base = OTHER
                     note = 2'-O-methyluridine
SEQUENCE: 223
tcgctcaaag caggctcgct t                                          21

SEQ ID NO: 224       moltype = RNA  length = 21
FEATURE              Location/Qualifiers
source               1..21
                     mol_type = other RNA
                     organism = synthetic construct
modified_base        1
                     mod_base = OTHER
                     note = 2'-fluorouridine phosphorothioate
modified_base        2
                     mod_base = OTHER
                     note = 2'-fluoroguanosine phosphorothioate
modified_base        3
                     mod_base = OTHER
                     note = 2'-O-methylcytidine
modified_base        4
                     mod_base = OTHER
                     note = 2'-O-methylcytidine
modified_base        5
                     mod_base = OTHER
                     note = 2'-O-methylguanosine
modified_base        6
                     mod_base = OTHER
                     note = 2'-fluorouridine
modified_base        7
                     mod_base = OTHER
                     note = 2'-O-methyluridine
modified_base        8
                     mod_base = OTHER
                     note = 2'-O-methylcytidine
modified_base        9
                     mod_base = OTHER
                     note = 2'-O-methyluridine
modified_base        10
                     mod_base = OTHER
                     note = 2'-O-methylcytidine
modified_base        11
                     mod_base = OTHER
                     note = 2'-O-methyluridine
modified_base        12
                     mod_base = OTHER
                     note = 2'-O-methylguanosine
modified_base        13
                     mod_base = OTHER
                     note = 2'-O-methylguanosine
modified_base        14
                     mod_base = OTHER
                     note = 2'-fluorouridine
modified_base        15
                     mod_base = OTHER
                     note = 2'-O-methylguanosine
modified_base        16
                     mod_base = OTHER
                     note = 2'-fluoroguanosine
modified_base        17
                     mod_base = OTHER
```

```
                         note = 2'-O-methylcytidine
modified_base            18
                         mod_base = OTHER
                         note = 2'-O-methylguanosine
modified_base            19
                         mod_base = OTHER
                         note = 2'-O-methyladenosine phosphorothioate
modified_base            20
                         mod_base = OTHER
                         note = 2'-O-methyluridine phosphorothioate
modified_base            21
                         mod_base = OTHER
                         note = 2'-O-methyluridine
SEQUENCE: 224
tgccgttctc tggtggcgat t                                          21

SEQ ID NO: 225           moltype = RNA  length = 21
FEATURE                  Location/Qualifiers
source                   1..21
                         mol_type = other RNA
                         organism = synthetic construct
modified_base            1
                         mod_base = OTHER
                         note = 2'-fluorouridine phosphorothioate
modified_base            2
                         mod_base = OTHER
                         note = 2'-fluorocytidine phosphorothioate
modified_base            3
                         mod_base = OTHER
                         note = 2'-O-methylguanosine
modified_base            4
                         mod_base = OTHER
                         note = 2'-O-methylguanosine
modified_base            5
                         mod_base = OTHER
                         note = 2'-O-methyladenosine
modified_base            6
                         mod_base = OTHER
                         note = 2'-fluoroadenosine
modified_base            7
                         mod_base = OTHER
                         note = 2'-O-methyluridine
modified_base            8
                         mod_base = OTHER
                         note = 2'-O-methylguanosine
modified_base            9
                         mod_base = OTHER
                         note = 2'-O-methylcytidine
modified_base            10
                         mod_base = OTHER
                         note = 2'-O-methylcytidine
modified_base            11
                         mod_base = OTHER
                         note = 2'-O-methylguanosine
modified_base            12
                         mod_base = OTHER
                         note = 2'-O-methyladenosine
modified_base            13
                         mod_base = OTHER
                         note = 2'-O-methyluridine
modified_base            14
                         mod_base = OTHER
                         note = 2'-fluoroguanosine
modified_base            15
                         mod_base = OTHER
                         note = 2'-O-methylguanosine
modified_base            16
                         mod_base = OTHER
                         note = 2'-fluorocytidine
modified_base            17
                         mod_base = OTHER
                         note = 2'-O-methylcytidine
modified_base            18
                         mod_base = OTHER
                         note = 2'-O-methyluridine
modified_base            19
                         mod_base = OTHER
                         note = 2'-O-methylguanosine phosphorothioate
modified_base            20
```

|  |  |
|---|---|
|  | mod_base = OTHER |
|  | note = 2'-O-methyluridine phosphorothioate |
| modified_base | 21 |
|  | mod_base = OTHER |
|  | note = 2'-O-methyluridine |
| SEQUENCE: 225 |  |
| tcggaatgcc gatggcctgt t | 21 |
|  |  |
| SEQ ID NO: 226 | moltype = RNA  length = 21 |
| FEATURE | Location/Qualifiers |
| source | 1..21 |
|  | mol_type = other RNA |
|  | organism = synthetic construct |
| modified_base | 1 |
|  | mod_base = OTHER |
|  | note = 2'-fluorouridine phosphorothioate |
| modified_base | 2 |
|  | mod_base = OTHER |
|  | note = 2'-fluorouridine phosphorothioate |
| modified_base | 3 |
|  | mod_base = OTHER |
|  | note = 2'-O-methylcytidine |
| modified_base | 4 |
|  | mod_base = OTHER |
|  | note = 2'-O-methylcytidine |
| modified_base | 5 |
|  | mod_base = OTHER |
|  | note = 2'-O-methylguanosine |
| modified_base | 6 |
|  | mod_base = OTHER |
|  | note = 2'-fluoroguanosine |
| modified_base | 7 |
|  | mod_base = OTHER |
|  | note = 2'-O-methyladenosine |
| modified_base | 8 |
|  | mod_base = OTHER |
|  | note = 2'-O-methyladenosine |
| modified_base | 9 |
|  | mod_base = OTHER |
|  | note = 2'-O-methyluridine |
| modified_base | 10 |
|  | mod_base = OTHER |
|  | note = 2'-O-methylguanosine |
| modified_base | 11 |
|  | mod_base = OTHER |
|  | note = 2'-O-methylcytidine |
| modified_base | 12 |
|  | mod_base = OTHER |
|  | note = 2'-O-methylcytidine |
| modified_base | 13 |
|  | mod_base = OTHER |
|  | note = 2'-O-methylguanosine |
| modified_base | 14 |
|  | mod_base = OTHER |
|  | note = 2'-fluoroadenosine |
| modified_base | 15 |
|  | mod_base = OTHER |
|  | note = 2'-O-methyluridine |
| modified_base | 16 |
|  | mod_base = OTHER |
|  | note = 2'-fluoroguanosine |
| modified_base | 17 |
|  | mod_base = OTHER |
|  | note = 2'-O-methylguanosine |
| modified_base | 18 |
|  | mod_base = OTHER |
|  | note = 2'-O-methylcytidine |
| modified_base | 19 |
|  | mod_base = OTHER |
|  | note = 2'-O-methylcytidine phosphorothioate |
| modified_base | 20 |
|  | mod_base = OTHER |
|  | note = 2'-O-methyluridine phosphorothioate |
| modified_base | 21 |
|  | mod_base = OTHER |
|  | note = 2'-O-methyluridine |
| SEQUENCE: 226 |  |
| ttccggaatg ccgatggcct t | 21 |

| | |
|---|---|
| SEQ ID NO: 227 | moltype = RNA  length = 21 |
| FEATURE | Location/Qualifiers |
| source | 1..21 |
| | mol_type = other RNA |
| | organism = synthetic construct |
| modified_base | 1 |
| | mod_base = OTHER |
| | note = 2'-fluorouridine phosphorothioate |
| modified_base | 2 |
| | mod_base = OTHER |
| | note = 2'-fluorocytidine phosphorothioate |
| modified_base | 3 |
| | mod_base = OTHER |
| | note = 2'-O-methyluridine |
| modified_base | 4 |
| | mod_base = OTHER |
| | note = 2'-O-methylcytidine |
| modified_base | 5 |
| | mod_base = OTHER |
| | note = 2'-O-methylcytidine |
| modified_base | 6 |
| | mod_base = OTHER |
| | note = 2'-fluoroguanosine |
| modified_base | 7 |
| | mod_base = OTHER |
| | note = 2'-O-methylguanosine |
| modified_base | 8 |
| | mod_base = OTHER |
| | note = 2'-O-methyladenosine |
| modified_base | 9 |
| | mod_base = OTHER |
| | note = 2'-O-methyladenosine |
| modified_base | 10 |
| | mod_base = OTHER |
| | note = 2'-O-methyluridine |
| modified_base | 11 |
| | mod_base = OTHER |
| | note = 2'-O-methylguanosine |
| modified_base | 12 |
| | mod_base = OTHER |
| | note = 2'-O-methylcytidine |
| modified_base | 13 |
| | mod_base = OTHER |
| | note = 2'-O-methylcytidine |
| modified_base | 14 |
| | mod_base = OTHER |
| | note = 2'-fluoroguanosine |
| modified_base | 15 |
| | mod_base = OTHER |
| | note = 2'-O-methyladenosine |
| modified_base | 16 |
| | mod_base = OTHER |
| | note = 2'-fluorouridine |
| modified_base | 17 |
| | mod_base = OTHER |
| | note = 2'-O-methylguanosine |
| modified_base | 18 |
| | mod_base = OTHER |
| | note = 2'-O-methylguanosine |
| modified_base | 19 |
| | mod_base = OTHER |
| | note = 2'-O-methylcytidine phosphorothioate |
| modified_base | 20 |
| | mod_base = OTHER |
| | note = 2'-O-methyluridine phosphorothioate |
| modified_base | 21 |
| | mod_base = OTHER |
| | note = 2'-O-methyluridine |
| SEQUENCE: 227 | |
| tctccggaat gccgatggct t | 21 |
| SEQ ID NO: 228 | moltype = RNA  length = 21 |
| FEATURE | Location/Qualifiers |
| source | 1..21 |
| | mol_type = other RNA |
| | organism = synthetic construct |
| modified_base | 1 |
| | mod_base = OTHER |
| | note = 2'-fluorouridine phosphorothioate |

-continued

```
modified_base    2
                 mod_base = OTHER
                 note = 2'-fluorocytidine phosphorothioate
modified_base    3
                 mod_base = OTHER
                 note = 2'-O-methylguanosine
modified_base    4
                 mod_base = OTHER
                 note = 2'-O-methyladenosine
modified_base    5
                 mod_base = OTHER
                 note = 2'-O-methylguanosine
modified_base    6
                 mod_base = OTHER
                 note = 2'-fluoroadenosine
modified_base    7
                 mod_base = OTHER
                 note = 2'-O-methyluridine
modified_base    8
                 mod_base = OTHER
                 note = 2'-O-methyluridine
modified_base    9
                 mod_base = OTHER
                 note = 2'-O-methylcytidine
modified_base    10
                 mod_base = OTHER
                 note = 2'-O-methylcytidine
modified_base    11
                 mod_base = OTHER
                 note = 2'-O-methylcytidine
modified_base    12
                 mod_base = OTHER
                 note = 2'-O-methylguanosine
modified_base    13
                 mod_base = OTHER
                 note = 2'-O-methylcytidine
modified_base    14
                 mod_base = OTHER
                 note = 2'-fluorocytidine
modified_base    15
                 mod_base = OTHER
                 note = 2'-O-methylguanosine
modified_base    16
                 mod_base = OTHER
                 note = 2'-fluoroguanosine
modified_base    17
                 mod_base = OTHER
                 note = 2'-O-methyluridine
modified_base    18
                 mod_base = OTHER
                 note = 2'-O-methylguanosine
modified_base    19
                 mod_base = OTHER
                 note = 2'-O-methylcytidine phosphorothioate
modified_base    20
                 mod_base = OTHER
                 note = 2'-O-methyluridine phosphorothioate
modified_base    21
                 mod_base = OTHER
                 note = 2'-O-methyluridine
SEQUENCE: 228
tcgagattcc cgccggtgct t                                      21

SEQ ID NO: 229   moltype = RNA   length = 21
FEATURE          Location/Qualifiers
source           1..21
                 mol_type = other RNA
                 organism = synthetic construct
modified_base    1
                 mod_base = OTHER
                 note = 2'-fluorouridine phosphorothioate
modified_base    2
                 mod_base = OTHER
                 note = 2'-fluorocytidine phosphorothioate
modified_base    3
                 mod_base = OTHER
                 note = 2'-O-methylcytidine
modified_base    4
                 mod_base = OTHER
```

```
                        note = 2'-O-methylguanosine
modified_base           5
                        mod_base = OTHER
                        note = 2'-O-methyladenosine
modified_base           6
                        mod_base = OTHER
                        note = 2'-fluoroguanosine
modified_base           7
                        mod_base = OTHER
                        note = 2'-O-methyladenosine
modified_base           8
                        mod_base = OTHER
                        note = 2'-O-methyluridine
modified_base           9
                        mod_base = OTHER
                        note = 2'-O-methyluridine
modified_base           10
                        mod_base = OTHER
                        note = 2'-O-methylcytidine
modified_base           11
                        mod_base = OTHER
                        note = 2'-O-methylcytidine
modified_base           12
                        mod_base = OTHER
                        note = 2'-O-methylcytidine
modified_base           13
                        mod_base = OTHER
                        note = 2'-O-methylguanosine
modified_base           14
                        mod_base = OTHER
                        note = 2'-fluorocytidine
modified_base           15
                        mod_base = OTHER
                        note = 2'-O-methylcytidine
modified_base           16
                        mod_base = OTHER
                        note = 2'-fluoroguanosine
modified_base           17
                        mod_base = OTHER
                        note = 2'-O-methylguanosine
modified_base           18
                        mod_base = OTHER
                        note = 2'-O-methyluridine
modified_base           19
                        mod_base = OTHER
                        note = 2'-O-methylguanosine phosphorothioate
modified_base           20
                        mod_base = OTHER
                        note = 2'-O-methyluridine phosphorothioate
modified_base           21
                        mod_base = OTHER
                        note = 2'-O-methyluridine
SEQUENCE: 229
tccgagattc ccgccggtgt t                                             21

SEQ ID NO: 230          moltype = RNA   length = 21
FEATURE                 Location/Qualifiers
source                  1..21
                        mol_type = other RNA
                        organism = synthetic construct
modified_base           1
                        mod_base = OTHER
                        note = 2'-fluorouridine phosphorothioate
modified_base           2
                        mod_base = OTHER
                        note = 2'-fluorocytidine phosphorothioate
modified_base           3
                        mod_base = OTHER
                        note = 2'-O-methyluridine
modified_base           4
                        mod_base = OTHER
                        note = 2'-O-methyluridine
modified_base           5
                        mod_base = OTHER
                        note = 2'-O-methyluridine
modified_base           6
                        mod_base = OTHER
                        note = 2'-fluorocytidine
modified_base           7
```

```
                        mod_base = OTHER
                        note = 2'-O-methylguanosine
modified_base           8
                        mod_base = OTHER
                        note = 2'-O-methylcytidine
modified_base           9
                        mod_base = OTHER
                        note = 2'-O-methylcytidine
modified_base           10
                        mod_base = OTHER
                        note = 2'-O-methylguanosine
modified_base           11
                        mod_base = OTHER
                        note = 2'-O-methylguanosine
modified_base           12
                        mod_base = OTHER
                        note = 2'-O-methylcytidine
modified_base           13
                        mod_base = OTHER
                        note = 2'-O-methylcytidine
modified_base           14
                        mod_base = OTHER
                        note = 2'-fluorouridine
modified_base           15
                        mod_base = OTHER
                        note = 2'-O-methyluridine
modified_base           16
                        mod_base = OTHER
                        note = 2'-fluorocytidine
modified_base           17
                        mod_base = OTHER
                        note = 2'-O-methyluridine
modified_base           18
                        mod_base = OTHER
                        note = 2'-O-methylguanosine
modified_base           19
                        mod_base = OTHER
                        note = 2'-O-methylguanosine phosphorothioate
modified_base           20
                        mod_base = OTHER
                        note = 2'-O-methyluridine phosphorothioate
modified_base           21
                        mod_base = OTHER
                        note = 2'-O-methyluridine
SEQUENCE: 230
tctttcgccg gccttctggt t                                              21

SEQ ID NO: 231          moltype = RNA   length = 21
FEATURE                 Location/Qualifiers
source                  1..21
                        mol_type = other RNA
                        organism = synthetic construct
modified_base           1
                        mod_base = OTHER
                        note = 2'-fluorouridine phosphorothioate
modified_base           2
                        mod_base = OTHER
                        note = 2'-fluorocytidine phosphorothioate
modified_base           3
                        mod_base = OTHER
                        note = 2'-O-methylguanosine
modified_base           4
                        mod_base = OTHER
                        note = 2'-O-methylcytidine
modified_base           5
                        mod_base = OTHER
                        note = 2'-O-methyluridine
modified_base           6
                        mod_base = OTHER
                        note = 2'-fluorouridine
modified_base           7
                        mod_base = OTHER
                        note = 2'-O-methyluridine
modified_base           8
                        mod_base = OTHER
                        note = 2'-O-methylcytidine
modified_base           9
                        mod_base = OTHER
                        note = 2'-O-methylguanosine
```

```
modified_base        10
                     mod_base = OTHER
                     note = 2'-O-methylcytidine
modified_base        11
                     mod_base = OTHER
                     note = 2'-O-methylcytidine
modified_base        12
                     mod_base = OTHER
                     note = 2'-O-methylguanosine
modified_base        13
                     mod_base = OTHER
                     note = 2'-O-methylguanosine
modified_base        14
                     mod_base = OTHER
                     note = 2'-fluorocytidine
modified_base        15
                     mod_base = OTHER
                     note = 2'-O-methylcytidine
modified_base        16
                     mod_base = OTHER
                     note = 2'-fluorouridine
modified_base        17
                     mod_base = OTHER
                     note = 2'-O-methyluridine
modified_base        18
                     mod_base = OTHER
                     note = 2'-O-methylcytidine
modified_base        19
                     mod_base = OTHER
                     note = 2'-O-methyluridine phosphorothioate
modified_base        20
                     mod_base = OTHER
                     note = 2'-O-methyluridine phosphorothioate
modified_base        21
                     mod_base = OTHER
                     note = 2'-O-methyluridine
SEQUENCE: 231
tcgctttcgc cggccttctt t                                              21

SEQ ID NO: 232       moltype = RNA   length = 21
FEATURE              Location/Qualifiers
source               1..21
                     mol_type = other RNA
                     organism = synthetic construct
modified_base        1
                     mod_base = OTHER
                     note = 2'-fluorouridine phosphorothioate
modified_base        2
                     mod_base = OTHER
                     note = 2'-fluorocytidine phosphorothioate
modified_base        3
                     mod_base = OTHER
                     note = 2'-O-methylcytidine
modified_base        4
                     mod_base = OTHER
                     note = 2'-O-methylguanosine
modified_base        5
                     mod_base = OTHER
                     note = 2'-O-methylcytidine
modified_base        6
                     mod_base = OTHER
                     note = 2'-fluorouridine
modified_base        7
                     mod_base = OTHER
                     note = 2'-O-methyluridine
modified_base        8
                     mod_base = OTHER
                     note = 2'-O-methyluridine
modified_base        9
                     mod_base = OTHER
                     note = 2'-O-methylcytidine
modified_base        10
                     mod_base = OTHER
                     note = 2'-O-methylguanosine
modified_base        11
                     mod_base = OTHER
                     note = 2'-O-methylcytidine
modified_base        12
                     mod_base = OTHER
```

|  |  |
|---|---|
| | note = 2'-O-methylcytidine |
| modified_base | 13 |
| | mod_base = OTHER |
| | note = 2'-O-methylguanosine |
| modified_base | 14 |
| | mod_base = OTHER |
| | note = 2'-fluoroguanosine |
| modified_base | 15 |
| | mod_base = OTHER |
| | note = 2'-O-methylcytidine |
| modified_base | 16 |
| | mod_base = OTHER |
| | note = 2'-fluorocytidine |
| modified_base | 17 |
| | mod_base = OTHER |
| | note = 2'-O-methyluridine |
| modified_base | 18 |
| | mod_base = OTHER |
| | note = 2'-O-methyluridine |
| modified_base | 19 |
| | mod_base = OTHER |
| | note = 2'-O-methylcytidine phosphorothioate |
| modified_base | 20 |
| | mod_base = OTHER |
| | note = 2'-O-methyluridine phosphorothioate |
| modified_base | 21 |
| | mod_base = OTHER |
| | note = 2'-O-methyluridine |
| SEQUENCE: 232 | |
| tccgctttcg ccggccttct t | 21 |
| | |
| SEQ ID NO: 233 | moltype = RNA  length = 21 |
| FEATURE | Location/Qualifiers |
| source | 1..21 |
| | mol_type = other RNA |
| | organism = synthetic construct |
| modified_base | 1 |
| | mod_base = OTHER |
| | note = 2'-fluorouridine phosphorothioate |
| modified_base | 2 |
| | mod_base = OTHER |
| | note = 2'-fluoroadenosine phosphorothioate |
| modified_base | 3 |
| | mod_base = OTHER |
| | note = 2'-O-methylcytidine |
| modified_base | 4 |
| | mod_base = OTHER |
| | note = 2'-O-methylguanosine |
| modified_base | 5 |
| | mod_base = OTHER |
| | note = 2'-O-methylguanosine |
| modified_base | 6 |
| | mod_base = OTHER |
| | note = 2'-fluorocytidine |
| modified_base | 7 |
| | mod_base = OTHER |
| | note = 2'-O-methylguanosine |
| modified_base | 8 |
| | mod_base = OTHER |
| | note = 2'-O-methylguanosine |
| modified_base | 9 |
| | mod_base = OTHER |
| | note = 2'-O-methyluridine |
| modified_base | 10 |
| | mod_base = OTHER |
| | note = 2'-O-methylcytidine |
| modified_base | 11 |
| | mod_base = OTHER |
| | note = 2'-O-methylcytidine |
| modified_base | 12 |
| | mod_base = OTHER |
| | note = 2'-O-methylguanosine |
| modified_base | 13 |
| | mod_base = OTHER |
| | note = 2'-O-methylcytidine |
| modified_base | 14 |
| | mod_base = OTHER |
| | note = 2'-fluorouridine |
| modified_base | 15 |

```
                        mod_base = OTHER
                        note = 2'-O-methyluridine
modified_base           16
                        mod_base = OTHER
                        note = 2'-fluorouridine
modified_base           17
                        mod_base = OTHER
                        note = 2'-O-methylcytidine
modified_base           18
                        mod_base = OTHER
                        note = 2'-O-methylguanosine
modified_base           19
                        mod_base = OTHER
                        note = 2'-O-methylcytidine phosphorothioate
modified_base           20
                        mod_base = OTHER
                        note = 2'-O-methyluridine phosphorothioate
modified_base           21
                        mod_base = OTHER
                        note = 2'-O-methyluridine
SEQUENCE: 233
tacggcggtc cgctttcgct t                                              21

SEQ ID NO: 234          moltype = RNA   length = 21
FEATURE                 Location/Qualifiers
source                  1..21
                        mol_type = other RNA
                        organism = synthetic construct
modified_base           1
                        mod_base = OTHER
                        note = 2'-fluorouridine phosphorothioate
modified_base           2
                        mod_base = OTHER
                        note = 2'-fluorouridine phosphorothioate
modified_base           3
                        mod_base = OTHER
                        note = 2'-O-methylguanosine
modified_base           4
                        mod_base = OTHER
                        note = 2'-O-methyladenosine
modified_base           5
                        mod_base = OTHER
                        note = 2'-O-methylcytidine
modified_base           6
                        mod_base = OTHER
                        note = 2'-fluoroguanosine
modified_base           7
                        mod_base = OTHER
                        note = 2'-O-methylguanosine
modified_base           8
                        mod_base = OTHER
                        note = 2'-O-methylcytidine
modified_base           9
                        mod_base = OTHER
                        note = 2'-O-methylguanosine
modified_base           10
                        mod_base = OTHER
                        note = 2'-O-methylguanosine
modified_base           11
                        mod_base = OTHER
                        note = 2'-O-methyluridine
modified_base           12
                        mod_base = OTHER
                        note = 2'-O-methylcytidine
modified_base           13
                        mod_base = OTHER
                        note = 2'-O-methylcytidine
modified_base           14
                        mod_base = OTHER
                        note = 2'-fluoroguanosine
modified_base           15
                        mod_base = OTHER
                        note = 2'-O-methylcytidine
modified_base           16
                        mod_base = OTHER
                        note = 2'-fluorouridine
modified_base           17
                        mod_base = OTHER
                        note = 2'-O-methyluridine
```

```
modified_base       18
                    mod_base = OTHER
                    note = 2'-O-methyluridine
modified_base       19
                    mod_base = OTHER
                    note = 2'-O-methylcytidine phosphorothioate
modified_base       20
                    mod_base = OTHER
                    note = 2'-O-methyluridine phosphorothioate
modified_base       21
                    mod_base = OTHER
                    note = 2'-O-methyluridine
SEQUENCE: 234
ttgacggcgg tccgctttct t                                              21

SEQ ID NO: 235      moltype = RNA  length = 21
FEATURE             Location/Qualifiers
source              1..21
                    mol_type = other RNA
                    organism = synthetic construct
modified_base       1
                    mod_base = OTHER
                    note = 2'-fluorouridine phosphorothioate
modified_base       2
                    mod_base = OTHER
                    note = 2'-fluorouridine phosphorothioate
modified_base       3
                    mod_base = OTHER
                    note = 2'-O-methylcytidine
modified_base       4
                    mod_base = OTHER
                    note = 2'-O-methylcytidine
modified_base       5
                    mod_base = OTHER
                    note = 2'-O-methylguanosine
modified_base       6
                    mod_base = OTHER
                    note = 2'-fluoroguanosine
modified_base       7
                    mod_base = OTHER
                    note = 2'-O-methyluridine
modified_base       8
                    mod_base = OTHER
                    note = 2'-O-methylguanosine
modified_base       9
                    mod_base = OTHER
                    note = 2'-O-methyladenosine
modified_base       10
                    mod_base = OTHER
                    note = 2'-O-methylcytidine
modified_base       11
                    mod_base = OTHER
                    note = 2'-O-methylguanosine
modified_base       12
                    mod_base = OTHER
                    note = 2'-O-methylguanosine
modified_base       13
                    mod_base = OTHER
                    note = 2'-O-methylcytidine
modified_base       14
                    mod_base = OTHER
                    note = 2'-fluoroguanosine
modified_base       15
                    mod_base = OTHER
                    note = 2'-O-methylguanosine
modified_base       16
                    mod_base = OTHER
                    note = 2'-fluorouridine
modified_base       17
                    mod_base = OTHER
                    note = 2'-O-methylcytidine
modified_base       18
                    mod_base = OTHER
                    note = 2'-O-methylcytidine
modified_base       19
                    mod_base = OTHER
                    note = 2'-O-methylguanosine phosphorothioate
modified_base       20
                    mod_base = OTHER
```

```
                              note = 2'-O-methyluridine phosphorothioate
modified_base                 21
                              mod_base = OTHER
                              note = 2'-O-methyluridine
SEQUENCE: 235
ttccggtgac ggcggtccgt t                                              21

SEQ ID NO: 236         moltype = RNA  length = 21
FEATURE                Location/Qualifiers
source                 1..21
                       mol_type = other RNA
                       organism = synthetic construct
modified_base          1
                       mod_base = OTHER
                       note = 2'-fluorouridine phosphorothioate
modified_base          2
                       mod_base = OTHER
                       note = 2'-fluoroadenosine phosphorothioate
modified_base          3
                       mod_base = OTHER
                       note = 2'-O-methyluridine
modified_base          4
                       mod_base = OTHER
                       note = 2'-O-methylcytidine
modified_base          5
                       mod_base = OTHER
                       note = 2'-O-methylcytidine
modified_base          6
                       mod_base = OTHER
                       note = 2'-fluoroguanosine
modified_base          7
                       mod_base = OTHER
                       note = 2'-O-methylguanosine
modified_base          8
                       mod_base = OTHER
                       note = 2'-O-methyluridine
modified_base          9
                       mod_base = OTHER
                       note = 2'-O-methylguanosine
modified_base          10
                       mod_base = OTHER
                       note = 2'-O-methyladenosine
modified_base          11
                       mod_base = OTHER
                       note = 2'-O-methylcytidine
modified_base          12
                       mod_base = OTHER
                       note = 2'-O-methylguanosine
modified_base          13
                       mod_base = OTHER
                       note = 2'-O-methylguanosine
modified_base          14
                       mod_base = OTHER
                       note = 2'-fluorocytidine
modified_base          15
                       mod_base = OTHER
                       note = 2'-O-methylguanosine
modified_base          16
                       mod_base = OTHER
                       note = 2'-fluoroguanosine
modified_base          17
                       mod_base = OTHER
                       note = 2'-O-methyluridine
modified_base          18
                       mod_base = OTHER
                       note = 2'-O-methylcytidine
modified_base          19
                       mod_base = OTHER
                       note = 2'-O-methylcytidine phosphorothioate
modified_base          20
                       mod_base = OTHER
                       note = 2'-O-methyluridine phosphorothioate
modified_base          21
                       mod_base = OTHER
                       note = 2'-O-methyluridine
SEQUENCE: 236
tatccggtga cggcggtcct t                                              21

SEQ ID NO: 237         moltype = RNA  length = 21
```

| FEATURE | Location/Qualifiers |
|---|---|
| source | 1..21 |
| | mol_type = other RNA |
| | organism = synthetic construct |
| modified_base | 1 |
| | mod_base = OTHER |
| | note = 2'-fluorouridine phosphorothioate |
| modified_base | 2 |
| | mod_base = OTHER |
| | note = 2'-fluoroguanosine phosphorothioate |
| modified_base | 3 |
| | mod_base = OTHER |
| | note = 2'-O-methyladenosine |
| modified_base | 4 |
| | mod_base = OTHER |
| | note = 2'-O-methyluridine |
| modified_base | 5 |
| | mod_base = OTHER |
| | note = 2'-O-methylcytidine |
| modified_base | 6 |
| | mod_base = OTHER |
| | note = 2'-fluorocytidine |
| modified_base | 7 |
| | mod_base = OTHER |
| | note = 2'-O-methylguanosine |
| modified_base | 8 |
| | mod_base = OTHER |
| | note = 2'-O-methylguanosine |
| modified_base | 9 |
| | mod_base = OTHER |
| | note = 2'-O-methyluridine |
| modified_base | 10 |
| | mod_base = OTHER |
| | note = 2'-O-methylguanosine |
| modified_base | 11 |
| | mod_base = OTHER |
| | note = 2'-O-methyladenosine |
| modified_base | 12 |
| | mod_base = OTHER |
| | note = 2'-O-methylcytidine |
| modified_base | 13 |
| | mod_base = OTHER |
| | note = 2'-O-methylguanosine |
| modified_base | 14 |
| | mod_base = OTHER |
| | note = 2'-fluoroguanosine |
| modified_base | 15 |
| | mod_base = OTHER |
| | note = 2'-O-methylcytidine |
| modified_base | 16 |
| | mod_base = OTHER |
| | note = 2'-fluoroguanosine |
| modified_base | 17 |
| | mod_base = OTHER |
| | note = 2'-O-methylguanosine |
| modified_base | 18 |
| | mod_base = OTHER |
| | note = 2'-O-methyluridine |
| modified_base | 19 |
| | mod_base = OTHER |
| | note = 2'-O-methylcytidine phosphorothioate |
| modified_base | 20 |
| | mod_base = OTHER |
| | note = 2'-O-methyluridine phosphorothioate |
| modified_base | 21 |
| | mod_base = OTHER |
| | note = 2'-O-methyluridine |
| SEQUENCE: 237 | |

```
tgatccggtg acggcggtct t                                    21
```

| SEQ ID NO: 238 | moltype = RNA  length = 21 |
|---|---|
| FEATURE | Location/Qualifiers |
| source | 1..21 |
| | mol_type = other RNA |
| | organism = synthetic construct |
| modified_base | 1 |
| | mod_base = OTHER |
| | note = 2'-fluorouridine phosphorothioate |
| modified_base | 2 |

| | | |
|---|---|---|
| | | mod_base = OTHER |
| | | note = 2'-fluoroadenosine phosphorothioate |
| modified_base | 3 | |
| | | mod_base = OTHER |
| | | note = 2'-O-methylcytidine |
| modified_base | 4 | |
| | | mod_base = OTHER |
| | | note = 2'-O-methyluridine |
| modified_base | 5 | |
| | | mod_base = OTHER |
| | | note = 2'-O-methylcytidine |
| modified_base | 6 | |
| | | mod_base = OTHER |
| | | note = 2'-fluorocytidine |
| modified_base | 7 | |
| | | mod_base = OTHER |
| | | note = 2'-O-methylguanosine |
| modified_base | 8 | |
| | | mod_base = OTHER |
| | | note = 2'-O-methylguanosine |
| modified_base | 9 | |
| | | mod_base = OTHER |
| | | note = 2'-O-methylguanosine |
| modified_base | 10 | |
| | | mod_base = OTHER |
| | | note = 2'-O-methyladenosine |
| modified_base | 11 | |
| | | mod_base = OTHER |
| | | note = 2'-O-methylguanosine |
| modified_base | 12 | |
| | | mod_base = OTHER |
| | | note = 2'-O-methylguanosine |
| modified_base | 13 | |
| | | mod_base = OTHER |
| | | note = 2'-O-methylcytidine |
| modified_base | 14 | |
| | | mod_base = OTHER |
| | | note = 2'-fluorocytidine |
| modified_base | 15 | |
| | | mod_base = OTHER |
| | | note = 2'-O-methylcytidine |
| modified_base | 16 | |
| | | mod_base = OTHER |
| | | note = 2'-fluoroguanosine |
| modified_base | 17 | |
| | | mod_base = OTHER |
| | | note = 2'-O-methyluridine |
| modified_base | 18 | |
| | | mod_base = OTHER |
| | | note = 2'-O-methylcytidine |
| modified_base | 19 | |
| | | mod_base = OTHER |
| | | note = 2'-O-methyluridine phosphorothioate |
| modified_base | 20 | |
| | | mod_base = OTHER |
| | | note = 2'-O-methyluridine phosphorothioate |
| modified_base | 21 | |
| | | mod_base = OTHER |
| | | note = 2'-O-methyluridine |
| SEQUENCE: 238 | | |
| tactccggga ggcccgtctt t | | 21 |
| SEQ ID NO: 239 | moltype = RNA  length = 21 | |
| FEATURE | Location/Qualifiers | |
| source | 1..21 | |
| | mol_type = other RNA | |
| | organism = synthetic construct | |
| modified_base | 1 | |
| | | mod_base = OTHER |
| | | note = 2'-fluorouridine phosphorothioate |
| modified_base | 2 | |
| | | mod_base = OTHER |
| | | note = 2'-fluorocytidine phosphorothioate |
| modified_base | 3 | |
| | | mod_base = OTHER |
| | | note = 2'-O-methylguanosine |
| modified_base | 4 | |
| | | mod_base = OTHER |
| | | note = 2'-O-methyladenosine |

```
                       -continued
modified_base          5
                       mod_base = OTHER
                       note = 2'-O-methyladenosine
modified_base          6
                       mod_base = OTHER
                       note = 2'-fluoroguanosine
modified_base          7
                       mod_base = OTHER
                       note = 2'-O-methylguanosine
modified_base          8
                       mod_base = OTHER
                       note = 2'-O-methylcytidine
modified_base          9
                       mod_base = OTHER
                       note = 2'-O-methylguanosine
modified_base          10
                       mod_base = OTHER
                       note = 2'-O-methyladenosine
modified_base          11
                       mod_base = OTHER
                       note = 2'-O-methylcytidine
modified_base          12
                       mod_base = OTHER
                       note = 2'-O-methylcytidine
modified_base          13
                       mod_base = OTHER
                       note = 2'-O-methylcytidine
modified_base          14
                       mod_base = OTHER
                       note = 2'-fluoroadenosine
modified_base          15
                       mod_base = OTHER
                       note = 2'-O-methylcytidine
modified_base          16
                       mod_base = OTHER
                       note = 2'-fluoroguanosine
modified_base          17
                       mod_base = OTHER
                       note = 2'-O-methyladenosine
modified_base          18
                       mod_base = OTHER
                       note = 2'-O-methylguanosine
modified_base          19
                       mod_base = OTHER
                       note = 2'-O-methylguanosine phosphorothioate
modified_base          20
                       mod_base = OTHER
                       note = 2'-O-methyluridine phosphorothioate
modified_base          21
                       mod_base = OTHER
                       note = 2'-O-methyluridine
SEQUENCE: 239
tcgaaggcga cccacgaggt t                                            21

SEQ ID NO: 240         moltype = RNA   length = 21
FEATURE                Location/Qualifiers
source                 1..21
                       mol_type = other RNA
                       organism = synthetic construct
modified_base          1
                       mod_base = OTHER
                       note = 2'-fluorouridine phosphorothioate
modified_base          2
                       mod_base = OTHER
                       note = 2'-fluoroguanosine phosphorothioate
modified_base          3
                       mod_base = OTHER
                       note = 2'-O-methylcytidine
modified_base          4
                       mod_base = OTHER
                       note = 2'-O-methylguanosine
modified_base          5
                       mod_base = OTHER
                       note = 2'-O-methyladenosine
modified_base          6
                       mod_base = OTHER
                       note = 2'-fluoroadenosine
modified_base          7
                       mod_base = OTHER
```

|  |  |
|---|---|
|  | note = 2'-O-methylguanosine |
| modified_base | 8 |
|  | mod_base = OTHER |
|  | note = 2'-O-methylguanosine |
| modified_base | 9 |
|  | mod_base = OTHER |
|  | note = 2'-O-methylcytidine |
| modified_base | 10 |
|  | mod_base = OTHER |
|  | note = 2'-O-methylguanosine |
| modified_base | 11 |
|  | mod_base = OTHER |
|  | note = 2'-O-methyladenosine |
| modified_base | 12 |
|  | mod_base = OTHER |
|  | note = 2'-O-methylcytidine |
| modified_base | 13 |
|  | mod_base = OTHER |
|  | note = 2'-O-methylcytidine |
| modified_base | 14 |
|  | mod_base = OTHER |
|  | note = 2'-fluorocytidine |
| modified_base | 15 |
|  | mod_base = OTHER |
|  | note = 2'-O-methyladenosine |
| modified_base | 16 |
|  | mod_base = OTHER |
|  | note = 2'-fluorocytidine |
| modified_base | 17 |
|  | mod_base = OTHER |
|  | note = 2'-O-methylguanosine |
| modified_base | 18 |
|  | mod_base = OTHER |
|  | note = 2'-O-methyladenosine |
| modified_base | 19 |
|  | mod_base = OTHER |
|  | note = 2'-O-methylguanosine phosphorothioate |
| modified_base | 20 |
|  | mod_base = OTHER |
|  | note = 2'-O-methyluridine phosphorothioate |
| modified_base | 21 |
|  | mod_base = OTHER |
|  | note = 2'-O-methyluridine |

SEQUENCE: 240
tgcgaaggcg acccacgagt t          21

| SEQ ID NO: 241 | moltype = RNA  length = 21 |
|---|---|
| FEATURE | Location/Qualifiers |
| source | 1..21 |
|  | mol_type = other RNA |
|  | organism = synthetic construct |
| modified_base | 1 |
|  | mod_base = OTHER |
|  | note = 2'-fluorouridine phosphorothioate |
| modified_base | 2 |
|  | mod_base = OTHER |
|  | note = 2'-fluoroadenosine phosphorothioate |
| modified_base | 3 |
|  | mod_base = OTHER |
|  | note = 2'-O-methylguanosine |
| modified_base | 4 |
|  | mod_base = OTHER |
|  | note = 2'-O-methylguanosine |
| modified_base | 5 |
|  | mod_base = OTHER |
|  | note = 2'-O-methyluridine |
| modified_base | 6 |
|  | mod_base = OTHER |
|  | note = 2'-fluorouridine |
| modified_base | 7 |
|  | mod_base = OTHER |
|  | note = 2'-O-methylguanosine |
| modified_base | 8 |
|  | mod_base = OTHER |
|  | note = 2'-O-methylguanosine |
| modified_base | 9 |
|  | mod_base = OTHER |
|  | note = 2'-O-methylguanosine |
| modified_base | 10 |

```
                        mod_base = OTHER
                        note = 2'-O-methyladenosine
modified_base           11
                        mod_base = OTHER
                        note = 2'-O-methylguanosine
modified_base           12
                        mod_base = OTHER
                        note = 2'-O-methyladenosine
modified_base           13
                        mod_base = OTHER
                        note = 2'-O-methyluridine
modified_base           14
                        mod_base = OTHER
                        note = 2'-fluorocytidine
modified_base           15
                        mod_base = OTHER
                        note = 2'-O-methylcytidine
modified_base           16
                        mod_base = OTHER
                        note = 2'-fluorocytidine
modified_base           17
                        mod_base = OTHER
                        note = 2'-O-methylcytidine
modified_base           18
                        mod_base = OTHER
                        note = 2'-O-methyluridine
modified_base           19
                        mod_base = OTHER
                        note = 2'-O-methylcytidine phosphorothioate
modified_base           20
                        mod_base = OTHER
                        note = 2'-O-methyluridine phosphorothioate
modified_base           21
                        mod_base = OTHER
                        note = 2'-O-methyluridine
SEQUENCE: 241
taggttggga gatcccctct t                                              21

SEQ ID NO: 242          moltype = RNA   length = 21
FEATURE                 Location/Qualifiers
source                  1..21
                        mol_type = other RNA
                        organism = synthetic construct
modified_base           1
                        mod_base = OTHER
                        note = 2'-fluorouridine phosphorothioate
modified_base           2
                        mod_base = OTHER
                        note = 2'-fluoroadenosine phosphorothioate
modified_base           3
                        mod_base = OTHER
                        note = 2'-O-methylguanosine
modified_base           4
                        mod_base = OTHER
                        note = 2'-O-methylguanosine
modified_base           5
                        mod_base = OTHER
                        note = 2'-O-methylcytidine
modified_base           6
                        mod_base = OTHER
                        note = 2'-fluoroguanosine
modified_base           7
                        mod_base = OTHER
                        note = 2'-O-methyladenosine
modified_base           8
                        mod_base = OTHER
                        note = 2'-O-methyladenosine
modified_base           9
                        mod_base = OTHER
                        note = 2'-O-methyladenosine
modified_base           10
                        mod_base = OTHER
                        note = 2'-O-methyluridine
modified_base           11
                        mod_base = OTHER
                        note = 2'-O-methylcytidine
modified_base           12
                        mod_base = OTHER
                        note = 2'-O-methylcytidine
```

```
modified_base          13
                       mod_base = OTHER
                       note = 2'-O-methylcytidine
modified_base          14
                       mod_base = OTHER
                       note = 2'-fluorocytidine
modified_base          15
                       mod_base = OTHER
                       note = 2'-O-methylguanosine
modified_base          16
                       mod_base = OTHER
                       note = 2'-fluorocytidine
modified_base          17
                       mod_base = OTHER
                       note = 2'-O-methylguanosine
modified_base          18
                       mod_base = OTHER
                       note = 2'-O-methylcytidine
modified_base          19
                       mod_base = OTHER
                       note = 2'-O-methylguanosine phosphorothioate
modified_base          20
                       mod_base = OTHER
                       note = 2'-O-methyluridine phosphorothioate
modified_base          21
                       mod_base = OTHER
                       note = 2'-O-methyluridine
SEQUENCE: 242
taggcgaaat ccccgcgcgt t                                        21

SEQ ID NO: 243         moltype = RNA  length = 21
FEATURE                Location/Qualifiers
source                 1..21
                       mol_type = other RNA
                       organism = synthetic construct
modified_base          1
                       mod_base = OTHER
                       note = 2'-fluorouridine phosphorothioate
modified_base          2
                       mod_base = OTHER
                       note = 2'-fluorouridine phosphorothioate
modified_base          3
                       mod_base = OTHER
                       note = 2'-O-methyladenosine
modified_base          4
                       mod_base = OTHER
                       note = 2'-O-methylguanosine
modified_base          5
                       mod_base = OTHER
                       note = 2'-O-methylguanosine
modified_base          6
                       mod_base = OTHER
                       note = 2'-fluorocytidine
modified_base          7
                       mod_base = OTHER
                       note = 2'-O-methylguanosine
modified_base          8
                       mod_base = OTHER
                       note = 2'-O-methyladenosine
modified_base          9
                       mod_base = OTHER
                       note = 2'-O-methyladenosine
modified_base          10
                       mod_base = OTHER
                       note = 2'-O-methyladenosine
modified_base          11
                       mod_base = OTHER
                       note = 2'-O-methyluridine
modified_base          12
                       mod_base = OTHER
                       note = 2'-O-methylcytidine
modified_base          13
                       mod_base = OTHER
                       note = 2'-O-methylcytidine
modified_base          14
                       mod_base = OTHER
                       note = 2'-fluorocytidine
modified_base          15
                       mod_base = OTHER
```

```
                        note = 2'-O-methylcytidine
modified_base           16
                        mod_base = OTHER
                        note = 2'-fluoroguanosine
modified_base           17
                        mod_base = OTHER
                        note = 2'-O-methylcytidine
modified_base           18
                        mod_base = OTHER
                        note = 2'-O-methylguanosine
modified_base           19
                        mod_base = OTHER
                        note = 2'-O-methylcytidine phosphorothioate
modified_base           20
                        mod_base = OTHER
                        note = 2'-O-methyluridine phosphorothioate
modified_base           21
                        mod_base = OTHER
                        note = 2'-O-methyluridine
SEQUENCE: 243
ttaggcgaaa tccccgcgct t                                              21

SEQ ID NO: 244          moltype = RNA   length = 21
FEATURE                 Location/Qualifiers
source                  1..21
                        mol_type = other RNA
                        organism = synthetic construct
modified_base           1
                        mod_base = OTHER
                        note = 2'-fluorouridine phosphorothioate
modified_base           2
                        mod_base = OTHER
                        note = 2'-fluoroguanosine phosphorothioate
modified_base           3
                        mod_base = OTHER
                        note = 2'-O-methylcytidine
modified_base           4
                        mod_base = OTHER
                        note = 2'-O-methylguanosine
modified_base           5
                        mod_base = OTHER
                        note = 2'-O-methyluridine
modified_base           6
                        mod_base = OTHER
                        note = 2'-fluoroadenosine
modified_base           7
                        mod_base = OTHER
                        note = 2'-O-methylguanosine
modified_base           8
                        mod_base = OTHER
                        note = 2'-O-methylguanosine
modified_base           9
                        mod_base = OTHER
                        note = 2'-O-methylcytidine
modified_base           10
                        mod_base = OTHER
                        note = 2'-O-methylguanosine
modified_base           11
                        mod_base = OTHER
                        note = 2'-O-methyladenosine
modified_base           12
                        mod_base = OTHER
                        note = 2'-O-methyladenosine
modified_base           13
                        mod_base = OTHER
                        note = 2'-O-methyladenosine
modified_base           14
                        mod_base = OTHER
                        note = 2'-fluorouridine
modified_base           15
                        mod_base = OTHER
                        note = 2'-O-methylcytidine
modified_base           16
                        mod_base = OTHER
                        note = 2'-fluorocytidine
modified_base           17
                        mod_base = OTHER
                        note = 2'-O-methylcytidine
modified_base           18
```

```
                        mod_base = OTHER
                        note = 2'-O-methylcytidine
modified_base           19
                        mod_base = OTHER
                        note = 2'-O-methylguanosine phosphorothioate
modified_base           20
                        mod_base = OTHER
                        note = 2'-O-methyluridine phosphorothioate
modified_base           21
                        mod_base = OTHER
                        note = 2'-O-methyluridine
SEQUENCE: 244
tgcgtaggcg aaatccccgt t                                              21

SEQ ID NO: 245          moltype = RNA   length = 21
FEATURE                 Location/Qualifiers
source                  1..21
                        mol_type = other RNA
                        organism = synthetic construct
modified_base           1
                        mod_base = OTHER
                        note = 2'-fluorouridine phosphorothioate
modified_base           2
                        mod_base = OTHER
                        note = 2'-fluoroadenosine phosphorothioate
modified_base           3
                        mod_base = OTHER
                        note = 2'-O-methylcytidine
modified_base           4
                        mod_base = OTHER
                        note = 2'-O-methylguanosine
modified_base           5
                        mod_base = OTHER
                        note = 2'-O-methyluridine
modified_base           6
                        mod_base = OTHER
                        note = 2'-fluoroguanosine
modified_base           7
                        mod_base = OTHER
                        note = 2'-O-methylguanosine
modified_base           8
                        mod_base = OTHER
                        note = 2'-O-methylguanosine
modified_base           9
                        mod_base = OTHER
                        note = 2'-O-methyluridine
modified_base           10
                        mod_base = OTHER
                        note = 2'-O-methylguanosine
modified_base           11
                        mod_base = OTHER
                        note = 2'-O-methylguanosine
modified_base           12
                        mod_base = OTHER
                        note = 2'-O-methylcytidine
modified_base           13
                        mod_base = OTHER
                        note = 2'-O-methylguanosine
modified_base           14
                        mod_base = OTHER
                        note = 2'-fluorocytidine
modified_base           15
                        mod_base = OTHER
                        note = 2'-O-methyladenosine
modified_base           16
                        mod_base = OTHER
                        note = 2'-fluoroadenosine
modified_base           17
                        mod_base = OTHER
                        note = 2'-O-methylguanosine
modified_base           18
                        mod_base = OTHER
                        note = 2'-O-methylcytidine
modified_base           19
                        mod_base = OTHER
                        note = 2'-O-methyladenosine phosphorothioate
modified_base           20
                        mod_base = OTHER
                        note = 2'-O-methyluridine phosphorothioate
```

|                | |                                                  |    |
|----------------|-|--------------------------------------------------|----|
| modified_base  | | 21                                               |    |
|                | | mod_base = OTHER                                 |    |
|                | | note = 2'-O-methyluridine                        |    |
| SEQUENCE: 245  | |                                                  |    |
| tacgtgggtg gcgcaagcat t | |                                         | 21 |

| | | |
|---|---|---|
| SEQ ID NO: 246 | moltype = RNA  length = 21 | |
| FEATURE | Location/Qualifiers | |
| source | 1..21 | |
|  | mol_type = other RNA | |
|  | organism = synthetic construct | |
| modified_base | 1 | |
|  | mod_base = OTHER | |
|  | note = 2'-fluorouridine phosphorothioate | |
| modified_base | 2 | |
|  | mod_base = OTHER | |
|  | note = 2'-fluoroadenosine phosphorothioate | |
| modified_base | 3 | |
|  | mod_base = OTHER | |
|  | note = 2'-O-methyladenosine | |
| modified_base | 4 | |
|  | mod_base = OTHER | |
|  | note = 2'-O-methyladenosine | |
| modified_base | 5 | |
|  | mod_base = OTHER | |
|  | note = 2'-O-methylcytidine | |
| modified_base | 6 | |
|  | mod_base = OTHER | |
|  | note = 2'-fluorouridine | |
| modified_base | 7 | |
|  | mod_base = OTHER | |
|  | note = 2'-O-methylcytidine | |
| modified_base | 8 | |
|  | mod_base = OTHER | |
|  | note = 2'-O-methylcytidine | |
| modified_base | 9 | |
|  | mod_base = OTHER | |
|  | note = 2'-O-methylguanosine | |
| modified_base | 10 | |
|  | mod_base = OTHER | |
|  | note = 2'-O-methylguanosine | |
| modified_base | 11 | |
|  | mod_base = OTHER | |
|  | note = 2'-O-methylguanosine | |
| modified_base | 12 | |
|  | mod_base = OTHER | |
|  | note = 2'-O-methylcytidine | |
| modified_base | 13 | |
|  | mod_base = OTHER | |
|  | note = 2'-O-methyluridine | |
| modified_base | 14 | |
|  | mod_base = OTHER | |
|  | note = 2'-fluorocytidine | |
| modified_base | 15 | |
|  | mod_base = OTHER | |
|  | note = 2'-O-methylguanosine | |
| modified_base | 16 | |
|  | mod_base = OTHER | |
|  | note = 2'-fluorocytidine | |
| modified_base | 17 | |
|  | mod_base = OTHER | |
|  | note = 2'-O-methylcytidine | |
| modified_base | 18 | |
|  | mod_base = OTHER | |
|  | note = 2'-O-methyladenosine | |
| modified_base | 19 | |
|  | mod_base = OTHER | |
|  | note = 2'-O-methylguanosine phosphorothioate | |
| modified_base | 20 | |
|  | mod_base = OTHER | |
|  | note = 2'-O-methyluridine phosphorothioate | |
| modified_base | 21 | |
|  | mod_base = OTHER | |
|  | note = 2'-O-methyluridine | |
| SEQUENCE: 246 | | |
| taaactccgg gctcgccagt t | | 21 |

| | | |
|---|---|---|
| SEQ ID NO: 247 | moltype = RNA  length = 21 | |
| FEATURE | Location/Qualifiers | |

| | | |
|---|---|---|
| source | 1..21 | |
| | mol_type = other RNA | |
| | organism = synthetic construct | |
| modified_base | 1 | |
| | mod_base = OTHER | |
| | note = 2'-fluorouridine phosphorothioate | |
| modified_base | 2 | |
| | mod_base = OTHER | |
| | note = 2'-fluoroadenosine phosphorothioate | |
| modified_base | 3 | |
| | mod_base = OTHER | |
| | note = 2'-O-methylguanosine | |
| modified_base | 4 | |
| | mod_base = OTHER | |
| | note = 2'-O-methyladenosine | |
| modified_base | 5 | |
| | mod_base = OTHER | |
| | note = 2'-O-methyladenosine | |
| modified_base | 6 | |
| | mod_base = OTHER | |
| | note = 2'-fluoroadenosine | |
| modified_base | 7 | |
| | mod_base = OTHER | |
| | note = 2'-O-methylcytidine | |
| modified_base | 8 | |
| | mod_base = OTHER | |
| | note = 2'-O-methyluridine | |
| modified_base | 9 | |
| | mod_base = OTHER | |
| | note = 2'-O-methylcytidine | |
| modified_base | 10 | |
| | mod_base = OTHER | |
| | note = 2'-O-methylcytidine | |
| modified_base | 11 | |
| | mod_base = OTHER | |
| | note = 2'-O-methylguanosine | |
| modified_base | 12 | |
| | mod_base = OTHER | |
| | note = 2'-O-methylguanosine | |
| modified_base | 13 | |
| | mod_base = OTHER | |
| | note = 2'-O-methylguanosine | |
| modified_base | 14 | |
| | mod_base = OTHER | |
| | note = 2'-fluorocytidine | |
| modified_base | 15 | |
| | mod_base = OTHER | |
| | note = 2'-O-methyluridine | |
| modified_base | 16 | |
| | mod_base = OTHER | |
| | note = 2'-fluorocytidine | |
| modified_base | 17 | |
| | mod_base = OTHER | |
| | note = 2'-O-methylguanosine | |
| modified_base | 18 | |
| | mod_base = OTHER | |
| | note = 2'-O-methylcytidine | |
| modified_base | 19 | |
| | mod_base = OTHER | |
| | note = 2'-O-methylcytidine phosphorothioate | |
| modified_base | 20 | |
| | mod_base = OTHER | |
| | note = 2'-O-methyluridine phosphorothioate | |
| modified_base | 21 | |
| | mod_base = OTHER | |
| | note = 2'-O-methyluridine | |
| SEQUENCE: 247 | | |
| tagaaactcc gggctcgcct t | | 21 |
| | | |
| SEQ ID NO: 248 | moltype = RNA  length = 21 | |
| FEATURE | Location/Qualifiers | |
| source | 1..21 | |
| | mol_type = other RNA | |
| | organism = synthetic construct | |
| modified_base | 1 | |
| | mod_base = OTHER | |
| | note = 2'-fluorouridine phosphorothioate | |
| modified_base | 2 | |
| | mod_base = OTHER | |

|  |  |
|---|---|
| | note = 2'-fluorouridine phosphorothioate |
| modified_base | 3 |
| | mod_base = OTHER |
| | note = 2'-O-methylcytidine |
| modified_base | 4 |
| | mod_base = OTHER |
| | note = 2'-O-methyluridine |
| modified_base | 5 |
| | mod_base = OTHER |
| | note = 2'-O-methyladenosine |
| modified_base | 6 |
| | mod_base = OTHER |
| | note = 2'-fluoroguanosine |
| modified_base | 7 |
| | mod_base = OTHER |
| | note = 2'-O-methylguanosine |
| modified_base | 8 |
| | mod_base = OTHER |
| | note = 2'-O-methyladenosine |
| modified_base | 9 |
| | mod_base = OTHER |
| | note = 2'-O-methylguanosine |
| modified_base | 10 |
| | mod_base = OTHER |
| | note = 2'-O-methyladenosine |
| modified_base | 11 |
| | mod_base = OTHER |
| | note = 2'-O-methylguanosine |
| modified_base | 12 |
| | mod_base = OTHER |
| | note = 2'-O-methylguanosine |
| modified_base | 13 |
| | mod_base = OTHER |
| | note = 2'-O-methyluridine |
| modified_base | 14 |
| | mod_base = OTHER |
| | note = 2'-fluorouridine |
| modified_base | 15 |
| | mod_base = OTHER |
| | note = 2'-O-methylguanosine |
| modified_base | 16 |
| | mod_base = OTHER |
| | note = 2'-fluorocytidine |
| modified_base | 17 |
| | mod_base = OTHER |
| | note = 2'-O-methylguanosine |
| modified_base | 18 |
| | mod_base = OTHER |
| | note = 2'-O-methylcytidine |
| modified_base | 19 |
| | mod_base = OTHER |
| | note = 2'-O-methylcytidine phosphorothioate |
| modified_base | 20 |
| | mod_base = OTHER |
| | note = 2'-O-methyluridine phosphorothioate |
| modified_base | 21 |
| | mod_base = OTHER |
| | note = 2'-O-methyluridine |
| SEQUENCE: 248 | |
| ttctaggaga ggttgcgcct t | 21 |
| | |
| SEQ ID NO: 249 | moltype = RNA length = 21 |
| FEATURE | Location/Qualifiers |
| source | 1..21 |
| | mol_type = other RNA |
| | organism = synthetic construct |
| modified_base | 1 |
| | mod_base = OTHER |
| | note = 2'-fluorouridine phosphorothioate |
| modified_base | 2 |
| | mod_base = OTHER |
| | note = 2'-fluorouridine phosphorothioate |
| modified_base | 3 |
| | mod_base = OTHER |
| | note = 2'-O-methyluridine |
| modified_base | 4 |
| | mod_base = OTHER |
| | note = 2'-O-methylcytidine |
| modified_base | 5 |

```
                        mod_base = OTHER
                        note = 2'-O-methyluridine
modified_base           6
                        mod_base = OTHER
                        note = 2'-fluoroadenosine
modified_base           7
                        mod_base = OTHER
                        note = 2'-O-methylguanosine
modified_base           8
                        mod_base = OTHER
                        note = 2'-O-methylguanosine
modified_base           9
                        mod_base = OTHER
                        note = 2'-O-methyladenosine
modified_base           10
                        mod_base = OTHER
                        note = 2'-O-methylguanosine
modified_base           11
                        mod_base = OTHER
                        note = 2'-O-methyladenosine
modified_base           12
                        mod_base = OTHER
                        note = 2'-O-methylguanosine
modified_base           13
                        mod_base = OTHER
                        note = 2'-O-methylguanosine
modified_base           14
                        mod_base = OTHER
                        note = 2'-fluorouridine
modified_base           15
                        mod_base = OTHER
                        note = 2'-O-methyluridine
modified_base           16
                        mod_base = OTHER
                        note = 2'-fluoroguanosine
modified_base           17
                        mod_base = OTHER
                        note = 2'-O-methylcytidine
modified_base           18
                        mod_base = OTHER
                        note = 2'-O-methylguanosine
modified_base           19
                        mod_base = OTHER
                        note = 2'-O-methylcytidine phosphorothioate
modified_base           20
                        mod_base = OTHER
                        note = 2'-O-methyluridine phosphorothioate
modified_base           21
                        mod_base = OTHER
                        note = 2'-O-methyluridine
SEQUENCE: 249
tttctaggag aggttgcgct t                                                  21

SEQ ID NO: 250          moltype = RNA   length = 21
FEATURE                 Location/Qualifiers
source                  1..21
                        mol_type = other RNA
                        organism = synthetic construct
modified_base           1
                        mod_base = OTHER
                        note = 2'-fluorouridine phosphorothioate
modified_base           2
                        mod_base = OTHER
                        note = 2'-fluorocytidine phosphorothioate
modified_base           3
                        mod_base = OTHER
                        note = 2'-O-methylcytidine
modified_base           4
                        mod_base = OTHER
                        note = 2'-O-methylguanosine
modified_base           5
                        mod_base = OTHER
                        note = 2'-O-methyluridine
modified_base           6
                        mod_base = OTHER
                        note = 2'-fluorouridine
modified_base           7
                        mod_base = OTHER
                        note = 2'-O-methyluridine
```

```
modified_base          8
                       mod_base = OTHER
                       note = 2'-O-methylcytidine
modified_base          9
                       mod_base = OTHER
                       note = 2'-O-methyluridine
modified_base          10
                       mod_base = OTHER
                       note = 2'-O-methyladenosine
modified_base          11
                       mod_base = OTHER
                       note = 2'-O-methylguanosine
modified_base          12
                       mod_base = OTHER
                       note = 2'-O-methylguanosine
modified_base          13
                       mod_base = OTHER
                       note = 2'-O-methyladenosine
modified_base          14
                       mod_base = OTHER
                       note = 2'-fluoroguanosine
modified_base          15
                       mod_base = OTHER
                       note = 2'-O-methyladenosine
modified_base          16
                       mod_base = OTHER
                       note = 2'-fluoroguanosine
modified_base          17
                       mod_base = OTHER
                       note = 2'-O-methylguanosine
modified_base          18
                       mod_base = OTHER
                       note = 2'-O-methyluridine
modified_base          19
                       mod_base = OTHER
                       note = 2'-O-methyluridine phosphorothioate
modified_base          20
                       mod_base = OTHER
                       note = 2'-O-methyluridine phosphorothioate
modified_base          21
                       mod_base = OTHER
                       note = 2'-O-methyluridine
SEQUENCE: 250
tccgtttcta ggagaggttt t                                             21

SEQ ID NO: 251         moltype = RNA  length = 21
FEATURE                Location/Qualifiers
source                 1..21
                       mol_type = other RNA
                       organism = synthetic construct
modified_base          1
                       mod_base = OTHER
                       note = 2'-fluorouridine phosphorothioate
modified_base          2
                       mod_base = OTHER
                       note = 2'-fluorocytidine phosphorothioate
modified_base          3
                       mod_base = OTHER
                       note = 2'-O-methylguanosine
modified_base          4
                       mod_base = OTHER
                       note = 2'-O-methylguanosine
modified_base          5
                       mod_base = OTHER
                       note = 2'-O-methyluridine
modified_base          6
                       mod_base = OTHER
                       note = 2'-fluoroadenosine
modified_base          7
                       mod_base = OTHER
                       note = 2'-O-methyluridine
modified_base          8
                       mod_base = OTHER
                       note = 2'-O-methyluridine
modified_base          9
                       mod_base = OTHER
                       note = 2'-O-methylcytidine
modified_base          10
                       mod_base = OTHER
```

|               | note = 2'-O-methyluridine |
| modified_base | 11 |
|               | mod_base = OTHER |
|               | note = 2'-O-methyluridine |
| modified_base | 12 |
|               | mod_base = OTHER |
|               | note = 2'-O-methylcytidine |
| modified_base | 13 |
|               | mod_base = OTHER |
|               | note = 2'-O-methylcytidine |
| modified_base | 14 |
|               | mod_base = OTHER |
|               | note = 2'-fluorouridine |
| modified_base | 15 |
|               | mod_base = OTHER |
|               | note = 2'-O-methylcytidine |
| modified_base | 16 |
|               | mod_base = OTHER |
|               | note = 2'-fluoroguanosine |
| modified_base | 17 |
|               | mod_base = OTHER |
|               | note = 2'-O-methylcytidine |
| modified_base | 18 |
|               | mod_base = OTHER |
|               | note = 2'-O-methyluridine |
| modified_base | 19 |
|               | mod_base = OTHER |
|               | note = 2'-O-methylguanosine phosphorothioate |
| modified_base | 20 |
|               | mod_base = OTHER |
|               | note = 2'-O-methyluridine phosphorothioate |
| modified_base | 21 |
|               | mod_base = OTHER |
|               | note = 2'-O-methyluridine |

SEQUENCE: 251
tcggtattct tcctcgctgt t         21

| SEQ ID NO: 252 | moltype = RNA length = 21 |
| FEATURE | Location/Qualifiers |
| source | 1..21 |
|        | mol_type = other RNA |
|        | organism = synthetic construct |
| modified_base | 1 |
|               | mod_base = OTHER |
|               | note = 2'-fluorouridine phosphorothioate |
| modified_base | 2 |
|               | mod_base = OTHER |
|               | note = 2'-fluorocytidine phosphorothioate |
| modified_base | 3 |
|               | mod_base = OTHER |
|               | note = 2'-O-methylcytidine |
| modified_base | 4 |
|               | mod_base = OTHER |
|               | note = 2'-O-methylguanosine |
| modified_base | 5 |
|               | mod_base = OTHER |
|               | note = 2'-O-methylguanosine |
| modified_base | 6 |
|               | mod_base = OTHER |
|               | note = 2'-fluorouridine |
| modified_base | 7 |
|               | mod_base = OTHER |
|               | note = 2'-O-methyladenosine |
| modified_base | 8 |
|               | mod_base = OTHER |
|               | note = 2'-O-methyluridine |
| modified_base | 9 |
|               | mod_base = OTHER |
|               | note = 2'-O-methyluridine |
| modified_base | 10 |
|               | mod_base = OTHER |
|               | note = 2'-O-methylcytidine |
| modified_base | 11 |
|               | mod_base = OTHER |
|               | note = 2'-O-methyluridine |
| modified_base | 12 |
|               | mod_base = OTHER |
|               | note = 2'-O-methyluridine |
| modified_base | 13 |

```
                        mod_base = OTHER
                        note = 2'-O-methylcytidine
modified_base           14
                        mod_base = OTHER
                        note = 2'-fluorocytidine
modified_base           15
                        mod_base = OTHER
                        note = 2'-O-methyluridine
modified_base           16
                        mod_base = OTHER
                        note = 2'-fluorocytidine
modified_base           17
                        mod_base = OTHER
                        note = 2'-O-methylguanosine
modified_base           18
                        mod_base = OTHER
                        note = 2'-O-methylcytidine
modified_base           19
                        mod_base = OTHER
                        note = 2'-O-methyluridine phosphorothioate
modified_base           20
                        mod_base = OTHER
                        note = 2'-O-methyluridine phosphorothioate
modified_base           21
                        mod_base = OTHER
                        note = 2'-O-methyluridine
SEQUENCE: 252
tccggtattc ttcctcgctt t                                              21

SEQ ID NO: 253          moltype = RNA   length = 21
FEATURE                 Location/Qualifiers
source                  1..21
                        mol_type = other RNA
                        organism = synthetic construct
modified_base           1
                        mod_base = OTHER
                        note = 2'-fluorouridine phosphorothioate
modified_base           2
                        mod_base = OTHER
                        note = 2'-fluorocytidine phosphorothioate
modified_base           3
                        mod_base = OTHER
                        note = 2'-O-methylcytidine
modified_base           4
                        mod_base = OTHER
                        note = 2'-O-methylcytidine
modified_base           5
                        mod_base = OTHER
                        note = 2'-O-methylguanosine
modified_base           6
                        mod_base = OTHER
                        note = 2'-fluoroguanosine
modified_base           7
                        mod_base = OTHER
                        note = 2'-O-methyluridine
modified_base           8
                        mod_base = OTHER
                        note = 2'-O-methyladenosine
modified_base           9
                        mod_base = OTHER
                        note = 2'-O-methyluridine
modified_base           10
                        mod_base = OTHER
                        note = 2'-O-methyluridine
modified_base           11
                        mod_base = OTHER
                        note = 2'-O-methylcytidine
modified_base           12
                        mod_base = OTHER
                        note = 2'-O-methyluridine
modified_base           13
                        mod_base = OTHER
                        note = 2'-O-methyluridine
modified_base           14
                        mod_base = OTHER
                        note = 2'-fluorocytidine
modified_base           15
                        mod_base = OTHER
                        note = 2'-O-methylcytidine
```

-continued

```
modified_base    16
                 mod_base = OTHER
                 note = 2'-fluorouridine
modified_base    17
                 mod_base = OTHER
                 note = 2'-O-methylcytidine
modified_base    18
                 mod_base = OTHER
                 note = 2'-O-methylguanosine
modified_base    19
                 mod_base = OTHER
                 note = 2'-O-methylcytidine phosphorothioate
modified_base    20
                 mod_base = OTHER
                 note = 2'-O-methyluridine phosphorothioate
modified_base    21
                 mod_base = OTHER
                 note = 2'-O-methyluridine
SEQUENCE: 253
tcccggtatt cttcctcgct t                                    21

SEQ ID NO: 254   moltype = RNA   length = 21
FEATURE          Location/Qualifiers
source           1..21
                 mol_type = other RNA
                 organism = synthetic construct
modified_base    1
                 mod_base = OTHER
                 note = 2'-fluorouridine phosphorothioate
modified_base    2
                 mod_base = OTHER
                 note = 2'-fluoroadenosine phosphorothioate
modified_base    3
                 mod_base = OTHER
                 note = 2'-O-methylcytidine
modified_base    4
                 mod_base = OTHER
                 note = 2'-O-methylcytidine
modified_base    5
                 mod_base = OTHER
                 note = 2'-O-methylcytidine
modified_base    6
                 mod_base = OTHER
                 note = 2'-fluoroguanosine
modified_base    7
                 mod_base = OTHER
                 note = 2'-O-methyladenosine
modified_base    8
                 mod_base = OTHER
                 note = 2'-O-methylcytidine
modified_base    9
                 mod_base = OTHER
                 note = 2'-O-methylcytidine
modified_base    10
                 mod_base = OTHER
                 note = 2'-O-methylcytidine
modified_base    11
                 mod_base = OTHER
                 note = 2'-O-methylcytidine
modified_base    12
                 mod_base = OTHER
                 note = 2'-O-methylguanosine
modified_base    13
                 mod_base = OTHER
                 note = 2'-O-methyluridine
modified_base    14
                 mod_base = OTHER
                 note = 2'-fluorocytidine
modified_base    15
                 mod_base = OTHER
                 note = 2'-O-methylcytidine
modified_base    16
                 mod_base = OTHER
                 note = 2'-fluorocytidine
modified_base    17
                 mod_base = OTHER
                 note = 2'-O-methyladenosine
modified_base    18
                 mod_base = OTHER
```

```
                        note = 2'-O-methyladenosine
modified_base           19
                        mod_base = OTHER
                        note = 2'-O-methylcytidine phosphorothioate
modified_base           20
                        mod_base = OTHER
                        note = 2'-O-methyluridine phosphorothioate
modified_base           21
                        mod_base = OTHER
                        note = 2'-O-methyluridine
SEQUENCE: 254
tacccgaccc cgtcccaact t                                                      21

SEQ ID NO: 255          moltype = RNA  length = 21
FEATURE                 Location/Qualifiers
source                  1..21
                        mol_type = other RNA
                        organism = synthetic construct
modified_base           1
                        mod_base = OTHER
                        note = 2'-fluorouridine phosphorothioate
modified_base           2
                        mod_base = OTHER
                        note = 2'-fluorocytidine phosphorothioate
modified_base           3
                        mod_base = OTHER
                        note = 2'-O-methylguanosine
modified_base           4
                        mod_base = OTHER
                        note = 2'-O-methyladenosine
modified_base           5
                        mod_base = OTHER
                        note = 2'-O-methyladenosine
modified_base           6
                        mod_base = OTHER
                        note = 2'-fluorocytidine
modified_base           7
                        mod_base = OTHER
                        note = 2'-O-methylcytidine
modified_base           8
                        mod_base = OTHER
                        note = 2'-O-methyladenosine
modified_base           9
                        mod_base = OTHER
                        note = 2'-O-methylcytidine
modified_base           10
                        mod_base = OTHER
                        note = 2'-O-methylcytidine
modified_base           11
                        mod_base = OTHER
                        note = 2'-O-methylcytidine
modified_base           12
                        mod_base = OTHER
                        note = 2'-O-methylguanosine
modified_base           13
                        mod_base = OTHER
                        note = 2'-O-methyladenosine
modified_base           14
                        mod_base = OTHER
                        note = 2'-fluorocytidine
modified_base           15
                        mod_base = OTHER
                        note = 2'-O-methylcytidine
modified_base           16
                        mod_base = OTHER
                        note = 2'-fluorocytidine
modified_base           17
                        mod_base = OTHER
                        note = 2'-O-methylcytidine
modified_base           18
                        mod_base = OTHER
                        note = 2'-O-methylguanosine
modified_base           19
                        mod_base = OTHER
                        note = 2'-O-methyluridine phosphorothioate
modified_base           20
                        mod_base = OTHER
                        note = 2'-O-methyluridine phosphorothioate
modified_base           21
```

```
                        mod_base = OTHER
                        note = 2'-O-methyluridine
SEQUENCE: 255
tcgaaccacc cgaccccgtt t                                              21

SEQ ID NO: 256          moltype = RNA  length = 21
FEATURE                 Location/Qualifiers
source                  1..21
                        mol_type = other RNA
                        organism = synthetic construct
modified_base           1
                        mod_base = OTHER
                        note = 2'-fluorouridine phosphorothioate
modified_base           2
                        mod_base = OTHER
                        note = 2'-fluoroguanosine phosphorothioate
modified_base           3
                        mod_base = OTHER
                        note = 2'-O-methylcytidine
modified_base           4
                        mod_base = OTHER
                        note = 2'-O-methylcytidine
modified_base           5
                        mod_base = OTHER
                        note = 2'-O-methylcytidine
modified_base           6
                        mod_base = OTHER
                        note = 2'-fluorocytidine
modified_base           7
                        mod_base = OTHER
                        note = 2'-O-methylguanosine
modified_base           8
                        mod_base = OTHER
                        note = 2'-O-methyladenosine
modified_base           9
                        mod_base = OTHER
                        note = 2'-O-methyladenosine
modified_base           10
                        mod_base = OTHER
                        note = 2'-O-methylcytidine
modified_base           11
                        mod_base = OTHER
                        note = 2'-O-methylcytidine
modified_base           12
                        mod_base = OTHER
                        note = 2'-O-methyladenosine
modified_base           13
                        mod_base = OTHER
                        note = 2'-O-methylcytidine
modified_base           14
                        mod_base = OTHER
                        note = 2'-fluorocytidine
modified_base           15
                        mod_base = OTHER
                        note = 2'-O-methylcytidine
modified_base           16
                        mod_base = OTHER
                        note = 2'-fluoroguanosine
modified_base           17
                        mod_base = OTHER
                        note = 2'-O-methyladenosine
modified_base           18
                        mod_base = OTHER
                        note = 2'-O-methylcytidine
modified_base           19
                        mod_base = OTHER
                        note = 2'-O-methylcytidine phosphorothioate
modified_base           20
                        mod_base = OTHER
                        note = 2'-O-methyluridine phosphorothioate
modified_base           21
                        mod_base = OTHER
                        note = 2'-O-methyluridine
SEQUENCE: 256
tgccccgaac cacccgacct t                                              21

SEQ ID NO: 257          moltype = RNA  length = 21
FEATURE                 Location/Qualifiers
source                  1..21
```

```
                        mol_type = other RNA
                        organism = synthetic construct
modified_base           1
                        mod_base = OTHER
                        note = 2'-fluorouridine phosphorothioate
modified_base           2
                        mod_base = OTHER
                        note = 2'-fluorouridine phosphorothioate
modified_base           3
                        mod_base = OTHER
                        note = 2'-O-methylguanosine
modified_base           4
                        mod_base = OTHER
                        note = 2'-O-methylcytidine
modified_base           5
                        mod_base = OTHER
                        note = 2'-O-methylcytidine
modified_base           6
                        mod_base = OTHER
                        note = 2'-fluorocytidine
modified_base           7
                        mod_base = OTHER
                        note = 2'-O-methylcytidine
modified_base           8
                        mod_base = OTHER
                        note = 2'-O-methylguanosine
modified_base           9
                        mod_base = OTHER
                        note = 2'-O-methyladenosine
modified_base           10
                        mod_base = OTHER
                        note = 2'-O-methyladenosine
modified_base           11
                        mod_base = OTHER
                        note = 2'-O-methylcytidine
modified_base           12
                        mod_base = OTHER
                        note = 2'-O-methylcytidine
modified_base           13
                        mod_base = OTHER
                        note = 2'-O-methyladenosine
modified_base           14
                        mod_base = OTHER
                        note = 2'-fluorocytidine
modified_base           15
                        mod_base = OTHER
                        note = 2'-O-methylcytidine
modified_base           16
                        mod_base = OTHER
                        note = 2'-fluorocytidine
modified_base           17
                        mod_base = OTHER
                        note = 2'-O-methylguanosine
modified_base           18
                        mod_base = OTHER
                        note = 2'-O-methyladenosine
modified_base           19
                        mod_base = OTHER
                        note = 2'-O-methylcytidine phosphorothioate
modified_base           20
                        mod_base = OTHER
                        note = 2'-O-methyluridine phosphorothioate
modified_base           21
                        mod_base = OTHER
                        note = 2'-O-methyluridine
SEQUENCE: 257
ttgccccgaa ccacccgact t                                                    21

SEQ ID NO: 258          moltype = RNA  length = 21
FEATURE                 Location/Qualifiers
source                  1..21
                        mol_type = other RNA
                        organism = synthetic construct
modified_base           1
                        mod_base = OTHER
                        note = 2'-fluorouridine phosphorothioate
modified_base           2
                        mod_base = OTHER
                        note = 2'-fluorocytidine phosphorothioate
```

```
                        -continued modified_base           3
                        mod_base = OTHER
                        note = 2'-O-methylguanosine
modified_base           4
                        mod_base = OTHER
                        note = 2'-O-methyladenosine
modified_base           5
                        mod_base = OTHER
                        note = 2'-O-methyladenosine
modified_base           6
                        mod_base = OTHER
                        note = 2'-fluoroadenosine
modified_base           7
                        mod_base = OTHER
                        note = 2'-O-methylguanosine
modified_base           8
                        mod_base = OTHER
                        note = 2'-O-methyladenosine
modified_base           9
                        mod_base = OTHER
                        note = 2'-O-methylguanosine
modified_base           10
                        mod_base = OTHER
                        note = 2'-O-methyladenosine
modified_base           11
                        mod_base = OTHER
                        note = 2'-O-methylguanosine
modified_base           12
                        mod_base = OTHER
                        note = 2'-O-methylguanosine
modified_base           13
                        mod_base = OTHER
                        note = 2'-O-methylcytidine
modified_base           14
                        mod_base = OTHER
                        note = 2'-fluorocytidine
modified_base           15
                        mod_base = OTHER
                        note = 2'-O-methyladenosine
modified_base           16
                        mod_base = OTHER
                        note = 2'-fluorocytidine
modified_base           17
                        mod_base = OTHER
                        note = 2'-O-methylcytidine
modified_base           18
                        mod_base = OTHER
                        note = 2'-O-methylguanosine
modified_base           19
                        mod_base = OTHER
                        note = 2'-O-methylcytidine phosphorothioate
modified_base           20
                        mod_base = OTHER
                        note = 2'-O-methyluridine phosphorothioate
modified_base           21
                        mod_base = OTHER
                        note = 2'-O-methyluridine
SEQUENCE: 258
tcgaaagaga ggccaccgct t                                             21

SEQ ID NO: 259          moltype = RNA   length = 21
FEATURE                 Location/Qualifiers
source                  1..21
                        mol_type = other RNA
                        organism = synthetic construct
modified_base           1
                        mod_base = OTHER
                        note = 2'-fluorouridine phosphorothioate
modified_base           2
                        mod_base = OTHER
                        note = 2'-fluoroguanosine phosphorothioate
modified_base           3
                        mod_base = OTHER
                        note = 2'-O-methylcytidine
modified_base           4
                        mod_base = OTHER
                        note = 2'-O-methylguanosine
modified_base           5
                        mod_base = OTHER
```

US 11,999,955 B2

367                                                                368
-continued

```
                        note = 2'-O-methyladenosine
modified_base           6
                        mod_base = OTHER
                        note = 2'-fluoroadenosine
modified_base           7
                        mod_base = OTHER
                        note = 2'-O-methyladenosine
modified_base           8
                        mod_base = OTHER
                        note = 2'-O-methylguanosine
modified_base           9
                        mod_base = OTHER
                        note = 2'-O-methyladenosine
modified_base           10
                        mod_base = OTHER
                        note = 2'-O-methylguanosine
modified_base           11
                        mod_base = OTHER
                        note = 2'-O-methyladenosine
modified_base           12
                        mod_base = OTHER
                        note = 2'-O-methylguanosine
modified_base           13
                        mod_base = OTHER
                        note = 2'-O-methylguanosine
modified_base           14
                        mod_base = OTHER
                        note = 2'-fluorocytidine
modified_base           15
                        mod_base = OTHER
                        note = 2'-O-methylcytidine
modified_base           16
                        mod_base = OTHER
                        note = 2'-fluoroadenosine
modified_base           17
                        mod_base = OTHER
                        note = 2'-O-methylcytidine
modified_base           18
                        mod_base = OTHER
                        note = 2'-O-methylcytidine
modified_base           19
                        mod_base = OTHER
                        note = 2'-O-methylguanosine phosphorothioate
modified_base           20
                        mod_base = OTHER
                        note = 2'-O-methyluridine phosphorothioate
modified_base           21
                        mod_base = OTHER
                        note = 2'-O-methyluridine
SEQUENCE: 259
tgcgaaagag aggccaccgt t                                              21

SEQ ID NO: 260          moltype = RNA  length = 21
FEATURE                 Location/Qualifiers
source                  1..21
                        mol_type = other RNA
                        organism = synthetic construct
modified_base           1
                        mod_base = OTHER
                        note = 2'-fluorouridine phosphorothioate
modified_base           2
                        mod_base = OTHER
                        note = 2'-fluorocytidine phosphorothioate
modified_base           3
                        mod_base = OTHER
                        note = 2'-O-methylguanosine
modified_base           4
                        mod_base = OTHER
                        note = 2'-O-methylcytidine
modified_base           5
                        mod_base = OTHER
                        note = 2'-O-methylguanosine
modified_base           6
                        mod_base = OTHER
                        note = 2'-fluoroadenosine
modified_base           7
                        mod_base = OTHER
                        note = 2'-O-methyladenosine
modified_base           8
```

```
                        mod_base = OTHER
                        note = 2'-O-methyladenosine
modified_base           9
                        mod_base = OTHER
                        note = 2'-O-methylguanosine
modified_base           10
                        mod_base = OTHER
                        note = 2'-O-methyladenosine
modified_base           11
                        mod_base = OTHER
                        note = 2'-O-methylguanosine
modified_base           12
                        mod_base = OTHER
                        note = 2'-O-methyladenosine
modified_base           13
                        mod_base = OTHER
                        note = 2'-O-methylguanosine
modified_base           14
                        mod_base = OTHER
                        note = 2'-fluoroguanosine
modified_base           15
                        mod_base = OTHER
                        note = 2'-O-methylcytidine
modified_base           16
                        mod_base = OTHER
                        note = 2'-fluorocytidine
modified_base           17
                        mod_base = OTHER
                        note = 2'-O-methyladenosine
modified_base           18
                        mod_base = OTHER
                        note = 2'-O-methylcytidine
modified_base           19
                        mod_base = OTHER
                        note = 2'-O-methylcytidine phosphorothioate
modified_base           20
                        mod_base = OTHER
                        note = 2'-O-methyluridine phosphorothioate
modified_base           21
                        mod_base = OTHER
                        note = 2'-O-methyluridine
SEQUENCE: 260
tcgcgaaaga gaggccacct t                                             21

SEQ ID NO: 261          moltype = RNA   length = 21
FEATURE                 Location/Qualifiers
source                  1..21
                        mol_type = other RNA
                        organism = synthetic construct
modified_base           1
                        mod_base = OTHER
                        note = 2'-fluorouridine phosphorothioate
modified_base           2
                        mod_base = OTHER
                        note = 2'-fluorouridine phosphorothioate
modified_base           3
                        mod_base = OTHER
                        note = 2'-O-methylcytidine
modified_base           4
                        mod_base = OTHER
                        note = 2'-O-methylcytidine
modified_base           5
                        mod_base = OTHER
                        note = 2'-O-methylcytidine
modified_base           6
                        mod_base = OTHER
                        note = 2'-fluorocytidine
modified_base           7
                        mod_base = OTHER
                        note = 2'-O-methylguanosine
modified_base           8
                        mod_base = OTHER
                        note = 2'-O-methylcytidine
modified_base           9
                        mod_base = OTHER
                        note = 2'-O-methylguanosine
modified_base           10
                        mod_base = OTHER
                        note = 2'-O-methyladenosine
```

| | |
|---|---|
| modified_base | 11<br>mod_base = OTHER<br>note = 2'-O-methyladenosine |
| modified_base | 12<br>mod_base = OTHER<br>note = 2'-O-methyladenosine |
| modified_base | 13<br>mod_base = OTHER<br>note = 2'-O-methylguanosine |
| modified_base | 14<br>mod_base = OTHER<br>note = 2'-fluoroadenosine |
| modified_base | 15<br>mod_base = OTHER<br>note = 2'-O-methylguanosine |
| modified_base | 16<br>mod_base = OTHER<br>note = 2'-fluoroadenosine |
| modified_base | 17<br>mod_base = OTHER<br>note = 2'-O-methylguanosine |
| modified_base | 18<br>mod_base = OTHER<br>note = 2'-O-methylguanosine |
| modified_base | 19<br>mod_base = OTHER<br>note = 2'-O-methylcytidine phosphorothioate |
| modified_base | 20<br>mod_base = OTHER<br>note = 2'-O-methyluridine phosphorothioate |
| modified_base | 21<br>mod_base = OTHER<br>note = 2'-O-methyluridine |
| SEQUENCE: 261 | |
| ttccccgcga aagagaggct t | 21 |
| SEQ ID NO: 262<br>FEATURE<br>source | moltype = RNA length = 21<br>Location/Qualifiers<br>1..21<br>mol_type = other RNA<br>organism = synthetic construct |
| modified_base | 1<br>mod_base = OTHER<br>note = 2'-fluorouridine phosphorothioate |
| modified_base | 2<br>mod_base = OTHER<br>note = 2'-fluorouridine phosphorothioate |
| modified_base | 3<br>mod_base = OTHER<br>note = 2'-O-methylcytidine |
| modified_base | 4<br>mod_base = OTHER<br>note = 2'-O-methylcytidine |
| modified_base | 5<br>mod_base = OTHER<br>note = 2'-O-methylguanosine |
| modified_base | 6<br>mod_base = OTHER<br>note = 2'-fluorouridine |
| modified_base | 7<br>mod_base = OTHER<br>note = 2'-O-methyladenosine |
| modified_base | 8<br>mod_base = OTHER<br>note = 2'-O-methylguanosine |
| modified_base | 9<br>mod_base = OTHER<br>note = 2'-O-methylcytidine |
| modified_base | 10<br>mod_base = OTHER<br>note = 2'-O-methylcytidine |
| modified_base | 11<br>mod_base = OTHER<br>note = 2'-O-methyladenosine |
| modified_base | 12<br>mod_base = OTHER<br>note = 2'-O-methylguanosine |
| modified_base | 13<br>mod_base = OTHER |

|                | note = 2'-O-methylcytidine |
| modified_base  | 14 |
|                | mod_base = OTHER |
|                | note = 2'-fluorocytidine |
| modified_base  | 15 |
|                | mod_base = OTHER |
|                | note = 2'-O-methyladenosine |
| modified_base  | 16 |
|                | mod_base = OTHER |
|                | note = 2'-fluoroguanosine |
| modified_base  | 17 |
|                | mod_base = OTHER |
|                | note = 2'-O-methylguanosine |
| modified_base  | 18 |
|                | mod_base = OTHER |
|                | note = 2'-O-methyluridine |
| modified_base  | 19 |
|                | mod_base = OTHER |
|                | note = 2'-O-methylguanosine phosphorothioate |
| modified_base  | 20 |
|                | mod_base = OTHER |
|                | note = 2'-O-methyluridine phosphorothioate |
| modified_base  | 21 |
|                | mod_base = OTHER |
|                | note = 2'-O-methyluridine |

SEQUENCE: 262
ttccgtagcc agccaggtgt t                                          21

| SEQ ID NO: 263 | moltype = RNA  length = 21 |
| FEATURE        | Location/Qualifiers |
| source         | 1..21 |
|                | mol_type = other RNA |
|                | organism = synthetic construct |
| modified_base  | 1 |
|                | mod_base = OTHER |
|                | note = 2'-fluorouridine phosphorothioate |
| modified_base  | 2 |
|                | mod_base = OTHER |
|                | note = 2'-fluoroguanosine phosphorothioate |
| modified_base  | 3 |
|                | mod_base = OTHER |
|                | note = 2'-O-methyladenosine |
| modified_base  | 4 |
|                | mod_base = OTHER |
|                | note = 2'-O-methylcytidine |
| modified_base  | 5 |
|                | mod_base = OTHER |
|                | note = 2'-O-methyladenosine |
| modified_base  | 6 |
|                | mod_base = OTHER |
|                | note = 2'-fluorocytidine |
| modified_base  | 7 |
|                | mod_base = OTHER |
|                | note = 2'-O-methylguanosine |
| modified_base  | 8 |
|                | mod_base = OTHER |
|                | note = 2'-O-methylcytidine |
| modified_base  | 9 |
|                | mod_base = OTHER |
|                | note = 2'-O-methylcytidine |
| modified_base  | 10 |
|                | mod_base = OTHER |
|                | note = 2'-O-methylcytidine |
| modified_base  | 11 |
|                | mod_base = OTHER |
|                | note = 2'-O-methylcytidine |
| modified_base  | 12 |
|                | mod_base = OTHER |
|                | note = 2'-O-methyluridine |
| modified_base  | 13 |
|                | mod_base = OTHER |
|                | note = 2'-O-methylcytidine |
| modified_base  | 14 |
|                | mod_base = OTHER |
|                | note = 2'-fluorocytidine |
| modified_base  | 15 |
|                | mod_base = OTHER |
|                | note = 2'-O-methylguanosine |
| modified_base  | 16 |

```
                      mod_base = OTHER
                      note = 2'-fluorouridine
modified_base         17
                      mod_base = OTHER
                      note = 2'-O-methyladenosine
modified_base         18
                      mod_base = OTHER
                      note = 2'-O-methylguanosine
modified_base         19
                      mod_base = OTHER
                      note = 2'-O-methylcytidine phosphorothioate
modified_base         20
                      mod_base = OTHER
                      note = 2'-O-methyluridine phosphorothioate
modified_base         21
                      mod_base = OTHER
                      note = 2'-O-methyluridine
SEQUENCE: 263
tgacacgccc ctccgtagct t                                            21

SEQ ID NO: 264        moltype = RNA   length = 21
FEATURE               Location/Qualifiers
source                1..21
                      mol_type = other RNA
                      organism = synthetic construct
modified_base         1
                      mod_base = OTHER
                      note = 2'-fluorouridine phosphorothioate
modified_base         2
                      mod_base = OTHER
                      note = 2'-fluoroadenosine phosphorothioate
modified_base         3
                      mod_base = OTHER
                      note = 2'-O-methylguanosine
modified_base         4
                      mod_base = OTHER
                      note = 2'-O-methyladenosine
modified_base         5
                      mod_base = OTHER
                      note = 2'-O-methylcytidine
modified_base         6
                      mod_base = OTHER
                      note = 2'-fluoroadenosine
modified_base         7
                      mod_base = OTHER
                      note = 2'-O-methylcytidine
modified_base         8
                      mod_base = OTHER
                      note = 2'-O-methylguanosine
modified_base         9
                      mod_base = OTHER
                      note = 2'-O-methylcytidine
modified_base         10
                      mod_base = OTHER
                      note = 2'-O-methylcytidine
modified_base         11
                      mod_base = OTHER
                      note = 2'-O-methylcytidine
modified_base         12
                      mod_base = OTHER
                      note = 2'-O-methylcytidine
modified_base         13
                      mod_base = OTHER
                      note = 2'-O-methyluridine
modified_base         14
                      mod_base = OTHER
                      note = 2'-fluorocytidine
modified_base         15
                      mod_base = OTHER
                      note = 2'-O-methylcytidine
modified_base         16
                      mod_base = OTHER
                      note = 2'-fluoroguanosine
modified_base         17
                      mod_base = OTHER
                      note = 2'-O-methyluridine
modified_base         18
                      mod_base = OTHER
                      note = 2'-O-methyladenosine
```

```
modified_base          19
                       mod_base = OTHER
                       note = 2'-O-methylguanosine phosphorothioate
modified_base          20
                       mod_base = OTHER
                       note = 2'-O-methyluridine phosphorothioate
modified_base          21
                       mod_base = OTHER
                       note = 2'-O-methyluridine
SEQUENCE: 264
tagacacgcc cctccgtagt t                                              21

SEQ ID NO: 265         moltype = RNA   length = 21
FEATURE                Location/Qualifiers
source                 1..21
                       mol_type = other RNA
                       organism = synthetic construct
modified_base          1
                       mod_base = OTHER
                       note = 2'-fluorouridine phosphorothioate
modified_base          2
                       mod_base = OTHER
                       note = 2'-fluoroguanosine phosphorothioate
modified_base          3
                       mod_base = OTHER
                       note = 2'-O-methylcytidine
modified_base          4
                       mod_base = OTHER
                       note = 2'-O-methylguanosine
modified_base          5
                       mod_base = OTHER
                       note = 2'-O-methyladenosine
modified_base          6
                       mod_base = OTHER
                       note = 2'-fluoroguanosine
modified_base          7
                       mod_base = OTHER
                       note = 2'-O-methylcytidine
modified_base          8
                       mod_base = OTHER
                       note = 2'-O-methyluridine
modified_base          9
                       mod_base = OTHER
                       note = 2'-O-methylcytidine
modified_base          10
                       mod_base = OTHER
                       note = 2'-O-methylcytidine
modified_base          11
                       mod_base = OTHER
                       note = 2'-O-methylcytidine
modified_base          12
                       mod_base = OTHER
                       note = 2'-O-methyluridine
modified_base          13
                       mod_base = OTHER
                       note = 2'-O-methyluridine
modified_base          14
                       mod_base = OTHER
                       note = 2'-fluoroguanosine
modified_base          15
                       mod_base = OTHER
                       note = 2'-O-methylcytidine
modified_base          16
                       mod_base = OTHER
                       note = 2'-fluoroadenosine
modified_base          17
                       mod_base = OTHER
                       note = 2'-O-methylcytidine
modified_base          18
                       mod_base = OTHER
                       note = 2'-O-methylguanosine
modified_base          19
                       mod_base = OTHER
                       note = 2'-O-methyluridine phosphorothioate
modified_base          20
                       mod_base = OTHER
                       note = 2'-O-methyluridine phosphorothioate
modified_base          21
                       mod_base = OTHER
``` note = 2'-O-methyluridine
SEQUENCE: 265
tgcgagctcc cttgcacgtt t                                              21

SEQ ID NO: 266           moltype = RNA   length = 21
FEATURE                  Location/Qualifiers
source                   1..21
                         mol_type = other RNA
                         organism = synthetic construct
modified_base            1
                         mod_base = OTHER
                         note = 2'-fluorouridine phosphorothioate
modified_base            2
                         mod_base = OTHER
                         note = 2'-fluoroadenosine phosphorothioate
modified_base            3
                         mod_base = OTHER
                         note = 2'-O-methylguanosine
modified_base            4
                         mod_base = OTHER
                         note = 2'-O-methylcytidine
modified_base            5
                         mod_base = OTHER
                         note = 2'-O-methylguanosine
modified_base            6
                         mod_base = OTHER
                         note = 2'-fluoroadenosine
modified_base            7
                         mod_base = OTHER
                         note = 2'-O-methylguanosine
modified_base            8
                         mod_base = OTHER
                         note = 2'-O-methylcytidine
modified_base            9
                         mod_base = OTHER
                         note = 2'-O-methyluridine
modified_base            10
                         mod_base = OTHER
                         note = 2'-O-methylcytidine
modified_base            11
                         mod_base = OTHER
                         note = 2'-O-methylcytidine
modified_base            12
                         mod_base = OTHER
                         note = 2'-O-methylcytidine
modified_base            13
                         mod_base = OTHER
                         note = 2'-O-methyluridine
modified_base            14
                         mod_base = OTHER
                         note = 2'-fluorouridine
modified_base            15
                         mod_base = OTHER
                         note = 2'-O-methylguanosine
modified_base            16
                         mod_base = OTHER
                         note = 2'-fluorocytidine
modified_base            17
                         mod_base = OTHER
                         note = 2'-O-methyladenosine
modified_base            18
                         mod_base = OTHER
                         note = 2'-O-methylcytidine
modified_base            19
                         mod_base = OTHER
                         note = 2'-O-methylguanosine phosphorothioate
modified_base            20
                         mod_base = OTHER
                         note = 2'-O-methyluridine phosphorothioate
modified_base            21
                         mod_base = OTHER
                         note = 2'-O-methyluridine
SEQUENCE: 266
tagcgagctc ccttgcacgt t                                              21

SEQ ID NO: 267           moltype = RNA   length = 21
FEATURE                  Location/Qualifiers
source                   1..21
                         mol_type = other RNA

|  |  |
|---|---|
| modified_base | 1<br>mod_base = OTHER<br>note = 2'-fluorouridine phosphorothioate |
| modified_base | 2<br>mod_base = OTHER<br>note = 2'-fluorocytidine phosphorothioate |
| modified_base | 3<br>mod_base = OTHER<br>note = 2'-O-methyladenosine |
| modified_base | 4<br>mod_base = OTHER<br>note = 2'-O-methylguanosine |
| modified_base | 5<br>mod_base = OTHER<br>note = 2'-O-methylcytidine |
| modified_base | 6<br>mod_base = OTHER<br>note = 2'-fluoroguanosine |
| modified_base | 7<br>mod_base = OTHER<br>note = 2'-O-methyladenosine |
| modified_base | 8<br>mod_base = OTHER<br>note = 2'-O-methylguanosine |
| modified_base | 9<br>mod_base = OTHER<br>note = 2'-O-methylcytidine |
| modified_base | 10<br>mod_base = OTHER<br>note = 2'-O-methyluridine |
| modified_base | 11<br>mod_base = OTHER<br>note = 2'-O-methylcytidine |
| modified_base | 12<br>mod_base = OTHER<br>note = 2'-O-methylcytidine |
| modified_base | 13<br>mod_base = OTHER<br>note = 2'-O-methylcytidine |
| modified_base | 14<br>mod_base = OTHER<br>note = 2'-fluorouridine |
| modified_base | 15<br>mod_base = OTHER<br>note = 2'-O-methyluridine |
| modified_base | 16<br>mod_base = OTHER<br>note = 2'-fluoroguanosine |
| modified_base | 17<br>mod_base = OTHER<br>note = 2'-O-methylcytidine |
| modified_base | 18<br>mod_base = OTHER<br>note = 2'-O-methyladenosine |
| modified_base | 19<br>mod_base = OTHER<br>note = 2'-O-methylcytidine phosphorothioate |
| modified_base | 20<br>mod_base = OTHER<br>note = 2'-O-methyluridine phosphorothioate |
| modified_base | 21<br>mod_base = OTHER<br>note = 2'-O-methyluridine |
| SEQUENCE: 267 | |
| tcagcgagct cccttgcact t | 21 |
| | |
| SEQ ID NO: 268 | moltype = RNA   length = 21 |
| FEATURE | Location/Qualifiers |
| source | 1..21<br>mol_type = other RNA<br>organism = synthetic construct |
| modified_base | 1<br>mod_base = OTHER<br>note = 2'-fluorouridine phosphorothioate |
| modified_base | 2<br>mod_base = OTHER<br>note = 2'-fluoroadenosine phosphorothioate |
| modified_base | 3 |

```
                        mod_base = OTHER
                        note = 2'-O-methylguanosine
modified_base           4
                        mod_base = OTHER
                        note = 2'-O-methyladenosine
modified_base           5
                        mod_base = OTHER
                        note = 2'-O-methylcytidine
modified_base           6
                        mod_base = OTHER
                        note = 2'-fluoroadenosine
modified_base           7
                        mod_base = OTHER
                        note = 2'-O-methylguanosine
modified_base           8
                        mod_base = OTHER
                        note = 2'-O-methylcytidine
modified_base           9
                        mod_base = OTHER
                        note = 2'-O-methylguanosine
modified_base           10
                        mod_base = OTHER
                        note = 2'-O-methyluridine
modified_base           11
                        mod_base = OTHER
                        note = 2'-O-methylcytidine
modified_base           12
                        mod_base = OTHER
                        note = 2'-O-methylguanosine
modified_base           13
                        mod_base = OTHER
                        note = 2'-O-methylguanosine
modified_base           14
                        mod_base = OTHER
                        note = 2'-fluoroadenosine
modified_base           15
                        mod_base = OTHER
                        note = 2'-O-methyladenosine
modified_base           16
                        mod_base = OTHER
                        note = 2'-fluoroguanosine
modified_base           17
                        mod_base = OTHER
                        note = 2'-O-methylguanosine
modified_base           18
                        mod_base = OTHER
                        note = 2'-O-methyluridine
modified_base           19
                        mod_base = OTHER
                        note = 2'-O-methylguanosine phosphorothioate
modified_base           20
                        mod_base = OTHER
                        note = 2'-O-methyluridine phosphorothioate
modified_base           21
                        mod_base = OTHER
                        note = 2'-O-methyluridine
SEQUENCE: 268
tagacagcgt cggaaggtgt t                                                  21

SEQ ID NO: 269          moltype = RNA   length = 21
FEATURE                 Location/Qualifiers
source                  1..21
                        mol_type = other RNA
                        organism = synthetic construct
modified_base           1
                        mod_base = OTHER
                        note = 2'-fluorouridine phosphorothioate
modified_base           2
                        mod_base = OTHER
                        note = 2'-fluorouridine phosphorothioate
modified_base           3
                        mod_base = OTHER
                        note = 2'-O-methyladenosine
modified_base           4
                        mod_base = OTHER
                        note = 2'-O-methylguanosine
modified_base           5
                        mod_base = OTHER
                        note = 2'-O-methyladenosine
```

```
modified_base    6
                 mod_base = OTHER
                 note = 2'-fluorocytidine
modified_base    7
                 mod_base = OTHER
                 note = 2'-O-methyladenosine
modified_base    8
                 mod_base = OTHER
                 note = 2'-O-methylguanosine
modified_base    9
                 mod_base = OTHER
                 note = 2'-O-methylcytidine
modified_base    10
                 mod_base = OTHER
                 note = 2'-O-methylguanosine
modified_base    11
                 mod_base = OTHER
                 note = 2'-O-methyluridine
modified_base    12
                 mod_base = OTHER
                 note = 2'-O-methylcytidine
modified_base    13
                 mod_base = OTHER
                 note = 2'-O-methylguanosine
modified_base    14
                 mod_base = OTHER
                 note = 2'-fluoroguanosine
modified_base    15
                 mod_base = OTHER
                 note = 2'-O-methyladenosine
modified_base    16
                 mod_base = OTHER
                 note = 2'-fluoroadenosine
modified_base    17
                 mod_base = OTHER
                 note = 2'-O-methylguanosine
modified_base    18
                 mod_base = OTHER
                 note = 2'-O-methylguanosine
modified_base    19
                 mod_base = OTHER
                 note = 2'-O-methyluridine phosphorothioate
modified_base    20
                 mod_base = OTHER
                 note = 2'-O-methyluridine phosphorothioate
modified_base    21
                 mod_base = OTHER
                 note = 2'-O-methyluridine
SEQUENCE: 269
ttagacagcg tcggaaggtt t                                          21

SEQ ID NO: 270      moltype = RNA  length = 21
FEATURE             Location/Qualifiers
source              1..21
                    mol_type = other RNA
                    organism = synthetic construct
modified_base       1
                    mod_base = OTHER
                    note = 2'-fluorouridine phosphorothioate
modified_base       2
                    mod_base = OTHER
                    note = 2'-fluorocytidine phosphorothioate
modified_base       3
                    mod_base = OTHER
                    note = 2'-O-methyluridine
modified_base       4
                    mod_base = OTHER
                    note = 2'-O-methyladenosine
modified_base       5
                    mod_base = OTHER
                    note = 2'-O-methylguanosine
modified_base       6
                    mod_base = OTHER
                    note = 2'-fluoroadenosine
modified_base       7
                    mod_base = OTHER
                    note = 2'-O-methylcytidine
modified_base       8
                    mod_base = OTHER
```

|                | note = 2'-O-methyladenosine |
| --- | --- |
| modified_base | 9 |
|                | mod_base = OTHER |
|                | note = 2'-O-methylguanosine |
| modified_base | 10 |
|                | mod_base = OTHER |
|                | note = 2'-O-methylcytidine |
| modified_base | 11 |
|                | mod_base = OTHER |
|                | note = 2'-O-methylguanosine |
| modified_base | 12 |
|                | mod_base = OTHER |
|                | note = 2'-O-methyluridine |
| modified_base | 13 |
|                | mod_base = OTHER |
|                | note = 2'-O-methylcytidine |
| modified_base | 14 |
|                | mod_base = OTHER |
|                | note = 2'-fluoroguanosine |
| modified_base | 15 |
|                | mod_base = OTHER |
|                | note = 2'-O-methylguanosine |
| modified_base | 16 |
|                | mod_base = OTHER |
|                | note = 2'-fluoroadenosine |
| modified_base | 17 |
|                | mod_base = OTHER |
|                | note = 2'-O-methyladenosine |
| modified_base | 18 |
|                | mod_base = OTHER |
|                | note = 2'-O-methylguanosine |
| modified_base | 19 |
|                | mod_base = OTHER |
|                | note = 2'-O-methylguanosine phosphorothioate |
| modified_base | 20 |
|                | mod_base = OTHER |
|                | note = 2'-O-methyluridine phosphorothioate |
| modified_base | 21 |
|                | mod_base = OTHER |
|                | note = 2'-O-methyluridine |

SEQUENCE: 270
tctagacagc gtcggaaggt t                                          21

| SEQ ID NO: 271 | moltype = RNA  length = 21 |
| --- | --- |
| FEATURE | Location/Qualifiers |
| source | 1..21 |
|  | mol_type = other RNA |
|  | organism = synthetic construct |
| modified_base | 1 |
|  | mod_base = OTHER |
|  | note = 2'-fluorouridine phosphorothioate |
| modified_base | 2 |
|  | mod_base = OTHER |
|  | note = 2'-fluorocytidine phosphorothioate |
| modified_base | 3 |
|  | mod_base = OTHER |
|  | note = 2'-O-methylcytidine |
| modified_base | 4 |
|  | mod_base = OTHER |
|  | note = 2'-O-methyluridine |
| modified_base | 5 |
|  | mod_base = OTHER |
|  | note = 2'-O-methyladenosine |
| modified_base | 6 |
|  | mod_base = OTHER |
|  | note = 2'-fluoroguanosine |
| modified_base | 7 |
|  | mod_base = OTHER |
|  | note = 2'-O-methyladenosine |
| modified_base | 8 |
|  | mod_base = OTHER |
|  | note = 2'-O-methylcytidine |
| modified_base | 9 |
|  | mod_base = OTHER |
|  | note = 2'-O-methyladenosine |
| modified_base | 10 |
|  | mod_base = OTHER |
|  | note = 2'-O-methylguanosine |
| modified_base | 11 |

|  |  |
|---|---|
|  | mod_base = OTHER |
|  | note = 2'-O-methylcytidine |
| modified_base | 12 |
|  | mod_base = OTHER |
|  | note = 2'-O-methylguanosine |
| modified_base | 13 |
|  | mod_base = OTHER |
|  | note = 2'-O-methyluridine |
| modified_base | 14 |
|  | mod_base = OTHER |
|  | note = 2'-fluorocytidine |
| modified_base | 15 |
|  | mod_base = OTHER |
|  | note = 2'-O-methylguanosine |
| modified_base | 16 |
|  | mod_base = OTHER |
|  | note = 2'-fluoroguanosine |
| modified_base | 17 |
|  | mod_base = OTHER |
|  | note = 2'-O-methyladenosine |
| modified_base | 18 |
|  | mod_base = OTHER |
|  | note = 2'-O-methyladenosine |
| modified_base | 19 |
|  | mod_base = OTHER |
|  | note = 2'-O-methylguanosine phosphorothioate |
| modified_base | 20 |
|  | mod_base = OTHER |
|  | note = 2'-O-methyluridine phosphorothioate |
| modified_base | 21 |
|  | mod_base = OTHER |
|  | note = 2'-O-methyluridine |
| SEQUENCE: 271 |  |
| tcctagacag cgtcggaagt t | 21 |
|  |  |
| SEQ ID NO: 272 | moltype = RNA length = 21 |
| FEATURE | Location/Qualifiers |
| source | 1..21 |
|  | mol_type = other RNA |
|  | organism = synthetic construct |
| modified_base | 1 |
|  | mod_base = OTHER |
|  | note = 2'-fluorouridine phosphorothioate |
| modified_base | 2 |
|  | mod_base = OTHER |
|  | note = 2'-fluorouridine phosphorothioate |
| modified_base | 3 |
|  | mod_base = OTHER |
|  | note = 2'-O-methylguanosine |
| modified_base | 4 |
|  | mod_base = OTHER |
|  | note = 2'-O-methylcytidine |
| modified_base | 5 |
|  | mod_base = OTHER |
|  | note = 2'-O-methylcytidine |
| modified_base | 6 |
|  | mod_base = OTHER |
|  | note = 2'-fluorouridine |
| modified_base | 7 |
|  | mod_base = OTHER |
|  | note = 2'-O-methyladenosine |
| modified_base | 8 |
|  | mod_base = OTHER |
|  | note = 2'-O-methylguanosine |
| modified_base | 9 |
|  | mod_base = OTHER |
|  | note = 2'-O-methyladenosine |
| modified_base | 10 |
|  | mod_base = OTHER |
|  | note = 2'-O-methylcytidine |
| modified_base | 11 |
|  | mod_base = OTHER |
|  | note = 2'-O-methyladenosine |
| modified_base | 12 |
|  | mod_base = OTHER |
|  | note = 2'-O-methylguanosine |
| modified_base | 13 |
|  | mod_base = OTHER |
|  | note = 2'-O-methylcytidine |

-continued

```
modified_base         14
                      mod_base = OTHER
                      note = 2'-fluoroguanosine
modified_base         15
                      mod_base = OTHER
                      note = 2'-O-methyluridine
modified_base         16
                      mod_base = OTHER
                      note = 2'-fluorocytidine
modified_base         17
                      mod_base = OTHER
                      note = 2'-O-methylguanosine
modified_base         18
                      mod_base = OTHER
                      note = 2'-O-methylguanosine
modified_base         19
                      mod_base = OTHER
                      note = 2'-O-methyladenosine phosphorothioate
modified_base         20
                      mod_base = OTHER
                      note = 2'-O-methyluridine phosphorothioate
modified_base         21
                      mod_base = OTHER
                      note = 2'-O-methyluridine
SEQUENCE: 272
ttgcctagac agcgtcggat t                                         21

SEQ ID NO: 273        moltype = RNA   length = 21
FEATURE               Location/Qualifiers
source                1..21
                      mol_type = other RNA
                      organism = synthetic construct
modified_base         1
                      mod_base = OTHER
                      note = 2'-fluorouridine phosphorothioate
modified_base         2
                      mod_base = OTHER
                      note = 2'-fluorouridine phosphorothioate
modified_base         3
                      mod_base = OTHER
                      note = 2'-O-methyluridine
modified_base         4
                      mod_base = OTHER
                      note = 2'-O-methylguanosine
modified_base         5
                      mod_base = OTHER
                      note = 2'-O-methylcytidine
modified_base         6
                      mod_base = OTHER
                      note = 2'-fluorocytidine
modified_base         7
                      mod_base = OTHER
                      note = 2'-O-methyluridine
modified_base         8
                      mod_base = OTHER
                      note = 2'-O-methyladenosine
modified_base         9
                      mod_base = OTHER
                      note = 2'-O-methylguanosine
modified_base         10
                      mod_base = OTHER
                      note = 2'-O-methyladenosine
modified_base         11
                      mod_base = OTHER
                      note = 2'-O-methylcytidine
modified_base         12
                      mod_base = OTHER
                      note = 2'-O-methyladenosine
modified_base         13
                      mod_base = OTHER
                      note = 2'-O-methylguanosine
modified_base         14
                      mod_base = OTHER
                      note = 2'-fluorocytidine
modified_base         15
                      mod_base = OTHER
                      note = 2'-O-methylguanosine
modified_base         16
                      mod_base = OTHER
```

```
                              note = 2'-fluorouridine
modified_base                 17
                              mod_base = OTHER
                              note = 2'-O-methylcytidine
modified_base                 18
                              mod_base = OTHER
                              note = 2'-O-methylguanosine
modified_base                 19
                              mod_base = OTHER
                              note = 2'-O-methylguanosine phosphorothioate
modified_base                 20
                              mod_base = OTHER
                              note = 2'-O-methyluridine phosphorothioate
modified_base                 21
                              mod_base = OTHER
                              note = 2'-O-methyluridine
SEQUENCE: 273
tttgcctaga cagcgtcggt t                                              21

SEQ ID NO: 274                moltype = RNA   length = 21
FEATURE                       Location/Qualifiers
source                        1..21
                              mol_type = other RNA
                              organism = synthetic construct
modified_base                 1
                              mod_base = OTHER
                              note = 2'-fluorouridine phosphorothioate
modified_base                 2
                              mod_base = OTHER
                              note = 2'-fluoroguanosine phosphorothioate
modified_base                 3
                              mod_base = OTHER
                              note = 2'-O-methylguanosine
modified_base                 4
                              mod_base = OTHER
                              note = 2'-O-methyluridine
modified_base                 5
                              mod_base = OTHER
                              note = 2'-O-methyluridine
modified_base                 6
                              mod_base = OTHER
                              note = 2'-fluorouridine
modified_base                 7
                              mod_base = OTHER
                              note = 2'-O-methylguanosine
modified_base                 8
                              mod_base = OTHER
                              note = 2'-O-methylcytidine
modified_base                 9
                              mod_base = OTHER
                              note = 2'-O-methylcytidine
modified_base                 10
                              mod_base = OTHER
                              note = 2'-O-methyluridine
modified_base                 11
                              mod_base = OTHER
                              note = 2'-O-methyladenosine
modified_base                 12
                              mod_base = OTHER
                              note = 2'-O-methylguanosine
modified_base                 13
                              mod_base = OTHER
                              note = 2'-O-methyladenosine
modified_base                 14
                              mod_base = OTHER
                              note = 2'-fluorocytidine
modified_base                 15
                              mod_base = OTHER
                              note = 2'-O-methyladenosine
modified_base                 16
                              mod_base = OTHER
                              note = 2'-fluoroguanosine
modified_base                 17
                              mod_base = OTHER
                              note = 2'-O-methylcytidine
modified_base                 18
                              mod_base = OTHER
                              note = 2'-O-methylguanosine
modified_base                 19
```

```
                        mod_base = OTHER
                        note = 2'-O-methyluridine phosphorothioate
modified_base           20
                        mod_base = OTHER
                        note = 2'-O-methyluridine phosphorothioate
modified_base           21
                        mod_base = OTHER
                        note = 2'-O-methyluridine
SEQUENCE: 274
tggtttgcct agacagcgtt t                                                21

SEQ ID NO: 275          moltype = RNA  length = 21
FEATURE                 Location/Qualifiers
source                  1..21
                        mol_type = other RNA
                        organism = synthetic construct
modified_base           1
                        mod_base = OTHER
                        note = 2'-fluorouridine phosphorothioate
modified_base           2
                        mod_base = OTHER
                        note = 2'-fluorouridine phosphorothioate
modified_base           3
                        mod_base = OTHER
                        note = 2'-O-methyladenosine
modified_base           4
                        mod_base = OTHER
                        note = 2'-O-methyladenosine
modified_base           5
                        mod_base = OTHER
                        note = 2'-O-methylcytidine
modified_base           6
                        mod_base = OTHER
                        note = 2'-fluorouridine
modified_base           7
                        mod_base = OTHER
                        note = 2'-O-methylcytidine
modified_base           8
                        mod_base = OTHER
                        note = 2'-O-methyluridine
modified_base           9
                        mod_base = OTHER
                        note = 2'-O-methyladenosine
modified_base           10
                        mod_base = OTHER
                        note = 2'-O-methyladenosine
modified_base           11
                        mod_base = OTHER
                        note = 2'-O-methyluridine
modified_base           12
                        mod_base = OTHER
                        note = 2'-O-methylcytidine
modified_base           13
                        mod_base = OTHER
                        note = 2'-O-methylcytidine
modified_base           14
                        mod_base = OTHER
                        note = 2'-fluoroadenosine
modified_base           15
                        mod_base = OTHER
                        note = 2'-O-methylguanosine
modified_base           16
                        mod_base = OTHER
                        note = 2'-fluoroguanosine
modified_base           17
                        mod_base = OTHER
                        note = 2'-O-methyluridine
modified_base           18
                        mod_base = OTHER
                        note = 2'-O-methyluridine
modified_base           19
                        mod_base = OTHER
                        note = 2'-O-methyluridine phosphorothioate
modified_base           20
                        mod_base = OTHER
                        note = 2'-O-methyluridine phosphorothioate
modified_base           21
                        mod_base = OTHER
                        note = 2'-O-methyluridine
```

```
SEQUENCE: 275
ttaactctaa tccaggtttt t                                          21

SEQ ID NO: 276          moltype = RNA  length = 21
FEATURE                 Location/Qualifiers
source                  1..21
                        mol_type = other RNA
                        organism = synthetic construct
modified_base           1
                        mod_base = OTHER
                        note = 2'-fluorouridine phosphorothioate
modified_base           2
                        mod_base = OTHER
                        note = 2'-fluoroadenosine phosphorothioate
modified_base           3
                        mod_base = OTHER
                        note = 2'-O-methyladenosine
modified_base           4
                        mod_base = OTHER
                        note = 2'-O-methylguanosine
modified_base           5
                        mod_base = OTHER
                        note = 2'-O-methylcytidine
modified_base           6
                        mod_base = OTHER
                        note = 2'-fluoroguanosine
modified_base           7
                        mod_base = OTHER
                        note = 2'-O-methyladenosine
modified_base           8
                        mod_base = OTHER
                        note = 2'-O-methyluridine
modified_base           9
                        mod_base = OTHER
                        note = 2'-O-methylcytidine
modified_base           10
                        mod_base = OTHER
                        note = 2'-O-methylcytidine
modified_base           11
                        mod_base = OTHER
                        note = 2'-O-methyluridine
modified_base           12
                        mod_base = OTHER
                        note = 2'-O-methyluridine
modified_base           13
                        mod_base = OTHER
                        note = 2'-O-methylcytidine
modified_base           14
                        mod_base = OTHER
                        note = 2'-fluorouridine
modified_base           15
                        mod_base = OTHER
                        note = 2'-O-methylcytidine
modified_base           16
                        mod_base = OTHER
                        note = 2'-fluoroadenosine
modified_base           17
                        mod_base = OTHER
                        note = 2'-O-methyladenosine
modified_base           18
                        mod_base = OTHER
                        note = 2'-O-methyladenosine
modified_base           19
                        mod_base = OTHER
                        note = 2'-O-methylguanosine phosphorothioate
modified_base           20
                        mod_base = OTHER
                        note = 2'-O-methyluridine phosphorothioate
modified_base           21
                        mod_base = OTHER
                        note = 2'-O-methyluridine
SEQUENCE: 276
taagcgatcc ttctcaaagt t                                          21

SEQ ID NO: 277          moltype = RNA  length = 21
FEATURE                 Location/Qualifiers
source                  1..21
                        mol_type = other RNA
                        organism = synthetic construct
```

| | |
|---|---|
| modified_base | 1<br>mod_base = OTHER<br>note = 2'-fluorouridine phosphorothioate |
| modified_base | 2<br>mod_base = OTHER<br>note = 2'-fluoroguanosine phosphorothioate |
| modified_base | 3<br>mod_base = OTHER<br>note = 2'-O-methyladenosine |
| modified_base | 4<br>mod_base = OTHER<br>note = 2'-O-methylguanosine |
| modified_base | 5<br>mod_base = OTHER<br>note = 2'-O-methyladenosine |
| modified_base | 6<br>mod_base = OTHER<br>note = 2'-fluorouridine |
| modified_base | 7<br>mod_base = OTHER<br>note = 2'-O-methylcytidine |
| modified_base | 8<br>mod_base = OTHER<br>note = 2'-O-methylcytidine |
| modified_base | 9<br>mod_base = OTHER<br>note = 2'-O-methylcytidine |
| modified_base | 10<br>mod_base = OTHER<br>note = 2'-O-methylcytidine |
| modified_base | 11<br>mod_base = OTHER<br>note = 2'-O-methyluridine |
| modified_base | 12<br>mod_base = OTHER<br>note = 2'-O-methylcytidine |
| modified_base | 13<br>mod_base = OTHER<br>note = 2'-O-methyluridine |
| modified_base | 14<br>mod_base = OTHER<br>note = 2'-fluoroguanosine |
| modified_base | 15<br>mod_base = OTHER<br>note = 2'-O-methylcytidine |
| modified_base | 16<br>mod_base = OTHER<br>note = 2'-fluorocytidine |
| modified_base | 17<br>mod_base = OTHER<br>note = 2'-O-methylguanosine |
| modified_base | 18<br>mod_base = OTHER<br>note = 2'-O-methylguanosine |
| modified_base | 19<br>mod_base = OTHER<br>note = 2'-O-methylcytidine phosphorothioate |
| modified_base | 20<br>mod_base = OTHER<br>note = 2'-O-methyluridine phosphorothioate |
| modified_base | 21<br>mod_base = OTHER<br>note = 2'-O-methyluridine |
| SEQUENCE: 277 | |
| tgagatcccc tctgccggct t | 21 |
| SEQ ID NO: 278<br>FEATURE<br>source | moltype = RNA  length = 21<br>Location/Qualifiers<br>1..21<br>mol_type = other RNA<br>organism = synthetic construct |
| modified_base | 1<br>mod_base = OTHER<br>note = 2'-fluorouridine phosphorothioate |
| modified_base | 2<br>mod_base = OTHER<br>note = 2'-fluoroguanosine phosphorothioate |
| modified_base | 3<br>mod_base = OTHER |

|                | |
|---|---|
| | note = 2'-O-methylcytidine |
| modified_base | 4 |
| | mod_base = OTHER |
| | note = 2'-O-methyladenosine |
| modified_base | 5 |
| | mod_base = OTHER |
| | note = 2'-O-methyladenosine |
| modified_base | 6 |
| | mod_base = OTHER |
| | note = 2'-fluoroguanosine |
| modified_base | 7 |
| | mod_base = OTHER |
| | note = 2'-O-methylcytidine |
| modified_base | 8 |
| | mod_base = OTHER |
| | note = 2'-O-methyladenosine |
| modified_base | 9 |
| | mod_base = OTHER |
| | note = 2'-O-methylcytidine |
| modified_base | 10 |
| | mod_base = OTHER |
| | note = 2'-O-methylcytidine |
| modified_base | 11 |
| | mod_base = OTHER |
| | note = 2'-O-methylcytidine |
| modified_base | 12 |
| | mod_base = OTHER |
| | note = 2'-O-methylcytidine |
| modified_base | 13 |
| | mod_base = OTHER |
| | note = 2'-O-methyluridine |
| modified_base | 14 |
| | mod_base = OTHER |
| | note = 2'-fluorouridine |
| modified_base | 15 |
| | mod_base = OTHER |
| | note = 2'-O-methylguanosine |
| modified_base | 16 |
| | mod_base = OTHER |
| | note = 2'-fluoroguanosine |
| modified_base | 17 |
| | mod_base = OTHER |
| | note = 2'-O-methylcytidine |
| modified_base | 18 |
| | mod_base = OTHER |
| | note = 2'-O-methylcytidine |
| modified_base | 19 |
| | mod_base = OTHER |
| | note = 2'-O-methylcytidine phosphorothioate |
| modified_base | 20 |
| | mod_base = OTHER |
| | note = 2'-O-methyluridine phosphorothioate |
| modified_base | 21 |
| | mod_base = OTHER |
| | note = 2'-O-methyluridine |
| SEQUENCE: 278 | |
| tgcaagcacc ccttggccct t | 21 |
| | |
| SEQ ID NO: 279 | moltype = RNA   length = 21 |
| FEATURE | Location/Qualifiers |
| source | 1..21 |
| | mol_type = other RNA |
| | organism = synthetic construct |
| modified_base | 1 |
| | mod_base = OTHER |
| | note = 2'-fluorouridine phosphorothioate |
| modified_base | 2 |
| | mod_base = OTHER |
| | note = 2'-fluoroguanosine phosphorothioate |
| modified_base | 3 |
| | mod_base = OTHER |
| | note = 2'-O-methylcytidine |
| modified_base | 4 |
| | mod_base = OTHER |
| | note = 2'-O-methylguanosine |
| modified_base | 5 |
| | mod_base = OTHER |
| | note = 2'-O-methylcytidine |
| modified_base | 6 |

```
                           mod_base = OTHER
                           note = 2'-fluoroadenosine
modified_base              7
                           mod_base = OTHER
                           note = 2'-O-methyladenosine
modified_base              8
                           mod_base = OTHER
                           note = 2'-O-methylguanosine
modified_base              9
                           mod_base = OTHER
                           note = 2'-O-methylcytidine
modified_base              10
                           mod_base = OTHER
                           note = 2'-O-methyladenosine
modified_base              11
                           mod_base = OTHER
                           note = 2'-O-methylcytidine
modified_base              12
                           mod_base = OTHER
                           note = 2'-O-methylcytidine
modified_base              13
                           mod_base = OTHER
                           note = 2'-O-methylcytidine
modified_base              14
                           mod_base = OTHER
                           note = 2'-fluorocytidine
modified_base              15
                           mod_base = OTHER
                           note = 2'-O-methyluridine
modified_base              16
                           mod_base = OTHER
                           note = 2'-fluorouridine
modified_base              17
                           mod_base = OTHER
                           note = 2'-O-methylguanosine
modified_base              18
                           mod_base = OTHER
                           note = 2'-O-methylguanosine
modified_base              19
                           mod_base = OTHER
                           note = 2'-O-methylcytidine phosphorothioate
modified_base              20
                           mod_base = OTHER
                           note = 2'-O-methyluridine phosphorothioate
modified_base              21
                           mod_base = OTHER
                           note = 2'-O-methyluridine
SEQUENCE: 279
tgcgcaagca ccccttggct t                                                21

SEQ ID NO: 280             moltype = RNA   length = 21
FEATURE                    Location/Qualifiers
source                     1..21
                           mol_type = other RNA
                           organism = synthetic construct
modified_base              1
                           mod_base = OTHER
                           note = 2'-fluorouridine phosphorothioate
modified_base              2
                           mod_base = OTHER
                           note = 2'-fluorocytidine phosphorothioate
modified_base              3
                           mod_base = OTHER
                           note = 2'-O-methylguanosine
modified_base              4
                           mod_base = OTHER
                           note = 2'-O-methylcytidine
modified_base              5
                           mod_base = OTHER
                           note = 2'-O-methylcytidine
modified_base              6
                           mod_base = OTHER
                           note = 2'-fluoroguanosine
modified_base              7
                           mod_base = OTHER
                           note = 2'-O-methylguanosine
modified_base              8
                           mod_base = OTHER
                           note = 2'-O-methylguanosine
```

```
modified_base      9
                   mod_base = OTHER
                   note = 2'-O-methyladenosine
modified_base      10
                   mod_base = OTHER
                   note = 2'-O-methyluridine
modified_base      11
                   mod_base = OTHER
                   note = 2'-O-methylguanosine
modified_base      12
                   mod_base = OTHER
                   note = 2'-O-methylcytidine
modified_base      13
                   mod_base = OTHER
                   note = 2'-O-methylcytidine
modified_base      14
                   mod_base = OTHER
                   note = 2'-fluorouridine
modified_base      15
                   mod_base = OTHER
                   note = 2'-O-methyluridine
modified_base      16
                   mod_base = OTHER
                   note = 2'-fluoroguanosine
modified_base      17
                   mod_base = OTHER
                   note = 2'-O-methylcytidine
modified_base      18
                   mod_base = OTHER
                   note = 2'-O-methyladenosine
modified_base      19
                   mod_base = OTHER
                   note = 2'-O-methyluridine phosphorothioate
modified_base      20
                   mod_base = OTHER
                   note = 2'-O-methyluridine phosphorothioate
modified_base      21
                   mod_base = OTHER
                   note = 2'-O-methyluridine
SEQUENCE: 280
tcgccgggat gccttgcatt t                                          21

SEQ ID NO: 281         moltype = AA   length = 9
FEATURE                Location/Qualifiers
source                 1..9
                       mol_type = protein
                       organism = synthetic construct
SEQUENCE: 281
YTFTNYWMH                                                        9

SEQ ID NO: 282         moltype = AA   length = 17
FEATURE                Location/Qualifiers
source                 1..17
                       mol_type = protein
                       organism = synthetic construct
SEQUENCE: 282
EINPINGRSN YAQKFQG                                               17

SEQ ID NO: 283         moltype = AA   length = 7
FEATURE                Location/Qualifiers
source                 1..7
                       mol_type = protein
                       organism = synthetic construct
SEQUENCE: 283
GTRAMHY                                                          7

SEQ ID NO: 284         moltype = AA   length = 17
FEATURE                Location/Qualifiers
source                 1..17
                       mol_type = protein
                       organism = synthetic construct
SEQUENCE: 284
EINPINGRSN YAEKFQG                                               17

SEQ ID NO: 285         moltype = AA   length = 17
FEATURE                Location/Qualifiers
source                 1..17
                       mol_type = protein
                       organism = synthetic construct
```

```
SEQUENCE: 285
EINPIQGRSN YAEKFQG                                                    17

SEQ ID NO: 286         moltype = AA  length = 11
FEATURE                Location/Qualifiers
source                 1..11
                       mol_type = protein
                       organism = synthetic construct
SEQUENCE: 286
RTSENIYNNL A                                                          11

SEQ ID NO: 287         moltype = AA  length = 7
FEATURE                Location/Qualifiers
source                 1..7
                       mol_type = protein
                       organism = synthetic construct
SEQUENCE: 287
AATNLAD                                                               7

SEQ ID NO: 288         moltype = AA  length = 9
FEATURE                Location/Qualifiers
source                 1..9
                       mol_type = protein
                       organism = synthetic construct
SEQUENCE: 288
QHFWGTPLT                                                             9

SEQ ID NO: 289         moltype = AA  length = 7
FEATURE                Location/Qualifiers
source                 1..7
                       mol_type = protein
                       organism = synthetic construct
SEQUENCE: 289
AATNLAE                                                               7

SEQ ID NO: 290         moltype = AA  length = 10
FEATURE                Location/Qualifiers
source                 1..10
                       mol_type = protein
                       organism = synthetic construct
SEQUENCE: 290
QHFWGTPLTF                                                            10

SEQ ID NO: 291         moltype = AA  length = 11
FEATURE                Location/Qualifiers
source                 1..11
                       mol_type = protein
                       organism = synthetic construct
SEQUENCE: 291
RTSENIYSNL A                                                          11

SEQ ID NO: 292         moltype = AA  length = 7
FEATURE                Location/Qualifiers
source                 1..7
                       mol_type = protein
                       organism = synthetic construct
SEQUENCE: 292
AGTNLAD                                                               7

SEQ ID NO: 293         moltype = AA  length = 116
FEATURE                Location/Qualifiers
source                 1..116
                       mol_type = protein
                       organism = synthetic construct
SEQUENCE: 293
QVQLVQSGAE VKKPGASVKV SCKASGYTFT NYWMHWVRQA PGQGLEWMGE INPINGRSNY      60
AQKFQGRVTL TVDTSISTAY MELSRLRSDD TAVYYCARGT RAMHYWGQGT LVTVSS         116

SEQ ID NO: 294         moltype = AA  length = 116
FEATURE                Location/Qualifiers
source                 1..116
                       mol_type = protein
                       organism = synthetic construct
SEQUENCE: 294
QVQLVQSGAE VKKPGASVKV SCKASGYTFT NYWMHWVRQA PGQGLEWIGE INPINGRSNY      60
AEKFQGRVTL TVDTSSSTAY MELSRLRSDD TAVYYCARGT RAMHYWGQGT LVTVSS         116

SEQ ID NO: 295         moltype = AA  length = 116
FEATURE                Location/Qualifiers
```

```
                          source          1..116
                                          mol_type = protein
                                          organism = synthetic construct
SEQUENCE: 295
QVQLVQSGAE VKKPGASVKV SCKASGYTFT NYWMHWVRQA PGQGLEWMGE INPIQGRSNY    60
AEKFQGRVTL TVDTSSSTAY MELSSLRSED TATYYCARGT RAMHYWGQGT LVTVSS       116

SEQ ID NO: 296            moltype = AA   length = 116
FEATURE                   Location/Qualifiers
source                    1..116
                          mol_type = protein
                          organism = synthetic construct
SEQUENCE: 296
QVQLVQSGAE VKKPGASVKV SCKASGYTFT NYWMHWVRQA PGQGLEWMGE INPINGRSNY    60
AEKFQGRVTL TVDTSSSTAY MELSSLRSED TATYYCARGT RAMHYWGQGT LVTVSS       116

SEQ ID NO: 297            moltype = AA   length = 116
FEATURE                   Location/Qualifiers
source                    1..116
                          mol_type = protein
                          organism = synthetic construct
SEQUENCE: 297
QVQLQQPGAE LVKPGASVKL SCKASGYTFT NYWMHWVKQR PGQGLEWIGE INPINGRSNY    60
GERFKTKATL TVDKSSSTAY MQLSSLTSED SAVYYCARGT RAMHYWGQGT SVTVSS       116

SEQ ID NO: 298            moltype = AA   length = 107
FEATURE                   Location/Qualifiers
source                    1..107
                          mol_type = protein
                          organism = synthetic construct
SEQUENCE: 298
DIQMTQSPSS LSASVGDRVT ITCRTSENIY NNLAWYQQKP GKSPKLLIYA ATNLADGVPS    60
RFSGSGSGTD YTLTISSLQP EDFATYYCQH FWGTPLTFGG GTKVEIK                 107

SEQ ID NO: 299            moltype = AA   length = 107
FEATURE                   Location/Qualifiers
source                    1..107
                          mol_type = protein
                          organism = synthetic construct
SEQUENCE: 299
DIQMTQSPSS LSASVGDRVT ITCRTSENIY NNLAWYQQKP GKAPKLLIYA ATNLADGVPS    60
RFSGSGSGTD YTLTISSLQP EDFATYYCQH FWGTPLTFGG GTKVEIK                 107

SEQ ID NO: 300            moltype = AA   length = 107
FEATURE                   Location/Qualifiers
source                    1..107
                          mol_type = protein
                          organism = synthetic construct
SEQUENCE: 300
DIQMTQSPSS LSASVGDRVT ITCRTSENIY NNLAWYQQKP GKAPKLLIYA ATNLAEGVPS    60
RFSGSGSGTD YTLTISSLQP EDFATYYCQH FWGTPLTFGG GTKVEIK                 107

SEQ ID NO: 301            moltype = AA   length = 107
FEATURE                   Location/Qualifiers
source                    1..107
                          mol_type = protein
                          organism = synthetic construct
SEQUENCE: 301
DIQMTQSPSS LSASVGDRVT ITCRTSENIY SNLAWYQQKP GKAPKLLIYA GTNLADGVPS    60
RFSGSGSGTD YTLTISSLQP EDFANYYCQH FWGTPLTFGG GTKVEIK                 107

SEQ ID NO: 302            moltype = AA   length = 107
FEATURE                   Location/Qualifiers
source                    1..107
                          mol_type = protein
                          organism = synthetic construct
SEQUENCE: 302
DIQMTQSPAS LSVSVGETVT ITCRTSENIY NNLAWYQQKQ GKSPQLLVYA ATNLADGVPS    60
RFSGSGSGTQ YSLKINSLQS EDFGNYYCQH FWGTPLTFGA GTKLELK                 107

SEQ ID NO: 303            moltype = AA   length = 445
FEATURE                   Location/Qualifiers
source                    1..445
                          mol_type = protein
                          organism = synthetic construct
SEQUENCE: 303
QVQLVQSGAE VKKPGASVKV SCKASGYTFT NYWMHWVRQA PGQGLEWMGE INPINGRSNY    60
AQKFQGRVTL TVDTSISTAY MELSRLRSDD TAVYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
```

```
LSSVVTVPSS SLGTQTYICN VNHKPSNTKV DKRVEPKSCD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 304          moltype = AA  length = 445
FEATURE                 Location/Qualifiers
source                  1..445
                        mol_type = protein
                        organism = synthetic construct
SEQUENCE: 304
QVQLVQSGAE VKKPGASVKV SCKASGYTFT NYWMHWVRQA PGQGLEWMGE INPINGRSNY    60
AQKFQGRVTL TVDTSISTAY MELSRLRSDD TAVYYCARGT RAMHYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSCD KTHTCPPCPA PEAAGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 305          moltype = AA  length = 445
FEATURE                 Location/Qualifiers
source                  1..445
                        mol_type = protein
                        organism = synthetic construct
SEQUENCE: 305
QVQLVQSGAE VKKPGASVKV SCKASGYTFT NYWMHWVRQA PGQGLEWMGE INPINGRSNY    60
AQKFQGRVTL TVDTSISTAY MELSRLRSDD TAVYYCARGT RAMHYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSCD KTHTCPPCPA PEAAGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC GVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 306          moltype = AA  length = 445
FEATURE                 Location/Qualifiers
source                  1..445
                        mol_type = protein
                        organism = synthetic construct
SEQUENCE: 306
QVQLVQSGAE VKKPGASVKV SCKASGYTFT NYWMHWVRQA PGQGLEWMGE INPINGRSNY    60
AQKFQGRVTL TVDTSISTAY MELSRLRSDD TAVYYCARGT RAMHYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSCD KTHTCPPCPA PEAAGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKARPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 307          moltype = AA  length = 445
FEATURE                 Location/Qualifiers
source                  1..445
                        mol_type = protein
                        organism = synthetic construct
SEQUENCE: 307
QVQLVQSGAE VKKPGASVKV SCKASGYTFT NYWMHWVRQA PGQGLEWMGE INPINGRSNY    60
AQKFQGRVTL TVDTSISTAY MELSRLRSDD TAVYYCARGT RAMHYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSCD KTHTCPPCPA PEAAGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALGAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 308          moltype = AA  length = 445
FEATURE                 Location/Qualifiers
source                  1..445
                        mol_type = protein
                        organism = synthetic construct
SEQUENCE: 308
QVQLVQSGAE VKKPGASVKV SCKASGYTFT NYWMHWVRQA PGQGLEWMGE INPINGRSNY    60
AQKFQGRVTL TVDTSISTAY MELSRLRSDD TAVYYCARGT RAMHYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSCD KTHTCPPCPA PELLGGPSVF    240
LFPPKPKDTL MISRTPEVTC VVVAVSHEDP EVKFNWYVDG VEVHNAKTKP REEQYGSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
```

```
VFSCSVMHEA LHNHYTQKSL SLSPG                                              445

SEQ ID NO: 309            moltype = AA  length = 445
FEATURE                   Location/Qualifiers
source                    1..445
                          mol_type = protein
                          organism = synthetic construct
SEQUENCE: 309
QVQLVQSGAE VKKPGASVKV SCKASGYTFT NYWMHWVRQA PGQGLEWIGE INPINGRSNY          60
AEKFQGRVTL TVDTSSSTAY MELSRLRSDD TAVYYCARGT RAMHYWGQGT LVTVSSASTK         120
GPSVFPLAPS SKSTSGGTAA LGCLVKDYFP EPVTVSWNSG ALTSGVHTFP AVLQSSGLYS         180
LSSVVTVPSS SLGTQTYICN VNHKPSNTKV DKRVEPKSCD KTHTCPPCPA PELLGGPSVF         240
LFPPKPKDTL MISRTPEVTC VVVDVSHEDP EVKFNWYVDG VEVHNAKTKP REEQYNSTYR         300
VVSVLTVLHQ DWLNGKEYKC KVSNKALPAP IEKTISKAKG QPREPQVYTL PPSREEMTKN         360
QVSLTCLVKG FYPSDIAVEW ESNGQPENNY KTTPPVLDSD GSFFLYSKLT VDKSRWQQGN         420
VFSCSVMHEA LHNHYTQKSL SLSPG                                              445

SEQ ID NO: 310            moltype = AA  length = 445
FEATURE                   Location/Qualifiers
source                    1..445
                          mol_type = protein
                          organism = synthetic construct
SEQUENCE: 310
QVQLVQSGAE VKKPGASVKV SCKASGYTFT NYWMHWVRQA PGQGLEWIGE INPINGRSNY          60
AEKFQGRVTL TVDTSSSTAY MELSRLRSDD TAVYYCARGT RAMHYWGQGT LVTVSSASTK         120
GPSVFPLAPS SKSTSGGTAA LGCLVKDYFP EPVTVSWNSG ALTSGVHTFP AVLQSSGLYS         180
LSSVVTVPSS SLGTQTYICN VNHKPSNTKV DKRVEPKSCD KTHTCPPCPA PEAAGGPSVF         240
LFPPKPKDTL MISRTPEVTC VVVDVSHEDP EVKFNWYVDG VEVHNAKTKP REEQYNSTYR         300
VVSVLTVLHQ DWLNGKEYKC KVSNKALPAP IEKTISKAKG QPREPQVYTL PPSREEMTKN         360
QVSLTCLVKG FYPSDIAVEW ESNGQPENNY KTTPPVLDSD GSFFLYSKLT VDKSRWQQGN         420
VFSCSVMHEA LHNHYTQKSL SLSPG                                              445

SEQ ID NO: 311            moltype = AA  length = 445
FEATURE                   Location/Qualifiers
source                    1..445
                          mol_type = protein
                          organism = synthetic construct
SEQUENCE: 311
QVQLVQSGAE VKKPGASVKV SCKASGYTFT NYWMHWVRQA PGQGLEWIGE INPINGRSNY          60
AEKFQGRVTL TVDTSSSTAY MELSRLRSDD TAVYYCARGT RAMHYWGQGT LVTVSSASTK         120
GPSVFPLAPS SKSTSGGTAA LGCLVKDYFP EPVTVSWNSG ALTSGVHTFP AVLQSSGLYS         180
LSSVVTVPSS SLGTQTYICN VNHKPSNTKV DKRVEPKSCD KTHTCPPCPA PEAAGGPSVF         240
LFPPKPKDTL MISRTPEVTC VVVDVSHEDP EVKFNWYVDG VEVHNAKTKP REEQYNSTYR         300
VVSVLTVLHQ DWLNGKEYKC GVSNKALPAP IEKTISKAKG QPREPQVYTL PPSREEMTKN         360
QVSLTCLVKG FYPSDIAVEW ESNGQPENNY KTTPPVLDSD GSFFLYSKLT VDKSRWQQGN         420
VFSCSVMHEA LHNHYTQKSL SLSPG                                              445

SEQ ID NO: 312            moltype = AA  length = 445
FEATURE                   Location/Qualifiers
source                    1..445
                          mol_type = protein
                          organism = synthetic construct
SEQUENCE: 312
QVQLVQSGAE VKKPGASVKV SCKASGYTFT NYWMHWVRQA PGQGLEWIGE INPINGRSNY          60
AEKFQGRVTL TVDTSSSTAY MELSRLRSDD TAVYYCARGT RAMHYWGQGT LVTVSSASTK         120
GPSVFPLAPS SKSTSGGTAA LGCLVKDYFP EPVTVSWNSG ALTSGVHTFP AVLQSSGLYS         180
LSSVVTVPSS SLGTQTYICN VNHKPSNTKV DKRVEPKSCD KTHTCPPCPA PEAAGGPSVF         240
LFPPKPKDTL MISRTPEVTC VVVDVSHEDP EVKFNWYVDG VEVHNAKTKP REEQYNSTYR         300
VVSVLTVLHQ DWLNGKEYKC KVSNKARPAP IEKTISKAKG QPREPQVYTL PPSREEMTKN         360
QVSLTCLVKG FYPSDIAVEW ESNGQPENNY KTTPPVLDSD GSFFLYSKLT VDKSRWQQGN         420
VFSCSVMHEA LHNHYTQKSL SLSPG                                              445

SEQ ID NO: 313            moltype = AA  length = 445
FEATURE                   Location/Qualifiers
source                    1..445
                          mol_type = protein
                          organism = synthetic construct
SEQUENCE: 313
QVQLVQSGAE VKKPGASVKV SCKASGYTFT NYWMHWVRQA PGQGLEWIGE INPINGRSNY          60
AEKFQGRVTL TVDTSSSTAY MELSRLRSDD TAVYYCARGT RAMHYWGQGT LVTVSSASTK         120
GPSVFPLAPS SKSTSGGTAA LGCLVKDYFP EPVTVSWNSG ALTSGVHTFP AVLQSSGLYS         180
LSSVVTVPSS SLGTQTYICN VNHKPSNTKV DKRVEPKSCD KTHTCPPCPA PEAAGGPSVF         240
LFPPKPKDTL MISRTPEVTC VVVDVSHEDP EVKFNWYVDG VEVHNAKTKP REEQYNSTYR         300
VVSVLTVLHQ DWLNGKEYKC KVSNKALGAP IEKTISKAKG QPREPQVYTL PPSREEMTKN         360
QVSLTCLVKG FYPSDIAVEW ESNGQPENNY KTTPPVLDSD GSFFLYSKLT VDKSRWQQGN         420
VFSCSVMHEA LHNHYTQKSL SLSPG                                              445

SEQ ID NO: 314            moltype = AA  length = 445
FEATURE                   Location/Qualifiers
```

```
source                      1..445
                            mol_type = protein
                            organism = synthetic construct
SEQUENCE: 314
QVQLVQSGAE VKKPGASVKV SCKASGYTFT NYWMHWVRQA PGQGLEWIGE INPINGRSNY    60
AEKFQGRVTL TVDTSSSTAY MELSRLRSDD TAVYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PELLGGPSVF   240
LFPPKPKDTL MISRTPEVTC VVVAVSHEDP EVKFNWYVDG VEVHNAKTKP REEQYGSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 315              moltype = AA  length = 445
FEATURE                     Location/Qualifiers
source                      1..445
                            mol_type = protein
                            organism = synthetic construct
SEQUENCE: 315
QVQLVQSGAE VKKPGASVKV SCKASGYTFT NYWMHWVRQA PGQGLEWMGE INPIQGRSNY    60
AEKFQGRVTL TVDTSSSTAY MELSSLRSED TATYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 316              moltype = AA  length = 445
FEATURE                     Location/Qualifiers
source                      1..445
                            mol_type = protein
                            organism = synthetic construct
SEQUENCE: 316
QVQLVQSGAE VKKPGASVKV SCKASGYTFT NYWMHWVRQA PGQGLEWMGE INPIQGRSNY    60
AEKFQGRVTL TVDTSSSTAY MELSSLRSED TATYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PEAAGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 317              moltype = AA  length = 445
FEATURE                     Location/Qualifiers
source                      1..445
                            mol_type = protein
                            organism = synthetic construct
SEQUENCE: 317
QVQLVQSGAE VKKPGASVKV SCKASGYTFT NYWMHWVRQA PGQGLEWMGE INPIQGRSNY    60
AEKFQGRVTL TVDTSSSTAY MELSSLRSED TATYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PEAAGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC GVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 318              moltype = AA  length = 445
FEATURE                     Location/Qualifiers
source                      1..445
                            mol_type = protein
                            organism = synthetic construct
SEQUENCE: 318
QVQLVQSGAE VKKPGASVKV SCKASGYTFT NYWMHWVRQA PGQGLEWMGE INPIQGRSNY    60
AEKFQGRVTL TVDTSSSTAY MELSSLRSED TATYYCARGT RAMHYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PEAAGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKARPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                        445

SEQ ID NO: 319              moltype = AA  length = 445
FEATURE                     Location/Qualifiers
source                      1..445
                            mol_type = protein
                            organism = synthetic construct
SEQUENCE: 319
```

```
QVQLVQSGAE VKKPGASVKV SCKASGYTFT NYWMHWVRQA PGQGLEWMGE INPIQGRSNY   60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALGAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 320            moltype = AA  length = 445
FEATURE                   Location/Qualifiers
source                    1..445
                          mol_type = protein
                          organism = synthetic construct
SEQUENCE: 320
QVQLVQSGAE VKKPGASVKV SCKASGYTFT NYWMHWVRQA PGQGLEWMGE INPIQGRSNY   60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVAVSHEDP EVKFNWYVDG VEVHNAKTKP REEQYGSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 321            moltype = AA  length = 445
FEATURE                   Location/Qualifiers
source                    1..445
                          mol_type = protein
                          organism = synthetic construct
SEQUENCE: 321
QVQLVQSGAE VKKPGASVKV SCKASGYTFT NYWMHWVRQA PGQGLEWMGE INPINGRSNY   60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 322            moltype = AA  length = 445
FEATURE                   Location/Qualifiers
source                    1..445
                          mol_type = protein
                          organism = synthetic construct
SEQUENCE: 322
QVQLVQSGAE VKKPGASVKV SCKASGYTFT NYWMHWVRQA PGQGLEWMGE INPINGRSNY   60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 323            moltype = AA  length = 445
FEATURE                   Location/Qualifiers
source                    1..445
                          mol_type = protein
                          organism = synthetic construct
SEQUENCE: 323
QVQLVQSGAE VKKPGASVKV SCKASGYTFT NYWMHWVRQA PGQGLEWMGE INPINGRSNY   60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC GVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 324            moltype = AA  length = 445
FEATURE                   Location/Qualifiers
source                    1..445
                          mol_type = protein
                          organism = synthetic construct
SEQUENCE: 324
QVQLVQSGAE VKKPGASVKV SCKASGYTFT NYWMHWVRQA PGQGLEWMGE INPINGRSNY   60
AEKFQGRVTL TVDTSSSTAY MELSSLRSED TATYYCARGT RAMHYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGGPSVF  240
```

```
LFPPKPKDTL MISRTPEVTC VVVDVSHEDP EVKFNWYVDG VEVHNAKTKP REEQYNSTYR    300
VVSVLTVLHQ DWLNGKEYKC KVSNKARPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 325          moltype = AA   length = 445
FEATURE                 Location/Qualifiers
source                  1..445
                        mol_type = protein
                        organism = synthetic construct
SEQUENCE: 325
QVQLVQSGAE VKKPGASVKV SCKASGYTFT NYWMHWVRQA PGQGLEWMGE INPINGRSNY     60
AEKFQGRVTL TVDTSSSTAY MELSSLRSED TATYYCARGT RAMHYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSCD KTHTCPPCPA PEAAGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALGAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 326          moltype = AA   length = 445
FEATURE                 Location/Qualifiers
source                  1..445
                        mol_type = protein
                        organism = synthetic construct
SEQUENCE: 326
QVQLVQSGAE VKKPGASVKV SCKASGYTFT NYWMHWVRQA PGQGLEWMGE INPINGRSNY     60
AEKFQGRVTL TVDTSSSTAY MELSSLRSED TATYYCARGT RAMHYWGQGT LVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSCD KTHTCPPCPA PELLGGPSVF    240
LFPPKPKDTL MISRTPEVTC VVVAVSHEDP EVKFNWYVDG VEVHNAKTKP REEQYGSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPG                                         445

SEQ ID NO: 327          moltype = AA   length = 214
FEATURE                 Location/Qualifiers
source                  1..214
                        mol_type = protein
                        organism = synthetic construct
SEQUENCE: 327
DIQMTQSPSS LSASVGDRVT ITCRTSENIY NNLAWYQQKP GKSPKLLIYA ATNLADGVPS     60
RFSGSGSGTD YTLTISSLQP EDFATYYCQH FWGTPLTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 328          moltype = AA   length = 214
FEATURE                 Location/Qualifiers
source                  1..214
                        mol_type = protein
                        organism = synthetic construct
SEQUENCE: 328
DIQMTQSPSS LSASVGDRVT ITCRTSENIY NNLAWYQQKP GKAPKLLIYA ATNLADGVPS     60
RFSGSGSGTD YTLTISSLQP EDFATYYCQH FWGTPLTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 329          moltype = AA   length = 214
FEATURE                 Location/Qualifiers
source                  1..214
                        mol_type = protein
                        organism = synthetic construct
SEQUENCE: 329
DIQMTQSPSS LSASVGDRVT ITCRTSENIY NNLAWYQQKP GKAPKLLIYA ATNLAEGVPS     60
RFSGSGSGTD YTLTISSLQP EDFATYYCQH FWGTPLTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 330          moltype = AA   length = 214
FEATURE                 Location/Qualifiers
source                  1..214
                        mol_type = protein
                        organism = synthetic construct
SEQUENCE: 330
DIQMTQSPSS LSASVGDRVT ITCRTSENIY SNLAWYQQKP GKAPKLLIYA GTNLADGVPS     60
RFSGSGSGTD YTLTISSLQP EDFANYYCQH FWGTPLTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214
```

| | | |
|---|---|---|
| SEQ ID NO: 331 | moltype = AA   length = 24 | |
| FEATURE | Location/Qualifiers | |
| source | 1..24 | |
| | mol_type = protein | |
| | organism = synthetic construct | |
| SEQUENCE: 331 | | |
| CGIFGEIEEL IEEGLENLID WGNA | | 24 |
| | | |
| SEQ ID NO: 332 | moltype = AA   length = 24 | |
| FEATURE | Location/Qualifiers | |
| source | 1..24 | |
| | mol_type = protein | |
| | organism = synthetic construct | |
| SEQUENCE: 332 | | |
| GLFEAIEGFI ENGWEGMIDG WYGC | | 24 |
| | | |
| SEQ ID NO: 333 | moltype = AA   length = 27 | |
| FEATURE | Location/Qualifiers | |
| source | 1..27 | |
| | mol_type = protein | |
| | organism = synthetic construct | |
| SEQUENCE: 333 | | |
| GLFEAIEGFI ENGWEGMIWD YGSGSCG | | 27 |
| | | |
| SEQ ID NO: 334 | moltype = AA   length = 23 | |
| FEATURE | Location/Qualifiers | |
| source | 1..23 | |
| | mol_type = protein | |
| | organism = synthetic construct | |
| SITE | 23 | |
| | note = Glycine hexaethylene glycol amide | |
| SEQUENCE: 334 | | |
| GLFEAIEGFI ENGWEGMIDG WYG | | 23 |
| | | |
| SEQ ID NO: 335 | moltype = AA   length = 27 | |
| FEATURE | Location/Qualifiers | |
| source | 1..27 | |
| | mol_type = protein | |
| | organism = synthetic construct | |
| CARBOHYD | 27 | |
| | note = Lysine N-linked | |
| | N-acetylgalactosaminyl-(1-3)-N-acetylgalactosamine | |
| SEQUENCE: 335 | | |
| GLFEAIEGFI ENGWEGMIWD YGSGSCK | | 27 |
| | | |
| SEQ ID NO: 336 | moltype = AA   length = 27 | |
| FEATURE | Location/Qualifiers | |
| source | 1..27 | |
| | mol_type = protein | |
| | organism = synthetic construct | |
| SEQUENCE: 336 | | |
| CLIGAILKVL ATGLPTLISW IKNKRKQ | | 27 |
| | | |
| SEQ ID NO: 337 | moltype = AA   length = 26 | |
| FEATURE | Location/Qualifiers | |
| source | 1..26 | |
| | mol_type = protein | |
| | organism = synthetic construct | |
| SEQUENCE: 337 | | |
| GIGAVLKVLT TGLPALISWI KRKRQQ | | 26 |
| | | |
| SEQ ID NO: 338 | moltype = AA   length = 13 | |
| FEATURE | Location/Qualifiers | |
| source | 1..13 | |
| | mol_type = protein | |
| | organism = synthetic construct | |
| SITE | 13 | |
| | note = Phenylalanine amide | |
| SEQUENCE: 338 | | |
| IFGAIAGLLK NIF | | 13 |
| | | |
| SEQ ID NO: 339 | moltype = AA   length = 18 | |
| FEATURE | Location/Qualifiers | |
| source | 1..18 | |
| | mol_type = protein | |
| | organism = synthetic construct | |
| SEQUENCE: 339 | | |
| FFGHLFKLAT KIIPSLFQ | | 18 |

| | | |
|---|---|---|
| SEQ ID NO: 340<br>FEATURE<br>source | moltype = AA length = 21<br>Location/Qualifiers<br>1..21<br>mol_type = protein<br>organism = synthetic construct | |
| SEQUENCE: 340<br>KETWWETWWT EWSQPKKKRK V | | 21 |
| SEQ ID NO: 341<br>FEATURE<br>source | moltype = AA length = 19<br>Location/Qualifiers<br>1..19<br>mol_type = protein<br>organism = synthetic construct | |
| SEQUENCE: 341<br>LLIILRRRRI RKQAHAHSK | | 19 |
| SEQ ID NO: 342<br>FEATURE<br>source | moltype = AA length = 26<br>Location/Qualifiers<br>1..26<br>mol_type = protein<br>organism = synthetic construct | |
| SEQUENCE: 342<br>DPKGDPKGVT VTVTVTVTGK GDPKPD | | 26 |
| SEQ ID NO: 343<br>FEATURE<br>source | moltype = AA length = 17<br>Location/Qualifiers<br>1..17<br>mol_type = protein<br>organism = synthetic construct | |
| SEQUENCE: 343<br>CSIPPEVKFN KPFVYLI | | 17 |
| SEQ ID NO: 344<br>FEATURE<br>source | moltype = AA length = 27<br>Location/Qualifiers<br>1..27<br>mol_type = protein<br>organism = synthetic construct | |
| SEQUENCE: 344<br>GWTLNSAGYL LGKINLKALA ALAKKIL | | 27 |
| SEQ ID NO: 345<br>FEATURE<br>source | moltype = AA length = 21<br>Location/Qualifiers<br>1..21<br>mol_type = protein<br>organism = synthetic construct | |
| SEQUENCE: 345<br>AGYLLGKINL KALAALAKKI L | | 21 |
| SEQ ID NO: 346<br>FEATURE<br>source | moltype = AA length = 17<br>Location/Qualifiers<br>1..17<br>mol_type = protein<br>organism = synthetic construct | |
| SEQUENCE: 346<br>GALFLGFLGA AGSTMGA | | 17 |
| SEQ ID NO: 347<br>FEATURE<br>source | moltype = AA length = 20<br>Location/Qualifiers<br>1..20<br>mol_type = protein<br>organism = synthetic construct | |
| SEQUENCE: 347<br>HGLASTLTRW AHYNALIRAF | | 20 |
| SEQ ID NO: 348<br>FEATURE<br>source | moltype = AA length = 20<br>Location/Qualifiers<br>1..20<br>mol_type = protein<br>organism = synthetic construct | |
| SEQUENCE: 348<br>GLWRALWRLL RSLWRLLWRA | | 20 |
| SEQ ID NO: 349<br>FEATURE<br>source | moltype = AA length = 30<br>Location/Qualifiers<br>1..30<br>mol_type = protein<br>organism = synthetic construct | |
| SEQUENCE: 349<br>WEAALAEALA EALAEHLAEA LAEALEALAA | | 30 |

```
SEQ ID NO: 350          moltype = AA  length = 24
FEATURE                 Location/Qualifiers
source                  1..24
                        mol_type = protein
                        organism = synthetic construct
SEQUENCE: 350
GLFEAIEGFI ENGWEGMIDG WYGC                                            24

SEQ ID NO: 351          moltype = AA  length = 23
FEATURE                 Location/Qualifiers
source                  1..23
                        mol_type = protein
                        organism = synthetic construct
SEQUENCE: 351
GLFGAIAGFI ENGWEGMIDG WYG                                             23

SEQ ID NO: 352          moltype = AA  length = 36
FEATURE                 Location/Qualifiers
source                  1..36
                        mol_type = protein
                        organism = synthetic construct
SITE                    36
                        note = Lysine amide
SEQUENCE: 352
GLFGAIAGFI ENGWEGMIDG RQIKIWFQNR RMKWKK                               36

SEQ ID NO: 353          moltype = AA  length = 26
FEATURE                 Location/Qualifiers
source                  1..26
                        mol_type = protein
                        organism = synthetic construct
SEQUENCE: 353
GLFGAIAGFI ENGWEGMIDG SSKKKK                                          26

SEQ ID NO: 354          moltype = AA  length = 24
FEATURE                 Location/Qualifiers
source                  1..24
                        mol_type = protein
                        organism = synthetic construct
SEQUENCE: 354
GLFEAIAGFI ENGWEGMIDG GGYC                                            24

SEQ ID NO: 355          moltype = AA  length = 23
FEATURE                 Location/Qualifiers
source                  1..23
                        mol_type = protein
                        organism = synthetic construct
SEQUENCE: 355
GLFHAIAHFI HGGWHGLIHG WYG                                             23

SEQ ID NO: 356          moltype = AA  length = 30
FEATURE                 Location/Qualifiers
source                  1..30
                        mol_type = protein
                        organism = synthetic construct
SITE                    30
                        note = Alanine hexaethylene glycol amide
SEQUENCE: 356
GLFEAIEGFI ENGWEGLAEA LAEALEALAA                                      30

SEQ ID NO: 357          moltype = AA  length = 29
FEATURE                 Location/Qualifiers
source                  1..29
                        mol_type = protein
                        organism = synthetic construct
SEQUENCE: 357
KWKLFKKIGA VLKVLTTGYG RKKRRQRRR                                       29

SEQ ID NO: 358          moltype = AA  length = 16
FEATURE                 Location/Qualifiers
source                  1..16
                        mol_type = protein
                        organism = synthetic construct
SEQUENCE: 358
RQIKIWFQNR RMKWKK                                                     16

SEQ ID NO: 359          moltype = AA  length = 13
FEATURE                 Location/Qualifiers
```

```
                                    -continued source                   1..13
                         mol_type = protein
                         organism = synthetic construct
SEQUENCE: 359
GRKKRRQRRR PPQ                                                              13

SEQ ID NO: 360           moltype = AA   length = 18
FEATURE                  Location/Qualifiers
source                   1..18
                         mol_type = protein
                         organism = synthetic construct
SEQUENCE: 360
LLIILRRRIR KQAHAHSK                                                         18

SEQ ID NO: 361           moltype = AA   length = 27
FEATURE                  Location/Qualifiers
source                   1..27
                         mol_type = protein
                         organism = synthetic construct
SEQUENCE: 361
GWTLNSAGYL LGKINLKALA ALAKKIL                                               27

SEQ ID NO: 362           moltype = AA   length = 27
FEATURE                  Location/Qualifiers
source                   1..27
                         mol_type = protein
                         organism = synthetic construct
SEQUENCE: 362
GALFLGFLGA AGSTMGAWSQ PKKKRKV                                               27

SEQ ID NO: 363           moltype = AA   length = 21
FEATURE                  Location/Qualifiers
source                   1..21
                         mol_type = protein
                         organism = synthetic construct
SEQUENCE: 363
KETWWETWWT EWSQPKKKRK V                                                     21

SEQ ID NO: 364           moltype = AA   length = 12
FEATURE                  Location/Qualifiers
source                   1..12
                         mol_type = protein
                         organism = synthetic construct
VARIANT                  1..12
                         note = This sequence may encompass 6-12 residues
SEQUENCE: 364
RRRRRRRRRR RR                                                               12

SEQ ID NO: 365           moltype = AA   length = 18
FEATURE                  Location/Qualifiers
source                   1..18
                         mol_type = protein
                         organism = synthetic construct
SEQUENCE: 365
KLALKLALKA LKAALKLA                                                         18

SEQ ID NO: 366           moltype = AA   length = 9
FEATURE                  Location/Qualifiers
source                   1..9
                         mol_type = protein
                         organism = synthetic construct
SEQUENCE: 366
RRWWRRWRR                                                                    9

SEQ ID NO: 367           moltype = AA   length = 13
FEATURE                  Location/Qualifiers
source                   1..13
                         mol_type = protein
                         organism = synthetic construct
SEQUENCE: 367
CGYGPKKKRK VGG                                                              13

SEQ ID NO: 368           moltype = AA   length = 8
FEATURE                  Location/Qualifiers
source                   1..8
                         mol_type = protein
                         organism = synthetic construct
SEQUENCE: 368
KKKKKKKK                                                                     8
```

```
SEQ ID NO: 369          moltype = AA  length = 22
FEATURE                 Location/Qualifiers
source                  1..22
                        mol_type = protein
                        organism = synthetic construct
SEQUENCE: 369
MVRRFLVTLR IRRACGPPRV RV                                              22

SEQ ID NO: 370          moltype = AA  length = 28
FEATURE                 Location/Qualifiers
source                  1..28
                        mol_type = protein
                        organism = synthetic construct
SEQUENCE: 370
LSTAADMQGV VTDGMASGLD KDYLKPDD                                        28

SEQ ID NO: 371          moltype = DNA  length = 19
FEATURE                 Location/Qualifiers
source                  1..19
                        mol_type = other DNA
                        organism = synthetic construct
SEQUENCE: 371
ctgcctctcc accagccca                                                  19

SEQ ID NO: 372          moltype = DNA  length = 19
FEATURE                 Location/Qualifiers
source                  1..19
                        mol_type = other DNA
                        organism = synthetic construct
SEQUENCE: 372
tgggctggtg gagaggcag                                                  19

SEQ ID NO: 373          moltype = DNA  length = 19
FEATURE                 Location/Qualifiers
source                  1..19
                        mol_type = other DNA
                        organism = synthetic construct
SEQUENCE: 373
gcagagatgg agagaggaa                                                  19

SEQ ID NO: 374          moltype = DNA  length = 19
FEATURE                 Location/Qualifiers
source                  1..19
                        mol_type = other DNA
                        organism = synthetic construct
SEQUENCE: 374
ttcctctctc catctctgc                                                  19

SEQ ID NO: 375          moltype = DNA  length = 19
FEATURE                 Location/Qualifiers
source                  1..19
                        mol_type = other DNA
                        organism = synthetic construct
SEQUENCE: 375
gcggtttcct ccgggacaa                                                  19

SEQ ID NO: 376          moltype = DNA  length = 19
FEATURE                 Location/Qualifiers
source                  1..19
                        mol_type = other DNA
                        organism = synthetic construct
SEQUENCE: 376
ttgtcccgga ggaaaccgc                                                  19

SEQ ID NO: 377          moltype = DNA  length = 19
FEATURE                 Location/Qualifiers
source                  1..19
                        mol_type = other DNA
                        organism = synthetic construct
SEQUENCE: 377
ggacgacgga ggcgtgatt                                                  19

SEQ ID NO: 378          moltype = DNA  length = 19
FEATURE                 Location/Qualifiers
source                  1..19
                        mol_type = other DNA
                        organism = synthetic construct
SEQUENCE: 378
```

```
aatcacgcct ccgtcgtcc                                              19

SEQ ID NO: 379          moltype = DNA   length = 25
FEATURE                 Location/Qualifiers
source                  1..25
                        mol_type = other DNA
                        organism = synthetic construct
SEQUENCE: 379
cgggcacccg gaaacatgca gggaa                                       25

SEQ ID NO: 380          moltype = DNA   length = 25
FEATURE                 Location/Qualifiers
source                  1..25
                        mol_type = other DNA
                        organism = synthetic construct
SEQUENCE: 380
ttccctgcat gtttccgggt gcccg                                       25

SEQ ID NO: 381          moltype = DNA   length = 19
FEATURE                 Location/Qualifiers
source                  1..19
                        mol_type = other DNA
                        organism = synthetic construct
SEQUENCE: 381
ccggaaacat gcagggaag                                              19

SEQ ID NO: 382          moltype = DNA   length = 19
FEATURE                 Location/Qualifiers
source                  1..19
                        mol_type = other DNA
                        organism = synthetic construct
SEQUENCE: 382
cttccctgca tgtttccgg                                              19

SEQ ID NO: 383          moltype = DNA   length = 19
FEATURE                 Location/Qualifiers
source                  1..19
                        mol_type = other DNA
                        organism = synthetic construct
SEQUENCE: 383
gaaatgaacg agagccaca                                              19

SEQ ID NO: 384          moltype = DNA   length = 19
FEATURE                 Location/Qualifiers
source                  1..19
                        mol_type = other DNA
                        organism = synthetic construct
SEQUENCE: 384
tgtggctctc gttcatttc                                              19

SEQ ID NO: 385          moltype = DNA   length = 25
FEATURE                 Location/Qualifiers
source                  1..25
                        mol_type = other DNA
                        organism = synthetic construct
SEQUENCE: 385
tggcacactc aagactccca cggag                                       25

SEQ ID NO: 386          moltype = DNA   length = 25
FEATURE                 Location/Qualifiers
source                  1..25
                        mol_type = other DNA
                        organism = synthetic construct
SEQUENCE: 386
ctccgtggga gtcttgagtg tgcca                                       25

SEQ ID NO: 387          moltype = DNA   length = 19
FEATURE                 Location/Qualifiers
source                  1..19
                        mol_type = other DNA
                        organism = synthetic construct
SEQUENCE: 387
ccacggaggt tcagttcca                                              19

SEQ ID NO: 388          moltype = DNA   length = 19
FEATURE                 Location/Qualifiers
source                  1..19
                        mol_type = other DNA
                        organism = synthetic construct
```

```
SEQUENCE: 388
tggaactgaa cctccgtgg                                                    19

SEQ ID NO: 389         moltype = DNA  length = 19
FEATURE                Location/Qualifiers
source                 1..19
                       mol_type = other DNA
                       organism = synthetic construct
SEQUENCE: 389
accaccacca ccaccacca                                                    19

SEQ ID NO: 390         moltype = DNA  length = 19
FEATURE                Location/Qualifiers
source                 1..19
                       mol_type = other DNA
                       organism = synthetic construct
SEQUENCE: 390
tggtggtggt ggtggtggt                                                    19

SEQ ID NO: 391         moltype = DNA  length = 19
FEATURE                Location/Qualifiers
source                 1..19
                       mol_type = other DNA
                       organism = synthetic construct
SEQUENCE: 391
cgccattcat gaaggggtg                                                    19

SEQ ID NO: 392         moltype = DNA  length = 19
FEATURE                Location/Qualifiers
source                 1..19
                       mol_type = other DNA
                       organism = synthetic construct
SEQUENCE: 392
cacccctcca tgaatggcg                                                    19

SEQ ID NO: 393         moltype = DNA  length = 19
FEATURE                Location/Qualifiers
source                 1..19
                       mol_type = other DNA
                       organism = synthetic construct
SEQUENCE: 393
catgaagggg tggagcctg                                                    19

SEQ ID NO: 394         moltype = DNA  length = 19
FEATURE                Location/Qualifiers
source                 1..19
                       mol_type = other DNA
                       organism = synthetic construct
SEQUENCE: 394
caggctccac cccttcatg                                                    19

SEQ ID NO: 395         moltype = DNA  length = 19
FEATURE                Location/Qualifiers
source                 1..19
                       mol_type = other DNA
                       organism = synthetic construct
SEQUENCE: 395
gagcctgctt tgagcggaa                                                    19

SEQ ID NO: 396         moltype = DNA  length = 19
FEATURE                Location/Qualifiers
source                 1..19
                       mol_type = other DNA
                       organism = synthetic construct
SEQUENCE: 396
ttccgctcaa agcaggctc                                                    19

SEQ ID NO: 397         moltype = DNA  length = 25
FEATURE                Location/Qualifiers
source                 1..25
                       mol_type = other DNA
                       organism = synthetic construct
SEQUENCE: 397
ccgagccttt gagaaggatc gcttt                                             25

SEQ ID NO: 398         moltype = DNA  length = 25
FEATURE                Location/Qualifiers
source                 1..25
                       mol_type = other DNA
```

```
                              organism = synthetic construct
SEQUENCE: 398
aaagcgatcc ttctcaaagg ctcgg                                                  25

SEQ ID NO: 399         moltype = DNA  length = 19
FEATURE                Location/Qualifiers
source                 1..19
                       mol_type = other DNA
                       organism = synthetic construct
SEQUENCE: 399
ggcagggcgc ccgcgcagg                                                         19

SEQ ID NO: 400         moltype = DNA  length = 19
FEATURE                Location/Qualifiers
source                 1..19
                       mol_type = other DNA
                       organism = synthetic construct
SEQUENCE: 400
cctgcgcggg cgccctgcc                                                         19

SEQ ID NO: 401         moltype = DNA  length = 19
FEATURE                Location/Qualifiers
source                 1..19
                       mol_type = other DNA
                       organism = synthetic construct
SEQUENCE: 401
gatgattagt tcagagata                                                         19

SEQ ID NO: 402         moltype = DNA  length = 19
FEATURE                Location/Qualifiers
source                 1..19
                       mol_type = other DNA
                       organism = synthetic construct
SEQUENCE: 402
tatctctgaa ctaatcatc                                                         19

SEQ ID NO: 403         moltype = AA  length = 4
FEATURE                Location/Qualifiers
source                 1..4
                       mol_type = protein
                       organism = synthetic construct
SEQUENCE: 403
GGFG                                                                          4

SEQ ID NO: 404         moltype = AA  length = 4
FEATURE                Location/Qualifiers
source                 1..4
                       mol_type = protein
                       organism = synthetic construct
SEQUENCE: 404
ALAL                                                                          4

SEQ ID NO: 405         moltype = AA  length = 4
FEATURE                Location/Qualifiers
source                 1..4
                       mol_type = protein
                       organism = synthetic construct
SEQUENCE: 405
GFLG                                                                          4

SEQ ID NO: 406         moltype = AA  length = 17
FEATURE                Location/Qualifiers
source                 1..17
                       mol_type = protein
                       organism = synthetic construct
VARIANT                6
                       note = N or Q
VARIANT                13
                       note = Q or E
SEQUENCE: 406
EINPIXGRSN YAXKFQG                                                           17

SEQ ID NO: 407         moltype = AA  length = 11
FEATURE                Location/Qualifiers
source                 1..11
                       mol_type = protein
                       organism = synthetic construct
VARIANT                8
                       note = N or S
```

```
SEQUENCE: 407
RTSENIYXNL A                                                                    11

SEQ ID NO: 408         moltype = AA  length = 7
FEATURE                Location/Qualifiers
source                 1..7
                       mol_type = protein
                       organism = synthetic construct
VARIANT                2
                       note = A or G
VARIANT                7
                       note = D or E
SEQUENCE: 408
AXTNLAX                                                                         7

SEQ ID NO: 409         moltype = AA  length = 10
FEATURE                Location/Qualifiers
source                 1..10
                       mol_type = protein
                       organism = synthetic construct
VARIANT                10
                       note = F or absent
SEQUENCE: 409
QHFWGTPLTX                                                                      10

SEQ ID NO: 410         moltype = AA  length = 7
FEATURE                Location/Qualifiers
source                 1..7
                       mol_type = protein
                       organism = synthetic construct
VARIANT                7
                       note = D or E
SEQUENCE: 410
AATNLAX                                                                         7
```

The invention claimed is:

1. A polynucleotide-antibody conjugate comprising an anti-transferrin receptor antibody or antigen binding fragment thereof conjugated to a polynucleotide, wherein the polynucleotide is from 19 to 30 nucleotides in length, wherein the polynucleotide comprises a nucleic acid sequence selected from a group consisting of SEQ ID NOs: 72, 76, 126, 131, 132, 134, 135, 136, 212, 216, 266, 271, 272, 274, 275, and 276 and wherein the polynucleotide mediates RNA interference against DUX4 mRNA and downregulation of DUX4 biomarker mRNA level.

2. The polynucleotide-antibody conjugate of claim 1, wherein the polynucleotide is a single stranded polynucleotide.

3. The polynucleotide-antibody conjugate of claim 2, wherein the single stranded polynucleotide is an antisense oligonucleotide (ASO) or a phosphorodiamidate morpholino oligomers (PMO).

4. The polynucleotide-antibody conjugate of claim 1, wherein the anti-transferrin receptor antibody or antigen binding fragment thereof binds to a transferrin receptor on a cell surface of a muscle cell.

5. The polynucleotide-antibody conjugate of claim 1, wherein the polynucleotide comprises at least one 2' modified nucleotide, at least one modified internucleotide linkage, or at least one inverted abasic moiety.

6. The polynucleotide-antibody conjugate of claim 1, wherein the polynucleotide hybridizes to at least 8 contiguous bases of the target sequence of a human DUX4 mRNA.

7. The polynucleotide-antibody conjugate of claim 1, wherein the polynucleotide is from 19 to 25 nucleotides in length.

8. The polynucleotide-antibody conjugate of claim 1, wherein the polynucleotide-antibody conjugate comprises a linker connecting the anti-transferrin receptor antibody or antigen binding fragment thereof to the polynucleotide.

9. The polynucleotide-antibody conjugate of claim 5, wherein the at least one 2' modified nucleotide comprises 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-ODMAOE), 2'-O-dimethylaminopropyl (2'-O-DMAP), 2'-O-dimethylaminoethyloxyethyl (2'-O-DMAEOE), 2'-O—N-methylacetamido (2'-O-NMA) modified nucleotide, locked nucleic acid (LNA), ethylene nucleic acid (ENA), or a combination thereof.

10. The polynucleotide-antibody conjugate of claim 5, wherein the at least one modified internucleotide linkage comprises a phosphorodithioate linkage.

11. The polynucleotide-antibody conjugate of claim 5, wherein the polynucleotide comprises three or more 2' modified nucleotides selected from 2-O-methyl modified nucleotide and 2'-deoxy-2'-fluoro modified nucleotide.

12. The polynucleotide-antibody conjugate of claim 1, wherein the polynucleotide-antibody conjugate has a polynucleotide to antibody ratio from 1 to 4.

13. The polynucleotide-antibody conjugate of claim 1, wherein the polynucleotide comprises a 5'-terminal vinylphosphonate modified nucleotide.

14. The polynucleotide-antibody conjugate of claim 1, wherein the polynucleotide-antibody conjugate is formulated for parenteral administration.

15. The polynucleotide-antibody conjugate of claim 1, wherein the downregulation of DUX4 biomarker mRNA level is evaluated by expression level of one or more DUX4 biomarker genes selected from a group consisting of MBD3L2, TRIM43, PRAMEF1, ZSCAN4, KHDC1L, and LEUTX.

16. The polynucleotide-antibody conjugate of claim 1, wherein the anti-transferrin receptor antibody or antigen binding fragment thereof is conjugated to the 5' end of the polynucleotide.

\* \* \* \* \*